(12) United States Patent
Alcaraz et al.

(10) Patent No.: US 8,629,271 B2
(45) Date of Patent: Jan. 14, 2014

(54) COMPOUNDS

(75) Inventors: Lilian Alcaraz, Leicestershire (GB); Nicholas David Kindon, Leicestershire (GB)

(73) Assignee: AstraZeneca AB, Cheshire (GB)

(*) Notice: Subject to any disclaimer, the term of this patent is extended or adjusted under 35 U.S.C. 154(b) by 0 days.

(21) Appl. No.: 13/437,410

(22) Filed: Apr. 2, 2012

(65) Prior Publication Data

US 2012/0322788 A1     Dec. 20, 2012

Related U.S. Application Data

(63) Continuation of application No. 12/365,570, filed on Feb. 4, 2009, now Pat. No. 8,148,373.

(30) Foreign Application Priority Data

| Feb. 6, 2008 | (GB) | 0802192.5 |
| Dec. 9, 2008 | (GB) | 0822437.0 |

(51) Int. Cl.
*C07D 498/10* (2006.01)

(52) U.S. Cl.
USPC .......................................................... 544/71

(58) Field of Classification Search
USPC .......................................................... 544/71
See application file for complete search history.

(56) References Cited

U.S. PATENT DOCUMENTS

| 2,707,186 A | 4/1955 | Duschinsky |
| 2011/0053909 A1 | 3/2011 | Alcaraz et al. |

FOREIGN PATENT DOCUMENTS

| WO | WO9733202 A1 | 9/1997 |
| WO | WO9746577 A1 | 12/1997 |
| WO | WO0112896 A1 | 2/2001 |
| WO | WO0144170 A1 | 6/2001 |
| WO | WO2005085226 A1 | 9/2005 |
| WO | WO2007027134 A1 | 3/2007 |
| WO | WO2007069986 A1 | 6/2007 |
| WO | WO2007102771 A1 | 9/2007 |
| WO | WO2008075025 A1 | 6/2008 |
| WO | WO2008096127 A2 | 8/2008 |
| WO | WO2008096129 A1 | 8/2008 |
| WO | WO2009098448 A1 | 8/2009 |
| WO | WO2011012897 A1 | 2/2011 |

OTHER PUBLICATIONS

Bauerlein et al. "Synthesis of Long-chain 1-Alkylimidazole-2-thiols, 1-Alkylimidazoles, and Some Related Benzimidazole Compounds" Liebigs Ann. Chem. 1979 (11) 1818-1827.
Birch et al. "A New Modification of the Pomeranz-Fritsch Isoquinoline Synthesis" J. Chem. Soc. Perkin I 1974 (19) 2185-2190.
Deng et al. "A Practical Synthesis of Enantiopure 7-Alkoxy-4-aryl-tetrahydroisoquinoline, a Dual Serotonin Reuptake Inhibitor/Histamine H3 Antagonist" Org. Proc. Res. Dev. 2007 (11) 1043-1050.
European Examiner José Cortés, European Search Report for Application No. PCT/GB2009/000298 dated Jun. 12, 2009, 4 pages.
Gao et al. "Synthesis and Structure Revision of Nakiterpiosin" J. Am. Chem. Soc. 2009 (131) 1410-1412.
Giles et al. "Development of a Manufacturing Process for Sibenadet Hydrochloride, the Active Ingredient of Viozan" Org. Proc. Res. Dev. 2004 (8) 628-642.
Kaye et al. "Preparation of N-Substituted Aminoacetals" J. Am. Chem. Soc. 1949 (71) 2272-2273.
Lindner et al. "Macrocyclic Di- and Tetranuclear Osmacycloferrocenophanes" Organometallics 2002 (21) 4217-4225.
Main, B.G. "β-Adrenergic Receptors" in Comprehensive Medicinal Chemistry (Alderley Park, UK Pergamon Press, 1990) pp. 187-228.
Plaue et al. "A new preparation of 4-(boc-aminoacyloxymethyl)phenylacetic acids for solid-phase peptide synthesis" Tet. Lett. 1987 (28) 1401-1404.
Van Noord et al. "Comparison of tiotropium once daily, formoterol twice daily and both combined once daily in patients with COPD" Eur. Respir. J. 2005 (26) 214-222.

*Primary Examiner* — Brian McDowell
(74) *Attorney, Agent, or Firm* — Fish & Richardson P.C.

(57) ABSTRACT

The present invention relates to spirocyclic amide derivatives of the formula I,

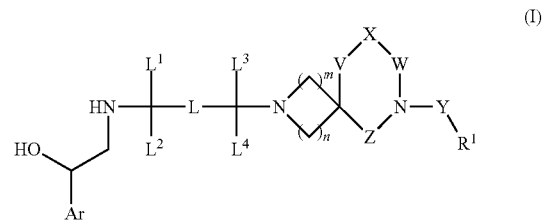

pharmaceutically acceptable salts thereof, a process for their preparation, pharmaceutical compositions containing them, and their use in therapy.

1 Claim, 2 Drawing Sheets

COMPOUNDS

CROSS REFERENCE TO RELATED APPLICATIONS

This application claims the benefit of from Great Britain Application Serial No. 0802192.5, filed on 6 Feb. 2008 and from Great Britain Application Serial No. 0822437.0, filed on 9 Dec. 2008. Each of these prior applications is incorporated herein by reference in its entirety.

The present invention relates to spirocyclic amide derivatives, a process for their preparation, pharmaceutical compositions containing them, a process for preparing such pharmaceutical compositions, their use in therapy, and intermediates for use in their preparation.

First-line treatment for a variety of pulmonary disorders including chronic obstructive pulmonary disease (COPD) and asthma is through the use of bronchodilators. Muscarinic-receptor antagonists (anti-cholinergics) are bronchodilators that exert their efficacy by reducing vagal cholinergic tone, the main reversible component of airway constriction in COPD. β-adrenoceptor agonists are also bronchodilators due to their ability to functionally antagonise the bronchoconstrictor responses to a range of mediators, including acetylcholine.

In addition to improving lung function, these agents improve dyspnoea (breathlessness), quality of life, exercise tolerance and they reduce exacerbations. A number of clinical studies have demonstrated that combined administration of an anti-cholinergic and a $\beta_2$-receptor agonist is more efficacious than either of the individual components (van Noord, J. A., Aumann, J-L., Janssens, E., Smeets, J. J., Verhaert, J., Disse, B., Mueller, A. & Cornelissen, P. J. G., 2005. "Comparison of tiotropium once daily, formoterol twice daily and both combined once daily in patients with COPD", *Eur. Respir. J.*, vol 26, pp 214-222.). A single molecule possessing activities at muscarinic and $\beta_2$-receptors (MABAs) may provide additional benefits to COPD patients in terms of efficacy and side-effect profile over either single agent. Moreover, a molecule possessing dual activity may also offer benefits in terms of ease-of-use and patient compliance over co-administration of the single therapies. A single agent may also be beneficial from the perspective of formulation compared to two separate compounds, also offering the potential, if combined with another therapeutic, for triple action therapies.

According to a first aspect of the invention we now provide a compound of formula I

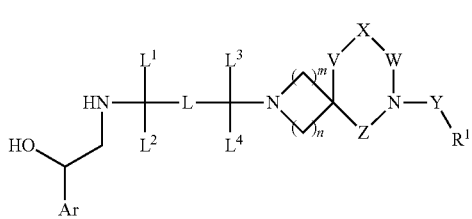

wherein Ar represents a β-adrenoceptor binding group;

L represents a linker comprising a straight or branched hydrocarbyl chain of up to 15 carbon atoms;

wherein up to three of the carbon atoms in the chain are optionally substituted by up to four substituents independently selected from halogen, $S(O)_{0-2}R^{56}$, $NR^{57}R^{58}$, $S(O)_2NR^{59}R^{60}$, $C(O)NR^{61}R^{62}$, $C(O)OR^{63}$, $NR^{64}S(O)_2R^{65}$, $NR^{66}C(O)R^{67}$, $NR^{68}C(O)OR^{69}$, $NR^{70}C(O)NR^{71}R^{72}$, $OR^{73}$, $C_{1-6}$ alkyl and $C_{3-6}$ cycloalkyl, and wherein $C_{1-6}$ alkyl and $C_{3-6}$ cycloalkyl may be optionally substituted by up to three substituents independently selected from halogen, hydroxyl and $C_{1-6}$ alkoxy;

wherein up to five carbon atoms of the chain may be replaced by groups independently selected from O, $NR^{45}$, S, S(O), $S(O)_2$, C(O)O, OC(O), $NR^{46}C(O)$, $C(O)NR^{47}$, $NR^{48}S(O)_2$, $S(O)_2NR^{49}$, $NR^{50}C(O)NR^{51}$, $NR^{52}S(O)_2NR^{53}$, OC(O)$NR^{54}$, $NR^{55}C(O)O$, provided that any such groups in the chain are separated by at least 2 carbon atoms; and wherein up to six carbon atoms of the chain may form part of a mono- or bicyclic aliphatic, heteroaliphatic, aromatic or heteroaromatic ring having up to four heteroatoms independently selected from N, O or S, said ring comprising up to 10 ring atoms, and wherein the ring is optionally substituted by up to three substituents independently selected from halogen, $S(O)O_{0-2}R^{56}$, $NR^{57}R^{58}$, $S(O)_2NR^{59}R^{60}$, $C(O)NR^{61}R^{62}$, $C(O)OR^{63}$, $NR^{64}S(O)_2R^{65}$, $NR^{66}C(O)R^{67}$, $NR^{68}C(O)OR^{69}$, $NR^{70}C(O)NR^{71}R^{72}$, $OR^{73}$, $C_{1-6}$ alkyl and $C_{3-6}$ cycloalkyl, and wherein $C_{1-6}$ alkyl and $C_{3-6}$ cycloalkyl may be optionally substituted by up to three substituents independently selected from halogen, hydroxyl and $C_{1-6}$ alkoxy;

and the chain may comprise up to three of such rings each selected independently;

wherein $R^{56}$, $R^{65}$ and $R^{69}$ each independently represent $C_{1-6}$ alkyl or $C_{3-6}$ cycloalkyl wherein the $C_{1-6}$ alkyl and $C_{3-6}$ cycloalkyl may be optionally substituted by up to three substituents independently selected from halogen, hydroxyl, $C_{1-6}$ alkoxy; and $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{57}$, $R^{58}$, $R^{59}$, $R^{60}$, $R^{61}$, $R^{62}$, $R^{63}$, $R^{64}$, $R^{66}$, $R^{67}$, $R^{68}$, $R^{70}$, $R^{71}$, $R^{72}$ and $R^{73}$ each independently represent hydrogen, $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen, hydroxyl, $C_{1-6}$ alkoxy; or any of $R^{57}$ and $R^{58}$, $R^{59}$ and $R^{60}$, $R^{61}$ and $R^{62}$ or $R^{71}$ and $R^{72}$, together with the nitrogen atom to which they are both attached, may form a 4 to 8 membered aliphatic heterocyclic ring, wherein the heterocyclic ring may comprise up to three heteroatoms independently selected from N, O and S, wherein the ring may be optionally substituted by up to three substituents independently selected from halogen, hydroxyl, $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen, hydroxyl and $C_{1-6}$ alkoxy; and wherein the chain may additionally comprise up to three carbon-carbon double bonds;

wherein the chain may additionally comprise up to three carbon-carbon triple bonds;

$L^1$ and $L^2$ independently represent hydrogen, $C_{1-6}$ alkyl or $C_{3-6}$ cycloalkyl;

$L^3$ and $L^4$ independently represent hydrogen, $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen, hydroxyl and $C_{1-6}$ alkoxy;

in addition $L^1$ and/or $L^3$ may be linked to carbon atoms of the hydrocarbyl chain in linker L to form aliphatic rings of up to 6 ring atoms, wherein each ring may comprise up to three heteroatoms independently selected from N, O and S;

$R^1$ represents a phenyl ring, a 4 to 8 membered heteroaliphatic ring, a 3 to 8 membered aliphatic ring or a 5 to 6 membered heteroaryl ring each having up to four heteroatoms independently selected from N, O or S, each of wherein the ring may be optionally substituted by up to three substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$, $C_{1-7}$ alkyl or $C_{3-8}$ cycloalkyl (each of wherein the $C_{1-7}$ alkyl and $C_{3-8}$ cycloalkyl may be optionally substituted by up to six substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$), a phenyl ring, a 4 to 8 membered heteroaliphatic ring, a 5 to 6 membered heteroaryl ring, each having up to four heteroatoms independently selected from N, O or S, each of which phenyl ring, 4 to 8 membered heteroaliphatic ring, 3 to 8 membered aliphatic ring or 5 to 6 membered heteroaryl ring may be optionally substituted by up to three substituents independently selected from halogen, cyano, nitro, SH, $S(O)_{0-2}R^5$, $S(O)_2NR^8R^9$, $C(O)NR^{10}R^{11}$, $C(O)OR^{12}$, $OR^{22}$, $C_{1-6}$ alkyl or $C_{3-6}$ cycloalkyl wherein the $C_{1-6}$ alkyl and $C_{3-6}$ cycloalkyl may be optionally substituted by up to three substituents independently selected from halogen, hydroxyl, $C_{1-6}$ alkoxy, cyano, nitro, $NH_2$, $NH(C_{1-6}$ alkyl) and $N(C_{1-6}$ alkyl)$_2$;

or $R^1$ represents a fused aliphatic, fused heteroaliphatic, fused aromatic or fused heteroaryl ring of up to 10 atoms and having up to four heteroatoms independently selected from N, O or S, each of wherein the ring may be optionally substituted by up to three substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$, $C_{1-6}$ alkyl or $C_{3-6}$ cycloalkyl wherein the $C_{1-6}$ alkyl and $C_{3-6}$ cycloalkyl may be optionally substituted by up to three substituents independently selected from halogen, hydroxyl, $C_{1-6}$ alkoxy, $NH_2$, $NH(C_{1-6}$ alkyl) and $N(C_{1-6}$ alkyl)$_2$;

or $R^1$ further represents a $C_{1-6}$ alkyl chain wherein one or two of the carbon atoms can be replaced by O, S or N and wherein $R^1$ may be substituted by up to three $C_{1-3}$ alkyl chains and two such chains may be joined to form a $C_{3-8}$ cycloalkyl chain wherein the $C_{1-3}$ alkyl and $C_{3-8}$ cycloalkyl chains may be optionally substituted up to three substituents independently selected from halogen, cyano, nitro; SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$, and wherein the $C_{1-6}$ alkyl chain is further optionally substituted by up to three substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{11}$, $NR^{19}C(O)NR^{20}R^{21}$, $OR^{22}$, a phenyl ring, a 4 to 8 membered heteroaliphatic ring, a 3 to 8 membered aliphatic ring, a 5 to 6 membered heteroaryl ring each having up to four heteroatoms independently selected from N, O or S, and wherein each ring is optionally substituted by up to three substituents independently selected from halogen, cyano, nitro, $S(O)_{0-2}R^5$, $S(O)_2NR^8R^9$, $C(O)NR^{10}R^{11}$, $C(O)OR^{12}$, $OR^{22}$, $C_{1-7}$ alkyl or $C_{3-7}$ cycloalkyl (each of wherein the $C_{1-7}$ alkyl and $C_{3-7}$ cycloalkyl may be optionally substituted by up to six substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$), a phenyl ring, a 4 to 8 membered heteroaliphatic ring, a 3 to 8 membered aliphatic ring, a 5 to 6 membered heteroaryl ring each having up to four heteroatoms independently selected from N, O or S, each of which phenyl ring, 4 to 8 membered heteroaliphatic ring, 3 to 8 membered aliphatic ring, or 5 to 6 membered heteroaryl ring may be optionally substituted by up to three substituents independently selected from halogen, cyano, nitro, $S(O)_{0-2}R^5$, $S(O)_2NR^8R^9$, $C(O)NR^{10}R^{11}$, $C(O)OR^{12}$, $OR^{22}$, $C_{1-6}$ alkyl or $C_{3-6}$ cycloalkyl, wherein $C_{1-6}$ alkyl and $C_{3-6}$ cycloalkyl may each be optionally substituted by up to three substituents independently selected from halogen, hydroxyl, $C_{1-6}$ alkoxy, $NH_2$, $NH(C_{1-6}$ alkyl) and $N(C_{1-6}$ alkyl)$_2$;

or the $C_{1-6}$ alkyl chain may be substituted by a fused aliphatic, fused heteroaliphatic, fused aromatic or fused heteroaryl ring of up to 10 atoms and having up to four heteroatoms independently selected from N, O or S, each of wherein the ring may be optionally substituted by up to three substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$, $C_{1-6}$ alkyl or $C_{3-6}$ cycloalkyl wherein the $C_{1-6}$ alkyl and $C_{3-6}$ cycloalkyl may be optionally substituted by up to three substituents independently selected from halogen, hydroxyl, $C_{1-6}$ alkoxy, $NH_2$, $NH(C_{1-6}$ alkyl) and $N(C_{1-6}$ alkyl)$_2$;

$R^5$, $R^{14}$ and $R^{18}$ independently represent $C_{1-6}$ alkyl or $C_{3-6}$ cycloalkyl, wherein the $C_{1-6}$ alkyl and $C_{3-6}$ cycloalkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$; and $R^6$, $R^7$, $R^8$, $R^9$, $R^{10}$, $R^{11}$, $R^{12}$, $R^{13}$, $R^{15}$, $R^{16}$, $R^{17}$, $R^{19}$, $R^{20}$, $R^{21}$ and $R^{22}$ each independently represent hydrogen, $C_{1-6}$ alkyl or $C_{3-6}$ cycloalkyl, wherein the $C_{1-6}$ alkyl or $C_{3-6}$ cycloalkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$; or any of $R^6$ and $R^7$, $R^8$ and $R^9$, $R^{10}$ and $R^{11}$, or $R^{20}$ and $R^{21}$ together with the nitrogen atom to which they are both attached, may form a 4 to 8 membered aliphatic heterocyclic ring, wherein the heterocyclic ring may be optionally substituted by one or more substituents independently selected from halogen, hydroxyl, $C_{1-6}$ alkyl, $C_{1-6}$ cycloalkyl and $C_{1-6}$ alkoxy, wherein the $C_{1-6}$ alkyl, $C_{1-6}$ cycloalkyl or $C_{1-6}$ alkoxy may be optionally substituted by one or more substituents independently selected from halogen, hydroxyl and $C_{1-6}$ alkoxy, $NH_2$, $NH(C_{1-6}$ alkyl) and $N(C_{1-6}$ alkyl)$_2$;

X represents O, S, $S(O)_o$ or $CR^{25}R^{26}$;

m=0, 1, 2 or 3;

n=1, 2, 3 or 4; provided that m+n is greater than or equal to 2 o=1, 2;

W represents $CR^{27}R^{28}CR^{29}R^{30}$ or $CR^{31}R^{32}CR^{33}R^{34}CR^{35}R^{36}$;

V and Z independently represent a bond, $CR^{37}R^{38}$ or $CR^{39}R^{40}CR^{41}R^{42}$, provided that when X represents either O, S, or $S(O)_o$ then m, V and Z are such that all the heteroatoms in the rings are separated by at least two carbon atoms (e.g. when V is a bond then m is not 0, Z is not a bond);

Y represents CO, $CONR^{43}$, $SO_2$ or $SO_2NR^{44}$;

$R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$ $R^{39}$, $R^{40}$, $R^{41}$, $R^{42}$, each independently represent hydrogen, fluorine or $C_{1-6}$ alkyl or $C_{3-6}$ cycloalkyl; and when they do not represent hydrogen or fluorine $R^{25}$ and $R^{26}$, $R^{27}$ and $R^{28}$, $R^{29}$ and $R^{30}$, $R^{31}$ and $R^{32}$, $R^{33}$ and $R^{34}$, $R^{35}$ and $R^{36}$, $R^{37}$ and $R^{38}$, $R^{39}$ and $R^{40}$ or $R^{41}$ and $R^{42}$ together with the carbon atom to which they are both attached, may additionally form a 3 to 6 membered aliphatic ring;

$R^{43}$ and $R^{44}$ each independently represent hydrogen, $C_{1-6}$ alkyl or $C_{3-6}$ cycloalkyl and pharmaceutically acceptable salts thereof.

By "β-adrenoceptor binding group" we mean a group capable of binding a β-adrenergic receptor; such as for example as outlined in the review article "β-adrenergic receptors in Comprehensive Medicinal Chemistry, 1990, B. E.

Main, p 187 (Pergamon Press). Such groups are also known from, for example in WO/2005092841, US/20050215542, WO/2005070872, WO/2006023460, WO/2006051373, WO/2006087315, WO/2006032627.

Examples of convenient β-adrenoceptor binding groups include

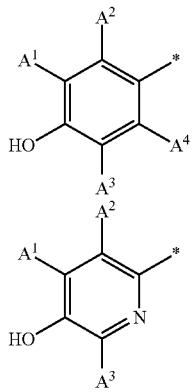 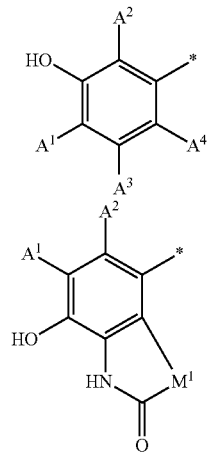

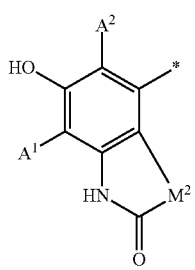

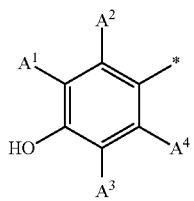 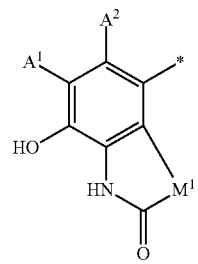

$M^1$ is S, C(O), $NA^5$, $CA^6A^7$, $CH_2CH_2$, CH=CH, $CH_2O$ or $OCH_2$;

$M^2$ is S, C(O), $NA^5$, $CA^6A^7$, $CH_2CH_2$, CH=CH, $CH_2O$ or $OCH_2$;

$A^1$, $A^2$, $A^3$ and $A^4$ are, independently, hydrogen, halogen, trifluoromethyl, cyano, carboxy, hydroxy, nitro, $S(O)_2A^8$, $NA^9S(O)_2A^{10}$, $C(O)NA^{11}A^{12}$, $NA^{13}C(O)A^{14}$, $C_{1-6}$ alkyl, $C_{1-6}$ alkoxy, $C(O)(C_{1-6}$ alkyl) or $C(O)OC_{1-6}$ alkyl;

$A^3$ can also be $CH_2OH$, NHCHO, $NHS(O)_2NA^{15}A^{16}$ or $NHSO_2A^{17}$;

$A^5$, $A^6$, $A^7$, $A^9$, $A^{11}$, $A^{12}$, $A^{13}$, $A^{14}$, $A^{15}$ or $A^{16}$ are, independently, hydrogen or $C_{1-6}$ alkyl;

$A^8$, $A^{10}$ and $A^{17}$ are, independently, $C_{1-6}$ alkyl;

More conveniently the β adrenergic receptor binding group Ar is selected from

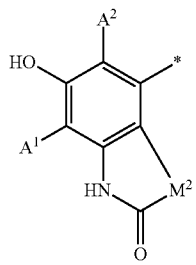

wherein $M^1$ is S, CH=CH, $CH_2O$ or $OCH_2$;

$M^2$ is S, CH=CH, $CH_2O$ or $OCH_2$;

$A^1$, $A^2$, and $A^4$ are, independently, hydrogen, halogen, $C_{1-6}$ alkyl, $C_{1-6}$ alkoxy;

$A^3$ can also be $CH_2OH$, NHCHO, $NHS(O)_2NA^{15}A^{16}$ or $NHSO_2A^{17}$;

$A^{15}$ or $A^{16}$ are independently selected from hydrogen, $C_{1-6}$ alkyl or $C_{3-4}$ cycloalkyl;

$A^{17}$ is $C_{1-6}$ alkyl or $C_{3-6}$ cycloalkyl;

Examples of $C_{1-6}$ alkyl include $C_{1-4}$ alkyl and $C_{1-2}$ alkyl.

Examples of $C_{3-6}$ cycloalkyl include $C_{3-5}$ cycloalkyl and $C_{3-4}$ cycloalkyl.

Examples of $C_{1-6}$ alkoxy include $C_{1-4}$ alkoxy and $C_{1-2}$ alkoxy.

More conveniently the β adrenergic receptor binding group Ar is selected from:

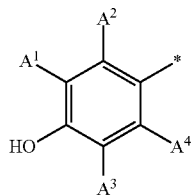 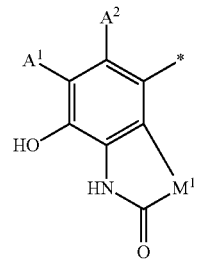

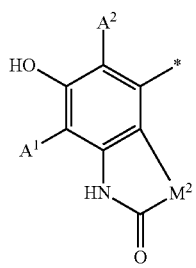

wherein $A^1$, $A^2$ and $A^4$ are all hydrogen, $A^3$ is $CH_2OH$, NHCHO, $M^1$ is S, CH=CH, or $OCH_2$; $M^2$ is S, CH=CH, or $OCH_2$.

More conveniently the β adrenergic receptor binding group Ar is selected from:

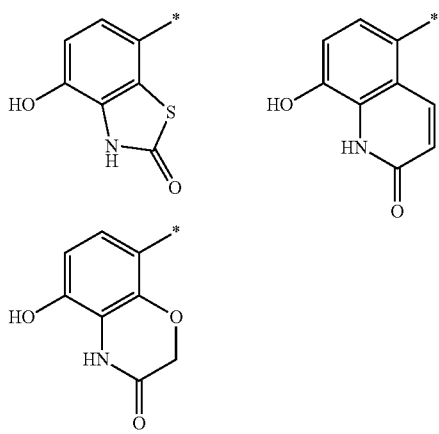

Conveniently L represents a linker comprising a straight or branched hydrocarbyl chain of up to 12 carbon atoms or of up to 10 carbon atoms or of up to 8 carbon atoms;

wherein up to two of the carbon atoms in the chain are optionally substituted by up to four substituents independently selected from halogen, $S(O)_{0-2}R^{56}$, $NR^{57}R^{58}$, $S(O)_2NR^{59}R^{60}$, $C(O)NR^{61}R^{62}$, $C(O)OR^{63}$, $NR^{64}S(O)_2R^{65}$, $NR^{66}C(O)R^{67}$, $NR^{68}C(O)OR^{69}$, $NR^{70}C(O)NR^{71}R^{72}$, $OR^{73}$, $C_{1-6}$ alkyl and $C_{3-6}$ cycloalkyl, and wherein $C_{1-6}$ alkyl and $C_{3-6}$ cycloalkyl may be optionally substituted by up to three substituents independently selected from halogen, hydroxyl and $C_{1-6}$ alkoxy;

Conveniently up to two carbon atoms of the chain may be replaced by groups independently selected from O, $NR^{45}$, S, S(O), $S(O)_2$, C(O)O, OC(O), $NR^{46}C(O)$, $C(O)NR^{47}$, $NR^{48}S(O)_2$, $S(O)_2NR^{49}$, $NR^{50}C(O)NR^{51}$, $NR^{52}S(O)_2NR^{53}$; or independently selected from O, S, S(O), $S(O)_2$, $NR^{46}C(O)$, $C(O)NR^{47}$; provided that in each case any such groups in the chain are separated by at least 2 carbon atoms;

Conveniently up to four carbon atoms of the chain may form part of a mono- or bicyclic aliphatic, heteroaliphatic, aromatic or heteroaromatic ring having up to three heteroatoms independently selected from N, O or S, said ring comprising up to 10 ring atoms, and wherein the ring is optionally substituted by up to three substituents independently selected from halogen, $S(O)_{0-2}R^{56}$, $NR^{57}R^{58}$, $S(O)_2NR^{59}R^{60}$, $C(O)NR^{61}R^{62}$, $C(O)OR^{63}$, $NR^{64}S(O)_2R^{65}$, $NR^{66}C(O)R^{67}$, $NR^{68}C(O)OR^{69}$, $NR^{70}C(O)NR^{71}R^{72}$, $OR^{73}$, $C_{1-6}$ alkyl and $C_{3-6}$ cycloalkyl, and wherein $C_{1-6}$ alkyl and $C_{3-6}$ cycloalkyl may be optionally substituted by up to three substituents independently selected from halogen, hydroxyl and $C_{1-6}$ alkoxy;

Conveniently the chain may comprise up to two, or one of such rings each selected independently;

Conveniently $R^{56}$, $R^{65}$ and $R^{69}$ each independently represent $C_{1-4}$ alkyl or $C_{3-6}$ cycloalkyl wherein the $C_{1-4}$ alkyl and $C_{3-6}$ cycloalkyl may be optionally substituted by up to three substituents independently selected from halogen, hydroxyl, $C_{1-4}$ alkoxy; and Conveniently $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{57}$, $R^{58}$, $R^{59}$, $R^{60}$, $R^{61}$, $R^{62}$, $R^{63}$, $R^{64}$, $R^{66}$, $R^{67}$, $R^{68}$, $R^{70}$, $R^{71}$, $R^{72}$ and $R^{73}$ each independently represent hydrogen, $C_{1-4}$ alkyl or $C_{3-6}$ cycloalkyl, wherein the $C_{1-4}$ alkyl and $C_{3-6}$ cycloalkyl may be optionally substituted by up to three substituents independently selected from halogen, hydroxyl, $C_{1-4}$ alkoxy; or any of $R^{57}$ and $R^{58}$, $R^{59}$ and $R^{60}$, $R^{61}$ and $R^{62}$ or $R^{71}$ and $R^{72}$, together with the nitrogen atom to which they are both attached, may form a 4 to 8 membered aliphatic heterocyclic ring, wherein the heterocyclic ring may be optionally substituted by up to three substituents independently selected from halogen, hydroxyl and $C_{1-4}$ alkyl or $C_{3-6}$ cycloalkyl, wherein the $C_{1-4}$ alkyl and $C_{3-6}$ cycloalkyl may be optionally substituted by up to three substituents independently selected from halogen, hydroxyl and $C_{1-4}$ alkoxy;

Examples of convenient ring systems which may be present as part of the hydrocarbyl linker include

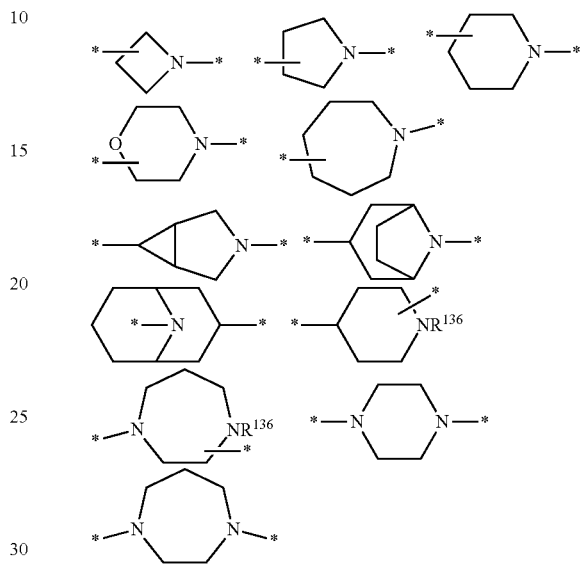

wherein the heterocyclyl ring is unsubstituted or substituted by 1 or 2 substituents independently selected from halogen, $C_{1-4}$ alkyl (optionally substituted by $OR^{121}$, $NR^{122}R^{123}$ or $NR^{124}C(O)R^{125}$), $OR^{126}$, $NR^{127}R^{128}$, $C(O)NR^{129}R^{130}$, $NR^{131}C(O)R^{132}$, CN, $S(O)_2R^{133}$ or $S(O)_2NR^{134}R^{135}$;

$R^{133}$ represents $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen, hydroxyl, $C_{1-6}$ alkoxy; and $R^{121}$, $R^{122}$, $R^{123}$, $R^{124}$, $R^{125}$, $R^{126}$, $R^{127}$, $R^{128}$, $R^{129}$, $R^{130}$, $R^{131}$, $R^{132}$, $R^{134}$, $R^{135}$ and $R^{136}$ each independently represent hydrogen, $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen, hydroxyl, $C_{1-6}$ alkoxy; or any of $R^{122}$ and $R^{123}$, $R^{127}$ and $R^{128}$, $R^{129}$ and $R^{130}$ or $R^{134}$ and $R^{135}$, together with the nitrogen atom to which they are both attached, may form a 4 to 8 membered aliphatic heterocyclic ring, wherein the heterocyclic ring may be optionally substituted by up to three substituents independently selected from halogen, hydroxyl, $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen and hydroxyl;

Conveniently the chain may additionally comprise up to two carbon-carbon double bonds or a single carbon-carbon double bond.

Conveniently the chain may additionally comprise up to two carbon-carbon triple bonds or a single carbon-carbon triple bond.

Conveniently each of $L^1$, $L^2$, $L^3$ and $L^4$ represent independently hydrogen, a $C_{1-4}$ alkyl or $C_{3-6}$ cycloalkyl group, wherein the $C_{1-4}$ alkyl and $C_{3-6}$ cycloalkyl may be optionally substituted by up to three substituents independently selected from halogen and hydroxyl; in addition $L^1$ and/or $L^3$ may be linked to a carbon atom of the hydrocarbyl chain in linker L to form an aliphatic ring of up to 6 ring atoms, wherein the ring may comprise up to two heteroatoms independently selected from N, O and S.

Where four carbon atoms of the chain form part of a mono- or bicyclic aliphatic, heteroaliphatic, aromatic or heteroaromatic ring having up to three heteroatoms independently selected from N, O or S, said ring may, if an aliphatic ring system, comprise up to 10, 9, 8, 7, 6, 5, 4 or 3 ring atoms; if an aromatic ring system then it may comprise 10, 9, 6 or 5 ring atoms; each selected independently;

$R^1$ represents a phenyl ring or a 5 to 6 membered heteroaryl ring each having up to three heteroatoms independently selected from N, O or S, or $R^1$ represents a fused aliphatic, fused heteroaliphatic, fused aromatic or fused heteroaryl ring of up to 10 atoms and having up to three heteroatoms independently selected from N, O or S, wherein each ring may be optionally substituted by up to three substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$, $C_{1-7}$ alkyl or $C_{3-8}$ cycloalkyl (each of wherein the $C_{1-7}$ alkyl and $C_{3-8}$ cycloalkyl may be optionally substituted by up to six substituents independently selected from halogen, cyano, nitro, SH, $S(O)_{0-2}R^5$, $NR^6R^7$, $S(O)_2NR^8R^9$, $C(O)NR^{10}R^{11}$, $C(O)OR^{12}$, $NR^{13}S(O)_2R^{14}$, $NR^{15}C(O)R^{16}$, $NR^{17}C(O)OR^{18}$, $NR^{19}C(O)NR^{20}R^{21}$, $OR^{22}$), a phenyl ring, optionally substituted by up to three substituents independently selected from halogen, cyano, nitro, SH, $S(O)_{0-2}R^5$, $S(O)_2NR^8R^9$, $C(O)NR^{10}R^{11}$, $C(O)OR^{12}$, $OR^{22}$, $C_{1-6}$ alkyl or $C_{3-6}$ cycloalkyl wherein the $C_{1-6}$ alkyl and $C_{3-6}$ cycloalkyl may be optionally substituted by up to three substituents independently selected from halogen, hydroxyl, $C_{1-6}$ alkoxy, cyano, nitro, $NH_2$, $NH(C_{1-6}$ alkyl) and $N(C_{1-6}$ alkyl)$_2$;

$R^5$, $R^{14}$, and $R^{18}$, represent $C_{1-6}$ alkyl or $C_{3-6}$ cycloalkyl optionally substituted by up to three substituents independently selected from halogen, hydroxyl or $C_{1-6}$ alkoxy;

$R^8$, $R^9$, $R^{10}$, $R^{11}$, $R^{12}$ and $R^{22}$ each independently represent hydrogen or $C_{1-6}$ alkyl or $C_{3-6}$ cycloalkyl, wherein the $C_{1-6}$ alkyl and $C_{3-6}$ cycloalkyl may be optionally substituted by up to three substituents independently selected from halogen, hydroxyl, $C_{1-6}$ alkoxy; or any of $R^8$ and $R^9$, or $R^{10}$ and $R^{11}$ together with the nitrogen atom to which they are both attached, may form a 4 to 6 membered aliphatic heterocyclic ring, wherein the heterocyclic ring may be optionally substituted by up to three substituents independently selected from halogen, hydroxyl, $C_{1-6}$ alkoxy and $C_{1-6}$ alkyl;

X represents O, S, or $S(O)_2$.

m=0, 1, 2 or 3;

n=1, 2 or 3;

W represents $CR^{27}R^{28}CR^{29}R^{30}$ or $CR^{31}R^{32}CR^{33}R^{34}CR^{35}R^{36}$.

V and Z independently represent a bond, $CR^{37}R^{38}$ or $CR^{39}R^{40}CR^{41}R^{42}$.

When X represents either O, S, or $S(O)_2$ then m, V and Z are such that all the heteroatoms in the rings are separated by at least two carbon atoms (e.g. When V is a bond then m is not 0, Z is not a bond).

Y represents CO, $CONR^{43}$, $SO_2$.

$R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}R^{39}$, $R^{40}$, $R^{41}$ and $R^{42}$ each independently represent hydrogen, fluorine, $C_{1-6}$ alkyl or $C_{3-6}$ cycloalkyl.

When they do not represent hydrogen or fluorine $R^{27}$ and $R^{28}$, $R^{29}$ and $R^{30}$, $R^{31}$ and $R^{32}$, $R^{33}$ and $R^{34}$, $R^{35}$ and $R^{36}$, $R^{37}$ and $R^{38}$, $R^{39}$ and $R^{40}$ or $R^{41}$ and $R^{42}$ together with the carbon atom to which they are both attached, may form a 3 to 6 membered aliphatic ring; and $R^{43}$ each independently represent hydrogen, $C_{1-6}$ alkyl or $C_{3-6}$ cycloalkyl More conveniently:

L represents a linker comprising a straight or branched hydrocarbyl chain of up to 8 carbon atoms such as of up to 7, 6, 5, or 4 carbon atoms. Examples of such chains include those of 4-7, 4-6, 4-5, 5-7, 6-7, and 5-6 carbon atoms.

L represents a $C_{4-8}$ alkyl chain optionally substituted by up to four (such as up to three, two or one) fluorine or methyl groups;

Conveniently up to two carbon atoms of the chain may be replaced by groups independently selected from O, S, $S(O)_2$, $NR^{46}C(O)$, $C(O)NR^{47}$, $NR^{48}S(O)_2$, $S(O)_2NR^{49}$ provided that in each case any such groups in the chain are separated by at least 2 carbon atoms;

Conveniently up to four carbon atoms, such as up to three or up to two carbon atoms of the chain may form part of a mono- or bicyclic aromatic or heteroaromatic ring having up to three heteroatoms independently selected from N, O or S, said ring comprising up to 10 ring atoms, and wherein the ring is optionally substituted by up to three substituents independently selected from halogen, $S(O)_{0-2}R^{56}$, $S(O)_2NR^{59}R^{60}$, $C(O)NR^{61}R^{62}$, $OR^{73}$, $C_{1-6}$ alkyl and $C_{3-6}$ cycloalkyl, and wherein $C_{1-6}$ alkyl and $C_{3-4}$ cycloalkyl may be optionally substituted by up to three substituents independently selected from halogen, hydroxyl and $C_{1-6}$ alkoxy;

Conveniently the chain may comprise one of such ring;

Conveniently $R^{56}$ represents $C_{1-4}$ alkyl or $C_{3-6}$ cycloalkyl wherein the $C_{1-4}$ alkyl and $C_{3-6}$ cycloalkyl may be optionally substituted by up to three substituents independently selected from halogen, hydroxyl, $C_{1-4}$ alkoxy; and Conveniently $R^{46}$, $R^{47}$, $R^{48}$, $R^{49}$, $R^{59}$, $R^{60}$, $R^{61}$, $R^{62}$ and $R^{73}$ each independently represent hydrogen, $C_{1-4}$ alkyl or $C_{3-6}$ cycloalkyl, wherein the $C_{1-4}$ alkyl and $C_{3-6}$ cycloalkyl may be optionally substituted by up to three substituents independently selected from halogen, hydroxyl, $C_{1-4}$ alkoxy; or any of $R^{59}$ and $R^{60}$, or $R^{61}$ and $R^{62}$, together with the nitrogen atom to which they are both attached, may form a 4 to 6 membered aliphatic heterocyclic ring, wherein the heterocyclic ring may be optionally substituted by up to two substituents independently selected from halogen, hydroxyl and $C_{1-4}$ alkyl or $C_{3-6}$ cycloalkyl, wherein the $C_{1-4}$ alkyl and $C_{3-6}$ cycloalkyl may be optionally substituted by one substituents independently selected from halogen, hydroxyl and $C_{1-4}$ alkoxy;

$L^1$, $L^2$, $L^3$ and $L^4$ independently represent hydrogen or methyl;

$R^1$ represents phenyl or a 5 to 6 membered heteroaryl ring having up to three heteroatoms independently selected from N, O or S, each of wherein the ring may be optionally substituted by up to three substituents independently selected from halogen, cyano, nitro, $C(O)OR^{12}$, $OR^{22}$, $C_{1-7}$ alkyl or $C_{3-8}$ cycloalkyl, wherein the $C_{1-7}$ alkyl and $C_{3-8}$ cycloalkyl may be optionally substituted by up to three substituents independently selected from halogen, cyano, hydroxyl or $C_{1-3}$ alkoxy;

or $R^1$ represents a fused aromatic or fused heteroaryl ring of up to 10 atoms having up to three heteroatoms independently selected from N, O or S, each of wherein the ring may be optionally substituted by up to three substituents independently selected from halogen, cyano, nitro, $C(O)OR^{12}$, $OR^{22}$, $C_{1-6}$ alkyl or $C_{3-6}$ cycloalkyl, wherein the $C_{1-4}$ alkyl and $C_{3-6}$ cycloalkyl may be optionally substituted by up to three substituents independently selected from halogen, cyano, hydroxyl or $C_{1-3}$ alkoxy; $R^{12}$ and $R^{22}$ each independently represent hydrogen, $C_{1-6}$ alkyl or $C_{3-6}$ cycloalkyl, wherein the $C_{1-6}$ alkyl or $C_{3-6}$ cycloalkyl may be optionally substituted by one substituent selected from halogen, hydroxyl or $C_{1-3}$ alkoxy;

More convenient ring substituents include halogen, for example fluorine and for example chlorine.

More conveniently the species -L- is represented by

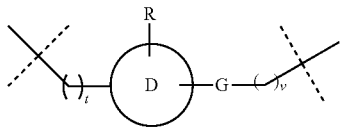

wherein ring D represents a phenyl, thiophene, furan or thiazole ring;

R represents up to three ring substituents each independently selected from H, F, Cl, $C_{1-4}$ alkyl, and $CF_3$; t=0 or 1; G=O, $CR^{43}R^{44}$ or S; when G=O or S then v=1 or 2; when G=C then v=0, 1 or 2, and wherein the species -L- is attached to adjacent atoms in either orientation.

More conveniently the species -L- is selected from
-(phen-1,4-ylene)$OCH_2$—, wherein phenyl is optionally substituted by 3, 2 or 1 methyl groups;
-(phen-1,4-ylene)$OCH_2CH_2$—;
—$CH_2$ (phen-1,4-ylene)$OCH_2$— wherein phenyl is optionally substituted by 3, 2 or 1 of Cl or F (selected independently);
—$CH_2$ (phen-1,4-ylene)-;
$CH_2$ (phen-1,4-ylene)$CH_2$—;
—$(CH_2)_7$—;
—$CH_2$ (phen-1,3-ylene)- wherein the phenyl ring is optionally substituted by up to three of $C_{1-3}$ alkyl, F, Cl, and $CF_3$ (selected independently);
—$CH_2$ (thien-2,5-ylene)$CH_2$—;
—$CH_2$ (thien-2,5-ylene)-;
—$CH_2$ (thien-3,5-ylene)-;
—$CH_2$ (thien-2,4-ylene)-;
—$CH_2O$ (phen-1,3-ylene)-; and
—$CH_2S$ (phen-1,3-ylene)-.
further convenient linkers include:
-(naphth-1,5-ylene)-
—$C(CH_3)2$-(phenyl-1,3-ylene)-
-(phen-1,3-ylene)$OCH_2CH_2$—
-(phen-1,3-ylene)
—$C(CH_3)_2$—$(CH_2)_4$—
—$C(CH_3)_2$—$(CH_2)_6$—
—$CH_2$ (phen-1,3-ylene)$OCH_2$—;
—$CH_2S(CH_2)_5$—;
Each of the above linkers taken alone represents an independent aspect of the invention.

More conveniently the species -L- is selected from:
—$CH_2$ (thien-2,5-ylene)-;
—$CH_2$ (phen-1,3-ylene)- wherein phenyl can be mono-substituted by F;
—$CH_2$ (thien-2,4-ylene)-; and
—$CH_2$ (thien-3,5-ylene)-;
more conveniently $L^1$, $L^2$, $L^3$, and $L^4$=H More conveniently $R^1$ is selected from any one of the individual species as provided in the Examples hereinafter.

X represents O or S.
m=1 or 2;
n=1 or 2;
W represents $CR^{27}R^{28}CR^{29}R^{30}$ or $CR^{31}R^{32}CR^{33}R^{34}CR^{35}R^{36}$.
V and Z independently represent a bond or $CR^{37}R^{38}$.

V and Z are such that all the heteroatoms in the rings are separated by at least two carbon atoms (e.g. When V is a bond then Z is $CR^{37}R^{38}$).

Y represents CO, $CONR^{43}$, $SO_2$; such as CO or $SO_2$, for example CO.

$R^{27}$, $R^{28}$, $R^{29}$, $R^{30}$, $R^{31}$, $R^{32}$, $R^{33}$, $R^{34}$, $R^{35}$, $R^{36}$, $R^{37}$ and $R^{38}$ each independently represent hydrogen, fluorine or $C_{1-3}$ alkyl or $C_3$ cycloalkyl.

When they do not represent hydrogen or fluorine $R^{27}$ and $R^{28}$, $R^{29}$ and $R^{30}$, $R^{31}$ and $R^{32}$, $R^{33}$ and $R^{34}$, $R^{35}$ and $R^{36}$, or $R^{37}$ and $R^{38}$ together with the carbon atom to which they are both attached, may form a 3 to 6 membered aliphatic ring.

$R^{43}$ each independently represent hydrogen or $C_{1-3}$ alkyl or $C_3$ cycloalkyl More conveniently the spirocycle encompassed by the bicyclic ring system comprising —N-(ˆ)m-C—V—X—W—N(Y—$R^1$)—Z—(C)-(ˆ)n- is wherein:
  (i) m and n=2, v=bond, Z=$CH_2$, X=O and W=$CH_2CH_2$
  (ii) m and n=2, v=bond, Z=$CH_2$, X=O and W=$CF_2CH_2$
  (iii) m and n=1, v=bond, Z=$CH_2$, X=O and W=$CH_2CH_2$
  (iv) m and n=2, v=bond, Z=$CH_2CH_2$, X=O and W=$CH_2CH_2$ More conveniently the spirocycle is selected from (i) and (ii) above.

More conveniently $R^1$ is selected from thiophene or thiazole or benzofuran each optionally substituted by one or two substituents. One of the optional substituents is conveniently selected from H, Cl, F and $C_{1-3}$ alkyl. The other optional substituent is selected from methyl, ethyl, propyl, butyl, $CF_3$, $CH_2CF_3$, $CH(CH_3)_2$, $CH(CH_2CH_3)_2$, $CH(CH_3)CH_2$, $CH_3$, $CH_2CH(CH_3)_2$, $C(CH_3)_3$, cyclopropyl, cyclobutyl and cyclopentyl;

Each exemplified compound of the invention represents a particular and independent aspect of the invention.

Convenient compounds of the invention include the compounds of Examples 1, 2, 3, 4, 5, 6, 7, 8, 9, 11, 12, 14, 15, 19, 22, 23, 25, 26, 27, 28, 29, 36, 37, 38, 40, 42, 44, 45, 47, 48, 52, 56, 57, 58, 66, 67, 70, 71, 75, 76, 82, 83, 84, 86, 87, 88, 91, 93, 99, 105, 109, 111, 115, 265, 266, 278 and 280.

Convenient compounds of the invention include the compounds of Examples 22, 23, 36, 40, 42, 44, 47, 48, 57, 66, 82, 83, 84, 86, 87, 99, 265 and 266.

Convenient compounds of the invention include the compounds of Examples 40, 42, 47, 48, 82, 84, 99 and 278.

It will be understood that certain compounds of the present invention may exist in solvated, for example hydrated, as well as unsolvated forms. It is to be understood that the present invention encompasses all such solvated forms. Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Conveniently the chiral centre at the hydroxy-substituted carbon atom adjacent to the β-adrenoceptor binding group has R-stereochemistry.

It is also to be understood that the present invention encompasses the replacement of any quaternary carbon, more specifically the quaternary carbon present in the spirocyclic system, by a silicon atom for example as disclosed in "Silicon switches of Marketed Drugs: Mini-reviews in Med. Chem.", 2006, 6, 1169-1177.

In the context of the present specification the term 'heteroaromatic' denotes a group or part of a group comprising an optionally substituted aromatic monocyclic or multicyclic organic moiety of from 5 to 14 ring atoms, preferably from 5 to 10 ring atoms, in which up to four of the ring atoms is/are element(s) other than carbon, for example nitrogen, oxygen or sulfur. Examples of such groups include benzimidazolyl, benzoxazolyl, benzothiazolyl, benzofuranyl, benzothienyl, furyl, imidazolyl, indolyl, indolizinyl, isoxazolyl, isoquinolinyl, isothiazolyl, oxazolyl, oxadiazolyl, pyrazinyl, pyridazinyl, pyrazolyl, pyridyl, pyrimidinyl, pyrrolyl, quinazolinyl, quinolinyl, tetrazolyl, 1,3,4-thiadiazolyl, thiazolyl, thienyl and triazolyl groups. The heteroaryl group may be substituted by one or more substituent groups. The heteroaryl group may be attached to the remainder of the compound of the invention by any available carbon or nitrogen atom.

The term 'Aliphatic heterocyclic ring' denotes non-aromatic rings comprising at least one heteroatom selected from the group consisting of nitrogen, oxygen and sulfur. Examples of 4-8 membered aliphatic heterocyclic rings according to the present invention include pyrrolidinyl, piperidinyl, piperazinyl, morpholinyl, homopiperazinyl, homopiperidinyl and azetidinyl.

Unless otherwise stated, in the context of the present specification alkyl groups and moieties may be straight or branched chain and include, for example, methyl, ethyl, n-propyl, iso-propyl, n-butyl, iso-butyl or tert-butyl. Cycloalkyl groups are monocyclic, for example cyclopentyl or cyclohexyl. Halogen is for example, fluoride, chloride or bromide.

In the context of the present specification, where it is stated that a group may be optionally substituted with up to three substituents, the group may be unsubstituted or substituted; when substituted the group will generally be substituted with one, two or three substituents. In general, a hydroxyl moiety will not be attached to a carbon atom which is adjacent to a nitrogen atom, another oxygen atom or a sulfur atom.

The invention further provides a process for the preparation of a compound of formula (I) or a pharmaceutically acceptable salt thereof as defined above which comprises:

(a) when $L^1$ represents hydrogen, reacting a compound of formula (II), or a suitable salt thereof,

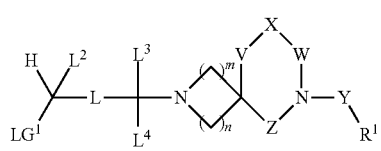

(II)

wherein $LG^1$ represents a leaving group (e.g. chloride, bromide, iodide, methanesulfonate or para-toluenesulfonate) and L, $L^2$, $L^3$, $L^4$, $R^1$, m, n, V, W, X, Y and Z are as defined in formula (I), with a compound of formula (III), or a suitable salt thereof (e.g. hydrobromide, acetate or hydrochloride),

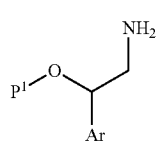

(III)

wherein Ar is as defined in formula (I) and $P^1$ is hydrogen or a protective group (eg. tert-butyldimethyl silyl) in the presence of a base (e.g. potassium carbonate, triethylamine or diisopropylethylamine), followed by removal of the protective group (e.g. using hydrofluoric acid-pyridine complex); or (b) when $L^1$ represents hydrogen, reacting a compound of formula (IV), or a suitable salt thereof,

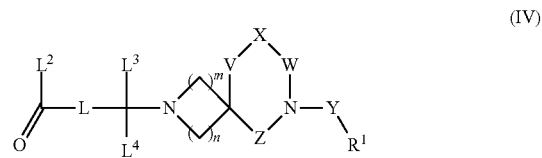

(IV)

wherein L, $L^2$, $L^3$, $L^4$, $R^1$, m, n, V, W, X, Y and Z are as defined in formula (I), with a compound of formula (III) or a suitable salt thereof in the presence of a suitable reducing agent (e.g. sodium cyanoborohydride, sodium triacetoxyborohydride, or hydrogen in the presence of a suitable palladium on carbon or platinum oxide catalyst); or (c) reacting a compound of formula (V), or a suitable salt thereof,

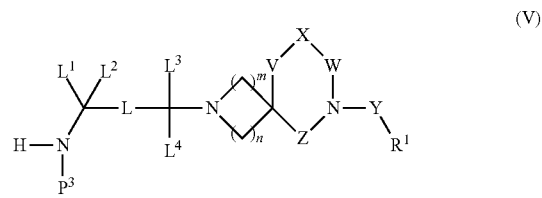

(V)

wherein L, $L^1$, $L^2$, $L^3$, $L^4$, $R^1$, m, n, V, W, X, Y and Z are as defined in formula (I), $P^3$ represents hydrogen or an activating group (e.g. 3-nitrophenylsulfonyl) with a compound of formula (VI), or a suitable salt thereof,

(VI)

wherein Ar is as defined in formula (I), $LG^2$ represents a leaving group (e.g. chloride, bromide, iodide, methanesulfonate or para-toluenesulfonate) and $P^1$ is as defined in formula (III) in the presence of a base (e.g. when $P^3$ is hydrogen, potassium carbonate, triethylamine, diisopropylethylamine and, when $P^3$ is 3-nitrophenylsulfonyl, sodium hydride or lithium di-iso-propylamide), followed by removal of the protective groups (e.g. using hydrofluoric acid-pyridine complex, thiophenol, thioacetic acid); or with a compound of formula (VII), or a suitable salt thereof,

(VII)

wherein Ar is as defined in formula (I) in the presence of a base (e.g. when $P^3$ is hydrogen, potassium carbonate, triethylamine, diisopropylethylamine and, when P³ is 3-nitrophenylsulfonyl, sodium hydride or lithium di-iso-propylamide), followed by removal of the protective groups (e.g. trifluoroacetic acid, thiophenol, thioacetic acid); or with a compound of formula (VIII), or a suitable salt thereof,

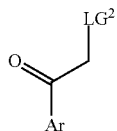
(VIII)

wherein Ar is as defined in formula (I), LG² represents a leaving group (e.g. chloride, bromide, iodide, methanesulfonate or para-toluenesulfonate) in the presence of a base (e.g. when P³ is hydrogen, potassium carbonate, triethylamine, diisopropylethylamine and, when P³ is 3-nitrophenylsulfonyl, sodium hydride or lithium di-iso-propylamide), followed by reduction of the ketone (e.g. using sodium borohydride or a borane/chiral catalyst complex), followed by removal of the protective groups (e.g. trifluoroacetic acid, thiophenol, thioacetic acid); or (d) when L³ and L⁴ each represents hydrogen, reacting a compound of formula (IX), or a suitable salt thereof,

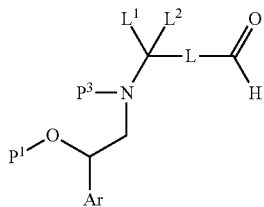
(IX)

wherein Ar, L, L¹ and L² are as defined in formula (I), P¹ is as defined in formula (III), P³ is represents a protective group (e.g. tert-butylcarbamate or 3-nitrophenylsulfonyl) with a compound of formula (X), or a suitable salt thereof, (X)

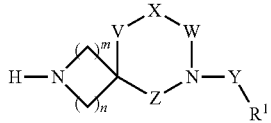

wherein R¹, m, n, V, W, X, Y and Z are as defined in formula (I), in the presence of a suitable reducing agent (e.g. sodium cyanoborohydride, sodium triacetoxyborohydride, or hydrogen in the presence of a suitable palladium on carbon or platinum oxide catalyst), followed by removal of the protective groups (e.g. treatment with hydrochloric or trifluoroacetic acid thiophenol, thioacetic acid); or (e) when one or both of L³ and L⁴ represents hydrogen, reacting a compound of formula (XI), or a suitable salt thereof,

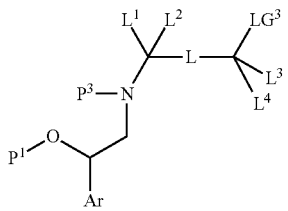
(XI)

wherein Ar, L, L¹ and L² are as defined in formula (I), P¹ is as defined in formula (III), P³ represents a protective group (e.g. tert-butylcarbonyl or 3-nitrophenylsulfonoyl), LG³ represents a leaving group (e.g. chloride, bromide, iodide, methanesulfonate or para-toluenesulfonate), with a compound of formula (X) or a suitable salt thereof, in the presence of a base (e.g. potassium carbonate, triethylamine, diisopropylethylamine), followed by removal of the protective groups (e.g. trifluoroacetic acid, thiophenol, thioacetic acid); or (f) when L¹ and L² each represent hydrogen, reacting a compound of formula (XII), or a suitable salt thereof,

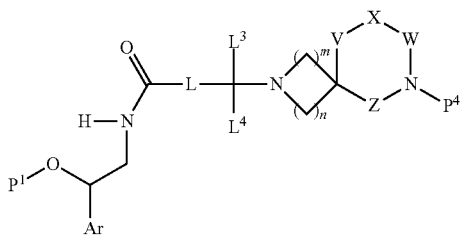
(XII)

wherein Ar, L, L³, L⁴, m, n, V, W, X, Y and Z are as defined in formula (I) and P¹ is as defined in formula (III) and P⁴ is a suitable nitrogen protective group (e.g. tert-Butylcarbonate) with a suitable reducing agent (e.g. borane tetrahydrofuran complex), followed by removal of the protective group (e.g. using hydrofluoric acid-pyridine complex) and reaction with a compound of formula (XIII), or a suitable salt thereof,

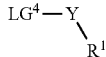
(XIII)

wherein R¹ and Y are as defined in formula (I) and LG⁴ represent hydroxyl or a leaving group (e.g. halide, chloride), or a suitable salt thereof, followed by removal of the protective groups (e.g. using hydrofluoric acid-pyridine complex, hydrochloric acid or trifluoroacetic acid).

When LG⁴ represents hydroxyl, the reaction is conveniently carried out in the presence of an activating reagent, for example, carbonyldiimidazole, 1-Propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in a presence of a base (e.g. triethylamine), at a temperature, for example in the range from 0 to 60° C., When $LG^4$ represents a halide (e.g. chloride), the reaction is conveniently carried out in the presence of a base, for example, triethylamine, diisopropylethylamine or pyridine in an organic solvent, for example, dichloromethane or tetrahydrofuran at a temperature, for example, in the range from 0 to 25° C.; and optionally after (a), (b), (c), (d), (e) or (f) carrying out one or more of the following:

converting the compound obtained to a further compound of the invention forming a pharmaceutically acceptable salt of the compound.

In processes (a), (c) and (e), the reaction may conveniently be carried out in an organic solvent such as N,N-dimethylformamide, ethanol, n-butanol or dimethyl sulfoxide, at a temperature, for example, in the range from 50 to 140° C.

In processes (b) and (d), the reaction may conveniently be carried out in an organic solvent such as methanol, ethanol, dichloromethane, acetic acid Nmethylpyrrolidinone, or N,N-dimethylformamide, containing up to 10% w of water and acetic acid.

In processes (f), the reaction may conveniently be carried out in an organic solvent such as tetrahydrofuran, at a temperature, for example, in the range from 0 to 80° C.

Alternatively, compounds of Formula I (represented in the schemes below as formulae A, B and C) may be prepared as follows:

Route A

Alternative Method for Making Compound A

Heck Reaction

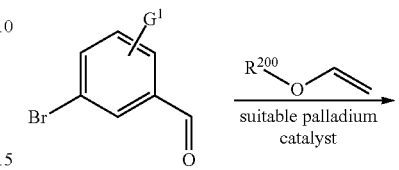

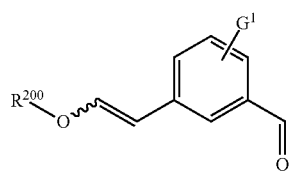

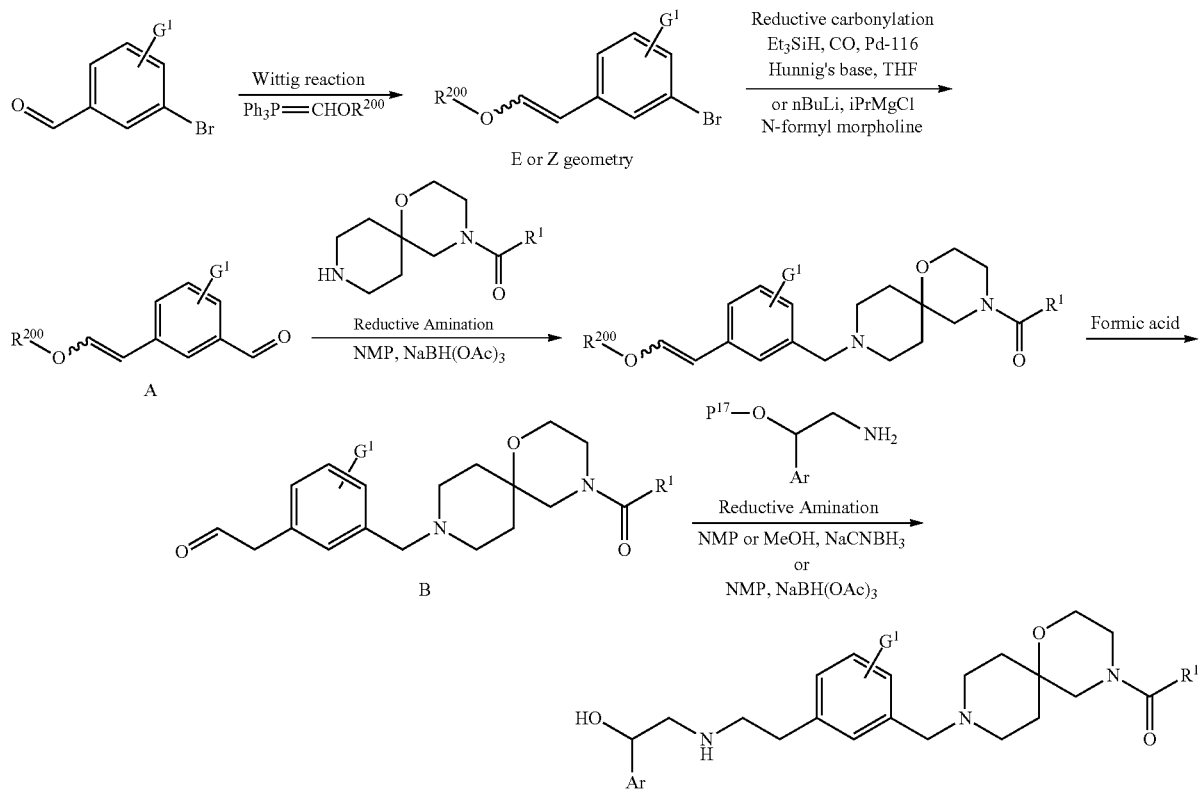

$G^1$ = H or F
$R^{200}$ = alkyl
$P^{17}$ = $P^{17}$ is H or a suitable protecting group that is removed after the reductive amination

Alternative Method for Making Compound B
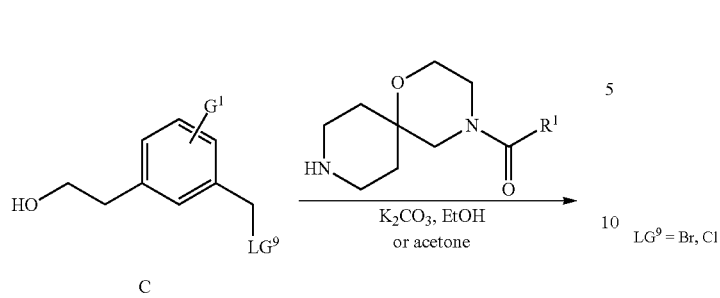
LG⁹ = suitable leaving group such as Br, Cl, OMs, OTs
Alternative Method for Making Compound B
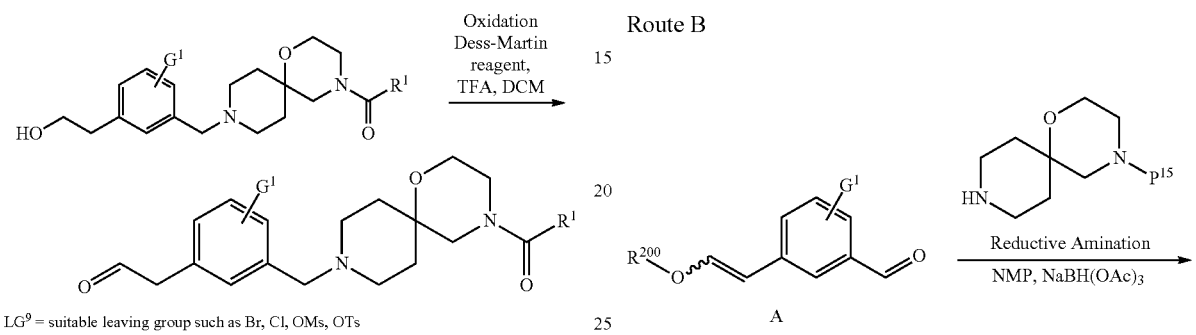
G¹ = H or F
R²⁰⁰ = alkyl
E or Z geometry
R²⁰¹ = alkyl
Method for Making Compound C where LG⁹ is Cl or Br
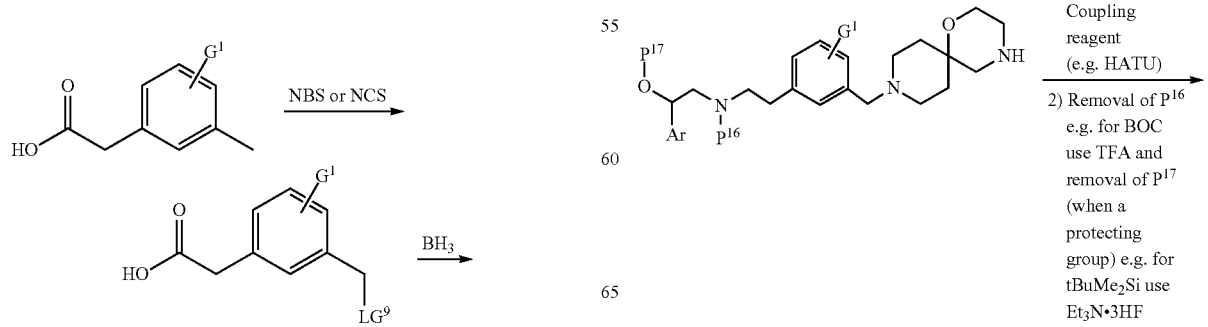
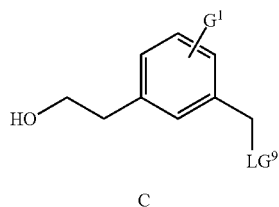
Route B
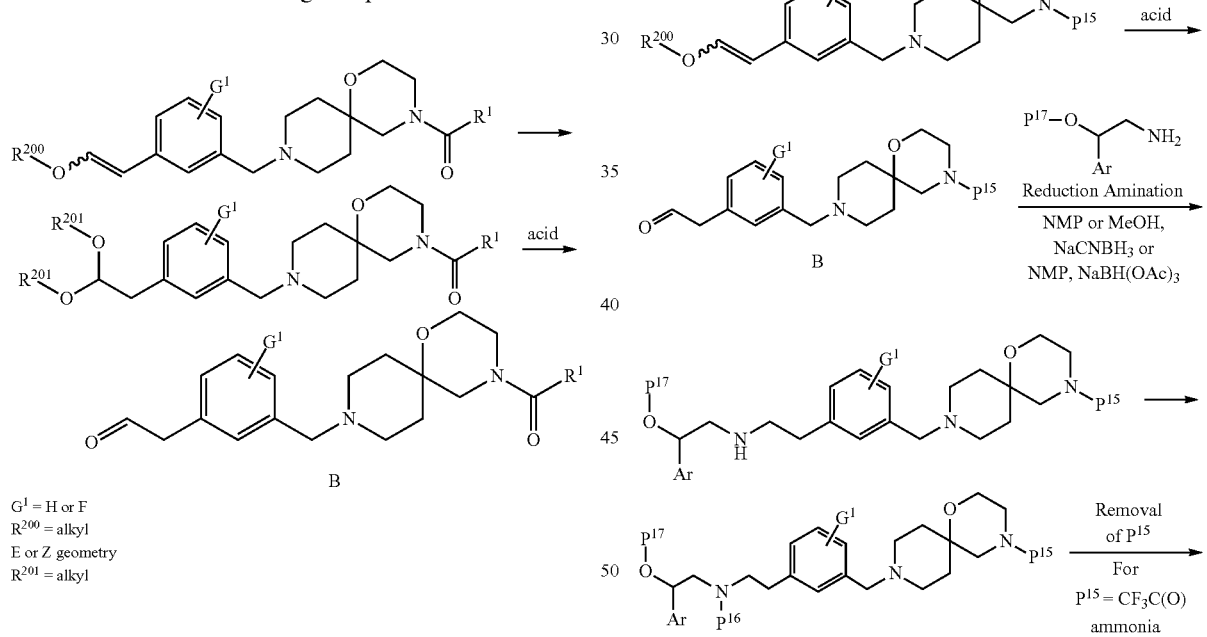

-continued

P<sup>15</sup> is a suitable protecting group such as CF$_3$C(O)
P<sup>17</sup> is H or a suitable protecting group
P<sup>16</sup> is a suitable protecting group such as BOC Route C LG<sup>10</sup> is a suitable leaving group such as halogen OMs or OTs 1) P$^{17}$O-CH(Ar)-CH$_2$-NH$_2$
2) Removal of P$^{17}$
(when a protecting group)
e.g. for tBuMe$_2$Si use NEt$_3$·3HF P$^{17}$ is H or suitable protecting group Compounds of formula (II) may be prepared by reacting a compound of formula (XIV), or a suitable salt thereof, (XIV)

wherein L, L$^3$, L$^4$, R$^1$, m, n, V, W, X, Y and Z are as defined in formula (II), with a compound of formula (XV)

L$^2$-Mt    (XV)

wherein L$^2$ is as defined in formula (II) and Mt represents a metal such as lithium or magnesium, or aluminium or boron (e.g. methyl lithium, methyl magnesium bromide, lithium aluminium hydride, sodium borohydride) in an organic solvent, for example, tetrahydrofuran or ether, at a temperature, for example in the range from 0 to 60° C., followed by conversion of the resulting hydroxyl group into a suitable leaving group (e.g. chloride, bromide, iodide, methanesulfonate or para-toluenesulfonate).

Compounds of formula (IV) may be prepared by reacting a compound of formula (XIV) with a compound of formula (XV) in an organic solvent, for example, tetrahydrofuran or ether, at a temperature, for example in the range from −10 to 60° C., followed by oxidation of the resulting hydroxyl group with a suitable oxidising agent (e.g. Swern reagent, Dess-Martin reagent or pyridinium chlorochromate) in an organic solvent such as dichloromethane, N,N-dimethylformamide or dimethylsulfoxide at a temperature, for example in the range from −78 to 60° C.

Compounds of formula (V) in wherein L$^1$ represents hydrogen and L, L$^2$, L$^3$, L$^4$, P$^3$, R$^1$, m, n, V, W, X, Y and Z as defined in formula (V) may be prepared by a) reacting a compound of formula (II) with sodium azide, in an organic solvent for example, tetrahydrofuran, N,N-dimethylformamide or dimethylsulfoxide at a temperature, for example in the range from 25 to 85° C., followed by reduction of the resulting azido compound using a suitable reducing agent (e.g. triphenylphosphine) in an organic solvent for example, tetrahydrofuran and water, and eventually followed by protection of the resulting amine (e.g. treatment with 3-nitrophenylsulfonyl chloride in the presence of a base such as pyridine); or, b) reacting a compound of formula (IV) with an amine (e.g. benzylamine, α-methyl benzylamine, 4-methoxybenzylamine or 2,4-methoxybenzylamine) followed by reduction of the resulting imine using a suitable reducing agent (e.g. sodium cyanoborohydride or sodium triacetoxyborohydride) in an organic solvent such as methanol, ethanol, dichloromethane, acetic acid, N-methylpyrrolidinone or N,N-dimethylformamide containing up to 10% w of water and acetic acid, followed by removal of the resulting benzyl protective group using the appropriate reagent (e.g. hydrogen and a suitable catalyst (Palladium on carbon or palladium hydroxide), 2,3-dichloro-5,6-dicyanobenzoquinone (DDQ), or ammonium cerium nitrate (CAN)) in an organic solvent, for example, ethanol, methanol, tetrahydrofuran, dichloromethane, acetonitrile, water, or a mixture thereof, at a temperature ranging from 25 to 80° C., and eventually followed by protection of the resulting amine (e.g. treatment with 3-nitrophenylsulfonyl chloride in the presence of a base such as pyridine);

Compounds of formula (V) in wherein L, L$^1$, L$^2$, L$^3$, L$^4$, P$^3$, R$^1$, m, n, V, W, X, Y and Z are as defined in formula (V) may be prepared by reacting a compound of formula (XVI), or a suitable salt thereof,

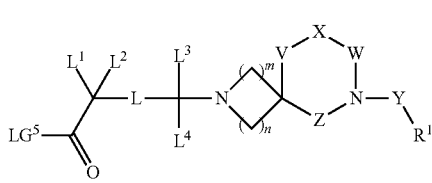

(XVI)

wherein LG$^5$ is a leaving group (e.g. hydroxyl or chlorine), L, L$^1$, L$^2$, L$^3$, L$^4$, R$^1$, m, n, V, W, X, Y and Z are as defined in formula (V), with reagents such as, when LG$^5$ is hydroxyl, diphenylphosphonic azide, in a presence of an amine (e.g. triethylamine), in an organic solvent, for example, tert-butanol, tetrahydrofuran, dichloromethane, water, or a mixture thereof, at a temperature ranging from 25 to 100° C., or when LG$^5$ is chlorine, sodium azide, in an organic solvent, for example, ether, tert-butanol, tetrahydrofuran, water, or a mixture thereof, at a temperature ranging from 25 to 100° C. (Angewandte Chemie, 2005, 54, 5188), eventually followed by protection of the resulting amine (e.g. treatment with 3-nitrophenylsulfonyl chloride in the presence of a base such as pyridine).

Compounds of formula (III), (VI), (VII), (VIII), (XIII) and (XV) are known in the literature or may be prepared using known techniques.

Compounds of formula (IX) can be prepared by a) reacting a compound of formula (XVII), or a suitable salt thereof,

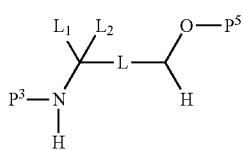

(XVII)

wherein P$^5$ is hydrogen or a protective group (e.g. tert-butyldimethylsilyl, tetrahydropyran) and P$^3$, L, L$^1$ and L$^2$ are as defined in formula (IX), with a compound of formula (VI), (VII) or (VIII), or a suitable salt thereof, in the presence of a base (e.g. potassium carbonate, triethylamine or diisopropylethylamine when P$^3$ is hydrogen and sodium hydride or lithium di-iso-propylamide when P$^3$ is 3-nitrophenylsulfonyl) in an organic solvent such as N,N-dimethylformamide, N-methylpyrrolidinone, tetrahydrofuran, ethanol, n-butanol Or dimethyl sulfoxide, at a temperature, for example, in the range from 50 to 140° C. When the reaction is carried out with compound of formula (VIII), a second step involving reduction of the ketone (e.g. using sodium borohydride or a borane/chiral catalyst complex) is required. Appropriate selective removal of the protective group (e.g. hydrofluoric acid-pyridine complex, tetrabutylamonium fluoride, diluted hydrochloric acid or amberlyst-15 resin in methanol) and oxidation of the resulting alcohol into the corresponding aldehyde with a suitable oxidising agent (pyridinium chlorochromate, Dess-Martin reagent or Swern reagent) lead to compound of formula (IX); or, b) reacting a compound of formula (XVIII), or a suitable salt thereof,

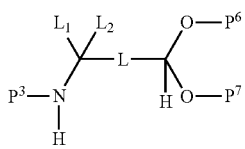

(XVIII)

wherein P$^6$ and P$^7$ represent an acyclic or cyclic carbonyl protective group (e.g. dimethoxy or diethoxy acetal, 1,3-dioxolane or 1,3-dioxane) and L, L$^1$, L$^2$, and P$^3$ are as defined in formula (IX), with a compound of formula (VI), (VII) or (VIII), or a suitable salt thereof, in the presence of a base (e.g. potassium carbonate, triethylamine or diisopropylethylamine when P$^3$ is hydrogen and sodium hydride or lithium di-iso-propylamide when P$^3$ is 3-nitrophenylsulfonyl) in an organic solvent such as N,N-dimethylformamide, N-methylpyrrolidinone, tetrahydrofuran, ethanol, n-butanol or dimethyl sulfoxide, at a temperature, for example, in the range from 50 to 140° C. When reacting with a compound of formula (VIII), this is followed by reduction of the ketone (e.g. using sodium borohydride or a borane/chiral catalyst complex). Removal of the protective group (e.g. diluted hydrochloric acid or amberlyst-15 resin in methanol) leads to a compound of formula (IX); or, c) when L$^1$ represents hydrogen, reacting a compound of formula (XIX), or a suitable salt thereof,

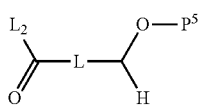

(XIX)

wherein P$^5$ is hydrogen or a protective group (e.g. tert-butyldimethylsilyl, tetrahydropyran) and, L and L$^2$ are as defined in formula (IX), with a compound of formula (III), or a suitable salt to thereof, in the presence of a suitable reducing agent (e.g. sodium cyanoborohydride, sodium triacetoxyborohydride, or hydrogen in the presence of a suitable palladium on carbon or platinum oxide catalyst) in an organic solvent such as methanol, ethanol, dichloromethane, acetic acid, N-methylpyrrolidinone or N,N-dimethylformamide, containing up to 10% w of water and acetic acid, followed by appropriate selective removal of the protective group (e.g. hydrofluoric acid-pyridine complex, tetrabutylamonium fluoride, diluted hydrochloric acid or amberlyst-15 resin in methanol) and oxidation of the resulting alcohol into the corresponding aldehyde with a suitable oxidising agent (pyridinium chlorochromate, Dess-Martin reagent or Swern reagent); or d) when L$^1$ represents hydrogen, reacting a compound of formula (XX), or a suitable salt thereof,

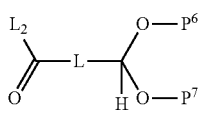

(XX)

wherein P$^6$ and P$^7$ represent an acyclic or cyclic carbonyl protective group (e.g. dimethoxy or diethoxy acetal, 1,3-dioxolane or 1,3-dioxane) and, L and L$^2$ are as defined in formula (IX), with a compound of formula (III), or a suitable salt thereof, in the presence of a suitable reducing agent (e.g. sodium cyanoborohydride, sodium triacetoxyborohydride, or hydrogen in the presence of a suitable palladium on carbon or platinum oxide catalyst) in an organic solvent, such as methanol, ethanol, dichloromethane, acetic acid, N-methypyrrolidinone or N,N-dimethylformamide, containing up to 10% w of water and acetic acid, followed by removal of the protective group (e.g. diluted hydrochloric acid or amberlyst-15 resin in methanol).

Compounds of formula (XI) can be prepared by converting a compound of formula (IX), or a precursor to compound of formula (IX) as described above, choosing an appropriate sequence of reactions, for example, reduction of an aldehyde to an alcohol (e.g. sodium borohydride), appropriate selective removal of the protective group (e.g. hydrofluoric acid-pyridine complex, tetrabutylamonium fluoride, diluted hydrochloric acid or amberlyst-15 resin in methanol) and conversion of an alcohol into a suitable leaving group (e.g. chloride, bromide, iodide, methanesulfonate or para-toluenesulfonate); or Compounds of formula (XII) can be prepared by reacting a compound of formula (XXI), or a suitable salt thereof,

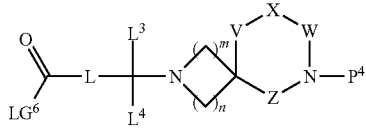

(XXI)

wherein L, $L^3$, $L^4$, $P^4$, m, n, V, W, X and Z are as defined in formula (XII), and $LG^6$ represent hydroxyl or a leaving group (e.g. chlorine) with a compound of formula (III), or a suitable salt thereof;

When $LG^6$ represents hydroxyl, the reaction is conveniently carried out in the presence of an activating reagent, for example, carbonyldiimidazole, 1-Propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in a presence of a base (e.g. triethylamine), at a temperature, for example in the range from 0 to 60° C., When $LG^6$ represents chlorine, the reaction is conveniently carried out in the presence of a base, for example, triethylamine or diisopropylethylamine in an organic solvent, for example, dichloromethane or tetrahydrofuran at a temperature, for example, in the range from 0 to 25° C.

Compounds of formula (V), (X), (XIV), (XVI), and (XXI) can be accessed through a general coupling reaction of a compound of formula (XIII) wherein $R^1$, Y are as defined in formula (I) and $LG^4$ represent hydroxyl or a leaving group (e.g. halide, chloride), or a suitable salt thereof, When $LG^4$ represents hydroxyl, the reaction is conveniently carried out in the presence of an activating reagent, for example, carbonyldiimidazole, 1-Propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in a presence of a base (e.g. triethylamine), at a temperature, for example in the range from 0 to 60° C., or When $LG^4$ represents a halide (e.g. chloride), the reaction is conveniently carried out in the presence of a base, for example, triethylamine, diisopropylethylamine or pyridine in an organic solvent, for example, dichloromethane or tetrahydrofuran at a temperature, for example, in the range from 0 to 25° C., with a compound of general formula (XXII), or a suitable salt thereof,

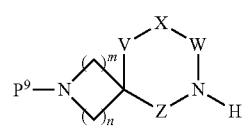

(XXII)

wherein m, n, V, W, X, Y and Z are as defined in formula (I) and, for compounds of formula (V), $P^9$ represents

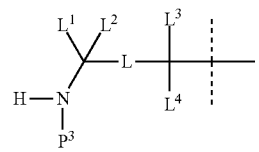

wherein L, $L^1$, $L^2$, $L^3$, $L^4$ and $P^3$ are as defined in formula (V);

for compounds of formula (X), $P^9$ represents an appropriate nitrogen protecting group, such as tert-butoxycarbonyl, or for compounds of formula (XIV), $P^9$ represents

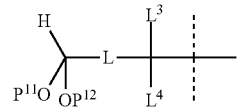

wherein L, $L^3$ and $L^4$ are as defined in formula (XIV), wherein $P^{11}$ and $P^{12}$ represent an acyclic or cyclic carbonyl protective group (e.g. dimethoxy or diethoxy acetal, 1,3-dioxolane or 1,3-dioxane), followed by suitable deprotection (e.g. diluted hydrochloric acid or amberlyst-15 resin in methanol);

for compounds of formula (XVI), $P^9$ represents

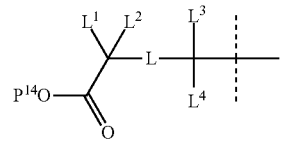

wherein L, $L^1$, $L^2$, $L^3$, and $L^4$ are as defined in formula (XVI), wherein $P^{14}$ represent an acid protective group (e.g. methyl, ethyl or tert-butyl), followed by suitable deprotection (e.g. lithium hydroxide or sodium hydroxide, trifluoroacetic acid, hydrochloric acid);

for compounds of formula (XXI), $P^9$ represents

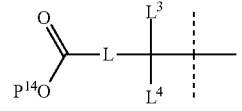

wherein L, L³ and L⁴ are as defined in formula (XXI), wherein P¹⁴ represent an acid protective group (e.g. tert-butyl), followed by suitable deprotection (e.g. trifluoroacetic acid, hydrochloric acid); A compound of general formula (XXII), wherein V represents a bond, X represents O, W represents $CR^{27}R^{28}CR^{29}R^{30}$, Z represents $CR^{37}R^{38}$, $R^{27}$, $R^{28}$, $R^{29}$, $R^{30}$, $R^{37}$, $R^{38}$ each represent hydrogen, and P⁹ represents an appropriate nitrogen protecting group such tert-butoxycarbonyl, can be prepared from a compound of formula (XXIII)

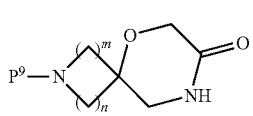
(XXIII)

wherein P⁹, m and n are as defined in compound of formula (XXII), by treatment with a suitable reducing agent such as borane-THF complex in a suitable solvent such as tetrahydrofuran at 30-70° C. with the resulting boron complex decomposed with a suitable amine such as N1,N2-dimethyleneamine-1,2-diamine in methanol at 60-90° C.

A compound of formula (XXIII) can be prepared from a compound of formula (XXIV)

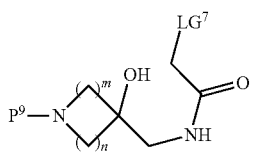
(XXIV)

wherein LG⁷ is a suitable leaving group such as halogen or tosylate and P⁹, m and n are as defined in compound of formula (XXIII), by treatment with a suitable base such as potassium tert-butoxide in a suitable solvent such as tetrahydrofuran at 50-90° C.

A compound of formula (XXIV) can be prepared by reacting a compound of formula (XXV) with a compound of formula (XXVI)

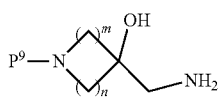
(XXV)

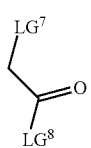
(XXVI)

wherein LG⁸ represents a hydroxyl or halogen group such as chloride and P⁹, m, n and LG⁷ are as defined in compound of formula (XXIV);

For the case where LG⁸ represents hydroxyl, the reaction is conveniently carried out in the presence of an activating reagent, for example, carbonyldiimidazole, 1-Propanephosphonic acid cyclic anhydride (T3P) or O-(7-azabenzotriazol-1-yl)-N,N,N',N'-tetramethyluroniumhexafluorophosphate (HATU), in an organic solvent, for example, N,N-dimethylformamide or dichloromethane, optionally in a presence of a base (e.g. triethylamine), at a temperature, for example in the range from 0 to 60° C.; For the case where LG⁸ represents chloride, the reaction is conveniently carried out in the presence of a base, for example, triethylamine or diisopropylethylamine in an organic solvent, for example, dichloromethane or tetrahydrofuran at a temperature, for example, in the range from 0 to 25° C.;

A compound of formula (XXV) can be prepared by reacting a compound of formula (XXVII)

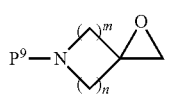
(XXVII)

wherein P⁹, m and n are as defined in compound of formula (XXV), with ammonia in a suitable solvent such as methanol at a temperature in the range from 20-60° C.;

A compound of formula (XXVII) can be prepared by reacting a compound of formula (XXVIII)

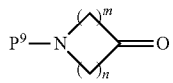
(XXVIII)

wherein P⁹, m and n are as defined in compound of formula (XXVII), with trimethyl sulfoxonium iodide in the presence of a suitable base such as sodium hydride or potassium tert-butoxide in a suitable solvent such as dimethylsulfoxide at a temperature in the range from 0-20° C.;

Also the process above refers to simple oxidation and reduction steps, these are performed under standard conditions well established in the literature (e.g. Dess-Martin, Swern, pyridinium chlorochromate, pyridinium sulfur trioxide complex oxidations). They can be conveniently performed in an organic solvent such as dichloromethane, in a range of temperature from −78 to 50° C. (Annual Reports on the Progress of Chemistry, Section B: Organic Chemistry, 2004, 100, 51-70).

A compound of general formula (XXII), wherein V represents a bond, X represents O, W represents $CR^{27}R^{28}CR^{29}R^{30}$, Z represents $CR^{37}R^{38}$, $R^{27}$, $R^{28}$, $R^{29}$, $R^{30}$, $R^{37}$, $R^{38}$ each represent hydrogen, and P⁹ represents an appropriate nitrogen protecting group can be prepared from a compound of formula (XXIX) under suitable reaction conditions such in strong acid

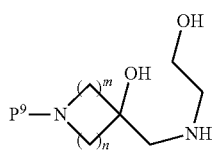
(XXIX)

A compound of general formula (XXIX) can be made by reacting a compound of formula (XXVII) with ethanolamine.

A compound of general formula (XXII), wherein V represents a bond, X represents O, W represents $CR^{27}R^{28}CR^{29}R^{30}$, Z represents $CR^{37}R^{38}$, $R^{27}$, $R^{28}$, $R^{29}$, $R^{30}$, $R^{37}$, $R^{38}$ each represent hydrogen, and $P^9$ represents an appropriate nitrogen protecting group can be prepared from a compound of formula (XXX) where $LG^{11}$ is a suitable leaving group such as halogen, OMs or OTs.

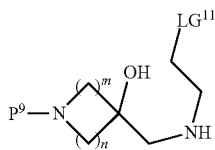
(XXX)

A compound of general formula (XXX) can be formed from a compound of formula (XXIX) under appropriate conditions.

A compound of formula (XIV) can be prepared from a compound of formula (XXXI) where $CH_2L^5$ is L and $R^{200}$ is alkyl or alkyl substituted with dialkylamine by treatment under acidic conditions such as formic acid.

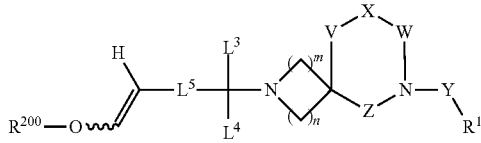
(XXXI)

A compound of formula (XXXI) can be prepared from a compound of formula (XXXII) where by treatment with a compound of formula (XXXIII).

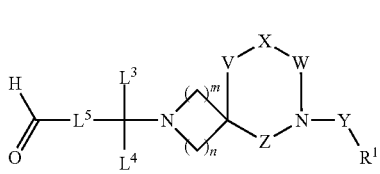
(XXXII)

$PPh_3=CHOR^{200}$ (XXXIII)

A compound of formula (IV) or (XIV) can be prepared from a compound of formula (XXXII) by oxidation of the alcohol under suitable conditions such as using the Dess-Martin reagent in a suitable solvent such as dichloromethane containing trifluoroacetic acid.

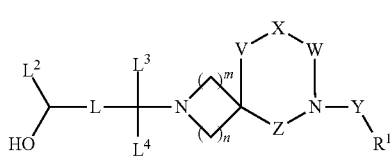
(XXXII)

A compound of formula (XXXII) can be made by reacting a compound of formula (XXXIII) where $P^{18}$ is a hydrogen or a suitable protecting group and $LG^{12}$ represents a leaving group (e.g. chloride, bromide, iodide, methanesulfonate or para-toluenesulfonate), with a compound of formula (X) or a suitable salt thereof, in the presence of a base (e.g. potassium carbonate, triethylamine, diisopropylethylamine), followed by removal of the protective groups (e.g. trifluoroacetic acid, thiophenol, thioacetic acid);

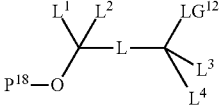
(XXXIII)

A compound of formula (XXXII) can be made by reacting a compound of formula (XXXIV) where $P^{18}$ represents hydrogen or a suitable protective group with a compound of formula (X), or a suitable salt thereof, in the presence of a suitable reducing agent (e.g. sodium cyanoborohydride, sodium triacetoxyborohydride, or hydrogen in the presence of a suitable palladium on carbon or platinum oxide catalyst), followed by removal of the protective groups (e.g. treatment with hydrochloric or trifluoroacetic acid thiophenol, thioacetic acid);

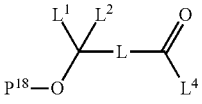
(XXXIV)

A compound of formula (XXXI) can be made by reacting a compound of formula (XXXV) where $CH_2L^5$ is L and $R^{200}$ is alkyl or alkyl substituted with dialkylamine and $LG^{13}$ represents a leaving group (e.g. chloride, bromide, iodide, methanesulfonate or para-toluenesulfonate), with a compound of formula (X) or a suitable salt thereof, in the presence of a base (e.g. potassium carbonate, triethylamine, diisopropylethylamine), followed by removal of the protective groups (e.g. trifluoroacetic acid, thiophenol, thioacetic acid);

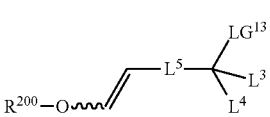
(XXXV)

A compound of formula (XXXI) can be made by reacting a compound of formula (XXXVI) where $CH_2L^5$ is L and $R^{200}$ is alkyl or alkyl substituted with dialkylamine with a compound of formula (X), or a suitable salt thereof, in the presence of a suitable reducing agent (e.g. sodium cyanoborohydride, sodium triacetoxyborohydride, or hydrogen in the presence of a suitable palladium on carbon or platinum oxide catalyst), followed by removal of the protective groups (e.g. treatment with hydrochloric or trifluoroacetic acid thiophenol, thioacetic acid);

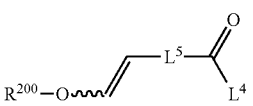
(XXXVI)

Convenient compounds of formula (IV) include those where m and n=2, V=bond, $Z=CH_2$, is $X=O$ and $W=CH_2CH_2$, $Y=CO$, $R^1$ is 4-thiazole optionally substituted in the 2-position of the thiazole by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; or R¹ is 3-thiophene optionally substituted in the 5-position of the thiophene by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; (XXXVII) represent R¹=4-thiazole and 3-thiophene

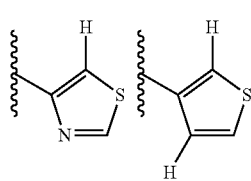

(XXXVII)

Convenient compounds of formula (X) and suitably nitrogen protected analogues include those where m and n=2, V=bond, Z=CH₂, X=O and W=CH₂CH₂, Y=CO, R¹ is 4-thiazole optionally substituted in the 2-position of the thiazole by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; or R¹ is 3-thiophene optionally substituted in the 5-position of the thiophene by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; R¹=4-thiazole and 3-thiophene are as represented in formula (XXXVII)

Convenient compounds of formula (XIV) include those where m and n=2, V=bond, Z=CH₂, X=O and W=CH₂CH₂, Y=CO, R¹ is 4-thiazole optionally substituted in the 2-position of the thiazole by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; or R¹ is 3-thiophene optionally substituted in the 5-position of the thiophene by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; R¹=4-thiazole and 3-thiophene are as represented in formula (XXXVII).

Convenient compounds of formula (XXXI) include those where m and n=2, V=bond, Z=CH₂, X=O and W=CH₂CH₂, Y=CO, R¹ is 4-thiazole optionally substituted in the 2-position of the thiazole by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; or R¹ is 3-thiophene optionally substituted in the 5-position of the thiophene by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; R¹=4-thiazole and 3-thiophene are as represented in formula (XXXVII)

Convenient compounds of formula (XXXII) include those where m and n=2, V=bond, Z=CH₂, X=O and W=CH₂CH₂, Y=CO, R¹ is 4-thiazole optionally substituted in the 2-position of the thiazole by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; or R¹ is 3-thiophene optionally substituted in the 5-position of the thiophene by methyl, ethyl, propyl, butyl, CF₃, CH₂CF₃, CH(CH₃)₂, CH(CH₂CH₃)₂, CH(CH₃)CH₂, CH₃, CH₂CH(CH₃)₂, C(CH₃)₃, cyclopropyl, cyclobutyl and cyclopentyl; R¹=4-thiazole and 3-thiophene are as represented in formula (XXXVII).

Compounds of formula (VI), (VII), (VIII), (XIII), (XV), (XVII), (XVIII), (XIX), (XX), (XXVI) and (XXVIII) are either commercially available, known in the literature, or can be readily prepare by those skilled in the art using one of the process described above or using known techniques.

Other intermediate compounds are novel and represent independent aspects of the invention. In particular, a number of the novel intermediate compounds described herein are compounds that are capable of causing blockade at M3 muscarinic receptors. Intermediate compounds of the present invention having activity as muscarinic antagonists include:
(9-(2-(4-(Hydroxymethyl)phenoxy)ethyl)-1-oxa-4,9-diazaspiro[5.5]undecan-4-yl)(2-methylthiazol-4-yl)methanone;
(9-(9-Hydroxynonyl)-1-oxa-4,9-diazaspiro[5.5]undecan-4-yl)(2-methylthiazol-4-yl)methanone;
(9-(2-(4-(2-Hydroxyethyl)phenoxy)ethyl)-1-oxa-4,9-diazaspiro[5.5]undecan-4-yl)(2-methylthiazol-4-yl)methanone;
(9-(2-(5-(2-Hydroxyethyl)thiophen-2-yl)ethyl)-1-oxa-4,9-diazaspiro[5.5]undecan-4-yl)(2-methylthiazol-4-yl)methanone;
(9-(4-(2-Hydroxyethyl)phenethyl)-1-oxa-4,9-diazaspiro[5.5]undecan-4-yl)(2-methylthiazol-4-yl)methanone;
9-(3-(2-Hydroxyethyl)benzyl)-1-oxa-4,9-diazaspiro[5.5]undecan-4-yl)(2-methylthiazol-4-yl)methanone;
(9-(3-(2-Hydroxyethyl)benzyl)-1-oxa-4,9-diazaspiro[5.5]undecan-4-yl)(5-methylthiophen-2-yl)methanone;
and pharmaceutically acceptable salts thereof.

It will be appreciated by those skilled in the art that in the processes of the present invention certain functional groups such as hydroxyl or amino groups in the reagents may need to be protected by protecting groups. Thus, the preparation of the compounds of formula (I) may involve, at an appropriate stage, the addition or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

Compounds of formula (I) can be converted into further compounds of formula (I) using standard procedures.

The compounds of formula I have activity as pharmaceuticals, in particular as dual adrenergic β receptor agonists and anticholinergic agents including muscarinic receptor (M1, M2, and M3) antagonists, in particular M3 antagonists. Diseases and conditions which may be treated with the compounds of formula (I) and their pharmaceutically acceptable salts include:
1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) or adenovirus; or eosinophilic esophagitis;

2. bone and joints: arthritides associated with or including osteoarthritis/osteoarthrosis, both primary and secondary to, for example, congenital hip dysplasia; cervical and lumbar spondylitis, and low back and neck pain; osteoporosis; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Thus, the present invention provides a compound of formula (I) or a pharmaceutically-acceptable salt thereof as hereinbefore defined for use in therapy.

In a further aspect, the present invention provides the use of a compound of formula (I) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating, or reducing the risk of, an inflammatory disease or condition (including a reversible obstructive airways disease or condition) which comprises administering to a patient in need thereof a therapeutically effective amount of a compound of formula (I) or a pharmaceutically acceptable salt thereof as hereinbefore defined.

In particular, the compounds of this invention may be used in the treatment of adult respiratory distress syndrome (ARDS), pulmonary emphysema, bronchitis, bronchiectasis, chronic obstructive pulmonary disease (COPD), asthma and rhinitis.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight ($\mu$g/kg) to 100 micrograms per kilogram body weight ($\mu$g/kg). Alternatively, if the compound is administered orally, then the daily dosage of the compound of the invention may be in the range from 0.01 micrograms per kilogram body weight ($\mu$g/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, Hydrofluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 $\mu$m, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

In particular, the compounds of the present invention and salts thereof may be used in the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The compounds of the invention may also be administered in conjunction with other compounds used for the treatment of the above conditions.

The invention therefore further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed above.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R) or T-Lymphocytes (CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, to MK-886, and BAY×1005.

The present invention further relates to the combination of a compound of the invention, or a pharmaceutically acceptable salt thereof, and a receptor antagonist for leukotrienes (LT) B4, LTC4, LTD4, and LTE4 selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; (xxvii) inhibitor of transcription factor activation such as NFkB, API or STATS; or (xxviii) a glucocorticoid receptor (GR-receptor) agonist.

In a further aspect the present invention provides a combination (for example for the treatment of COPD, asthma or allergic rhinitis) of a compound of formula (I) and one or more agents selected from the list comprising:

a non-steroidal glucocorticoid receptor (GR-receptor) agonist;

a PDE4 inhibitor including an inhibitor of the isoform PDE4D;

a modulator of chemokine receptor function (such as a CCR1 receptor antagonist);

a steroid (such as budesonide); and an inhibitor of p38 kinase function.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The compounds of formula (I) above may be converted to a pharmaceutically acceptable salt thereof, for example an acid addition salt such as a hydrochloride (for example a dihydrochloride), hydrobromide (for example a dihydrobromide), trifluoroacetate (for example a di-trifluoroacetate), sulphate, phosphate, acetate, fumarate, maleate, tartrate, lactate, citrate, pyruvate, succinate, oxalate, methanesulphonate or p-toluenesulphonate.

The invention will now be illustrated but not limited by reference to the following Examples wherein the following General Methods were used:

General Methods $^1$H NMR spectra were recorded on a Varian Inova 400 MHz or a Varian Mercury-VX 300 MHz instrument. The central peaks of chloroform-d ($\delta_H$ 7.27 ppm), dimethylsulfoxide-d$_6$ ($\delta_H$ 2.50 ppm), acetonitrile-d$_3$ ($\delta_H$ 1.95 ppm) or methanol-d$_4$ ($\delta_H$ 3.31 ppm) were used as internal references. Column chromatography was carried out using silica gel: Fisher Scientific silica 60A, particle size 35-70 micron, Davisil® or 0.040-0.63 mm, pre-packed biotage KP-Sil cartridges. Unless stated otherwise, starting materials were commercially available. All solvents and commercial reagents were of laboratory grade and were used as received.

The following method was used for LC/MS analysis:
Instrument Agilent 1100; Column Waters Symmetry $C_{18}$, 2.1×50 mm; Mass APCI or multimode (APCI+ESI; Flow rate 1 mL/min; Wavelength 220 nm; Solvent A: water+0.1% TFA; Solvent B: acetonitrile+0.1% TFA; Gradient 5-95%/B over 8 min.

Purification by reversed phase preparative HPLC was carried out using a gradient of acetonitrile or methanol in 0.2% aqueous TFA solution or 0.1% aqueous formic acid using either a SunFire™ prep C8 OBD™ 5 μm 30×100 mm column (Waters Corporation) at a flow rate of 35 mL/min or a gradient of acetonitrile or methanol in 0.1% aqueous ammonium acetate solution or 0.1% aqueous formic acid using a Xbridge®50×19 mm column (Waters Corporation) at a flow rate of 18.5 mL/min.

General Methods for Examples 101-115 and 279-285

The following method was used for LC/MS analysis:
Final compounds were analyzed using MS3 and intermediates using MS4

MS3: Instrument Waters Micromass ZQ quadrupole mass spectrometer linked to a Hewlett Packard HP1100 LC system. Sample injection is done by a Gilson 215 autosampler. The spectrometer has an electrospray source operating in positive and negative ion mode. Additional detection is achieved using a Sedex 55 evaporative light scattering detector. Flow rate 1 ml/min; Wavelength 254 nm;
Solvent A: water+0.1% formic acid; Solvent B: acetonitrile+0.1% formic acid; Gradient 5-95% B over 20 min MS4: Instrument Finnigan AQA single quadrupole mass spectrometer linked to a Hewlett Packard 1050 LC system with UV diode array detector and autosampler. The spectrometer has an electrospray source operating in positive ion mode. Additional detection is achieved using a Sedex 65 evaporative light scattering detector. Flow rate 1 ml/min; Wavelength 254 nm; Solvent A: water+0.1% formic acid; Solvent B: acetonitrile+0.1% formic acid; Gradient 5-95% B over 5 min.

NMR spectra were recorded on one of three instruments:
A Varian Unity Inova 400 spectrometer operating at 400 MHz for $^1$H equipped with a 5 mm inverse detection triple resonance probe for detection of $^1$H, $^{13}$C, $^{31}$P with the magnetic field provided by a 9.4 Tesla Oxford instruments super-conducting magnet and Sun Microsystems SunBlade 1000 workstation as host.

A Bruker Avance DRX 400 spectrometer operating at 400 MHz for $^1$H equipped with a 5 mm inverse detection triple resonance TXI probe for detection of $^1$H, $^{13}$C, $^{15}$N with the magnetic field provided by a 9.4 Tesla Oxford instruments super-conducting magnet and an HP workstation wx5000 operating under Windows XP with the WIN-NMR software as host computer.

A Bruker Avance DPX 300 spectrometer operating at 300 MHz for H1 equipped with a standard 5 mm dual frequency probe for detection of H1 and C13 with the magnetic field provided by a 7.05 Tesla Bruker super-conducting magnet and an HP workstation operating under Windows 2000 with the Bruker XWIN-NMR software as host.

Column chromatography was carried out using silica gel: Fluka silica gel 60, particle size 35-70 micron, pre-packed Teledyne Isco, Inc. RediSep® Rf cartridges or pre-packed Isolute Flash Si II SPE cartridges. All solvents and commercial reagents were of laboratory grade and were used as received. Purification by reversed phase preparative HPLC was carried out using a gradient of acetonitrile in 0.1% aqueous TFA solution or 0.1% aqueous formic acid using a Phenomenex Gemini® C18 column (250×21.2 mm, 5 micron) as stationary phase at a flow rate of 18 mL/min.

The abbreviations or terms used in the examples have the following meanings:

SCX: Strong cation exchange—Silica based solid phase extraction with a sulfonic acid sorbent HPLC: High performance liquid chromatography DCM: Dichloromethane DMF: N,N-Dimethylformamide NMP: 1-Methylpyrrolidin-2-one THF: tetrahydrofuran TFA: trifluoroacetic acid DMSO: dimethylsulphoxide aq: aqueous h: hours min: minutes g: grammes mL: milliliters RT: room temperature MP-TsOH65: macroporous polymer bound ion exchange resin supplied by Biotage.

HATU O-(7-Azabenzotriazol-1-yl)-N,N,N',N'-tetramethyluronium hexafluorophosphate NBS N-bromosuccinimide T3P Propane phosphonic acid anhydride TBAF tetrabutylammonium fluoride CDI 1,1'-Carbonyldiimidazole MTBE Methyl tert-butyl ether MCPBA meta-Chloroperbenzoic acid Varian bond elute NH$_2$ cartridge: strong anion exchange. Silica based solid phase extraction with a NH$_2$ sorbent tert-butyl 1-oxa-4,9-diazaspiro[5.5]undecane-9-carboxylate hydrochloride salt was purchased from WuXi Pharma Tech 7-[(1R)-2-Amino-1-hydroxy-ethyl]-4-hydroxy-3H-benzothiazol-2-one acetate or HCl salt (WO2007027134, example 1, step d) is 86-94% ee (R)-5-(2-amino-1-(tert-butyldimethylsilyloxy)ethyl)-8-hydroxyquinolin-2(H)-one (WO2004106333) is 92-96% ee Naming Package for Title/Subtitled Compounds:
Struct=Name 9.0.7 from CambridgeSoft Corporation

EXAMPLE 1

(R)-4-Hydroxy-7-(1-hydroxy-2-(4-(2-(4-(2-methylthiazole-4-carbonyl)-1-oxa-4,9-diazaspiro[5.5]undecan-9-yl)ethoxy)benzylamino)ethyl)benzo[d]thiazol-2(3H)-one ditrifluoroacetate

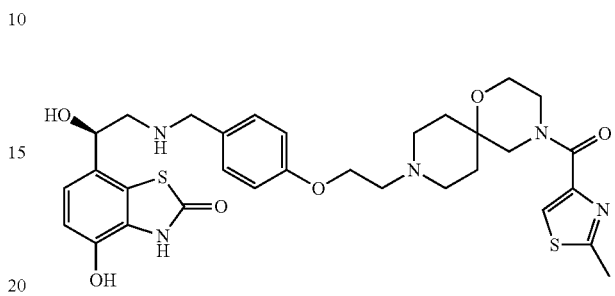

a) 7-(2-Chloro-acetyl)-4-hydroxy-3H-benzothiazol-2-one

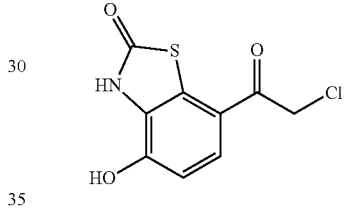

Ethanol (1500 mL) was added to a mixture of 7-acetyl-4-hydroxy-3H-benzothiazol-2-one (150 g) (WO2004/016578) and benzyltrimethylammonium dichloroiodate (374 g) in a flask fitted with an overhead stirrer. The mixture was heated to 78° C. for 1 h and left to cool to room temperature overnight. The mixture was poured into water (2 L), and the precipitate collected by filtration, washed with water, filtered to near dryness, and suspended in ethyl acetate. The mixture was heated to reflux and allowed to cool to room temperature with stirring. The solid was collected by filtration, washed with cold ethyl acetate (200 mL) then re-suspended in diethyl ether (1 L). The solid was collected, filtered again and washed with ether (200 mL) and dried in vacuo to give the subtitled compound. Yield 164 g.

m/z 244 (M+H)$^+$ (APCI)

b) 7-(2-Azido-acetyl)-4-hydroxy-3H-benzothiazol-2-one

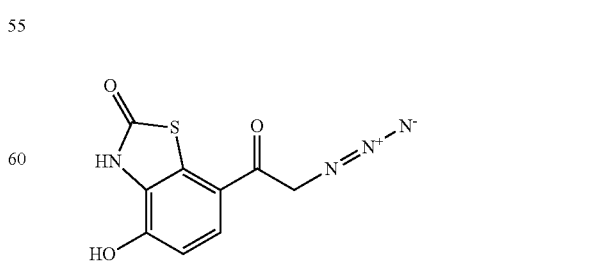

7-(2-Chloro-acetyl)-4-hydroxy-3H-benzothiazol-2-one (example 1, step a) (331 g) was dissolved in N,N-dimethylformamide (1800 mL) and stirred in an ice bath for 10 minutes. Sodium azide (88.3 g) was added portionwise over 15 minutes. The reaction was stirred for 72 hours and then the reaction mixture was divided into 3 equal portions and each quenched separately into ice and water (2.5 L). The solid was filtered off and washed with water (1 L) and re-suspended in acetonitrile (1.5 L). The solvent was evaporated and a further portion of acetonitrile (1 L) added and solvent evaporated again to dry the product. Diethyl ether (1.5 L) was added and the mixture stirred to achieve an homogeneous suspension. The solid was collected and dried in vacuo at 35° C. for 24 hours to give the subtitled compound. Yield 285 g.

m/z 251 (M+H)$^+$ (APCI)

c) 7-[(1R)-2-Azido-1-hydroxy-ethyl]-4-hydroxy-3H-benzothiazol-2-one

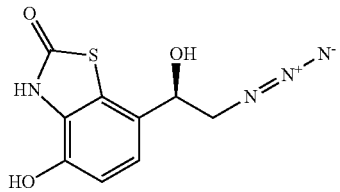 [SMILES: [NH-][NH+]=NC[C@H](O)c1ccc(O)c2[nH]c(=O)sc12]

(1R,2S)-(+)-cis-1-Amino-2-indanol (149 g) was added portion wise to borane-tetrahydrofuran complex (1M in tetrahydrofuran, 2997 mL) over 25 minutes maintaining a temperature of 20-25° C. The mixture was stirred at 20° C. for a further 30 minutes, cooled to 0° C. and 7-(2-azido-acetyl)-4-hydroxy-3H-benzothiazol-2-one (example 1, step b) (250 g) added portionwise maintaining the temperature 0-5° C. The reaction mixture was stirred for a further 1 h at 0° C. and then quenched dropwise with methanol (350 g, 442 mL) (caution effervescence!). An exotherm brought the temperature to 17° C. The reaction was evaporated to a brown foam and re-dissolved in ethyl acetate (1.2 L). Aqueous hydrochloric acid (87 mL conc. HCl in 1.2 L water) was added and the mixture stirred vigorously for 30 minutes. The aqueous layer was separated and washed with fresh ethyl acetate (2×600 mL). The combined organic solution was washed with water (1.2 L). The aqueous layer was filtered through Celite and extracted with ethyl acetate (600 mL). The ethyl acetate solutions were combined, dried over Na$_2$SO$_4$, filtered and evaporated. The resulting solid was suspended in 5% ethanol/dichloromethane (2 L), stirred for 3 h, filtered and dried in vacuo to give the subtitled compound. Yield 213 g.

m/z 253 (M+H)$^+$ (APCI)

d) 7-[(1R)-2-Amino-1-hydroxy-ethyl]-4-hydroxy-3H-benzothiazol-2-one, acetate salt

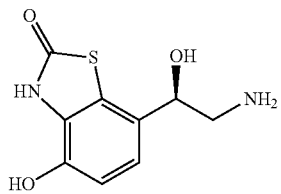 [SMILES: NC[C@H](O)c1ccc(O)c2[nH]c(=O)sc12]

5% Palladium on carbon type 87L paste (22 g) was added to 7-[(1R)-2-azido-1-hydroxy-ethyl]-4-hydroxy-3H-benzothiazol-2-one (example 1, step c) (225 g) dissolved in ethanol (3 L). The reaction was stirred under hydrogen (3 bar) for 48 h. A further 10 g of the catalyst was added and hydrogenation continued for a further 5 days. The reaction mixture was filtered and the solid (product+catalyst) suspended in ethanol (2.5 L) then acetic acid (150 mL) was added and the whole stirred overnight. The mixture was filtered again to remove the palladium on carbon catalyst. The solution was evaporated to dryness and azeotroped with toluene (2×1 L). The solid was slurried in tetrahydrofuran (1 L) for 4 hours, filtered and dried at 40° C. in vacuo to give the subtitled compound. Yield 57 g.

$^1$H NMR (400 MHz, D$_6$-DMSO) δ 6.85 (d, 1H), 6.69 (d, 1H), 4.54 (dd, 1H), 2.78-2.67 (m, 2H)+5 exchangeable protons e) tert-Butyl 4-(2-methylthiazole-4-carbonyl)-1-oxa-4,9-diazaspiro[5.5]undecane-9-carboxylate

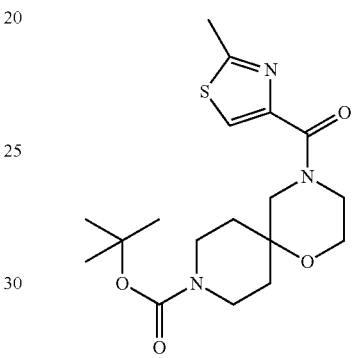

1-Propanephosphonic acid cyclic anhydride (1.57M solution in THF, 4.18 mL) was added to a solution of tert-butyl 1-oxa-4,9-diazaspiro[5.5]undecane-9-carboxylate hydrochloride (WuXi PharmaTech) (1.92 g), 2-methylthiazole-4-carboxylic acid (0.94 g) and triethylamine (5.48 mL) in DMF (70 mL) and the resulting mixture stirred for 16 h. The reaction mixture was poured into water (500 mL) and extracted with ethyl acetate (3×200 mL). The combined organic solutions were washed with water (2×100 mL) and brine (100 mL), dried over magnesium sulphate, filtered and evaporated in vacuo. Purification was by silica gel chromatography eluting with ethyl acetate to give the subtitled compound as a clear oil. Yield 2.30 g.

$^1$H NMR (400 MHz, D$_6$-DMSO, 90° C.) δ 7.95 (s, 1H), 3.80-3.45 (m, 8H), 3.18-2.96 (m, 2H), 2.67 (s, 3H), 1.77-1.62 (m, 2H), 1.43-1.31 (m, 11H)

f) (2-Methylthiazol-4-yl)(1-oxa-4,9-diazaspiro[5.5] undecan-4-yl)methanone hydrochloride

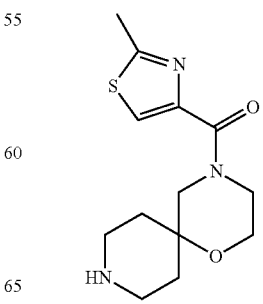

Trifluoroacetic acid (10 mL) was added to a solution of tert-butyl 4-(2-methylthiazole-4-carbonyl)-1-oxa-4,9-diazaspiro[5.5]undecane-9-carboxylate (example 1, step e) (2.3 g) in DCM (50 mL) at 0° C. and the resulting mixture was stirred for 16 h. The solvent was evaporated in vacuo. Toluene (50 mL) was added and the mixture evaporated in vacuo. The residue was dissolved in methanol (20 mL) and applied to a SCX cartridge pre-wetted with methanol. The cartridge was washed with methanol (250 mL) and eluted with 3M ammonia in methanol solution (150 mL). The eluent was evaporated in vacuo and the residue, dissolved in MeCN (100 mL). HCl (1M solution in diethyl ether, 10 mL) was added and the solvent was evaporated in vacuo to give the subtitled compound as a yellow solid. Yield 1.90 g.

$^1$H NMR (400 MHz, D$_6$-DMSO, 90° C.) δ 9.16 (s, 2H), 7.92 (s, 1H), 4.25 (s, 4H), 3.66-3.58 (m, 2H), 3.12-2.90 (m, 4H), 2.69 (s, 3H), 2.01-1.89 (m, 2H), 1.85-1.73 (m, 2H).

g) [4-(2,2-Diethoxy-ethoxy)-phenyl]-methanol

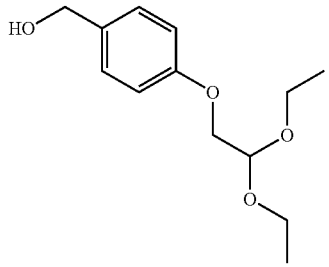 [SMILES: CCOC(COc1ccc(CO)cc1)OCC]

Caesium carbonate (39.4 g) was added to a solution of 4-hydroxymethyl-phenol (10 g) and 2-bromo-1,1-diethoxyethane (12.73 mL) in DMF (200 mL) and the resulting mixture stirred at 90° C. for 16 h. The reaction was poured into water (500 mL) and extracted with ethyl acetate (3×250 mL). The combined organic solutions were washed with water (250 mL) and brine (250 mL), then dried over sodium sulphate, filtered and evaporated in vacuo. Purification was by silica gel chromatography eluting with an isohexane to diethyl ether gradient to give the subtitled compound as a yellow oil. Yield 9.5 g.

$^1$H NMR (400 MHz, CDCl$_3$) δ 7.29-7.25 (m, 2H), 6.93-6.88 (m, 2H), 4.83 (t, J=5.2 Hz, 1H), 4.61 (s, 2H), 4.00 (d, J=5.2 Hz, 2H), 3.81-3.72 (m, 2H), 3.68-3.58 (m, 2H), 1.25 (t, J=7.0 Hz, 6H). One exchangeable proton not observed.

h) 2-(4-(Hydroxymethyl)phenoxy)acetaldehyde

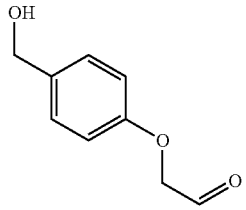 [SMILES: O=CCOc1ccc(CO)cc1]

2M HCl (4 mL) was added to a solution of (4-(2,2-diethoxyethoxy)phenyl)methanol (example 1, step g) (0.9 g) in acetone (20 mL) and the resulting mixture was stirred for 16 h at room temperature. The reaction was concentrated in vacuo and the resulting aqueous solution extracted with ethyl acetate (3×20 mL). The combined organic solutions were dried over magnesium sulphate, filtered and evaporated in vacuo to give the subtitled compound as a clear gum, which was used directly in the next step. Yield 0.50 g.

i) (9-(2-(4-(Hydroxymethyl)phenoxy)ethyl)-1-oxa-4,9-diazaspiro[5.5]undecan-4-yl)(2-methylthiazol-4-yl)methanone

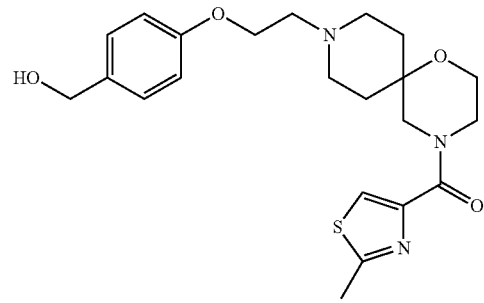 [SMILES: Cc1nc(C(=O)N2CCOC3(CCN(CCOc4ccc(CO)cc4)CC3)C2)cs1]

(2-Methylthiazol-4-yl)(1-oxa-4,9-diazaspiro[5.5]undecan-4-yl)methanone hydrochloride (example 1, step f) (0.38 g) was added to a solution of 2-(4-(hydroxymethyl)phenoxy)acetaldehyde (example 1, step h) (0.17 g) in NMP (10 mL) and acetic acid (0.06 mL). The resulting mixture was stirred for 30 min then cooled in an ice bath. Sodium triacetoxyborohydride (0.32 g) was then added and the reaction allowed to warm to room temperature and stirred for 16 h. The reaction was diluted with methanol (30 mL) and applied to a SCX cartridge pre-wetted with methanol. The cartridge was washed with methanol (250 mL) and eluted with 3M ammonia in methanol solution (150 mL). The eluent was evaporated in vacuo and the residue purified by column chromatography eluting with 95:5 ethyl acetate:triethylamine to give the subtitled compound as a gum. Yield 0.32 g.

$^1$H NMR (300 MHz, D$_6$-DMSO) δ 7.86 (s, 1H), 7.23-7.16 (m, 2H), 6.85 (dt, J=8.7, 1.1 Hz, 2H), 4.72-4.62 (m, 1H), 4.44-4.38 (m, 2H), 4.10-3.99 (m, 2H), 3.66 (d, J=6.7 Hz, 4H), 3.61-3.55 (m, 2H), 2.71-2.64 (m, 5H), 2.47-2.42 (m, 4H), 1.76-1.64 (m, 2H), 1.59-1.45 (m, 2H).

j) 4-(2-(4-(2-Methylthiazole-4-carbonyl)-1-oxa-4,9-diazaspiro[5.5]undecan-9-yl)ethoxy)benzaldehyde

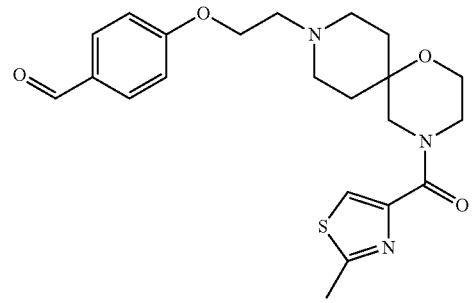 [SMILES: Cc1nc(C(=O)N2CCOC3(CCN(CCOc4ccc(C=O)cc4)CC3)C2)cs1]

Manganese dioxide (0.65 g) was added to a solution of (9-(2-(4-(hydroxymethyl)phenoxy)ethyl)-1-oxa-4,9-diazaspiro[5.5]undecan-4-yl)(2-methylthiazol-4-yl)methanone (0.32 g) (example 1, step i) in DCM (20 mL) and the resulting black suspension heated under reflux for 1 h. After cooling the reaction mixture was passed through a pad of Celite. The pad was washed with DCM (2×30 mL) and the combined filtrate and washings evaporated in vacuo to give the subtitled compound as a gum. Yield 0.25 g.

m/z 430 (M+H)$^+$ (APCI)

¹H NMR (300 MHz, D₆-DMSO) δ 9.86 (s, 1H), 7.96 (s, 1H), 7.88-7.83 (m, 2H), 7.13 (d, J=8.5 Hz, 2H), 4.26-4.11 (m, 2H), 3.77-3.46 (m, 6H), 2.78-2.65 (m, 5H), 2.48-2.34 (m, 4H), 1.76-1.36 (m, 4H).

k) (R)-4-Hydroxy-7-(1-hydroxy-2-(4-(2-(4-(2-methylthiazole-4-carbonyl)-1-oxa-4,9-diazaspiro[5.5]undecan-9-yl)ethoxy)benzylamino)ethyl)benzo[d]thiazol-2(3H)-one ditrifluoroacetate

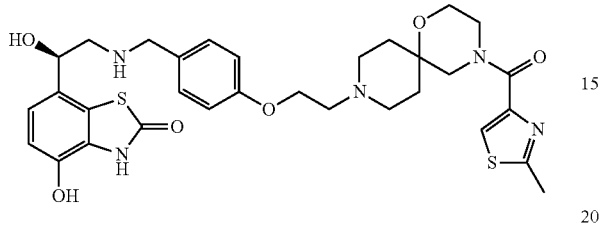

HCl (2M solution in ether, 0.29 mL) was added to a solution of (R)-7-(2-amino-1-hydroxyethyl)-4-hydroxybenzo[d]thiazol-2(3H)-one acetate (example 1, step d) (0.17 g) in NMP (1 mL) and the mixture stirred for 10 min. The resulting solution was added to a solution of 4-(2-(4-(2-methylthiazole-4-carbonyl)-1-oxa-4,9-diazaspiro[5.5]undecan-9-yl)ethoxy)benzaldehyde (example 1, step j) (0.25 g) in NMP (4 mL) and stirred for 1 h. The reaction was cooled to 0° C. and sodium triacetoxyborohydride (0.19 g) was added portionwise. The resulting mixture was allowed to warm to room temperature and stirred for 16 h. The reaction was partitioned between pH 7.2 phosphate buffer (50 mL) and ethyl acetate (50 mL). The layers were separated and the aqueous extracted with ethyl acetate (2×50 mL). The aqueous phase was basified with sodium bicarbonate and extracted with ethyl acetate (3×50 mL). The combined organic solutions were evaporated in vacuo. The residue was redissolved in acetonitrile (50 mL) and acidified with trifluoroacetic acid (1 mL). Toluene (50 mL) was added and the mixture evaporated in vacuo. The resulting gum was dissolved in a mixture of acetonitrile and water (1:1, 10 mL) and filtered. Purification was by preparative HPLC (Sunfire™, Gradient: 5-30% acetonitrile in 0.2% aqueous TFA). The fractions containing product were combined, evaporated and the residue triturated with ether and evaporated in vacuo to give the titled compound as a white solid. Yield 0.35 g.

m/z 640 (M+H)⁺ (APCI)

¹H NMR (400 MHz, D₆-DMSO, 90° C.) δ 11.26 (s, 1H), 7.91 (s, 1H), 7.46 (d, J=8.5 Hz, 2H), 7.03 (d, J=8.5 Hz, 2H), 6.89 (d, J=8.5 Hz, 1H), 6.75 (d, J=8.2 Hz, 1H), 4.93-4.87 (m, 1H), 4.40-4.35 (m, 2H), 4.19-4.13 (m, 2H), 3.76-3.63 (m, 6H), 3.58-3.51 (m, 2H), 3.43-3.35 (m, 2H), 3.30-3.14 (m, 2H), 3.03-2.96 (m, 2H), 2.68 (s, 3H), 2.11-1.99 (m, 2H), 1.92-1.78 (m, 2H). Five exchangeable protons not observed.

EXAMPLE 2

(R)-4-Hydroxy-7-(1-hydroxy-2-(9-(4-(2-methylthiazole-4-carbonyl)-1-oxa-4,9-diazaspiro[5.5]undecan-9-yl)nonylamino)ethyl)benzo[d]thiazol-2(3H)-one ditrifluoroacetate

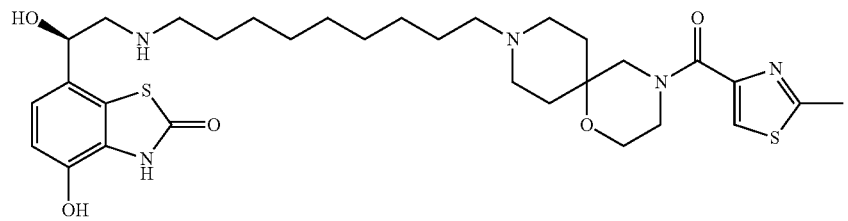 [SMILES: Cc1nc(C(=O)N2CCOC3(CCN(CCCCCCCCCNC[C@H](O)c4ccc(O)c5[nH]c(=O)sc45)CC3)C2)cs1]

a) (9-(9-Hydroxynonyl)-1-oxa-4,9-diazaspiro[5.5]undecan-4-yl)(2-methylthiazol-4-yl)methanone

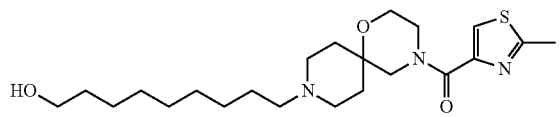 [SMILES: Cc1nc(C(=O)N2CCOC3(CCN(CCCCCCCCCO)CC3)C2)cs1]

9-Bromononan-1-ol (0.29 g) was added to a suspension of (2-methylthiazol-4-yl)(1-oxa-4,9-diazaspiro[5.5]undecan-4-yl)methanone hydrochloride (example 1, step f) (0.4 g) in a mixture of triethylamine (0.41 mL) and acetonitrile (10 mL). The resulting mixture was stirred for 16 h at 50° C. The solvent was evaporated in vacuo and the residue partitioned between ethyl acetate (30 mL) and saturated sodium bicarbonate solution (30 mL). The layers were separated and the aqueous extracted with ethyl acetate (2×30 mL). The combined organic solutions were washed with brine (30 mL), dried over sodium sulphate, filtered and evaporated in vacuo. The residue was dissolved in methanol (10 mL) and applied to a SCX cartridge pre-wetted with methanol. The cartridge was washed with methanol (10 mL) and eluted with 3M ammonia in methanol solution (100 mL). The eluent was evaporated in vacuo to give the subtitled compound a yellow oil. Yield 0.32 g.

¹H NMR (300 MHz, D₆-DMSO) δ 7.95 (s, 1H), 4.30 (t, J=5.1 Hz, 1H), 3.78-3.44 (m, 8H), 3.42-3.33 (m, 2H), 2.69 (s, 3H), 2.35-2.14 (m, 8H), 1.71-1.57 (m, 2H), 1.55-1.19 (m, 12H).

b) 9-(4-(2-Methylthiazole-4-carbonyl)-1-oxa-4,9-diazaspiro[5.5]undecan-9-yl)nonanal

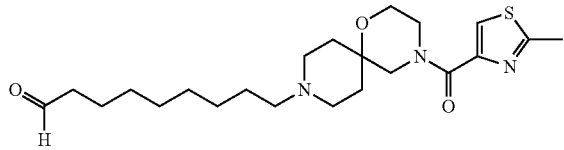 [SMILES: Cc1nc(C(=O)N2CCOC3(CCN(CCCCCCCCC=O)CC3)C2)cs1]

DMSO (0.32 mL) and triethylamine (0.32 mL) were added to a solution of (9-(9-hydroxynonyl)-1-oxa-4,9-diazaspiro[5.5]undecan-4-yl)(2-methylthiazol-4-yl)methanone (example 2, step a) (0.32 g) in dichloromethane (5 mL). The mixture was cooled in an ice-salt bath and pyridine sulphur trioxide (0.36 g) was added. The reaction was stirred at −10° C. for 1 h then allowed to warm to room temperature and stirred for a further 3 h. The reaction was diluted with DCM (20 mL) then poured into brine (20 mL). The layers were separated and the organic layer washed with brine (20 mL), dried over sodium sulphate, filtered and evaporated in vacuo. Purification was by silica gel chromatography eluting with 47.5:47.5:5 isohexane:ethyl acetate:triethylamine to 95:5 ethyl acetate:triethylamine gradient to give the subtitled compound as a yellow oil. Yield 0.25 g.

$^1$H NMR (300 MHz, D$_6$-DMSO) δ 9.66 (t, J=1.6 Hz, 1H), 7.95 (s, 1H), 3.72-3.46 (m, 8H), 3.31 (s, 2H), 2.69 (s, 3H), 2.44-2.18 (m, 8H), 1.73-1.14 (m, 12H)

c) (R)-4-Hydroxy-7-(1-hydroxy-2-(9-(4-(2-methylthiazole-4-carbonyl)-1-oxa-4,9-diazaspiro[5.5]undecan-9-yl)nonylamino)ethyl)benzo[d]thiazol-2(3H)-one ditrifluoroacetate

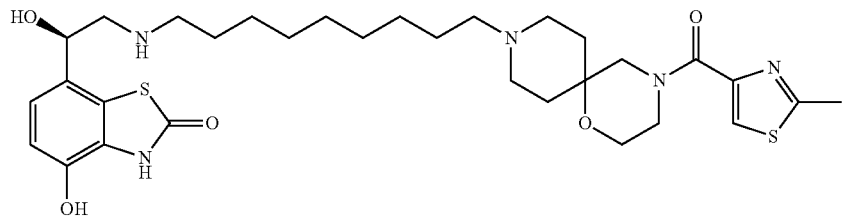 [SMILES: Cc1nc(C(=O)N2CCOC3(CCN(CCCCCCCCCNC[C@H](O)c4ccc(O)c5[nH]c(=O)sc45)CC3)C2)cs1]

(R)-7-(2-Amino-1-hydroxyethyl)-4-hydroxybenzo[d]thiazol-2(3H)-one hydrochloride (WO2007027134, example 1, step d) (0.17 g) was added to a solution of 9-(4-(2-methylthiazole-4-carbonyl)-1-oxa-4,9-diazaspiro[5.5]undecan-9-yl)nonanal (example 2, step b) (0.23 g) and acetic acid (0.03 mL) in methanol (15 mL). The resulting mixture was stirred for 10 min and cooled to 0° C. Sodium triacetoxyborohydride (0.17 g) was then added and the mixture stirred for 16 h. The reaction was concentrated in vacuo and the residue dissolved in a mixture of water and acetonitrile (1:1, 5 mL). Purification was by preparative HPLC (Sunfire™, Gradient: 5-30% acetonitrile in 0.2% aqueous TFA). The fractions containing product were combined and evaporated in vacuo. The residue was triturated with ether and evaporated to give the titled compound as a white solid. Yield 0.15 g.

m/z 632 (M+H)$^+$ (APCI)

$^1$H NMR (300 MHz, D$_6$-DMSO, 90° C.) δ 11.42 (s, 1H), 10.75 (s, 1H), 9.01 (s, 1H), 8.72 (s, 1H), 7.92 (s, 1H), 6.94 (d, J=8.5 Hz, 1H), 6.78 (d, J=8.5 Hz, 1H), 5.02-4.93 (m, 1H), 3.78-3.56 (m, 6H), 3.33-3.23 (m, 1H), 3.07-2.88 (m, 8H), 2.69 (s, 3H), 2.07-1.89 (m, 4H), 1.75-1.62 (m, 4H), 1.3-1.24 (m, 10H)+1 proton obscured by the solvent peak.

EXAMPLE 3

(R)-4-Hydroxy-7-(1-hydroxy-2-(4-(2-(4-(2-methylthiazole-4-carbonyl)-1-oxa-4,9-diazaspiro[5.5]undecan-9-yl)ethoxy)phenethylamino)ethyl)benzo[d]thiazol-2(3H)-one dihydrochloride

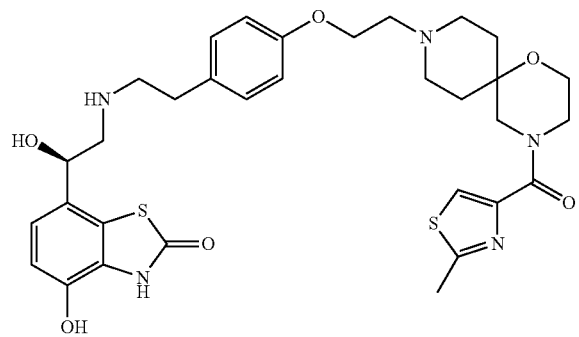 [SMILES: Cc1nc(C(=O)N2CCOC3(CCN(CCOc4ccc(CCNC[C@H](O)c5ccc(O)c6[nH]c(=O)sc56)cc4)CC3)C2)cs1]

a) 2-(4-(2,2-Diethoxyethoxy)phenyl)ethanol

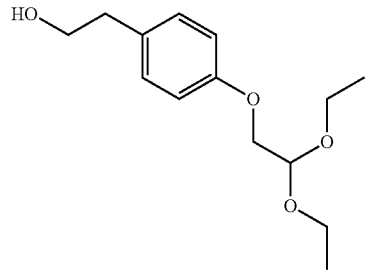 [SMILES: CCOC(COc1ccc(CCO)cc1)OCC]

Caesium carbonate (28.3 g) was added to a solution of 4-(2-hydroxyethyl)phenol (10 g) and 2-bromo-1,1-diethoxyethane (11.79 mL) in DMF (150 mL). The resulting suspension was heated at 90° C. for 16 h. The reaction was poured into water (500 mL). The aqueous phase was extracted with ethyl acetate (3×200 mL). The combined organic solutions were washed with water (200 mL) and brine (200 mL), then dried over magnesium sulfate, filtered and evaporated in vacuo. Purification was by silica gel chromatography eluting with isohexane to 1:1 ethyl acetate:isohexane gradient to give the subtitled compound as a yellow oil. Yield 10 g.

$^1$H NMR (300 MHz, CDCl$_3$) δ 7.14 (d, J=6.9 Hz, 2H), 6.88 (d, J=6.9 Hz, 2H), 4.83 (t, J=5.0 Hz, 1H), 4.00 (d, J=5.0 Hz, 2H), 3.87-3.70 (m, 4H), 3.70-3.56 (m, 2H), 2.81 (t, J=6.4 Hz, 2H), 1.25 (t, J=6.9 Hz, 6H). OH not observed.

b) 2-(4-(2-Hydroxyethyl)phenoxy)acetaldehyde

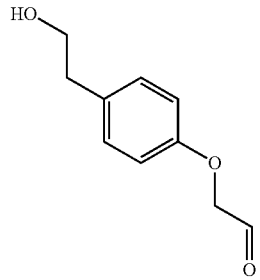

Concentrated hydrochloric acid (5 mL) was added to a solution of 2-(4-(2,2-diethoxyethoxy)phenyl)ethanol (example 3, step a) (0.76 g) in 1,4-dioxane (10 mL) and the resulting mixture was stirred for 1 h. The reaction was diluted with water (50 mL) and extracted with ethyl acetate (3×50 mL). The combined organic solutions were washed with water (50 mL) and brine (50 mL), then dried over sodium sulphate, filtered and evaporated in vacuo to give the subtitled compound, which was used directly. Yield 0.35 g.

c) (9-(2-(4-(2-Hydroxyethyl)phenoxy)ethyl)-1-oxa-4,9-diazaspiro[5.5]undecan-4-yl)(2-methylthiazol-4-yl)methanone

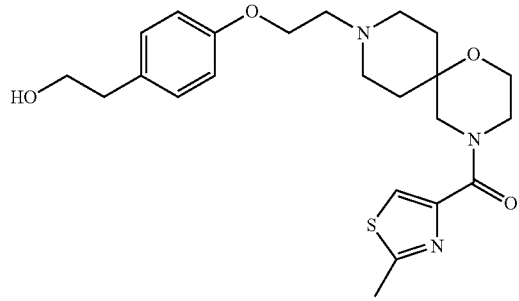 [SMILES: Cc1nc(C(=O)N2CCOC3(CCN(CCOc4ccc(CCO)cc4)CC3)C2)cs1]

(2-Methylthiazol-4-yl)(1-oxa-4,9-diazaspiro[5.5]undecan-4-yl)methanone hydrochloride (example 1, step f) (0.63 g) was added to a solution of 2-(4-(2-hydroxyethyl)phenoxy)acetaldehyde (example 3, step b) (0.541 g) in a mixture of NMP (10 mL) and acetic acid (0.11 mL). The resulting mixture was stirred at room temperature for 30 min then cooled in an ice bath. Sodium triacetoxyborohydride (0.64 g) was then added and the reaction was allowed to warm to room temperature and stirred for 16 h. The reaction was diluted with methanol (30 mL) and applied to a SCX cartridge pre-wetted with methanol. The cartridge was washed with methanol (100 mL) and eluted with 3M ammonia in methanol solution (100 mL). The eluent was evaporated in vacuo and the residue purified by silica gel chromatography, eluting with 95:5 ethyl acetate:triethylamine to give the subtitled compound as a brown oil. Yield 0.74 g.

$^1$H NMR (300 MHz, D$_6$-DMSO) δ 7.86 (s, 1H), 7.09 (d, J=8.4 Hz, 2H), 6.84-6.77 (m, 2H), 4.24-4.15 (m, 1H), 4.02 (t, J=6.0 Hz, 2H), 3.68-3.54 (m, 8H), 3.00 (s, 2H), 2.71-2.61 (m, 5H), 2.51-2.42 (m, 4H), 1.75-1.65 (m, 2H), 1.59-1.45 (m, 2H).

d) 2-(4-(2-(4-(2-Methylthiazole-4-carbonyl)-1-oxa-4,9-diazaspiro[5.5]undecan-9-yl)ethoxy)phenyl)acetaldehyde

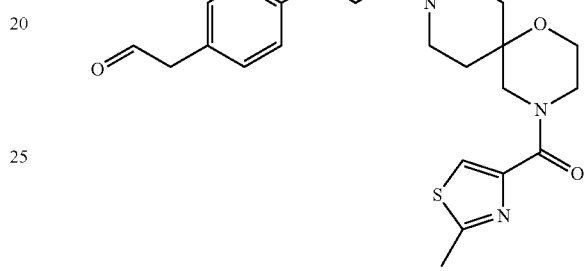

Trifluoroacetic acid (0.04 mL) was added to a solution of 9-(2-(4-(2-hydroxyethyl)phenoxy)ethyl)-4-(2-methylthiazole-4-carbonyl)-1-oxa-4-aza-9-azoniaspiro[5.5]undecane (example 3, step c) (0.22 g) in DCM (3 mL) and the resulting mixture was stirred for 5 min. Dess-Martin periodinane (0.31 g) was then added and the resulting mixture stirred for 5 min. A mixture of saturated sodium thiosulphate solution (0.5 mL), sodium bicarbonate solution (0.5 mL) and ether (5 mL) was then added and the resulting mixture stirred for 5 min. The organic layer was separated and washed with sodium bicarbonate solution (1 mL) and water (1 mL), then dried over sodium sulphate, filtered and evaporated in vacuo to give the subtitled compound as a clear oil which was used immediately. Yield 0.19 g.

e) (R)-4-Hydroxy-7-(1-hydroxy-2-(4-(2-(4-(2-methylthiazole-4-carbonyl)-1-oxa-4,9-diazaspiro[5.5]undecan-9-yl)ethoxy)phenethylamino)ethyl)benzo[d]thiazol-2(3H)-one dihydrochloride

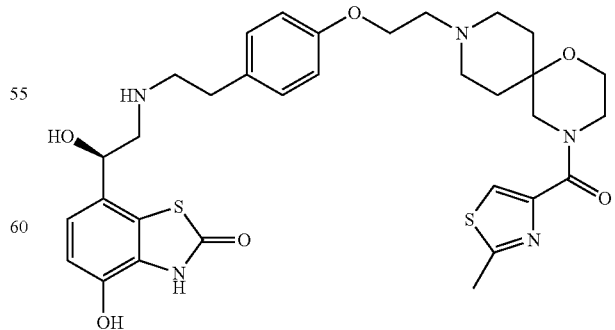

(R)-7-(2-Amino-1-hydroxyethyl)-4-hydroxybenzo[d]thiazol-2(3H)-one hydrochloride (WO2007027134, example 1, step d) (0.10 g) was added to a solution of 2-(4-(2-(4-(2-methylthiazole-4-carbonyl)-1-oxa-4,9-diazaspiro[5.5]undecan-9-yl)ethoxy)phenyl)acetaldehyde (example 3, step d) (0.14 g) and acetic acid (0.02 mL) in methanol (1 mL) and the resulting mixture stirred for 5 min. Sodium triacetoxyborohydride (0.103 g) was then added, the reaction was stirred for 10 min and evaporated in vacuo. The residue was dissolved in a mixture of acetonitrile and water (1:1, 5 mL). Purification was by preparative HPLC (Sunfire™, Gradient: 5-50% acetonitrile in 0.2% aqueous TFA). The fractions containing product were combined and evaporated in vacuo. The residue was dissolved in acetonitrile (5 mL) and HCl in ether (1M, 2 mL) was added, then the solvent was evaporated in vacuo. The residue was triturated with ether and evaporated in vacuo to give the titled compound as a white solid. Yield 0.075 g.

m/z 654 (M+H)+ (APCI)

$^1$H NMR (400 MHz, D$_6$-DMSO) δ 11.50-11.14 (m, 2H), 9.22 (s, 1H), 8.87 (s, 1H), 7.91 (s, 1H), 7.20 (d, J=8.5 Hz, 2H), 6.98-6.92 (m, 3H), 6.78 (d, J=8.5 Hz, 1H), 5.0-4.96 (m, 1H), 4.42 (t, J=5.1 Hz, 2H), 3.83-3.55 (m, 5H), 3.52-3.43 (m, 5H), 3.22-3.04 (m, 4H), 3.01-2.93 (m, 2H), 2.69 (s, 3H), 2.11-1.93 (m, 4H)+2 protons obscured by the solvent.

EXAMPLE 4

(R)-4-Hydroxy-7-(1-hydroxy-2-(2-(5-(2-(4-(2-methylthiazole-4-carbonyl)-1-oxa-4,9-diazaspiro[5.5]undecan-9-yl)ethyl)thiophen-2-yl)ethylamino)ethyl)benzo[d]thiazol-2(3H)-one ditrifluoroacetate

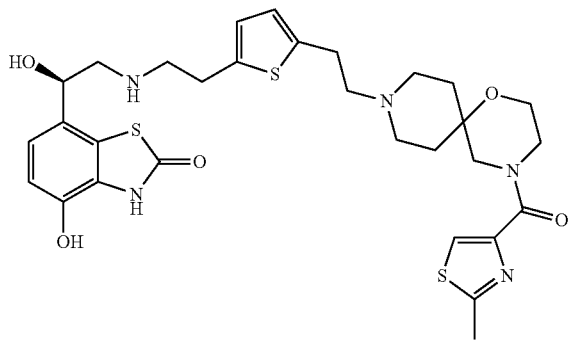 [SMILES: Cc1nc(C(=O)N2CCOC3(CCN(CCc4ccc(CCNC[C@H](O)c5ccc(O)c6[nH]c(=O)sc56)s4)CC3)C2)cs1]

a) tert-Butyldimethyl(2-(thiophen-2-yl)ethoxy)silane

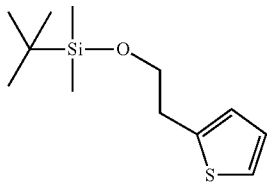

tert-Butyldimethylsilyl chloride (12.66 g) was added portionwise to 2-(2-thienyl)ethanol (9.0 g) and imidazole (5.7 g) in DMF (35 mL). The resulting solution was stirred for 18 h. The reaction mixture was partitioned between ethyl acetate and water. The organic layer was washed with water, dried over sodium sulphate and the solvents evaporated in vacuo. Purification was by silica gel chromatography, eluting with 99:1 to 96:4 ethyl acetate:isohexane to give the subtitled compound as a clear oil. Yield 16 g.

$^1$H NMR (400 MHz, CDCl$_3$) δ 7.13 (d, 1H), 6.92 (dd, J=5.0, 3.2 Hz, 1H), 6.83-6.82 (m, 1H), 3.82 (t, J=6.7 Hz, 2H), 3.03 (t, J=6.8 Hz, 2H), 0.97 (s, 9H), 0.03 (s, 6H).

b) 5-(2-(tert-Butyldimethylsilyloxy)ethyl)thiophene-2-carbaldehyde

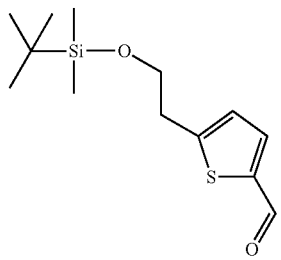 [SMILES: CC(C)(C)[Si](C)(C)OCCc1ccc(C=O)s1]

n-Butyllithium (2.5M in hexanes, 30 mL) was added dropwise to a solution of tert-butyldimethyl(2-(thiophen-2-yl)ethoxy)silane (example 4, step a) (16 g) in tetrahydrofuran (250 mL) at −78° C. The reaction mixture was allowed to warm to 0° C. and stirred for 1 h. The reaction was then cooled to −78° C. and DMF (34 mL) was added over 10 min. The reaction mixture was allowed to warm to room temperature and stirred for 18 h. The reaction mixture was partitioned between water and ethyl acetate. The organic layer was separated, washed with water, dried over sodium sulphate, filtered and the solvent evaporated in vacuo. Purification was by silica gel chromatography, eluting with 93:7 isohexane:ethyl acetate to give the subtitled compound as a colourless oil. Yield 15.4 g.

$^1$H NMR (400 MHz, CDCl$_3$) δ 9.83 (s, 1H), 7.61 (d, J=3.6 Hz, 1H), 6.96 (d, 1H), 3.86 (t, J=6.3 Hz, 2H), 3.06 (td, J=6.1, 0.1 Hz, 2H), 0.88 (t, J=2.9 Hz, 9H), 0.02 (s, 6H).

c) (5-(2-(tert-Butyldimethylsilyloxy)ethyl)thiophen-2-yl)methanol

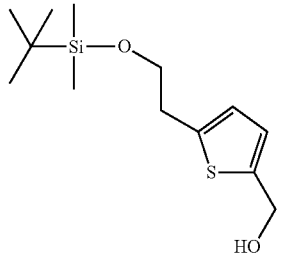 [SMILES: CC(C)(C)[Si](C)(C)OCCc1ccc(CO)s1]

Sodium borohydride (1.74 g) was added to a solution of 5-(2-(tert-butyldimethylsilyloxy)ethyl)thiophene-2-carbaldehyde (12.4 g) (example 4, step b) in ethanol (120 mL) at 0° C. The resulting solution was stirred at 0° C. for 1 h. The reaction mixture was partitioned between brine and ethyl acetate. The organic layer was separated, dried over sodium sulphate, filtered and the solvent evaporated in vacuo to give the subtitled compound. Yield 12.1 g.

$^1$H NMR (400 MHz, CDCl$_3$) δ 6.82 (d, J=3.6 Hz, 1H), 6.69 (d, J=3.3 Hz, 1H), 4.75 (d, J=4.9 Hz, 2H), 3.81 (t, J=6.7 Hz,

2H), 2.99 (t, J=6.8 Hz, 2H), 1.65 (t, J=5.5 Hz, 1H), 0.89 (d, J=2.8 Hz, 9H), 0.03 (d, J=3.1 Hz, 6H).

d) 2-(5-(2-(tert-Butyldimethylsilyloxy)ethyl)thiophen-2-yl)acetonitrile

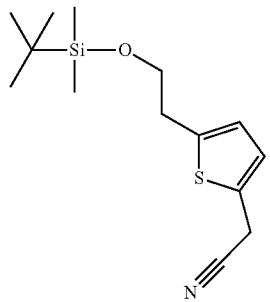 [SMILES: CC(C)(C)[Si](C)(C)OCCc1ccc(CC#N)s1]

Triphenylphosphine (13.04 g) and carbon tetrabromide (15.71 g) were added in one portion to a solution of (5-(2-(tert-butyldimethylsilyloxy)ethyl)thiophen-2-yl)methanol (example 4, step c) (10.94 g) in DCM (20 mL) at 0° C. The resulting solution was stirred at room temperature for 1 h. The reaction mixture was cooled to 0° C. and tetraethylammonium cyanide (8.96 g) was added. The mixture was diluted with dichloromethane (10 mL) and stirred at room temperature for 40 min. The reaction mixture was partitioned between dichloromethane and brine. The organic layer was separated, dried over sodium sulphate, filtered and the solvent evaporated in vacuo. Purification was by silica gel chromatography, eluting with 95:5 to 94:6 isohexane:ethyl acetate gradient to give the subtitled compound as a yellow oil. Yield 7.6 g.

$^1$H NMR (400 MHz, CDCl$_3$) δ 6.87-6.84 (m, 1H), 6.70-6.68 (m, 1H), 3.84 (d, J=0.8 Hz, 2H), 3.80 (t, J=6.4 Hz, 2H), 2.97 (t, J=6.5 Hz, 2H), 0.89 (s, 9H), 0.03 (s, 6H).

e) 2-(5-(2-Hydroxyethyl)thiophen-2-yl)acetic acid

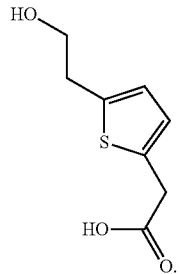

A solution of 2-(5-(2-(tert-butyldimethylsilyloxy)ethyl)thiophen-2-yl)acetonitrile (example 4, step d) (3 g) in ethanol (30 mL) was added to a stirred solution of potassium hydroxide (1.20 g) in water (30 mL). The resulting mixture was stirred at 100° C. for 4 hours. The reaction was concentrated in vacuo and the resulting mixture was partitioned between brine and ethyl acetate. The aqueous layer was cooled with ice, acidified by dropwise addition of concentrated hydrochloric acid and extracted with yl acetate three times. The combined organic solutions were washed with brine, dried over sodium sulphate, filtered and the solvent evaporated in vacuo to give the subtitled compound as a yellow solid. Yield 1.75 g.

$^1$H NMR (400 MHz, D$_6$-DMSO) δ 12.44 (s, 1H), 6.72 (d, J=3.3 Hz, 1H), 6.67 (d, J=3.3 Hz, 1H), 4.76 (s, 1H), 3.71 (s, 2H), 3.61-3.55 (m, 2H), 2.86 (t, J=6.8 Hz, 2H).

f) 2-(5-(2-(tert-Butyldimethylsilyloxy)ethyl)thiophen-2-yl)ethanol

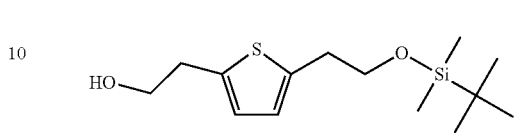

tert-Butyldimethylsilyl chloride (6.63 g) was added portionwise to a solution of imidazole (2.99 g) and 2-(5-(2-hydroxyethyl)thiophen-2-yl)acetic acid (3.9 g) (example 4, step e) in DMF (50 mL) over 20 minutes. The resulting solution was stirred for 1 h. THF (50 mL) was then added and the reaction cooled in an ice bath. A solution of potassium carbonate (4.05 g) in water (50 mL) was then added and the mixture stirred for 20 min. The reaction was partitioned between ethyl acetate and brine. The organic layer was separated and washed twice with brine, dried over sodium sulphate, filtered and the solvent evaporated in vacuo. The residue was dissolved in THF (80 mL) and borane tetrahydrofuran complex (1M solution in THF, 62.8 mL) was added dropwise. The resulting solution was stirred for 2 h and quenched by dropwise addition of methanol (30 mL). The solvents were then evaporated in vacuo. Purification was by silica gel chromatography, eluting with 83:17 isohexane:ethyl acetate to give the subtitled compound as a yellow liquid. Yield 4.6 g.

$^1$H NMR (300 MHz, CDCl$_3$) δ 6.69-6.63 (m, 2H), 3.87-3.75 (m, 4H), 3.05-2.91 (m, 4H), 0.89 (s, 9H), 0.03 (s, 6H)+ exchangeable protons g) 2-(5-(2-(tert-Butyldimethylsilyloxy)ethyl)thiophen-2-yl)acetaldehyde

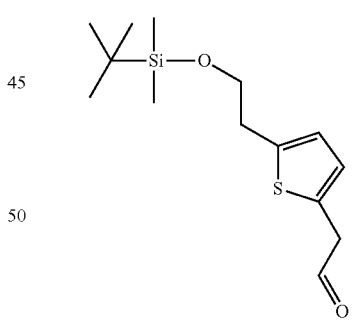

Dess-Martin periodinane (0.38 g) was added to a solution of 2-(5-(2-(tert-butyldimethylsilyloxy)ethyl)thiophen-2-yl)ethanol (example 4, step f) (0.22 g) in dichloromethane (5 mL) and the resulting mixture stirred for 30 min. A mixture of saturated sodium thiosulphate solution (5 mL), saturated sodium bicarbonate solution (5 mL) and ethyl acetate (25 mL) were added and the resulting mixture stirred for 10 min. The organic layer was separated and washed with a solution of saturated sodium bicarbonate solution (10 mL), and brine (10 mL), then dried over sodium sulphate, filtered and evaporated in vacuo to give the subtitled compound as a clear oil which was used immediately. Yield 0.21 g.

¹H NMR (400 MHz, CDCl₃) δ 9.70 (t, J=2.2 Hz, 1H), 6.73 (s, 2H), 3.83-3.78 (m, 4H), 2.98 (t, J=6.7 Hz, 2H), 0.89 (s, 9H), 0.02 (s, 6H)

h) (2-Methylthiazol-4-yl)(1-oxa-4,9-diazaspiro[5.5]undecan-4-yl)methanone trifluoroacetate

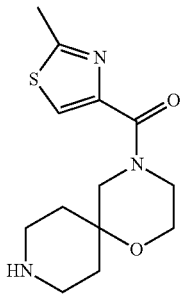

1-Propanephosphonic acid cyclic anhydride (1.57M solution in THF, 2.49 mL) was added to a solution of tert-butyl 1-oxa-4,9-diazaspiro[5.5]undecane-9-carboxylate hydrochloride (WuXi PharmaTech) (1 g), 2-methylthiazole-4-carboxylic acid (0.56 g) and triethylamine (3.26 mL) in DMF (30 mL) and the resulting mixture stirred for 16 hours at room temperature. The reaction was partitioned between water (500 mL) and ethyl acetate (200 mL). The layers were separated and the aqueous layer extracted with ethyl acetate (2×150 mL). The combined organic solutions were washed with water (2×100 mL), and brine (100 mL), then dried over magnesium sulphate, filtered and evaporated in vacuo. Purification was by silica gel chromatography eluting with ethyl acetate. The resulting oil was dissolved in dichloromethane (30 mL) and trifluoroacetic acid (3 mL) was added dropwise. This was then stirred for 1 hour and concentrated in vacuo. The residue was azeotroped twice with toluene (20 mL). The resulting gum was triturated with ether to give the subtitled compound as a white solid. Yield 1.20 g.

m/z 282 (M+H)⁺ (APCI)

¹H NMR (300 MHz, D₆-DMSO) δ 8.59-8.18 (m, 2H), 8.00 (s, 1H), 3.86-3.49 (m, 6H), 3.22-2.86 (m, 4H), 2.69 (s, 3H), 2.00-1.90 (m, 2H), 1.74-1.58 (m, 2H).

i) (9-(2-(5-(2-(tert-Butyldimethylsilyloxy)ethyl)thiophen-2-yl)ethyl)-1-oxa-4,9-diazaspiro[5.5]undecan-4-yl)(2-methylthiazol-4-yl)methanone

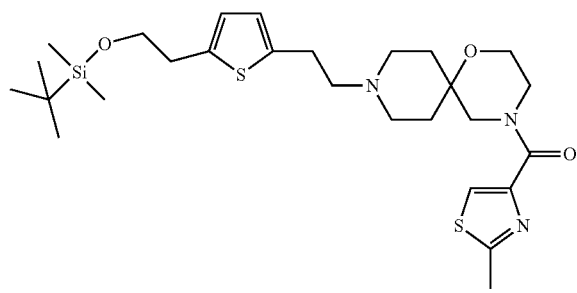 [SMILES: Cc1nc(C(=O)N2CCOC3(CCN(CCc4ccc(CCO[Si](C)(C)C(C)(C)C)s4)CC3)C2)cs1]

(2-Methylthiazol-4-yl)(1-oxa-4,9-diazaspiro[5.5]undecan-4-yl)methanone trifluoroacetate (example 4, step h) (0.25 g) was added to a solution of 2-(5-(2-(tert-butyldimethylsily- loxy)ethyl)thiophen-2-yl)acetaldehyde (0.2 g) (example 4, step g) in a mixture of NMP (5 mL) and acetic acid (0.04 mL). The resulting mixture was stirred for 5 min then sodium triacetoxyborohydride (0.22 g) was added. The mixture was stirred for 1 h and poured into pH 7.2 buffer (50 mL). The aqueous phase was extracted with ethyl acetate (3×50 mL). The combined organics were washed with pH 7.2 buffer (50 mL) and brine (50 mL), then dried over sodium sulphate, filtered and evaporated in vacuo. Purification was by silica gel chromatography eluting with 4:1:0.05 isohexane:ethyl acetate:triethylamine to 95:5 ethyl acetate:triethylamine to give the subtitled compound as a yellow oil. Yield 0.23 g.

¹H NMR (400 MHz, D₆-DMSO) δ 7.86 (s, 1H), 6.62 (s, 2H), 3.76 (t, J=6.5 Hz, 2H), 3.70-3.57 (m, 6H), 3.30 (t, J=7.0 Hz, 2H), 2.91-2.81 (m, 4H), 2.68 (s, 3H), 2.44-2.37 (m, 4H), 1.74-1.66 (m, 2H), 1.58-1.49 (m, 2H), 0.88-0.84 (m, 9H), 0.01-0.00 (m, 6H).

j) (9-(2-(5-(2-Hydroxyethyl)thiophen-2-yl)ethyl)-1-oxa-4,9-diazaspiro[5.5]undecan-4-yl)(2-methylthiazol-4-yl)methanone

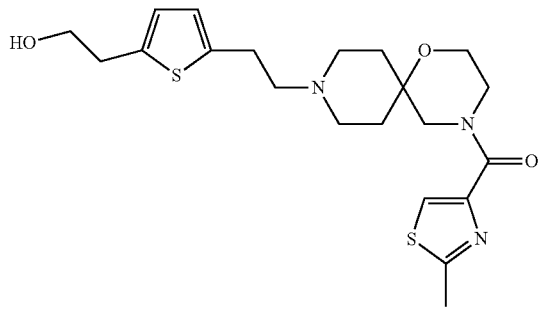 [SMILES: Cc1nc(C(=O)N2CCOC3(CCN(CCc4ccc(CCO)s4)CC3)C2)cs1]

Concentrated hydrochloric-acid (0.5 mL) was added to a solution of (9-(2-(5-(2-(tert-butyldimethylsilyloxy)ethyl)thiophen-2-yl)ethyl)-1-oxa-4,9-diazaspiro[5.5]undecan-4-yl)(2-methylthiazol-4-yl)methanone (example 4, step i) (0.235 g) in methanol (5 mL) and the resulting solution stirred for 1 h. The solvent was evaporated in vacuo and the residue azeotroped with toluene and re-dissolved in methanol (~2 mL). The residue was dissolved in methanol (10 mL) and applied to a SCX cartridge pre-wetted with methanol. The cartridge was washed with methanol (100 mL) and eluted with 1M ammonia in methanol solution (100 mL). The eluent was evaporated in vacuo to give the subtitled compound as a yellow oil. Yield 0.12 g.

¹H NMR (300 MHz, D₆-DMSO) δ 7.87 (s, 1H), 6.64 (s, 2H), 4.38 (t, J=4.9 Hz, 1H), 3.70-3.51 (m, 8H), 2.84 (t, J=6.7 Hz, 4H), 2.68 (s, 3H), 2.60-2.52 (m, 2H), 2.4-2.38 (m, 4H), 1.76-1.65 (m, 2H), 1.60-1.49 (m, 2H).

k) (R)-4-Hydroxy-7-(1-hydroxy-2-(2-(5-(2-(4-(2-methylthiazole-4-carbonyl)-1-oxa-4,9-diazaspiro[5.5]undecan-9-yl)ethyl)thiophen-2-yl)ethylamino)ethyl)benzo[d]thiazol-2(3H)-one ditrifluoroacetate

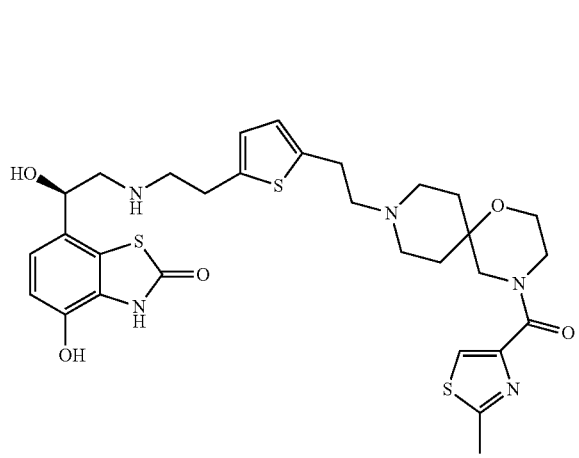 [SMILES: Cc1nc(C(=O)N2CCOC3(CCN(CCc4ccc(CCNC[C@H](O)c5ccc(O)c6[nH]c(=O)sc56)s4)CC3)C2)cs1]

Trifluoroacetic acid (0.02 mL) was added to a solution of (9-(2-(5-(2-hydroxyethyl)thiophen-2-yl)ethyl)-1-oxa-4,9-diazaspiro[5.5]undecan-4-yl)(2-methylthiazol-4-yl)methanone (example 4, step j) (0.128 g) in DCM (5 mL) at 0° C. and the resulting mixture stirred for 5 min. Dess-Martin periodinane (0.15 g) was then added and the mixture stirred for 10 min. A mixture of saturated sodium thiosulphate solution (5 mL), saturated sodium bicarbonate solution (5 mL) and ethyl acetate (25 mL) were added and the mixture stirred for 10 min. The aqueous phase was separated and extracted with ethyl acetate (20 mL). The combined organic solutions were washed with a saturated solution of sodium bicarbonate solution (10 mL), and brine (10 mL), then dried over sodium sulphate, filtered and evaporated in vacuo. The residue was redissolved in MeOH (1 mL). Acetic acid (0.04 mL) was added followed by (R)-7-(2-amino-1-hydroxyethyl)-4-hydroxybenzo[d]thiazol-2(3H)-one hydrochloride (WO2007027134, example 1, step d) (0.19 g) and the mixture was cooled to 0° C. Sodium triacetoxyborohydride (0.157 g) was added and the resulting mixture stirred for 1 h then concentrated in vacuo. The residue was dissolved in a mixture of acetonitrile and water (1:1, 5 mL). Purification was by preparative HPLC (Sunfire™, Gradient: 5-50% acetonitrile in 0.2% aqueous TFA). The fractions containing product were combined, evaporated in vacuo and the residue triturated with ether and evaporated in vacuo to give the titled compound as a white solid. Yield 0.04 g.

m/z 644 (M+H)$^+$ (APCI)

$^1$H NMR (300 MHz, D$_6$-DMSO, 90° C.) δ 7.92 (s, 1H), 6.93 (d, J=8.5 Hz, 1H), 6.84-6.73 (m, 3H), 4.89 (dd, J=7.9, 5.4 Hz, 1H), 3.74-3.62 (m, 6H), 3.44-3.07 (m, 14H), 2.68 (s, 3H), 2.11-1.93 (m, 2H), 1.89-1.72 (m, 2H). Six exchangeable protons not observed.

EXAMPLE 5

(R)-4-Hydroxy-7-(1-hydroxy-2-(4-(2-(4-(2-methylthiazole-4-carbonyl)-1-oxa-4,9-diazaspiro[5.5]undecan-9-yl)ethyl)phenethylamino)ethyl)benzo[d]thiazol-2(3H)-one ditrifluoroacetate

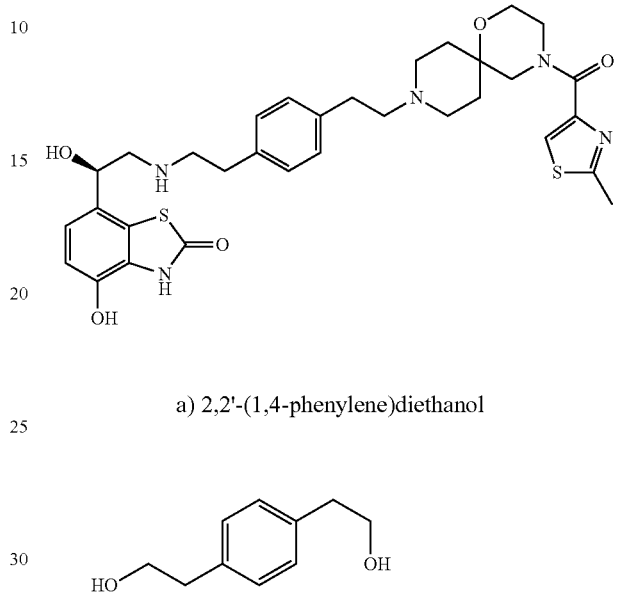

a) 2,2'-(1,4-phenylene)diethanol

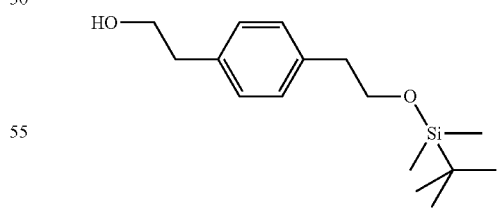

Borane-methyl sulfide complex (2M solution in tetrahydrofuran, 80 mL) was added over 20 min to a stirred solution of 2,2'-(1,4-phenylene)diacetic acid (10.20 g) in tetrahydrofuran (100 mL) cooled in an ice bath. After 16 h, the reaction mixture was carefully quenched with methanol (40 mL). The solution was evaporated in vacuo and the resulting gum was partitioned between ethyl acetate and saturated aqueous ammonium chloride. The ethyl acetate solution was separated, dried over magnesium sulphate, filtered and evaporated in vacuo to give the subtitled compound as gum. Yield 8.64 g.

$^1$H NMR (300 MHz, CDCl$_3$) δ 7.18 (s, 4H), 3.86 (t, 4H), 2.85 (t, 4H)+2 exchangeable protons.

b) 2-{4-[2-(tert-Butyl-dimethyl-silanyloxy)-ethyl]-phenyl}-ethanol tert-Butyldimethylchlorosilane (9.68 mL) was added to a solution of 2,2'-(1,4-phenylene)diethanol (example 5, step a) (8.64 g) and imidazole (10.21 g) in dry DMF (100 mL) cooled in an ice bath. After 45 min, the reaction mixture was diluted with ethyl acetate, washed three times with water and evaporated in vacuo. Purification was by silica gel chromatography, eluting with 5:1 isohexane:ethyl acetate to give the subtitled compound as a colourless oil. Yield 6.20 g.

c) 2-(4-(2-(tert-Butyldimethylsilyloxy)ethyl)phenyl) acetaldehyde

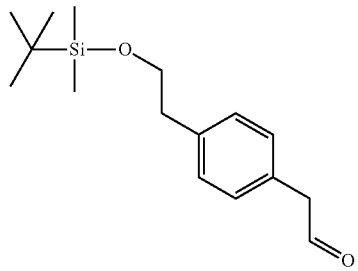 [SMILES: CC(C)(C)[Si](C)(C)OCCc1ccc(CC=O)cc1]

Dess-Martin periodinane (0.38 g) was added to a solution of 2-(4-(2-(tert-butyldimethylsilyloxy)ethyl)phenyl)ethanol (example 5, step b) (0.21 g) in dichloromethane (5 mL) and the resulting mixture stirred for 30 min. A mixture of saturated sodium thiosulphate solution (5 mL), saturated sodium bicarbonate solution (5 mL) and ethyl acetate (25 mL) were added and the resulting mixture stirred for 10 min. The organic phase was separated and washed with saturated sodium bicarbonate solution (2×10 mL) and brine (10 mL), then dried over sodium sulphate, filtered and evaporated to give the subtitled compound as a clear oil which was used immediately. Yield 0.20 g.

$^1$H NMR (300 MHz, CDCl$_3$) δ 9.74 (t, J=2.4 Hz, 1H), 7.23 (d, J=8.2 Hz, 2H), 7.15 (d, J=8.2 Hz, 2H), 3.82 (t, J=7.1 Hz, 2H), 3.67 (d, J=2.6 Hz, 2H), 2.83 (t, J=7.1 Hz, 2H), 0.88 (s, 9H), 0.00 (s, 6H).

d) (9-(4-(2-(tert-Butyldimethylsilyloxy)ethyl)phenethyl)-1-oxa-4,9-diazaspiro[5.5]undecan-4-yl)(2-methylthiazol-4-yl)methanone

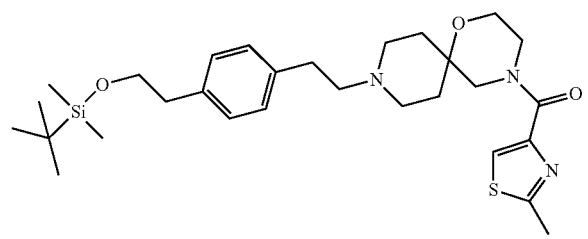 [SMILES: Cc1nc(C(=O)N2CCOC3(CCN(CCc4ccc(CCO[Si](C)(C)C(C)(C)C)cc4)CC3)C2)cs1]

(2-Methylthiazol-4-yl)(1-oxa-4,9-diazaspiro[5.5]undecan-4-yl)methanone trifluoroacetate (example 4, step h) (0.26 g) was added to a solution of 2-(4-(2-(tert-butyldimethylsilyloxy)ethyl)phenyl)acetaldehyde (example 5, step c) (0.2 g) and acetic acid (0.04 mL) in NMP (5 mL). The resulting mixture was stirred for 5 min then sodium triacetoxyborohydride (0.23 g) was added. The mixture was stirred for 1 h, poured into pH 7.2 buffer (50 mL) and extracted with ethyl acetate (3×50 mL). The combined organic solutions were washed with pH 7.2 buffer (50 mL) and brine (50 mL), then dried over sodium sulphate, filtered and evaporated in vacuo. Purification was by silica gel chromatography eluting with 80:15:5 isohexane:ethyl acetate:triethylamine to 95:5 ethyl acetate:triethylamine to give the subtitled compound as a yellow oil. Yield 0.30 g.

$^1$H NMR (400 MHz, D$_6$-DMSO, 90° C.) δ 7.90 (s, 1H), 7.12 (s, 4H), 3.80 (t, J=6.8 Hz, 2H), 3.71-3.60 (m, 6H), 2.77-2.67 (m, 7H), 2.46-2.41 (m, 2H), 1.76-1.67 (m, 2H), 1.61-1.51 (m, 2H), 0.87 (s, 9H), 0.02 (s, 6H)+4 protons obscured by solvent peaks.

e) (9-(4-(2-Hydroxyethyl)phenethyl)-1-oxa-4,9-diazaspiro[5.5]undecan-4-yl)(2-methylthiazol-4-yl)methanone

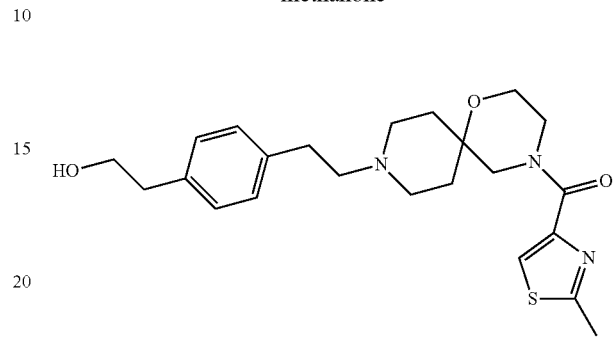

Concentrated hydrochloric acid (0.5 mL) was added to a solution of (9-(4-(2-(tert-butyldimethylsilyloxy)ethyl)phenethyl)-1-oxa-4,9-diazaspiro[5.5]undecan-4-yl)(2-methylthiazol-4-yl)methanone (example 5, step d) (0.3 g) in methanol (5 mL) and the resulting solution stirred for 1 h.

The solvent was evaporated in vacuo and the residue azeotroped with toluene and redissolved in methanol (~2 mL). The residue was diluted with methanol (10 mL) and applied to a SCX cartridge pre-wetted with methanol. The cartridge was washed with methanol (100 mL) and eluted with 1M ammonia in methanol solution (100 mL). The eluent was evaporated in vacuo to give the subtitled compound as a clear oil. Yield 0.2 g.

$^1$H NMR (400 MHz, D$_6$-DMSO) δ 7.86 (s, 1H), 7.09 (s, 4H), 4.24 (t, J=5.0 Hz, 1H), 3.69-3.55 (m, 8H), 2.68 (s, 3H), 2.45-2.38 (m, 4H), 1.74-1.65 (m, 2H), 1.57-1.48 (m, 2H)+6 protons obscured by solvent peaks.

f) (R)-4-Hydroxy-7-(1-hydroxy-2-(4-(2-(4-(2-methylthiazole-4-carbonyl)-1-oxa-4,9-diazaspiro[5.5]undecan-9-yl)ethyl)phenethylamino)ethyl)benzo[d]thiazol-2(3H)-one ditrifluoroacetate

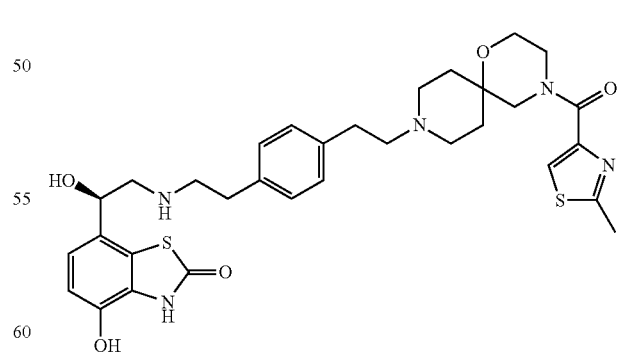

Trifluoroacetic acid (0.04 mL) was added to a solution of (9-(4-(2-hydroxyethyl)phenethyl)-1-oxa-4,9-diazaspiro[5.5]undecan-4-yl)(2-methylthiazol-4-yl)methanone (example 5, step e) (0.21 g) in DCM (5 mL) at 0° C. and the resulting mixture stirred for 5 min. Dess-Martin periodinane (0.25 g)

was then added and the mixture stirred for 10 min. A mixture of saturated sodium thiosulphate solution (5 mL), saturated sodium bicarbonate solution (5 mL) and ethyl acetate (25 mL) was added and the mixture stirred for 10 min. The aqueous was separated and extracted with ethyl acetate (20 mL). The combined organic solutions were washed with saturated sodium bicarbonate solution (10 mL) and brine (10 mL), then dried over sodium sulphate, filtered and evaporated in vacuo. The residue was redissolved in MeOH (1 mL). Acetic acid (0.04 mL) was added, followed by (R)-7-(2-amino-1-hydroxyethyl)-4-hydroxybenzo[d]thiazol-2(3H)-one hydrochloride (WO2007027134, example 1, step d) (0.19 g) and the mixture was cooled to 0° C. Sodium triacetoxyborohydride (0.157 g) was added and the resulting mixture stirred for 1 h then concentrated in vacuo. The residue was dissolved in a mixture of acetonitrile and water (1:1, 5 mL). Purification was by preparative HPLC (Sunfire™, Gradient: 5-50% acetonitrile in 0.2% aqueous TFA). The fractions containing product were combined, evaporated in vacuo and the residue triturated with ether and evaporated in vacuo to give the titled compound as a white solid. Yield 0.17 g.

m/z 638 (M+H)$^+$ (APCI)

$^1$H NMR (300 MHz, D$_6$-DMSO) δ 7.92 (s, 1H), 7.26-7.18 (m, 4H), 6.93 (d, J=8.5 Hz, 1H), 6.77 (d, J=8.5 Hz, 1H), 4.96-4.87 (m, 1H), 3.76-2.90 (m, 20H), 2.68 (s, 3H), 2.14-1.75 (m, 4H). Six exchangeable protons not observed.

EXAMPLE 6

(R)-4-Hydroxy-7-(1-hydroxy-2-(3-((4-(2-methylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

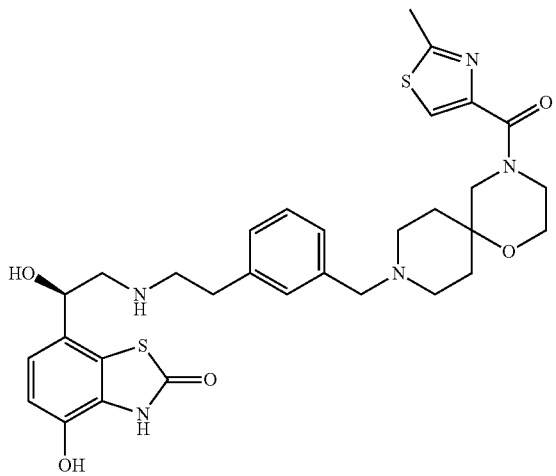 [SMILES: Cc1nc(C(=O)N2CCOC3(CCN(Cc4cccc(CCNC[C@H](O)c5ccc(O)c6[nH]c(=O)sc56)c4)CC3)C2)cs1]

a) 2-(3-(Bromomethyl)phenyl)ethanol

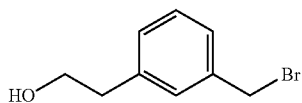 [SMILES: OCCc1cccc(CBr)c1]

Borane dimethylsulphide complex (2M solution in THF, 5.78 mL) was added dropwise to a solution of 2-(3-(bromomethyl)phenyl)acetic acid (1.06 g) in THF (10 mL) at 0° C. and the resulting mixture stirred for 10 min. The reaction was then allowed to warm to room temperature and stirred overnight. Methanol (5 mL) was then added and the mixture concentrated in vacuo. Purification was by silica gel chromatography eluting with isohexane to diethyl ether gradient to give the subtitled compound as a white solid. Yield 1 g.

$^1$H NMR (300 MHz, CDCl$_3$) δ 7.34-7.24 (m, 3H), 7.22-7.12 (m, 1H), 4.48 (s, 2H), 3.87 (t, J=6.5 Hz, 2H), 2.87 (t, J=6.5 Hz, 2H), OH not observed.

b) 9-(3-(2-Hydroxyethyl)benzyl)-1-oxa-4,9-diazaspiro[5.5]undecan-4-yl)(2-methylthiazol-4-yl)methanone

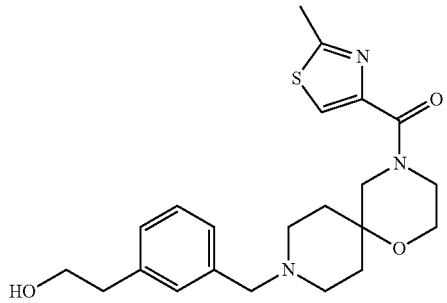 [SMILES: Cc1nc(C(=O)N2CCOC3(CCN(Cc4cccc(CCO)c4)CC3)C2)cs1]

2-(3-(Bromomethyl)phenyl)ethanol (example 6, step a) (0.11 g) was added to a solution of (2-methylthiazol-4-yl)(1-oxa-4,9-diazaspiro[5.5]undecan-4-yl)methanone trifluoroacetate (example 4, step h) (0.2 g) and triethylamine (0.17 mL) in acetonitrile (5 mL) and the resulting mixture stirred overnight at room temperature. The solvent was evaporated in vacuo and the residue partitioned between ethyl acetate (25 mL) and saturated sodium bicarbonate solution (25 mL). The aqueous layer was separated and extracted with ethyl acetate (2×25 mL). The combined organic solutions were washed with brine (25 mL), dried over sodium sulphate, filtered and evaporated in vacuo. Purification was by silica gel chromatography eluting with 80:15:5 isohexane:ethyl acetate:triethylamine to 95:5 ethyl acetate:triethylamine gradient to give the subtitled compound as a yellow oil. Yield 0.15 g.

$^1$H NMR (400 MHz, D$_6$-DMSO) δ 7.85 (s, 1H), 7.18 (t, J=7.4 Hz, 1H), 7.12-7.04 (m, 3H), 4.24 (t, J=5.1 Hz, 1H), 3.71-3.54 (m, 8H), 3.42 (s, 2H), 2.71 (t, J=6.9 Hz, 2H), 2.68 (s, 3H), 2.38-2.27 (m, 4H), 1.74-1.64 (m, 2H), 1.57-1.47 (m, 2H).

c) (R)-4-Hydroxy-7-(1-hydroxy-2-(3-((4-(2-methylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

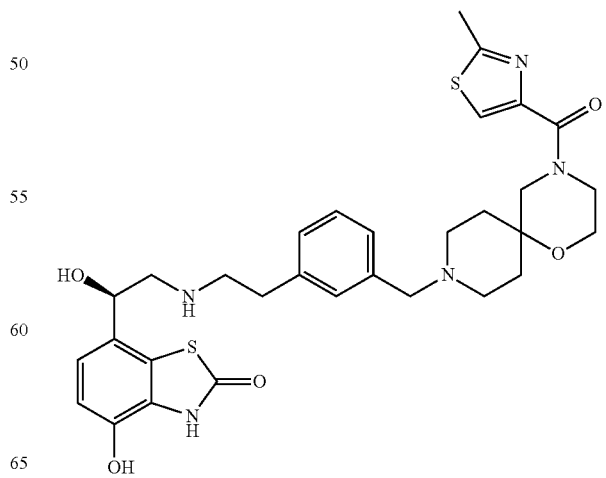

Trifluoroacetic acid (0.03 mL) was added to a solution of (9-(3-(2-hydroxyethyl)benzyl)-1-oxa-4,9-diazaspiro[5.5]undecan-4-yl)(2-methylthiazol-4-yl)methanone (example 6, step b) (0.17 g) in DCM (5 mL) at 0° C. and the resulting mixture stirred for 5 min. Dess-Martin periodinane (0.21 g) was then added and the mixture stirred for 10 min. A mixture of saturated sodium thiosulphate solution (5 mL), saturated sodium bicarbonate solution (5 mL) and ethyl acetate (25 mL) was added and the mixture stirred for 10 min. The aqueous phase was separated and extracted with ethyl acetate (20 mL). The combined organic solutions were washed with saturated sodium bicarbonate solution (10 mL), and brine (10 mL), then dried over sodium sulphate, filtered and evaporated. The residue was redissolved in methanol (25 mL). Acetic acid (0.04 mL) was added followed by (R)-7-(2-amino-1-hydroxyethyl)-4-hydroxybenzo[d]thiazol-2(3H)-one hydrochloride (WO2007027134, example 1, step d) (0.16 g) and the mixture cooled to 0° C. in an ice bath before addition of sodium triacetoxyborohydride (0.16 g). The resulting mixture was stirred for 1 h and concentrated. The residue was dissolved in a mixture of acetonitrile and water (1:1, 5 mL). Purification was by preparative HPLC (Sunfire™, Gradient: 5-50% acetonitrile in 0.2% aqueous TFA). The fractions containing product were combined, evaporated in vacuo and the residue triturated with ether and evaporated in vacuo to give the titled compound as a white solid. Yield 0.125 g.

m/z 624 (M+H)$^+$ (APCI)

$^1$H NMR (400 MHz, D$_6$-DMSO, 90° C.) δ 11.27 (s, 1H), 7.90 (s, 1H), 7.45-7.31 (m, 4H), 6.93 (d, J=8.2 Hz, 1H), 6.77 (d, J=8.2 Hz, 1H), 4.92 (dd, J=7.9, 5.1 Hz, 1H), 4.30 (s, 2H), 3.74-3.58 (m, 6H), 3.29-2.97 (m, 10H), 2.67 (s, 3H), 2.13-1.95 (m, 2H), 1.88-1.70 (m, 2H). Five exchangeable protons not observed.

EXAMPLE 7

(R)-8-Hydroxy-5-(1-hydroxy-2-(3-((4-(2-methylthiazole-4-carbonyl)-1-oxa-4,9-diazaspiro[5.5]undecan-9-yl)methyl)phenethylamino)ethyl)quinolin-2(1H)-one ditrifluoroacetate

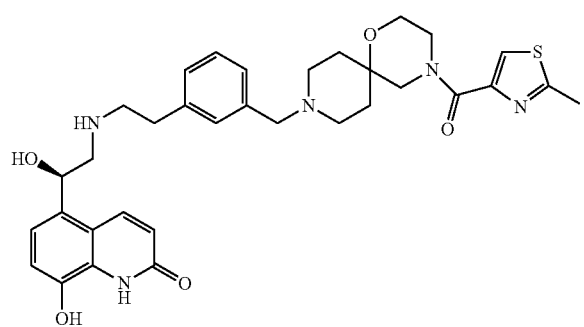 [SMILES: Cc1nc(C(=O)N2CCOC3(CCN(Cc4cccc(CCNC[C@H](O)c5ccc(O)c6[nH]c(=O)ccc56)c4)CC3)C2)cs1]

Trifluoroacetic acid (0.02 mL) was added to a solution of (9-(3-(2-hydroxyethyl)benzyl)-1-oxa-4,9-diazaspiro[5.5]undecan-4-yl)(2-methylthiazol-4-yl)methanone (example 6, step b) (0.11 g) in DCM (5 mL) at 0° C. and the resulting mixture stirred for 5 min. Dess-Martin periodinane (0.14 g) was then added and the mixture stirred for 10 min. A mixture of saturated sodium thiosulphate solution (5 mL), saturated sodium bicarbonate solution (5 mL) and ethyl acetate (25 mL) were added and the mixture was stirred for 10 min. The aqueous layer was separated and extracted with ethyl acetate (20 mL). The combined organic solutions were washed with saturated sodium bicarbonate solution (10 mL), brine (10 mL), dried over sodium sulphate, filtered and evaporated in vacuo. The residue was redissolved in methanol (25 mL). Acetic acid (0.02 mL) was added followed by (R)-5-(2-amino-1-(tert-butyldimethylsilyloxy)ethyl)-8-hydroxyquinolin-2(1H)-one (WO2004106333) (0.09 g) and the mixture cooled to 0° C. in an ice bath before addition of sodium triacetoxyborohydride (0.08 g). The resulting mixture was stirred for 1 h and concentrated in vacuo. The residue was partitioned between ethyl acetate (50 mL) and pH 7.2 buffer (50 mL). The aqueous was separated and extracted with ethyl acetate (2×50 mL). The combined organic solutions were washed with brine (20 mL), dried over sodium sulphate, filtered and evaporated. Purification was by silica gel chromatography eluting with 95:5:0.5 to 92:8:0.8 DCM:methanol:'880' aqueous ammonia gradient. The fractions containing product were combined, evaporated and dissolved in THF (1 mL). Triethylamine trihydrofluoride (0.05 mL) was added and the mixture stirred overnight. The solvent was evaporated in vacuo and the residue was dissolved in a mixture of acetonitrile and water (1:1, 5 mL). Purification was by preparative HPLC (Sunfire™, Gradient: 5-50% acetonitrile in 0.2% aqueous TFA). The fractions containing product were combined, evaporated in vacuo and the residue triturated with ether and evaporated in vacuo to give the titled compound as a white solid. Yield 0.06 g.

m/z 618 (M+H)$^+$ (APCI)

$^1$H NMR (400 MHz, D$_6$-DMSO) δ 8.16 (d, J=10.0 Hz, 1H), 7.90 (s, 1H), 7.47-7.30 (m, 4H), 7.13 (d, J=8.2 Hz, 1H), 6.99 (d, J=8.2 Hz, 1H), 6.54 (d, J=10.0 Hz, 1H), 5.35 (dd, J=8.5, 4.1 Hz, 1H), 4.30 (s, 2H), 3.74-3.57 (m, 4H), 3.32-2.98 (m, 12H), 2.67 (s, 3H), 2.12-1.92 (m, 2H), 1.87-1.67 (m, 2H). Six exchangeable protons not observed.

EXAMPLE 8

(R)-4-Hydroxy-7-(1-hydroxy-2-(4-(3-(4-(2-methylthiazole-4-carbonyl)-1-oxa-4,9-diazaspiro[5.5]undecan-9-yl)propoxy)benzylamino)ethyl)benzo[d]thiazol-2(3H)-one ditrifluoroacetate

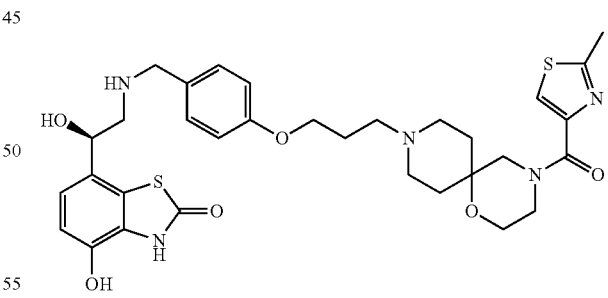

a) 4-(3-Bromopropoxy)benzaldehyde

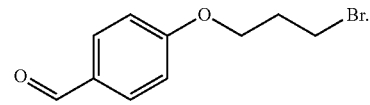 [SMILES: O=Cc1ccc(OCCCBr)cc1]

1,3-dibromopropane (20.0 g) was added to a stirred suspension of 4-hydroxybenzaldehyde (4.0 g) and potassium carbonate (7.0 g) in acetone (80 mL). After 16 h, the mixture was heated under reflux for a further 2 h, cooled, filtered to remove the inorganics, and the solution was evaporated in vacuo. Purification was by silica gel chromatography eluting with isohexane to remove the 1,3-dibromopropane and then dichloromethane:isohexane, 2:1 to collect the subtitled compound. Yield 3.45 g.

$^1$H NMR (300 MHz, CDCl$_3$) δ 9.89 (s, 1H), 7.84 (d, J=9.2 Hz, 2H), 7.01 (d, J=9.2 Hz, 2H), 4.21 (t, J=5.6 Hz, 2H), 3.62 (t, J=6.0 Hz, 2H), 2.36 (quintet, J=6.1 Hz, 2H)

b) 4-(3-(4-(2-Methylthiazole-4-carbonyl)-1-oxa-4,9-diazaspiro[5.5]undecan-9-yl)propoxy)benzaldehyde

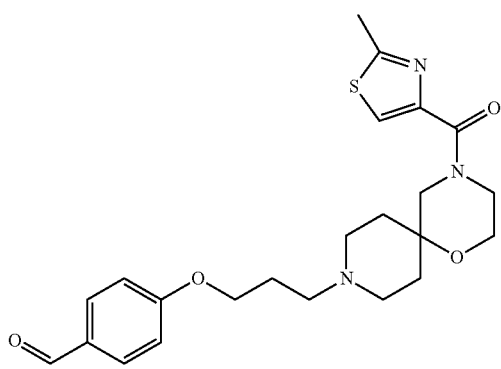 [SMILES: Cc1nc(C(=O)N2CCOC3(CCN(CCCOc4ccc(C=O)cc4)CC3)C2)cs1]

A mixture of (2-methylthiazol-4-yl)(1-oxa-4,9-diazaspiro[5.5]undecan-4-yl)methanone trifluoroacetate (example 4, step h) (0.244 g), 4-(3-bromopropoxy)benzaldehyde (example 8, step a) (0.15 g) and triethylamine (0.344 mL) in MeCN (2 mL) was heated at 60° C. After 16 h, the reaction mixture was evaporated in vacuo. Purification was by silica gel chromatography eluting with ethyl acetate:triethylamine, 10:1 to give the subtitled compound as an oil. Yield 0.24 g.

m/z 444 (M+H)$^+$ (APCI)

c) (R)-4-Hydroxy-7-(1-hydroxy-2-(4-(3-(4-(2-methylthiazole-4-carbonyl)-1-oxa-4,9-diazaspiro[5.5]undecan-9-yl)propoxy)benzylamino)ethyl)benzo[d]thiazol-2(3H)-one ditrifluoroacetate

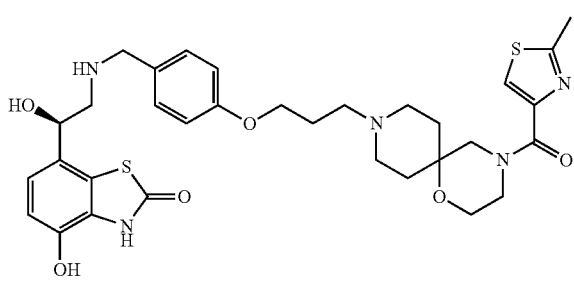 [SMILES: Cc1nc(C(=O)N2CCOC3(CCN(CCCOc4ccc(CNC[C@H](O)c5ccc(O)c6[nH]c(=O)sc56)cc4)CC3)C2)cs1]

Hydrogen chloride (0.4 mL of a 1M solution in diethyl ether) was added to a stirred solution of 4-(3-(4-(2-methylthiazole-4-carbonyl)-1-oxa-4,9-diazaspiro[5.5]undecan-9-yl)propoxy)benzaldehyde (example 8, step b) (0.15 g) and (R)-7-(2-amino-1-hydroxyethyl)-4-hydroxybenzo[d]thiazol-2 (3H)-one acetate (example 1, step d) (0.15 g) in MeOH (15 mL). After 5 minutes sodium cyanoborohydride (0.05 g) was added. After 16 h the solution was concentrated to ~2 mL and then partitioned between ethyl acetate and pH 7.2 phosphate buffer (20 mL). The ethyl acetate solution was washed with brine, dried over sodium sulphate, filtered and evaporated in vacuo. The residue was dissolved in a mixture of acetonitrile and water (1:1, 5 mL). Purification was by preparative HPLC (Sunfire™, Gradient: 5-35% acetonitrile in 0.2% aqueous TFA). The fractions containing product were combined, evaporated in vacuo and the residue triturated with ether and evaporated in vacuo to give the titled compound as a white solid. Yield 0.045 g.

m/z 654 (M+H)$^+$ (APCI)

$^1$H NMR (400 MHz, D$_6$-DMSO) δ 7.92 (s, 1H), 7.42 (d, J=8.7 Hz, 2H), 6.98 (d, J=8.7 Hz, 2H), 6.89 (d, J=8.5 Hz, 1H), 6.75 (d, J=8.2 Hz, 1H), 4.91-4.84 (m, 1H), 4.18-4.04 (m, 4H), 3.78-2.94 (m, 14H), 2.71 (s, 3H), 2.19-2.00 (m, 4H), 1.85-1.66 (m, 2H). Six exchangeable protons not observed.

EXAMPLE 9

(R)-8-Hydroxy-5-(1-hydroxy-2-(3-((4-(5-methylthiophene-2-carbonyl)-1-oxa-4,9-diazaspiro[5.5]undecan-9-yl)methyl)phenethylamino)ethyl)quinolin-2(1H)-one ditrifluoracetate

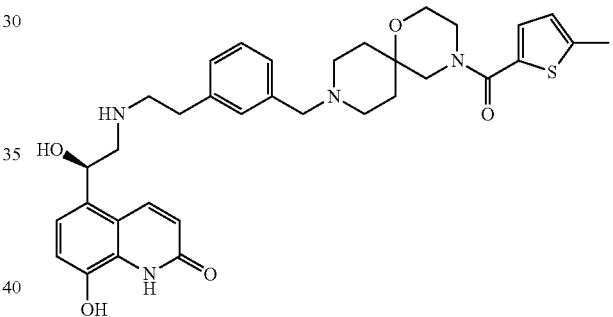

a) tert-Butyl 4-(5-methylthiophene-2-carbonyl)-1-oxa-4,9-diazaspiro[5.5]undecane-9-carboxylate

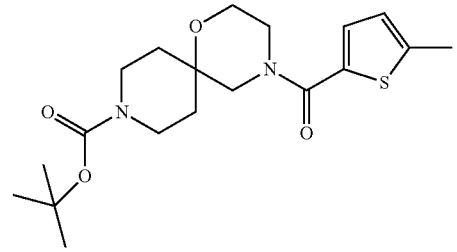 [SMILES: Cc1ccc(C(=O)N2CCOC3(CCN(C(=O)OC(C)(C)C)CC3)C2)s1]

1-Propanephosphonic acid cyclic anhydride (1.57M solution in THF, 0.64 mL) was added to a solution of tert-butyl 1-oxa-4,9-diazaspiro[5.5]undecane-9-carboxylate hydrochloride (WuXi PharmaTech) (0.26 g), 5-methylthiophene-2-carboxylic acid (0.142 g) and triethylamine (0.84 mL) in DMF (8 mL) and the resulting mixture stirred for 16 h. The reaction mixture was poured into water (100 mL) and extracted with ethyl acetate (3×200 mL). The combined organic solutions were washed with water (2×100 mL) and brine (100 mL), then dried over magnesium sulphate, filtered and evaporated in vacuo. Purification was by silica gel chromatography eluting with ethyl acetate:isohexane, 1:1 to give the subtitled compound as a clear oil. Yield 0.32 g.

$^1$H NMR (400 MHz, CDCl$_3$) δ 7.11 (d, J=3.6 Hz, 1H), 6.72-6.69 (m, 1H), 3.78-3.67 (m, 8H), 3.60-3.51 (m, 2H), 3.19-3.10 (m, 2H), 2.51 (s, 3H), 1.86-1.79 (m, 2H), 1.45 (s, 9H).

b) (5-Methylthiophen-2-yl)(1-oxa-4,9-diazaspiro[5.5]undecan-4-yl)methanone trifluoroacetate

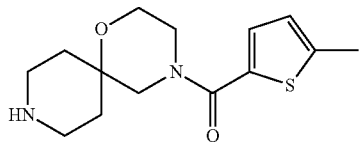 [SMILES: Cc1ccc(C(=O)N2CCOC3(CCNCC3)C2)s1]

tert-Butyl 4-(5-methylthiophene-2-carbonyl)-1-oxa-4,9-diazaspiro[5.5]undecane-9-carboxylate (example 9, step a) (0.32 g) in DCM (3 mL) was treated with trifluoroacetic acid (1.0 g). After 2 h, the reaction mixture was evaporated in vacuo and azeotroped twice with toluene to yield the subtitled compound which was used directly. Yield 0.32 g.

c) (9-(3-(2-Hydroxyethyl)benzyl)-1-oxa-4,9-diazaspiro[5.5]undecan-4-yl)(5-methylthiophen-2-yl)methanone

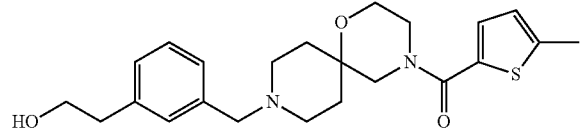 [SMILES: Cc1ccc(C(=O)N2CCOC3(CCN(Cc4cccc(CCO)c4)CC3)C2)s1]

2-(3-(Bromomethyl)phenyl)ethanol (example 6, step a) (0.136 g) was added to a stirred solution of (5-methylthiophen-2-yl)(1-oxa-4,9-diazaspiro[5.5]undecan-4-yl)methanone trifluoroacetate (example 9, step b) (0.250 g) and triethylamine (0.278 mL) in MeCN (5 mL). After 1 h, the reaction mixture was concentrated and applied to a silica gel column eluting with ethyl acetate:triethylamine, 95:5 to give the subtitled compound. Yield 0.24 g.

$^1$H NMR (400 MHz, CDCl$_3$) δ 7.28-7.24 (m, 2H), 7.18-7.15 (m, 1H), 7.11-7.08 (m, 2H), 6.70-6.67 (m, 1H), 3.86 (t, J=6.6 Hz, 2H), 3.77-3.69 (m, 4H), 3.56 (s, 2H), 3.48 (s, 2H), 2.86 (t, J=7.0 Hz, 2H), 2.55-2.48 (m, 5H), 2.40-2.32 (m, 2H), 1.89-1.82 (m, 2H), 1.70-1.50 (2Hs under water peak). One exchangeable proton not observed.

d) 2-(3-((4-(5-Methylthiophene-2-carbonyl)-1-oxa-4,9-diazaspiro[5.5]undecan-9-yl)methyl)phenyl)acetaldehyde

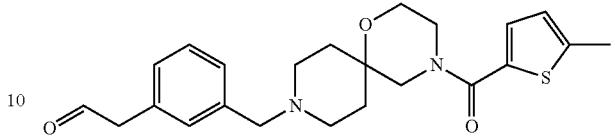

Dess-Martin periodinane (0.16 g) was added to a stirred solution of (9-(3-(2-hydroxyethyl)benzyl)-1-oxa-4,9-diazaspiro[5.5]undecan-4-yl)(5-methylthiophen-2-yl)methanone (0.13 g) (example 9, step c) and trifluoroacetic acid (0.036 g) in DCM (4 mL) under nitrogen. After 0.5 h, saturated sodium thiosulphate solution (5 mL) and saturated sodium bicarbonate solution (5 mL) were added and the reaction mixture extracted twice with ethyl acetate. The combined organic extracts were washed with saturated sodium bicarbonate and brine, dried over sodium sulphate, filtered and evaporated in vacuo to give the subtitled compound. Yield 0.13 g. Used directly.

e) (R)-8-Hydroxy-5-(1-hydroxy-2-(3-((4-(5-methylthiophene-2-carbonyl)-1-oxa-4,9-diazaspiro[5.5]undecan-9-yl)methyl)phenethylamino)ethyl)quinolin-2(1H)-one ditrifluoroacetate

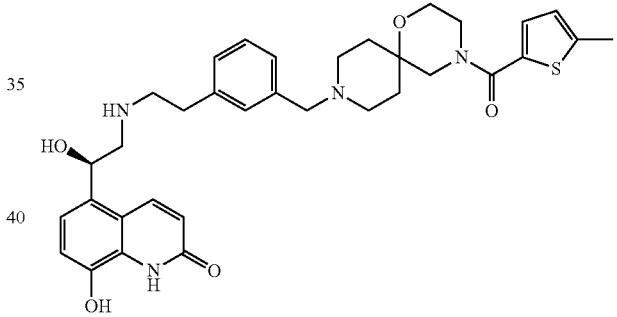

(R)-5-(2-Amino-1-(tert-butyldimethylsilyloxy)ethyl)-8-hydroxyquinolin-2(1H)-one (WO2004106333) (0.179 g) was added to stirred solution of 2-(3-((4-(5-methylthiophene-2-carbonyl)-1-oxa-4,9-diazaspiro[5.5]undecan-9-yl)methyl)phenyl)acetaldehyde (example 9, step d) (0.13 g) and acetic acid (0.031 mL) in MeOH (5 mL). After 5 minutes, sodium triacetoxyborohydride (0.114 g) was added. After another 15 min. ethyl acetate (30 mL) was added and the reaction mixture was washed with pH 7 buffer (30 mL) and evaporated in vacuo. Purification was by silica gel chromatography eluting with 92:7:1, DCM:MeOH:'880' aqueous ammonia to give the silylated intermediate. This intermediate was dissolved in THF (2 mL) and triethylamine trihydrofluoride (0.062 mL) added. After 16 h, the reaction was evaporated in vacuo, toluene (150 mL) added and the mixture evaporated in vacuo. The residue was dissolved in a mixture of acetonitrile and water (1:1, 5 mL). Purification was by preparative HPLC (Sunfire™, Gradient: 5-50% acetonitrile in 0.2% aqueous TFA). The fractions containing product were combined, evaporated in vacuo and the residue triturated with diethyl ether and evaporated in vacuo to give the titled compound as a white solid. Yield 0.05 g.

m/z 617 (M+H)$^+$ (APCI)

¹H NMR (400 MHz, D₆-DMSO) δ 10.55-10.45 (m, 2H), 9.95-9.84 (m, 0.2H), 9.68-9.57 (m, 0.8H) (rotormers), 8.97-8.74 (m, 2H), 8.16 (d, J=9.5 Hz, 1H), 7.49-7.33 (m, 4H), 7.29-7.26 (m, 0.2H), 7.25-7.21 (m, 0.8H)) (rotormers), 7.15 (d, J=9.5 Hz, 1H), 6.99 (d, J=9.5 Hz, 1H), 6.86-6.81 (m, 1H), 6.58 (d, J=10.1 Hz, 1H), 6.27-6.18 (m, 1H), 5.37-5.30 (m, 2H), 4.44-4.40 (m, 0.5H), 4.35-4.29 (m, 1.5H), 3.73-3.63 (m, 4H), 3.51-3.46 (m, 2H), 3.31-2.94 (m, 8H), 2.46 (s, 3H), 2.12-2.00 (m, 2H), 1.70-1.58 (m, 2H). One exchangeable proton not observed.

EXAMPLE 10

(R)-4-Hydroxy-7-(1-hydroxy-2-(3-(2-(4-(2-methylthiazole-4-carbonyl)-1-oxa-4,9-diazaspiro[5.5]undecan-9-yl)ethoxy)benzylamino)ethyl)benzo[d]thiazol-2(3H)-one ditrifluoroacetate

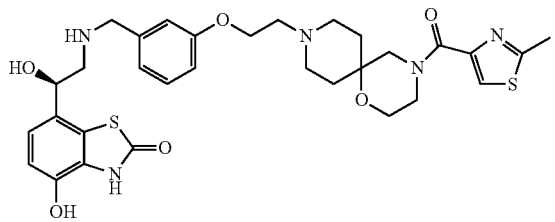 [SMILES: Cc1nc(C(=O)N2CCOC3(CCN(CCOc4cccc(CNC[C@H](O)c5ccc(O)c6[nH]c(=O)sc56)c4)CC3)C2)cs1]

a) 2-(3-Formylphenoxy)ethyl methanesulfonate

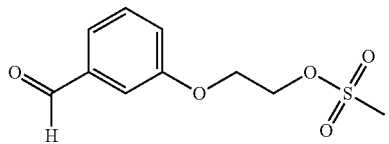 [SMILES: CS(=O)(=O)OCCOc1cccc(C=O)c1]

2-Bromoethanol (10.23 g) and potassium carbonate (11.32 g) were added to a solution of 3-hydroxybenzaldehyde (5 g) in acetonitrile (100 mL) and the resulting mixture stirred at reflux for 72 h. The reaction mixture was cooled and partitioned between ethyl acetate and ice-cold, dilute aqueous sodium hydroxide. The organic layer was separated, washed with brine, dried over sodium sulphate, filtered and the solvent removed in vacuo. The residue was dissolved in DCM (30 mL) and triethylamine (3.44 mL) was added. The solution was cooled to 0° C. and treated dropwise with methanesulfonyl chloride (1.89 mL). The reaction mixture was stirred at 0° C. for 10 minutes and then allowed to warm to room temperature and stirred for 1 h. The mixture was washed twice with brine, dried over sodium sulphate, filtered and the solvent evaporated in vacuo. Purification was by silica gel chromatography eluting with 6:4 ethyl acetate:isohexane. Pure fractions were evaporated in vacuo to give the subtitled compound as a colourless oil. Yield 3.50 g.

¹H NMR (400 MHz, CDCl₃) δ 9.98 (d, J=8.2 Hz, 1H), 7.53-7.46 (m, 2H), 7.41-7.39 (m, 1H), 7.22-7.19 (m, 1H), 4.62-4.59 (m, 2H), 4.34-4.30 (m, 2H), 3.10 (s, 3H).

b) 3-(2-(4-(2-Methylthiazole-4-carbonyl)-1-oxa-4,9-diazaspiro[5.5]undecan-9-yl)ethoxy)benzaldehyde

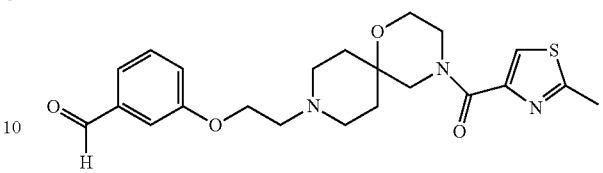

2-(3-Formylphenoxy)ethyl methanesulfonate (example 10, step a) (0.38 g) was added to a solution of (2-methylthiazol-4-yl)(1-oxa-4,9-diazaspiro[5.5]undecan-4-yl)methanone trifluoroacetate (example 4, step h) (0.62 g) and triethylamine (0.55 mL) in acetonitrile (5 mL) and the resulting mixture stirred for 16 h at 65° C. The solvent was evaporated in vacuo and the residue partitioned between ethyl acetate (25 mL) and saturated sodium bicarbonate solution (25 mL). The aqueous phase was separated and extracted with ethyl acetate (2×25 mL). The organic phases were combined, washed with brine (25 mL), dried over sodium sulphate, filtered and evaporated in vacuo. Purification was by silica gel chromatography eluting with 47.5:47:5:5 isohexane:ethyl acetate:triethylamine to 95:5 ethyl acetate:triethylamine gradient to give the subtitled compound as a yellow oil. Yield 0.48 g.

¹H NMR (400 MHz, D₆-DMSO) δ 9.97 (s, 1H), 7.96 (s, 1H), 7.56-7.40 (m, 3H), 7.32-7.25 (m, 1H), 4.14 (s, 2H), 3.75-3.47 (m, 6H), 2.80-2.62 (m, 5H), 2.55-2.37 (m, 4H), 1.74-1.40 (m, 4H).

c) (R)-4-Hydroxy-7-(1-hydroxy-2-(3-(2-(4-(2-methylthiazole-4-carbonyl)-1-oxa-4,9-diazaspiro[5.5]undecan-9-yl)ethoxy)benzylamino)ethyl)benzo[d]thiazol-2(3H)-one ditrifluoroacetate

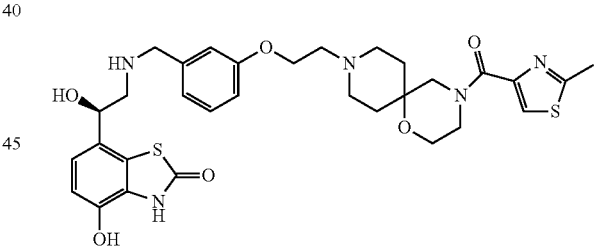

3-(2-(4-(2-Methylthiazole-4-carbonyl)-1-oxa-4,9-diazaspiro[5.5]undecan-9-yl)ethoxy)benzaldehyde (example 10, step b) (0.24 g) was added to a mixture of (R)-7-(2-amino-1-hydroxyethyl)-4-hydroxybenzo[d]thiazol-2(3H)-one hydrochloride (WO2007027134, example 1, step d) (0.15 g) and acetic acid (0.032 mL) in methanol (2 mL). The mixture was stirred for 30 min then cooled in an ice bath. Sodium triacetoxyborohydride (0.18 g) was then added and the mixture stirred for 2 h. The solvent was evaporated in vacuo and the residue partitioned between ethyl acetate (50 mL) and pH 7.2 phosphate buffer (50 mL). The aqueous phase was separated and extracted with ethyl acetate (2×50 mL). The combined organic phases were washed with brine (20 mL), dried over sodium sulphate, filtered and evaporated in vacuo. Purification was by preparative HPLC (Sunfire™, Gradient: 5-50% acetonitrile in 0.2% aqueous TFA). The fractions containing product were combined, evaporated in vacuo and the residue triturated with ether and evaporated in vacuo to give the titled compound as a white solid. Yield 0.21 g.

m/z 640 (M+H)+ (APCI)

$^1$H NMR (400 MHz, D$_6$-DMSO, 90° C.) δ 11.27 (s, 1H), 7.92 (s, 1H), 7.37 (t, J=7.8 Hz, 1H), 7.19-7.12 (m, 2H), 7.05 (d, J=8.2 Hz, 1H), 6.90 (d, J=8.2 Hz, 1H), 6.76 (d, J=8.2 Hz, 1H), 4.92 (t, J=6.5 Hz, 1H), 4.45-4.31 (m, 2H), 4.26-4.12 (m, 2H), 3.76-3.53 (m, 8H), 3.45-3.36 (m, 2H), 3.31-3.20 (m, 2H), 3.06-3.00 (m, 2H), 2.68 (s, 3H), 2.1-1.97 (m, 2H), 1.92-1.80 (m, 2H). Five exchangeable protons not observed.

EXAMPLE 11

5-Hydroxy-8-(1-hydroxy-2-(3-((4-(2-methylthiazole-4-carbonyl)-1-oxa-4,9-diazaspiro[5.5]undecan-9-yl)methyl)phenethylamino)ethyl)-2H-benzo[b][1,4]oxazin-3(4H)-one ditrifluoroacetate, Isomer 1

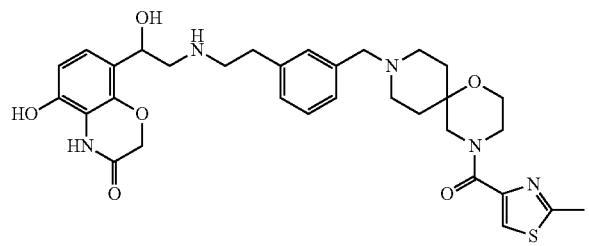 [SMILES: Cc1nc(C(=O)N2CCOC3(CCN(Cc4cccc(CCNCC(O)c5ccc(O)c6c5OCC(=O)N6)c4)CC3)C2)cs1]

a) 1-(2,4-Dihydroxy-3-nitrophenyl)ethanone

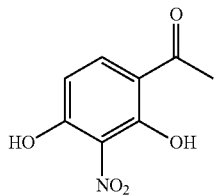

2-Nitrobenzene-1,3-diol (24.5 g) was added portionwise over 15 minutes to a vigorously stirred solution of aluminum chloride (46.3 g) in nitrobenzene (325 mL). Acetic anhydride (15.7 mL) was then added dropwise to the mixture over a further 15 minutes and the mixture then heated at 100° C. for 5 h. The reaction was cooled to ambient temperature and carefully quenched with ice cold 2M hydrochloric acid (300 mL). The mixture was extracted with diethyl ether (2×500 mL) and the combined diethyl ether extracts then extracted with 2M aqueous sodium hydroxide (2×400 mL). The combined basic extracts were washed with diethyl ether (4×500 mL) and then acidified to pH 1 with 2M hydrochloric acid (700 mL). The resulting precipitate was filtered off, washed with water, and dried under vacuum at 40° C. to afford the subtitled compound as a yellow-brown solid. Yield 29.5 g.

$^1$H NMR (400 MHz, D$_6$-DMSO) δ 13.32 (s, 1H), 12.31 (s, 1H), 7.98 (d, J=9.2 Hz, 1H), 6.63 (d, J=28.2 Hz, 1H), 2.59 (s, 3H).

b) 1-(4-(Benzyloxy)-2-hydroxy-3-nitrophenyl)ethanone

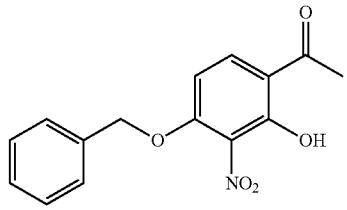 [SMILES: CC(=O)c1ccc(OCc2ccccc2)c([N+](=O)[O-])c1O]

Lithium tert-butoxide (4.06 g) was added to a stirred solution of 1-(2,4-dihydroxy-3-nitrophenyl)ethanone (example 11, step a) (10 g) in DMF (100 mL), under nitrogen, whilst maintaining the internal temperature below 30° C. After stirring for a further 10 minutes at ambient temperature, benzyl bromide (6.03 mL) was added and the mixture stirred for a further 20 h. Further benzyl bromide (3 mL) was added and the mixture stirred for 24 h. The reaction was quenched with water (300 mL), 1M aqueous sodium hydroxide (50 mL) was added and the mixture was washed with diethyl ether (2×300 mL), filtering through Celite to aid separation. The basic solution was cooled in ice/water, acidified with ice cold 2M hydrochloric acid (200 mL) and the resulting precipitate filtered off, washed with water and dried to afford a light brown solid. The solid was slurried with ethanol (100 mL) for 1 h and the solid filtered off, washed with cold ethanol (20 mL), and dried under vacuum at 40° C. to afford the subtitled compound as a light brown solid. Yield 6.8 g.

$^1$H NMR (400 MHz, D$_6$-DMSO) δ 13.04 (s, 1H), 8.14 (d, J=9.2 Hz, 1H), 7.45-7.32 (m, 5H), 7.01 (d, J=9.2 Hz, 1H), 5.42 (s, 2H), 2.64 (s, 3H)+3 exchangeable protons not observed.

c) 1-(3-Amino-4-(benzyloxy)-2-hydroxyphenyl)ethanone

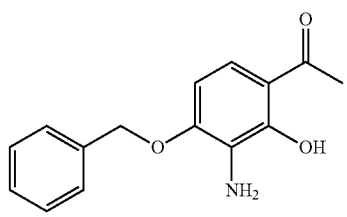 [SMILES: CC(=O)c1ccc(OCc2ccccc2)c(N)c1O]

Zinc dust (5.5 g) was added portionwise to a suspension of 1-(4-(benzyloxy)-2-hydroxy-3-nitrophenyl)ethanone (example 11, step b) (5.5 g) in acetic acid (55 mL) over 15 minutes, whilst maintaining the internal temperature below 40° C. with an ice bath. The mixture was allowed to attain ambient temperature and stirred for 2 h. The mixture was filtered through Celite (Caution: Gets hot—do not allow to dry), washed with acetic acid, and the filtrate poured onto ice/water (500 mL). The resulting precipitate was filtered off, washed with water, and dried under vacuum at 40° C. to afford the subtitled compound as a light brown solid. Yield 4.8 g.

$^1$H NMR (300 MHz, D$_6$-DMSO) δ 7.53 (m, 2H), 7.48-7.33 (m, 3H), 7.28 (d, J=9.0 Hz, 1H), 6.72 (d, J=9.0 Hz, 1H), 5.29 (s, 2H), 2.59 (s, 3H).

d) 8-Acetyl-5-(benzyloxy)-2H-benzo[b][1,4]oxazin-3(4H)-one

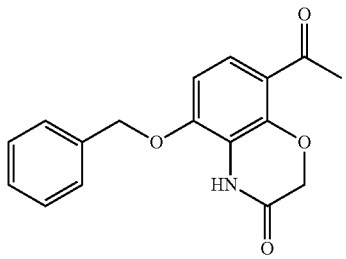 [SMILES: CC(=O)c1ccc(OCc2ccccc2)c2c1OCC(=O)N2]

2-Chloroacetyl chloride (1.8 mL) was added dropwise to a stirred mixture of 1-(3-amino-4-(benzyloxy)-2-hydroxyphenyl)ethanone (example 11, step c) (5.2 g) and sodium hydrogen carbonate (3.74 g) in DMF (30 mL) and then stirred for 2 h. Cesium carbonate (7.90 g) was added and the mixture heated at 100° C. for 20 h. The mixture was cooled to ambient temperature, quenched with water (500 mL), extracted with ethyl acetate (2×200 mL), washed with water (3×300 mL) and brine, dried over anhydrous sodium sulphate, filtered and evaporated under vacuum. The solid residue was treated with diethyl ether, filtered and dried to afford the subtitled compound as a beige solid. Yield 5.7 g.

$^1$H NMR (400 MHz, D$_6$-DMSO) δ 10.33 (s, 1H), 7.55 (m, 2H), 7.39 (m, 2H), 7.34 (d, J=8.8 Hz, 1H), 7.33 (m, 1H), 6.89 (d, J=9.2 Hz, 1H), 5.27 (s, 2H), 4.67 (s, 2H), 3.32 (s, 3H).

e) 5-(Benzyloxy)-8-(2-chloroacetyl)-2H-benzo[b][1,4]oxazin-3(4H)-one

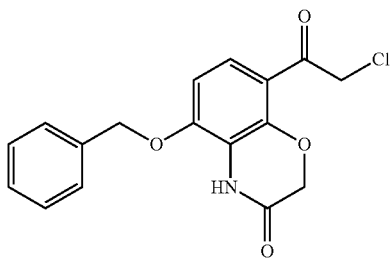 [SMILES: O=C1COc2c(C(=O)CCl)ccc(OCc3ccccc3)c2N1]

Benzyltrimethylammonium dichloroiodate (14.17 g) was added to a stirred solution of 8-acetyl-5-(benzyloxy)-2H-benzo[b][1,4]oxazin-3(4H)-one (example 11, step d) (5.5 g) in a mixture of dichloromethane (100 mL), acetic acid (33 mL) and water (5.5 mL) and the reaction mixture stirred at 65° C. for 20 h. The reaction was cooled to ambient temperature, treated with aqueous sodium bisulphite (5.78 g in 100 mL) and stirred for a further 30 min. The mixture was diluted with diethyl ether (200 mL) and the resulting solid collected by filtration, washed with water and diethyl ether, and dried under vacuum at 40° C. to afford the subtitled compound as a light brown solid. Yield 5.6 g.

$^1$H NMR (300 MHz, D$_6$-DMSO) δ 10.41 (s, 1H), 7.55 (m, 2H), 7.44 (d, J=9.4 Hz, 1H), 7.39 (m, 2H), 7.32 (m, 1H), 6.95 (d, J=9.4 Hz, 1H), 5.30 (s, 2H), 4.96 (s, 2H), 4.69 (s, 2H).

f) 8-(2-Azidoacetyl)-5-(benzyloxy)-2H-benzo[b][1,4]oxazin-3(4H)-one

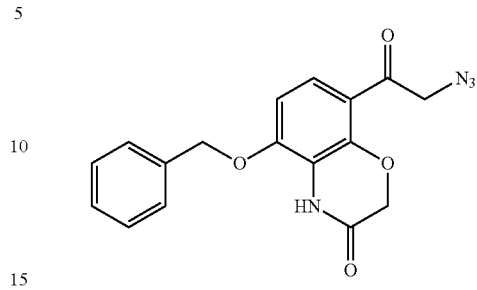

Sodium azide (1.176 g) was added to a suspension of 5-(benzyloxy)-8-(2-chloroacetyl)-2H-benzo[b][1,4]oxazin-3(4H)-one (example 11, step e) (4.8 g) in DMF (50 mL) and stirred for 2 h. The mixture was poured onto ice/water and the resulting solid collected by filtration, washed with water and dried under vacuum at 40° C. to afford the subtitled compound as a light brown solid. Yield 4.6 g.

$^1$H NMR (300 MHz, D$_6$-DMSO) δ 10.42 (s, 1H), 7.55 (m, 2H), 7.48 (m, 1H), 7.43-7.29 (m, 3H), 6.97 (m, 1H), 5.31 (s, 2H), 4.69 (s, 2H), 4.63 (s, 2H).

g) 8-(2-Azido-1-hydroxyethyl)-5-(benzyloxy)-2H-benzo[b][1,4]oxazin-3(4H)-one, Isomer 1

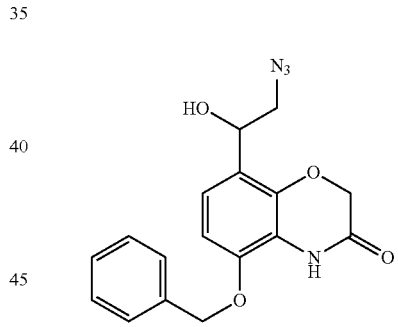

A suspension of 8-(2-azidoacetyl)-5-(benzyloxy)-2H-benzo[b][1,4]oxazin-3(4H)-one (example 11, step f) (2 g) in ethanol (80 mL) was treated with sodium borohydride (0.224 g) and the resultant mixture stirred at 20° C. for 1.5 hours. The mixture was partitioned between ethyl acetate and brine, the organic layer was dried over sodium sulphate, filtered and the solvent evaporated under reduced pressure. The crude solid was triturated with acetone (20 mL) to afford 1.6 g of racemic product.

Separation of Racemic Mixture:

Racemic 8-(2-azido-1-hydroxyethyl)-5-(benzyloxy)-2H-benzo[b][1,4]oxazin-3(4H)-one (2.5 g) was dissolved in methanol at a concentration of 10 mg/mL and separated by chiral HPLC using a Chiralpak®AS (250×50 mm ID, 20 μm particle size) column eluted with ethanol. Fractions containing the first eluting isomer were combined and concentrated in vacuo to afford the subtitled compound. Yield 0.67 g.

m/z 339 (M–H)$^-$ (APCI)

h) 8-(2-Amino-1-hydroxyethyl)-5-hydroxy-2H-benzo[b][1,4]oxazin-3(4H)-one acetate, Isomer 1

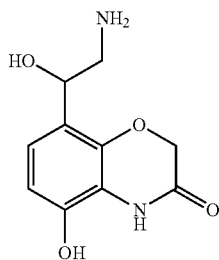

A mixture of 8-(2-azido-1-hydroxyethyl)-5-(benzyloxy)-2H-benzo[b][1,4]oxazin-3(4H)-one, Isomer 1 (example 11, step g) (0.67 g) in ethanol (30 mL) with 10% palladium on carbon catalyst (0.210 g) was stirred vigorously under 4 bar pressure of hydrogen for 18 hours. The catalyst was filtered off and the solvent evaporated off under reduced pressure. The residue was dissolved in acetic acid (15 mL) and ethanol (15 mL) and the mixture stirred with 10% palladium on carbon catalyst (0.210 g) under 4 bar pressure of hydrogen for 18 hours. The mixture was filtered and fresh 10% palladium on carbon catalyst (0.210 g) was added and stirring under 4 bar pressure of hydrogen was continued for 18 hours. The mixture was filtered and fresh 10% palladium on carbon catalyst (0.210 g) added and stirring under 4 bar pressure of hydrogen was continued for 18 hours. The mixture was filtered and the solvent removed under reduced pressure. The residue was triturated with acetonitrile (30 mL) to afford the subtitled compound. Yield 0.33 g.

$^1$H NMR (400 MHz, D$_6$-DMSO) δ 6.85 (d, 1H), 6.50 (d, 1H), 4.74-4.69 (m, 1H), 4.52-4.42 (m, 2H), 2.74-2.50 (m, 2H), 1.83 (s, 3H). Six exchangeable protons not observed.

i) 5-Hydroxy-8-(1-hydroxy-2-(3-((4-(2-methylthiazole-4-carbonyl)-1-oxa-4,9-diazaspiro[5.5]undecan-9-yl)methyl)phenethylamino)ethyl)-2H-benzo[b][1,4]oxazin-3(4H)-one ditrifluoroacetate, Isomer 1

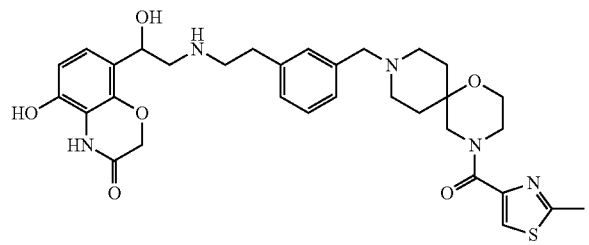 [SMILES: Cc1nc(C(=O)N2CCOC3(CCN(Cc4cccc(CCNCC(O)c5ccc(O)c6c5OCC(=O)N6)c4)CC3)C2)cs1]

A solution of (9-(3-(2-hydroxyethyl)benzyl)-1-oxa-4,9-diazaspiro[5.5]undecan-4-yl)(2-methylthiazol-4-yl)methanone (example 6, step b) (0.198 g) in DCM (7 mL) was cooled in an ice bath and treated with trifluoroacetic acid (0.037 mL) followed by Dess-Martin periodinane (303 mg). The mixture was stirred at 20° C. for 30 minutes. Further Dess-Martin periodinane (303 mg) was added and stirring continued for a further 30 minutes. The mixture was treated with saturated sodium thiosulphate solution (7 mL) and saturated sodium bicarbonate solution (7 mL) and the whole stirred vigorously for minutes. The mixture was extracted twice with ethyl acetate, the combined organics were washed with saturated sodium bicarbonate solution, dried over sodium sulphate, filtered and the solvent evaporated under reduced pressure. The residue was dissolved in methanol (2 mL) and added dropwise to a solution of 8-(2-amino-1-hydroxyethyl)-5-hydroxy-2H-benzo[b][1,4]oxazin-3(4H)-one acetate, Isomer 1 (example 11, step h) (110 mg) in methanol (5 mL) which had been cooled to 0° C. and treated with acetic acid (0.022 mL) followed by HCl (1M in ether, 0.387 mL) and then sodium cyanoborohydride (37 mg). The reaction mixture was stirred at 20° C. for 2 hours. The mixture was evaporated down to a volume of 3 mL and partitioned between ethyl acetate (30 mL) and aqueous phosphate buffer (pH=7.2) (50 mL). The aqueous layer was acidified by addition of acetic acid and passed through a 10 g SCX cartridge. The column was washed with water and then flushed with 7N ammonia in methanol to elute the product. The solvent was evaporated under reduced pressure. The crude product was dissolved in methanol, treated with acetic acid (0.5 mL) and the solvents removed under reduced pressure. The residue was purified by preparative HPLC (Sunfire™, Gradient: 5-35% acetonitrile in 0.2% aqueous TFA). The fractions containing the desired compound were evaporated to dryness to afford the titled compound. Yield 0.059 g.

m/z 622 (M+H)$^+$ (APCI)

$^1$H NMR (400 MHz, D$_6$-DMSO, 90° C.) δ 9.46 (s, 1H), 7.90 (s, 1H), 7.46-7.30 (m, 4H), 6.93-6.89 (m, 1H), 6.58-6.55 (m, 1H), 5.13-5.05 (m, 1H), 4.52 (s, 2H), 4.28 (s, 2H), 3.70 (s, 4H), 3.63 (s, 2H), 3.29-2.98 (m, 10H), 2.68 (s, 3H), 2.09-1.95 (m, 2H), 1.85-1.70 (m, 2H). Five exchangeable protons not observed.

EXAMPLE 12

(R)-5-(2-(3-((4-(5-Ethylthiophene-2-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

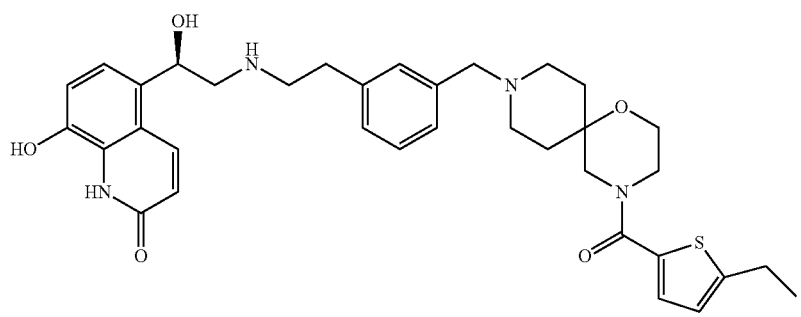 [SMILES: CCc1ccc(C(=O)N2CCOC3(CCN(Cc4cccc(CCNC[C@H](O)c5ccc(O)c6[nH]c(=O)ccc56)c4)CC3)C2)s1]

a) tert-Butyl 3-oxo-1-oxa-4,9-diazaspiro[5.5]undecane-9-carboxylate

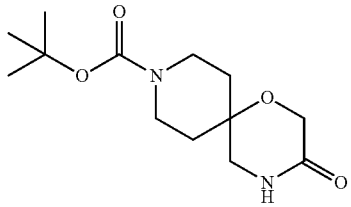 [SMILES: CC(C)(C)OC(=O)N1CCC2(CC1)CNC(=O)CO2]

Chloroacetyl chloride (4.88 mL) was added dropwise to a vigorously stirred mixture at 0° C. of potassium carbonate (17.43 g) in water (78 mL) and tert-butyl 4-(aminomethyl)-4-hydroxypiperidine-1-carboxylate (10.4 g) in ethyl acetate (92 mL). After 30 minutes at 0° C. the mixture was extracted with ethyl acetate and the organic layer dried over sodium sulfate, filtered and the solvent evaporated under reduced pressure. The residue was dissolved in THF (200 mL) and added dropwise over 3 hours to a stirred solution under nitrogen and heated at reflux of potassium tert-butoxide (1M in tert-butanol, 75 mL) and THF (250 mL). The mixture was cooled to room temperature and allowed to stir for 18 hours. Most of the solvent was removed under reduced pressure and the residue partitioned between ethyl acetate and brine, the aqueous layer was re-extracted with ethyl acetate and the combined organics were dried over sodium sulfate, filtered and the solvent removed under reduced pressure. The residue was purified by trituration with a mixture of ether (30 mL) and isohexane (20 mL) to afford the subtitled product. Yield 8.20 g.

$^1$H NMR (400 MHz, D$_6$-DMSO) δ 7.95 (s, 1H), 3.97 (s, 2H), 3.72-3.62 (m, 2H), 3.10 (d, 2H), 3.05-2.93 (m, 2H), 1.77-1.69 (m, 2H), 1.53-1.43 (m, 2H), 1.40 (s, 9H).

b) tert-Butyl 1-oxa-4,9-diazaspiro[5.5]undecane-9-carboxylate

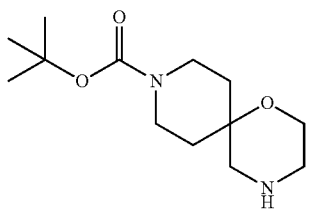 [SMILES: CC(C)(C)OC(=O)N1CCC2(CC1)CNCCO2]

A solution of tert-butyl 3-oxo-1-oxa-4,9-diazaspiro[5.5]undecane-9-carboxylate (example 12, step a) (8.2 g) in THF (100 mL) was treated dropwise with borane THF complex (1M in THF, 91 mL) and the resultant mixture heated at 55° C. for 2 hours. Borane dimethylsulfide complex (2M in THF, 15.17 mL) was added and the resultant mixture heated at 55° C. for 2 hours. The mixture was cooled to room temperature and quenched with methanol, then the solvents were evaporated under reduced pressure. The residue was dissolved in methanol (250 mL) and the solution treated with N1,N2-dimethylethane-1,2-diamine (10 g) and the resultant mixture was heated at reflux for 6 hours. Further N1,N2-dimethylethane-1,2-diamine (3 g) was added and heated at reflux continued for 6 hours. The mixture was cooled to room temperature and the solvents evaporated under reduced pressure, the residue was purified by flash silica chromatography eluting with 1% triethylamine and 5% methanol in dichloromethane. Pure fractions were evaporated to dryness to afford the subtitled compound. Yield 7.40 g.

$^1$H NMR (400 MHz, CDCl$_3$) δ 3.72 (s, 2H), 3.68-3.64 (m, 2H), 3.14 (t, J=20 Hz, 2H), 2.87-2.81 (m, 2H), 2.68 (s, 2H), 1.97-1.88 (m, 2H), 1.46 (s, 9H), 1.44-1.36 (m, 2H). One exchangeable proton not observed.

c) tert-Butyl 4-(2,2,2-trifluoroacetyl)-1-oxa-4,9-diazaspiro[5.5]undecane-9-carboxylate

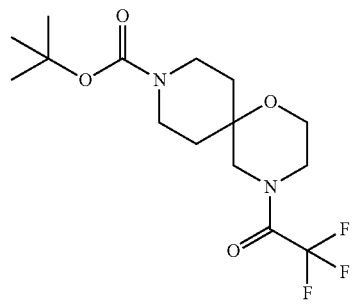 [SMILES: CC(C)(C)OC(=O)N1CCC2(CC1)CN(C(=O)C(F)(F)F)CCO2]

A solution of trifluoroacetic anhydride (0.496 mL) dissolved in DCM (3 mL) was added dropwise to a stirred solution of triethylamine (0.538 mL) and tert-butyl 1-oxa-4,9-diazaspiro[5.5]undecane-9-carboxylate (example 12, step b) (0.9 g) in DCM (20 mL) at 0° C., over a period of 5 minutes under nitrogen. The resulting solution was stirred at 0° C. for 30 minutes. Water (20 mL) was added and the mixture stirred vigorously stirred for 10 minutes. The organic layer was separated, dried over sodium sulfate, filtered and the solvent evaporated under reduced pressure. The crude product was purified by flash silica chromatography eluting with 40% ethyl acetate in isohexane. Pure fractions were evaporated to dryness to afford the subtitled compound. Yield 1 g. Used directly without purification.

d) 2,2,2-Trifluoro-1-(1-oxa-4,9-diazaspiro[5.5]undecan-4-yl)ethanone trifluoroacetate

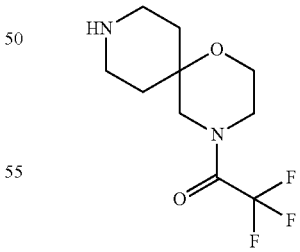

Trifluoroacetic acid (15 mL) was added to a stirred solution of tert-butyl 4-(2,2,2-trifluoroacetyl)-1-oxa-4,9-diazaspiro[5.5]undecane-9-carboxylate (example 12, step c) (1 g) in DCM (15 mL) at 20° C. The resulting solution was stirred at 20° C. for 10 minutes. Toluene (50 mL) was added and the solvents were evaporated under reduced pressure to afford the subtitled compound. Yield 1.4 g.

m/z 253 (M+H)$^+$ (APCI)

e) 2,2,2-Trifluoro-1-(9-(3-(2-hydroxyethyl)benzyl)-1-oxa-4,9-diazaspiro[5.5]undecan-4-yl)ethanone

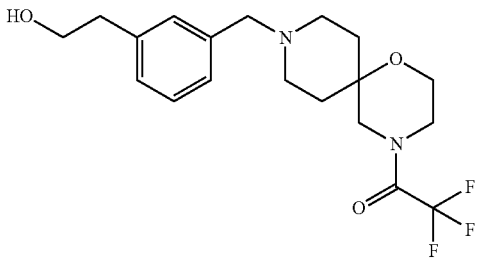 [SMILES: O=C(N1CCOC2(CCN(Cc3cccc(CCO)c3)CC2)C1)C(F)(F)F]

A solution of 2-(3-(bromomethyl)phenyl)ethanol (example 6, step a) (0.223 g) dissolved in acetonitrile (1 mL) was added dropwise to a stirred solution of triethylamine (0.318 mL) and 2,2,2-trifluoro-1-(1-oxa-4,9-diazaspiro[5.5]undecan-4-yl)ethanone trifluoroacetate (example 12, step d) (0.38 g) in acetonitrile (2 mL) at 20° C., over a period of 2 minutes. The resulting mixture was stirred at 20° C. for 3 hours. The solvent was evaporated off and residue partitioned between dichloromethane and water, the aqueous layer was re-extracted twice with DCM and the combined organics were dried over sodium sulfate, filtered and the solvent evaporated under reduced pressure. The crude product was purified by flash silica chromatography eluting with 6% methanol and 1% triethylamine in dichloromethane. Pure fractions were evaporated to dryness to afford the subtitled compound. Yield 0.260 g.

m/z 387 (M+H)⁺ (APCI)

f) (R)-5-(1-(tert-Butyldimethylsilyloxy)-2-(3-((4-(2,2,2-trifluoroacetyl)-1-oxa-4,9-diazaspiro[5.5]undecan-9-yl)methyl)phenethylamino)ethyl)-8-hydroxyquinolin-2(1H)-one

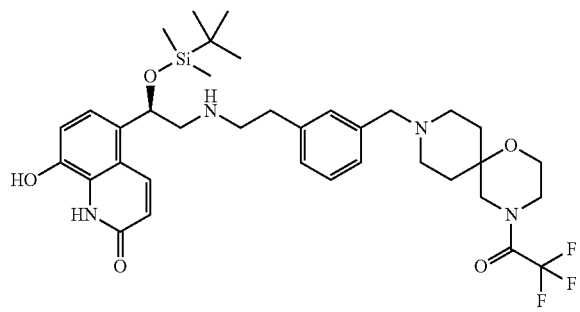 [SMILES: CC(C)(C)[Si](C)(C)O[C@@H](CNCCc1cccc(CN2CCC3(CC2)CN(C(=O)C(F)(F)F)CCO3)c1)c1ccc(O)c2[nH]c(=O)ccc12]

Trifluoroacetic acid (0.052 mL) was added to a solution of 2,2,2-trifluoro-1-(9-(3-(2-hydroxyethyl)benzyl)-1-oxa-4,9-diazaspiro[5.5]undecan-4-yl)ethanone (example 12, step e) (0.26 g) in dichloromethane (7.0 mL) at 20° C. The mixture was treated with Dess-Martin periodinane (0.428 g) and stirred for 30 minutes at 20° C. The mixture was treated with saturated sodium thiosulphate solution (7.0 mL) and saturated sodium bicarbonate solution (7.0 mL) and the mixture stirred vigorously for 10 minutes. The mixture was extracted twice with ethyl acetate, the combined organic phases were washed with saturated sodium bicarbonate solution, dried over sodium sulfate, filtered and the solvent evaporated under reduced pressure. The residue was dissolved in methanol (7.0 mL), and (R)-5-(2-amino-1-(tert-butyldimethylsilyloxy)ethyl)-8-hydroxyquinolin-2(1H)-one (WO2004106333) (0.225 g) and acetic acid (0.039 mL) were added to the mixture colled at 0° C. Sodium triacetoxyborohydride (0.214 g) was added and the resultant mixture was stirred at 20° C. for 90 minutes. Most of the methanol was evaporated off and the remainder partitioned between ethyl acetate and aqueous phosphate buffer (pH=7.2), the organic layer was dried over sodium sulfate, filtered and the solvent evaporated under reduced pressure. The crude product was purified by flash silica chromatography eluting with 1% concentrated aqueous ammonia and 10% methanol in dichloromethane. Pure fractions were evaporated to dryness to afford the subtitled compound. Yield 0.144 g.

m/z 703 (M+H)⁺ (APCI)

g) (R)-tert-Butyl 2-hydroxy-2-(8-hydroxy-2-oxo-1,2-dihydroquinolin-5-yl)ethyl(3-((4-(2,2,2-trifluoroacetyl)-1-oxa-4,9-diazaspiro[5.5]undecan-9-yl)methyl)phenethyl)carbamate

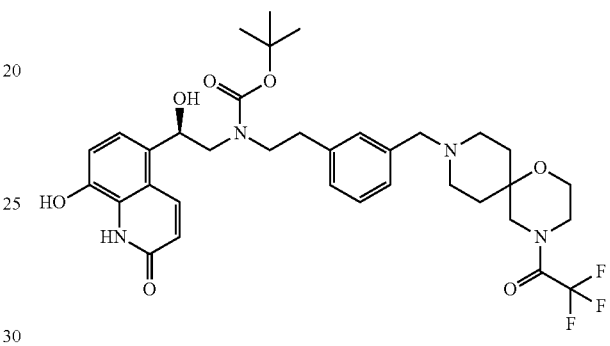

A solution of triethylamine trihydrofluoride (0.044 mL) dissolved in methanol (1 mL) was added to a stirred solution of (R)-5-(1-(tert-butyldimethylsilyloxy)-2-(3-((4-(2,2,2-trifluoroacetyl)-1-oxa-4,9-diazaspiro[5.5]undecan-9-yl)methyl)phenethylamino)ethyl)-8-hydroxyquinolin-2(1H)-one (example 12, step f) (0.140 g), in THF (4 mL) at 20° C. The resulting solution was stirred at 20° C. for 18 hours. The reaction mixture was treated with triethylamine (0.111 mL) followed by a solution of di-tert-butyl dicarbonate (0.048 mL) in methanol (1 mL). The mixture was stirred at 20° C. for 3 hours and the solvents then evaporated off under reduced pressure. The residue was purified by flash silica chromatography eluting with 1% "880" aqueous ammonia and 10% methanol in dichloromethane. Pure fractions were evaporated to dryness to afford the subtitled compound. Yield 0.100 g.

m/z 689 (M+H)⁺ (APCI)

h) (R)-tert-Butyl 3-(1-oxa-4,9-diazaspiro[5.5]undecan-9-ylmethyl)phenethyl(2-hydroxy-2-(8-hydroxy-2-oxo-1,2-dihydroquinolin-5-yl)ethyl)carbamate

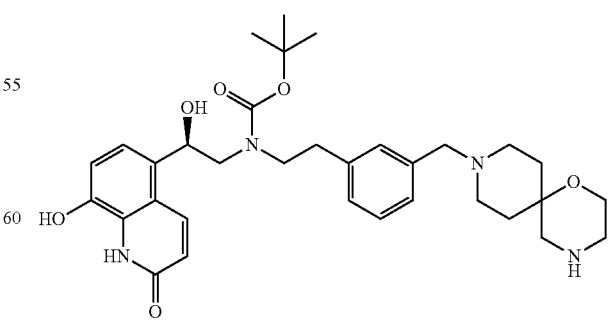

A solution of (R)-tert-butyl 2-hydroxy-2-(8-hydroxy-2-oxo-1,2-dihydroquinolin-5-yl)ethyl(3-((4-(2,2,2-trifluoroacetyl)-1-oxa-4,9-diazaspiro[5.5]undecan-9-yl)methyl) phenethyl)carbamate (example 12, step g) (0.100 g) in methanol (5.0 mL) was treated with a solution of potassium carbonate (0.035 g) in water (5.0 mL) and the resultant mixture stirred at 20° C. for 5 hours. The methanol was evaporated off under a stream of nitrogen and further water (5.0 mL) was added. The solution was acidified by addition of acetic acid and then passed through a 10 g cartridge of C18 silica. The cartridge was washed with water and then flushed with methanol to bring off the product. The solvent was evaporated off under reduced pressure to yield 0.090 g of the acetic acid salt. This solid was dissolved in methanol (2 mL) and passed through 0.700 g of VARIAN Bond Elut $NH_2$ resin and the solvent was evaporated off under reduced pressure to afford the subtitled compound. Yield 0.074 g.

m/z 593 (M+H)+ (APCI)

and the solution treated with trifluoroacetic acid (1 mL). The solution was allowed to stand at 20° C. for 10 minutes, toluene (20 mL) was added and the solvents were evaporated under reduced pressure, the residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.039 g.

m/z 631 (M+H)+ (APCI)

$^1$H NMR (400 MHz, $D_6$-DMSO, 90° C.) δ 8.18 (d, J=10.0 Hz, 1H), 7.46-7.33 (m, 4H), 7.23 (d, 1H), 7.14 (d, 1H), 7.00 (d, 1H), 6.84 (d, 1H), 6.55 (d, 1H), 5.39-5.33 (m, 1H), 4.29 (s, 2H), 3.74-3.63 (m, 4H), 3.54 (s, 2H), 3.29 (t, 2H), 3.21-3.00 (m, 8H), 2.83 (q, 2H), 2.10-1.96 (m, 2H), 1.84-1.69 (m, 2H), 1.26 (td, 3H). Six exchangeable protons not observed.

EXAMPLE 13

5-Hydroxy-8-(1-hydroxy-2-(3-((4-(2-methylthiazole-4-carbonyl)-1-oxa-4,9-diazaspiro[5.5]undecan-9-yl) methyl)phenethylamino)ethyl)-2H-benzo[b][1,4] oxazin-3(4H)-one ditrifluoroacetate, Isomer 2 i) (R)-5-(2-(3-((4-(5-Ethylthiophene-2-carbonyl)-1-oxa-4,9-diazaspiro[5.5]undecan-9-yl)methyl)phenethylamino)-1-hydroxyethyl)-8-hydroxyquinolin-2 (1H)-one ditrifluoroacetate

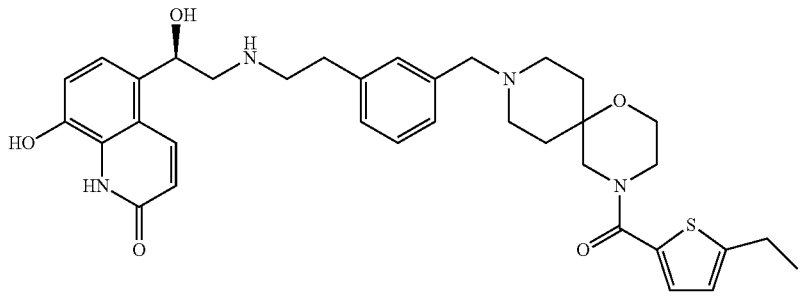 [SMILES: CCc1ccc(C(=O)N2CCOC3(CCN(Cc4cccc(CCNC[C@H](O)c5ccc(O)c6[nH]c(=O)ccc56)c4)CC3)C2)s1]

A solution of (R)-tert-butyl 3-(1-oxa-4,9-diazaspiro[5.5] undecan-9-ylmethyl)phenethyl(2-hydroxy-2-(8-hydroxy-2-oxo-1,2-dihydroquinolin-5-yl)ethyl)carbamate (example 12, step h) (0.068 g) in DMF (2.0 mL) was treated with triethylamine (0.048 mL) followed by 5-ethylthiophene-2-carboxylic acid (0.018 g) and then HATU (0.057 g). The mixture was stirred at 20° C. for 2 hours. "880" aqueous ammonia (4 drops) was added and stirring continued for 1 hour. The mixture was partitioned between ethyl acetate and brine, the organic layer was washed with brine, dried over sodium sulfate, filtered, and the solvent evaporated under reduced pressure. The residue was dissolved in dichloromethane (1 mL)

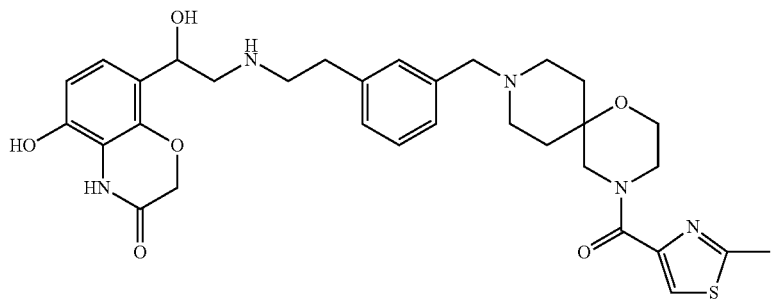 [SMILES: Cc1nc(C(=O)N2CCOC3(CCN(Cc4cccc(CCNCC(O)c5ccc(O)c6c5OCC(=O)N6)c4)CC3)C2)cs1]

a) 8-(2-Azido-1-hydroxyethyl)-5-(benzyloxy)-2H-benzo[b][1,4]oxazin-3(4H)-one, Isomer 2

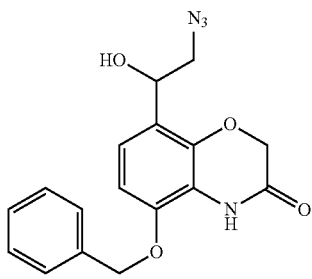 [SMILES: [N-]=[N+]=NCC(O)c1ccc(OCc2ccccc2)c2c1OCC(=O)N2]

Isomer 2 was obtained as the second eluting isomer from the chiral HPLC separation detailed in example 11, step g. Fractions containing the second eluting isomer were combined and concentrated in vacuo to afford the subtitled compound. Yield 0.72 g.

m/z 339 (M–H)⁻ (APCI)

b) (S)-8-(2-Amino-1-hydroxyethyl)-5-hydroxy-2H-benzo[b][1,4]oxazin-3(4H)-one acetate, Isomer 2

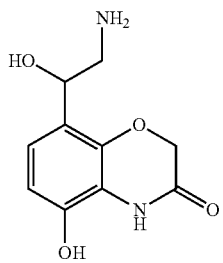

A solution of 8-(2-azido-1-hydroxyethyl)-5-(benzyloxy)-2H-benzo[b][1,4]oxazin-3(4H)-one, Isomer 2 (example 13, step a) (0.72 g) in a mixture of acetic acid (10 mL) and ethanol (10 mL) was stirred vigorously with 10% palladium on carbon catalyst (0.225 g) under 4 bar pressure of hydrogen for 18 hours. The mixture was filtered and fresh 10% palladium on carbon catalyst (0.225 g) added and stirring under 4 bar pressure of hydrogen was continued for 18 hours. The mixture was filtered and fresh 10% palladium on carbon catalyst (0.225 g) added and stirring under 4 bar pressure of hydrogen was continued for 18 hours. The mixture was filtered and the solvent removed under reduced pressure. The residue was triturated with acetonitrile (30 mL) to afford the subtitled compound. Yield 0.28 g.

m/z 222 (M–H)⁻ (APCI)

c) 5-Hydroxy-8-(1-hydroxy-2-(3-((4-(2-methylthiazole-4-carbonyl)-1-oxa-4,9-diazaspiro[5.5]undecan-9-yl)methyl)phenethylamino)ethyl)-2H-benzo[b][1,4]oxazin-3(4H)-one ditrifluoroacetate, Isomer 2

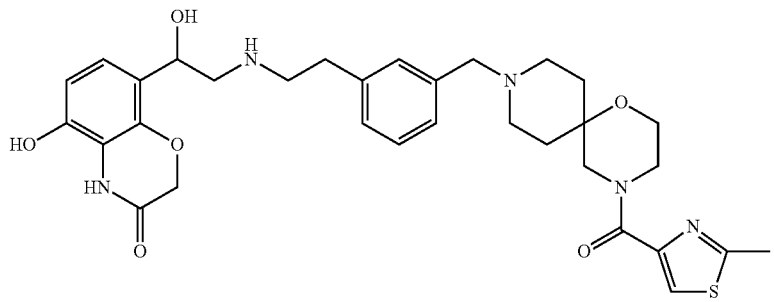 [SMILES: Cc1nc(C(=O)N2CCOC3(CCN(Cc4cccc(CCNCC(O)c5ccc(O)c6c5OCC(=O)N6)c4)CC3)C2)cs1]

A solution of (9-(3-(2-hydroxyethyl)benzyl)-1-oxa-4,9-diazaspiro[5.5]undecan-4-yl)(2-methylthiazol-4-yl)methanone (example 6, step b) (0.163 g) in DCM (7.0 mL) was cooled in an ice bath and treated with trifluoroacetic acid (0.030 mL) followed by Dess-Martin periodinane (0.246 g). The mixture was stirred at 20° C. for 30 minutes, treated with further Dess-Martin periodinane (0.246 g), and stirred for an additional 30 minutes at 20° C. The mixture was treated with saturated sodium thiosulphate solution (7.0 mL) and saturated sodium bicarbonate solution (7.0 mL) and stirred vigorously for 10 minutes. The mixture was extracted twice with ethyl acetate, the combined organics were washed with saturated sodium bicarbonate solution, dried over sodium sulfate, filtered and the solvent evaporated under reduced pressure. The residue was dissolved in methanol (2.0 mL) and added dropwise to a solution of 8-(2-amino-1-hydroxyethyl)-5-hydroxy-2H-benzo[b][1,4]oxazin-3(4H)-one acetate, Isomer 2 (example 13, step b) (0.090 g) in methanol (5.0 mL) which had been cooled to 0° C. and treated with acetic acid (0.018 mL) followed by HCl (1M in ether, 0.32 mL) and then sodium cyanoborohydride (0.030 g). The mixture was stirred at 20° C. for 2 hours. The mixture was evaporated down to a volume of 3 mL and partitioned between ethyl acetate (30 mL) and aqueous phosphate buffer (pH=7.2) (50 mL). The aqueous layer was acidified by addition of acetic acid and passed through a 10 g SCX cartridge. The column was washed with water and then flushed with 7N ammonia in methanol to elute the product. The solvent was evaporated under reduced pressure. The crude product was dissolved in methanol, treated with acetic acid (0.5 mL) and the solvents removed under reduced pressure. The residue was purified by preparative HPLC (Sunfire™, Gradient: 5-35% acetonitrile in 0.2% aqueous TFA). The fractions containing the desired product were evaporated to dryness to afford the titled compound. Yield 0.053 g.

m/z 622 (M+H)⁺ (APCI)

$^1$H NMR (400 MHz, D$_6$-DMSO, 90° C.) δ 9.45 (s, 1H), 7.90 (d, J=4.6 Hz, 1H), 7.45-7.31 (m, 4H), 6.95-6.88 (m, 1H), 6.60-6.54 (m, 1H), 5.14-5.07 (m, 1H), 4.54 (s, 2H), 4.30 (s, 2H), 3.70 (s, 4H), 3.64 (s, 2H), 3.28-2.98 (m, 10H), 2.68 (s, 3H), 2.08-1.97 (m, 2H), 1.88-1.71 (m, 2H). Five exchangeable protons not observed.

EXAMPLE 14

(R)-8-Hydroxy-5-(1-hydroxy-2-(2-(5-((4-(2-methylthiazole-4-carbonyl)-1-oxa-4,9-diazaspiro[5.5]undecan-9-yl)methyl)thiophen-2-yl)ethylamino)ethyl)quinolin-2(1H)-one ditrifluoroacetate

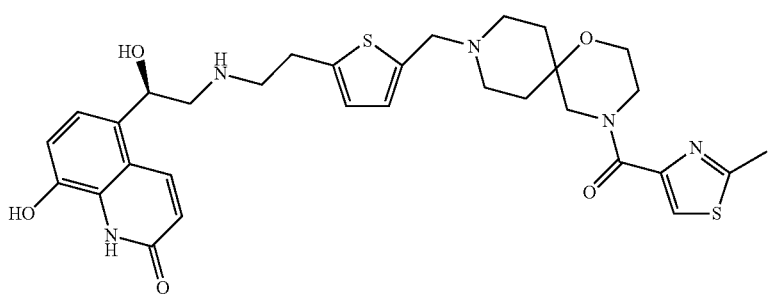 [SMILES: Cc1nc(C(=O)N2CCOC3(CCN(Cc4ccc(CCNC[C@H](O)c5ccc(O)c6[nH]c(=O)ccc56)s4)CC3)C2)cs1]

a) 5-(2-(tert-Butyldimethylsilyloxy)ethyl)thiophene-2-carbaldehyde

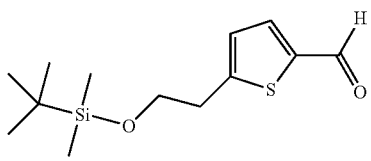 [SMILES: CC(C)(C)[Si](C)(C)OCCc1ccc(C=O)s1]

tert-Butyldimethylsilylchloride (2.82 g) was added portionwise to a stirred solution of 2-(thiophen-2-yl)ethanol (2 g) and imidazole (1.275 g) in DMF (20 mL) at 20° C. over a period of 20 minutes. The mixture was stirred at 20° C. for 18 hours and then partitioned between ethyl acetate and water, the organic layer was washed with water, dried over sodium sulphate, filtered and the solvent evaporated under reduced pressure. The residue was purified by flash silica chromatography, elution gradient 1-4% ethyl acetate in isohexane. The residue (2.7 g) was dissolved in THF (50 mL) and the solution cooled to −78° C., n-butyllithium (2.5M in hexanes, 5.06 mL) was added dropwise over 10 minutes and the resultant mixture stirred at 0° C. for 1 hour. The reaction mixture was cooled to −78° C. and DMF (5.7 mL) was added dropwise over 5 minutes. The mixture was stirred at 20° C. for 3 hours. The reaction mixture was partitioned between water and ethyl acetate, the organic layer was washed with water, dried over sodium sulphate and the solvent removed under reduced pressure. The crude product was purified by flash silica chromatography, eluting with 7% ethyl acetate in isohexane. Pure fractions were evaporated to dryness to afford the subtitled compound. Yield 2.3 g.

$^1$H NMR (400 MHz, CDCl$_3$) δ 9.83 (s, 1H), 7.61 (d, 1H), 6.96 (d, 1H), 3.86 (t, 2H), 3.07 (t, 2H), 0.88 (s, 9H), 0.02 (s, 6H).

b) (9-((5-(2-(tert-Butyldimethylsilyloxy)ethyl)thiophen-2-yl)methyl)-1-oxa-4,9-diazaspiro[5.5]undecan-4-yl)(2-methylthiazol-4-yl)methanone

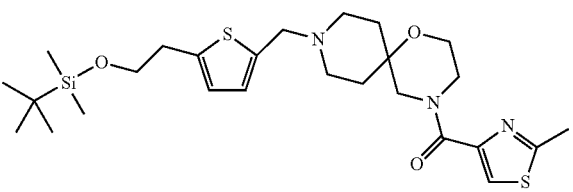 [SMILES: Cc1nc(C(=O)N2CCOC3(CCN(Cc4ccc(CCO[Si](C)(C)C(C)(C)C)s4)CC3)C2)cs1]

A solution of (2-methylthiazol-4-yl)(1-oxa-4,9-diazaspiro[5.5]undecan-4-yl)methanone trifluoroacetate (example 4, step h) (0.25 g) and 5-(2-(tert-butyldimethylsilyloxy)ethyl)thiophene-2-carbaldehyde (example 14, step a) (0.171 g) in NMP (5 mL) with acetic acid (0.036 mL) was treated with sodium triacetoxyborohydride (0.201 g) and the resultant mixture stirred at 20° C. for 18 hours. The mixture was partitioned between ethyl acetate and saturated sodium bicarbonate solution, the organic layer was washed with brine, dried over sodium sulphate, filtered and the solvent evaporated under reduced pressure to afford the subtitled compound. Yield 0.3 g.

m/z 536 (M+H)$^+$ (APCI)

c) (9-((5-(2-Hydroxyethyl)thiophen-2-yl)methyl)-1-oxa-4,9-diazaspiro[5.5]undecan-4-yl)(2-methylthiazol-4-yl)methanone

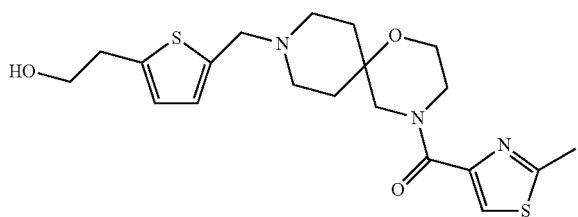 [SMILES: Cc1nc(C(=O)N2CCOC3(CCN(Cc4ccc(CCO)s4)CC3)C2)cs1]

A solution of (9-((5-(2-(tert-butyldimethylsilyloxy)ethyl)thiophen-2-yl)methyl)-1-oxa-4,9-diazaspiro[5.5]undecan-4-yl)(2-methylthiazol-4-yl)methanone (example 14, step b) (0.3 g) in THF (5 mL) was treated dropwise with a solution of tetrabutylammonium fluoride (1M in THF, 0.672 mL). The mixture was allowed to stand at 20° C. for 30 minutes. The solvents were evaporated using a stream of nitrogen and the residue was purified by flash silica chromatography, elution gradient 1% triethylamine and 2.5% methanol in dichloromethane. Pure fractions were evaporated to dryness to afford the subtitled compound. Yield 0.187 g.

m/z 422 (M+H)$^+$ (APCI)

A solution of (9-((5-(2-hydroxyethyl)thiophen-2-yl)methyl)-1-oxa-4,9-diazaspiro[5.5]undecan-4-yl)(2-methylthiazol-4-yl)methanone (example 14, step c) (0.18 g) in dichloromethane (10 mL) at 20° C. was treated with trifluoroacetic acid (0.033 mL) followed by Dess-Martin periodinane (0.254 g) and the mixture stirred at 20° C. for 90 minutes. The mixture was then treated with saturated sodium thiosulphate solution (10 mL) and saturated sodium bicarbonate solution (10 mL) and stirred vigorously for 10 minutes. The mixture was extracted twice with ethyl acetate, the combined organics were washed with saturated sodium bicarbonate solution, dried over sodium sulphate, filtered and the solvent evaporated under reduced pressure. The residue was dissolved in methanol (2 mL) and added to a solution of (R)-5-(2-amino-1-(tert-butyldimethylsilyloxy)ethyl)-8-hydroxyquinolin-2(1H)-one (WO2004106333) (0.143 g) and acetic acid (0.024 mL) in methanol (7 mL). The mixture was cooled in an ice bath and sodium triacetoxyborohydride (0.136 g) was added. The ice bath was removed and the mixture stirred at room temperature for 1 hour. Most of the methanol was evaporated off and the residue partitioned between ethyl acetate and saturated sodium bicarbonate solution, the organic layer was dried over sodium sulphate, filtered and the solvent evaporated under reduced pressure. The crude product was purified by flash silica chromatography eluting with 9% methanol and 1% '880' aqueous ammonia in dichloromethane. Pure fractions were evaporated to dryness to afford the subtitled compound. Yield 0.078 g.

m/z 738 (M+H)$^+$ (APCI)

d) (R)-5-(1-(tert-Butyldimethylsilyloxy)-2-(2-(5-((4-(2-methylthiazole-4-carbonyl)-1-oxa-4,9-diazaspiro[5.5]undecan-9-yl)methyl)thiophen-2-yl)ethylamino)ethyl)-8-hydroxyquinolin-2(1H)-one

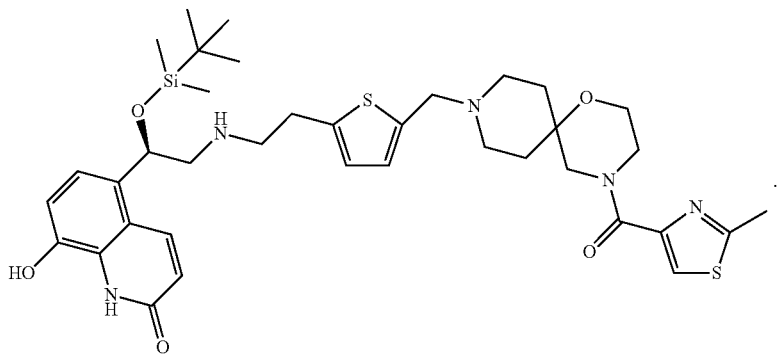 [SMILES: Cc1nc(C(=O)N2CCOC3(CCN(Cc4ccc(CCNC[C@H](O[Si](C)(C)C(C)(C)C)c5ccc(O)c6[nH]c(=O)ccc56)s4)CC3)C2)cs1]

e) (R)-8-Hydroxy-5-(1-hydroxy-2-(2-(5-((4-(2-methylthiazole-4-carbonyl)-1-oxa-4,9-diazaspiro[5.5]undecan-9-yl)methyl)thiophen-2-yl)ethylamino)ethyl)quinolin-2(1H)-one ditrifluoroacetate

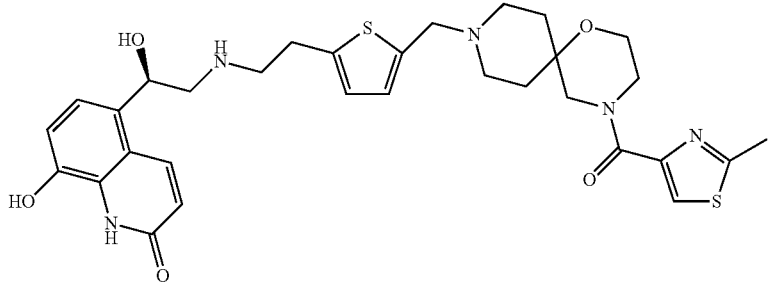 [SMILES: Cc1nc(C(=O)N2CCOC3(CCN(Cc4ccc(CCNC[C@H](O)c5ccc(O)c6[nH]c(=O)ccc56)s4)CC3)C2)cs1]

A solution of (R)-5-(1-(tert-butyldimethylsilyloxy)-2-(2-(5-((4-(2-methylthiazole-4-carbonyl)-1-oxa-4,9-diazaspiro[5.5]undecan-9-yl)methyl)thiophen-2-yl)ethylamino)ethyl)-8-hydroxyquinolin-2(1H)-one (example 14, step d) (0.078 g) in a mixture of THF (4 mL) and methanol (1 mL) was treated with triethylamine trihydrofluoride (0.022 mL) and the mixture allowed to stand at 20° C. for 18 hours. The solvents were evaporated under reduced pressure and the residue azeotroped with toluene. The crude product was purified by preparative HPLC (Sunfire™, Gradient: 10-30% acetonitrile in 0.2% aqueous TFA). The fractions containing the desired product were evaporated to dryness to afford the titled compound. Yield 0.021 g.

m/z 624 (M+H)⁺ (APCI)

¹H NMR (400 MHz, D₆-DMSO) δ 10.50 (s, 2H), 10.15-9.84 (m, 1H), 8.91 (s, 1H), 8.80 (s, 1H), 8.16 (d, J=10.0 Hz, 1H), 8.00 (s, 1H), 7.26-7.12 (m, 2H), 7.02-6.94 (m, 2H), 6.58 (d, J=9.7 Hz, 1H), 6.21 (s, 1H), 5.36-5.31 (m, 1H), 4.53 (s, 2H), 3.83-3.48 (m, 6H), 3.33-2.93 (m, 10H), 2.68 (s, 3H), 2.16-2.04 (m, 2H), 1.79-1.59 (m, 2H).

EXAMPLE 15

(R)-4-Hydroxy-7-(1-hydroxy-2-(3-((4-(5-methylthiophene-2-carbonyl)-1-oxa-4,9-diazaspiro[5.5]undecan-9-yl)methyl)phenethylamino)ethyl)benzo[d]thiazol-2(3H)-one trifluoroacetate

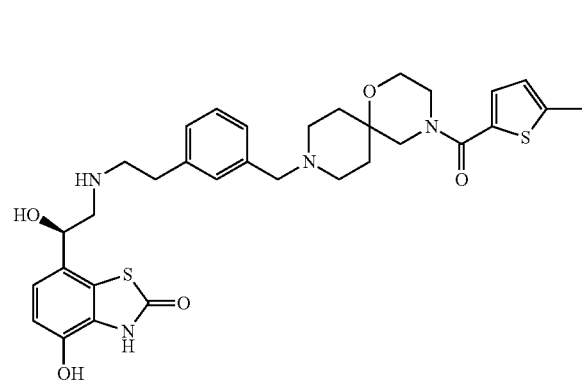 [SMILES: Cc1ccc(C(=O)N2CCOC3(CCN(Cc4cccc(CCNC[C@H](O)c5ccc(O)c6[nH]c(=O)sc56)c4)CC3)C2)s1]

Hydrogen chloride (2M in diethyl ether, 0.504 mL) was added to a stirred solution of (R)-7-(2-amino-1-hydroxyethyl)-4-hydroxybenzo[d]thiazol-2(3H)-one acetate (example 1, step d) (0.222 g) and 2-(3-((4-(5-methylthiophene-2-carbonyl)-1-oxa-4,9-diazaspiro[5.5]undecan-9-yl)methyl)phenyl)acetaldehyde (example 9, step d) (0.320 g) in methanol (10 mL). After 5 min, sodium cyanoborohydride (0.100 g) was added and the reaction mixture stirred overnight. The solution was concentrated to 3 mL and partitioned between pH 7.2 buffer (80 mL) and ethyl acetate. Saturated sodium bicarbonate solution was added to the aqueous layer which was then extracted with ethyl acetate. The ethyl acetate solutions were combined, dried over sodium sulphate, filtered and evaporated to dryness. Purification was by preparative HPLC (Sunfire™, Gradient: 25-65% acetonitrile in 0.2% aqueous TFA). The fractions containing the product were combined and evaporated to dryness in vacuo. Acetonitrile was added, the solution was evaporated in vacuo, and this process was repeated. Diethyl ether was added and the gum triturated to give the titled compound as a solid. Yield 0.017 g.

m/z 623 (M+H)⁺ (APCI)

¹H NMR (400 MHz, D₆-DMSO) δ 11.67 (s, 1H), 10.25 (s, 1H), 9.73-9.63 (m, 1H), 8.99-8.89 (m, 1H), 8.85-8.76 (m, 1H), 7.46-7.32 (m, 3H), 7.30-7.20 (m, 1H), 6.93 (d, J=8.3 Hz, 1H), 6.86-6.81 (m, 1H), 6.77 (d, J=8.3 Hz, 1H), 6.53-6.45 (m, 1H), 4.93-4.86 (m, 1H), 4.45-4.39 (m, 0.4H), 4.35-4.28 (m, 1.6H), 3.74-3.60 (m, 4H), 3.49 (s, 2H), 3.27-3.14 (m, 4H), 3.13-2.89 (m, 6H), 2.46 (s, 3H), 2.12-2.03 (m, 2H), 1.70-1.59 (m, 2H). One exchangeable proton not observed.

EXAMPLE 16

(R)-4-Hydroxy-7-(1-hydroxy-2-(4-((4-(2-methylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

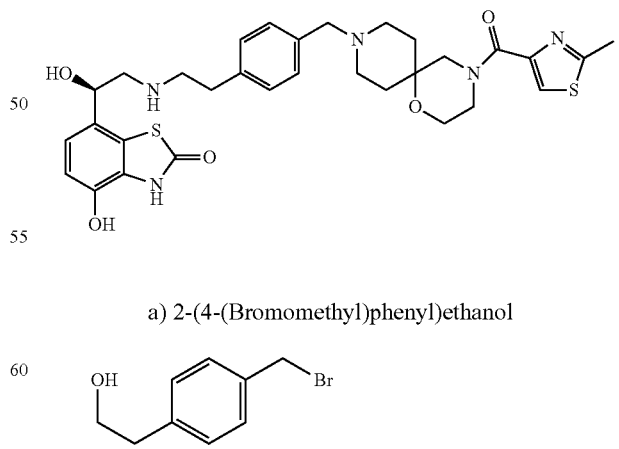

a) 2-(4-(Bromomethyl)phenyl)ethanol

Borane dimethylsulphide complex (2M in THF, 4.37 mL) was added dropwise to a solution of 2-(4-(bromomethyl)phenyl)acetic acid (1.0 g) in THF (20 mL) at 20° C. and the mixture stirred for 1 hour. Methanol was added dropwise until bubbling ceased and the solvent evaporated in vacuo. Purification was by silica gel chromatography eluting with 30% ethyl acetate in isohexane. The fractions containing product were combined and evaporated in vacuo to give the subtitled compound as a white crystalline solid. Yield 0.86 g.

¹H NMR (400 MHz, D₆-DMSO) δ 7.36-7.32 (m, 2H), 7.20 (d, J=8.2 Hz, 2H), 4.68 (s, 2H), 4.64 (t, J=5.1 Hz, 1H), 3.64-3.55 (m, 2H), 2.75-2.67 (m, 2H).

b) (9-(4-(2-Hydroxyethyl)benzyl)-1-oxa-4,9-diazaspiro[5.5]undecan-4-yl)(2-methylthiazol-4-yl)methanone

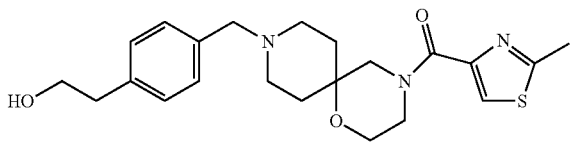 [SMILES: Cc1nc(C(=O)N2CCOC3(CCN(Cc4ccc(CCO)cc4)CC3)C2)cs1]

To a solution of (2-methylthiazol-4-yl)(1-oxa-4,9-diazaspiro[5.5]undecan-4-yl)methanone trifluoroacetate (example 4, step h) (0.791 g) and triethylamine (0.697 mL) in acetonitrile (10 mL) was added 2-(4-(bromomethyl)phenyl)ethanol (example 16, step a) and the resulting mixture stirred overnight. The solvent was evaporated in vacuo. The residue was partitioned between ethyl acetate (25 mL) and saturated sodium bicarbonate solution (25 mL). The aqueous phase was separated and extracted with ethyl acetate (2×25 mL). The combined organic solutions were washed with brine (25 mL), dried over sodium sulphate, filtered and evaporated in vacuo to give the subtitled compound as a yellow oil. Yield 0.76 g.

m/z 416 (M+H)⁺ (APCI)

c) 2-(4-((4-(2-Methylthiazole-4-carbonyl)-1-oxa-4,9-diazaspiro[5.5]undecan-9-yl)methyl)phenyl)acetaldehyde

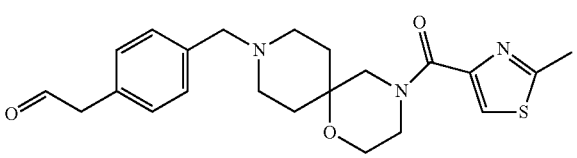 [SMILES: Cc1nc(C(=O)N2CCOC3(CCN(Cc4ccc(CC=O)cc4)CC3)C2)cs1]

TFA (0.030 mL) was added to a solution of (9-(4-(2-hydroxyethyl)benzyl)-1-oxa-4,9-diazaspiro[5.5]undecan-4-yl)(2-methylthiazol-4-yl)methanone (example 16, step b) (0.16 g) in DCM (5 mL) at 0° C. and the resulting mixture stirred for 5 min. Dess-Martin periodinane (0.245 g) was added and the mixture allowed to warm to room temperature and stirred for 45 min. A mixture of saturated sodium thiosulphate solution (5 mL), saturated sodium bicabonate solution (5 mL) and ethyl acetate (20 mL) was then added and the resulting mixture stirred for 10 min. The aqueous phase was separated and extracted with ethyl acetate (20 mL). The combined organic solutions were washed with brine. AcOH (0.1 mL) was then added and the mixture dried over sodium sulphate, filtered and evaporated in vacuo to give the subtitled compound as a clear oil which was used immediately. Yield 0.16 g.

d) (R)-4-Hydroxy-7-(1-hydroxy-2-(4-((4-(2-methylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

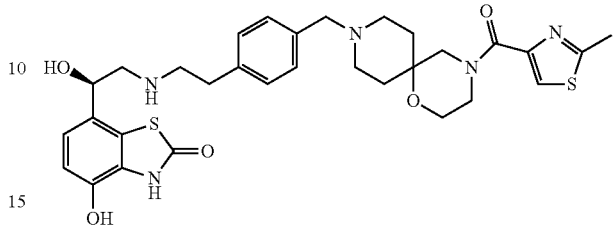

A solution of 2-(4-((4-(2-methylthiazole-4-carbonyl)-1-oxa-4,9-diazaspiro[5.5]undecan-9-yl)methyl)phenyl)acetaldehyde (example 16, step c) (0.08 g) in methanol (2 mL) was added to a mixture of (R)-7-(2-amino-1-hydroxyethyl)-4-hydroxybenzo[d]thiazol-2(3H)-one hydrochloride (WO2007027134, example 1, step d) (0.076 g) and acetic acid (0.017 mL) in methanol (0.5 mL). The resulting mixture was stirred for 5 min then cooled to 0° C. Sodium cyanoborohydride (0.012 g) was then added and the mixture allowed to warm to room temperature and stirred for 2 hours. The reaction mixture was applied to C18 cartridge (Varian 10 g). The cartridge was washed with water (50 mL) and eluted with methanol (50 mL). Purification was by preparative HPLC (Sunfire™, Gradient: 5-50% acetonitrile in 0.2% aqueous TFA). The fractions containing product were combined, evaporated in vacuo and the residue triturated with ether to give the titled compound as a white solid. Yield 0.66 g.

m/z 624 (M+H)⁺ (APCI)

¹H NMR (300 MHz, D₆-DMSO, 90° C.) δ 11.28 (s, 1H), 7.90 (s, 1H), 7.48 (d, J=7.1 Hz, 2H), 7.34 (d, J=7.3 Hz, 2H), 6.94 (d, J=8.1 Hz, 1H), 6.78 (d, J=8.1 Hz, 1H), 4.99-4.88 (m, 1H), 4.31 (s, 2H), 3.76-3.55 (m, 6H), 3.32-2.91 (m, 10H), 2.67 (s, 3H), 2.10-1.67 (m, 4H). Five exchangeable protons not observed.

EXAMPLE 17

(R)-8-Hydroxy-5-(1-hydroxy-2-(4-((4-(2-methylthiazole-4-carbonyl)-1-oxa-4,9-diazaspiro[5.5]undecan-9-yl)methyl)phenethylamino)ethyl)quinolin-2(1H)-one ditrifluoroacetate

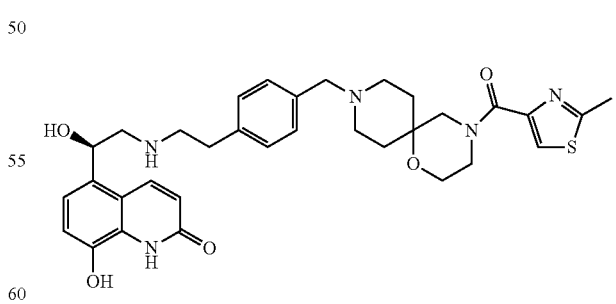

A solution of 2-(4-((4-(2-methylthiazole-4-carbonyl)-1-oxa-4,9-diazaspiro[5.5]undecan-9-yl)methyl)phenyl)acetaldehyde (example 16, step c) (0.08 g) in methanol (2 mL) was added to a mixture of (R)-5-(2-amino-1-(tert-butyldimethylsilyloxy)ethyl)-8-hydroxyquinolin-2(1H)-one (WO02004106333) (0.097 g) and acetic acid (0.017 mL) in methanol (0.5 mL). The resulting mixture was stirred for 5 min then cooled to 0° C. Sodium cyanoborohydride (0.018 g) was then added and the mixture allowed to warm to room temperature and stirred for 2 hours. The reaction mixture was applied to C18 cartridge (Varian 10 g). The cartridge was washed with water (50 mL) and eluted with methanol (50 mL). The fractions were combined, evaporated and purified by silica gel chromatography eluting with 95:5:0.5 to 89:10:1 DCM:methanol:'880' ammonia solution. The residue was dissolved in THF (2 mL), triethylamine trihydrofluoride (0.047 mL) was added and the mixture stirred overnight. Purification was by preparative HPLC (Sunfire™, Gradient: 5-50% acetonitrile in 0.2% aqueous TFA). The fractions containing product were combined, evaporated in vacuo and the residue triturated with ether to give the titled compounds as a white solid. Yield 0.07 g.

m/z 618 (M+H)$^+$ (APCI)

$^1$H NMR (400 MHz, D$_6$-DMSO, 90° C.) δ 8.18 (d, J=9.7 Hz, 1H), 7.90 (s, 1H), 7.48 (d, J=7.7 Hz, 2H), 7.34 (d, J=7.9 Hz, 2H), 7.14 (d, J=8.2 Hz, 1H), 7.00 (d, J=7.9 Hz, 1H), 6.54 (d, J=10.0 Hz, 1H), 5.36 (dd, J=8.6, 4.0 Hz, 1H), 4.31 (s, 2H), 3.75-3.58 (m, 6H), 3.33-2.97 (m, 10H), 2.67 (s, 3H), 2.11-1.67 (m, 4H). Six exchangeable protons not observed.

EXAMPLE 18

(R)-7-(2-(2,5-Dimethyl-4-(2-(4-(2-methylthiazole-4-carbonyl)-1-oxa-4,9-diazaspiro[5.5]undecan-9-yl)ethoxy)benzylamino)-1-hydroxyethyl)-4-hydroxybenzo[d]thiazol-2(3H)-one ditrifluoroacetate

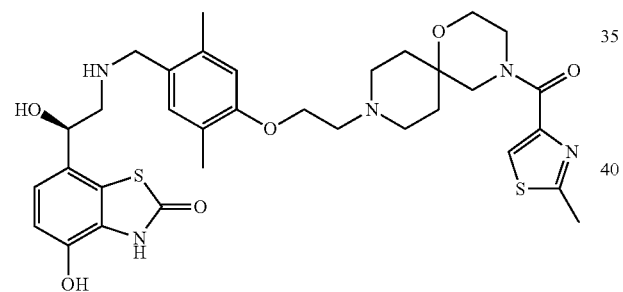

a) 4-Hydroxy-2,5-dimethylbenzoic acid

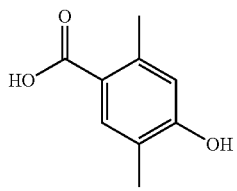

Boron tribromide solution (1M in DCM, 7.21 mL) was added dropwise to suspension of 4-methoxy-2,5-dimethylbenzoic acid (1 g) in DCM (5 mL) at −78° C. The reaction was allowed to warm to RT and stirred overnight. The reaction was cooled to −78° C. and boron tribromide solution (1M in DCM, 7.21 mL) was added. The reaction was allowed to warm to RT and stirred overnight. The reaction was cautiously poured onto ice (~50 mL). The resulting aqueous solution was extracted with DCM (5×50 mL). The organic solutions were combined, washed with brine (50 mL), dried over magnesium sulphate, filtered and evaporated to give the subtitled compound as a tan solid. Yield 0.75 g.

$^1$H NMR (300 MHz, D$_6$-DMSO) δ 12.19 (s, 1H), 9.91 (s, 1H), 7.64 (s, 1H), 6.65 (s, 1H), 2.43 (s, 3H), 2.09 (s, 3H).

b) Methyl 4-hydroxy-2,5-dimethylbenzoate

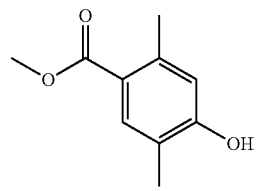

Acetyl chloride (0.107 mL) was added dropwise to a solution of 4-hydroxy-2,5-dimethylbenzoic acid (example 18, step a) (0.249 g) in methanol (15 mL) and the resulting mixture stirred at room temperature for 72 h. Acetyl chloride (0.107 mL) was then added and the reaction heated to 50° C. and stirred at this temperature overnight. The reaction was concentrated and the residue purified by silica gel chromatography eluting with 1:1 isohexane:ethyl acetate to 100% ethyl acetate gradient. The fractions containing product were combined and evaporated in vacuo to give the subtitled compound as a white solid. Yield 0.25 g.

$^1$H NMR (300 MHz, D$_6$-DMSO) δ 10.04 (s, 1H), 7.64 (s, 1H), 6.67 (s, 1H), 3.74 (s, 3H), 2.42 (s, 3H), 2.09 (s, 3H).

c) Methyl 4-(2,2-diethoxyethoxy)-2,5-dimethylbenzoate

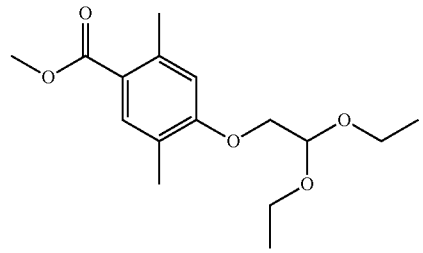 [SMILES: CCOC(COc1cc(C)c(C(=O)OC)cc1C)OCC]

2-Bromo-1,1-diethoxyethane (0.31 mL) was added to a mixture of methyl 4-hydroxy-2,5-dimethylbenzoate (example 18, step b) (0.25 g) and caesium carbonate (0.68 g) in DMF (20 mL). The resulting mixture was stirred at 85° C. for 16 h. The reaction was partitioned between water (200 mL) and ethyl acetate (100 mL). The aqueous phase was separated and extracted with ethyl acetate (2×100 mL). The combined organic solutions were washed with water (2×100 mL) and brine (100 mL), dried over magnesium sulphate, filtered and evaporated. The residue was purified by silica gel chromatography eluting with isohexane to 10:1 isohexane:ethyl acetate gradient. The fractions containing product were combined and evaporated in vacuo to give the subtitled compound as a clear oil. Yield 0.26 g.

$^1$H NMR (300 MHz, CDCl$_3$) δ 7.75 (s, 1H), 6.64 (s, 1H), 4.86 (t, J=5.2 Hz, 1H), 4.04 (d, J=5.4 Hz, 2H), 3.88-3.58 (m, 7H), 2.58 (s, 3H), 2.20 (s, 3H), 1.25 (t, J=7.0 Hz, 6H).

d) (4-(2,2-Diethoxyethoxy)-2,5-dimethylphenyl)methanol

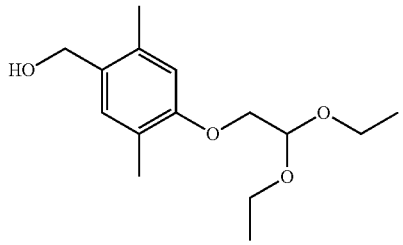 [SMILES: CCOC(COc1cc(C)c(CO)cc1C)OCC]

Lithium aluminium hydride solution (1M in THF, 1.17 mL) was added dropwise to a solution of methyl 4-(2,2-diethoxyethoxy)-2,5-dimethylbenzoate (example 18, step c) (0.231 g) in THF (20 mL) at 0° C. The resulting mixture was allowed to warm to RT and stirred for 1 h. Ethanol (0.5 mL) was cautiously added and the reaction concentrated. The residue was partitioned between 1M NaOH (50 mL) and ethyl acetate (100 mL). The aqueous was separated and extracted with ethyl acetate (2×50 mL). The combined organics were washed with brine (50 mL), dried over magnesium sulphate, filtered and evaporated to give the subtitled compound as a clear oil. Yield 0.20 g.

$^1$H NMR (300 MHz, CDCl$_3$) δ 7.08 (s, 1H), 6.66 (s, 1H), 4.85 (t, J=5.3 Hz, 1H), 4.60 (s, 2H), 4.00 (d, J=5.2 Hz, 2H), 3.84-3.58 (m, 4H), 2.33 (s, 3H), 2.20 (s, 3H), 1.25 (t, J=7.0 Hz, 6H). One exchangeable proton not observed.

e) (9-(2-(4-(Hydroxymethyl)-2,5-dimethylphenoxy)ethyl)-1-oxa-4,9-diazaspiro[5.5]undecan-4-yl)(2-methylthiazol-4-yl)methanone

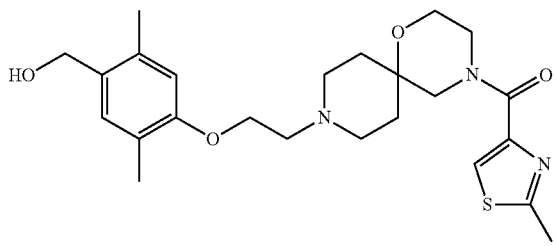 [SMILES: Cc1nc(C(=O)N2CCOC3(CCN(CCOc4cc(C)c(CO)cc4C)CC3)C2)cs1]

A solution of (4-(2,2-diethoxyethoxy)-2,5-dimethylphenyl)methanol (example 18, step d) (0.2 g) in a mixture of acetic acid (5 mL) and water (5 mL) was heated at 65° C. for 1 h and allowed to cool to RT. The reaction mixture was poured into saturated sodium bicarbonate solution (50 mL) and extracted with ethyl acetate (3×25 mL). The combined organic solutions were washed with brine (25 mL), dried over sodium sulphate, filtered and evaporated. The residue was redissolved in methanol (5 mL), acetic acid (5 mL) was added followed by (2-methylthiazol-4-yl)(1-oxa-4,9-diazaspiro[5.5]undecan-4-yl)methanone trifluoroacetate (example 4, step h) (0.35 g). The resulting mixture was stirred for 15 min then sodium cyanoborohydride (0.07 g) was added and the mixture stirred overnight. The solvent was evaporated and the residue partitioned between ethyl acetate (50 mL) and saturated sodium bicarbonate solution (20 mL). The layers were separated and the aqueous phase was extracted with ethyl acetate (2×30 mL). The combined organic solutions were washed with brine (20 mL), dried over sodium sulphate, filtered and evaporated. The residue was purified by silica gel chromatography eluting with 47.5:47.5:5 ethyl acetate:isohexane:triethylamine to 95:5 ethyl acetate:triethylamine gradient. The fractions containing product were combined and evaporated in vacuo to give the subtitled compound as a yellow oil. Yield 0.12 g.

m/z 460 (M+H)$^+$ (APCI)

f) 2,5-Dimethyl-4-(2-(4-(2-methylthiazole-4-carbonyl)-1-oxa-4,9-diazaspiro[5.5]undecan-9-yl)ethoxy)benzaldehyde

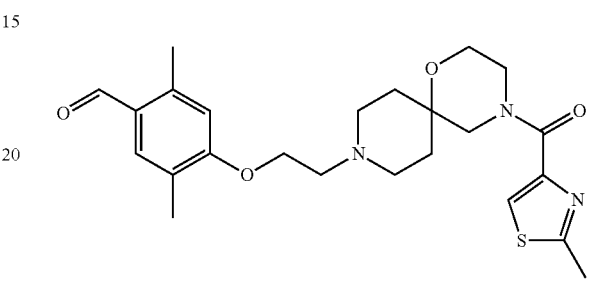

Manganese dioxide (0.32 g) was added to a solution of (9-(2-(4-(hydroxymethyl)-2,5-dimethylphenoxy)ethyl)-1-oxa-4,9-diazaspiro[5.5]undecan-4-yl)(2-methylthiazol-4-yl)methanone (example 18, step e) (0.17 g) in DCM (10 mL). The resulting mixture was heated at reflux for 4 h. The reaction was filtered through Celite and the filter pad washed with DCM (2×50 mL). The mother liquors and the washings were combined and evaporated to give the subtitled compound as a yellow gum. Yield 0.17 g.

m/z 458 (M+H)$^+$ (APCI)

g) (R)-7-(2-(2,5-Dimethyl-4-(2-(4-(2-methylthiazole-4-carbonyl)-1-oxa-4,9-diazaspiro[5.5]undecan-9-yl)ethoxy)benzylamino)-1-hydroxyethyl)-4-hydroxybenzo[d]thiazol-2(3H)-one ditrifluoroacetate

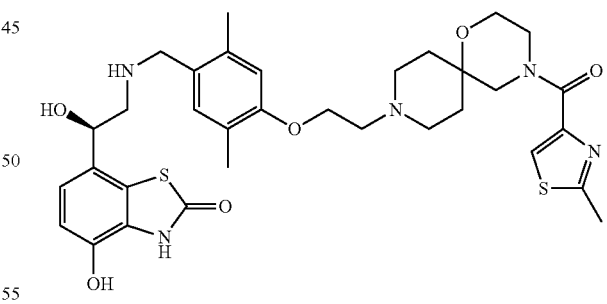

2,5-Dimethyl-4-(2-(4-(2-methylthiazole-4-carbonyl)-1-oxa-4,9-diazaspiro[5.5]undecan-9-yl)ethoxy)benzaldehyde (example 18, step f) (0.08 g) was added to a mixture of (R)-7-(2-amino-1-hydroxyethyl)-4-hydroxybenzo[d]thiazol-2(3H)-one hydrochloride (WO2007027134, example 1, step d) (0.07 g) and acetic acid (0.010 mL) in methanol (2 mL). The mixture was stirred for 30 min then cooled in an ice bath. Sodium cyanoborohydride (0.016 g) was then added and the mixture stirred for 2 h. The solvent was evaporated in vacuo and the residue partitioned between ethyl acetate (50 mL) and pH 7.2 phosphate buffer (50 mL). The aqueous was separated and extracted with ethyl acetate (2×50 mL). The combined organic solutions were washed with brine (20 mL), dried over sodium sulphate, filtered and evaporated in vacuo. The residue was purified by silica gel chromatography eluting with 95:5:0.5 to 92:8:0.8 DCM:methanol:'880' aqueous ammonia gradient. The fractions containing product were combined and evaporated in vacuo. Further purification was by preparative HPLC (Sunfire™, Gradient: 5-50% acetonitrile in 0.2% aqueous TFA). The fractions containing product were combined, evaporated in vacuo and the residue triturated with ether to give the titled compound as a white solid. Yield 0.069 g.

m/z 668 (M+H)+ (APCI)

$^1$H NMR (400 MHz, D$_6$-DMSO, 90° C.) δ 11.34-11.14 (m, 1H), 7.92 (s, 1H), 7.26 (s, 1H), 6.93 (d, J=8.2 Hz, 1H), 6.86 (s, 1H), 6.76 (d, J=8.2 Hz, 1H), 4.94 (t, J=6.5 Hz, 1H), 4.39-4.31 (m, 2H), 4.23-4.09 (m, 2H), 3.78-3.63 (m, 6H), 3.61-3.55 (m, 2H), 3.49-3.20 (m, 4H), 3.13-3.03 (m, 2H), 2.68 (s, 3H), 2.33 (s, 3H), 2.21-2.01 (m, 5H), 1.94-1.78 (m, 2H). Five exchangeable protons not observed.

EXAMPLE 19

(R)-7-(2-(3-Fluoro-5-((4-(2-methylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

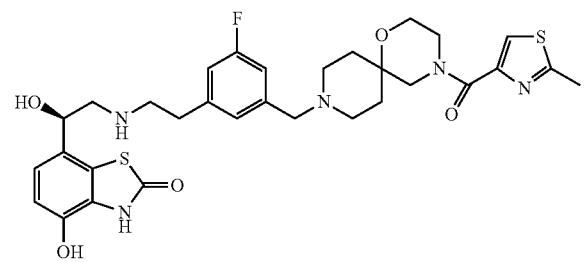 [SMILES: Cc1nc(C(=O)N2CCOC3(CCN(Cc4cc(F)cc(CCNC[C@H](O)c5ccc(O)c6[nH]c(=O)sc56)c4)CC3)C2)cs1]

a) 2-(3-(Bromomethyl)-5-fluorophenyl)acetic acid

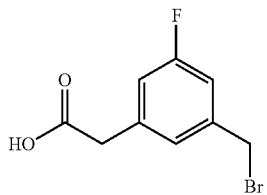 [SMILES: O=C(O)Cc1cc(F)cc(CBr)c1]

Benzoyl peroxide (0.05 g) was added to a mixture of 2-(3-fluoro-5-methylphenyl)acetic acid (0.518 g) and N-bromosuccinimide (0.6 g) in DCM (10 mL). The reaction was heated at reflux for 1 h. DCM (10 mL) and water (20 mL) were added and the organic phase separated. The organic layer was washed with brine (20 mL), dried over sodium sulphate, filtered and evaporated in vacuo. The residue was triturated with toluene and the resulting white solid removed by filtration. The mother liquors were evaporated in vacuo to give the subtitled compound as a white solid which was used in the next step without further purification. Yield 0.38 g.

b) (9-(3-Fluoro-5-(2-hydroxyethyl)benzyl)-1-oxa-4,9-diazaspiro[5.5]undecan-4-yl)(2-methylthiazol-4-yl)methanone

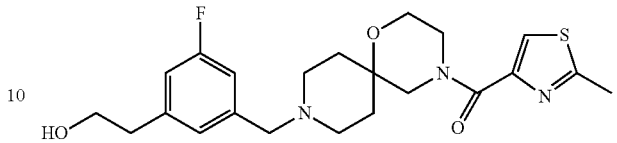

A solution of borane dimethylsulfide complex (2M in THF, 3.85 mL) was added dropwise to a solution of 2-(3-(bromomethyl)-5-fluorophenyl)acetic acid (example 19, step a) (0.38 g) in THF (10 mL) at 0° C. The resulting mixture was allowed to warm to RT and stirred for 1 h. The reaction was cooled to 0° C. and methanol (1 mL) was added dropwise until bubbling ceased. The solvent was evaporated in vacuo and the residue redissolved in MeCN (10 mL). (2-Methylthiazol-4-yl)(1-oxa-4,9-diazaspiro[5.5]undecan-4-yl)methanone trifluoroacetate (example 4, step h) (0.61 g) was then added followed by triethylamine (0.54 mL) and the resulting mixture stirred for 70 h. The solvent was then evaporated in vacuo. Purification was by silica gel chromatography eluting with 99:1:0.1 to 94.5:5:0.5 DCM:methanol:'880' aqueous ammonia gradient. The fractions containing product were combined and evaporated in vacuo to give the subtitled compound as a yellow foam. Yield 0.57 g.

m/z 434 (M+H)+ (APCI)

c) 2-(3-Fluoro-5-((4-(2-methylthiazole-4-carbonyl)-1-oxa-4,9-diazaspiro[5.5]undecan-9-yl)methyl)phenyl)acetaldehyde

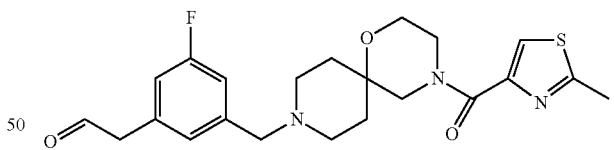

TFA (0.08 mL) was added to a solution of (9-(3-fluoro-5-(2-hydroxyethyl)benzyl)-1-oxa-4,9-diazaspiro[5.5]undecan-4-yl)(2-methylthiazol-4-yl)methanone (example 19, step b) (0.46 g) in DCM (5 mL) at 0° C. and the resulting mixture stirred for 5 min. Dess-Martin periodinane (0.68 g) was then added and the mixture stirred at RT for 45 min. Saturated sodium thiosulphate solution (5 mL), saturated sodium bicabonate solution (5 mL) and ethyl acetate (20 mL) were then added and the mixture stirred for 10 min. The aqueous phase was separated and extracted with ethyl acetate (20 mL). The combined organic solutions were washed with brine, acidified with acetic acid (0.1 mL), dried over sodium sulphate, filtered and evaporated in vacuo to give the subtitled compound as a yellow gum. Yield 0.4 g.

m/z 432 (M+H)+ (APCI)

d) (R)-7-(2-(3-Fluoro-5-((4-(2-methylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

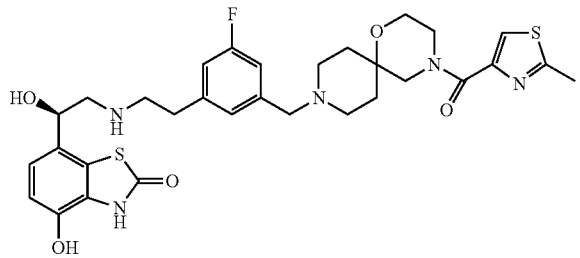 [SMILES: Cc1nc(C(=O)N2CCOC3(CCN(Cc4cc(F)cc(CCNC[C@H](O)c5ccc(O)c6[nH]c(=O)sc56)c4)CC3)C2)cs1]

A solution of 2-(3-fluoro-5-((4-(2-methylthiazole-4-carbonyl)-1-oxa-4,9-diazaspiro[5.5]undecan-9-yl)methyl)phenyl)acetaldehyde (example 19, step c) (0.2 g) in methanol (3 mL) was added to a mixture of (R)-7-(2-amino-1-hydroxyethyl)-4-hydroxybenzo[d]thiazol-2(3H)-one hydrochloride (WO2007027134, example 1, step d) (0.18 g) and acetic acid (0.04 mL) in methanol (0.5 mL). The resulting mixture was stirred for 5 min then cooled to 0° C. Sodium cyanoborohydride (0.03 g) was then added and the mixture allowed to warm to RT and stirred for 2 h. The solvent was evaporated in vacuo and purification was by silica gel chromatography eluting with 95:5:0.5 to 89:10:1 DCM:methanol:'880' aqueous ammonia gradient. The fractions containing product were combined, evaporated in vacuo and purified by preparative HPLC (Sunfire™, Gradient: 5-50% acetonitrile in 0.2% aqueous TFA). The fractions containing product were combined, evaporated in vacuo and the residue triturated with ether to give the titled compound as a white solid. Yield 0.018 g.

m/z 642 (M+H)+ (APCI)

$^1$H NMR (400 MHz, D$_6$-DMSO, 90° C.) δ 7.89 (s, 1H), 7.26-7.12 (m, 3H), 6.93 (d, J=8.5 Hz, 1H), 6.77 (d, J=8.2 Hz, 1H), 4.94-4.85 (m, 1H), 4.26-4.13 (m, 2H), 3.74-3.59 (m, 6H), 3.35-2.94 (m, 10H), 2.67 (s, 3H), 2.06-1.91 (m, 2H), 1.83-1.68 (m, 2H). Six exchangeable protons not observed.

EXAMPLE 20

(R)-4-Hydroxy-7-(1-hydroxy-2-(3-(2-(4-(5-methylthiophene-2-carbonyl)-1-oxa-4,9-diazaspiro[5.5]undecan-9-yl)ethyl)benzylamino)ethyl)benzo[d]thiazol-2(3H)-one ditrifluoroacetate

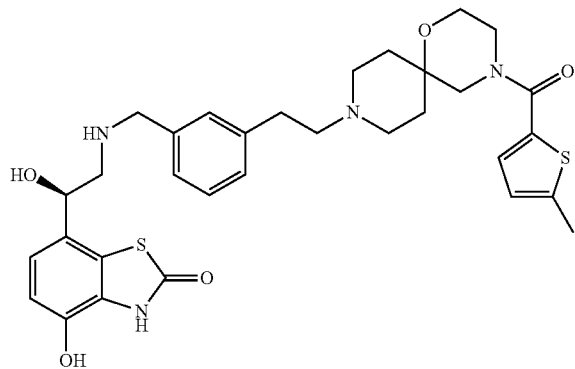 [SMILES: Cc1ccc(C(=O)N2CCOC3(CCN(CCc4cccc(CNC[C@H](O)c5ccc(O)c6[nH]c(=O)sc56)c4)CC3)C2)s1]

a) 2-(3-(Hydroxymethyl)phenyl)ethanol

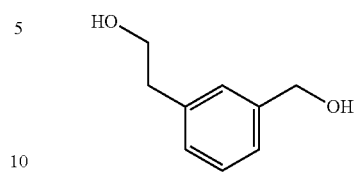

Lithium aluminum hydride (1M in diethyl ether, 5.55 mL) was added dropwise over 5 min to a stirred solution of methyl 3-(2-hydroxyethyl)benzoate (1.0 g) in tetrahydrofuran (15 mL) cooled in an ice bath. After 1 h, the reaction mixture was quenched with methanol and evaporated in vacuo. Purification was by silica gel chromatography eluting with ethyl acetate:isohexane, 2:1, then ethyl acetate to give the subtitled compound as a gum. Yield 0.5 g.

$^1$H NMR (300 MHz, CDCl$_3$) δ 7.31 (t, J=7.7 Hz, 1H), 7.26-7.20 (m, 2H), 7.16 (d, J=7.7 Hz, 1H), 4.67 (s, 2H), 3.86 (t, J=6.9 Hz, 2H), 2.87 (t, J=6.9 Hz, 2H). Two exchangeable protons not observed.

b) 3-(2-Hydroxyethyl)benzaldehyde

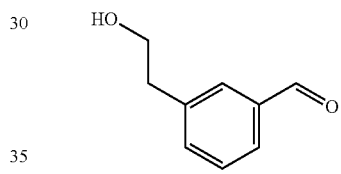

Manganese (IV) dioxide (2.0 g) was added to a stirred solution of 2-(3-(hydroxymethyl)phenyl)ethanol (example 20, step a) (0.50 g) in DCM (10 mL) at room temperature. After 6 h, the reaction mixture was filtered through Celite eluting with DCM. The solution was evaporated in vacuo to give the subtitled compound as a gum. Used directly. Yield 0.46 g.

c) 2-(3-(Diethoxymethyl)phenyl)ethanol

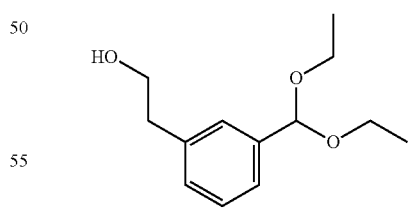

Ammonium chloride (0.08 g) was added to a solution of 3-(2-hydroxyethyl)benzaldehyde (example 20, step b) (0.45 g) and triethoxymethane (0.55 g) in EtOH (8 mL) and the reaction mixture heated at 70° C. for 3 h. After cooling, the reaction mixture was partitioned between ethyl acetate and saturated sodium bicarbonate solution. The ethyl acetate solution was dried over sodium sulphate, filtered and evaporated in vacuo to give the subtitled compound as a gum. Yield 0.24 g.

¹H NMR (300 MHz, CDCl₃) δ 7.38-7.25 (m, 3H), 7.22-7.16 (m, 1H), 5.50-5.47 (m, 1H), 3.93-3.82 (m, 2H), 3.71-3.47 (m, 4H), 2.94-2.86 (m, 2H), 1.29-1.21 (m, 6H). One exchangeable proton not observed.

d) 3-(Diethoxymethyl)phenethyl methanesulfonate

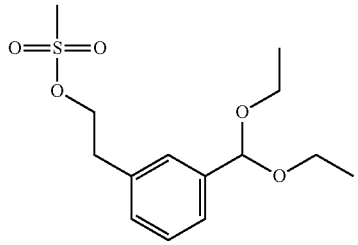 [SMILES: CCOC(OCC)c1cccc(CCOS(C)(=O)=O)c1]

Methanesulfonyl chloride (0.18 g) in dichloromethane (0.2 mL) was added to a stirred solution of 2-(3-(diethoxymethyl)phenyl)ethanol (example 20, step c) (0.23 g) and triethylamine (0.429 mL) in dichloromethane (2.5 mL) cooled in an ice bath. After 1 h, the reaction mixture was partitioned between ethyl acetate and saturated sodium bicarbonate solution. The ethyl acetate layer was washed with saturated sodium bicarbonate solution and brine, dried over sodium sulphate, filtered and evaporated in vacuo to give the subtitled compound as a gum. Yield 0.28 g.
¹H NMR (300 MHz, CDCl₃) δ 7.40-7.29 (m, 3H), 7.19 (d, J=7.4 Hz, 1H), 5.47 (s, 1H), 4.42 (t, J=6.9 Hz, 2H), 3.67-3.48 (m, 4H), 3.07 (t, J=6.9 Hz, 2H), 2.86 (s, 3H), 1.24 (t, J=6.8 Hz, 6H).

e) (9-(3-(Diethoxymethyl)phenethyl)-1-oxa-4,9-diazaspiro[5.5]undecan-4-yl)(5-methylthiophen-2-yl)methanone

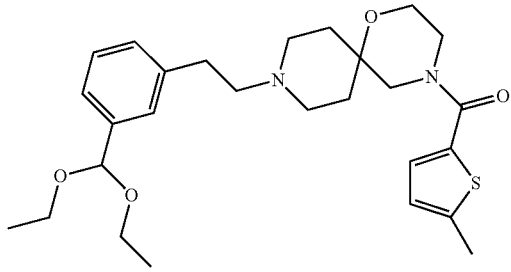 [SMILES: CCOC(OCC)c1cccc(CCN2CCC3(CC2)CN(C(=O)c2ccc(C)s2)CCO3)c1]

3-(Diethoxymethyl)phenethyl methanesulfonate (example 20, step d) (0.30 g) in acetonitrile (1.5 mL) was added to a stirred solution of (5-methylthiophen-2-yl)(1-oxa-4,9-diazaspiro[5.5]undecan-4-yl)methanone trifluoroacetate (example 9, step b) (0.391 g) and triethylamine (0.415 mL) in acetonitrile (1.5 mL) and the solution heated at 70° C. for 48 h. After cooling, the solution was evaporated in vacuo and applied to a silica gel column for purification, eluting with ethyl acetate:isohexane:triethylamine, 60:40:5 giving the subtitled compound as a gum. Yield 0.2 g.
¹H NMR (400 MHz, CDCl₃) δ 7.30-7.24 (m, 3H), 7.14 (d, J=7.6 Hz, 1H), 7.11 (d, J=3.7 Hz, 1H), 6.69 (dd, J=3.7 Hz, 1.1 Hz, 1H), 5.46 (s, 1H), 3.78-3.71 (m, 4H), 3.65-3.49 (m, 6H), 2.82-2.77 (m, 2H), 2.65-2.57 (m, 4H), 2.50 (s, 3H), 2.48-2.39 (m, 2H), 1.94-1.86 (m, 2H), 1.67-1.56 (m, 2H), 1.23 (t, J=7.2 Hz, 6H).

f) 3-(2-(4-(5-methylthiophene-2-carbonyl)-1-oxa-4,9-diazaspiro[5.5]undecan-9-yl)ethyl)benzaldehyde

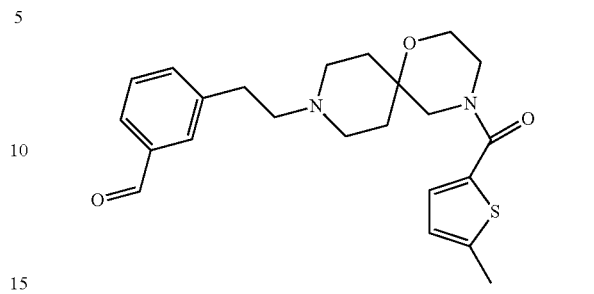

Formic acid (2 mL) was added to stirred solution of (9-(3-(diethoxymethyl)phenethyl)-1-oxa-4,9-diazaspiro[5.5]undecan-4-yl)(5-methylthiophen-2-yl)methanone (example 20, step e) (0.20 g) in tetrahydrofuran (3 mL) and water (1 mL) cooled in an ice bath. After 10 min, the reaction mixture was evaporated in vacuo, toluene was added and the reaction mixture was evaporated in vacuo. The residue was dissolved in acetonitrile and then evaporated in vacuo, and this process was repeated to give the subtitled compound as an oil that was used directly. Yield 0.16 g.
m/z 413 (M+H)⁺ (APCI)

g) (R)-4-Hydroxy-7-(1-hydroxy-2-(3-(2-(4-(5-methylthiophene-2-carbonyl)-1-oxa-4,9-diazaspiro[5.5]undecan-9-yl)ethyl)benzylamino)ethyl)benzo[d]thiazol-2(3H)-one ditrifluoroacetate

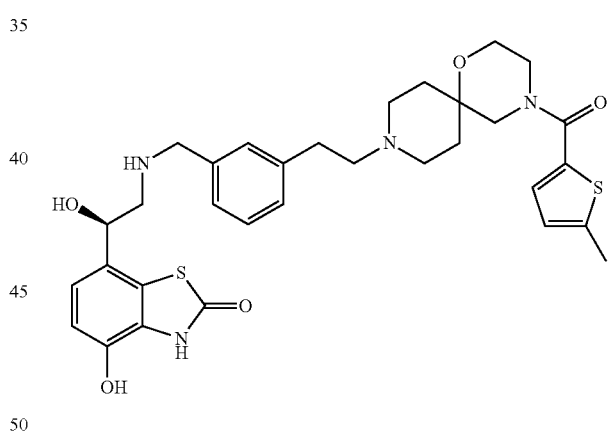

Acetic acid (0.033 mL) was added to a stirred solution of 3-(2-(4-(5-methylthiophene-2-carbonyl)-1-oxa-4,9-diazaspiro[5.5]undecan-9-yl)ethyl)benzaldehyde (example 20, step f) (0.17 g) and (R)-7-(2-amino-1-hydroxyethyl)-4-hydroxybenzo[d]thiazol-2(3H)-one hydrochloride (WO2007027134, example 1, step d) (0.15 g) in methanol (10 mL). After 2 min, sodium cyanoborohydride (0.10 g) was added and the reaction mixture stirred at room temperature overnight. The methanol solution was concentrated to ~3 mL and diluted with ethyl acetate. A gummy precipitate formed. The ethyl acetate was decanted off and washed with saturated sodium bicarbonate solution and brine and dried over sodium sulphate. The gum was dissolved in a small amount of methanol and added to the ethyl acetate. The ethyl acetate was filtered and evaporated in vacuo to give a white solid. The solid was dissolved in methanol and purified by preparative HPLC (Sunfire™, Gradient: 15-50% acetonitrile in 0.2% aqueous TFA). The fractions containing pure product were combined and evaporated to dryness. Trituration with diethyl ether gave the titled compound as a white solid. Yield 0.11 g.

m/z 623 (M+H)+ (APCI)

$^1$H NMR (400 MHz, D$_6$-DMSO, 90° C.) δ 11.67 (s, 1H), 10.23 (s, 1H), 9.85-9.75 and 9.61-9.50 (m, total 1H), 9.18-8.98 (m, 2H), 7.45-7.31 (m, 4H), 7.29-7.24 (m, 1H), 6.89 (d, J=7.4 Hz, 1H), 6.86-6.83 (m, 1H), 6.75 (d, J=7.4 Hz, 1H), 6.48-6.44 (m, 1H), 4.93-4.85 (m, 1H), 4.21-4.14 (m, 2H), 3.74-3.64 (m, 4H), 3.53 (s, 2H), 3.48-3.40 (m, 2H), 3.36-3.27 (m, 2H), 3.08-2.92 (m, 6H), 2.47 (s, 3H), 2.16-2.08 (m, 2H), 1.74-1.61 (m, 2H).

EXAMPLE 21

(R)-4-Hydroxy-7-(1-hydroxy-2-((5-(2-(4-(2-methylthiazole-4-carbonyl)-1-oxa-4,9-diazaspiro[5.5]undecan-9-yl)ethyl)thiophen-2-yl)methylamino)ethyl)benzo[d]thiazol-2(3H)-one ditrifluoroacetate

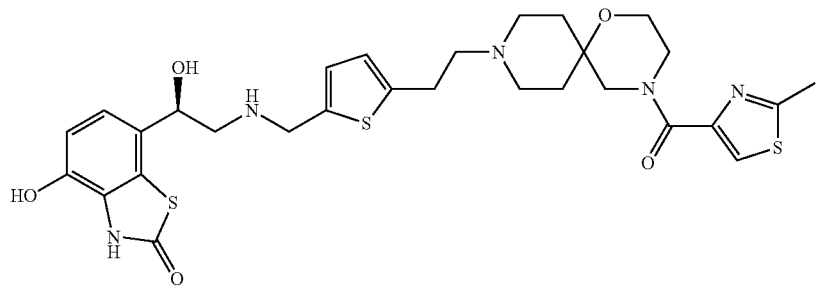 [SMILES: Cc1nc(C(=O)N2CCOC3(CCN(CCc4ccc(CNC[C@H](O)c5ccc(O)c6[nH]c(=O)sc56)s4)CC3)C2)cs1]

a) 5-(2-(tert-Butyldimethylsilyloxy)ethyl)thiophene-2-carbaldehyde

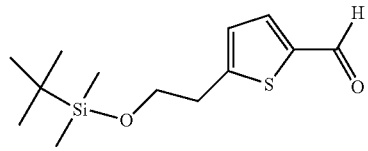 [SMILES: CC(C)(C)[Si](C)(C)OCCc1ccc(C=O)s1]

tert-Butyldimethylsilylchloride (2.82 g) was added portionwise to a stirred solution of 2-(thiophen-2-yl)ethanol (2 g) and imidazole (1.275 g) in DMF (20 mL) at 20° C. over a period of 20 minutes. The mixture was stirred at 20° C. for 18 hours and then partitioned between ethyl acetate and water, the organic layer was washed with water, dried over sodium sulphate, filtered and the solvent evaporated under reduced pressure. The residue was purified by flash silica chromatography, elution gradient 1-4% ethyl acetate in isohexane. The residue (2.7 g) was dissolved in THF (50 mL) and the solution cooled to −78° C., n-butyllithium (2.5M in hexanes, 5.06 mL) was added dropwise over 10 minutes and the resultant mixture stirred at 0° C. for 1 hour. The reaction mixture was cooled to −78° C. and DMF (5.7 mL) was added dropwise over 5 minutes. The mixture was stirred at 20° C. for 3 hours. The reaction mixture was partitioned between water and ethyl acetate, the organic layer was washed with water, dried over sodium sulphate and the solvent removed under reduced pressure. The crude product was purified by flash silica chroma-tography, eluting with 7% ethyl acetate in isohexane. Pure fractions were evaporated to dryness to afford the subtitled compound. Yield 2.3 g.

$^1$H NMR (400 MHz, CDCl$_3$) δ 9.83 (s, 1H), 7.61 (d, 1H), 6.96 (d, 1H), 3.86 (t, 2H), 3.07 (t, 2H), 0.88 (s, 9H), 0.02 (s, 6H).

b) 2-(5-(Diethoxymethyl)thiophen-2-yl)ethanol

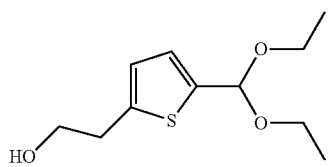

A mixture of 5-(2-(tert-butyldimethylsilyloxy)ethyl)thiophene-2-carbaldehyde (example 21, step a) (1.37 g) and ammonium chloride (0.135 g) and triethyl orthoformate (0.928 mL) in ethanol (15 mL) was heated at reflux under nitrogen for 3 hours. Most of the ethanol was removed under reduced pressure and the remaining mixture was partitioned between ethyl acetate and saturated sodium bicarbonate solution, the organic layer was dried over sodium sulphate, filtered and the solvent removed under reduced pressure. The residue was dissolved in THF (20 mL) and tetrabutylammonium fluoride (1M in THF, 5.07 mL) was added dropwise over 1 minute. The mixture was allowed to stand at room temperature for 30 minutes. The solvent was removed under reduced pressure and the residue was purified by flash silica chromatography eluting with 25% ethyl acetate in isohexane. Pure fractions were evaporated to dryness to afford the subtitled compound. Yield 0.940 g.

$^1$H NMR (400 MHz, D$_6$-DMSO) δ 6.85 (d, 1H), 6.73 (d, 1H), 5.64 (s, 1H), 4.79-4.74 (m, 1H), 3.62-3.43 (m, 6H), 2.87 (t, 2H), 1.13 (t, 6H).

c) 5-(2-(4-(2-Methylthiazole-4-carbonyl)-1-oxa-4,9-diazaspiro[5.5]undecan-9-yl)ethyl)thiophene-2-carbaldehyde

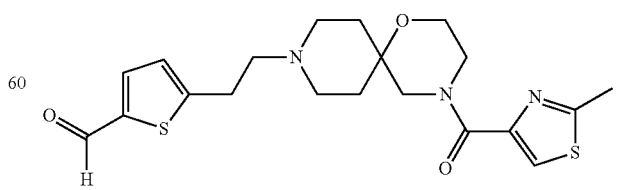

A solution of 2-(5-(diethoxymethyl)thiophen-2-yl)ethanol (example 21, step b) (0.54 g) in dichloromethane (20 mL) was treated with triethylamine (0.359 mL) and the mixture cooled in an ice bath. A solution of methanesulphonyl chloride (0.183 mL) in dichloromethane (3 mL) was then added dropwise over 2 minutes and the reaction mixture stirred at 0° C. for 1 hour. The mixture was washed with water and the organic layer dried over sodium sulphate, filtered and the solvent evaporated under reduced pressure. The residue was dissolved in a mixture of acetonitrile (7 mL) and DMF (1 mL) and triethylamine (0.654 mL) was added followed by (2-methylthiazol-4-yl)(1-oxa-4,9-diazaspiro[5.5]undecan-4-yl) methanone trifluoroacetate (example 4, step h) (0.5 g) and heated at 70° C. for 10 hours. The mixture was partitioned between ethyl acetate and saturated sodium bicarbonate solution, the organic layer was dried over sodium sulphate, filtered and the solvent evaporated under reduced pressure. The residue was dissolved in THF (5 mL) and cooled in an ice bath, formic acid (4 mL) was added followed by water (1 mL). The mixture was allowed to stand at 0° C. for 10 minutes. The solvent was removed under reduced pressure and the residue azeotroped twice with toluene and twice with acetonitrile. The crude product was purified by flash silica chromatography using 1% triethylamine and 2% methanol in dichloromethane as solvent. Pure fractions were evaporated to dryness to afford the subtitled compound. Yield 0.52 g.

m/z 420 (M+H)$^+$ (APCI)

d) (R)-4-Hydroxy-7-(1-hydroxy-2-((5-(2-(4-(2-methylthiazole-4-carbonyl)-1-oxa-4,9-diazaspiro[5.5]undecan-9-yl)ethyl)thiophen-2-yl)methylamino)ethyl)benzo[d]thiazol-2(3H)-one ditrifluoroacetate hyde (example 21, step c) (0.3 g) in methanol (2 mL). The mixture was cooled in an ice bath and treated with sodium cyanoborohydride (0.067 g). The mixture was then stirred at room temperature for 18 hours. Most of the methanol was evaporated under reduced pressure and the remainder partitioned between THF (50 mL), brine (10 mL) and saturated sodium bicarbonate solution (1 mL). The organic layer was dried over sodium sulphate, filtered and the solvent removed under reduced pressure. The crude product was purified by preparative HPLC (Sunfire™, Gradient: 10-40% acetonitrile in 0.2% aqueous TFA). The fractions containing the desired product were evaporated to dryness to afford the titled compound. Yield 0.08 g.

m/z 630 (M+H)$^+$ (APCI)

$^1$H NMR (400 MHz, D$_6$-DMSO, 90° C.) δ 11.27 (s, 1H), 7.92 (s, 1H), 7.14 (d, 1H), 6.94-6.88 (m, 2H), 6.76 (d, 1H), 4.91-4.85 (m, 1H), 4.37 (s, 2H), 3.70 (s, 4H), 3.66 (s, 2H), 3.40-3.30 (m, 4H), 3.26-3.07 (m, 4H), 3.04-3.02 (m, 2H), 2.68 (s, 3H), 2.09-1.99 (m, 2H), 1.87-1.73 (m, 2H). Five exchangeable protons not observed.

EXAMPLE 22

(R)-4-Hydroxy-7-(1-hydroxy-2-(3-((4-(2-isopropylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

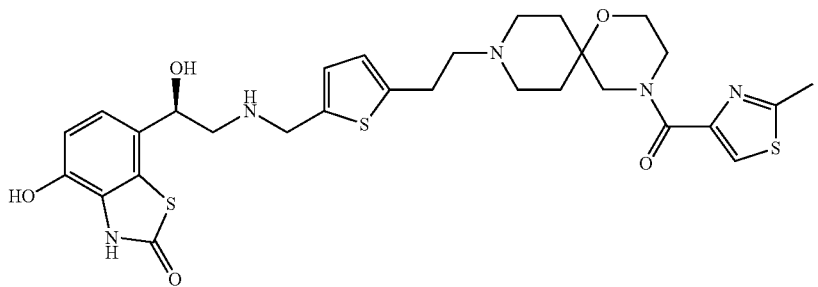 [SMILES: Cc1nc(C(=O)N2CCOC3(CCN(CCc4ccc(CNC[C@H](O)c5ccc(O)c6[nH]c(=O)sc56)s4)CC3)C2)cs1]

A solution of (R)-7-(2-amino-1-hydroxyethyl)-4-hydroxybenzo[d]thiazol-2(3H)-one hydrochloride (WO2007027134, example 1, step d) (0.22 g) in methanol (8 mL) was treated with acetic acid (0.041 mL) followed by a solution of 5-(2-(4-(2-methylthiazole-4-carbonyl)-1-oxa-4,9-diazaspiro[5.5]undecan-9-yl)ethyl)thiophene-2-carbalde-

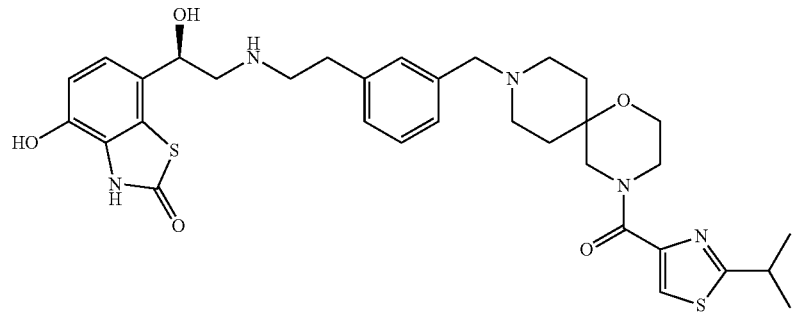 [SMILES: CC(C)c1nc(C(=O)N2CCOC3(CCN(Cc4cccc(CCNC[C@H](O)c5ccc(O)c6[nH]c(=O)sc56)c4)CC3)C2)cs1]

a) tert-Butyl 4-(2-isopropylthiazole-4-carbonyl)-1-oxa-4,9-diazaspiro[5.5]undecane-9-carboxylate

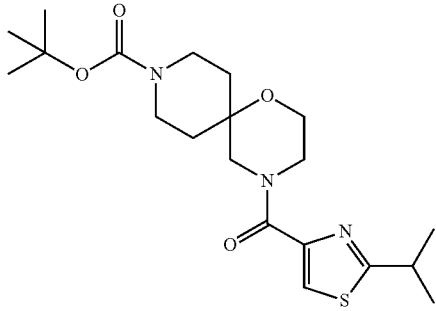 [SMILES: CC(C)c1nc(C(=O)N2CCOC3(CCN(C(=O)OC(C)(C)C)CC3)C2)cs1]

A solution of 2-isopropylthiazole-4-carboxylic acid (1 g) and tert-butyl 1-oxa-4,9-diazaspiro[5.5]undecane-9-carboxylate hydrochloride (WuXi PharmaTech) (1.71 g) in DMF (30 mL) was cooled in an ice bath and treated with triethylamine (2.442 mL) followed by HATU (2.89 g). The ice bath was removed and the mixture was stirred at 20° C. for 1 hour. The mixture was partitioned between ethyl acetate and brine, the organic layer was washed twice with brine, dried over sodium sulphate, filtered and the solvent evaporated under reduced pressure. The crude product was purified by flash silica chromatography using 70% ethyl acetate in isohexane as solvent. Pure fractions were evaporated to dryness to afford the subtitled compound. Yield 2 g.
$^1$H NMR (400 MHz, D$_6$-DMSO, 90° C.) δ 7.93 (s, 1H), 3.71-3.63 (m, 6H), 3.51-3.44 (m, 2H), 3.35-3.26 (m, 1H), 3.18-3.10 (m, 2H), 1.74-1.67 (m, 2H), 1.49-1.41 (m, 2H), 1.39 (s, 9H), 1.34 (d, J=7.6 Hz, 6H).

b) (2-Isopropylthiazol-4-yl)(1-oxa-4,9-diazaspiro[5.5]undecan-4-yl)methanone trifluoroacetate

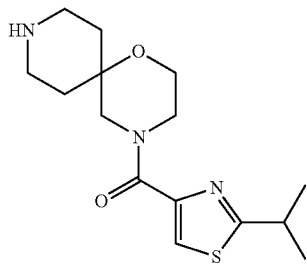 [SMILES: CC(C)c1nc(C(=O)N2CCOC3(CCNCC3)C2)cs1]

A solution of tert-butyl 4-(2-isopropylthiazole-4-carbonyl)-1-oxa-4,9-diazaspiro[5.5]undecane-9-carboxylate (example 22, step a) (2.3 g) in a mixture of dichloromethane (40 mL) and trifluoroacetic acid (10 mL) was allowed to stand at 20° C. for 30 minutes. Toluene (50 mL) was added and the solvents were evaporated, then this process was repeated with further toluene (50 mL). The residue was triturated with ether. The gum was then dissolved in acetonitrile and the solvent evaporated to afford the subtitled compound. Yield 1.64 g.
m/z 310 (M+H)$^+$ (APCI)

c) (9-(3-(2-Hydroxyethyl)benzyl)-1-oxa-4,9-diazaspiro[5.5]undecan-4-yl)(2-isopropylthiazol-4-yl)methanone

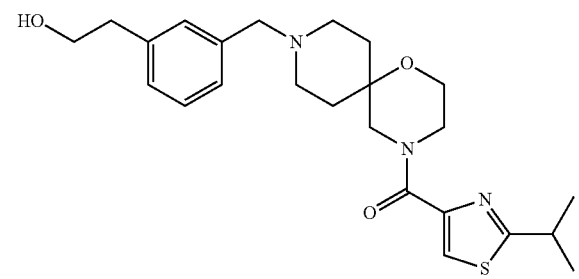 [SMILES: CC(C)c1nc(C(=O)N2CCOC3(CCN(Cc4cccc(CCO)c4)CC3)C2)cs1]

A mixture of (2-isopropylthiazol-4-yl)(1-oxa-4,9-diazaspiro[5.5]undecan-4-yl)methanone trifluoroacetate (example 22, step b) (0.85 g) and 2-(3-(bromomethyl)phenyl)ethanol (example 6, step a) (0.432 g) in acetonitrile (10 mL) at 20° C. was treated with triethylamine (0.616 mL) and then stirred for 2 hours. The solvent was evaporated under reduced pressure and the residue partitioned between ethyl acetate and brine, the organic layer was dried over sodium sulphate, filtered and the solvent evaporated under reduced pressure. The crude product was purified by flash silica chromatography, elution gradient 1% triethylamine and 3% methanol in dichloromethane. Pure fractions were evaporated to dryness to afford the subtitled compound. Yield 0.71 g.
m/z 444 (M+H)$^+$ (APCI)

d) (R)-4-Hydroxy-7-(1-hydroxy-2-(3-((4-(2-isopropylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

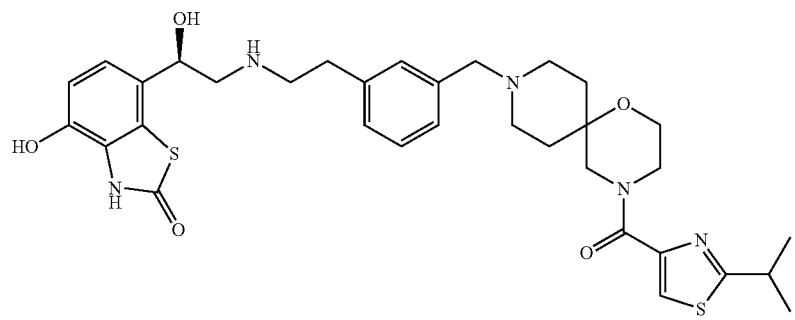

A solution of (9-(3-(2-hydroxyethyl)benzyl)-1-oxa-4,9-diazaspiro[5.5]undecan-4-yl)(2-isopropylthiazol-4-yl)methanone (example 22, step c) (0.3 g) in dichloromethane (10 mL) was treated with trifluoroacetic acid (0.052 mL) followed by Dess-Martin periodinane (0.402 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.039 mL) and the solvent evaporated under reduced pressure. The residue was dissolved in methanol (2 mL) and added to a solution at 0° C. of (R)-7-(2-amino-1-hydroxyethyl)-4-hydroxybenzo[d]thiazol-2(3H)-one hydrochloride (WO2007027134, example 1, step d) (0.2 g) and acetic acid (0.039 mL) in methanol (10 mL). Sodium cyanoborohydride (0.064 g) was added and the mixture stirred at room temperature for 18 hours. Most of the methanol was evaporated under reduced pressure and the remainder partitioned between THF (50 mL), brine (10 mL) and saturated sodium bicarbonate solution (1 mL). The organic layer was dried over sodium sulphate, filtered and the solvent removed under reduced pressure. The crude product was purified by preparative HPLC (Sunfire™, Gradient: 10-40% acetonitrile in 0.2% aqueous TFA). The fractions containing the desired product were evaporated to dryness to afford the titled compound. Yield 0.170 g.

m/z 652 (M+H)$^+$ (APCI)

$^1$H NMR (400 MHz, D$_6$-DMSO, 90° C.) δ 11.27 (s, 1H), 7.94 (s, 1H), 7.45-7.31 (m, 4H), 6.93 (d, J=31.1 Hz, 1H), 6.77 (d, J=24.6 Hz, 1H), 4.96-4.87 (m, 1H), 4.27 (s, 2H), 3.70 (s, 4H), 3.65 (s, 2H), 3.35-2.97 (m, 11H), 2.08-1.96 (m, 2H), 1.84-1.67 (m, 2H), 1.35 (d, J=20.7 Hz, 6H). Five exchangeable protons not observed.

EXAMPLE 23

(R)-8-Hydroxy-5-(1-hydroxy-2-(3-((4-(2-isopropylthiazole-4-carbonyl)-1-oxa-4,9-diazaspiro[5.5]undecan-9-yl)methyl)phenethylamino)ethyl)quinolin-2(1H)-one ditrifluoroacetate

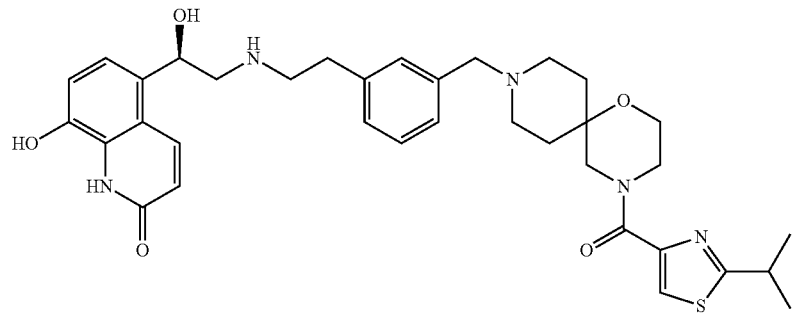 [SMILES: CC(C)c1nc(C(=O)N2CCOC3(CCN(Cc4cccc(CCNC[C@H](O)c5ccc(O)c6[nH]c(=O)ccc56)c4)CC3)C2)cs1]

a) (R)-5-(1-(tert-Butyldimethylsilyloxy)-2-(3-((4-(2-isopropylthiazole-4-carbonyl)-1-oxa-4,9-diazaspiro[5.5]undecan-9-yl)methyl)phenethylamino)ethyl)-8-hydroxyquinolin-2(1H)-one

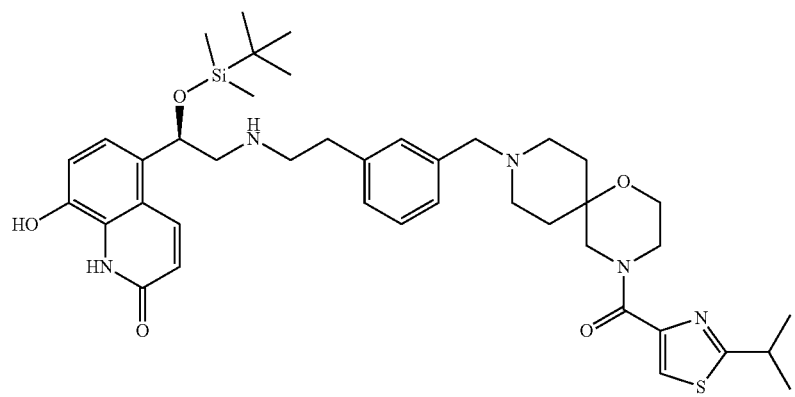 [SMILES: CC(C)c1nc(C(=O)N2CCOC3(CCN(Cc4cccc(CCNC[C@H](O[Si](C)(C)C(C)(C)C)c5ccc(O)c6[nH]c(=O)ccc56)c4)CC3)C2)cs1]

A solution of (9-(3-(2-hydroxyethyl)benzyl)-1-oxa-4,9-diazaspiro[5.5]undecan-4-yl)(2-isopropylthiazol-4-yl)methanone (example 22, step c) (0.159 g) in DCM (10 mL) was treated with trifluoroacetic acid (0.028 mL) followed by Dess-Martin periodinane (0.213 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.039 mL) and the solvent evaporated under reduced pressure. The residue was dissolved in methanol (2 mL) and added to a solution of (R)-5-(2-amino-1-(tert-butyldimethylsilyloxy)ethyl)-8-hydroxyquinolin-2(1H)-one (WO2004106333) (0.12 g) and acetic acid (0.021 mL) in methanol (10 mL). The mixture was cooled in an ice bath and treated with sodium triacetoxyborohydride (0.114 g), then the mixture was stirred at room temperature for 18 hours. The methanol was removed under reduced pressure and the residue was partitioned between saturated sodium bicarbonate solution and ethyl acetate, the organic layer was dried over sodium sulphate, filtered and the solvent removed under reduced pressure. The crude product was purified by flash silica chromatography using 1% '880' aqueous ammonia and 8% methanol in dichloromethane as solvent. Pure fractions were evaporated to dryness to afford the subtitled compound. Yield 0.127 g.

m/z 760 (M+H)$^+$ (APCI)

b) (R)-8-Hydroxy-5-(1-hydroxy-2-(3-((4-(2-isopropylthiazole-4-carbonyl)-1-oxa-4,9-diazaspiro[5.5]undecan-9-yl)methyl)phenethylamino)ethyl)quinolin-2(1H)-one ditrifluoroacetate

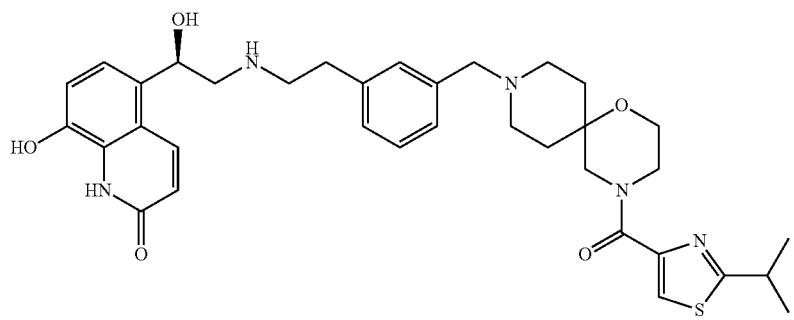 [SMILES: CC(C)c1nc(C(=O)N2CCOC3(CCN(Cc4cccc(CCNC[C@H](O)c5ccc(O)c6[nH]c(=O)ccc56)c4)CC3)C2)cs1]

A solution of (R)-5-(1-(tert-butyldimethylsilyloxy)-2-(3-((4-(2-isopropylthiazole-4-carbonyl)-1-oxa-4,9-diazaspiro[5.5]undecan-9-yl)methyl)phenethylamino)ethyl)-8-hydroxyquinolin-2(1H)-one (example 23, step a) (0.127 g) in THF (4 mL) was treated with a solution of triethylamine trihydrofluoride (0.035 mL) in methanol (1 mL) and the resultant mixture was allowed to stand at 20° C. for 18 hours. The solvents were removed under reduced pressure and the crude product was purified by preparative HPLC (Sunfire™, Gradient: 10-40% acetonitrile in 0.2% aqueous TFA). The fractions containing the desired compound were evaporated to dryness to afford the titled compound. Yield 0.085 g.

m/z 646 (M+H)$^+$ (APCI)

$^1$H NMR (400 MHz, D$_6$-DMSO, 90° C.) δ 8.16 (d, J=36.5 Hz, 1H), 7.94 (s, 1H), 7.45-7.33 (m, 4H), 7.13 (d, J=26.1 Hz, 1H), 6.99 (d, J=24.2 Hz, 1H), 6.54 (d, J=24.2 Hz, 1H), 5.38-5.32 (m, 1H), 4.29 (s, 2H), 3.70 (s, 4H), 3.64 (s, 2H), 3.32-3.24 (m, 3H), 3.21-3.00 (m, 8H), 2.08-1.97 (m, 2H), 1.82-1.68 (m, 2H), 1.34 (d, J=25.7 Hz, 6H). Six exchangeable protons not observed.

EXAMPLE 24

(R)-4-Hydroxy-7-(1-hydroxy-2-(3-(2-(4-(2-methylthiazole-4-carbonyl)-1-oxa-4,9-diazaspiro[5.5]undecan-9-yl)ethoxy)phenethylamino)ethyl)benzo[d]thiazol-2(3H)-one ditrifluoroacetate

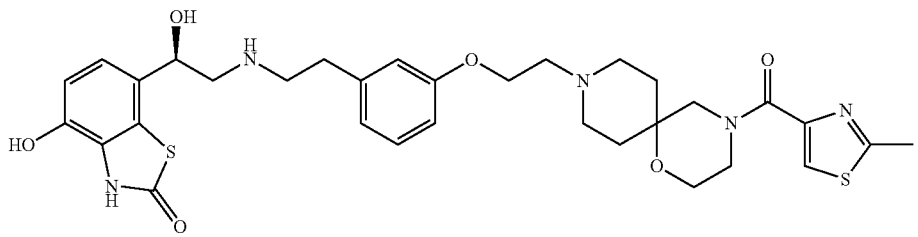 [SMILES: Cc1nc(C(=O)N2CCOC3(CCN(CCOc4cccc(CCNC[C@H](O)c5ccc(O)c6[nH]c(=O)sc56)c4)CC3)C2)cs1]

a) 2-(3-(2,2-Diethoxyethoxy)phenyl)ethanol

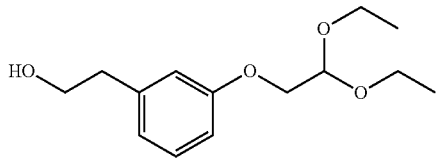 [SMILES: CCOC(COc1cccc(CCO)c1)OCC]

Caesium carbonate (8.84 g) was added to a solution of 3-(2-hydroxyethyl)phenol (2.5 g) and 2-bromo-1,1-diethoxyethane (3.74 g) in DMF (50 mL), and the resulting mixture was stirred at 90° C. overnight, then allowed to cool. The mixture was poured into water and extracted three times with ethyl acetate. The combined extracts were washed with water and brine, then dried over anhydrous sodium sulphate and purified by flash chromatography on silica eluted with a gradient of diethyl ether in isohexane to afford the subtitled compound as a pale yellow oil. Yield 3.0 g.

$^1$H NMR (400 MHz, CDCl$_3$) δ 7.21-7.16 (m, 1H), 6.82-6.72 (m, 3H), 4.80 (t, J=5.3 Hz, 1H), 3.97 (d, J=5.1 Hz, 2H), 3.81 (t, J=6.5 Hz, 2H), 3.78-3.69 (m, 2H), 3.65-3.56 (m, 2H), 2.80 (t, J=6.5 Hz, 2H), 1.21 (t, J=6.9 Hz, 6H). One exchangeable proton not observed.

b) 2-(3-(2-Hydroxyethyl)phenoxy)acetaldehyde

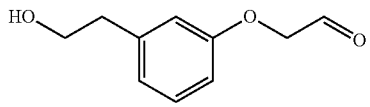 [SMILES: O=CCOc1cccc(CCO)c1]

Concentrated hydrochloric acid (1.5 mL) was added to a solution of 2-(3-(2,2-diethoxyethoxy)phenyl)ethanol (example 24 step a) (0.256 g) in 1,4-dioxane (3 mL) and the resulting mixture was stirred at room temperature for 1.5 hours. The solution was then diluted with water and extracted twice with ethyl acetate. The combined extracts were washed with brine, dried over anhydrous magnesium sulphate and concentrated in vacuo to afford the subtitled compound as a white foam. Yield 0.150 g.

$^1$H NMR (400 MHz, CDCl$_3$) δ 9.86 (s, 1H), 7.28-7.13 (m, 1H), 6.92-6.66 (m, 3H), 4.57 (s, 2H), 3.87 (t, J=6.5 Hz, 2H), 2.86 (t, J=6.5 Hz, 2H). One exchangeable proton not observed.

c) (9-(2-(3-(2-Hydroxyethyl)phenoxy)ethyl)-1-oxa-4,9-diazaspiro[5.5]undecan-4-yl)(2-methylthiazol-4-yl)methanone

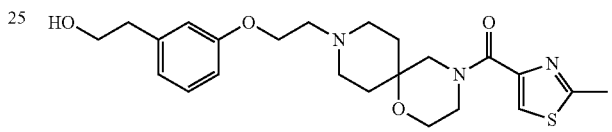

A suspension of 2-(3-(2-hydroxyethyl)phenoxy)acetaldehyde (example 24, step b) (0.143 g) and (2-methylthiazol-4-yl)(1-oxa-4,9-diazaspiro[5.5]undecan-4-yl)methanone trifluoroacetate (example 4, step h) (0.314 g) in methanol (10 mL) was treated with acetic acid (0.045 mL) and stirred at room temperature for 30 minutes. The mixture was cooled in ice-water, treated with sodium triacetoxyborohydride (0.254 g) and stirred over 3 days, allowing the ice-bath to expire. The resulting solution was purified by flash chromatography on silica eluted with 1:15:84 triethylamine:methanol:dichloromethane to afford the crude product (0.243 g). A second purification by flash chromatography on silica eluted with 1:5:94 triethylamine:methanol:dichloromethane afforded the slightly impure subtitled compound as a brown gum. Yield 0.122 g.

m/z 446 (M+H)$^+$ (APCI)

d) 2-(3-(2-(4-(2-Methylthiazole-4-carbonyl)-1-oxa-4,9-diazaspiro[5.5]undecan-9-yl)ethoxy)phenyl)acetaldehyde

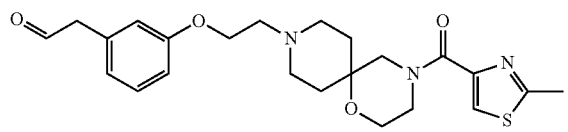 [SMILES: Cc1nc(C(=O)N2CCOC3(CCN(CCOc4cccc(CC=O)c4)CC3)C2)cs1]

A solution of (9-(2-(3-(2-hydroxyethyl)phenoxy)ethyl)-1-oxa-4,9-diazaspiro[5.5]undecan-4-yl)(2-methylthiazol-4-yl)methanone (example 24, step c) (0.152 g) in DCM (5 mL) was cooled in ice-water and treated with trifluoroacetic acid (0.039 mL) and stirred for 5 minutes. Dess-Martin periodinane (0.221 g) was added and the mixture was removed from the cooling bath and stirred at room temperature for 25 minutes. The reaction was quenched by the addition of saturated sodium thiosulphate solution (5 mL), saturated sodium bicarbonate solution (5 mL) and ethyl acetate (5 mL), and the resulting two-phase mixture was stirred for 10 minutes. The mixture was then extracted twice with ethyl acetate, and the combined organic extracts washed with brine. Acetic acid (0.1 mL) was added, and then the acidified extracts were dried over anhydrous magnesium sulphate and concentrated in vacuo to afford the subtitled compound as a brown gum. Yield 0.118 g.

m/z 444 (M+H)$^+$ (APCI)

e) (R)-4-Hydroxy-7-(1-hydroxy-2-(3-(2-(4-(2-methylthiazole-4-carbonyl)-1-oxa-4,9-diazaspiro[5.5]undecan-9-yl)ethoxy)phenethylamino)ethyl)benzo[d]thiazol-2(3H)-one ditrifluoroacetate hour. More sodium triacetoxyborohydride (0.506 g) was added and the mixture was stirred overnight, allowing it to slowly warm to room temperature. The next day, the mixture was cooled again in ice-water, and treated with sodium triacetoxyborohydride (0.254 g) and stirred in ice-water for 45 minutes then concentrated in vacuo. The residue was dissolved in a mixture of acetonitrile (3 mL) and water (1.5 mL) and purified by preparative HPLC (Sunfire™, Gradient: 5-50% acetonitrile in 0.2% aqueous TFA). Fractions containing product were concentrated in vacuo and co-evaporated from acetonitrile twice to give a colourless residue. The residue was triturated with diethyl ether to give a solid, which was collected by filtration, washed with diethyl ether and dried in vacuo at room temperature to afford the titled compound as a white solid. Yield 0.011 g.

m/z 654 (M+H)$^+$ (APCI)

$^1$H NMR (400 MHz, D$_6$-DMSO) δ 11.68 (br s, 1H), 10.22 (br s, 1H), 8.00 (s, 1H), 7.29 (t, J=7.9 Hz, 1H), 6.96-6.84 (m, 4H), 6.77 (d, J=8.5 Hz, 1H), 6.48 (br s, 1H), 4.93-4.85 (m,

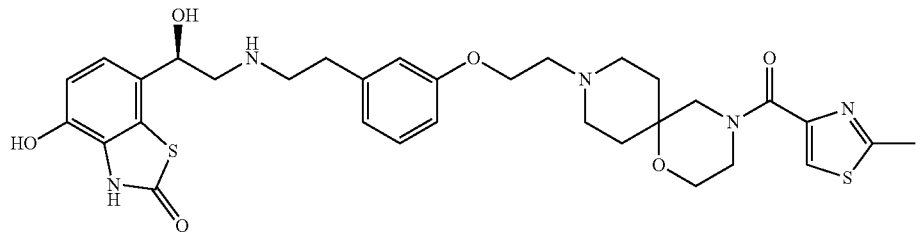 [SMILES: Cc1nc(C(=O)N2CCOC3(CCN(CCOc4cccc(CCNC[C@H](O)c5ccc(O)c6[nH]c(=O)sc56)c4)CC3)C2)cs1]

A solution of (R)-7-(2-amino-1-hydroxyethyl)-4-hydroxybenzo[d]thiazol-2(3H)-one hydrochloride (WO2007027134, example 1, step d) (0.105 g) in methanol (2 mL) was treated with acetic acid (0.023 mL) and stirred for 5 minutes. A solution of 2-(3-(2-(4-(2-methylthiazole-4-carbonyl)-1-oxa-4,9-diazaspiro[5.5]undecan-9-yl)ethoxy)phenyl)acetaldehyde (example 24, step d) (0.117 g) in methanol (3 mL) was then added and the resulting mixture was stirred at room temperature for 1 hour, before cooling in ice-water and treating with sodium triacetoxyborohydride (0.085 g). The mixture was stirred in ice for 1 hour, and then more sodium triacetoxyborohydride (0.086 g) was added. The mixture was stirred in ice for 1 hour, then more sodium triacetoxyborohydride (0.169 g) was added and the mixture was stirred for 1

1H), 4.36-4.27 (m, 2H), 3.83-3.61 (m, 6H), 3.60-3.51 (m, 2H), 3.50-3.42 (m, 2H), 3.24-3.02 (m, 6H), 3.02-2.84 (m, 2H), 2.69 (s, 3H), 2.15-2.06 (m, 2H), 1.88-1.67 (m, 2H). Three exchangeable protons not observed.

EXAMPLE 25

(R)-8-Hydroxy-5-(1-hydroxy-2-(3-((4-(2-(trifluoromethyl)thiazole-4-carbonyl)-1-oxa-4,9-diazaspiro[5.5]undecan-9-yl)methyl)phenethylamino)ethyl)quinolin-2(1H)-one ditrifluoroacetate

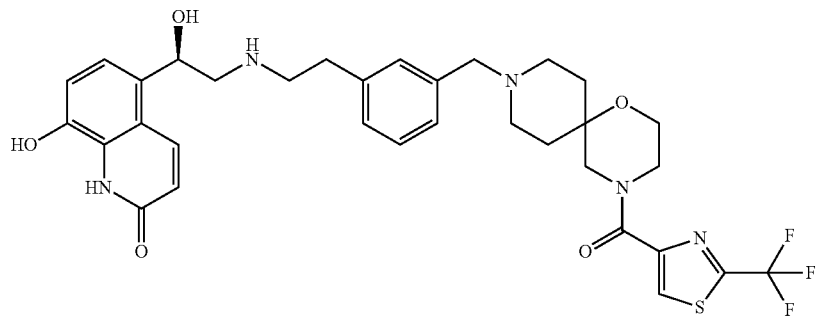 [SMILES: O=C(c1csc(C(F)(F)F)n1)N1CCOC2(CCN(Cc3cccc(CCNC[C@H](O)c4ccc(O)c5[nH]c(=O)ccc45)c3)CC2)C1]

a) 1-Oxa-4,9-diazaspiro[5.5]undecan-4-yl(2-(trifluoromethyl)thiazol-4-yl)methanone trifluoroacetate

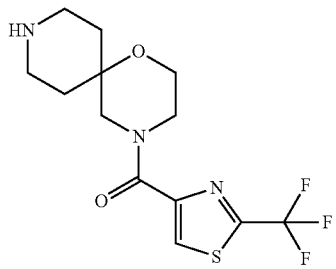 [SMILES: O=C(c1csc(C(F)(F)F)n1)N1CCOC2(CCNCC2)C1]

A solution of tert-butyl 1-oxa-4,9-diazaspiro[5.5]undecane-9-carboxylate hydrochloride (WuXi PharmaTech) (0.594 g) and 2-(trifluoromethyl)thiazole-4-carboxylic acid (0.4 g) in DMF (10 mL) was treated with triethylamine (0.848 mL) and cooled to 0° C. HATU (1.003 g) was added and the mixture stirred at 20° C. for 2 hours. The mixture was partitioned between ethyl acetate and brine, the organic layer was washed twice with brine, dried over sodium sulphate, filtered and the solvent evaporated under reduced pressure. The crude product was purified by flash silica chromatography eluting with 40% ethyl acetate in isohexane to yield the product as the free base. This was dissolved in dichloromethane (40 mL) and treated with trifluoroacetic acid (10 mL) and then the mixture was allowed to stand at 20° C. for 1 hour. Toluene (60 mL) was added and the solvent removed under reduced pressure to afford the subtitled compound. Yield 0.740 g.

m/z 336 (M+H)$^+$ (APCI)

b) (9-(3-(2-Hydroxyethyl)benzyl)-1-oxa-4,9-diazaspiro[5.5]undecan-4-yl)(2-(trifluoromethyl)thiazol-4-yl)methanone

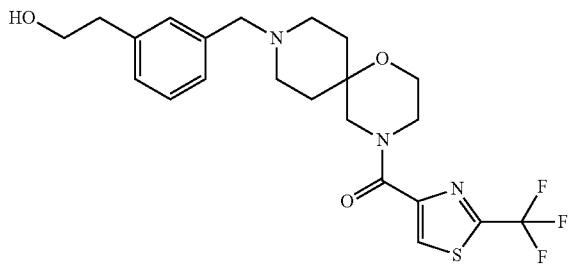 [SMILES: O=C(c1csc(C(F)(F)F)n1)N1CCOC2(CCN(Cc3cccc(CCO)c3)CC2)C1]

2-(3-(Bromomethyl)phenyl)ethanol (example 6, step a) (0.354 g) was added to a solution of 1-oxa-4,9-diazaspiro[5.5]undecan-4-yl(2-(trifluoromethyl)thiazol-4-yl)methanone trifluoroacetate (example 25, step a) (0.74 g) and triethylamine (0.689 mL) in acetonitrile (15 mL) and the mixture stirred at 20° C. for 2 hours. The solvent was evaporated under reduced pressure and the residue partitioned between ethyl acetate and saturated sodium bicarbonate solution, the organic layer was dried over sodium sulphate, filtered and the solvent evaporated under reduced pressure. The crude product was purified by flash silica chromatography using 1% triethylamine and 3% methanol in dichloromethane as solvent. Pure fractions were evaporated to dryness to afford the subtitled compound. Yield 0.640 g.

m/z 470 (M+H)$^+$ (APCI)

c) (R)-5-(1-(tert-Butyldimethylsilyloxy)-2-(3-((4-(2-(trifluoromethyl)thiazole-4-carbonyl)-1-oxa-4,9-diazaspiro[5.5]undecan-9-yl)methyl)phenethylamino)ethyl)-8-hydroxyquinolin-2(1H)-one

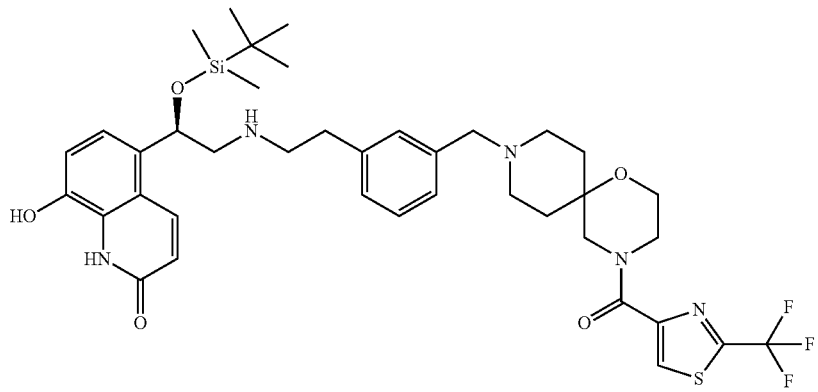 [SMILES: CC(C)(C)[Si](C)(C)O[C@@H](CNCCc1cccc(CN2CCC3(CC2)CN(C(=O)c2csc(C(F)(F)F)n2)CCO3)c1)c1ccc(O)c2[nH]c(=O)ccc12]

A solution of (9-(3-(2-hydroxyethyl)benzyl)-1-oxa-4,9-diazaspiro[5.5]undecan-4-yl)(2-(trifluoromethyl)thiazol-4-yl)methanone (example 25, step b) (0.211 g) in dichloromethane (10 mL) was treated with trifluoroacetic acid (0.035 mL) followed by Dess-Martin periodinane (0.266 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.026 mL) and the solvent evaporated under reduced pressure. The residue was dissolved in methanol (2 mL) and added to a solution of (R)-5-(2-amino-1-(tert-butyldimethylsilyloxy)ethyl)-8-hydroxyquinolin-2(1H)-one (WO2004106333) (0.150 g) and acetic acid (0.026 mL) in methanol (10 mL). The mixture was cooled in an ice bath and treated with sodium triacetoxyborohydride (0.143 g) and then the mixture was stirred at room temperature for 18 hours. The methanol was removed under reduced pressure and the residue was partitioned between saturated sodium bicarbonate solution and ethyl acetate, the organic layer was dried over sodium sulphate, filtered and the solvent removed under reduced pressure. The crude product was purified by flash silica chromatography using 1% '880' aqueous ammonia and 8% methanol in dichloromethane as solvent. Pure fractions were evaporated to dryness to afford the subtitled compound. Yield 0.11 g.

m/z 786 (M+H)$^+$ (APCI)

d) (R)-8-Hydroxy-5-(1-hydroxy-2-(3-((4-(2-(trifluoromethyl)thiazole-4-carbonyl)-1-oxa-4,9-diazaspiro[5.5]undecan-9-yl)methyl)phenethylamino)ethyl)quinolin-2(1H)-one ditrifluoroacetate

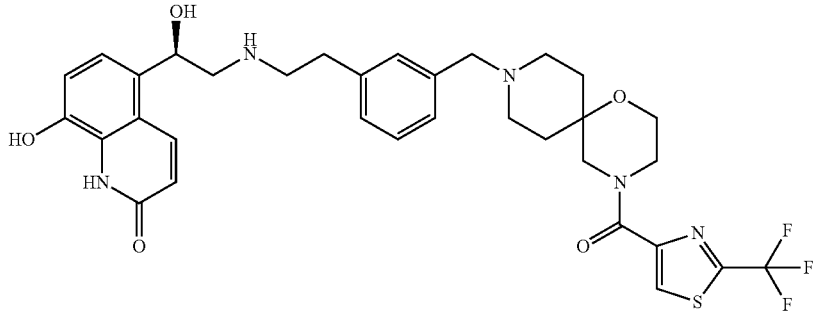 [SMILES: O=C(c1csc(C(F)(F)F)n1)N1CCOC2(CCN(Cc3cccc(CCNC[C@H](O)c4ccc(O)c5[nH]c(=O)ccc45)c3)CC2)C1]

Triethylamine trihydrofluoride (0.030 mL) in methanol (1 mL) was added to a solution of (R)-5-(1-(tert-butyldimethylsilyloxy)-2-(3-((4-(2-(trifluoromethyl)thiazole-4-carbonyl)-1-oxa-4,9-diazaspiro[5.5]undecan-9-yl)methyl)phenethylamino)ethyl)-8-hydroxyquinolin-2(1H)-one (example 25, step c) (0.11 g) in THF (4 mL) and the resultant solution allowed to stand at 20° C. for 18 hours. The solvents were removed under reduced pressure and the crude product was purified by preparative HPLC (Sunfire™, Gradient: 10-40% acetonitrile in 0.2% aqueous TFA). The fractions containing the desired compound were evaporated to dryness to afford the titled compound 0.075 g.

m/z 672 (M+H)⁺ (APCI)

¹H NMR (400 MHz, D₆-DMSO, 90° C.) δ 8.78 (s, 1H), 8.52 (s, 1H), 8.18 (d, J=49.2 Hz, 1H), 7.45-7.33 (m, 4H), 7.14 (d, J=21.8 Hz, 1H), 7.00 (d, J=19.8 Hz, 1H), 6.54 (d, J=21.9 Hz, 1H), 5.39-5.33 (m, 1H), 4.29 (s, 2H), 3.75-3.63 (m, 4H), 3.59 (s, 2H), 3.28 (t, J=8.1 Hz, 2H), 3.21-3.00 (m, 8H), 2.10-1.97 (m, 2H), 1.84-1.67 (m, 2H). Five exchangeable protons not observed.

EXAMPLE 26

(R)-4-Hydroxy-7-(1-hydroxy-2-(3-((4-(2-(trifluoromethyl)thiazole-4-carbonyl)-1-oxa-4,9-diazaspiro[5.5]undecan-9-yl)methyl)phenethylamino)ethyl)benzo[d]thiazol-2(3H)-one ditrifluoroacetate

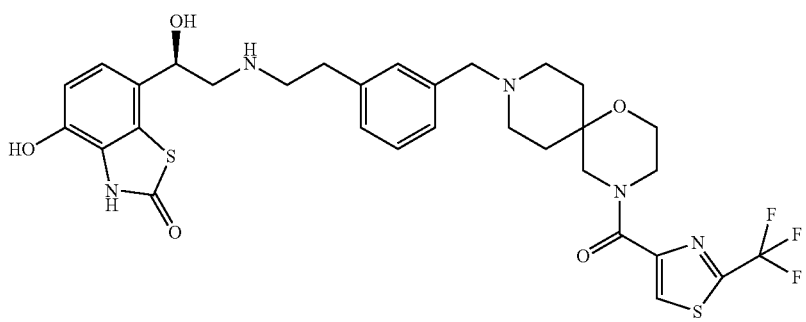 [SMILES: O=C(c1csc(C(F)(F)F)n1)N1CCOC2(CCN(Cc3cccc(CCNC[C@H](O)c4ccc(O)c5[nH]c(=O)sc45)c3)CC2)C1]

A solution of (9-(3-(2-hydroxyethyl)benzyl)-1-oxa-4,9-diazaspiro[5.5]undecan-4-yl)(2-(trifluoromethyl)thiazol-4-yl)methanone (example 25, step b) (0.268 g) in dichloromethane (10 mL) was treated with trifluoroacetic acid (0.044 mL) followed by Dess-Martin periodinane (0.339 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.033 mL) and the solvent evaporated under reduced pressure. The residue was dissolved in methanol (2 mL) and added to a solution at 0° C. of (R)-7-(2-amino-1-hydroxyethyl)-4-hydroxybenzo[d]thiazol-2(3H)-one hydrochloride (WO2007027134, example 1, step d) (0.15 g) and acetic acid (0.033 mL) in methanol (10 mL). Sodium cyanoborohydride (0.054 g) was added and the mixture stirred at room temperature for 18 hours. Most of the methanol was evaporated under reduced pressure and the remainder partitioned between THF (50 mL), brine (10 mL) and saturated sodium bicarbonate solution (1 mL). The organic layer was dried over sodium sulphate, filtered and the solvent removed under reduced pressure. The crude product was purified by preparative HPLC (Sunfire™, Gradient: 10-40% acetonitrile in 0.2% aqueous TFA). The fractions containing the desired compound were evaporated to dryness to afford the titled compound. Yield 0.13 g.

m/z 678 (M+H)⁺ (APCI)

¹H NMR (400 MHz, D₆-DMSO, 90° C.) δ 11.27 (s, 1H), 8.74 (s, 1H), 8.52 (s, 1H), 7.45-7.31 (m, 4H), 6.93 (d, J=41.1 Hz, 1H), 6.77 (d, J=36.9 Hz, 1H), 4.97-4.87 (m, 1H), 4.27 (s, 2H), 3.74-3.69 (m, 2H), 3.69-3.64 (m, 2H), 3.59 (s, 2H), 3.25

(t, J=14.5 Hz, 2H), 3.19-2.99 (m, 8H), 2.09-1.97 (m, 2H), 1.84-1.69 (m, 2H). Four exchangeable protons not observed.

EXAMPLE 27

(R)-4-Hydroxy-7-(1-hydroxy-2-(2-(5-((4-(5-methylthiophene-2-carbonyl)-1-oxa-4,9-diazaspiro[5.5]undecan-9-yl)methyl)thiophen-3-yl)ethylamino)ethyl)benzo[d]thiazol-2(3H)-one ditrifluoroacetate

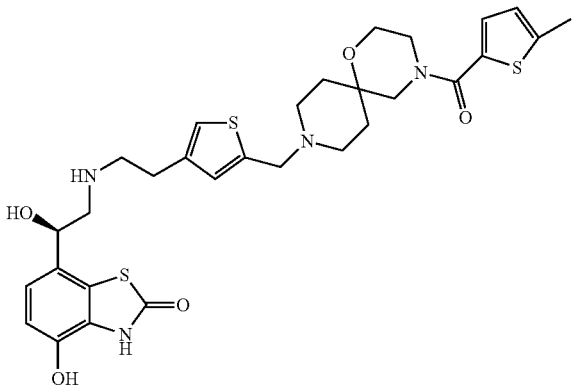 [SMILES: Cc1ccc(C(=O)N2CCOC3(CCN(Cc4cc(CCNC[C@H](O)c5ccc(O)c6[nH]c(=O)sc56)cs4)CC3)C2)s1]

a) tert-Butyldimethyl(2-(thiophen-3-yl)ethoxy)silane

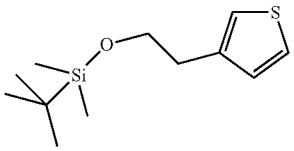

tert-Butylchlorodimethylsilane (3.88 g) was added to a stirred solution of 2-(thiophen-3-yl)ethanol (3.00 g) and 1H-imidazole (4.78 g) in DMF (30 mL) cooled in ice bath. After 16 h, the reaction mixture was diluted with ethyl acetate (300 mL), washed with water (3×150 mL) and evaporated in vacuo. Purification was by silica gel chromatography eluting with isohexane and then 1:5 ethyl acetate:isohexane, to collect the subtitled compound as an oil. Yield 5.2 g.

$^1$H NMR (300 MHz, CDCl$_3$) δ 7.23 (dd, J=2.9, 4.9 Hz, 1H), 7.01-6.99 (m, 1H), 6.97 (dd, J=1.3, 4.9 Hz, 1H), 3.80 (t, J=6.8 Hz, 2H), 2.85 (t, J=6.8 Hz, 2H), 0.88 (s, 9H), 0.01 (s, 6H).

b) Mixture of 4-(2-(tert-butyldimethylsilyloxy)ethyl)thiophene-2-carbaldehyde with 3-(2-(tert-butyldimethylsilyloxy)ethyl)thiophene-2-carbaldehyde

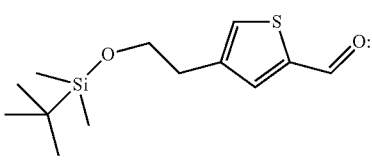

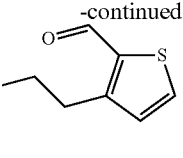

n-Butyllithium (1.6M in hexanes, 7 mL) was added dropwise to stirred solution of tert-butyldimethyl(2-(thiophen-3-yl)ethoxy)silane (example 27, step a) (2.210 g) in tetrahydrofuran (60 mL) cooled at −78° C. After the addition, the reaction mixture was stirred in an ice bath for 1 h and then cooled to −78° C. N,N-dimethylformamide (9.00 g) was added dropwise over 5 min and after a further 10 min the cooling bath was removed. After 1 h, the reaction mixture was partitioned between water and ethyl acetate and the ethyl acetate solution washed twice with water, once with brine, dried over sodium sulphate, filtered and evaporated in vacuo. Purification by silica gel chromatography eluting with 1:20 ethyl acetate:isohexane, gave a 4:1 mixture of 4-(2-(tert-butyldimethylsilyloxy)ethyl)thiophene-2-carbaldehyde and 3-(2-(tert-butyldimethylsilyloxy)ethyl)thiophene-2-carbaldehyde by $^1$H NMR as an oil. Yield 1.3 g.

4-(2-(tert-butyldimethylsilyloxy)ethyl)thiophene-2-carbaldehyde $^1$H NMR (400 MHz, CDCl$_3$) δ 9.93 (d, J=1.2 Hz, 1H), 7.71 (d, J=1.5 Hz, 1H), 7.52 (s, 1H), 3.92-3.84 (m, 2H), 2.91 (t, J=6.5 Hz, 2H), 0.92 (s, 9H), 0.04 (s, 6H).

3-(2-(tert-butyldimethylsilyloxy)ethyl)thiophene-2-carbaldehyde $^1$H NMR (400 MHz, CDCl$_3$) δ 10.08 (s, 1H), 7.69 (d, J=5.0 Hz, 1H), 7.09 (d, J=5.0 Hz, 1H), 3.92-3.84 (m, 2H), 3.22 (t, J=6.5 Hz, 2H), 0.89 (s, 9H), −0.01 (s, 6H).

c) (9-((4-(2-(tert-Butyldimethylsilyloxy)ethyl)thiophen-2-yl)methyl)-1-oxa-4,9-diazaspiro[5.5]undecan-4-yl)(5-methylthiophen-2-yl)methanone

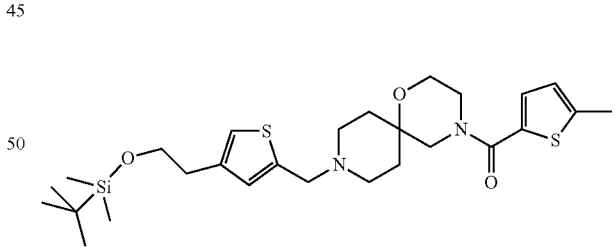

(5-Methylthiophen-2-yl)(1-oxa-4,9-diazaspiro[5.5]undecan-4-yl)methanone trifluoroacetate (example 9, step b) (0.230 g) was added to a stirred solution of a 4:1 mixture of 4-(2-(tert-butyldimethylsilyloxy)ethyl)thiophene-2-carbaldehyde and 3-(2-(tert-butyldimethylsilyloxy)ethyl)thiophene-2-carbaldehyde (example 27, step b) (0.20 g) and AcOH (0.033 mL) in N-methyl-2-pyrrolidinone (3 mL). After 5 min, sodium triacetoxyborohydride (0.35 g) was added. After 16 h water was added and the mixture extracted with ethyl acetate. The ethyl acetate layer was washed three times with water and evaporated in vacuo. Purification by silica gel chromatography eluting with 20:80:5 ethyl acetate:

isohexane:triethylamine, separated the two isomeric products and gave the subtitled compound as a gum. Yield 0.21 g.

$^1$H NMR (400 MHz, CDCl$_3$) δ 7.09 (d, J=3.8 Hz, 1H), 6.86 (s, 1H), 6.75 (s, 1H), 6.69 (d, J=3.8 Hz, 1H), 3.78 (t, J=6.6 Hz, 2H), 3.76-3.69 (m, 4H), 3.64 (s, 2H), 3.56 (s, 2H), 2.76 (t, J=7.1 Hz, 2H), 2.62-2.54 (m, 2H), 2.50 (s, 3H), 2.41-2.32 (m, 2H), 1.90-1.82 (m, 2H), 1.63-1.52 (m, 2H), 0.88 (s, 9H), 0.01 (s, 6H).

d) (9-((4-(2-Hydroxyethyl)thiophen-2-yl)methyl)-1-oxa-4,9-diazaspiro[5.5]undecan-4-yl)(5-methylthiophen-2-yl)methanone

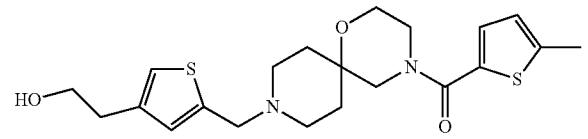 [SMILES: Cc1ccc(C(=O)N2CCOC3(CCN(Cc4cc(CCO)cs4)CC3)C2)s1]

Tetrabutylammonium fluoride (1M in tetrahydrofuran, 2 mL) was added to a solution of (9-((4-(2-(tert-butyldimethylsilyloxy)ethyl)thiophen-2-yl)methyl)-1-oxa-4,9-diazaspiro[5.5]undecan-4-yl)(5-methylthiophen-2-yl)methanone (example 27, step c) (0.65 g) in tetrahydrofuran (7 mL). After 1 h, the solution was evaporated in vacuo. Purification by silica gel chromatography, eluting with 20:1 ethyl acetate:triethylamine, gave the subtitled compound as a gum. Yield 0.45 g.

$^1$H NMR (400 MHz, CDCl$_3$) δ 7.09 (d, J=3.7 Hz, 1H), 6.92 (s, 1H), 6.77 (s, 1H), 6.69 (dd, J=1.0, 3.7 Hz, 1H), 3.83 (t, J=6.4 Hz, 2H), 3.76-3.70 (m, 4H), 3.66 (s, 2H), 3.56 (s, 2H), 2.82 (t, J=6.4 Hz, 2H), 2.62-2.55 (m, 2H), 2.50 (s, 3H), 2.43-2.33 (m, 2H), 1.91-1.82 (m, 2H), 1.65-1.50 (m, 2H). One exchangeable proton not observed.

e) 2-(5-((4-(5-Methylthiophene-2-carbonyl)-1-oxa-4,9-diazaspiro[5.5]undecan-9-yl)methyl)thiophen-3-yl)acetaldehyde

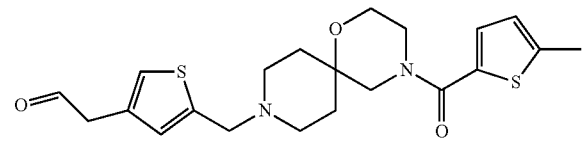 [SMILES: Cc1ccc(C(=O)N2CCOC3(CCN(Cc4cc(CC=O)cs4)CC3)C2)s1]

Dess-Martin periodinane (0.35 g) was added to a stirred solution of (9-((4-(2-hydroxyethyl)thiophen-2-yl)methyl)-1-oxa-4,9-diazaspiro[5.5]undecan-4-yl)(5-methylthiophen-2-yl)methanone (example 27, step d) (0.19 g) and trifluoroacetic acid (0.052 mL) in DCM (5 mL). After 1 h, ethyl acetate (30 mL) was added followed by a mixture of saturated sodium thiosulphate solution (5 mL) and saturated sodium bicarbonate solution (5 mL). The reaction mixture was shaken well and separated. The ethyl acetate solution was washed with saturated sodium bicarbonate solution, water and brine. Acetic acid (0.07 mL) was added, the solution dried over sodium sulphate, filtered and evaporated in vacuo (bath temperature ~30° C.) to give the subtitled compound as a gum. Yield 0.19 g. Used directly.

f) (R)-4-Hydroxy-7-(1-hydroxy-2-(2-(5-((4-(5-methylthiophene-2-carbonyl)-1-oxa-4,9-diazaspiro[5.5]undecan-9-yl)methyl)thiophen-3-yl)ethylamino)ethyl)benzo[d]thiazol-2(3H)-one ditrifluoroacetate

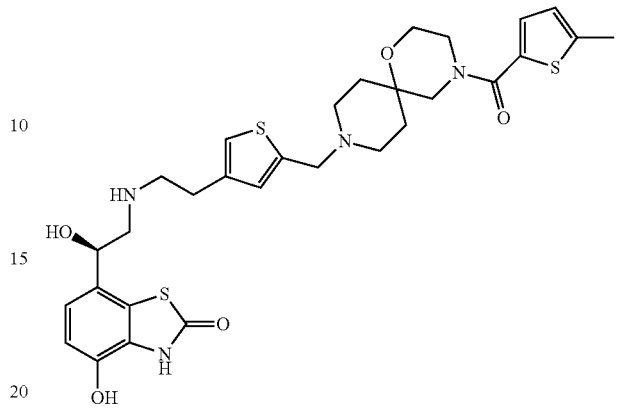

Acetic acid (0.039 g) was added to a stirred solution of (R)-7-(2-amino-1-hydroxyethyl)-4-hydroxybenzo[d]thiazol-2(3H)-one hydrochloride (WO2007027134, example 1, step d) (0.17 g) and 2-(5-((4-(5-methylthiophene-2-carbonyl)-1-oxa-4,9-diazaspiro[5.5]undecan-9-yl)methyl)thiophen-3-yl)acetaldehyde (example 27, step e) (0.19 g) in MeOH (10 mL). After 1 min, sodium cyanoborohydride (0.10 g) was added. After 3 h, the reaction mixture was concentrated in vacuo to ~2 mL, THF (20 mL) was added and the solution washed with a mixture of brine (10 mL) and saturated sodium bicarbonate solution (2 mL). The organic solution was dried over sodium sulphate, filtered and evaporated in vacuo. The solid was dissolved in methanol and purified by preparative HPLC (Sunfire™, Gradient: 10-40% acetonitrile in 0.2% aqueous TFA). The fractions containing the product were combined and evaporated to dryness in vacuo. Acetonitrile was added and the solution evaporated in vacuo, and this process was repeated. Diethyl ether was added and the gum triturated to give the titled compound as a solid. Yield 0.097 g.
m/z 629 (M+H)$^+$ (APCI)

$^1$H NMR (400 MHz, D$_6$-DMSO) δ 11.67 (s, 1H), 10.23 (s, 1H), 9.82-9.67 (m, 1H), 8.93-8.67 (m, 2H), 7.46 (s, 1H), 7.25-7.22 (m, 1H), 7.17 (s, 1H), 6.93 (d, J=8.8 Hz, 1H), 6.77 (d, J=8.8 Hz, 1H), 6.60-6.46 (m, 1H), 6.51-6.46 (m, 1H), 4.92-4.86 (m, 1H), 4.68-4.51 (m, 2H), 3.74-2.88 (m, 16H), 2.46 (s, 3H), 2.15-2.04 (m, 2H), 1.69-1.56 (m, 2H).

EXAMPLE 28

(R)-5-(2-(3-Fluoro-5-((4-(2-methylthiazole-4-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

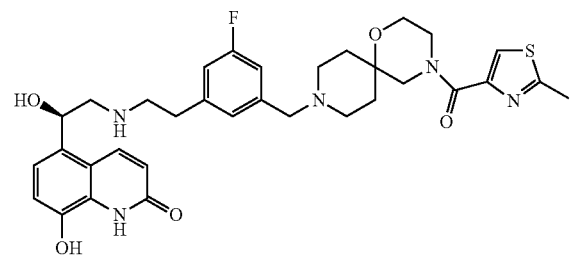

A solution of 2-(3-fluoro-5-((4-(2-methylthiazole-4-carbonyl)-1-oxa-4,9-diazaspiro[5.5]undecan-9-yl)methyl)phenyl)acetaldehyde (example 19, step c) (0.2 g) in methanol (3 mL) was added to a mixture of (R)-5-(2-amino-1-(tert-butyldimethylsilyloxy)ethyl)-8-hydroxyquinolin-2(1H)-one (WO2004106333) (0.23 g) and acetic acid (0.027 mL) in methanol (3 mL). The resulting mixture was stirred for 5 min then cooled to 0° C. Sodium cyanoborohydride (0.044 g) was then added and the mixture allowed to warm to RT and stirred for 2 h. The solvent was evaporated in vacuo and purification was by silica gel chromatography eluting with 95:5:0.5 to 89:10:1 DCM:methanol:'880' aqueous ammonia gradient. The fractions containing product were combined and evaporated in vacuo. The residue was dissolved in THF (3 mL), triethylamine trihydrofluoride (0.11 mL) was added and the mixture stirred overnight. The reaction was concentrated in vacuo. Purification was by preparative HPLC (Sunfire™, Gradient: 5-50% acetonitrile in 0.2% aqueous TFA). The fractions containing product were combined and evaporated to give the titled compound as a white solid. Yield 0.021 g.

m/z 636 (M+H)+ (APCI)

$^1$H NMR (400 MHz, D$_6$-DMSO, 90° C.) δ 8.15 (d, J=10.0 Hz, 1H), 7.90 (s, 1H), 7.29-7.17 (m, 3H), 7.13 (d, J=8.2 Hz, 1H), 6.99 (d, J=8.2 Hz, 1H), 6.55 (d, J=9.7 Hz, 1H), 5.37-5.29 (m, 1H), 4.35-4.19 (m, 2H), 3.75-3.59 (m, 6H), 3.34-2.98 (m, 10H), 2.67 (s, 3H), 2.06-1.93 (m, 2H), 1.83-1.69 (m, 2H). Six exchangeable protons not observed.

EXAMPLE 29

(R)-7-(2-(4-Fluoro-3-((4-(5-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

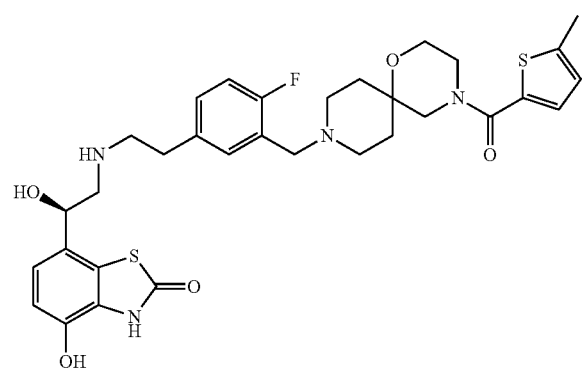 [SMILES: Cc1ccc(C(=O)N2CCOC3(CCN(Cc4cc(CCNC[C@H](O)c5ccc(O)c6[nH]c(=O)sc56)ccc4F)CC3)C2)s1]

a) 2-(4-Fluoro-3-methylphenyl)acetic acid

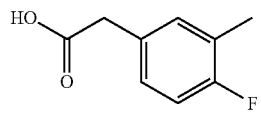

2-(4-Fluoro-3-methylphenyl)acetonitrile (1 g) and sodium hydroxide (0.8 g) were combined in a mixture of methanol (10 mL) and water (3 mL). The resulting mixture was then heated at reflux overnight. The reaction was concentrated in vacuo and the residue dissolved in water (25 mL). The aqueous phase was washed with ether (2×25 mL), acidified with concentrated hydrochloric acid and extracted with ether (3×25 mL). The combined organic solutions were washed with brine, dried over sodium sulphate, filtered and evaporated in vacuo to afford the subtitled compound as a white solid. Yield 1.1 g.

$^1$H NMR (300 MHz, D$_6$-DMSO) δ 12.31 (s, 1H), 7.20-6.99 (m, 3H), 3.52 (s, 2H), 2.21 (s, 3H).

b) (9-(2-Fluoro-5-(2-hydroxyethyl)benzyl)-1-oxa-4,9-diazaspiro[5.5]undecan-4-yl)(5-methylthiophen-2-yl)methanone

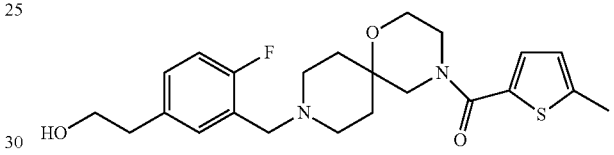

Benzoyl peroxide (0.058 g) was added to a mixture of 2-(4-fluoro-3-methylphenyl)acetic acid (0.6 g) (example 29, step a) and N-bromosuccinimide (0.7 g) in DCM (10 mL). The resulting mixture was heated at reflux for 4 h. DCM (10 mL) and water (20 mL) were added and the organic phase separated. The organic phase was washed with brine (20 mL), dried over sodium sulphate, filtered and evaporated in vacuo. The residue was redissolved in THF (10 mL) and cooled in an ice bath. A solution of borane dimethyl sulfide (2M in THF, 4.46 mL) was added dropwise and the mixture stirred for 1 h. Methanol (2 mL) was cautiously added, and once bubbling had ceased the solvent was evaporated in vacuo. The residue was redissolved in acetonitrile (10 mL) and (5-methylthiophen-2-yl)(1-oxa-4,9-diazaspiro[5.5]undecan-4-yl)methanone trifluoroacetate (example 9, step b) (0.7 g) was added, followed by triethylamine (1.49 mL). The resulting mixture was stirred overnight and then concentrated in vacuo. Purification was by silica gel chromatography eluting with 99:1:0.1 to 97:3:0.3 DCM:methanol:'880' aqueous ammonia gradient. The fractions containing product were combined and evaporated to give the subtitled compound as a foam. Yield 0.46 g.

m/z 433 (M+H)+ (APCI)

$^1$H NMR (400 MHz, D$_6$-DMSO) δ 7.22-7.16 (m, 2H), 7.14-7.07 (m, 1H), 6.97 (dd, J=10.0, 8.5 Hz, 1H), 6.80-6.76 (m, 1H), 3.67-3.57 (m, 6H), 3.50-3.45 (m, 4H), 2.70 (t, J=6.8 Hz, 2H), 2.46 (s, 3H), 2.41-2.35 (m, 4H), 1.76-1.67 (m, 2H), 1.55-1.45 (m, 2H). One exchangeable proton not observed.

c) (R)-7-(2-(4-Fluoro-3-((4-(5-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

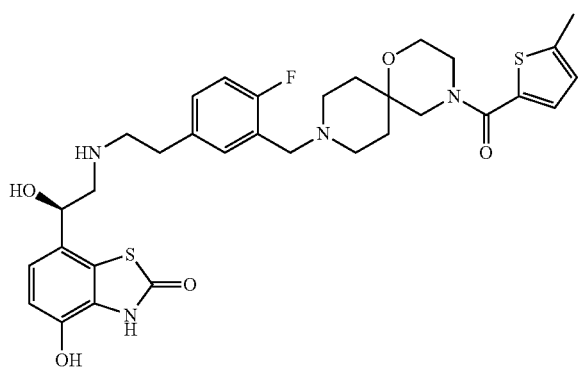 [SMILES: Cc1ccc(C(=O)N2CCOC3(CCN(Cc4cc(CCNC[C@H](O)c5ccc(O)c6[nH]c(=O)sc56)ccc4F)CC3)C2)s1]

TFA (0.032 mL) was added to a solution of (9-(2-fluoro-5-(2-hydroxyethyl)benzyl)-1-oxa-4,9-diazaspiro[5.5]undecan-4-yl)(5-methylthiophen-2-yl)methanone (example 29, step b) (0.18 g) in DCM (5 mL) at 0° C. The mixture was stirred for 5 min then Dess-Martin periodinane (0.27 g) was added. The resulting yellow solution was allowed to warm to RT and stirred for 1 h. A mixture of saturated sodium thiosulphate solution (5 mL), saturated sodium bicarbonate solution (5 mL) and ethyl acetate (25 mL) was then added and the resulting mixture stirred vigorously for 10 min. The aqueous phase was separated and extracted with ethyl acetate (25 mL). The combined organic solutions were washed with brine, acidified with a few drops of acetic acid, dried over sodium sulphate, filtered and evaporated in vacuo. The residue was dissolved in methanol (5 mL), acetic acid (0.012 mL) and (R)-7-(2-amino-1-hydroxyethyl)-4-hydroxybenzo[d]thiazol-2(3H)-one hydrochloride (WO2007027134, example 1, step d) (0.17 g) were then added and the mixture stirred for 5 min before cooling in an ice bath. Sodium cyanoborohydride (0.039 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined, evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethyl ether to give the titled compound as a white solid. Yield 0.11 g.

m/z 641 (M+H)⁺ (APCI)

$^1$H NMR (400 MHz, D$_6$-DMSO, 90° C.) δ 7.47-7.35 (m, 2H), 7.29-7.17 (m, 2H), 6.93 (d, J=8.2 Hz, 1H), 6.82-6.75 (m, 2H), 4.91 (dd, J=8.1, 5.3 Hz, 1H), 4.32-4.20 (m, 2H), 3.74-3.61 (m, 4H), 3.53 (s, 2H), 3.28-2.93 (m, 10H), 2.46 (s, 3H), 2.05-1.97 (m, 2H), 1.82-1.74 (m, 2H). Six exchangeable protons not observed.

EXAMPLE 30

(R)-methyl 5-(9-(3-(2-(2-hydroxy-2-(4-hydroxy-2-oxo-2,3-dihydrobenzo[d]thiazol-7-yl)ethylamino)ethyl)benzyl)-1-oxa-4,9-diazaspiro[5.5]undecane-4-carbonyl)thiophene-2-carboxylate ditrifluoroacetate

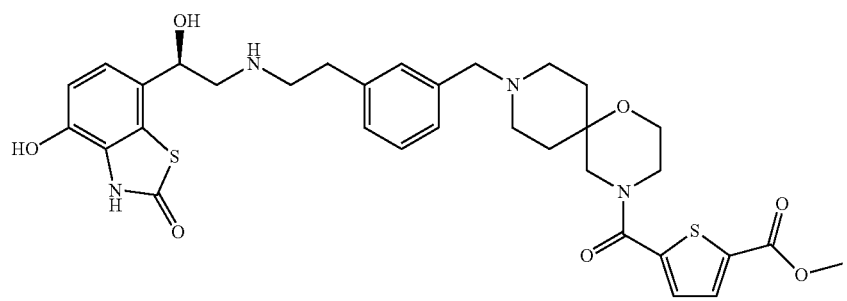 [SMILES: COC(=O)c1ccc(C(=O)N2CCOC3(CCN(Cc4cccc(CCNC[C@H](O)c5ccc(O)c6[nH]c(=O)sc56)c4)CC3)C2)s1]

a) tert-Butyl 4-(5-(methoxycarbonyl)thiophene-2-carbonyl)-1-oxa-4,9-diazaspiro[5.5]undecane-9-carboxylate

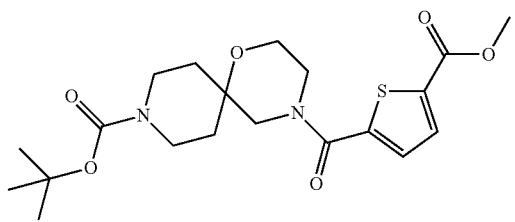 [SMILES: COC(=O)c1ccc(C(=O)N2CCOC3(CCN(C(=O)OC(C)(C)C)CC3)C2)s1]

A solution of tert-butyl 1-oxa-4,9-diazaspiro[5.5]undecane-9-carboxylate hydrochloride (WuXi PharmaTech) (0.6 g) and thiophene-2,5-dicarboxylic acid (1.7 g) in DMF (10 mL) was treated with triethylamine (2.75 mL) and cooled to 0° C. HATU (1.013 g) was added and the mixture stirred at 20° C. for 2 hours. The mixture was partitioned between ethyl acetate and brine containing acetic acid (2 mL), the organic layer was washed twice with brine, dried over sodium sulphate, filtered and the solvent evaporated under reduced pressure. The residue was purified by flash silica chromatography using 1% acetic acid in ethyl acetate as solvent. This material was dissolved in THF (30 mL), treated with carbonyldiimidazole (0.332 g) and the mixture was allowed to stand at 45° C. for 1 hour. Methanol (20 mL) was added and the reaction heated at 50° C. for 30 minutes. The solvent was removed under reduced pressure and the residue was partitioned between ethyl acetate and brine. The organic layer was dried over sodium sulphate, filtered and the solvent evaporated under reduced pressure. The crude product was purified by flash silica chromatography using 40% ethyl acetate in isohexane as solvent. Pure fractions were evaporated to dryness to afford the subtitled compound. Yield 0.45 g.

$^1$H NMR (400 MHz, D$_6$-DMSO, 90° C.) δ 7.72 (d, J=3.8 Hz, 1H), 7.40 (d, J=3.8 Hz, 1H), 3.85 (s, 3H), 3.72-3.68 (m, 2H), 3.63-3.59 (m, 2H), 3.58-3.51 (m, 2H), 3.49 (s, 2H), 3.12-3.04 (m, 2H), 1.77-1.70 (m, 2H), 1.46-1.40 (m, 2H), 1.39 (s, 9H).

b) Methyl 5-(1-oxa-4,9-diazaspiro[5.5]undecane-4-carbonyl)thiophene-2-carboxylate trifluoroacetate

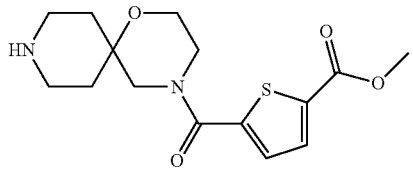

Trifluoroacetic acid (10 mL) was added to a solution of tert-butyl 4-(5-(methoxycarbonyl)thiophene-2-carbonyl)-1-oxa-4,9-diazaspiro[5.5]undecane-9-carboxylate (example 30, step a) (0.45 g) in dichloromethane (40 mL) and the resultant mixture was allowed to stand at 20° C. for 1 hour. Toluene (50 mL) was added and the solvents removed under reduced pressure to afford the subtitled compound. Yield 0.46 g.

m/z 325 (M+H)$^+$ (APCI)

c) Methyl 5-(9-(3-(2-hydroxyethyl)benzyl)-1-oxa-4,9-diazaspiro[5.5]undecane-4-carbonyl)thiophene-2-carboxylate

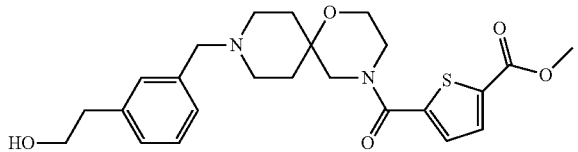 [SMILES: COC(=O)c1ccc(C(=O)N2CCOC3(CCN(Cc4cccc(CCO)c4)CC3)C2)s1]

A solution of methyl 5-(1-oxa-4,9-diazaspiro[5.5]undecane-4-carbonyl)thiophene-2-carboxylate trifluoroacetate (example 30, step b) (0.46 g) and 2-(3-(bromomethyl)phenyl)ethanol (example 6, step a) (0.226 g) in acetonitrile (10 mL) was treated with triethylamine (0.44 mL) and the mixture stirred at 20° C. for 2 hours. The solvent was evaporated under reduced pressure and the residue partitioned between ethyl acetate and saturated sodium bicarbonate solution. The organic layer was dried over sodium sulphate, filtered and the solvent evaporated under reduced pressure. The crude product was purified by flash silica chromatography using 1% triethylamine and 3% methanol in dichloromethane as solvent. Pure fractions were evaporated to dryness to afford the subtitled compound. Yield 0.41 g.

m/z 459 (M+H)$^+$ (APCI)

d) (R)-Methyl 5-(9-(3-(2-(2-hydroxy-2-(4-hydroxy-2-oxo-2,3-dihydrobenzo[d]thiazol-7-yl)ethylamino)ethyl)benzyl)-1-oxa-4,9-diazaspiro[5.5]undecane-4-carbonyl)thiophene-2-carboxylate ditrifluoroacetate

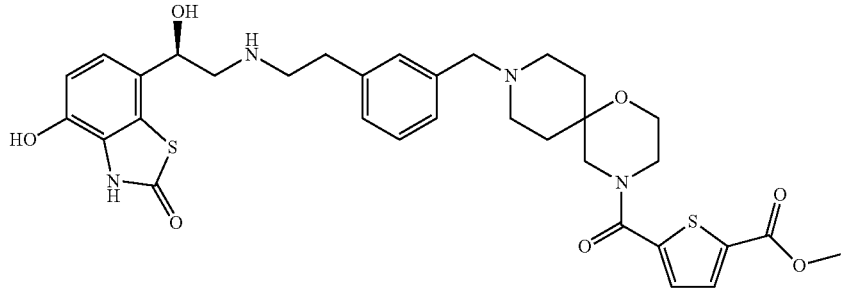 [SMILES: COC(=O)c1ccc(C(=O)N2CCOC3(CCN(Cc4cccc(CCNC[C@H](O)c5ccc(O)c6[nH]c(=O)sc56)c4)CC3)C2)s1]

A solution of methyl 5-(9-(3-(2-hydroxyethyl)benzyl)-1-oxa-4,9-diazaspiro[5.5]undecane-4-carbonyl)thiophene-2-carboxylate (example 30, step c) (0.262 g) in dichloromethane (10 mL) was treated with trifluoroacetic acid (0.044 mL) followed by Dess-Martin periodinane (0.339 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.033 mL) and the solvent evaporated under reduced pressure. The residue was dissolved in methanol (2 mL) and added to a solution at 0° C. of (R)-7-(2-amino-1-hydroxyethyl)-4-hydroxybenzo[d]thiazol-2(3H)-one hydrochloride (WO2007027134, example 1, step d) (0.15 g) and acetic acid (0.033 mL) in methanol (10 mL). Sodium cyanoborohydride (0.054 g) was added and the mixture stirred at room temperature for 18 hours. Most of the methanol was evaporated under reduced pressure and the remainder partitioned between THF (50 mL), brine (10 mL) and saturated sodium bicarbonate solution (1 mL). The organic layer was dried over sodium sulphate, filtered and the solvent removed under reduced pressure. The crude product was purified by preparative HPLC (Sunfire™, Gradient: 10-40% acetonitrile in 0.2% aqueous TFA). The fractions containing the desired compound were evaporated to dryness to afford the titled compound. Yield 0.175 g.

m/z 667 (M+H)+ (APCI)

$^1$H NMR (400 MHz, D$_6$-DMSO, 90° C.) δ 11.27 (s, 1H), 7.72 (d, J=3.8 Hz, 1H), 7.44-7.33 (m, 5H), 6.93 (d, J=8.5 Hz, 1H), 6.77 (d, J=8.2 Hz, 1H), 4.95-4.89 (m, 1H), 4.30 (s, 2H), 3.85 (s, 3H), 3.74-3.69 (m, 2H), 3.66-3.61 (m, 2H), 3.53 (s, 2H), 3.28-2.98 (m, 10H), 2.09-1.99 (m, 2H), 1.77 (s, 2H). Five exchangeable protons not observed.

EXAMPLE 31

(R)-Methyl 5-(9-(3-(2-(2-hydroxy-2-(8-hydroxy-2-oxo-1,2-dihydroquinolin-5-yl)ethylamino)ethyl)benzyl)-1-oxa-4,9-diazaspiro[5.5]undecane-4-carbonyl)thiophene-2-carboxylate ditrifluoroacetate

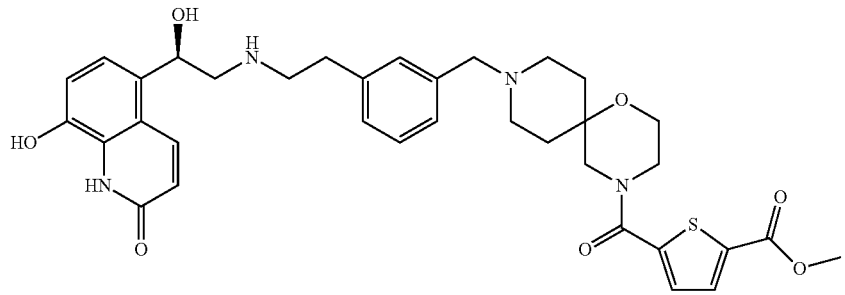 [SMILES: COC(=O)c1ccc(C(=O)N2CCOC3(CCN(Cc4cccc(CCNC[C@H](O)c5ccc(O)c6[nH]c(=O)ccc56)c4)CC3)C2)s1]

a) (R)-Methyl 5-(9-(3-(2-(2-(tert-butyldimethylsilyloxy)-2-(8-hydroxy-2-oxo-1,2-dihydroquinolin-5-yl)ethylamino)ethyl)benzyl)-1-oxa-4,9-diazaspiro[5.5]undecane-4-carbonyl)thiophene-2-carboxylate

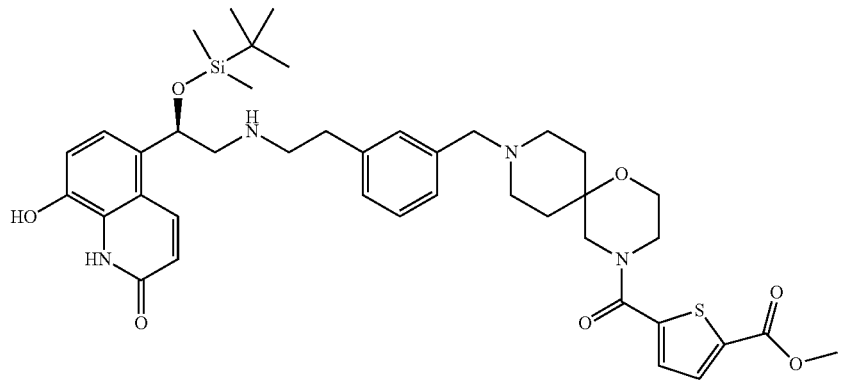 [SMILES: COC(=O)c1ccc(C(=O)N2CCOC3(CCN(Cc4cccc(CCNC[C@H](O[Si](C)(C)C(C)(C)C)c5ccc(O)c6[nH]c(=O)ccc56)c4)CC3)C2)s1]

A solution of methyl 5-(9-(3-(2-hydroxyethyl)benzyl)-1-oxa-4,9-diazaspiro[5.5]undecane-4-carbonyl)thiophene-2-carboxylate (example 30, step c) (0.137 g) in dichloromethane (10 mL) was treated with trifluoroacetic acid (0.023 mL) followed by Dess-Martin periodinane (0.178 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.017 mL) and the solvent evaporated under reduced pressure to yield the crude intermediate aldehyde (0.13 g). The aldehyde was dissolved in methanol (2 mL) and added to a solution of (R)-5-(2-amino-1-(tert-butyldimethylsilyloxy)ethyl)-8-hydroxyquinolin-2(1H)-one (WO2004106333) (0.10 g) and acetic acid (0.017 mL) in methanol (10 mL). The mixture was cooled in an ice bath and treated with sodium triacetoxyborohydride (0.095 g) and then the mixture was stirred at room temperature for 18 hours. The methanol was removed under reduced pressure and the residue was partitioned between saturated sodium bicarbonate solution and ethyl acetate, the organic layer was dried over sodium sulphate, filtered and the solvent removed under to reduced pressure. The crude product was purified by flash silica chromatography using 1% '880' aqueous ammonia and 9% methanol in dichloromethane as solvent. Pure fractions were evaporated to dryness to afford the subtitled compound. Yield 0.108 g.

m/z 775 (M+H)+ (APCI)

b) (R)-Methyl 5-(9-(3-(2-(2-hydroxy-2-(8-hydroxy-2-oxo-1,2-dihydroquinolin-5-yl)ethylamino)ethyl)benzyl)-1-oxa-4,9-diazaspiro[5.5]undecane-4-carbonyl)thiophene-2-carboxylate ditrifluoroacetate

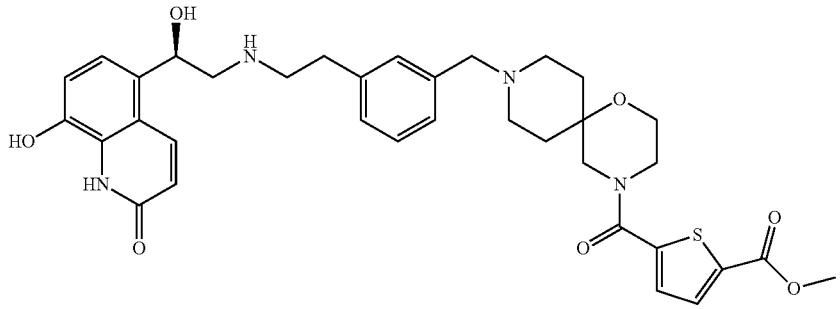 [SMILES: COC(=O)c1ccc(C(=O)N2CCOC3(CCN(Cc4cccc(CCNC[C@H](O)c5ccc(O)c6[nH]c(=O)ccc56)c4)CC3)C2)s1]

(R)-Methyl 5-(9-(3-(2-(2-(tert-butyldimethylsilyloxy)-2-(8-hydroxy-2-oxo-1,2-dihydroquinolin-5-yl)ethylamino)ethyl)benzyl)-1-oxa-4,9-diazaspiro[5.5]undecane-4-carbonyl)thiophene-2-carboxylate (example 31, step a) (0.108 g) in THF (4 mL) was treated with triethylamine trihydrofluoride (0.029 mL) in methanol (1 mL) and the solution allowed to stand at 20° C. for 18 hours. The solvents were removed under reduced pressure and the crude product was purified by preparative HPLC (Sunfire™, Gradient: 10-40% acetonitrile in 0.2% aqueous TFA). The fractions containing the desired compound were evaporated to dryness to afford the titled compound. Yield 0.055 g.

m/z 661 (M+H)+ (APCI)

$^1$H NMR (400 MHz, D$_6$-DMSO, 90° C.) δ 8.18 (d, J=9.7 Hz, 1H), 7.72 (d, J=3.8 Hz, 1H), 7.45-7.32 (m, 5H), 7.14 (d, J=8.2 Hz, 1H), 7.00 (d, J=8.2 Hz, 1H), 6.54 (d, J=9.7 Hz, 1H), 5.40-5.34 (m, 1H), 4.30 (s, 2H), 3.85 (s, 3H), 3.75-3.70 (m, 2H), 3.66-3.61 (m, 2H), 3.53 (s, 2H), 3.29 (t, J=8.1 Hz, 2H), 3.22-3.01 (m, 8H), 2.10-1.99 (m, 2H), 1.78 (s, 2H). Six exchangeable protons not observed.

EXAMPLE 32

(R)-7-(2-(3,4-Difluoro-5-((4-(5-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

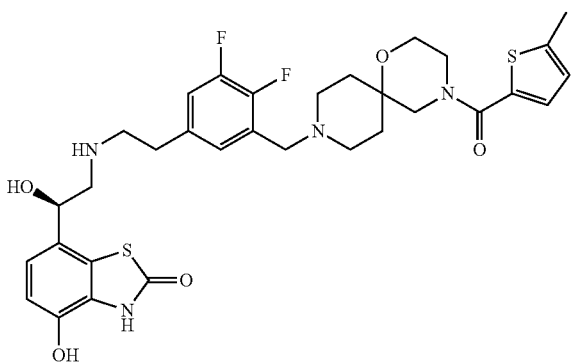

a) 2-(3,4-Difluorophenyl)ethanol

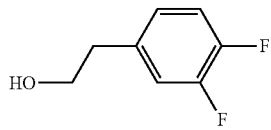 [SMILES: OCCc1ccc(F)c(F)c1]

A solution of borane dimethyl sulfide (2M in THF, 18.30 mL) was added cautiously to a solution of 2-(3,4-difluorophenyl)acetic acid (2.1 g) in THF (20 mL) at 0° C. The resulting mixture was allowed to warm to RT and stirred for 1 h. The reaction was cooled in an ice bath and methanol (5 mL) was added dropwise. The reaction was stirred until bubbling ceased and the solvent evaporated in vacuo. Purification was by silica gel chromatography eluting with isohexane to 4:1 isohexane:ethyl acetate. The fractions containing product were combined and evaporated in vacuo to give the subtitled compound as a clear oil. Yield 1.92 g.

$^1$H NMR (300 MHz, CDCl$_3$) δ 7.14-7.00 (m, 2H), 6.98-6.90 (m, 1H), 3.85 (t, J=6.4 Hz, 2H), 2.82 (t, J=6.4 Hz, 2H). One exchangeable proton not observed.

b) 2,3-Difluoro-5-(2-hydroxyethyl)benzaldehyde

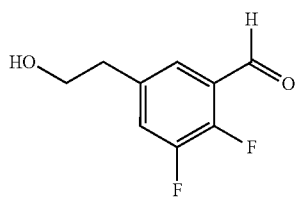 [SMILES: O=Cc1cc(CCO)cc(F)c1F]

2,2,6,6-Tetramethylpiperidine (6.15 mL) was added to a solution of n-butyllithium in hexanes (1.6M, 22.8 mL) at −70° C. A solution of 2-(3,4-difluorophenyl)ethanol (example 32, step a) (1.92 g) in THF (25 mL) was added dropwise. THF (25 mL) was added and the mixture stirred at −70° C. for 6 h. DMF (4.7 mL) was then added and the mixture stirred for 1 h at −70° C. The mixture was then allowed to warm to RT and stirred for 70 h. Aqueous HCl solution (2M, 10 mL) was added followed by ethyl acetate (20 mL) and the layers separated. The aqueous phase was extracted with ethyl acetate (2×20 mL). The combined organic solutions were washed with brine (20 mL), dried over magnesium sulphate, filtered and evaporated in vacuo. Purification was by silica gel chromatography eluting with 4:1 to 2:1 isohexane:diethyl ether gradient. The fractions containing product were combined and evaporated in vacuo to give the subtitled compound as a yellow oil. Yield 1.9 g.

¹H NMR (400 MHz, CDCl₃) δ 10.33 (s, 1H), 7.54-7.47 (m, 1H), 7.39-7.32 (m, 1H), 3.92-3.86 (m, 2H), 2.88 (t, J=6.3 Hz, 2H). One exchangeable proton not observed.

c) (9-(2,3-Difluoro-5-(2-hydroxyethyl)benzyl)-1-oxa-4,9-diazaspiro[5.5]undecan-4-yl)(5-methylthiophen-2-yl)methanone

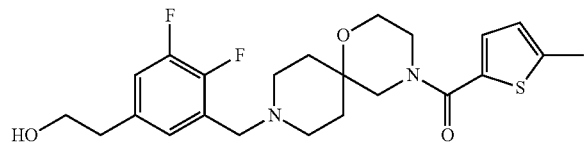 [SMILES: Cc1ccc(C(=O)N2CCOC3(CCN(Cc4cc(CCO)cc(F)c4F)CC3)C2)s1]

(5-Methylthiophen-2-yl)(1-oxa-4,9-diazaspiro[5.5]undecan-4-yl)methanone trifluoroacetate (example 9, step b) (0.53 g) was added to a solution of 2,3-difluoro-5-(2-hydroxyethyl) benzaldehyde (example 32, step b) (0.25 g) and acetic acid (0.08 mL) in methanol (5 mL). The reaction was stirred for 30 min and cooled in an ice bath. Sodium cyanoborohydride (0.13 g) was then added, the mixture allowed to warm to RT and stirred for 18 h. The reaction was concentrated in vacuo. Purification was by silica gel chromatography eluting with 99:1:0.1 to 97:3:0.3 DCM:methanol:'880' aqueous ammonia gradient. The fractions containing product were combined and evaporated in vacuo to give the subtitled compound as a gum. Yield 0.08 g.

m/z 451 (M+H)⁺ (APCI)

¹H NMR (400 MHz, D₆-DMSO, 90° C.) δ 7.18 (d, J=3.6 Hz, 1H), 7.14-7.06 (m, 1H), 7.04-6.99 (m, 1H), 6.80-6.77 (m, 1H), 4.34-4.29 (m, 1H), 3.68-3.57 (m, 6H), 3.53-3.46 (m, 4H), 2.70 (t, J=6.7 Hz, 2H), 2.47-2.34 (m, 7H), 1.77-1.67 (m, 2H), 1.55-1.45 (m, 2H).

d) (R)-7-(2-(3,4-Difluoro-5-((4-(5-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

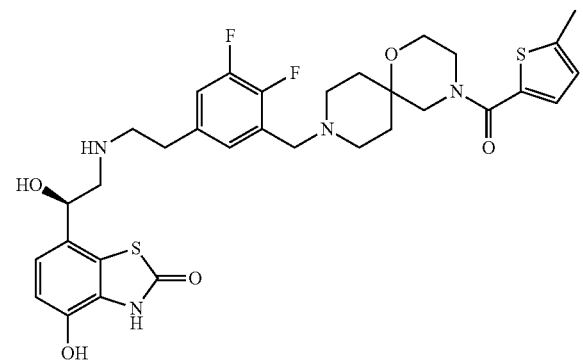

TFA (0.013 mL) was added to a solution of (9-(2,3-difluoro-5-(2-hydroxyethyl)benzyl)-1-oxa-4,9-diazaspiro[5.5]undecan-4-yl)(5-methylthiophen-2-yl)methanone (example 32, step c) (0.077 g) in DCM (2 mL) at 0° C. The mixture was stirred for 5 min then Dess-Martin periodinane (0.11 g) was added. The resulting yellow solution was allowed to warm to RT and stirred for 1 h. A mixture of saturated sodium thiosulphate solution (1 mL), saturated sodium bicarbonate solution (1 mL) and ethyl acetate (5 mL) was then added and the resulting mixture stirred vigorously for 10 min. The aqueous phase was separated and extracted with ethyl acetate (25 mL). The combined organic solutions were washed with brine, acidified with a few drops of acetic acid, dried over sodium sulphate, filtered and evaporated in vacuo. The residue was dissolved in methanol (5 mL), acetic acid (0.005 mL) and (R)-7-(2-amino-1-hydroxyethyl)-4-hydroxybenzo[d]thiazol-2(3H)-one hydrochloride (WO2007027134, example 1, step d) (0.045 g) were then added and the mixture stirred for 5 min before cooling in an ice bath. Sodium cyanoborohydride (0.016 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with ether to give the titled compound as a white solid. Yield 0.052 g.

m/z 659 (M+H)⁺ (APCI)

¹H NMR (400 MHz, D₆-DMSO, 90° C.) δ 11.27 (s, 1H), 7.46-7.37 (m, 1H), 7.28-7.23 (m, 1H), 7.20 (d, J=3.6 Hz, 1H), 6.93 (d, J=8.2 Hz, 1H), 6.81-6.74 (m, 2H), 4.91 (dd, J=8.1, 5.0 Hz, 1H), 4.28-4.19 (m, 2H), 3.74-3.62 (m, 4H), 3.53 (s, 2H), 3.25 (t, J=7.9 Hz, 2H), 3.15-2.95 (m, 8H), 2.46 (s, 3H), 2.01-1.93 (m, 2H), 1.80-1.67 (m, 2H). Five exchangeable protons not observed.

EXAMPLE 33

(R)-4-Hydroxy-7-(1-hydroxy-2-(3-((8-(5-methylthiophene-2-carbonyl)-5-oxa-2,8-diazaspiro[3.5]nonan-2-yl)methyl)phenethylamino)ethyl)benzo[d]thiazol-2(3H)-one ditrifluoroacetate

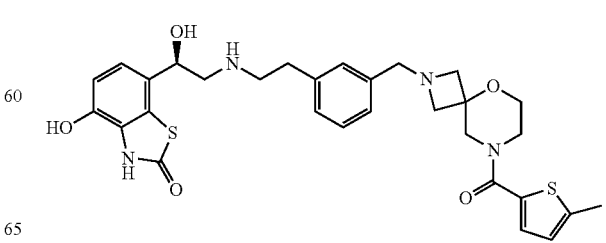

a) 1-Benzhydrylazetidin-3-one

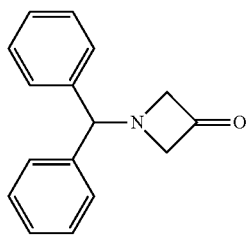 [SMILES: O=C1CN(C(c2ccccc2)c2ccccc2)C1]

Triethylamine (24.7 mL) was added to a solution of 1-benzhydrylazetidin-3-ol (5 g) in DMSO (25 mL). A solution of pyridine sulphur trioxide (18 g) in DMSO (65 mL) was added dropwise and the mixture stirred at 20° C. for 90 minutes. The mixture was poured onto ice/water and extracted twice with ethyl acetate, the combined organics were washed three times with brine before being dried over sodium sulphate, filtered and the solvent removed under reduced pressure. The crude product was purified by flash silica chromatography using 2% triethylamine in isohexane as solvent. Pure fractions were evaporated to dryness to afford the subtitled compound. Yield 2.9 g.

$^1$H NMR (400 MHz, CDCl$_3$) δ 7.50-7.46 (m, 4H), 7.30 (t, J=11.4 Hz, 4H), 7.24-7.19 (m, 2H), 4.59 (s, 1H), 4.00 (s, 4H).

b) 1-Benzhydryl-3-(trimethylsilyloxy)azetidine-3-carbonitrile

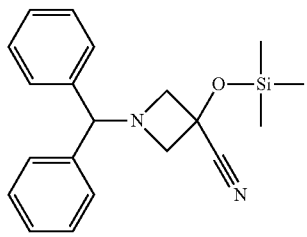 [SMILES: C[Si](C)(C)OC1(C#N)CN(C(c2ccccc2)c2ccccc2)C1]

Tetrabutylammonium cyanide (0.283 g) in dichloromethane (50 mL) was added dropwise over 15 minutes to a stirred solution of 1-benzhydrylazetidin-3-one (example 33, step a) (2.5 g) and trimethylsilyl cyanide (2.82 mL) in dichloromethane (50 mL) at 20° C. under nitrogen. The mixture was stirred at 20° C. for 1 hour. The reaction mixture was washed with water, the organic layer was dried over sodium sulphate, filtered and the solvent evaporated under reduced pressure to afford the subtitled compound. Yield 3.5 g. Used directly without purification.

c) 3-(Aminomethyl)-1-benzhydrylazetidin-3-ol

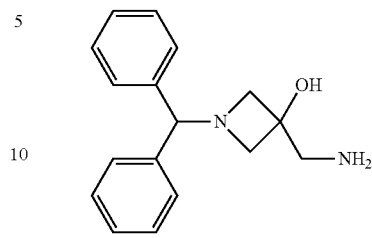

A solution of 1-benzhydryl-3-(trimethylsilyloxy)azetidine-3-carbonitrile (example 33, step b) (3.5 g) in THF (50 mL) was treated with borane methylsulfide complex (2M in THF, 20.8 mL) and the resultant mixture heated at 70° C. for 1 hour under nitrogen. The mixture was cooled to room temperature and quenched carefully with methanol (50 mL) followed by treatment with ethylenediamine (2.81 mL). This mixture was stirred at 20° C. for 1 hour and then at 55° C. for 1 hour. The mixture was cooled to room temperature and treated with tetrabutylammonium fluoride (1M in THF, 15.6 mL), then stirred at room temperature for 40 minutes. Solvents were evaporated under reduced pressure and the residue partitioned between ethyl acetate and brine. The organic layer was dried over sodium sulphate, filtered and the solvent evaporated under reduced pressure. The crude product was purified by flash silica chromatography, elution gradient 6 to 7% methanol in dichloromethane with 1% triethylamine. Pure fractions were evaporated to dryness to afford the subtitled compound. Yield 1.95 g.

m/z 269 (M+H)$^+$ (APCI)

d) N-((1-Benzhydryl-3-hydroxyazetidine-3-yl)methyl)-2-chloroacetamide

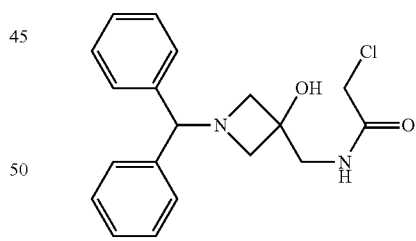

Chloroacetyl chloride (0.846 mL) was added dropwise over 30 minutes to a vigorously stirred mixture of 3-(aminomethyl)-1-benzhydrylazetidin-3-ol (example 33, step c) (2.1 g) in ethyl acetate (100 mL) and potassium carbonate (3.03 g) in water (100 mL) at 0° C. The mixture was stirred for a further 30 minutes at 0° C. and then extracted with ethyl acetate, the organic layer was dried over sodium sulphate, filtered and the solvent evaporated under reduced pressure to afford the subtitled compound. Yield 2.6 g.

m/z 345 (M+H)$^+$ (APCI)

e) 2-Benzhydryl-5-oxa-2,8-diazaspiro[3.5]nonan-7-one

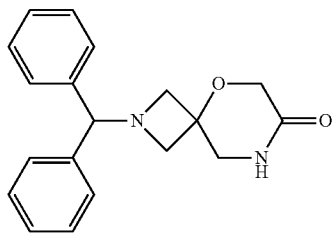 [SMILES: O=C1COC2(CN1)CN(C(c1ccccc1)c1ccccc1)C2]

N-((1-Benzhydryl-3-hydroxyazetidine-3-yl)methyl)-2-chloroacetamide (example 33, step d) (2.6 g) in THF (50 mL) was added dropwise over 90 minutes to a vigorously stirred solution at 75° C. of potassium tert-butoxide (1M in tert-butanol, 15.08 mL) and THF (150 mL) under nitrogen. After the addition was complete the mixture was stirred at 75° C. for 10 minutes and then cooled to room temperature. The solvents were removed under reduced pressure and the residue was partitioned between ethyl acetate and brine. The organic layer was dried over sodium sulphate, filtered and the solvent removed under reduced pressure to afford the subtitled compound. Yield 2.05 g.

m/z 309 (M+H)$^+$ (APCI)

f) 2-Benzhydryl-5-oxa-2,8-diazaspiro[3.5]nonane

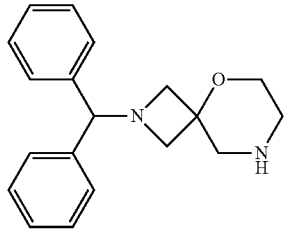 [SMILES: c1ccc(C(c2ccccc2)N2CC3(CNCCO3)C2)cc1]

Borane methyl sulfide complex (2M in THF, 10.7 mL) was added to a solution of 2-benzhydryl-5-oxa-2,8-diazaspiro[3.5]nonan-7-one (example 33, step e) (2 g) in dry THF (40 mL) and the resultant solution was stirred at 70° C. under nitrogen for 50 minutes. The mixture was cooled to room temperature and treated dropwise with methanol (40 mL) followed by N1,N2-dimethylethane-1,2-diamine (3.43 g). The mixture was heated at 70° C. for 6 hours. The solvent was removed under reduced pressure and the residue partitioned between ethyl acetate and brine. The organic layer was dried over sodium sulphate, filtered and the solvent evaporated under reduced pressure. The crude product was purified by flash silica chromatography using 1% triethylamine and 5% methanol in dichloromethane as solvent. Pure fractions were evaporated to dryness to afford the subtitled compound. Yield 1.35 g.

m/z 295 (M+H)$^+$ (APCI)

g) (2-Benzhydryl-5-oxa-2,8-diazaspiro[3.5]nonan-8-yl)(5-methylthiophen-2-yl)methanone

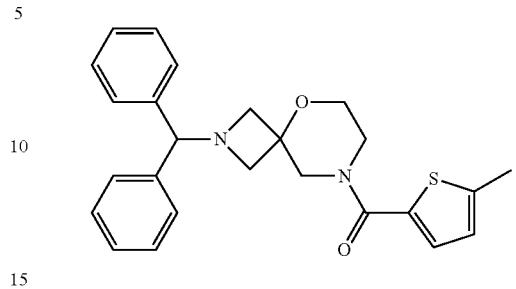

HATU (2.267 g) was added in one portion to a solution of 5-methylthiophene-2-carboxylic acid (0.652 g) and 2-benzhydryl-5-oxa-2,8-diazaspiro[3.5]nonane (example 33, step f) (1.35 g) and triethylamine (1.917 mL) in DMF (20 mL) at 0° C. The cooling bath was removed and the mixture stirred at room temperature for 2 hours. The mixture was partitioned between ethyl acetate and brine, the organic layer was washed twice with brine before being dried over sodium sulphate, filtered and the solvent removed under reduced pressure. The crude product was purified by flash silica chromatography, elution gradient 0.4 to 5% methanol in dichloromethane. Pure fractions were evaporated to dryness to afford the subtitled compound. Yield 1.5 g.

m/z 419 (M+H)$^+$ (APCI)

h) (5-Methylthiophen-2-yl)(5-oxa-2,8-diazaspiro[3.5]nonan-8-yl)methanone hydrochloride

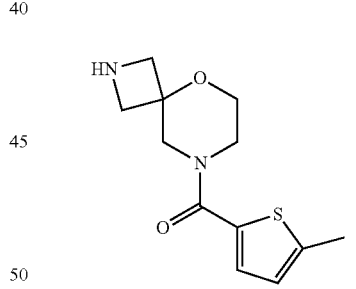

1-Chloroethyl chloroformate (0.508 mL) was added dropwise to a solution of (2-benzhydryl-5-oxa-2,8-diazaspiro[3.5]nonan-8-yl)(5-methylthiophen-2-yl)methanone (example 33, step g) (1.5 g) in acetonitrile (30 mL) at 0° C. The mixture was then heated at reflux for 1 hour under nitrogen. The solvent was removed under reduced pressure and the residue dissolved in methanol (50 mL). This solution was heated at reflux under nitrogen for 30 minutes. The solvent was removed under reduced pressure and the residue triturated with ethyl acetate (40 mL) and then with acetonitrile (7 mL) to yield the subtitled compound. Yield 0.29 g.

m/z 253 (M+H)$^+$ (APCI)

i) (2-(3-(2-Hydroxyethyl)benzyl)-5-oxa-2,8-diazaspiro[3.5]nonan-8-yl)(5-methylthiophen-2-yl)methanone

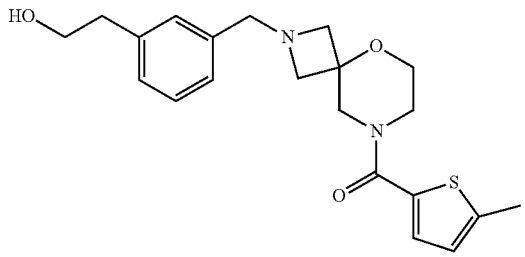 [SMILES: Cc1ccc(C(=O)N2CCOC3(CN(Cc4cccc(CCO)c4)C3)C2)s1]

2-(3-(Bromomethyl)phenyl)ethanol (example 6, step a) (0.281 g) was added to a solution of (5-methylthiophen-2-yl)(5-oxa-2,8-diazaspiro[3.5]nonan-8-yl)methanone hydrochloride (example 33, step h) (0.29 g) and triethylamine (0.42 mL) in acetonitrile (15 mL) at 20° C. and the resultant mixture stirred for 3 hours at 20° C. The solvent was removed under reduced pressure and the residue partitioned between ethyl acetate and brine. The organic layer was dried over sodium sulphate, filtered and the solvent removed under reduced pressure. The crude product was purified by flash silica chromatography using 3% methanol in dichloromethane with 1% triethylamine as solvent. Pure fractions were evaporated to dryness to afford the subtitled compound. Yield 0.32 g.

m/z 387 (M+H)$^+$ (APCI)

j) (R)-4-Hydroxy-7-(1-hydroxy-2-(3-((8-(5-methylthiophene-2-carbonyl)-5-oxa-2,8-diazaspiro[3.5]nonan-2-yl)methyl)phenethylamino)ethyl)benzo[d]thiazol-2(3H)-one ditrifluoroacetate

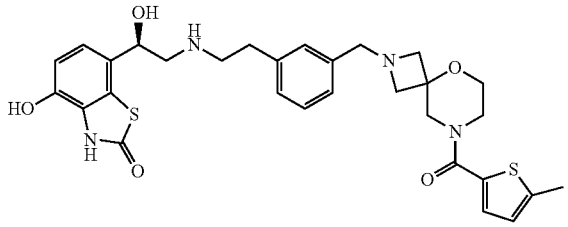 [SMILES: Cc1ccc(C(=O)N2CCOC3(CN(Cc4cccc(CCNC[C@H](O)c5ccc(O)c6[nH]c(=O)sc56)c4)C3)C2)s1]

A solution of (2-(3-(2-hydroxyethyl)benzyl)-5-oxa-2,8-diazaspiro[3.5]nonan-8-yl)(5-methylthiophen-2-yl)methanone (example 33, step i) (0.16 g) in dichloromethane (10 mL) was treated with trifluoroacetic acid (0.032 mL) followed by Dess-Martin periodinane (0.246 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.024 mL) and the solvent evaporated under reduced pressure. The residue was dissolved in methanol (2 mL) and added to a solution at 0° C. of (R)-7-(2-amino-1-hydroxyethyl)-4-hydroxybenzo[d]thiazol-2(3H)-one hydrochloride (WO2007027134, example 1, step d) (0.15 g) and acetic acid (0.024 mL) in methanol (10 mL). Sodium cyanoborohydride (0.039 g) was added and the mixture stirred at room temperature for 18 hours. Most of the methanol was evaporated under reduced pressure and the remainder partitioned between THF (50 mL), brine (10 mL) and saturated sodium bicarbonate solution (1 mL). The organic layer was dried over sodium sulphate, filtered and the solvent removed under reduced pressure. The crude product was purified by preparative HPLC (Sunfire™, Gradient: 10-40% acetonitrile in 0.2% aqueous TFA). The fractions containing the desired compound were evaporated to dryness to afford the titled compound. Yield 0.13 g.

m/z 595 (M+H)$^+$ (APCI)

$^1$H NMR (400 MHz, D$_6$-DMSO, 90° C.) δ 11.26 (s, 1H), 7.42-7.29 (m, 4H), 7.24 (d, J=3.6 Hz, 1H), 6.93 (d, J=8.5 Hz, 1H), 6.82-6.75 (m, 2H), 4.95-4.88 (m, 1H), 4.36 (s, 2H), 4.09-3.97 (m, 4H), 3.87 (s, 2H), 3.73-3.69 (m, 2H), 3.66-3.62 (m, 2H), 3.24 (t, J=8.1 Hz, 2H), 3.15-2.97 (m, 4H), 2.46 (s, 3H). Five exchangeable protons not observed.

EXAMPLE 34

(R)-7-(2-(2,6-Difluoro-3-((4-(5-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

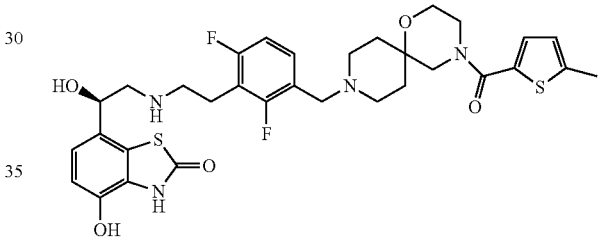

a) (9-(2,4-Difluoro-3-(2-hydroxyethyl)benzyl)-1-oxa-4,9-diazaspiro[5.5]undecan-4-yl)(5-methylthiophen-2-yl)methanone

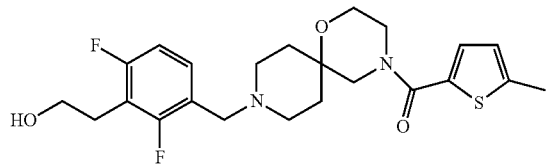 [SMILES: Cc1ccc(C(=O)N2CCOC3(CCN(Cc4ccc(F)c(CCO)c4F)CC3)C2)s1]

Dibenzoyl peroxide (0.03 g) was added to a mixture of NBS (0.53 g) and 2-(2,6-difluoro-3-methylphenyl)acetic acid (0.5 g) in DCM (10 mL). The reaction was heated at reflux for 4 h. DCM (10 mL) and water (20 mL) were added and the organic phase separated. The organic phase was washed with brine (20 mL), dried over sodium sulphate, filtered and evaporated. The residue was redissolved in THF (10 mL) and cooled in an ice bath. A solution of borane dimethyl sulfide complex (2M in THF, 4 mL) was added dropwise and the mixture stirred for 1 h. Methanol (2 mL) was cautiously added dropwise and once bubbling had ceased the solvent was evaporated. The residue was redissolved in acetonitrile (10 mL) and (5-methylthiophen-2-yl)(1-oxa-4,9-diazaspiro[5.5]undecan-4-yl)methanone trifluoroacetate (example 9, step b) (0.8 g) was added followed by triethylamine (1.12 mL). The resulting mixture was stirred overnight, evaporated and purified by silica gel chromatography eluting with 99:1:0.1 to 97:3:0.3 DCM:methanol:'880' aqueous ammonia gradient to give the subtitled compound as a clear foam. Yield 0.37 g.

m/z 451 (M+H)$^+$ (APCI)

b) 2-(2,6-Difluoro-3-((4-(5-methylthiophene-2-carbonyl)-1-oxa-4,9-diazaspiro[5.5]undecan-9-yl)methyl)phenyl)acetaldehyde

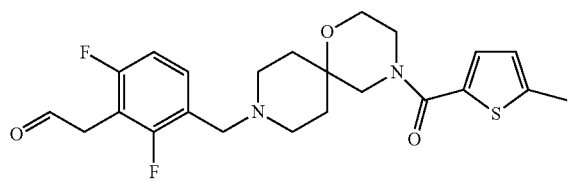 [SMILES: Cc1ccc(C(=O)N2CCOC3(CCN(Cc4ccc(F)c(CC=O)c4F)CC3)C2)s1]

TFA (0.05 mL) was added to a solution of (9-(2,4-difluoro-3-(2-hydroxyethyl)benzyl)-1-oxa-4,9-diazaspiro[5.5]undecan-4-yl)(5-methylthiophen-2-yl)methanone (example 34, step a) (0.27 g) in DCM (5 mL) at 0° C. and the resulting mixture stirred for 5 min. Dess-Martin periodinane (0.38 g) was then added and the mixture stirred at RT for 45 min. Saturated sodium thiosulphate solution (5 mL), saturated sodium bicabonate solution (5 mL) and ethyl acetate (20 mL) were then added and the mixture stirred vigorously for 10 min. The aqueous phase was separated and extracted with ethyl acetate (20 mL). The combined organic solutions were washed with brine (20 mL), acidified with a few drops of acetic acid, dried over sodium sulphate, filtered and evaporated to give the subtitled compound as a clear gum. Yield 0.27 g.

m/z 449 (M+H)$^+$ (APCI)

c) (R)-7-(2-(2,6-Difluoro-3-((4-(5-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

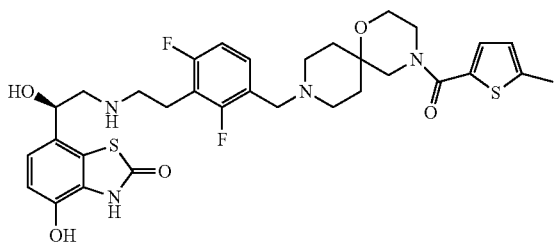

A solution of 2-(2,6-difluoro-3-((4-(5-methylthiophene-2-carbonyl)-1-oxa-4,9-diazaspiro[5.5]undecan-9-yl)methyl)phenyl)acetaldehyde (example 34, step b) (0.135 g) in methanol (3 mL) was added to a mixture of (R)-7-(2-amino-1-hydroxyethyl)-4-hydroxybenzo[d]thiazol-2(3H)-one hydrochloride (WO2007027134, example 1, step d) (0.11 g) and acetic acid (0:015 mL) in methanol (0.5 mL). The resulting mixture was stirred for 5 min then cooled to 0° C. Sodium cyanoborohydride (0.025 g) was then added and the mixture allowed to warm to RT and stirred for 2 h. The reaction was concentrated and purified by silica gel chromatography eluting with 95:5:0.5 to 89:10:1 DCM:methanol:'880' aqueous ammonia gradient. The fractions containing product were combined, evaporated and purified by preparative HPLC (Sunfire™, Gradient: 5-50% acetonitrile in 0.2% aqueous TFA) to give the titled compound as a white solid. Yield 0.1 g.

m/z 659 (M+H)$^+$ (APCI)

$^1$H NMR (400 MHz, D$_6$-DMSO, 90° C.) δ 11.27 (s, 1H), 7.64-7.50 (m, 1H), 7.26-7.12 (m, 2H), 6.93 (d, J=8.2 Hz, 1H), 6.84-6.69 (m, 2H), 4.91 (dd, J=8.5, 4.9 Hz, 1H), 4.30 (s, 2H), 3.77-3.47 (m, 6H), 3.29-2.99 (m, 10H), 2.46 (s, 3H), 2.10-1.90 (m, 2H), 1.88-1.68 (m, 2H). Five exchangeable protons not observed.

EXAMPLE 35

(R)-5-(2-(2,6-Difluoro-3-((4-(5-methylthiophene-2-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

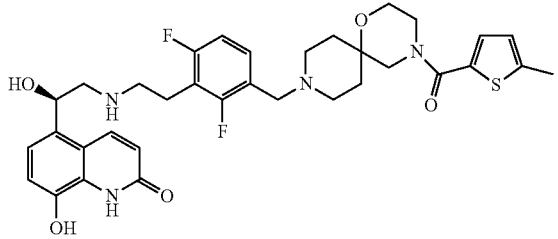

A solution of 2-(2,6-difluoro-3-((4-(5-methylthiophene-2-carbonyl)-1-oxa-4,9-diazaspiro[5.5]undecan-9-yl)methyl)phenyl)acetaldehyde (example 34, step b) (0.135 g) in methanol (3 mL) was added to a mixture of (R)-5-(2-amino-1-(tert-butyldimethylsilyloxy)ethyl)-8-hydroxyquinolin-2(1H)-one (WO2004106333) (0.12 g) and acetic acid (0.017 mL) in methanol (3 mL). The resulting mixture was stirred for 5 min then cooled to 0° C. Sodium cyanoborohydride (0.028 g) was then added and the mixture allowed to warm to RT and stirred for 2 h. The reaction was concentrated and the residue purified by silica gel chromatography eluting with 95:5:0.5 to 89:10:1 DCM:methanol:'880' aqueous ammonia gradient. The fractions containing product were combined, evaporated and the residue was dissolved in THF (3 mL), triethylamine trihydrofluoride (0.074 mL) was added and the mixture stirred overnight. The reaction was concentrated and the residue purified by preparative HPLC (Sunfire™, Gradient: 5-50% acetonitrile in 0.2% aqueous TFA). The fractions containing product were combined and evaporated to give the titled compound as a white solid. Yield 0.12 g.

m/z 653 (M+H)$^+$ (APCI)

$^1$H NMR (400 MHz, D$_6$-DMSO, 90° C.) δ 8.18 (d, J=9.7 Hz, 1H), 7.64-7.51 (m, 1H), 7.22-7.10 (m, 3H), 7.00 (d, J=8.2 Hz, 1H), 6.80 (d, J=3.3 Hz, 1H), 6.54 (d, J=10.0 Hz, 1H), 5.36 (dd, J=8.7, 4.1 Hz, 1H), 4.34 (s, 2H), 3.76-3.46 (m, 6H), 3.33-3.03 (m, 10H), 2.46 (s, 3H), 2.09-1.95 (m, 2H), 1.87-1.66 (m, 2H). Six exchangeable protons not observed.

EXAMPLE 36

(R)-4-Hydroxy-7-(1-hydroxy-2-(2-(5-((4-(2-isopropylthiazole-4-carbonyl)-1-oxa-4,9-diazaspiro[5.5]undecan-9-yl)methyl)thiophen-3-yl)ethylamino)ethyl)benzo[d]thiazol-2(3H)-one ditrifluoroacetate

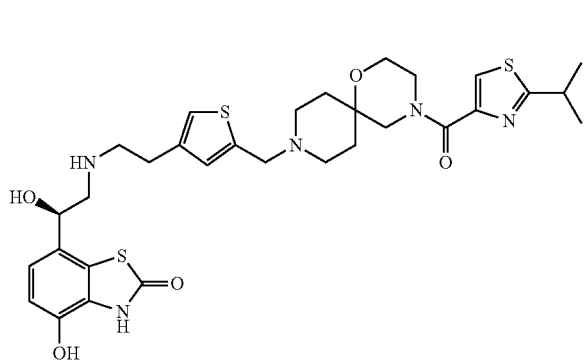 [SMILES: CC(C)c1nc(C(=O)N2CCOC3(CCN(Cc4cc(CCNC[C@H](O)c5ccc(O)c6[nH]c(=O)sc56)cs4)CC3)C2)cs1]

a) (9-((4-(2-(tert-Butyldimethylsilyloxy)ethyl)thiophen-2-yl)methyl)-1-oxa-4,9-diazaspiro[5.5]undecan-4-yl)(2-isopropylthiazol-4-yl)methanone

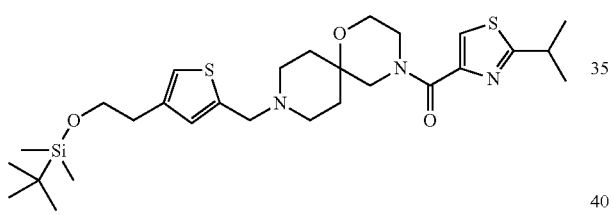

(2-Isopropylthiazol-4-yl)(1-oxa-4,9-diazaspiro[5.5]undecan-4-yl)methanone trifluoroacetate (example 22, step b) (0.50 g) was added to a stirred solution of a 4:1 mixture of 4-(2-(tert-butyldimethylsilyloxy)ethyl)thiophene-2-carbaldehyde and 3-(2-(tert-butyldimethylsilyloxy)ethyl)thiophene-2-carbaldehyde (example 27, step b) (0.40 g) and AcOH (0.085 mL) in N-methyl-2-pyrrolidinone (6 mL). After 5 min, sodium triacetoxyborohydride (0.48 g) was added. After 16 h water was added and the mixture was extracted with ethyl acetate. The ethyl acetate layer was washed three times with water and evaporated in vacuo. Purification by silica gel chromatography eluting with ethyl acetate:isohexane:triethylamine, 20:80:5 separated the two isomeric products and gave the subtitled compound as a gum. Yield 0.27 g.

$^1$H NMR (400 MHz, CDCl$_3$) δ 7.81 (s, 1H), 6.86 (s, 1H), 6.75 (s, 1H), 3.99-3.91 (m, 1H), 3.88-3.82 (m, 1H), 3.81-3.72 (m, 5H), 3.69-3.58 (m, 3H), 3.37-3.25 (m, 1H), 2.76 (t, J=7.1 Hz, 2H), 2.59-2.44 (m, 3H), 2.41-2.29 (m, 1H), 1.89-1.81 (m, 2H), 1.78-1.67 (m, 1H), 1.56-1.50 (m, 1H) 1.46-1.34 (m, 6H), 0.87 (s, 9H), 0.00 (s, 6H).

b) (9-((4-(2-Hydroxyethyl)thiophen-2-yl)methyl)-1-oxa-4,9-diazaspiro[5.5]undecan-4-yl)(2-isopropylthiazol-4-yl)methanone

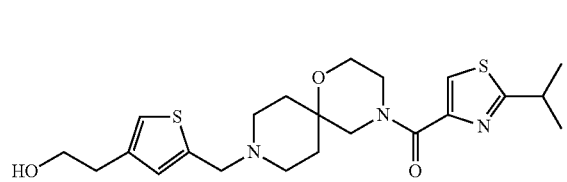 [SMILES: CC(C)c1nc(C(=O)N2CCOC3(CCN(Cc4cc(CCO)cs4)CC3)C2)cs1]

Tetrabutylammonium fluoride (1M in tetrahydrofuran, 2 mL) was added to a solution of (9-((4-(2-(tert-butyldimethylsilyloxy)ethyl)thiophen-2-yl)methyl)-1-oxa-4,9-diazaspiro[5.5]undecan-4-yl)(2-isopropylthiazol-4-yl)methanone (example 36, step a) (0.27 g) in tetrahydrofuran (4 mL). After 1 h, the solution was evaporated in vacuo. Purification by silica gel chromatography eluting with ethyl acetate:triethylamine, 20:1 gave the subtitled compound as a gum. Yield 0.18 g.

$^1$H NMR (400 MHz, CDCl$_3$) δ 7.81 (s, 1H), 6.91 (s, 1H), 6.77 (s, 1H), 4.00-3.90 (m, 1H), 3.87-3.80 (m, 3H), 3.79-3.72 (m, 3H), 3.71-3.60 (m, 3H), 3.36-3.25 (m, 1H), 2.82 (t, J=6.6 Hz, 3H), 2.61-2.42 (m, 3H), 2.42-2.30 (m, 1H), 1.90-1.82 (m, 2H), 1.78-1.67 (m, 1H), 1.67-1.58 (m, 1H), 1.44-1.36 (m, 6H).

c) 2-(5-((4-(2-Isopropylthiazole-4-carbonyl)-1-oxa-4,9-diazaspiro[5.5]undecan-9-yl)methyl)thiophen-3-yl)acetaldehyde

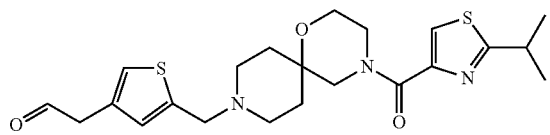 [SMILES: CC(C)c1nc(C(=O)N2CCOC3(CCN(Cc4cc(CC=O)cs4)CC3)C2)cs1]

Dess-Martin periodinane (0.25 g) was added to a stirred solution of (9-((4-(2-hydroxyethyl)thiophen-2-yl)methyl)-1-oxa-4,9-diazaspiro[5.5]undecan-4-yl)(2-isopropylthiazol-4-yl)methanone (example 36, step b) (0.17 g) and trifluoroacetic acid (0.07 mL) in DCM (5 mL). After 1 h, ethyl acetate (30 mL) was added followed by a mixture of saturated sodium thiosulphate solution (5 mL) and saturated sodium bicarbonate solution (5 mL). The reaction mixture was shaken well and separated. The ethyl acetate solution was washed with saturated sodium bicarbonate solution, water and brine. Acetic acid (0.07 mL) was added, the solution dried over sodium sulphate, filtered and evaporated in vacuo (bath temperature ~30° C.) to give the subtitled compound as a gum. Yield 0.19 g. Used directly d) (R)-4-Hydroxy-7-(1-hydroxy-2-(2-(5-((4-(2-isopropylthiazole-4-carbonyl)-1-oxa-4,9-diazaspiro[5.5]undecan-9-yl)methyl)thiophen-3-yl)ethylamino)ethyl)benzo[d]thiazol-2(3H)-one ditrifluoroacetate

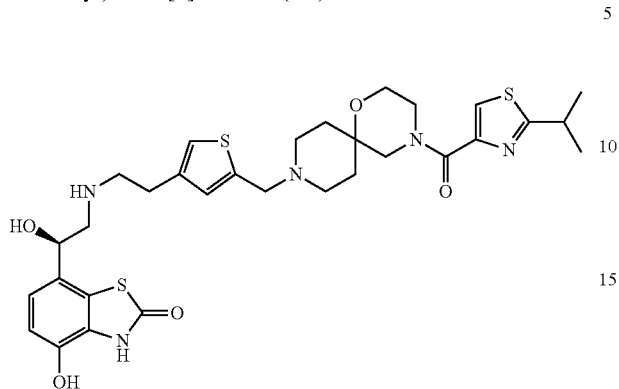

Acetic acid (0.037 mL) was added to a stirred solution of (R)-7-(2-amino-1-hydroxyethyl)-4-hydroxybenzo[d]thiazol-2(3H)-one hydrochloride (WO2007027134, example 1, step d) (0.170 g) and 2-(5-((4-(2-isopropylthiazole-4-carbonyl)-1-oxa-4,9-diazaspiro[5.5]undecan-9-yl)methyl)thiophen-3-yl)acetaldehyde (example 36, step c) (0.170 g) in methanol (8 mL). After 1 min, sodium cyanoborohydride (0.08 g) was added. After 3 h, the reaction mixture was concentrated in vacuo to ~2 mL, THF (20 mL) added and the solution washed with a mixture of brine (10 mL) and saturated sodium bicarbonate solution (2 mL). The organic solution was dried over sodium sulphate, filtered and evaporated in vacuo. The solid was dissolved in methanol and purified by preparative HPLC (Sunfire™, Gradient: 10-40% acetonitrile in 0.2% aqueous TFA). The fractions containing pure product were combined and evaporated to dryness. Trituration with diethyl ether gave the titled compound as a white solid. Yield 0.026 g.

m/z 658 (M+H)$^+$ (APCI)

$^1$H NMR (400 MHz, D$_6$-DMSO) δ 11.67 (s, 1H), 10.24 (s, 1H), 10.09-9.78 (m, 1H), 8.91-8.68 (m, 2H), 8.03 (s, 1H), 7.46 (s, 1H), 7.17 (s, 1H), 6.93 (d, J=8.9 Hz, 1H), 6.77 (d, J=8.9 Hz, 1H), 6.51-6.46 (m, 1H), 4.93-4.85 (m, 1H), 4.67-4.51 (m, 2H), 3.85-2.88 (m, 17H), 2.14-2.05 (m, 2H), 1.82-1.58 (m, 2H), 1.34 (d, J=6.8 Hz, 6H).

EXAMPLE 37

(R)-5-(2-(3-((2,2-Difluoro-4-(5-methylthiophene-2-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

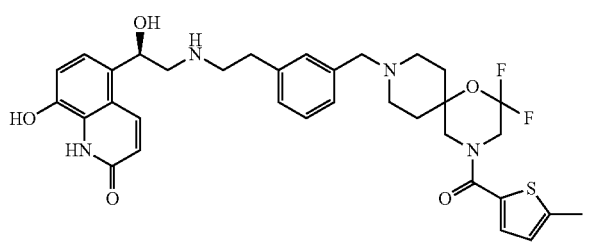 [SMILES: Cc1ccc(C(=O)N2CC(F)(F)OC3(CCN(Cc4cccc(CCNC[C@H](O)c5ccc(O)c6[nH]c(=O)ccc56)c4)CC3)C2)s1]

a) tert-Butyl 4-((2-bromo-2,2-difluoroacetamido)methyl)-4-hydroxypiperidine-1-carboxylate

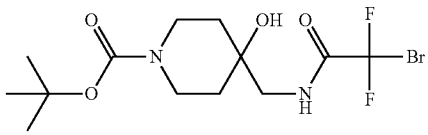 [SMILES: CC(C)(C)OC(=O)N1CCC(O)(CNC(=O)C(F)(F)Br)CC1]

A solution of tert-butyl 4-(aminomethyl)-4-hydroxypiperidine-1-carboxylate (1.702 g) in DMF (20 mL) at 20° C. was treated with ethyl 2-bromo-2,2-difluoroacetate (1.5 g) and the mixture stirred for 90 minutes at 20° C. under nitrogen. The mixture was partitioned between ethyl acetate and brine, the organic layer was washed twice with brine, dried over sodium sulphate, filtered and the solvent evaporated under reduced pressure to afford the subtitled compound. Yield 2.5 g.

m/z 385/387 (M−H)$^−$ (APCI)

b) tert-Butyl 2,2-difluoro-3-oxo-1-oxa-4,9-diazaspiro[5.5]undecane-9-carboxylate

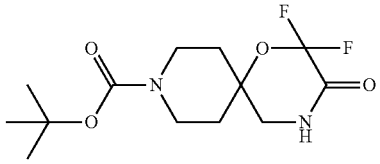 [SMILES: CC(C)(C)OC(=O)N1CCC2(CC1)CNC(=O)C(F)(F)O2]

A solution of tert-butyl 4-((2-bromo-2,2-difluoroacetamido)methyl)-4-hydroxypiperidine-1-carboxylate (example 37, step a) (3.2 g) in THF (40 mL) was added dropwise over 15 minutes to a stirred solution of potassium tert-butoxide (1M in t-butanol, 16.53 mL) and THF (60 mL) at 70° C. under nitrogen. At the end of the addition the mixture was heated for a further 10 minutes and then cooled to room temperature. The mixture was partitioned between ethyl acetate and brine, the organic layer was dried over sodium sulphate, filtered and the solvent evaporated under reduced pressure. The crude product was purified by flash silica chromatography using 30% isohexane in ethyl acetate. Pure fractions were evaporated to dryness to afford the subtitled compound. Yield 0.55 g.

m/z 305 (M−H)$^−$ (APCI)

$^1$H NMR (400 MHz, D$_6$-DMSO) δ 8.98 (s, 1H), 3.74 (d, J=13.3 Hz, 2H), 3.43 (d, J=2.8 Hz, 2H), 3.05 (s, 2H), 1.81-1.73 (m, 2H), 1.70-1.61 (m, 2H), 1.40 (s, 9H).

c) tert-Butyl 2,2-difluoro-1-oxa-4,9-diazaspiro[5.5]undecane-9-carboxylate

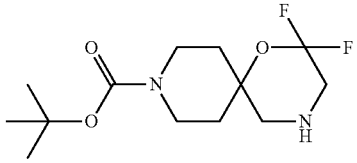 [SMILES: CC(C)(C)OC(=O)N1CCC2(CC1)CNCC(F)(F)O2]

Borane methyl sulfide complex (2M in THF, 2.69 mL) was added dropwise to a solution of tert-butyl 2,2-difluoro-3-oxo-1-oxa-4,9-diazaspiro[5.5]undecane-9-carboxylate (example 37, step b) (0.55 g) in THF (15 mL). The reaction mixture was heated at 55° C. under nitrogen for 25 minutes and then cooled to room temperature. The mixture was quenched by careful dropwise addition of methanol (5 mL). N1,N2-dimethylethane-1,2-diamine (0.633 g) was then added and the mixture heated at 70° C. for minutes. The solvents were removed under reduced pressure and the residue was purified by flash silica chromatography using 4% methanol in dichloromethane with 1% triethylamine as solvent. Pure fractions were evaporated to dryness to afford the subtitled compound. Yield 0.32 g. Used directly.

d) tert-Butyl 2,2-difluoro-4-(5-methylthiophene-2-carbonyl)-1-oxa-4,9-diazaspiro[5.5]undecane-9-carboxylate

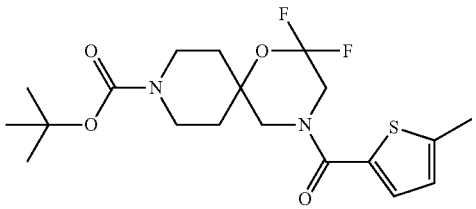 [SMILES: Cc1ccc(C(=O)N2CC(F)(F)OC3(CCN(C(=O)OC(C)(C)C)CC3)C2)s1]

HATU (0.541 g) was added in one portion to a stirred solution at 0° C. of tert-butyl 2,2-difluoro-1-oxa-4,9-diazaspiro[5.5]undecane-9-carboxylate (example 37, step c) (0.32 g) and 5-methylthiophene-2-carboxylic acid (0.171 g) and triethylamine (0.458 mL) in DMF (20 mL). The mixture was then stirred at 20° C. for 7 hours. The mixture was partitioned between ethyl acetate and brine, the organic layer was washed twice with brine, dried over sodium sulphate, filtered and the solvent evaporated under reduced pressure. The crude product was purified by flash silica chromatography, elution gradient 0.5 to 5% methanol in dichloromethane. Pure fractions were evaporated to dryness to afford the subtitled compound. Yield 0.4 g.

$^1$H NMR (400 MHz, D$_6$-DMSO, 90° C.) δ 7.29 (d, J=3.6 Hz, 1H), 6.84 (dd, J=3.6, 1.0 Hz, 1H), 4.08 (t, J=8.8 Hz, 2H), 3.79 (s, 2H), 3.65-3.58 (m, 2H), 3.21-3.11 (m, 2H), 1.81-1.73 (m, 2H), 1.66-1.56 (m, 2H), 1.39 (s, 9H)+3H (methyl) not observed (under solvent).

e) (2,2-Difluoro-1-oxa-4,9-diazaspiro[5.5]undecan-4-yl)(5-methylthiophen-2-yl)methanone trifluoroacetate

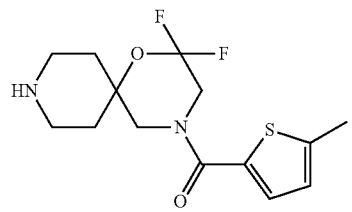

Trifluoroacetic acid (5 mL) was added to a solution of tert-butyl 2,2-difluoro-4-(5-methylthiophene-2-carbonyl)-1-oxa-4,9-diazaspiro[5.5]undecane-9-carboxylate (example 37, step d) (0.4 g) in dichloromethane (20 mL) at 20° C. The solution was allowed to stand at 20° C. for 25 minutes. Toluene (40 mL) was added and the solvents were removed under reduced pressure. The residue was evaporated down twice with acetonitrile. The resultant gum was triturated with ether to afford the subtitled compound. Yield 0.39 g.

m/z 317 (M+H)$^+$ (APCI)

$^1$H NMR (400 MHz, D$_6$-DMSO, 90° C.) δ 8.53 (s, 2H), 7.31 (d, J=3.8 Hz, 1H), 6.88-6.85 (m, 1H), 4.14 (t, J=8.8 Hz, 2H), 3.84 (s, 2H), 3.27-3.21 (m, 2H), 3.13-3.04 (m, 2H), 2.05-1.98 (m, 2H), 1.91-1.81 (m, 2H). Methyl protons not observed (under solvent).

f) (2,2-Difluoro-9-(3-(2-hydroxyethyl)benzyl)-1-oxa-4,9-diazaspiro[5.5]undecan-4-yl)(5-methylthiophen-2-yl)methanone

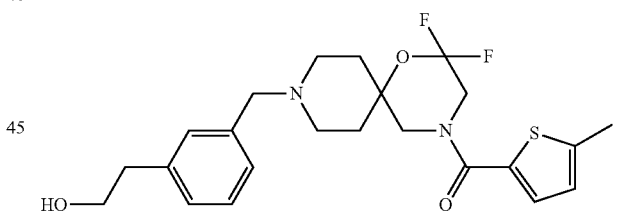

2-(3-(Bromomethyl)phenyl)ethanol (example 6, step a) (0.095 g) was added to a solution of (2,2-difluoro-1-oxa-4,9-diazaspiro[5.5]undecan-4-yl)(5-methylthiophen-2-yl)methanone trifluoroacetate (example 37, step e) (0.19 g) and triethylamine (0.185 mL) in acetonitrile (10 mL) and the reaction mixture stirred at 20° C. for 3 hours. The solvent was evaporated under reduced pressure and the residue partitioned between ethyl acetate and brine, the organic layer was dried over sodium sulphate, filtered and the solvent evaporated under reduced pressure. The crude product was purified by flash silica chromatography using 2.5% methanol in dichloromethane with 1% triethylamine as solvent. Pure fractions were evaporated to dryness to afford the subtitled compound. Yield 0.188 g.

m/z 451 (M+H)$^+$ (APCI)

g) (R)-5-(1-(tert-Butyldimethylsilyloxy)-2-(3-((2,2-difluoro-4-(5-methylthiophene-2-carbonyl)-1-oxa-4,9-diazaspiro[5.5]undecan-9-yl)methyl)phenethylamino)ethyl)-8-hydroxyquinolin-2(1H)-one

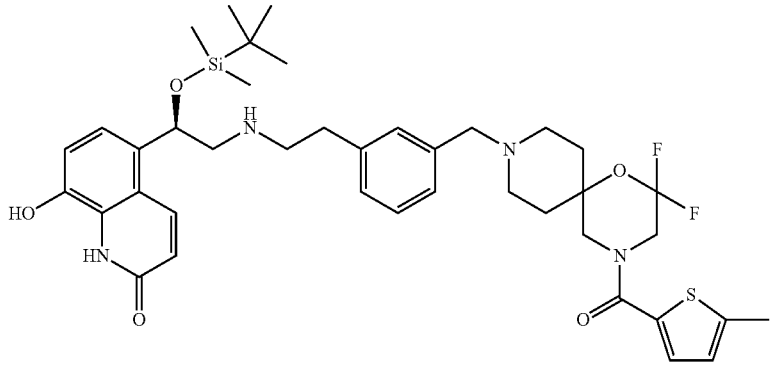 [SMILES: Cc1ccc(C(=O)N2CC(F)(F)OC3(CCN(Cc4cccc(CCNC[C@H](O[Si](C)(C)C(C)(C)C)c5ccc(O)c6[nH]c(=O)ccc56)c4)CC3)C2)s1]

A solution of (2,2-difluoro-9-(3-(2-hydroxyethyl)benzyl)-1-oxa-4,9-diazaspiro[5.5]undecan-4-yl)(5 methylthiophen-2-yl)methanone (example 37, step f) (0.188 g) in dichloromethane (10 mL) was treated with trifluoroacetic acid (0.032 mL) followed by Dess-Martin periodinane (0.248 g) and the resultant mixture stirred at 20° C. for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted twice with ethyl acetate, the combined organics were washed with saturated sodium bicarbonate solution, dried over sodium sulphate, filtered, treated with acetic acid (0.024 mL) and the solvent evaporated under reduced pressure. The residue was dissolved in methanol (2 mL) and added to a solution of (R)-5-(2-amino-1-(tert-butyldimethylsilyloxy)ethyl)-8-hydroxyquinolin-2(1H)-one (WO2004106333) (0.14 g) and acetic acid (0.024 mL) in methanol (10 mL). The mixture was cooled in an ice bath and treated with sodium triacetoxyborohydride (0.133 g), and stirred at room temperature for 18 hours. The methanol was removed under reduced pressure and the residue was partitioned between saturated sodium bicarbonate solution and ethyl acetate, the organic layer was dried over sodium sulphate, filtered and the solvent removed under reduced pressure. The crude product was purified by flash silica chromatography using 1% '880' aqueous ammonia and 8% methanol in dichloromethane. Pure fractions were evaporated to dryness to afford the subtitled compound. Yield 0.114 g.

m/z 767 (M+H)+ (APCI)

h) (R)-5-(2-(3-((2,2-Difluoro-4-(5-methylthiophene-2-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

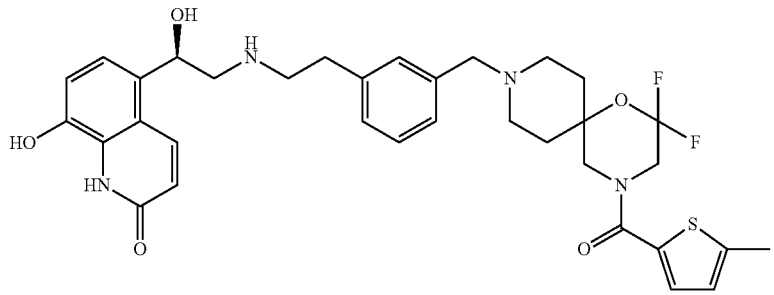 [SMILES: Cc1ccc(C(=O)N2CC(F)(F)OC3(CCN(Cc4cccc(CCNC[C@H](O)c5ccc(O)c6[nH]c(=O)ccc56)c4)CC3)C2)s1]

Triethylamine trihydrofluoride (0.03 mL) in methanol (1 mL) was added to a solution of (R)-5-(1-(tert-butyldimethylsilyloxy)-2-(3-((2,2-difluoro-4-(5-methylthiophene-2-carbonyl)-1-oxa-4,9-diazaspiro[5.5]undecan-9-yl)methyl)phenethylamino)ethyl)-8-hydroxyquinolin-2(1H)-one (example 37, step g) (0.114 g) in THF (4 mL) and the resultant solution was allowed to stand at 20° C. for 18 hours. The solvents were removed under reduced pressure, the crude product was purified by preparative HPLC (Sunfire™, Gradient: 10-40% acetonitrile in 0.2% aqueous TFA). The fractions containing the desired compound were evaporated to dryness to afford the titled compound. Yield 0.080 g.

m/z 653 (M+H)+ (APCI)

$^1$H NMR (400 MHz, D$_6$-DMSO, 90° C.) δ 8.16 (d, J=9.7 Hz, 1H), 7.46-7.26 (m, 5H), 7.14 (d, J=8.2 Hz, 1H), 6.99 (d, J=8.2 Hz, 1H), 6.86-6.83 (m, 1H), 6.57-6.52 (m, 1H), 5.37-5.31 (m, 1H), 4.25 (s, 2H), 4.13 (t, J=8.8 Hz, 2H), 3.82 (s, 2H), 3.30-2.99 (m, 10H), 2.10-1.88 (m, 4H). Six exchangeable protons not observed. Methyl protons not observed (under solvent).

EXAMPLE 38

(R)-4-Hydroxy-7-(1-hydroxy-2-(2-(3-((4-(5-methylthiophene-2-carbonyl)-1-oxa-4,9-diazaspiro[5.5]undecan-9-yl)methyl)phenoxy)ethylamino)ethyl)benzo[d]thiazol-2(3H)-one ditrifluoroacetate

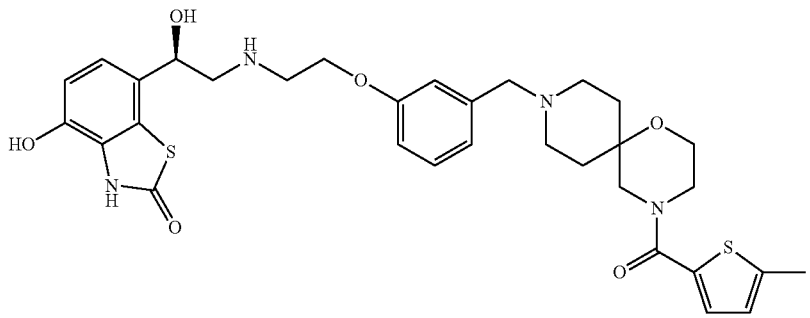 [SMILES: Cc1ccc(C(=O)N2CCOC3(CCN(Cc4cccc(OCCNC[C@H](O)c5ccc(O)c6[nH]c(=O)sc56)c4)CC3)C2)s1]

a) (3-(2,2-Diethoxyethoxy)phenyl)methanol

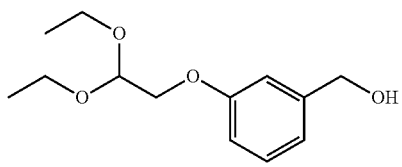 [SMILES: CCOC(COc1cccc(CO)c1)OCC]

Cesium carbonate (7.87 g) was added to a solution of 3-(hydroxymethyl)phenol (2.5 g) and 2-bromo-1,1-diethoxyethane (3.97 g) in DMF (40 mL) and the resultant mixture was heated at 90° C. for 18 hours. The mixture was cooled to room temperature and partitioned between ethyl acetate and brine, the organic layer was washed twice with brine, dried over sodium sulphate, filtered and the solvent evaporated under reduced pressure. The crude product was purified by flash silica chromatography using 30% ethyl acetate in isohexane as solvent. Pure fractions were evaporated to dryness to afford the subtitled compound. Yield 1.9 g.

$^1$H NMR (400 MHz, $D_6$-DMSO) δ 7.21 (t, J=7.9 Hz, 1H), 6.91-6.86 (m, 2H), 6.82-6.78 (m, 1H), 5.14 (t, J=5.9 Hz, 1H), 4.79 (t, J=5.1 Hz, 1H), 4.46 (d, J=5.9 Hz, 2H), 3.93 (d, J=5.1 Hz, 2H), 3.71-3.63 (m, 2H), 3.61-3.52 (m, 2H), 1.14 (t, J=7.0 Hz, 6H).

b) (9-(3-(2,2-Diethoxyethoxy)benzyl)-1-oxa-4,9-diazaspiro[5.5]undecan-4-yl)(5-methylthiophen-2-yl)methanone

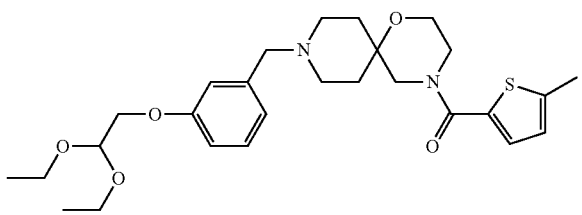 [SMILES: CCOC(COc1cccc(CN2CCC3(CC2)CN(C(=O)c2ccc(C)s2)CCO3)c1)OCC]

Methanesulphonyl chloride (0.1 mL) was added dropwise to a stirred solution at 0° C. of (3-(2,2-diethoxyethoxy)phenyl)methanol (example 38, step a) (0.307 g) and triethylamine (0.178 mL) in dichloromethane (30 mL). The resultant mixture was stirred at 20° C. for 1 hour. The mixture was washed with water and the organic layer was dried over sodium sulphate, filtered and the solvent evaporated under reduced pressure. The residue was dissolved in acetonitrile (30 mL) and treated with triethylamine (1 mL) followed by (5-methylthiophen-2-yl)(1-oxa-4,9-diazaspiro[5.5]undecan-4-yl)methanone trifluoroacetate (example 9, step b) (0.42 g). The mixture was stirred at 20° C. for 2 hours. The solvent was removed under reduced pressure and the residue partitioned between ethyl acetate and brine, the organic layer was dried over sodium sulphate, filtered and the solvent removed under reduced pressure. The crude product was purified by flash silica chromatography using 3% methanol in dichloromethane with 1% triethylamine as solvent. Pure fractions were evaporated to dryness to afford the subtitled compound. Yield 0.45 g.

m/z 503 (M+H)$^+$ (APCI)

c) 2-(3-((4-(5-Methylthiophene-2-carbonyl)-1-oxa-4,9-diazaspiro[5.5]undecan-9-yl)methyl)phenoxy)acetaldehyde

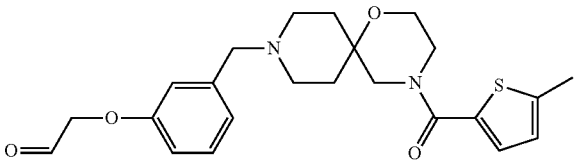 [SMILES: Cc1ccc(C(=O)N2CCOC3(CCN(Cc4cccc(OCC=O)c4)CC3)C2)s1]

A solution of (9-(3-(2,2-diethoxyethoxy)benzyl)-1-oxa-4,9-diazaspiro[5.5]undecan-4-yl)(5-methylthiophen-2-yl)methanone (example 38, step b) (0.45 g) in a mixture of acetic acid (25 mL) and water (25 mL) was heated at 65° C. under nitrogen for 16 hours. Most of the solvents were removed under reduced pressure and the residue partitioned between ethyl acetate and excess saturated sodium bicarbonate solution. The organic layer was dried over sodium sulphate and filtered, acetic acid (0.051 mL) was added and the solvent removed under reduced pressure to afford the subtitled compound. Yield 0.38 g. Used directly.

d) (R)-4-Hydroxy-7-(1-hydroxy-2-(2-(3-((4-(5-methylthiophene-2-carbonyl)-1-oxa-4,9-diazaspiro[5.5]undecan-9-yl)methyl)phenoxy)ethylamino)ethyl)benzo[d]thiazol-2(3H)-one ditrifluoroacetate

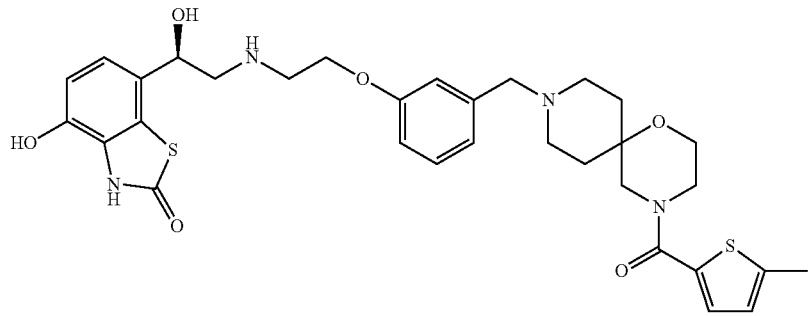 [SMILES: Cc1ccc(C(=O)N2CCOC3(CCN(Cc4cccc(OCCNC[C@H](O)c5ccc(O)c6[nH]c(=O)sc56)c4)CC3)C2)s1]

Sodium cyanoborohydride (0.084 g) was added to a stirred solution at 20° C. of (R)-7-(2-amino-1-hydroxyethyl)-4-hydroxybenzo[d]thiazol-2(3H)-one hydrochloride (WO2007027134, example 1, step d) (0.303 g) and 2-(3-((4-(5-methylthiophene-2-carbonyl)-1-oxa-4,9-diazaspiro[5.5]undecan-9-yl)methyl)phenoxy)acetaldehyde (example 38, step c) (0.38 g) and acetic acid (0.051 mL) in methanol (12 mL). The reaction mixture was stirred at 20° C. for 5 hours. The reaction mixture was evaporated under reduced pressure to a volume of 3 mL and then partitioned between ethyl acetate (20 mL) and water (20 mL). The aqueous layer was treated with saturated sodium bicarbonate solution (3 mL). The aqueous mixture was then treated with solid sodium chloride to give a saturated solution, which was extracted with THF (20 mL). The THF layer was dried over sodium sulphate, filtered and the solvent evaporated under reduced pressure. The crude product was purified by preparative HPLC (Sunfire™, Gradient: 10-40% acetonitrile in 0.2% aqueous TFA). The fractions containing the desired compound were evaporated to dryness to afford the titled compound. Yield 0.1 g.

m/z 639 (M+H)$^+$ (APCI)

$^1$H NMR (400 MHz, D$_6$-DMSO, 90° C.) δ 11.28 (s, 1H), 7.43-7.36 (m, 1H), 7.21 (s, 1H), 7.14 (s, 2H), 7.07 (d, J=8.5 Hz, 1H), 6.95 (d, J=8.2 Hz, 1H), 6.82-6.76 (m, 2H), 5.00-4.91 (m, 1H), 4.36-4.28 (m, 4H), 3.73-3.69 (m, 2H), 3.68-3.63 (m, 2H), 3.54 (s, 2H), 3.45 (s, 2H), 3.25-3.04 (m, 6H), 2.46 (s, 3H), 2.09-1.98 (m, 2H), 1.87-1.72 (m, 2H). Five exchangeable protons not observed.

EXAMPLE 39

7-((1R)-2-(2-Fluoro-2-(3-((4-(2-isopropylthiazole-4-carbonyl)-1-oxa-4,9-diazaspiro[5.5]undecan-9-yl)methyl)phenyl)ethylamino)-1-hydroxyethyl)-4-hydroxybenzo[d]thiazol-2(3H)-one ditrifluoroacetate

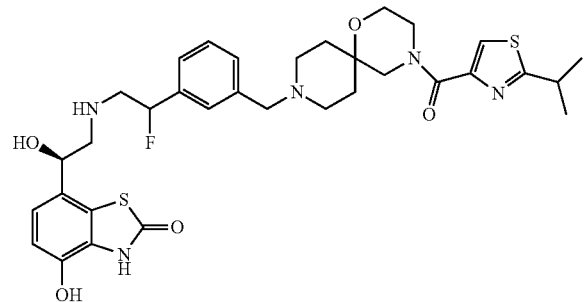 [SMILES: CC(C)c1nc(C(=O)N2CCOC3(CCN(Cc4cccc(C(F)CNC[C@H](O)c5ccc(O)c6[nH]c(=O)sc56)c4)CC3)C2)cs1]

a) Ethyl 2-(3-bromophenyl)-2-fluoroacetate

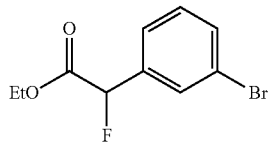

A solution of ethyl 2-(3-bromophenyl)acetate (1.00 g) and tert-butyldimethylchlorosilane (0.749 g) in THF (4 mL) was cooled to −78° C. under an atmosphere of nitrogen and treated with lithium bis(trimethylsilyl)amide (1M in THF, 4.6 mL), added dropwise over 10 minutes. The solution was stirred at −78° C. for 5 minutes, then removed from the cooling bath and allowed to warm to room temperature over 30 minutes. The solution was concentrated in vacuo and the residue suspended in isohexane and filtered to remove precipitated lithium chloride. The filtrate was concentrated in vacuo the give an oil (1.49 g), which was dissolved in acetonitrile (2 mL) and added dropwise to a stirred suspension of Selectfluor™ fluorinating reagent (1.93 g) in acetonitrile (17 mL) at room temperature, completing the addition with acetonitrile (3×1 mL). The resulting mixture was stirred for 1.5 hours, then concentrated onto silica and purified by flash chromatography on silica eluted with 10% diethyl ether in isohexane, to afford the subtitled compound contaminated with starting material as a colourless oil. Yield 0.884 g.

$^1$H NMR (400 MHz, CDCl$_3$) δ 7.63 (s, 1H), 7.53 (d, J=7.9 Hz, 1H), 7.28 (t, J=8.0 Hz, 2H), 5.73 (d, J=47.7 Hz, 1H), 4.33-4.19 (m, 2H), 1.28 (t, J=7.1 Hz, 3H).

b) 2-(3-Bromophenyl)-2-fluoroethanol

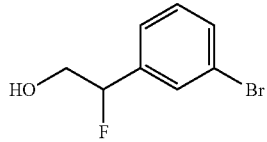 [SMILES: OCC(F)c1cccc(Br)c1]

Lithium aluminum hydride (1M in THF, 13.0 mL) was added portionwise over 7 minutes to a solution of ethyl 2-(3- bromophenyl)-2-fluoroacetate (example 39, step a) (2.94 g) in THF (35 mL), pre-cooled in ice-water. The resulting mixture was stirred in ice-water for 30 minutes, then quenched by the careful addition of methanol (5 mL), added portionwise over 30 minutes. The mixture was poured into 2 molar aqueous HCl and extracted three times with ethyl, acetate. The combined organic extracts were washed with brine, dried over anhydrous magnesium sulphate and purified by flash chromatography on silica eluted with 25% diethyl ether in isohexane to afford the subtitled compound as colourless oil. Yield 1.39 g.

$^1$H NMR (400 MHz, CDCl$_3$) δ 7.53-7.46 (m, 2H), 7.30-7.24 (m, 2H), 5.53 (ddd, J=48.2, 7.2, 3.3 Hz, 1H), 3.97-3.77 (m, 2H), 1.95 (dd, J=8.2, 5.1 Hz, 1H).

c) (2-(3-Bromophenyl)-2-fluoroethoxy)(tert-butyl)dimethylsilane

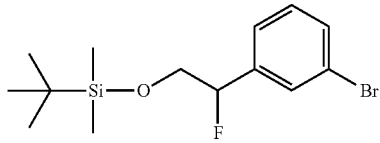 [SMILES: CC(C)(C)[Si](C)(C)OCC(F)c1cccc(Br)c1]

A solution of 2-(3-bromophenyl)-2-fluoroethanol (example 39, step b) (1.38 g) and imidazole (1.29 g) in DMF (14 mL) was cooled in ice-water, treated with tert-butyldimethylchlorosilane (1.049 g), then removed from the cooling bath and stirred at room temperature overnight. The solution was poured into water and extracted twice with diethyl ether. The combined organic extracts were washed twice with water, once with brine, then dried over anhydrous magnesium sulphate and purified by flash chromatography on silica eluted with 10% dichloromethane in isohexane to afford the subtitled compound as a colourless oil. Yield 1.94 g.

$^1$H NMR (400 MHz, CDCl$_3$) δ 7.51-7.49 (m, 1H), 7.46 (dt, J=7.0, 2.0 Hz, 1H), 7.28-7.21 (m, 2H), 5.43 (ddd, J=47.5, 6.5, 3.8 Hz, 1H), 3.95-3.76 (m, 2H), 0.88 (s, 9H), 0.03 (d, J=4.6 Hz, 6H).

d) 3-(2-(tert-Butyldimethylsilyloxy)-1-fluoroethyl)benzaldehyde

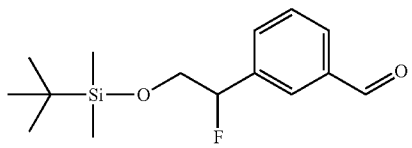 [SMILES: CC(C)(C)[Si](C)(C)OCC(F)c1cccc(C=O)c1]

A solution of (2-(3-bromophenyl)-2-fluoroethoxy)(tert-butyl)dimethylsilane (example 39, step c) (1.8 g) in THF (36 mL) was cooled to −78° C. under an atmosphere of nitrogen and treated with butyllithium (1.8M in hexanes, 3.3 mL), added dropwise over 5 minutes. The solution was stirred at −78° C. for 30 minutes, treated with N,N-dimethylformamide (0.63 mL), stirred at −78° C. for a further 30 minutes, then removed from the cooling bath and allowed to warm to room temperature over 140 minutes. The solution was quenched by the addition of 10% aqueous ammonium chloride, and the resulting mixture was extracted twice with diethyl ether. The combined organic phases were washed with brine, dried over anhydrous magnesium sulphate and purified by flash chromatography on silica eluted with 50% dichloromethane in isohexane to afford the subtitled compound as a colourless oil. Yield 1.26 g.

$^1$H NMR (400 MHz, CDCl$_3$) δ 10.04 (s, 1H), 7.88-7.84 (m, 2H), 7.63 (d, J=7.4 Hz, 1H), 7.56 (t, J=7.4 Hz, 1H), 5.55 (ddd, J=47.3, 6.2, 4.0 Hz, 1H), 4.00-3.83 (m, 2H), 0.87 (s, 9H), 0.02 (d, J=3.9 Hz, 6H).

e) (9-(3-(2-(tert-Butyldimethylsilyloxy)-1-fluoroethyl)benzyl)-1-oxa-4,9-diazaspiro[5.5]undecan-4-yl)(2-isopropylthiazol-4-yl)methanone

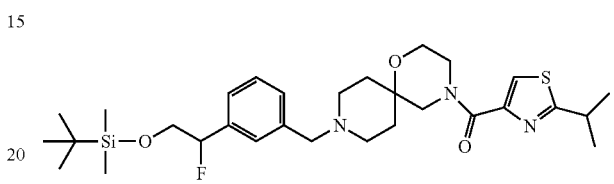

A solution of 3-(2-(tert-butyldimethylsilyloxy)-1-fluoroethyl)benzaldehyde (example 39, step d) (0.329 g) in MeOH (4 mL) was treated with acetic acid (0.055 mL) followed by (2-isopropylthiazol-4-yl)(1-oxa-4,9-diazaspiro[5.5]undecan-4-yl)methanone trifluoroacetate (example 22, step b) (0.408 g) and stirred at room temperature for 5 minutes. The solution was cooled in an ice-water bath, treated with sodium triacetoxyborohydride (0.309 g), stirred in ice-water for 135 minutes, then removed from the cooling bath and stirred at room temperature for a further 65 minutes. The solution was cooled back down in ice-water, treated with more sodium triacetoxyborohydride (0.310 g) and stirred in ice-water for 75 minutes. More sodium triacetoxyborohydride (0.312 g) was added and the mixture was stirred for 70 minutes. More sodium triacetoxyborohydride (0.619 g) was added and the mixture was stirred overnight, allowing the cooling bath to slowly expire. The next day, more sodium triacetoxyborohydride (0.307 g) was added and the mixture was stirred for 70 minutes. More acetic acid (0.055 mL) was added and the mixture was stirred for 80 minutes. The mixture was warmed to 40° C. and stirred at that temperature for 25 minutes, then it was concentrated onto flash silica in vacuo. The residue was purified by flash chromatography on silica eluted with 5% methanol in dichloromethane to afford the subtitled compound as a sticky white solid. Yield 0.344 g.

$^1$H NMR (400 MHz, D$_6$-DMSO, 90° C.) δ 7.93 (s, 1H), 7.57-7.11 (m, 4H), 5.64-5.43 (m, 1H), 4.00-3.81 (m, 2H), 3.77-3.55 (m, 6H), 3.31 (septet, J=6.8 Hz, 1H), 3.13-2.88 (m, 2H), 2.57-2.35 (m, 4H), 2.16-1.94 (m, 2H), 1.74-1.54 (m, 2H), 1.36 (d, J=6.7 Hz, 6H), 0.84 (s, 9H), 0.01 (s, 6H).

f) (9-(3-(1-Fluoro-2-hydroxyethyl)benzyl)-1-oxa-4,9-diazaspiro[5.5]undecan-4-yl)(2-isopropylthiazol-4-yl)methanone

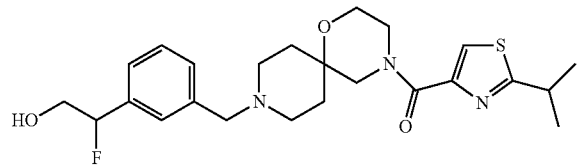 [SMILES: CC(C)c1nc(C(=O)N2CCOC3(CCN(Cc4cccc(C(F)CO)c4)CC3)C2)cs1]

A solution of (9-(3-(2-(tert-butyldimethylsilyloxy)-1-fluoroethyl)benzyl)-1-oxa-4,9-diazaspiro[5.5]undecan-4-yl)(2-isopropylthiazol-4-yl)methanone (example 39, step e) (0.33 g) in THF (5 mL) was treated with tetrabutylammonium fluoride (1M in THF, 0.69 mL) and stirred at room temperature for 50 minutes. More tetrabutylammonium fluoride (1M in THF, 0.69 mL) was added and the mixture was stirred for a further 80 minutes. The solution was then concentrated onto flash silica and the residue was purified by flash chromatography on silica eluted with 7.5% methanol in dichloromethane to afford the subtitled compound as a white foam. Yield 0.221 g.

$^1$H NMR (400 MHz, D$_6$-DMSO, 90° C.) δ 7.91 (d, J=1.5 Hz, 1H), 7.36-7.19 (m, 4H), 5.45 (ddd, J=48.5, 6.6, 3.7 Hz, 1H), 4.86-4.76 (m, 1H), 3.80-3.58 (m, 9H), 3.58-3.44 (m, 1H), 3.31 (septet, J=6.8 Hz, 1H), 2.46-2.28 (m, 4H), 1.79-1.67 (m, 2H), 1.66-1.50 (m, 2H), 1.36 (d, J=6.9 Hz, 6H).

g) 2-Fluoro-2-(3-((4-(2-isopropylthiazole-4-carbonyl)-1-oxa-4,9-diazaspiro[5.5]undecan-9-yl)methyl)phenyl)acetaldehyde A solution of (9-(3-(1-fluoro-2-hydroxyethyl)benzyl)-1-oxa-4,9-diazaspiro[5.5]undecan-4-yl)(2-isopropylthiazol-4-yl)methanone (example 39, step f) (0.213 g) in DCM (5 mL) was cooled in ice-water and treated with trifluoroacetic acid (0.053 mL) and stirred for 5 minutes. Dess-Martin periodinane (0.296 g) was added and the mixture was removed from the cooling bath and stirred at room temperature for 20 minutes. More Dess-Martin periodinane (0.295 g) was added and the mixture was stirred at room temperature for an additional 30 minutes. The reaction was then quenched by the addition of saturated sodium thiosulphate solution (5 mL), saturated sodium bicarbonate solution (5 mL) and ethyl acetate (5 mL), and the resulting two-phase mixture was stirred for 10 minutes. The mixture was then extracted twice with ethyl acetate, and the combined organic extracts washed with brine. Acetic acid (0.1 mL) was added, then the acidified extracts were dried over anhydrous magnesium sulphate and concentrated in vacuo to afford the crude subtitled product as an off-white foam. Yield 0.240 g.

m/z 460 (M+H)$^+$ (APCI)

h) 7-((1R)-2-(2-Fluoro-2-(3-((4-(2-isopropylthiazole-4-carbonyl)-1-oxa-4,9-diazaspiro[5.5]undecan-9-yl)methyl)phenyl)ethylamino)-1-hydroxyethyl)-4-hydroxybenzo[d]thiazol-2(3H)-one ditrifluoroacetate A solution of (R)-7-(2-amino-1-hydroxyethyl)-4-hydroxybenzo[d]thiazol-2(3H)-one hydrochloride (WO2007027134, example 1 step d) (0.182 g) in methanol (3 mL) was treated with acetic acid (0.039 mL) and stirred for 5 minutes. A solution of 2-fluoro-2-(3-((4-(2-isopropylthiazole-4-carbonyl)-1-oxa-4,9-diazaspiro[5.5]undecan-9-yl)methyl)phenyl)acetaldehyde (example 39, step g) (0.239 g) in methanol (4 mL) was then added and the resulting mixture was stirred at room temperature for 5 minutes, before cooling in ice-water and treating with sodium triacetoxyborohydride (0.146 g). The mixture was stirred in ice for 25 minutes, then more sodium triacetoxyborohydride (0.444 g) was added. The mixture was then stirred over the weekend, allowing it to slowly warm to room temperature. The following Monday the mixture was concentrated in vacuo. The residue was dissolved in a mixture of methanol (3 mL) and water (1.5 mL) and purified by preparative HPLC (Sunfire™, Gradient: 15-50% acetonitrile in 0.2% aqueous TFA). Fractions containing product were concentrated in vacuo and co-evaporated from acetonitrile three times to give a colourless residue. The residue was triturated with diethyl ether to give a solid, which was removed by filtration, washed with diethyl ether and dried in vacuo at room temperature to afford the titled product as a white solid (0.03 g.)

m/z 670 (M+H)$^+$ (APCI)

$^1$H NMR (400 MHz, D$_6$-DMSO, 90° C.) δ 7.94 (s, 1H), 7.60-7.45 (m, 4H), 6.93 (dd, J=8.2, 2.3 Hz, 1H), 6.77 (d, J=7.9 Hz, 1H), 5.97 (dt, J=49.2, 9.7 Hz, 1H), 4.99-4.89 (m, 1H), 4.36-4.17 (m, 2H), 3.75-3.62 (m, 6H), 3.60-2.90 (m, 9H), 2.08-1.92 (m, 2H), 1.81-1.64 (m, 2H), 1.35 (d, J=6.9 Hz, 6H). Six exchangeable protons not observed.

EXAMPLE 40

(R)-7-(2-(4-Fluoro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

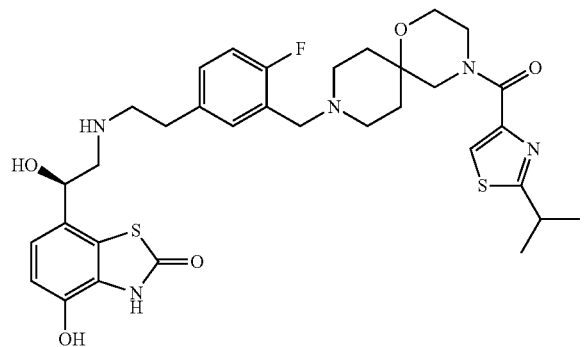 [SMILES: CC(C)c1nc(C(=O)N2CCOC3(CCN(Cc4cc(CCNC[C@H](O)c5ccc(O)c6[nH]c(=O)sc56)ccc4F)CC3)C2)cs1]

a) 2-Fluoro-5-(2-hydroxyethyl)benzaldehyde

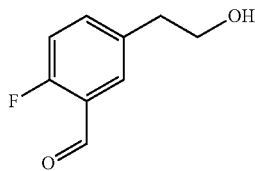

2,2,6,6-Tetramethylpiperidine (3.0 g) was added dropwise to a stirred solution of n-butyllithium (1.6M in hexanes, 13 mL) in dry tetrahydrofuran (12 mL) at −78° C. After 10 min, 2-(4-fluorophenyl)ethanol (1.00 g) was added dropwise. The reaction mixture was stirred at −78° C. for 5 h and then dry DMF (3.18 mL) was added dropwise over 5 min. The cooling bath was removed and the reaction mixture allowed to warm to room temperature overnight. Ethyl acetate and aqueous HCl (2M) were added and the solution separated. The ethyl acetate layer was washed with water, brine, dried over sodium sulphate, filtered and evaporated in vacuo. Purification was by silica gel chromatography eluting with ethyl acetate:isohexane, 1:1 to give the subtitled compound as an oil. Yield 0.43 g.

$^1$H NMR (300 MHz, CDCl$_3$) δ 10.35 (s, 1H), 7.73 (dd, J=6.4 & 2.0 Hz, 1H), 7.52-7.46 (m, 1H), 7.12 (dd, J=10.0 & 8.4 Hz, 1H), 3.88 (t, J=6.5 Hz, 2H), 2.90 (t, J=6.5 Hz, 2H). One exchangeable proton not observed.

b) (9-(2-Fluoro-5-(2-hydroxyethyl)benzyl)-1-oxa-4,9-diazaspiro[5.5]undecan-4-yl)(2-isopropylthiazol-4-yl)methanone

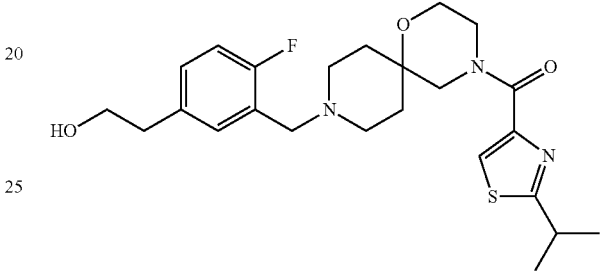

Sodium triacetoxyborohydride (0.339 g) was added to a stirred solution of 2-fluoro-5-(2-hydroxyethyl)benzaldehyde (example 40, step a) (0.135 g), (2-isopropylthiazol-4-yl)(1-oxa-4,9-diazaspiro[5.5]undecan-4-yl)methanone trifluoroacetate (example 22, step b) (0.339 g) and acetic acid (0.046 mL) in NMP (7 mL). After 16 h, more 2-fluoro-5-(2-hydroxyethyl)benzaldehyde (example 40, step a) (0.135 g) was added followed by sodium triacetoxyborohydride (0.339 g). After 2 h, the reaction mixture was diluted with ethyl acetate (60 mL) and washed with saturated sodium bicarbonate solution (30 mL). The aqueous layer was extracted with ethyl acetate. The combined ethyl acetate solution was evaporated in vacuo. Purification was by silica gel chromatography eluting with ethyl acetate:triethylamine, 10:1 to give the subtitled compound as a gum that contained NMP. The NMP was removed by applying the gum to a 10 g SCX cartridge eluting first with methanol and then 20% '880' aqueous ammonia in methanol to collect the subtitled compound. The solution was evaporated to dryness and the resulting gum applied to a silica gel column eluting with ethyl acetate:triethylamine, 10:1 to give the subtitled compound as a gum. Yield 0.31 g.

$^1$H NMR (400 MHz, D$_6$-DMSO, 90° C.) δ 7.90 (s, 1H), 7.19 (d, J=7.3 Hz, 1H), 7.13-7.07 (m, 1H), 6.97 (t, J=9.3 Hz, 1H), 4.28-4.24 (m, 1H), 3.71-3.55 (m, 6H), 3.46 (s, 2H), 3.35-3.26 (m, 1H), 3.00 (s, 2H), 2.70 (t, J=6.7 Hz, 2H), 2.45-2.26 (m, 4H), 1.74-1.65 (m, 2H), 1.59-1.49 (m, 2H), 1.36 (d, J=7.0 Hz, 6H).

c) 2-(4-Fluoro-3-((4-(2-isopropylthiazole-4-carbonyl)-1-oxa-4,9-diazaspiro[5.5]undecan-9-yl)methyl)phenyl)acetaldehyde

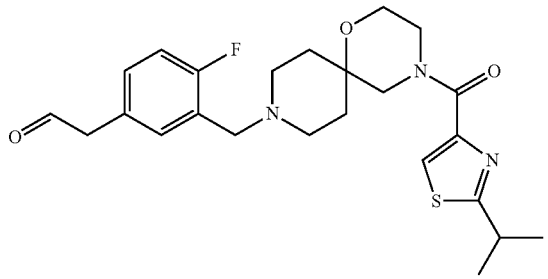 [SMILES: CC(C)c1nc(C(=O)N2CCOC3(CCN(Cc4cc(CC=O)ccc4F)CC3)C2)cs1]

Dess-Martin periodinane (0.284 g) was added to a stirred solution of (9-(2-fluoro-5-(2-hydroxyethyl)benzyl)-1-oxa-4,9-diazaspiro[5.5]undecan-4-yl)(2-isopropylthiazol-4-yl)methanone (example 40, step b) (0.21 g) and trifluoroacetic acid (0.046 mL) in DCM (5 mL). After 1 h, ethyl acetate (30 mL) was added followed by a mixture of saturated sodium thiosulphate solution (5 mL) and saturated sodium bicarbonate solution (5 mL). The reaction mixture was shaken well and separated. The ethyl acetate solution was washed with saturated sodium bicarbonate solution, water and brine. Acetic acid (0.07 mL) was added, the solution dried over sodium sulphate, filtered and evaporated in vacuo (bath temperature ~30° C.) to give the subtitled compound as a gum. Yield 0.2 g. Used directly.

m/z 460 (M+H)$^+$ (APCI)

d) (R)-7-(2-(4-Fluoro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

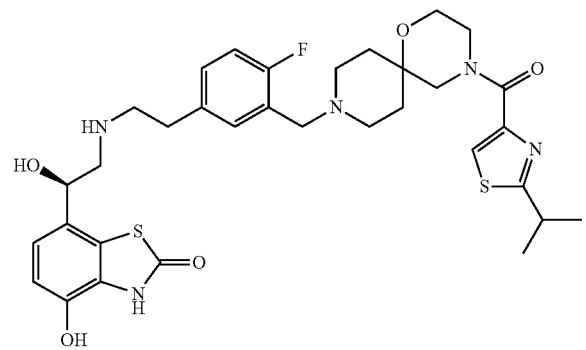 [SMILES: CC(C)c1nc(C(=O)N2CCOC3(CCN(Cc4cc(CCNC[C@H](O)c5ccc(O)c6[nH]c(=O)sc56)ccc4F)CC3)C2)cs1]

Acetic acid (0.037 mL) was added to a stirred solution of (R)-7-(2-amino-1-hydroxyethyl)-4-hydroxybenzo[d]thiazol-2(3H)-one hydrochloride (WO2007027134, example 1, step d) (0.17 g) and 2-(4-fluoro-3-((4-(2-isopropylthiazole-4-carbonyl)-1-oxa-4,9-diazaspiro[5.5]undecan-9-yl)methyl)phenyl)acetaldehyde (example 40, step c) (0.20 g) in methanol (8 mL). After 1 min, sodium cyanoborohydride (0.10 g) was added. After 3 h, the reaction mixture was concentrated in vacuo to ~2 mL, THF (20 mL) was added and the solution washed with a mixture of brine (10 mL) and saturated sodium bicarbonate solution (2 mL). The aqueous layer was extracted with ethyl acetate. The THF and ethyl acetate solutions were combined and evaporated in vacuo. The gum was dissolved in methanol and purified by preparative HPLC (Sunfire™, Gradient: 10-35% acetonitrile in 0.2% aqueous TFA). The fractions containing pure product were combined and evaporated to dryness. Trituration with diethyl ether gave the titled compound as a white solid. Yield 0.126 g.

m/z 670 (M+H)$^+$ (APCI)

$^1$H NMR (400 MHz, D$_6$-DMSO, 90° C.) δ 11.33-11.22 (m, 1H), 7.94 (s, 1H), 7.46-7.36 (m, 2H), 7.25 (t, J=9.0 Hz, 1H), 6.93 (d, J=8.4 Hz, 1H), 6.77 (d, J=8.4 Hz, 1H), 4.93-4.88 (m, 1H), 4.30-4.20 (m, 2H), 3.70 (s, 4H), 3.66 (s, 2H), 3.35-2.93 (m, 11H), 2.05-1.95 (m, 2H), 1.83-1.67 (m, 2H), 1.35 (d, J=7.0 Hz, 6H). Five exchangeable protons not observed.

EXAMPLE 41

(R)-7-(2-(3-Fluoro-5-((4-(2-phenylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

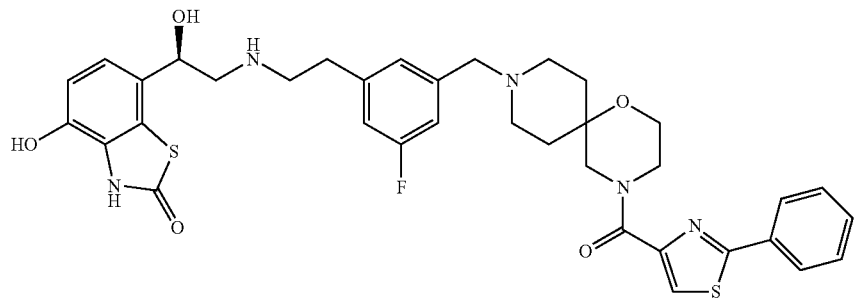 [SMILES: O=C(c1csc(-c2ccccc2)n1)N1CCOC2(CCN(Cc3cc(F)cc(CCNC[C@H](O)c4ccc(O)c5[nH]c(=O)sc45)c3)CC2)C1]

a) 2-(3-(Bromomethyl)-5-fluorophenyl)acetic acid

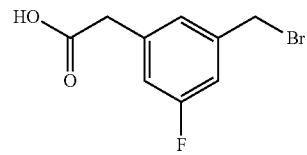 [SMILES: O=C(O)Cc1cc(F)cc(CBr)c1]

Benzoyl peroxide (0.5 g) was added to a stirred mixture of 2-(3-fluoro-5-methylphenyl)acetic acid (5.19 g) and NBS (6.04 g) in dichloromethane (100 mL). The resultant mixture was heated at reflux for 5 hours. The reaction mixture was cooled to room temperature and then washed twice with water, the organic layer was dried over sodium sulphate, filtered and the solvent evaporated under reduced pressure. The crude product was purified by flash silica chromatography using 1% acetic acid and 17% ethyl acetate in isohexane as solvent. Pure fractions were evaporated to dryness to afford the subtitled compound. Yield 4.3 g.

$^1$H NMR (400 MHz, D$_6$-DMSO) δ 7.22-7.17 (m, 2H), 7.09-7.05 (m, 1H), 4.68 (s, 2H), 3.61 (s, 2H). One exchangeable proton not observed.

b) 2-(3-(Bromomethyl)-5-fluorophenyl)ethanol

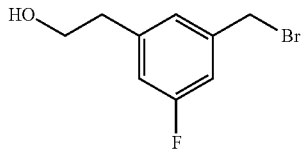 [SMILES: OCCc1cc(F)cc(CBr)c1]

Borane-methyl sulfide complex (2M in THF, 17.4 mL) was added dropwise over 10 minutes to a solution of 2-(3-(bromomethyl)-5-fluorophenyl)acetic acid (example 41, step a) (4.3 g) in THF (60 mL) at 0° C. The mixture was stirred at 0° C. for 10 minutes and then at 20° C. for 1 hour. The reaction mixture was quenched by dropwise addition of methanol and the solvents were removed under reduced pressure. The crude product was purified by flash silica chromatography using 30% ethyl acetate in isohexane as solvent. Pure fractions were evaporated to dryness to afford the subtitled compound. Yield 3.7 g.

$^1$H NMR (400 MHz, $D_6$-DMSO) δ 7.15 (s, 1H), 7.14-7.09 (m, 1H), 7.05-6.99 (m, 1H), 4.66 (s, 2H), 3.61 (t, J=6.8 Hz, 2H), 2.72 (t, J=6.7 Hz, 2H). One exchangeable proton not observed.

c) 2,2,2-Trifluoro-1-(9-(3-fluoro-5-(2-hydroxyethyl)benzyl)-1-oxa-4,9-diazaspiro[5.5]undecan-4-yl)ethanone

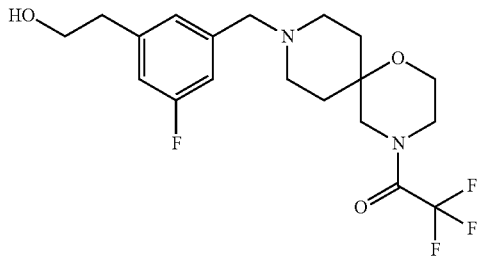 [SMILES: O=C(N1CCOC2(CCN(Cc3cc(F)cc(CCO)c3)CC2)C1)C(F)(F)F]

A solution of 2-(3-(bromomethyl)-5-fluorophenyl)ethanol (example 41, step b) (3.6 g) and 2,2,2-trifluoro-1-(1-oxa-4,9-diazaspiro[5.5]undecan-4-yl)ethanone trifluoroacetate (example 12, step d) (5.66 g) in acetonitrile (80 mL) was treated with triethylamine (5.38 mL) and the mixture stirred at 20° C. for 20 hours. The solvent was evaporated under reduced pressure and the residue partitioned between ethyl acetate and brine. The organic layer was dried over sodium sulphate, filtered and the solvent removed under reduced pressure. The crude product was purified by flash silica chromatography using 2.5% methanol in dichloromethane with 1% triethylamine as solvent. Pure fractions were evaporated to dryness to afford the subtitled compound. Yield 4.9 g.

m/z 405 (M+H)$^+$ (APCI)

d) (9-(3-Fluoro-5-(2-hydroxyethyl)benzyl)-1-oxa-4,9-diazaspiro[5.5]undecan-4-yl)(2-phenylthiazol-4-yl)methanone

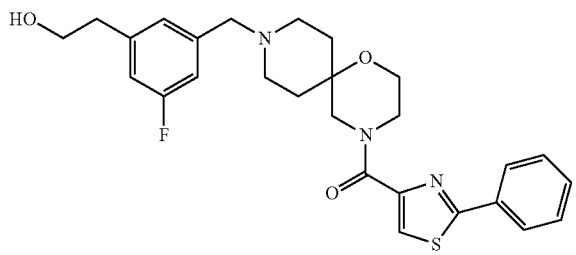 [SMILES: O=C(c1csc(-c2ccccc2)n1)N1CCOC2(CCN(Cc3cc(F)cc(CCO)c3)CC2)C1]

A solution of 2,2,2-trifluoro-1-(9-(3-fluoro-5-(2-hydroxyethyl)benzyl)-1-oxa-4,9-diazaspiro[5.5]undecan-4-yl)ethanone (example 41, step c) (0.21 g) in methanol (3 mL) was added to ammonia (35% aqueous solution, 15 mL) and the reaction mixture stirred at 20° C. for 1 hour. The mixture was evaporated to dryness under reduced pressure and the residue azeotroped three times with acetonitrile. The residue was dissolved in DMF (7 mL) and treated with 2-phenylthiazole-4-carboxylic acid (0.117 g) followed by triethylamine (0.29 mL) and then HATU (0.257 g) and the resultant mixture stirred at 20° C. for 1 hour. The mixture was partitioned between ethyl acetate and brine, the organic layer was washed twice with brine, dried over sodium sulphate, filtered and the solvent evaporated under reduced pressure to afford the subtitled compound. Yield 0.27 g.

m/z 496 (M+H)$^+$ (APCI)

e) (R)-7-(2-(3-Fluoro-5-((4-(2-phenylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

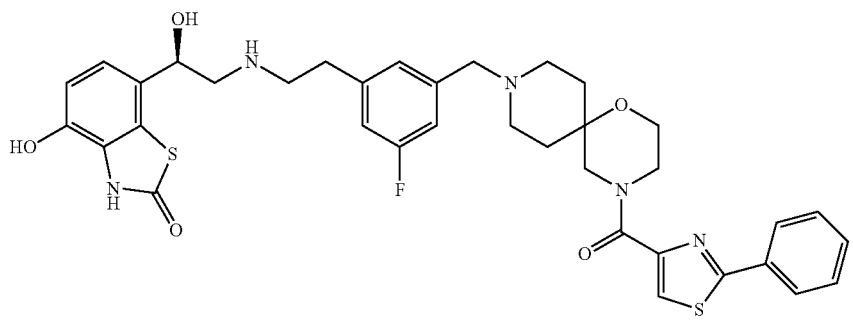 [SMILES: O=C(c1csc(-c2ccccc2)n1)N1CCOC2(CCN(Cc3cc(F)cc(CCNC[C@H](O)c4ccc(O)c5[nH]c(=O)sc45)c3)CC2)C1]

A solution of (9-(3-fluoro-5-(2-hydroxyethyl)benzyl)-1-oxa-4,9-diazaspiro[5.5]undecan-4-yl)(2-phenylthiazol-4-yl)methanone (example 41, step d) (0.25 g) in dichloromethane (20 mL) was treated with trifluoroacetic acid (0.039 mL) followed by Dess-Martin periodinane (0.278 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.029 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.199 g) and acetic acid (0.029 mL) in methanol (15 mL). The mixture was cooled in an ice bath and treated with sodium cyanoborohydride (0.063 g). The cooling bath was removed and the mixture stirred at 20° C. for 3 hours. The solvent was evaporated under reduced pressure to a volume of 3 mL and THF (20 mL) was added. The mixture was washed with a mixture of brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.19 g.

m/z 704 (M+H)⁺ (APCI)

¹H NMR (400 MHz, D₆-DMSO, 90° C.) δ 11.28 (s, 1H), 8.14 (s, 1H), 7.96-7.91 (m, 2H), 7.54-7.49 (m, 3H), 7.28-7.18 (m, 3H), 6.93 (d, J=8.5 Hz, 1H), 6.77 (d, J=8.5 Hz, 1H), 4.94-4.87 (m, 1H), 4.28 (s, 2H), 3.83-3.66 (m, 6H), 3.26 (t, J=7.9 Hz, 2H), 3.21-2.99 (m, 8H), 2.10-2.00 (m, 2H), 1.84-1.69 (m, 2H). Five exchangeable protons not observed.

EXAMPLE 42

(R)-7-(2-(3-Fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

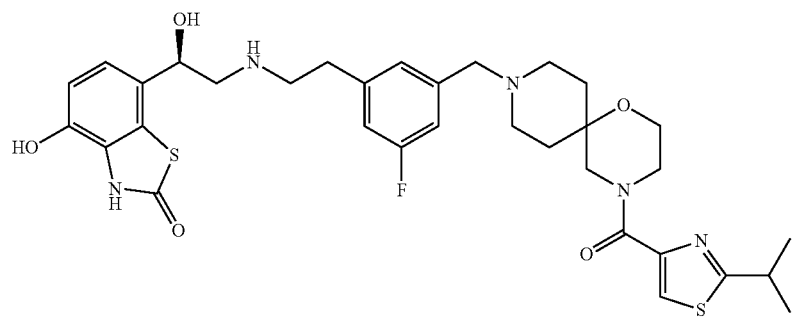

a) (9-(3-Fluoro-5-(2-hydroxyethyl)benzyl)-1-oxa-4,9-diazaspiro[5.5]undecan-4-yl)(2-isopropylthiazol-4-yl)methanone

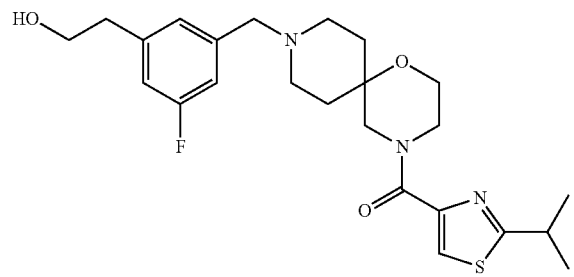

A solution of 2,2,2-trifluoro-1-(9-(3-fluoro-5-(2-hydroxyethyl)benzyl)-1-oxa-4,9-diazaspiro[5.5]undecan-4-yl)ethanone (example 41, step d) (0.21 g) in methanol (3 mL) was added to ammonia (35% aqueous solution, 15 mL) and the reaction mixture stirred at 20° C. for 1 hour. The mixture was evaporated to dryness under reduced pressure and the residue azeotroped three times with acetonitrile. The residue was dissolved in DMF (7 mL) and treated with 2-isopropylthiazole-4-carboxylic acid (0.098 g) followed by triethylamine (0.290 mL) and then HATU (0.257 g) and the resultant mixture stirred at 20° C. for 1 hour. The mixture was partitioned between ethyl acetate and brine, the organic layer was washed twice with brine, dried over sodium sulphate, filtered and the solvent evaporated under reduced pressure to afford the subtitled compound. Yield 0.25 g.

m/z 462 (M+H)+ (APCI)

b) (R)-7-(2-(3-Fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

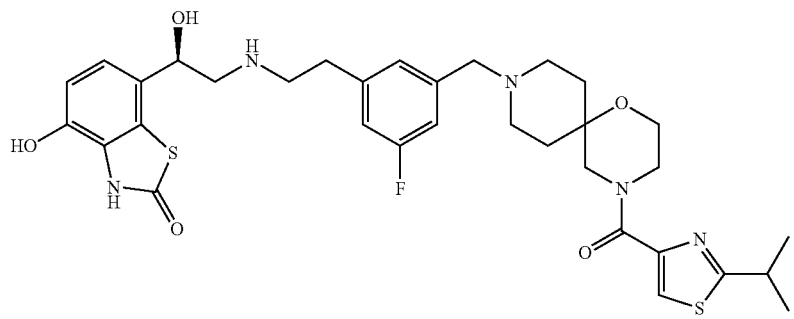

A solution of (9-(3-fluoro-5-(2-hydroxyethyl)benzyl)-1-oxa-4,9-diazaspiro[5.5]undecan-4-yl)(2-isopropylthiazol-4-yl)methanone (example 42, step a) (0.23 g) in DCM (20 mL) was treated with trifluoroacetic acid (0.038 mL) followed by Dess-Martin periodinane (0.275 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.029 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.196 g) and acetic acid (0.029 mL) in methanol (15 mL). The mixture was cooled in an ice bath and treated with sodium cyanoborohydride (0.063 g). The cooling bath was removed and the mixture stirred at 20° C. for 3 hours. The solvent was evaporated under reduced pressure to a volume of 3 mL and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.15 g.

m/z 670 (M+H)+ (APCI)
1H NMR (400 MHz, D6-DMSO, 90° C.) δ 11.27 (s, 1H), 7.94 (s, 1H), 7.28-7.16 (m, 3H), 6.93 (d, J=8.5 Hz, 1H), 6.77 (d, J=8.2 Hz, 1H), 4.94-4.88 (m, 1H), 4.27 (s, 2H), 3.70 (s, 4H), 3.66 (s, 2H), 3.32-3.23 (m, 3H), 3.17-2.99 (m, 8H), 2.07-1.96 (m, 2H), 1.81-1.69 (m, 2H), 1.35 (d, 6H). Five exchangeable protons not observed.

EXAMPLE 43

(R)-7-(2-(2-(5-((4-(2-tert-Butylthiazole-4-carbonyl)-1-oxa-4,9-diazaspiro[5.5]undecan-9-yl)methyl)thiophen-3-yl)ethylamino)-1-hydroxyethyl)-4-hydroxybenzo[d]thiazol-2(3H)-one ditrifluoroacetate

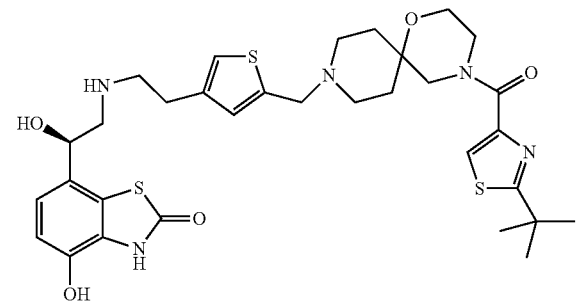 [SMILES: CC(C)(C)c1nc(C(=O)N2CCOC3(CCN(Cc4cc(CCNC[C@H](O)c5ccc(O)c6[nH]c(=O)sc56)cs4)CC3)C2)cs1]

a) 1-(9-((4-(2-(tert-Butyldimethylsilyloxy)ethyl)thiophen-2-yl)methyl)-1-oxa-4,9-diazaspiro[5.5]undecan-4-yl)-2,2,2-trifluoroethanone

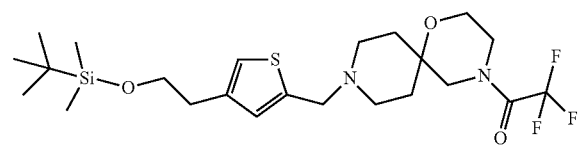 [SMILES: CC(C)(C)[Si](C)(C)OCCc1csc(CN2CCC3(CC2)CN(C(=O)C(F)(F)F)CCO3)c1]

2,2,2-Trifluoro-1-(1-oxa-4,9-diazaspiro[5.5]undecan-4-yl)ethanone trifluoroacetate (example 12, step d) (1.084 g) was added to a stirred solution of a 4:1 mixture of 4-(2-(tert-butyldimethylsilyloxy)ethyl)thiophene-2-carbaldehyde and 3-(2-(tert-butyldimethylsilyloxy)ethyl)thiophene-2-carbaldehyde (example 27, step b) (1.0 g), and AcOH (0.16 mL) in N-methyl-2-pyrrolidinone (15 mL). After 5 min, sodium triacetoxyborohydride (1.57 g) was added. After 16 h water was added and the mixture extracted with ethyl acetate. The ethyl acetate layer was washed three times with water and evaporated in vacuo. Purification by silica gel chromatography eluting with ethyl acetate:isohexane:triethylamine, 1:20:1 separated the two isomeric products and gave the subtitled compound as an oil. Yield 1.04 g.

$^1$H NMR (400 MHz, CDCl$_3$) δ 6.87 (s, 1H), 6.75 (d, J=3.7 Hz, 1H), 3.79-3.72 (m, 4H), 3.65 (s, 3H), 3.59-3.55 (m, 1H), 3.52 (s, 1H), 3.37 (s, 1H), 2.76 (t, J=6.9 Hz, 2H), 2.68-2.61 (m, 1H), 2.57-2.50 (m, 1H), 2.46-2.38 (m, 1H), 2.31 (t, J=11.5 Hz, 1H), 1.89-1.75 (m, 2H), 1.68-1.52 (m, 2H), 0.87 (s, 9H), 0.00 (s, 6H).

b) 9-((4-(2-(tert-Butyldimethylsilyloxy)ethyl)thiophen-2-yl)methyl)-1-oxa-4,9-diazaspiro[5.5]undecane

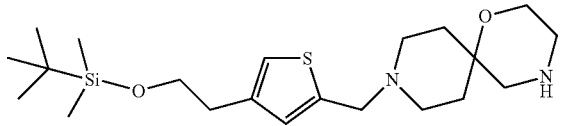 [SMILES: CC(C)(C)[Si](C)(C)OCCc1csc(CN2CCC3(CC2)CNCCO3)c1]

'880' Aqueous ammonia (1.5 mL) was added to stirred solution of 1-(9-((4-(2-(tert-butyldimethylsilyloxy)ethyl)thiophen-2-yl)methyl)-1-oxa-4,9-diazaspiro[5.5]undecan-4-yl)-2,2,2-trifluoroethanone (example 43, step a) (1.0 g) in methanol (5 mL). After 16 h the reaction mixture was evaporated to dryness. Acetonitrile was added, the solution evaporated to dryness in vacuo, and this process was repeated three times to give the subtitled compound as a white solid. Yield 0.78 g.

$^1$H NMR (400 MHz, CDCl$_3$) δ 6.94 (s, 1H), 6.87 (s, 1H), 3.91-3.85 (m, 2H), 3.78 (t, J=7.1 Hz, 2H), 3.72-3.68 (m, 2H), 2.93-2.82 (m, 4H), 2.80-2.73 (m, 4H), 2.62-2.53 (m, 2H), 2.11-2.01 (m, 2H), 1.76-1.64 (m, 2H), 0.87 (s, 9H), 0.00 (s, 6H)+1 exchangeable proton not observed.

c) (9-((4-(2-(tert-Butyldimethylsilyloxy)ethyl)thiophen-2-yl)methyl)-1-oxa-4,9-diazaspiro[5.5]undecan-4-yl)(2-tert-butylthiazol-4-yl)methanone

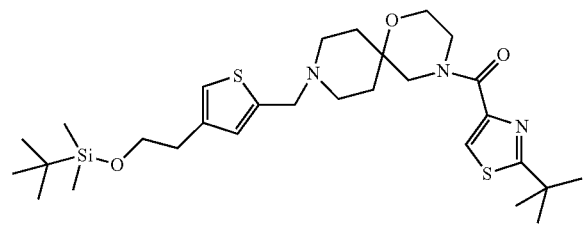 [SMILES: CC(C)(C)c1nc(C(=O)N2CCOC3(CCN(Cc4cc(CCO[Si](C)(C)C(C)(C)C)cs4)CC3)C2)cs1]

HATU (0.306 g) was added to stirred solution of 2-tert-butylthiazole-4-carboxylic acid (0.16 g), 9-((4-(2-(tert-butyldimethylsilyloxy)ethyl)thiophen-2-yl)methyl)-1-oxa-4,9-diazaspiro[5.5]undecane (example 43, step b) (0.300 g) and triethylamine (0.41 mL) in DMF (3 mL). After 1 h, the reaction mixture was partitioned between water and ethyl acetate. The ethyl acetate layer was washed twice with water and brine, dried over magnesium sulphate, filtered and evaporated in vacuo. Purification by silica gel chromatography eluting with ethyl acetate:isohexane:triethylamine, 12:90:10 gave the subtitled compound as a gum. Yield 0.3 g.

$^1$H NMR (300 MHz, CDCl$_3$) δ 7.82 (s, 1H), 6.85 (s, 1H), 6.74 (s, 1H), 4.01-3.92 (m, 1H), 3.92-3.84 (m, 1H), 3.82-3.71 (m, 7H), 3.69-3.58 (m, 3H), 2.79-2.71 (m, 2H), 2.60-2.28 (m, 4H), 1.93-1.79 (m, 2H), 1.44 (s, 9H), 0.87 (s, 9H), −0.01 (s, 6H).

d) (2-tert-Butylthiazol-4-yl)(9-((4-(2-hydroxyethyl)thiophen-2-yl)methyl)-1-oxa-4,9-diazaspiro[5.5]undecan-4-yl)methanone

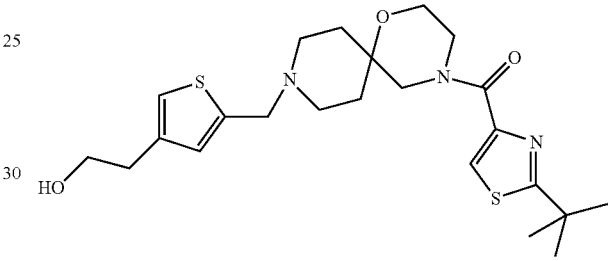

TBAF (1.5 mL of a 1M solution in THF) was added to stirred solution of (9-((4-(2-(tert-butyldimethylsilyloxy)ethyl)thiophen-2-yl)methyl)-1-oxa-4,9-diazaspiro[5.5]undecan-4-yl)(2-tert-butylthiazol-4-yl)methanone (example 43, step c) (0.300 g) in THF (3 mL). After 1 h the reaction was evaporated to a gum. Purification by silica gel chromatography eluting with ethyl acetate:triethylamine, 20:1 gave the subtitled compound as a gum. Yield 0.22 g.

$^1$H NMR (400 MHz, D$_6$-DMSO) δ 8.00 (s, 1H), 7.01 (s, 1H), 6.84-6.73 (m, 1H), 4.59 (t, J=5.3 Hz, 1H), 3.77-3.48 (m, 10H), 2.64 (t, J=7.0 Hz, 2H), 2.54-2.16 (m, 4H), 1.74-1.63 (m, 2H), 1.58-1.43 (m, 2H), 1.41 (s, 9H).

e) 2-(5-((4-(2-tert-Butylthiazole-4-carbonyl)-1-oxa-4,9-diazaspiro[5.5]undecan-9-yl)methyl)thiophen-3-yl)acetaldehyde

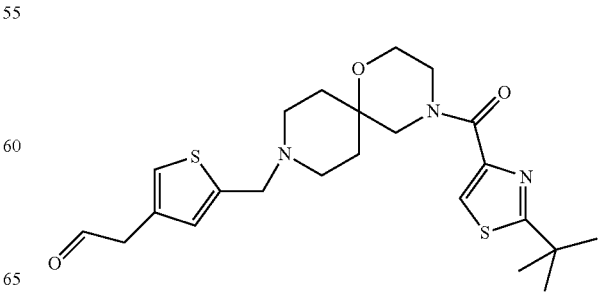

Dess-Martin periodinane (0.316 g) was added to stirred solution of (2-tert-butylthiazol-4-yl)(9-((4-(2-hydroxyethyl)thiophen-2-yl)methyl)-1-oxa-4,9-diazaspiro[5.5]undecan-4-yl)methanone (example 43, step d) (0.23 g) and TFA (0.05 mL) in DCM (5 mL). After 40 min the reaction mixture was treated with aqueous saturated sodium thiosulphate solution (5 mL), saturated sodium bicarbonate solution (5 mL) and ethyl acetate (30 mL). The mixture was extracted twice with ethyl acetate, the combined organics were washed with saturated sodium bicarbonate solution, acetic acid (0.08 mL) was added, then the solution was dried over sodium sulphate, filtered, and then evaporated in vacuo to afford the subtitled compound. Yield 0.23 g. Used directly.

m/z 462 (M+H)+ (APCI)

f) (R)-7-(2-(2-(5-((4-(2-tert-Butylthiazole-4-carbonyl)-1-oxa-4,9-diazaspiro[5.5]undecan-9-yl)methyl)thiophen-3-yl)ethylamino)-1-hydroxyethyl)-4-hydroxybenzo[d]thiazol-2(3H)-one ditrifluoroacetate

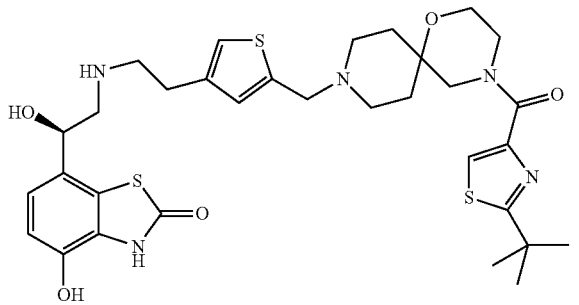 [SMILES: CC(C)(C)c1nc(C(=O)N2CCOC3(CCN(Cc4cc(CCNC[C@H](O)c5ccc(O)c6[nH]c(=O)sc56)cs4)CC3)C2)cs1]

Acetic acid (0.039 mL) was added to a stirred solution of (R)-7-(2-amino-1-hydroxyethyl)-4-hydroxybenzo[d]thiazol-2(3H)-one hydrochloride (WO2007027134, example 1, step d) (0.180 g) and 2-(5-((4-(2-tert-butylthiazole-4-carbonyl)-1-oxa-4,9-diazaspiro[5.5]undecan-9-yl)methyl)thiophen-3-yl)acetaldehyde (example 43, step e) (0.230 g) in MeOH (8 mL). After 1 min, sodium cyanoborohydride (0.125 g) was added. After 3 h, the reaction mixture was filtered and purified by preparative HPLC (Sunfire™, Gradient: 10-35% acetonitrile in 0.2% aqueous TFA). The fractions containing pure product were combined and evaporated to dryness. Trituration with diethyl ether gave the titled compound as a white solid. Yield 0.14 g.

m/z 672 (M+H)+ (APCI)

$^1$H NMR (400 MHz, D$_6$-DMSO) δ 11.67 (s, 1H), 10.24 (s, 1H), 8.91-8.71 (m, 2H), 8.04 (s, 1H), 7.46 (s, 1H), 7.18 (s, 1H), 6.93 (d, J=8.4 Hz, 1H), 6.77 (d, J=8.4 Hz, 1H), 6.54-6.44 (m, 1H), 4.93-4.86 (m, 1H), 4.68-4.51 (m, 2H), 3.82-3.47 (m, 8H), 3.32-3.15 (m, 4H), 3.12-2.87 (m, 5H), 2.15-2.07 (m, 2H), 1.83-1.54 (m, 2H), 1.39 (s, 9H).

EXAMPLE 44

(R)-5-(2-(3-((2,2-Difluoro-4-(2-isopropylthiazole-4-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

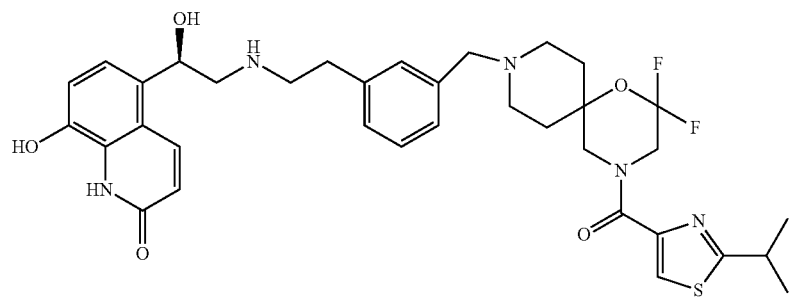 [SMILES: CC(C)c1nc(C(=O)N2CC(F)(F)OC3(CCN(Cc4cccc(CCNC[C@H](O)c5ccc(O)c6[nH]c(=O)ccc56)c4)CC3)C2)cs1]

a) tert-Butyl 2,2-difluoro-4-(2-isopropylthiazole-4-carbonyl)-1-oxa-4,9-diazaspiro[5.5]undecane-9-carboxylate

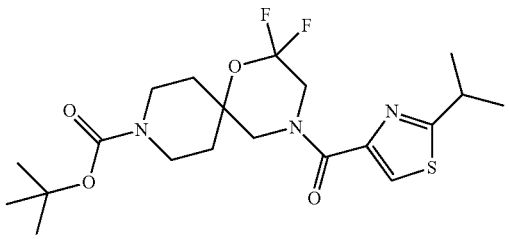 [SMILES: CC(C)c1nc(C(=O)N2CC(F)(F)OC3(CCN(C(=O)OC(C)(C)C)CC3)C2)cs1]

HATU (1.184 g) was added to a solution of tert-butyl 2,2-difluoro-1-oxa-4,9-diazaspiro[5.5]undecane-9-carboxylate (example 37, step c) (0.7 g) and 2-isopropylthiazole-4-carboxylic acid (0.41 g) and triethylamine (1 mL) in DMF (12 mL) at 20° C. and the resultant mixture stirred for 1 hour. The mixture was partitioned between ethyl acetate and brine, the organic layer was washed twice with brine, dried over sodium sulphate, filtered and the solvent evaporated under reduced pressure. The crude product was purified by flash silica chromatography using 30% ethyl acetate in isohexane as solvent. Pure fractions were evaporated to dryness to afford the subtitled compound. Yield 0.78 g.

$^1$H NMR (400 MHz, D$_6$-DMSO, 90° C.) δ 8.11 (s, 1H), 4.29-4.20 (m, 2H), 4.03-3.98 (m, 2H), 3.58-3.51 (m, 2H), 3.37-3.30 (m, 1H), 3.26-3.17 (m, 2H), 1.81-1.74 (m, 2H), 1.66-1.57 (m, 2H), 1.40 (s, 9H), 1.35 (d, 6H)

b) (2,2-Difluoro-1-oxa-4,9-diazaspiro[5.5]undecan-4-yl)(2-isopropylthiazol-4-yl)methanone trifluoroacetate

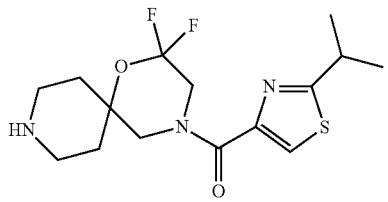 [SMILES: CC(C)c1nc(C(=O)N2CC(F)(F)OC3(CCNCC3)C2)cs1]

A solution of tert-butyl-2,2-difluoro-4-(2-isopropylthiazole-4-carbonyl)-1-oxa-4,9-diazaspiro[5.5]undecane-9-carboxylate (example 44, step a) (0.78 g) in DCM (20 mL) was treated with trifluoroacetic acid (5 mL) and the reaction mixture allowed to stand at 20° C. for 30 minutes. Toluene (40 mL) was added and the solvents evaporated under reduced pressure. The residue was azeotroped twice with acetonitrile to afford the subtitled compound. Yield 0.8 g.

m/z 346 (M+H)+ (APCI)

$^1$H NMR (300 MHz, D$_6$-DMSO, 90° C.) δ 8.57 (s, 2H), 8.16 (s, 1H), 4.39-4.22 (m, 2H), 4.04 (s, 2H), 3.39-3.28 (m, 1H), 3.27-3.19 (m, 2H), 3.16-3.04 (m, 2H), 2.07-1.97 (m, 2H), 1.93-1.80 (m, 2H), 1.37 (d, 6H).

c) (2,2-Difluoro-9-(3-(2-hydroxyethyl)benzyl)-1-oxa-4,9-diazaspiro[5.5]undecan-4-yl)(2-isopropylthiazol-4-yl)methanone

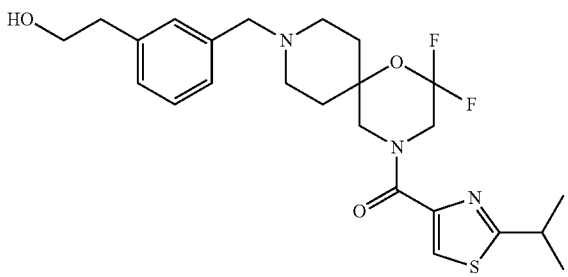 [SMILES: CC(C)c1nc(C(=O)N2CC(F)(F)OC3(CCN(Cc4cccc(CCO)c4)CC3)C2)cs1]

2-(3-(Bromomethyl)phenyl)ethanol (example 6, step a) (0.21 g) was added to a mixture of (2,2-difluoro-1-oxa-4,9-diazaspiro[5.5]undecan-4-yl)(2-isopropylthiazol-4-yl)methanone trifluoroacetate (example 44, step b) (0.40 g) and triethylamine (0.37 mL) in acetonitrile (15 mL). The reaction mixture was stirred at 20° C. for 2 hours. The solvent was evaporated under reduced pressure and the residue partitioned between ethyl acetate and brine, the organic layer was dried over sodium sulphate, filtered and the solvent evaporated under reduced pressure. The crude product was purified by flash silica chromatography using 2.5% methanol in dichloromethane with 1% triethylamine as solvent. Pure fractions were evaporated to dryness to afford the subtitled compound. Yield 0.40 g.

m/z 480 (M+H)+ (APCI)

d) (R)-5-(1-(tert-Butyldimethylsilyloxy)-2-(3-((2,2-difluoro-4-(2-isopropylthiazole-4-carbonyl)-1-oxa-4,9-diazaspiro[5.5]undecan-9-yl)methyl)phenethylamino)ethyl)-8-hydroxyquinolin-2(1H)-one

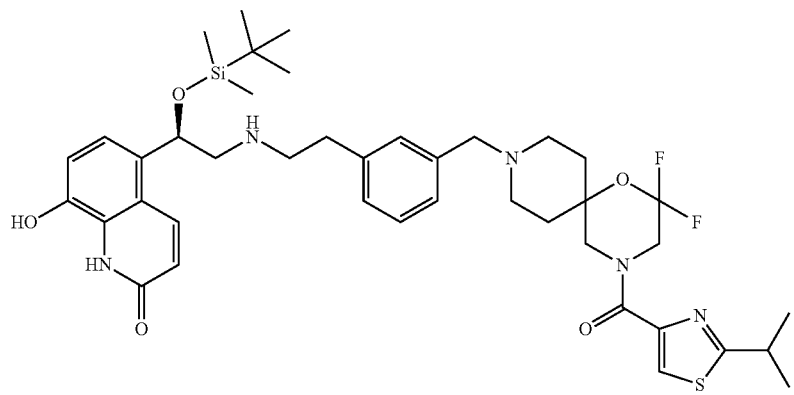 [SMILES: CC(C)c1nc(C(=O)N2CC(F)(F)OC3(CCN(Cc4cccc(CCNC[C@H](O[Si](C)(C)C(C)(C)C)c5ccc(O)c6[nH]c(=O)ccc56)c4)CC3)C2)cs1]

A solution of (2,2-difluoro-9-(3-(2-hydroxyethyl)benzyl)-1-oxa-4,9-diazaspiro[5.5]undecan-4-yl)(2-isopropylthiazol-4-yl)methanone (example 44, step c) (0.38 g) in DCM (20 mL) was treated with trifluoroacetic acid (0.061 mL) followed by Dess-Martin periodinane (0.437 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.045 mL) was added to this solution and the solvent then removed under reduced pressure. The residue was dissolved in methanol (3 mL) and added to a solution of (R)-5-(2-amino-1-(tert-butyldimethylsilyloxy)ethyl)-8-hydroxyquinolin-2(1H)-one (WO2004106333) (0.345 g) in methanol (15 mL). The mixture was cooled to 0° C. and sodium triacetoxyborohydride (0.252 g) was added in one portion. The reaction mixture was stirred at 20° C. for 3 hours. The solvent was removed under reduced pressure and the residue partitioned between ethyl acetate and saturated sodium bicarbonate solution, the organic layer was dried over sodium sulphate, filtered and the solvent removed under reduced pressure. The crude product was purified by flash silica chromatography using 10% methanol in dichloromethane with 1% "880" aqueous ammonia as solvent. Pure fractions were evaporated to dryness to afford the subtitled compound. Yield 0.32 g.

m/z 796 (M+H)+ (APCI)

e) (R)-5-(2-(3-((2,2-Difluoro-4-(2-isopropylthiazole-4-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

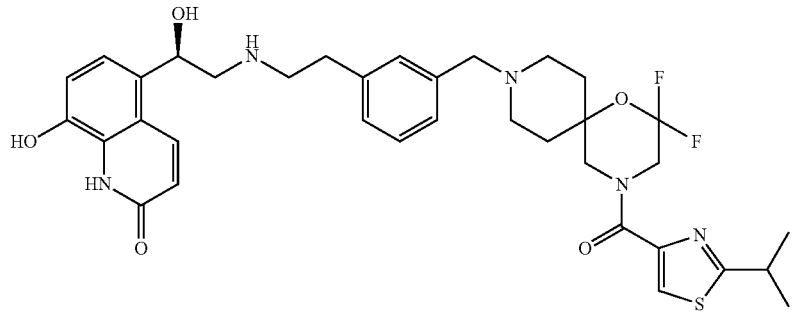 [SMILES: CC(C)c1nc(C(=O)N2CC(F)(F)OC3(CCN(Cc4cccc(CCNC[C@H](O)c5ccc(O)c6[nH]c(=O)ccc56)c4)CC3)C2)cs1]

Triethylamine trihydrofluoride (0.082 mL) in methanol (2 mL) was added to a solution of (R)-5-(1-(tert-butyldimethylsilyloxy)-2-(3-((2,2-difluoro-4-(2-isopropylthiazole-4-carbonyl)-1-oxa-4,9-diazaspiro[5.5]undecan-9-yl)methyl)phenethylamino)ethyl)-8-hydroxyquinolin-2(1H)-one (example 44, step d) (0.32 g) in THF (8 mL) and the reaction mixture allowed to stand at 20° C. for 18 hours. The solvent was removed under reduced pressure and the crude product was purified by preparative HPLC (Sunfire™, Gradient: 10-40% acetonitrile in 0.2% aqueous TFA). The fractions containing the desired compound were evaporated to dryness to afford the titled compound. Yield 0.21 g.

m/z 682 (M+H)$^+$ (APCI)

$^1$H NMR (400 MHz, D$_6$-DMSO, 90° C.) δ 8.18-8.11 (m, 2H), 7.44-7.31 (m, 4H), 7.14 (d, J=8.2 Hz, 1H), 6.99 (d, J=7.9 Hz, 1H), 6.55 (d, J=10.0 Hz, 1H), 5.37-5.31 (m, 1H), 4.31 (s, 2H), 4.23 (s, 2H), 4.01 (s, 2H), 3.40-2.98 (m, 11H), 2.08-1.99 (m, 2H), 1.98-1.88 (m, 2H), 1.36 (d, 6H). Six exchangeable protons not observed.

EXAMPLE 45

(R)-7-(2-(2,6-Difluoro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

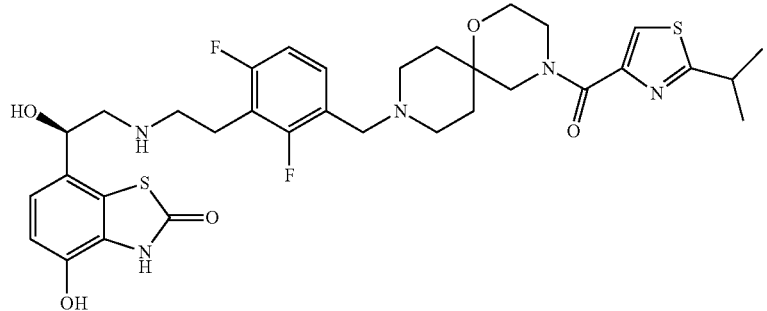 [SMILES: CC(C)c1nc(C(=O)N2CCOC3(CCN(Cc4ccc(F)c(CCNC[C@H](O)c5ccc(O)c6[nH]c(=O)sc56)c4F)CC3)C2)cs1]

a) 2-(2,6-Difluorophenyl)ethanol

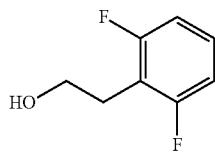 [SMILES: OCCc1c(F)cccc1F]

A solution of borane dimethyl sulfide complex (2M in THF, 26 mL) was added cautiously to a solution of 2-(2,6-difluorophenyl)acetic acid (3 g) in THF (50 mL) at 0° C. The reaction was then allowed to warm to RT and stirred for 3 h. The reaction was cooled in an ice bath and cautiously quenched with methanol (10 mL). The solvent was evaporated and the residue purified by silica gel chromatography eluting with 9:1 to 4:1 isohexane:ethyl acetate gradient. The fractions containing product were combined and evaporated to give the subtitled compound as a clear oil. Yield 2.2 g.

$^1$H NMR (400 MHz, CDCl$_3$) δ 7.20-7.13 (m, 1H), 6.94-6.82 (m, 2H), 3.85 (t, J=6.8 Hz, 2H), 2.97 (t, J=6.7 Hz, 2H). One exchangeable proton not observed.

b) 2,4-Difluoro-3-(2-hydroxyethyl)benzaldehyde

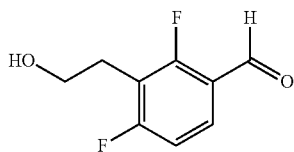 [SMILES: O=Cc1ccc(F)c(CCO)c1F]

2,2,6,6-Tetramethylpiperidine (5 mL) was added to a solution of butyllithium (1.6M in hexanes, 19 mL) in THF (25 mL) at −70° C. A solution of 2-(2,6-difluorophenyl)ethanol (example 45, step a) (1.6 g) in THF (25 mL) was added dropwise and the resulting mixture stirred for 2 h. DMF (3.9 mL) was then added and the mixture stirred for 1 h at −70° C. The mixture was then allowed to warm to RT and stirred for 70 h. The reaction was quenched with HCl solution (2M, 50 mL), diluted with ethyl acetate (100 mL) and the layers separated. The aqueous phase was extracted with ethyl acetate (2×50 mL). The combined organics were washed with brine (100 mL), dried over magnesium sulphate, filtered and evaporated. The residue was purified by silica gel chromatography eluting with 4:1 to 2:1 isohexane:ether gradient. The fractions containing product were combined and evaporated. The resulting oil was dissolved in ethyl acetate (50 mL) and washed with HCl solution (2M, 30 mL), brine (30 mL), dried over magnesium sulphate, filtered and evaporated to give the subtitled compound as a clear oil. Yield 1.1 g.

$^1$H NMR (300 MHz, CDCl$_3$) δ 10.28 (s, 1H), 7.84-7.74 (m, 1H), 7.05-6.95 (m, 1H), 3.89 (t, J=6.6 Hz, 2H), 3.01 (t, J=6.6 Hz, 2H). One exchangeable proton not observed.

c) (9-(2,4-Difluoro-3-(2-hydroxyethyl)benzyl)-1-oxa-4,9-diazaspiro[5.5]undecan-4-yl)(2-isopropylthiazol-4-yl)methanone

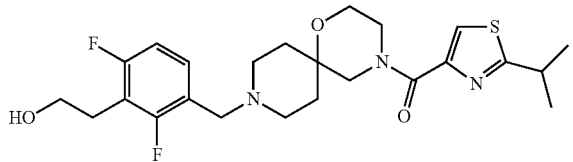 [SMILES: CC(C)c1nc(C(=O)N2CCOC3(CCN(Cc4ccc(F)c(CCO)c4F)CC3)C2)cs1]

2,4-Difluoro-3-(2-hydroxyethyl)benzaldehyde (example 45, step b) (0.35 g) was added to a solution of (2-isopropylthiazol-4-yl)(1-oxa-4,9-diazaspiro[5.5]undecan-4-yl)methanone trifluoroacetate (example 22, step b) (0.67 g) and acetic acid (0.09 mL) in N-methyl-2-pyrrolidinone (1 mL). The resulting mixture was stirred for 1 h then quenched by portionwise addition of sodium triacetoxyborohydride (0.335 g) over 5 min. The resulting mixture was stirred overnight, diluted with acetonitrile (20 mL) and applied to a SCX cartridge (10 g Varian, pre-wetted with acetonitrile, (50 mL)). The cartridge was washed with acetonitrile (50 mL) and eluted with 10% '880' aqueous ammonia in acetonitrile solution (50 mL). The eluent was evaporated, azeotroped with toluene and purified by silica gel chromatography eluting with 77.5:17.5:5 isohexane:ethyl acetate:triethylamine to 95:5 ethyl acetate:triethylamine gradient to give the subtitled compound as a yellow gum. Yield 0.74 g.

m/z 480 (M+H)$^+$ (APCI)

$^1$H NMR (300 MHz, D$_6$-DMSO) δ 8.00 (s, 1H), 7.32-7.16 (m, 1H), 7.00 (t, J=8.7 Hz, 1H), 4.80 (t, J=5.5 Hz, 1H), 3.78-3.38 (m, 11H), 2.77 (t, J=7.0 Hz, 2H), 2.46-2.26 (m, 4H), 1.76-1.40 (m, 4H), 1.35 (d, J=6.9 Hz, 6H).

d) 2-(2,6-Difluoro-3-((4-(2-isopropylthiazole-4-carbonyl)-1-oxa-4,9-diazaspiro[5.5]undecan-9-yl)methyl)phenyl)acetaldehyde

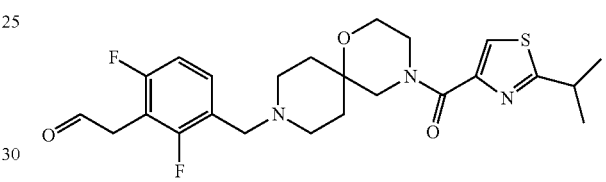

TFA (0.11 mL) was added to a solution of (9-(2,4-difluoro-3-(2-hydroxyethyl)benzyl)-1-oxa-4,9-diazaspiro[5.5]undecan-4-yl)(2-isopropylthiazol-4-yl)methanone (example 45, step c) (0.7 g) in DCM (5 mL) at 0° C. and the resulting mixture stirred for 5 min. Dess-Martin periodinane (0.93 g) was then added and the mixture stirred at RT for 45 min. Saturated sodium thiosulphate solution (5 mL), saturated sodium bicabonate solution (5 mL) and ethyl acetate (20 mL) was then added and the mixture stirred for 10 min. The aqueous layer was separated and extracted with ethyl acetate (20 mL). The combined organics were washed with brine, acidified with a few drops of acetic acid, the mixture dried over sodium sulphate, filtered and evaporated to give the subtitled compound as a clear gum. Yield 0.64 g.

m/z 478 (M+H)$^+$ (APCI)

e) (R)-7-(2-(2-(2,6-Difluoro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

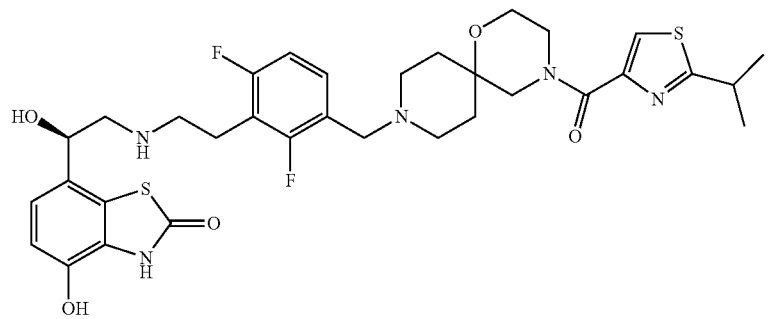 [SMILES: CC(C)c1nc(C(=O)N2CCOC3(CCN(Cc4ccc(F)c(CCNC[C@H](O)c5ccc(O)c6[nH]c(=O)sc56)c4F)CC3)C2)cs1]

A solution of 2-(2,6-difluoro-3-((4-(2-isopropylthiazole-4-carbonyl)-1-oxa-4,9-diazaspiro[5.5]undecan-9-yl)methyl)phenyl)acetaldehyde (example 45, step d) (0.323 g) in methanol (3 mL) was added to a mixture of (R)-7-(2-amino-1-hydroxyethyl)-4-hydroxybenzo[d]thiazol-2(3H)-one hydrochloride (WO2007027134, example 1, step d) (0.23 g) and acetic acid (0.034 mL) in methanol (2 mL). The resulting mixture was stirred for 5 min then cooled to 0° C. Sodium cyanoborohydride (0.057 g) was added and the mixture allowed to warm to RT and stirred for 2 h. The solvents were evaporated and the residue purified by silica gel chromatography eluting with 95:5:0.5 to 89:10:1 DCM:methanol:'880' aqueous ammonia gradient. The fractions containing product were combined, evaporated and purified by preparative HPLC (Sunfire™, Gradient: 5-50% acetonitrile in 0.2% aqueous TFA). The fractions containing product were combined, evaporated and triturated with ether to give the titled compound as a white solid. Yield 0.21 g.

m/z 688 (M+H)$^+$ (APCI)

$^1$H NMR (400 MHz, D$_6$-DMSO, 90° C.) δ 11.27 (s, 1H), 7.94 (s, 1H), 7.62-7.53 (m, 1H), 7.23-7.14 (m, 1H), 6.93 (d, J=8.2 Hz, 1H), 6.78 (d, J=8.2 Hz, 1H), 4.92 (dd, J=8.1, 4.7 Hz, 1H), 4.31 (s, 2H), 3.75-3.61 (m, 6H), 3.34-3.02 (m, 11H), 2.10-1.95 (m, 2H), 1.86-1.71 (m, 2H), 1.34 (d, J=6.7 Hz, 6H). Five exchangeable protons not observed.

EXAMPLE 46

(R)-5-(2-(2,6-Difluoro-3-((4-(2-isopropylthiazole-4-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

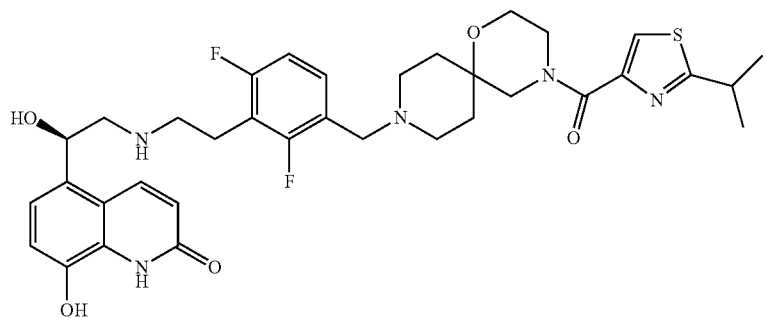 [SMILES: CC(C)c1nc(C(=O)N2CCOC3(CCN(Cc4ccc(F)c(CCNC[C@H](O)c5ccc(O)c6[nH]c(=O)ccc56)c4F)CC3)C2)cs1]

A solution of 2-(2,6-difluoro-3-((4-(2-isopropylthiazole-4-carbonyl)-1-oxa-4,9-diazaspiro[5.5]undecan-9-yl)methyl)phenyl)acetaldehyde (example 45, step d) (0.29 g) in methanol (3 mL) was added to a mixture of (R)-5-(2-amino-1-(tert-butyldimethylsilyloxy)ethyl)-8-hydroxyquinolin-2(1H)-one (WO2004106333) (0.20 g) and acetic acid (0.034 mL) in methanol (3 mL). The resulting mixture was stirred for 5 min then cooled to 0° C. Sodium cyanoborohydride (0.057 g) was then added and the mixture allowed to warm to RT and stirred for 2 h. The solvent was evaporated and the residue purified by silica gel chromatography eluting with 95:5:0.5 to 89:10:1 DCM:methanol:'880' aqueous ammonia gradient. The fractions containing product were combined and evaporated. The residue was dissolved in THF (3 mL), triethylamine trihydrofluoride (0.29 mL) was added and the mixture stirred overnight. The reaction was concentrated and the residue purified by preparative HPLC (Sunfire™, Gradient: 5-50% acetonitrile in 0.2% aqueous TFA). The fractions containing product were combined, evaporated and triturated with diethylether to give the titled compound as a white solid. Yield 0.23 g.

m/z 682 (M+H)$^+$ (APCI)

$^1$H NMR (400 MHz, D$_6$-DMSO, 90° C.) δ 8.19 (d, J=10.0 Hz, 1H), 7.94 (s, 1H), 7.65-7.51 (m, 1H), 7.24-7.10 (m, 2H), 7.01 (d, J=7.9 Hz, 1H), 6.53 (d, J=10.0 Hz, 1H), 5.37 (dd, J=8.6, 4.0 Hz, 1H), 4.34 (s, 2H), 3.75-3.59 (m, 6H), 3.34-3.03 (m, 11H), 2.11-1.95 (m, 2H), 1.88-1.72 (m, 2H), 1.34 (d, J=6.9 Hz, 6H). Six exchangeable protons not observed.

EXAMPLE 47

(R)-7-(2-(2-Fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

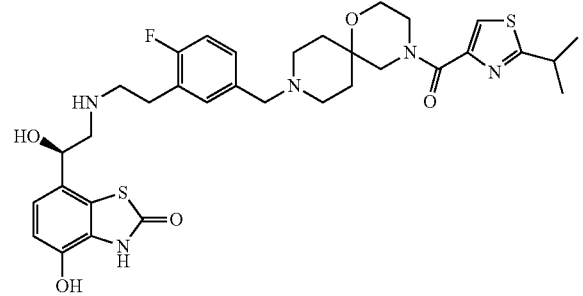 [SMILES: CC(C)c1nc(C(=O)N2CCOC3(CCN(Cc4ccc(F)c(CCNC[C@H](O)c5ccc(O)c6[nH]c(=O)sc56)c4)CC3)C2)cs1]

a) 2-(5-(Bromomethyl)-2-fluorophenyl)ethanol

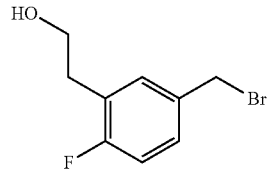 [SMILES: OCCc1cc(CBr)ccc1F]

Dibenzoyl peroxide (0.14 g) was added to a solution of NBS (1.53 g) and 2-(2-fluoro-5-methylphenyl)acetic acid (1.45 g) in DCM (50 mL) and the resulting mixture was heated at reflux for 12 h. The solvent was evaporated and the white solid partitioned between ethyl acetate (100 mL) and 10% sodium chloride solution (50 mL). The layers were separated and the organic phase washed with 10% sodium chloride solution (50 mL), dried over sodium sulphate, filtered and evaporated. The white solid obtained was redissolved in tetrahydrofuran (25 mL) and cooled in an ice bath. A solution of borane dimethyl sulfide complex (2M in THF, 13 mL) was added cautiously and the mixture was then allowed to warm to RT and stirred for 2 h. The reaction was cooled in an ice bath and cautiously quenched with methanol. Once bubbling had ceased the solvent was evaporated and the residue purified by silica gel chromatography eluting with 9:1 to 4:1 ethyl acetate:isohexane gradient to give the subtitled compound as a clear oil. Yield 1.35 g.

$^1$H NMR (300 MHz, CDCl$_3$) δ 7.32-7.21 (m, 2H), 7.04-6.97 (m, 1H), 4.46 (s, 2H), 3.87 (t, J=6.5 Hz, 2H), 2.93-2.87 (m, 2H). One exchangeable proton not observed.

b) (9-(4-Fluoro-3-(2-hydroxyethyl)benzyl)-1-oxa-4,9-diazaspiro[5.5]undecan-4-yl)(2-isopropylthiazol-4-yl)methanone

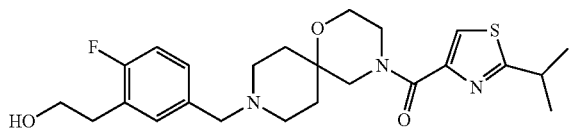 [SMILES: CC(C)c1nc(C(=O)N2CCOC3(CCN(Cc4ccc(F)c(CCO)c4)CC3)C2)cs1]

2-(5-(Bromomethyl)-2-fluorophenyl)ethanol (example 47, step a) (0.16 g) was added to a solution of (2-isopropylthiazol-4-yl)(1-oxa-4,9-diazaspiro[5.5]undecan-4-yl)methanone trifluoroacetate (example 22, step b) (0.3 g) and triethylamine (0.3 mL) in acetonitrile (10 mL). The resulting mixture was stirred overnight, diluted with acetonitrile (20 mL) and applied to a SCX cartridge (10 g Varian, pre-wetted with acetonitrile (50 mL)). The cartridge was washed with acetonitrile (50 mL) and eluted with 10% '880' aqueous ammonia in acetonitrile solution (50 mL). The eluent was evaporated, azeotroped with toluene and purified by silica gel chromatography eluting with 77.5:17.5:5 isohexane:ethyl acetate:triethylamine to 95:5 ethyl acetate:triethylamine gradient. The fractions containing product were combined and evaporated to give to the subtitled compound as a yellow gum. Yield 0.22 g.

m/z 462 (M+H)$^+$ (APCI)

$^1$H NMR (400 MHz, D$_6$-DMSO, 90° C.) δ 7.91 (s, 1H), 7.22-7.14 (m, 1H), 7.14-7.06 (m, 1H), 7.00 (dd, J=10.0, 8.3 Hz, 1H), 4.40 (t, J=5.3 Hz, 1H), 3.72-3.52 (m, 8H), 3.43-3.23 (m, 3H), 2.74 (t, J=7.0 Hz, 2H), 2.42-2.23 (m, 4H), 1.75-1.65 (m, 2H), 1.59-1.47 (m, 2H), 1.36 (d, J=6.9 Hz, 6H).

c) (R)-7-(2-(2-Fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

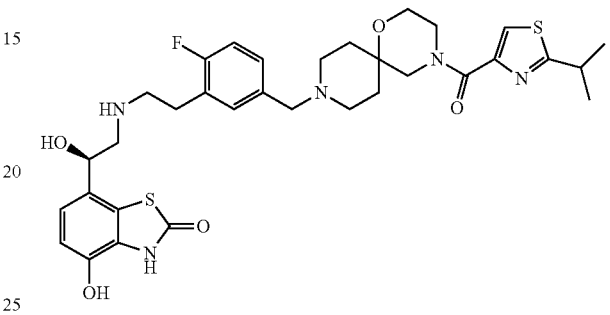

Trifluoroacetic acid (0.033 mL) was added to a solution of (9-(4-fluoro-3-(2-hydroxyethyl)benzyl)-1-oxa-4,9-diazaspiro[5.5]undecan-4-yl)(2-isopropylthiazol-4-yl)methanone (example 47, step b) (0.2 g) in DCM (5 mL) at 0° C. The mixture was stirred for 5 min then Dess-Martin periodinane (0.28 g) was added. The resulting yellow solution was allowed to warm to RT and stirred for 1 h. A mixture of saturated sodium thiosulphate solution (1 mL), saturated sodium bicarbonate solution (1 mL) and ethyl acetate (5 mL) was then added and the resulting mixture stirred vigorously for 10 min. The aqueous phase was separated and extracted with ethyl acetate (5 mL). The combined organic solutions were washed with brine (5 mL), acidified with a few drops of acetic acid, dried over sodium sulphate, filtered and evaporated in vacuo. The residue was dissolved in methanol (2 mL), acetic acid (0.025 mL) and (R)-7-(2-amino-1-hydroxyethyl)-4-hydroxybenzo[d]thiazol-2(3H)-one hydrochloride (WO2007027134, example 1, step d) (0.17 g) were then added and the mixture stirred for 5 min before cooling in an ice bath. Sodium cyanoborohydride (0.04 g) was then added, the mixture allowed to warm to RT and stirred overnight. The solvent was evaporated in vacuo. Purification was by silica gel chromatography eluting with 94.5:5:0.5 to 89:10:1 DCM:Methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethylether to give the titled compound as a white solid. Yield 0.14 g.

m/z 670 (M+H)$^+$ (APCI)

$^1$H NMR (400 MHz, D$_6$-DMSO, 90° C.) δ 11.27 (s, 1H), 7.94 (s, 1H), 7.52-7.42 (m, 2H), 7.25 (t, J=9.2 Hz, 1H), 6.94 (d, J=8.2 Hz, 1H), 6.78 (d, J=8.2 Hz, 1H), 4.93 (dd, J=7.9, 4.6 Hz, 1H), 4.29 (s, 2H), 3.80-3.58 (m, 6H), 3.34-2.95 (m, 11H), 2.11-1.95 (m, 2H), 1.87-1.64 (m, 2H), 1.34 (d, J=6.7 Hz, 6H). Five exchangeable protons not observed.

EXAMPLE 47A (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one a) 2-(5-(Bromomethyl)-2-fluorophenyl)ethanol

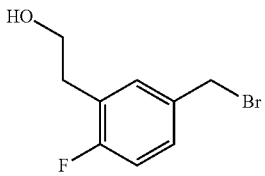 [SMILES: OCCc1cc(CBr)ccc1F]

Dibenzoyl peroxide (1 g) was added to a solution of NBS (10.6 g) and 2-(2-fluoro-5-methylphenyl)acetic acid (10 g) in DCM (250 mL) and the resulting mixture was heated under reflux for 12 h. The solvent was evaporated and the white solid partitioned between ethyl acetate (250 mL) and 10% sodium chloride solution (500 mL). The layers were separated and the organic phase washed with 10% sodium chloride solution (500 mL), dried over magnesium sulphate, filtered and evaporated. The white solid obtained was redissolved in tetrahydrofuran (150 mL) and cooled in an ice bath. A solution of borane dimethyl sulfide complex (2M in THF, 89 mL) was added cautiously and the mixture was then allowed to warm to RT and stirred for overnight. The reaction was cooled in an ice bath and cautiously quenched with methanol. Once bubbling had ceased the solvent was evaporated and the residue was triturated with a 4:1 mixture of iso-hexanes and ether. Purification was by silica gel chromatography eluting with 9:1 to 4:1 ethyl acetate:isohexane gradient to give the subtitled compound as a clear oil. Yield 6.5 g.

$^1$H NMR (300 MHz, CDCl$_3$) δ 7.32-7.21 (m, 2H), 7.04-6.97 (m, 1H), 4.46 (s, 2H), 3.87 (t, J=6.5 Hz, 2H), 2.93-2.87 (m, 2H). One exchangeable proton not observed.

b) (9-(4-Fluoro-3-(2-hydroxyethyl)benzyl)-1-oxa-4,9-diazaspiro[5.5]undecan-4-yl)(2-isopropylthiazol-4-yl)methanone

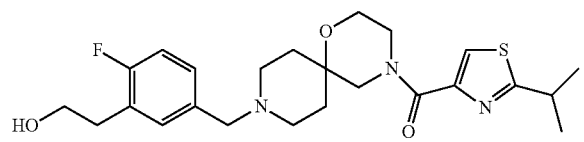 [SMILES: CC(C)c1nc(C(=O)N2CCOC3(CCN(Cc4ccc(F)c(CCO)c4)CC3)C2)cs1]

2-(5-(Bromomethyl)-2-fluorophenyl)ethanol (example 47A, step a) (5.2 g) was added to a suspension of (2-isopropylthiazol-4-yl)(1-oxa-4,9-diazaspiro[5.5]undecan-4-yl)methanone trifluoroacetate (example 22, step b) (9.4 g) and potassium carbonate (6.8 g) in ethanol (75 mL). The resulting mixture was stirred overnight and filtered. The filter cake was washed with ethanol (50 mL) and the combined filtrate and washings were evaporated. The residue was partioned between water (100 mL) and ethyl acetate (250 mL). The layers were separated and the organic washed with brine (100 mL), dried over sodium sulphate, filtered and evaporated. Purification was by silica gel chromatography eluting with 95:5 ethyl acetate:triethylamine gradient. The fractions containing product were combined and evaporated to give to the subtitled compound as a yellow gum. Yield 7.9 g.

m/z 462 (M+H)$^+$ (APCI)

$^1$H NMR (400 MHz, D$_6$-DMSO, 90° C.) δ 7.91 (s, 1H), 7.22-7.14 (m, 1H), 7.14-7.06 (m, 1H), 7.00 (dd, J=10.0, 8.3 Hz, 1H), 4.40 (t, J=5.3 Hz, 1H), 3.72-3.52 (m, 8H), 3.43-3.23 (m, 3H), 2.74 (t, J=7.0 Hz, 2H), 2.42-2.23 (m, 4H), 1.75-1.65 (m, 2H), 1.59-1.47 (m, 2H), 1.36 (d, J=6.9 Hz, 6H).

c) (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one Trifluoroacetic acid (1.32 mL) was added to a solution of (9-(4-fluoro-3-(2-hydroxyethyl)benzyl)-1-oxa-4,9-diazaspiro[5.5]undecan-4-yl)(2-isopropylthiazol-4-yl)methanone (example 47A, step b) (7.9 g) in DCM (200 mL) at 0° C. The mixture was stirred for 5 min then Dess-Martin periodinane (12.3 g) was added. The resulting yellow solution was allowed to warm to RT and stirred for 1 h. A mixture of saturated sodium thiosulphate solution (100 mL), saturated sodium bicarbonate solution (100 mL) and ethyl acetate (500 mL) was then added and the resulting mixture stirred vigorously for 10 min. The aqueous phase was separated and extracted with ethyl acetate (100 mL). The combined organic solutions were washed with brine (100 mL), acidified with acetic acid (2 mL), dried over sodium sulphate, filtered and evaporated in vacuo. The residue was dissolved in methanol (140 mL) and (R)-7-(2-amino-1-hydroxyethyl)-4-hydroxybenzo[d]thiazol-2(3H)-one hydrochloride (WO2007027134, example 1, step d) (4.5 g) was then added and the mixture stirred for 5 min before cooling in an ice bath. Sodium cyanoborohydride (1.6 g) was then added, the mixture allowed to warm to RT and stirred overnight. The reaction mixture was concentrated in vacuo and partioned between THF (100 mL) and a mixture of brine and saturated sodium bicarbonate solution (10:1, 100 mL). The layers were separated and the organic layer was dried over sodium sulphate, filtered, evaporated and the residue azeotroped with acetonitrile. Purification was by silica gel chromatography eluting with 94.5:5:0.5 to 89:10:1 DCM:Methanol:'880' aqueous ammonia gradient. The fractions containing the product were combined and evaporated in vacuo to give the titled compound as a white solid. Yield 4.1 g m/z 670 (M+H)$^+$ (APCI)

$^1$H NMR (400 MHz, D$_6$-DMSO, 90° C.) δ 11.27 (s, 1H), 7.94 (s, 1H), 7.52-7.42 (m, 2H), 7.25 (t, J=9.2 Hz, 1H), 6.94 (d, J=8.2 Hz, 1H), 6.78 (d, J=8.2 Hz, 1H), 4.93 (dd, J=7.9, 4.6 Hz, 1H), 4.29 (s, 2H), 3.80-3.58 (m, 6H), 3.34-2.95 (m, 11H), 2.11-1.95 (m, 2H), 1.87-1.64 (m, 2H), 1.34 (d, J=6.7 Hz, 6H). Five exchangeable protons not observed.

EXAMPLE 47B (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one di(1S)-(+)-10-camphorsulfonic acid salt 1S-(+)-Camphorsulphonic acid (41 mg) was added to a solution of (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one (example 47A) (59 mg) in ethanol (5 mL) and the resulting clear solution evaporated to dryness to give (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one dicamphorsulfonic acid salt as an amorphous white solid. Yield 0.1 g Iso-propanol (1 mL) was added to (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one dicamphorsulfonic acid salt (20 mg) and the resulting clear solution was stirred 2 days. A white solid was formed and the suspension was stirred for a further 5 days. The solid was isolated by centrifugal filtration and dried under high vacuum to give (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one dicamphorsulfonic acid salt as a white crystalline solid. Yield 5 mg.

A mixture of (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one (4.3 g, 6.42 mmol) (example 47A), (1S)-(+)-10-camphorsulfonic acid (2.98 g, 12.84 mmol) and iso-propanol (300 mL) was heated at 50° C. until a clear solution formed, seeded, allowed to cool to RT and stirred for 4 days. The solid was isolated by filtration, washed with iso-propanol (100 mL), ether (2×200 mL) and sucked dry to give the titled compound as a white crystalline solid. Yield 5.1 g The enantiomeric excess of the title compound is higher than the compound obtained in example 47A. (example 47A=86% ee, title compound >96% ee)

Analytical Chiral Method: Chiralcel OJ-H 4.6×250 mm, 80:20 isohexane:ethanol+0.1% ethylenediamine, 1 ml/min, 35 C, 225+−10 nm over 30 min.

Retention time for the R enantiomer=15.91 min
Retention time for the S enantiomer=22.85 min $^1$H NMR (300 MHz, DMSO, 90° C.) δ 11.42 (s, 1H), 9.95 (s, 1H), 8.89 (s, 2H), 7.95 (s, 1H), 7.61-7.54 (m, 1H), 7.53-7.46 (m, 1H), 7.27 (t, J=9.2 Hz, 1H), 6.94 (d, J=8.5 Hz, 1H), 6.77 (d, J=8.3 Hz, 1H), 4.97-4.90 (m, 1H), 4.30 (s, 2H), 3.74-3.59 (m, 6H), 3.35-3.02 (m, 9H), 2.93 (d, J=14.6 Hz, 2H), 2.76-2.61 (m, 2H), 2.44 (d, J=14.6 Hz, 2H), 2.29-2.23 (m, 2H), 2.22-2.16 (m, 2H), 2.13-2.00 (m, 2H), 1.96-1.68 (m, 6H), 1.34 (d, J=6.9 Hz, 6H), 1.32-1.20 (m, 4H), 1.06 (s, 6H), 0.76 (s, 6H) two exchangeable protons not observed.

An XRPD pattern of di(1S)-(+)-10-camphorsulfonic acid salt modification A is presented in FIG. 1.

Some characteristic peaks for modification A

| Pos. [°2Th.] | d-spacing [Å] |
| --- | --- |
| 4.9 | 18.1 |
| 9.8 | 9.1 |
| 12.5 | 7.1 |
| 16.1 | 5.5 |
| 17.3 | 5.1 |

EXAMPLE 47C (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one fumarate Modification A A solution of (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one (13 mg) (example 47D, step a) and fumaric acid (2 mg) in methanol (0.75 mL) was stirred at RT for 7 days. The resulting white solid formed was isolated by filtration and dried under high vacuum to give the titled compound as a white solid. Yield 5 mg.

m/z 670 (M+H)$^+$ (APCI)

An XRPD pattern of fumarate salt modification A is presented in FIG. 2.

Some characteristic peaks for the fumarate salt modification A

| Pos. [°2Th.] | d-spacing [Å] |
| --- | --- |
| 6.1 | 14.4 |
| 8.9 | 9.9 |
| 13.8 | 6.4 |
| 21.5 | 4.1 |
| 23.5 | 3.8 |

EXAMPLE 47D (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one mono fumarate Modification B a) (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one di(1S)-(+)-10-camphorsulfonic acid salt (Example 47B) (4.1 g) was partioned between freshly distilled 2-methyl-THF (100 mL) and saturated sodium bicarbonate solution (100 mL). The layers were separated and the organic layer washed with saturated sodium bicarbonate solution (100 mL), brine (100 mL), dried over sodium sulphate, filtered and evaporated in vacuo. The resulting glassy solid was triturated thrice with ether to give the subtitle compound as a white solid. Yield 2.6 g.

b) (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one mono fumarate Modification B (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one (2.4 g) was dissolved in ethanol (240 mL) at 50° C. Fumaric acid (0.416 g) was added and the mixture heated under reflux until a clear solution formed. The resulting solution was allowed to cool to 60° C. and seeded with form A (example 47C) (50 mg). The resulting mixture was stirred overnight at 50° C. and then allowed to cool to RT over 3 hrs. The resulting white solid was isolated by filtration, washed with ethanol (50 mL), ether (2×200 mL) and sucked dry to give the titled compound as a white solid. Yield 2.3 g.

m/z 670 (M+H)+ (APCI)

¹H NMR (400 MHz, DMSO, 90° C.) δ 7.89 (s, 1H), 7.19-7.09 (m, 2H), 7.01 (dd, J=9.9, 8.3 Hz, 1H), 6.86 (d, J=8.2 Hz, 1H), 6.69 (d, J=8.5 Hz, 1H), 6.59 (d, J=1.0 Hz, 2H), 4.65-4.59 (m, 1H), 3.73-3.56 (m, 6H), 3.41 (s, 2H), 3.30 (septet, J=3.3 Hz, 1H), 2.90-2.71 (m, 6H), 2.42-2.26 (m, 4H), 1.75-1.64 (m, 2H), 1.59-1.48 (m, 2H), 1.35 (dd, J=6.8, 1.2 Hz, 6H)+6 exchangables not observed An XRPD pattern of fumarate salt modification B is presented in FIG. 3.

Some characteristic peaks for the fumarate salt modification B

| Pos. [°2Th.] | d-spacing [Å] |
|---|---|
| 14.3 | 6.2 |
| 16.3 | 5.4 |
| 18.0 | 4.9 |
| 19.6 | 4.5 |
| 23.0 | 3.9 |
| 26.1 | 3.4 |

XRPD—PANalytical CubiX PRO

XRPD data was collected with a PANalytical CubiX PRO machine in θ-2θ configuration over the scan range 2° to 40° 2θ with 100-second exposure per 0.020 increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

EXAMPLE 47E (R)-7-(2-(2-Fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one a) tert-Butyl 4-(2-isopropylthiazole-4-carbonyl)-1-oxa-4,9-diazaspiro[5.5]undecane-9-carboxylate

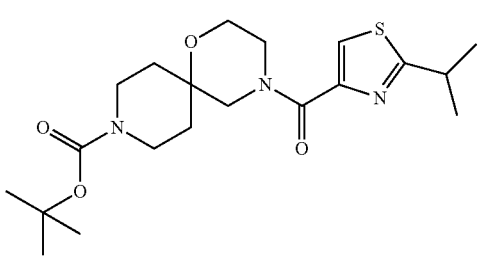 [SMILES: CC(C)c1nc(C(=O)N2CCOC3(CCN(C(=O)OC(C)(C)C)CC3)C2)cs1]

A mixture of tert-butyl 1-oxa-4,9-diazaspiro[5.5]undecane-9-carboxylate hydrochloride (limiting reagent) and 2-isopropylthiazole-4-carboxylic acid (1.1 molar equivalents) was suspended in 2-MeTHF (10 volumes) and cooled to 10-15° C. Triethylamine (7.2 molar equivalents) was added in portions at 10-15° C. The thick suspension was cooled to 5-10° C. and T3P (1.3 molar equivalents of a 1.57M solution in THF) was added dropwise at 5-10° C. over 0.5 hr. The reaction mixture was allowed to warm to ambient temperature (35 min) and stirred for 2.5 hr. The mixture was diluted with water (10 volumes, 5° C. exotherm) and the mixture vigorously stirred; the aqueous (pH 10) was separated and extracted with 2-MeTHF (2×2 volumes). The combined organics were washed with saturated aq sodium bicarbonate soln (2 volumes) and water (2×2 volumes). The organic phase was evaporated and azeotroped with MeCN (2×2 volumes) to give a brown gum, which was dried at 35° C. in vacuo for 24 hr. Yield: 89% of theoretical.

¹H NMR (300 MHz, DMSO) δ 8.03 (s, 1H), 3.76-3.44 (m, 8H), 3.37-3.25 (m, 3H), 3.16-3.00 (m, 2H), 1.76-1.66 (m, 2H), 1.39 (s, 9H), 1.33 (d, J=6.9 Hz, 6H)

b) (2-Isopropylthiazol-4-yl)(1-oxa-4,9-diazaspiro[5.5]undecan-4-yl)methanone, trifluoroacetate salt

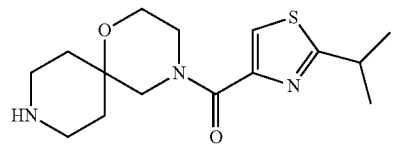 [SMILES: CC(C)c1nc(C(=O)N2CCOC3(CCNCC3)C2)cs1]

To a solution of tert-butyl 4-(2-isopropylthiazole-4-carbonyl)-1-oxa-4,9-diazaspiro[5.5]undecane-9-carboxylate (limiting reagent) (step a) in DCM (5 volumes) was added trifluoroacetic acid (13.4 molar equivalents) in portions at 10-15° C. The solution was allowed to warm to ambient and stirred for 16 hr. Solvent was evaporated and the residue was dissolved in diethyl ether (10 volumes). The solution was cooled in ice and scratched to give precipitation; the slurry was stirred at 0°-10° C. for 0.5 hr then filtered cold. The cake was washed with diethyl ether (5 volumes) and dried in vacuo at 35° C. to give a beige coloured powder. Yield: 91% of theoretical.

1H NMR (300 MHz, DMSO) δ 8.70-8.37 (m, 2H), 8.05 (s, 1H), 3.82-3.52 (m, 6H), 3.42-3.25 (m, 1H), 3.19-3.07 (m, 2H), 3.05-2.90 (m, 2H), 2.02-1.91 (m, 2H), 1.74-1.54 (m, 2H), 1.35 (d, J=6.7 Hz, 6H)

c) 4-Bromo-1-fluoro-2-(2-methoxyvinyl)benzene (mixture of cis and trans isomers)

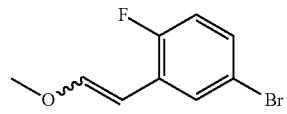

Potassium tert-butoxide (1.2 molar equivalents) was added portionwise, over 30 minutes, to a stirred suspension of (methoxymethyl)triphenylphosphonium chloride (1.3 molar equivalents) in THF (2.5 volumes) at −3° C. (+ or −2° C.). A deep red colour developed. The temperature was ramped to 18° C. over 0.5 hour and the reaction stirred for a further 1.5 hours. 5-Bromo-2-fluorobenzaldehyde (limiting reagent) as a solution in THF (5 volumes) was then added over 90 minutes, such that the temperature of the reaction did not exceed 24° C. The reaction was then stirred for 2 hours at room temperature. The reaction mixture was poured into saturated aqueous ammonium chloride solution (10 volumes) and extracted with t-BME (2×2.5 volumes). The combined extracts were washed with brine (3×2 volumes), dried (Na$_2$SO$_4$), filtered and evaporated in vacuo. The oily residue was extracted with iso-hexane (8×0.5 volumes). Combined iso-hexane extracts were filtered, then washed with glacial acetic acid (2 volumes) and 50% glacial acetic acid in water (2 volumes). After drying (Na$_2$SO$_4$) and filtering, the solvent was removed on a rotary evaporator to give a pale orange oil. Yield was 90% of theoretical.

Cis-isomer: $^1$H NMR (300 MHz, D6-DMSO) δ 8.07 (d, J=9.4 Hz, 1H), 7.41-7.39 (m, 1H), 7.13 (q, J=1.8 Hz, 1H), 6.54 (d, J=7.1 Hz, 1H), 5.31 (d, J=7.1 Hz, 1H), 3.83 (s, 3H)

Trans-isomer: $^1$H NMR (300 MHz, D6-DMSO) δ 7.73-7.68 (m, 1H), 7.44 (d, J=12.9 Hz, 1H), 7.41-7.39 (m, 1H), 7.18-7.09 (m, 1H), 5.79 (d, J=12.9 Hz, 1H), 3.67 (s, 3H)

d) 4-Fluoro-3-(2-methoxyvinyl)benzaldehyde

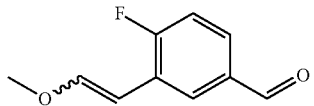

4-Bromo-1-fluoro-2-(2-methoxyvinyl)benzene (limiting reagent) (step c) was dissolved in 2-methyltetrahydrofuran (5 volumes) and the solution cooled to −10° C. Iso-propylmagnesium chloride (0.37 molar equivalents of a 2M solution in THF) was added dropwise, keeping the temperature at −7° C. (+ or −2° C.), over about 30 minutes, followed by Butyllithium (0.74 molar equivalents of a 1.5M solution in hexane), controlling the temperature at −6° C. (+ or −2° C.), over about 1 hour. Stirred for 45 minutes then added to a solution of 4-formylmorpholine (2 molar equivalents) in 2-methyltetrahydrofuran (7 volumes) at −5° C. This addition took about 90 minutes. The reaction was then stirred for 1 hour, during which time the internal temperature rose to 5° C. The reaction mixture was poured into saturated aq. ammonium chloride solution (10 volumes) and extracted with t-BME (2×3 volumes). Combined extracts were washed with sat'd aq. ammonium chloride (until the pH of the washing was approx 6) (2×3 volumes), water (5 volumes), dried (Na$_2$SO$_4$), filtered and evaporated to give a mobile orange oil.

The oil was chromatographed on silica using 5% ethyl acetate in iso-hexane as eluent. Yield was 80% of theoretical.

Trans-isomer: $^1$H NMR (400 MHz, CDCL$_3$) δ 9.93 (s, 1H), 7.83 (d, J=9.5 Hz, 1H), 7.66-7.61 (m, 1H), 7.25 (d, J=13.1 Hz, 1H), 7.17 (d, J=10.3 Hz, 1H), 5.87 (d, J=13.1 Hz, 1H), 3.74 (s, 3H)

Cis-isomer: $^1$H NMR (400 MHz, CDCL$_3$) δ 9.95 (s, 1H), 8.57 (d, J=9.5 Hz, 1H), 7.70-7.66 (m, 1H), 7.12 (d, J=11.5 Hz, 1H), 6.34 (d, J=7.2 Hz, 1H), 5.48 (d, J=6.9 Hz, 1H), 3.86 (s, 3H)

e) (9-(4-Fluoro-3-(2-methoxyvinyl)benzyl)-1-oxa-4,9-diazaspiro[5.5]undecan-4-yl)(2-isopropylthiazol-4-yl)methanone

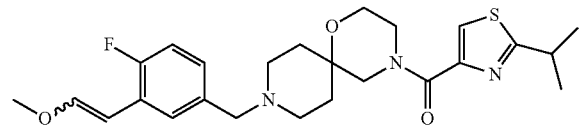 [SMILES: COC=Cc1cc(CN2CCC3(CC2)CN(C(=O)c2csc(C(C)C)n2)CCO3)ccc1F]

To a suspension of 4-fluoro-3-(2-methoxyvinyl)benzaldehyde (limiting reagent) (step d) and (2-isopropylthiazol-4-yl)(1-oxa-4,9-diazaspiro[5.5]undecan-4-yl)methanone trifluoroacetate (1.05 molar equivalents) (step b) in 2-methyltetrahydrofuran (25 volumes) was added triethylamine (1.73 molar equivalents) in one portion (4° C. exotherm). The mixture was stirred for 0.5 hr; sodium triacetoxyborohydride (1.5 molar equivalents) was then added in one portion (no exotherm) and the resultant solution was stirred for 16 hr.

Saturated aq NaHCO$_3$ (25 volumes) was added and the mixture vigorously stirred. The organic phase was separated and the aqueous (pH8) was extracted with 2-MeTHF (100 mL); the combined organics were washed with water (2×50 mL) and dried (Na$_2$SO$_4$), filtered and evaporated to give a dark oil. Yield: 78% of theoretical.

$^1$H NMR (300 MHz, D6-DMSO) mixture of cis and trans isomers: δ 7.97 (s, 1H), 7.86-7.79 (m, 0.5H), 7.34-7.20 (m, 1H), 7.07-6.98 (m, 2H), 6.41 (d, J=7.1 Hz, 0.5H), 5.82 (d, J=12.9 Hz, 0.5H), 5.32 (d, J=6.9 Hz, 0.5H), 3.77 (s, 0.5H), 3.66 (s, 2.5H), 3.42-3.19 (m, 7H), 2.41-2.26 (m, 4H), 1.76-1.63 (m, 3H), 1.59-1.45 (m, 3H), 1.35 (d, J=6.7 Hz, 6H)

f) (R)-7-(2-(2-Fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one

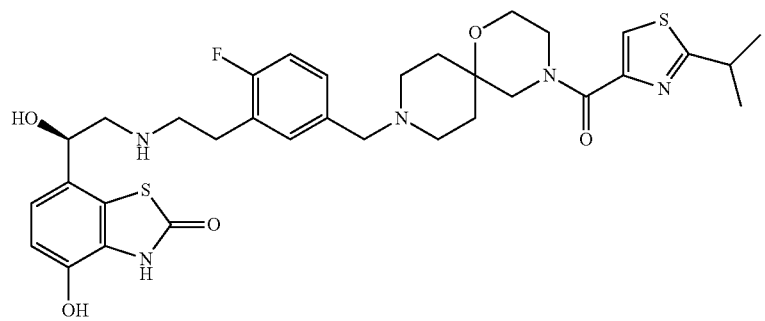 [SMILES: CC(C)c1nc(C(=O)N2CCOC3(CCN(Cc4ccc(F)c(CCNC[C@H](O)c5ccc(O)c6[nH]c(=O)sc56)c4)CC3)C2)cs1]

A solution of (9-(4-fluoro-3-(2-methoxyvinyl)benzyl)-1-oxa-4,9-diazaspiro[5.5]undecan-4-yl)(2-isopropylthiazol-4-yl)methanone (limiting reagent) (step e) in THF (5 volumes) was treated with water (2.5 volumes) followed by conc. hydrochloric acid (6 molar equivalents). The solution was heated at 55-60° C. for 1.5 hr; the solution was cooled to ambient and diluted with water (2.5 volumes). The THF was removed by evaporation and the aqueous residue was added to a stirred mixture of sodium bicarbonate (7 molar equivalents), water (5 volumes) and DCM (10 volumes).

The organic was separated and the aqueous (pH8) was extracted with DCM (5 volumes). The combined organic was washed with satd aq NaHCO₃ soln (5 volumes), water (2×5 volumes), dried (sodium sulphate) and filtered. The filtrate was diluted with MeOH (10 volumes) and the DCM evaporated at 35° C./405 mbar. The methanol solution of aldehyde was treated with acetic acid (2 molar equivalents) and added to (R)-7-(2-amino-1-hydroxyethyl)-4-hydroxybenzo[d]thiazol-2(3H)-one hydrochloride (1 molar equivalent) in one portion; the mixture was cooled to 0-5° C. and stirred for 5 min to give a solution. To this was added sodium cyanoborohydride (1.5 molar equivalents) in one portion and the mixture was stirred at 5° C. for 0.5 hr then warmed to ambient and stirred for 0.5 hr. Solvent was evaporated and the residue was partitioned between 2-MeTHF (10 volumes) and satd NaHCO3 soln (5 volumes); the organics were washed with 20% brine soln (5 volumes), dried (Na₂SO₄), filtered and evaporated. Gave a yellow foam which was slurried in ethyl acetate (13 volumes) and the resultant solid was collected by filtration and dried in vacuo. Gave a pale yellow solid which was purified on silica (20 times weight of crude reaction mixture), eluent DCM/10-15% MeOH/1-1.5% ammonia.

Yield: 29% of theoretical.

m/z 670 (M+H)⁺ (APCI)

¹H NMR (300 MHz, D6-DMSO) δ 7.99 (s, 1H), 7.23-7.02 (m, 3H), 6.84 (d, J=8.3 Hz, 1H), 6.69 (d, J=8.3 Hz, 1H), 4.58 (q, J=4.1 Hz, 1H), 3.75-3.24 (br m, 10H), 2.80-2.59 (m, 6H), 2.41-2.11 (m, 7H), 1.76-1.41 (m, 4H), 1.34 (d, J=6.9 Hz, 6H)

EXAMPLE 48

(R)-7-(2-(2-Fluoro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

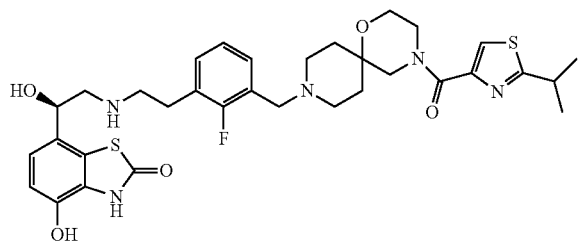 [SMILES: CC(C)c1nc(C(=O)N2CCOC3(CCN(Cc4cccc(CCNC[C@H](O)c5ccc(O)c6[nH]c(=O)sc56)c4F)CC3)C2)cs1]

a) 2-Fluoro-3-(2-hydroxyethyl)benzaldehyde

2,2,6,6-Tetramethylpiperidine (10.8 mL) was added to a solution of butyllithium (1.6M in hexanes, 40.1 mL) in THF (40 mL) at −70° C. A solution of 2-(2-fluorophenyl)ethanol (3 g) in THF (40 mL) was added dropwise and the resulting mixture stirred for 6 h at −70° C. DMF (8.29 mL) was then added and the mixture stirred for 1 h at −70° C. The mixture was then allowed to warm to RT and stirred for 70 h. The reaction was quenched with HCl solution (2M, 50 mL), diluted with ethyl acetate (100 mL) and the layers separated. The aqueous phase was extracted with ethyl acetate (2×100 mL). The combined organic solutions were washed with HCl solution (2M, 50 mL), brine (20 mL), dried over magnesium sulphate, filtered and evaporated. The residue was purified by silica gel chromatography eluting with 4:1 to 2:1 isohexane:ethyl acetate gradient. The fractions containing product were combined and evaporated to give the subtitled compound as a yellow oil. Yield 1.2 g.

¹H NMR (300 MHz, CDCl₃) δ 10.37 (s, 1H), 7.80-7.71 (m, 1H), 7.54 (td, J=7.4, 1.9 Hz, 1H), 7.22 (t, J=7.6 Hz, 1H), 3.96-3.87 (m, 2H), 2.99 (td, J=6.5, 1.2 Hz, 2H), 1.53 (t, J=5.6 Hz, 1H).

b) (9-(2-Fluoro-3-(2-hydroxyethyl)benzyl)-1-oxa-4,9-diazaspiro[5.5]undecan-4-yl)(2-isopropylthiazol-4-yl)methanone

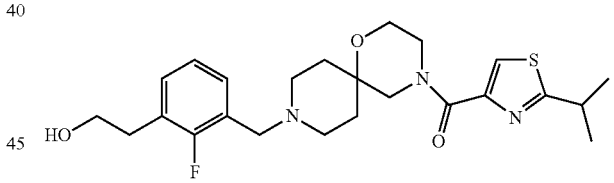

2-Fluoro-3-(2-hydroxyethyl)benzaldehyde (example 48, step a) (0.19 g) was added to a solution of (2-isopropylthiazol-4-yl)(1-oxa-4,9-diazaspiro[5.5]undecan-4-yl)methanone trifluoroacetate (example 22, step b) (0.32 g) and acetic acid (0.043 mL) in N-methyl-2-pyrrolidinone (5 mL). The resulting mixture was stirred for 1 h then sodium triacetoxyborohydride (0.24 g) was added portionwise over 5 min. The resulting mixture was stirred overnight, diluted with acetonitrile (20 mL) and applied to a SCX cartridge (10 g Varian, pre-wetted with acetonitrile (50 mL)). The cartridge was washed with acetonitrile (50 mL) and eluted with 10% '880' aqueous ammonia in acetonitrile solution (50 mL). The eluent was evaporated, azeotroped with toluene and purified by silica gel chromatography eluting with 77.5:17.5:5 isohexane:ethyl acetate:triethylamine to 95:5 ethyl acetate:triethylamine gradient. The fractions containing product were combined and evaporated to give the subtitled compound as a yellow gum. Yield 0.33 g.

m/z 462 (M+H)⁺ (APCI)

¹H NMR (400 MHz, D₆-DMSO, 90° C.) δ 7.91 (s, 1H), 7.23-7.13 (m, 2H), 7.03 (t, J=7.5 Hz, 1H), 4.40 (t, J=5.3 Hz, 1H), 3.72-3.56 (m, 9H), 3.48 (s, 2H), 2.75 (t, J=6.9 Hz, 2H), 2.46-2.26 (m, 4H), 1.75-1.63 (m, 2H), 1.59-1.46 (m, 2H), 1.35 (d, J=6.9 Hz, 6H).

c) (R)-7-(2-(2-Fluoro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

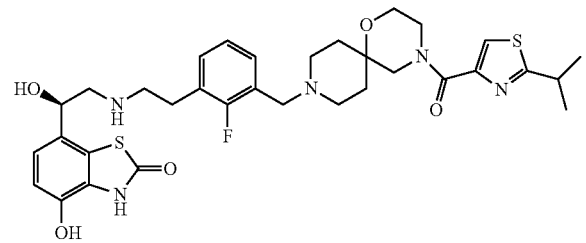 [SMILES: CC(C)c1nc(C(=O)N2CCOC3(CCN(Cc4cccc(CCNC[C@H](O)c5ccc(O)c6[nH]c(=O)sc56)c4F)CC3)C2)cs1]

TFA (0.044 mL) was added to a solution (9-(2-fluoro-3-(2-hydroxyethyl)benzyl)-1-oxa-4,9-diazaspiro[5.5]undecan-4-yl)(2-isopropylthiazol-4-yl)methanone (example 48, step b) (0.3 g) in DCM (5 mL) at 0° C. The mixture was stirred for 5 min then Dess-Martin periodinane (0.37 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (5 mL). The combined organic solutions were washed with brine (20 mL), acidified with a few drops of acetic acid, dried over sodium sulfate, filtered and evaporated in vacuo. The residue was dissolved in methanol (2 mL), acetic acid (0.033 mL) and (R)-7-(2-amino-1-hydroxyethyl)-4-hydroxybenzo[d]thiazol-2(3H)-one hydrochloride (WO2007027134, example 1, step d) (0.28 g) were then added and the mixture stirred for 5 min before cooling in an ice bath. Sodium cyanoborohydride (0.054 g) was then added and the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with ether to give the titled compound as a white solid. Yield 0.14 g.

m/z 670 (M+H)⁺ (APCI)

¹H NMR (400 MHz, D₆-DMSO, 90° C.) δ 11.27 (s, 1H), 7.94 (s, 1H), 7.51 (t, J=6.9 Hz, 1H), 7.44 (t, J=7.0 Hz, 1H), 7.25 (t, J=7.7 Hz, 1H), 6.94 (d, J=8.2 Hz, 1H), 6.78 (d, J=8.5 Hz, 1H), 4.93 (dd, J=8.3, 4.7 Hz, 1H), 4.34 (s, 2H), 3.77-3.60 (m, 6H), 3.36-3.04 (m, 11H), 2.09-1.97 (m, 2H), 1.87-1.72 (m, 2H), 1.35 (d, J=6.9 Hz, 6H). Five exchangeable protons not observed.

EXAMPLE 49

(R)-4-Hydroxy-7-(1-hydroxy-2-(2-(5-((4-(2-methylbenzo[d]thiazole-5-carbonyl)-1-oxa-4,9-diazaspiro[5.5]undecan-9-yl)methyl)thiophen-3-yl)ethylamino)ethyl)benzo[d]thiazol-2(3H)-one ditrifluoroacetate

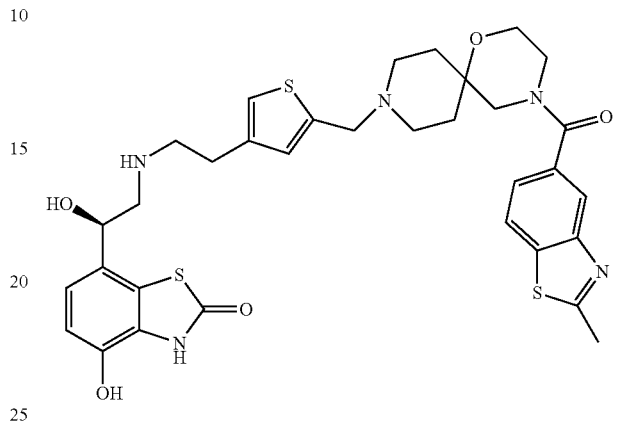

a) (9-((4-(2-(tert-Butyldimethylsilyloxy)ethyl)thiophen-2-yl)methyl)-1-oxa-4,9-diazaspiro[5.5]undecan-4-yl)(2-methylbenzo[d]thiazol-5-yl)methanone

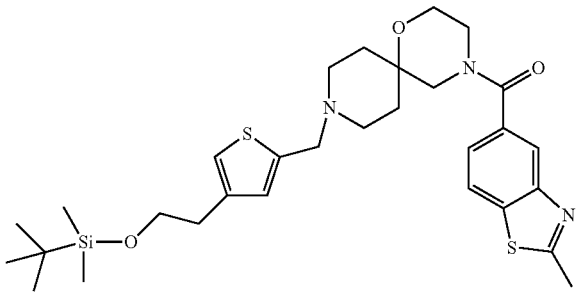 [SMILES: Cc1nc2cc(C(=O)N3CCOC4(CCN(Cc5cc(CCO[Si](C)(C)C(C)(C)C)cs5)CC4)C3)ccc2s1]

HATU (0.333 g) was added to stirred solution of 2-methylbenzo[d]thiazole-5-carboxylic acid (0.17 g), 9-((4-(2-(tert-butyldimethylsilyloxy)ethyl)thiophen-2-yl)methyl)-1-oxa-4,9-diazaspiro[5.5]undecane (example 43, step b) (0.3 g) and triethylamine (0.407 mL) in DMF (3 mL). After 1 h, the reaction mixture was partitioned between water and ethyl acetate. The ethyl acetate layer was washed twice with water, once with brine, dried over magnesium sulphate, filtered and evaporated in vacuo. Purification by silica gel chromatography eluting with ethyl acetate:isohexane:triethylamine, 2:8:1 gave the subtitled compound as a gum. Yield 0.36 g.

¹H NMR (400 MHz, D₆-DMSO, 90° C.) δ 8.06 (d, J=8.3 Hz, 1H), 7.38 (d, J=8.3 Hz, 1H), 7.87 (s, 1H), 6.96 (s, 1H), 6.78 (s, 1H), 3.77 (t, J=6.7 Hz, 2H), 3.68-3.63 (m, 2H), 3.58 (s, 2H), 3.53-3.46 (m, 2H), 3.42-3.36 (m, 2H), 2.82 (s, 3H), 2.70 (t, J=6.8 Hz, 2H), 2.42-2.31 (m, 4H), 1.81-1.72 (m, 2H), 1.52-1.41 (m, 2H), 0.86 (s, 9H), 0.00 (s, 6H).

b) (9-((4-(2-Hydroxyethyl)thiophen-2-yl)methyl)-1-oxa-4,9-diazaspiro[5.5]undecan-4-yl)(2-methylbenzo[d]thiazol-5-yl)methanone

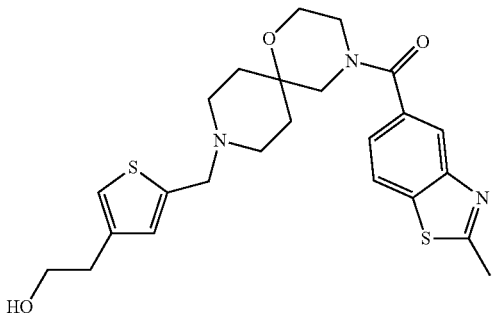 [SMILES: Cc1nc2cc(C(=O)N3CCOC4(CCN(Cc5cc(CCO)cs5)CC4)C3)ccc2s1]

TBAF (1M solution in THF, 1.5 mL) was added to stirred solution of (9-((4-(2-(tert-butyldimethylsilyloxy)ethyl)thiophen-2-yl)methyl)-1-oxa-4,9-diazaspiro[5.5]undecan-4-yl)(2-methylbenzo[d]thiazol-5-yl)methanone (example 49, step a) (0.36 g) in THF (2 mL). After 1 h, the reaction was evaporated to a gum. Purification by silica gel chromatography eluting with ethyl acetate:triethylamine, 20:1 gave the subtitled compound as a gum. Yield 0.2 g.

$^1$H NMR (400 MHz, D$_6$-DMSO, 90° C.) δ 8.05 (d, J=7.5 Hz, 1H), 7.37 (d, J=7.5 Hz, 1H), 7.86 (s, 1H), 6.94 (s, 1H), 6.76 (s, 1H), 4.30-4.23 (m, 1H), 3.68-3.54 (m, 6H), 3.54-3.44 (m, 2H), 3.43-3.33 (m, 2H), 2.81 (s, 3H), 2.71-2.62 (m, 2H), 2.47-2.29 (m, 4H), 1.81-1.71 (m, 2H), 1.55-1.40 (m, 2H).

c) 2-(5-((4-(2-Methylbenzo[d]thiazole-5-carbonyl)-1-oxa-4,9-diazaspiro[5.5]undecan-9-yl)methyl)thiophen-3-yl)acetaldehyde

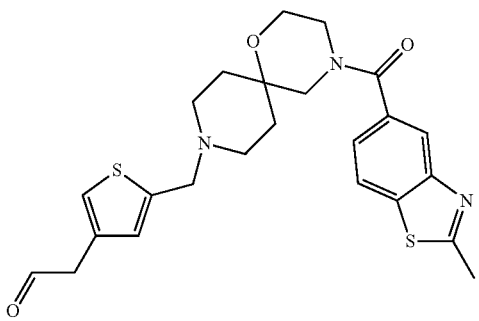 [SMILES: Cc1nc2cc(C(=O)N3CCOC4(CCN(Cc5cc(CC=O)cs5)CC4)C3)ccc2s1]

Dess-Martin periodinane (0.27 g) was added to stirred solution of (9-((4-(2-hydroxyethyl)thiophen-2-yl)methyl)-1-oxa-4,9-diazaspiro[5.5]undecan-4-yl)(2-methylbenzo[d]thiazol-5-yl)methanone (example 49, step b) (0.20 g) and trifluoroacetic acid (0.033 mL) in DCM (5 mL). After 40 min, the reaction mixture was treated with aqueous saturated sodium thiosulphate solution (5 mL), saturated sodium bicarbonate solution (5 mL) and ethyl acetate (30 mL). The mixture was extracted twice with ethyl acetate, the combined organics were washed with saturated sodium bicarbonate solution, acetic acid (0.08 mL) was added, then the solution was dried over sodium sulphate, filtered, and evaporated in vacuo. Yield 0.2 g. Used directly in the next step.

m/z 470 (M+H)$^+$ (APCI)

d) (R)-4-Hydroxy-7-(1-hydroxy-2-(2-(5-((4-(2-methylbenzo[d]thiazole-5-carbonyl)-1-oxa-4,9-diazaspiro[5.5]undecan-9-yl)methyl)thiophen-3-yl)ethylamino)ethyl)benzo[d]thiazol-2(3H)-one ditrifluoroacetate

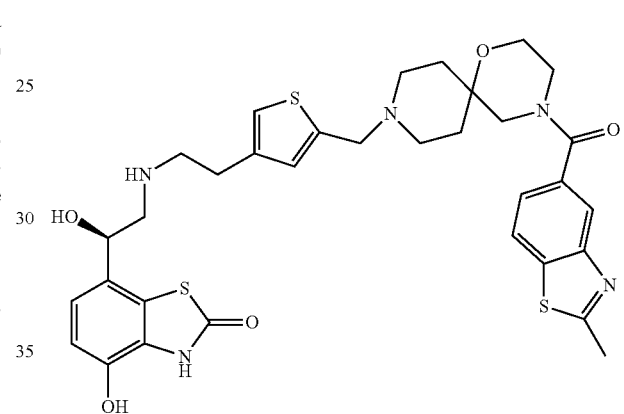

Acetic acid (0.037 mL) was added to a stirred solution of (R)-7-(2-amino-1-hydroxyethyl)-4-hydroxybenzo[d]thiazol-2(3H)-one hydrochloride (WO2007027134, example 1, step d) (0.168 g) and 2-(5-((4-(2-methylbenzo[d]thiazole-5-carbonyl)-1-oxa-4,9-diazaspiro[5.5]undecan-9-yl)methyl)thiophen-3-yl)acetaldehyde (example 49, step c) (0.200 g) in MeOH (8 mL). After 1 min, sodium cyanoborohydride (0.107 g) was added. After 3 h, the reaction mixture was filtered and purified by preparative HPLC (Sunfire™, Gradient: 10-35% acetonitrile in 0.2% aqueous TFA). The fractions containing pure product were combined and evaporated to dryness. Trituration with diethyl ether gave the titled compound as a white solid. Yield 0.15 g.

m/z 680 (M+H)$^+$ (APCI)

$^1$H NMR (400 MHz, D$_6$-DMSO, 90° C.) δ 11.29 (s, 1H), 8.07 (d, J=8.2 Hz, 1H), 7.90 (s, 1H), 7.42-7.37 (m, 2H), 7.15 (s, 1H), 6.93 (d, J=8.7 Hz, 1H), 6.77 (d, J=8.7 Hz, 1H), 4.94-4.86 (m, 1H), 4.50-4.41 (m, 2H), 3.73-3.63 (m, 2H), 3.58-3.33 (m, 4H), 3.29-2.90 (m, 10H), 2.81 (s, 3H), 2.16-2.00 (m, 2H), 1.78-1.62 (m, 2H). 4 exchangeable protons not observed.

EXAMPLE 50

(R)-7-(2-(3-((4-(2-tert-Butylthiazole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

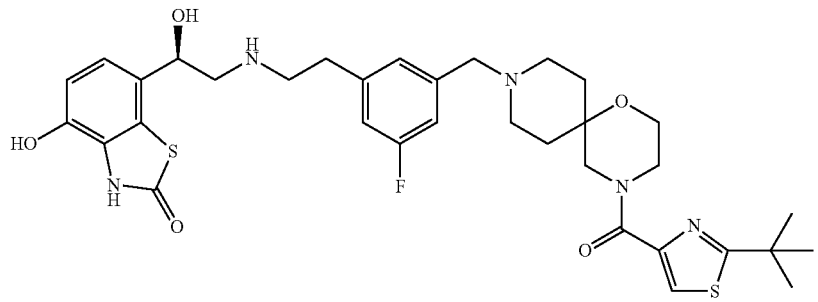 [SMILES: CC(C)(C)c1nc(C(=O)N2CCOC3(CCN(Cc4cc(F)cc(CCNC[C@H](O)c5ccc(O)c6[nH]c(=O)sc56)c4)CC3)C2)cs1]

a) (2-tert-Butylthiazol-4-yl)(9-(3-fluoro-5-(2-hydroxyethyl)benzyl)-1-oxa-4,9-diazaspiro[5.5]undecan-4-yl)methanone

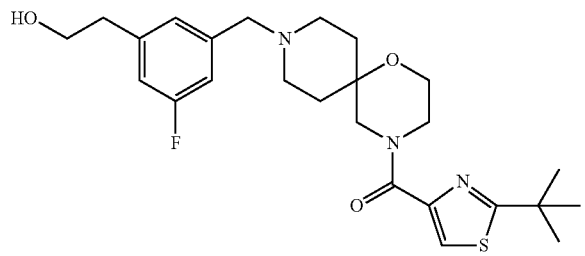 [SMILES: CC(C)(C)c1nc(C(=O)N2CCOC3(CCN(Cc4cc(F)cc(CCO)c4)CC3)C2)cs1]

A solution of 2,2,2-trifluoro-1-(9-(3-fluoro-5-(2-hydroxyethyl)benzyl)-1-oxa-4,9-diazaspiro[5.5]undecan-4-yl)ethanone (example 41, step d) (0.21 g) in methanol (3 mL) was added to ammonia (35% aqueous solution, 15 mL) and the reaction mixture stirred at 20° C. for 1 hour. The mixture was evaporated to dryness under reduced pressure and the residue azeotroped three times with acetonitrile. The residue was dissolved in DMF (7 mL) and treated with 2-tert-butylthiazole-4-carboxylic acid (0.096 g) followed by triethylamine (0.290 mL) and then HATU (0.257 g) and the resultant mixture stirred at 20° C. for 1 hour. The mixture was partitioned between ethyl acetate and brine, the organic layer was washed twice with brine, dried over sodium sulphate, filtered and the solvent evaporated under reduced pressure to afford the sub-titled compound. Yield 0.22 g.

m/z 476 (M+H)$^+$ (APCI)

b) (R)-7-(2-(3-((4-(2-tert-Butylthiazole-4-carbonyl)-1-oxa-4,9-diazaspiro[5.5]undecan-9-yl)methyl)-5-fluorophenethylamino)-11)-4-hydroxybenzo[d]thiazol-2(3H)-one ditrifluoroacetate

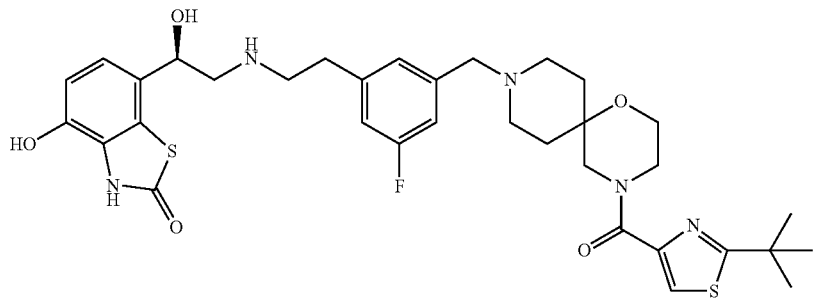 [SMILES: CC(C)(C)c1nc(C(=O)N2CCOC3(CCN(Cc4cc(F)cc(CCNC[C@H](O)c5ccc(O)c6[nH]c(=O)sc56)c4)CC3)C2)cs1]

A solution of (2-tert-butylthiazol-4-yl)(9-(3-fluoro-5-(2-hydroxyethyl)benzyl)-1-oxa-4,9-diazaspiro[5.5]undecan-4-yl)methanone (example 50, step a) (0.22 g) in DCM (20 mL) was treated with trifluoroacetic acid (0.036 mL) followed by Dess-Martin periodinane (0.255 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.026 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.182 g) and acetic acid (0.026 mL) in methanol (15 mL). The mixture was cooled in an ice bath and treated with sodium cyanoborohydride (0.058 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.135 g.

m/z 684 (M+H)$^+$ (APCI)

$^1$H NMR (400 MHz, D$_6$-DMSO, 90° C.) δ 7.95 (s, 1H), 7.27-7.16 (m, 3H), 6.93 (d, J=8.5 Hz, 1H), 6.77 (d, J=8.5 Hz, 1H), 4.94-4.88 (m, 1H), 4.21 (s, 2H), 3.71 (s, 4H), 3.66 (s, 2H), 3.26 (t, J=7.9 Hz, 2H), 3.15-2.98 (m, 8H), 2.06-1.95 (m, 2H), 1.79-1.67 (m, 2H), 1.41 (s, 9H). Six exchangeable protons not observed.

EXAMPLE 51

(R)-5-(2-(2-(5-((2,2-Difluoro-4-(2-isopropylthiazole-4-carbonyl)-1-oxa-4,9-diazaspiro[5.5]undecan-9-yl)methyl)thiophen-3-yl)ethylamino)-1-hydroxyethyl)-8-hydroxyquinolin-2(1H)-one ditrifluoroacetate

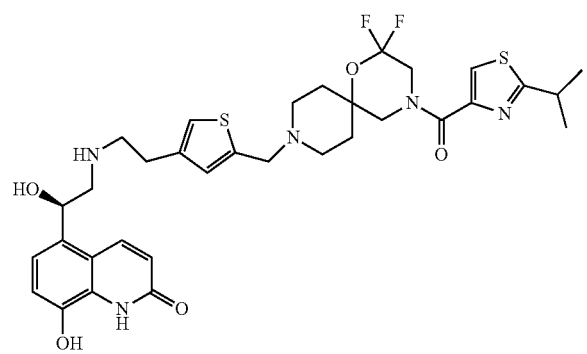 [SMILES: CC(C)c1nc(C(=O)N2CC(F)(F)OC3(CCN(Cc4cc(CCNC[C@H](O)c5ccc(O)c6[nH]c(=O)ccc56)cs4)CC3)C2)cs1]

a) (9-((4-(2-(tert-Butyldimethylsilyloxy)ethyl)thiophen-2-yl)methyl)-2,2-difluoro-1-oxa-4,9-diazaspiro[5.5]undecan-4-yl)(2-isopropylthiazol-4-yl)methanone

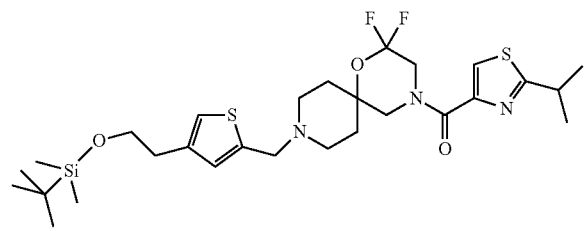 [SMILES: CC(C)c1nc(C(=O)N2CC(F)(F)OC3(CCN(Cc4cc(CCO[Si](C)(C)C(C)(C)C)cs4)CC3)C2)cs1]

(2,2-Difluoro-1-oxa-4,9-diazaspiro[5.5]undecan-4-yl)(2-isopropylthiazol-4-yl)methanone trifluoroacetate (example 44, step b) (0.40 g) was added to a stirred solution of a 4:1 mixture of 4-(2-(tert-butyldimethylsilyloxy)ethyl)thiophene-2-carbaldehyde and 3-(2-(tert-butyldimethylsilyloxy)ethyl)thiophene-2-carbaldehyde (example 27, step b) (0.36 g) and AcOH (0.05 mL) in N-methyl-2-pyrrolidinone (5 mL). After 5 min, sodium triacetoxyborohydride (0.28 g) was added. After 16 h water was added and the mixture extracted with ethyl acetate. The ethyl acetate layer was washed three times with water and evaporated in vacuo. Purification by silica gel chromatography eluting with 20:80:5 ethyl acetate:isohexane:triethylamine separated the two isomeric products and gave the subtitled compound as a gum. Yield 0.24 g.

$^1$H NMR (400 MHz, D$_6$-DMSO, 90° C.) δ 8.11 (s, 1H), 7.00 (s, 1H), 6.82 (s, 1H), 4.28-4.16 (m, 2H), 4.05-3.95 (m, 2H), 3.78 (t, J=6.6 Hz, 2H), 3.64 (s, 2H), 3.40-3.31 (m, 1H), 2.71 (t, J=6.6 Hz, 2H), 1.85-1.77 (m, 2H), 1.74-1.64 (m, 2H), 1.39 (d, J=6.8 Hz, 6H), 0.86 (s, 9H), 0.86 (s, 6H), 4 protons under solvent peaks.

b) (2,2-Difluoro-9-((4-(2-hydroxyethyl)thiophen-2-yl)methyl)-1-oxa-4,9-diazaspiro[5.5]undecan-4-yl)(2-isopropylthiazol-4-yl)methanone

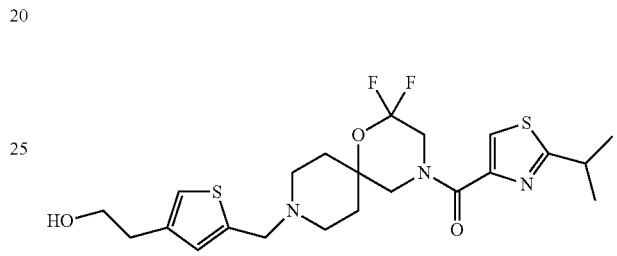

TBAF (1M in THF, 1.5 mL) was added to a stirred solution of (9-((4-(2-(tert-butyldimethylsilyloxy)ethyl)thiophen-2-yl)methyl)-2,2-difluoro-1-oxa-4,9-diazaspiro[5.5]undecan-4-yl)(2-isopropylthiazol-4-yl)methanone (example 51, step a) (0.30 g) in THF (3 mL). After 1 h, the reaction was evaporated in vacuo to a gum. Purification by silica gel chromatography eluting with ethyl acetate:triethylamine, 20:1 gave the subtitled compound as a gum. Yield 0.2 g.

$^1$H NMR (400 MHz, D$_6$-DMSO) δ 8.19 (s, 1H), 7.02 (s, 1H), 6.81 (s, 1H), 4.60 (t, J=5.3 Hz, 1H), 4.54-4.39 (m, 1H), 4.20-3.98 (m, 3H), 3.88-3.75 (m, 1H), 3.66-3.53 (m, 5H), 2.65 (t, J=7.0 Hz, 3H), 1.81-1.73 (m, 2H), 1.72-1.60 (m, 2H), 1.36 (d, J=6.4 Hz, 6H). 2 protons obscured by solvent peaks.

c) 2-(5-((2,2-Difluoro-4-(2-isopropylthiazole-4-carbonyl)-1-oxa-4,9-diazaspiro[5.5]undecan-9-yl)methyl)thiophen-3-yl)acetaldehyde

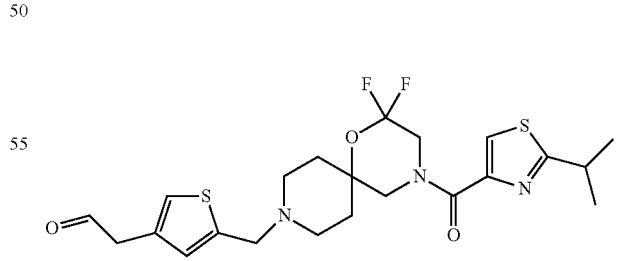

Dess-Martin periodinane (0.20 g) was added to stirred solution of (2,2-difluoro-9-((4-(2-hydroxyethyl)thiophen-2-yl)methyl)-1-oxa-4,9-diazaspiro[5.5]undecan-4-yl)(2-isopropylthiazol-4-yl)methanone (example 51, step b) (0.15 g) and trifluoroacetic acid (0.031 mL) in DCM (4 mL). After 40 min, the reaction mixture was treated with aqueous saturated sodium thiosulphate solution (5 mL), saturated sodium bicarbonate solution (5 mL) and ethyl acetate (30 mL). The mixture was extracted twice with ethyl acetate, the combined organics were washed with saturated sodium bicarbonate solution, acetic acid (0.08 mL) was added, then the solvent was dried over sodium sulphate, filtered, and evaporated in vacuo. Yield 0.19 g. Used directly.

m/z 484 (M+H)+ (APCI)

d) (R)-5-(2-(2-(5-((2,2-Difluoro-4-(2-isopropylthiazole-4-carbonyl)-1-oxa-4,9-diazaspiro[5.5]undecan-9-yl)methyl)thiophen-3-yl)ethylamino)-1-hydroxyethyl)-8-hydroxyquinolin-2(1H)-one ditrifluoroacetate

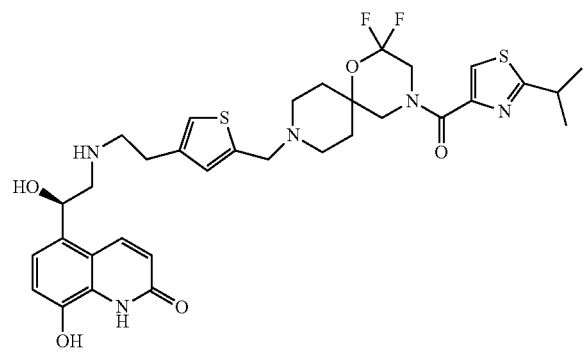 [SMILES: CC(C)c1nc(C(=O)N2CC(F)(F)OC3(CCN(Cc4cc(CCNC[C@H](O)c5ccc(O)c6[nH]c(=O)ccc56)cs4)CC3)C2)cs1]

(R)-5-(2-Amino-1-(tert-butyldimethylsilyloxy)ethyl)-8-hydroxyquinolin-2(1H)-one (WO2004106333) (0.156 g) was added to stirred solution of 2-(5-((2,2-difluoro-4-(2-isopropylthiazole-4-carbonyl)-1-oxa-4,9-diazaspiro[5.5]undecan-9-yl)methyl)thiophen-3-yl)acetaldehyde (example 51, step c) (0.15 g) and acetic acid (0.027 mL) in methanol (8 mL). After 5 minutes sodium cyanoborohydride (0.078 g) was added. After 3 h, the reaction mixture was evaporated in vacuo to ~3 mL and partitioned between ethyl acetate and saturated sodium bicarbonate. The ethyl acetate solution was washed with brine, dried over sodium sulphate, filtered and evaporated in vacuo. The resulting gum was dissolved in THF (2 mL) and triethylamine trihydrofluoride (0.064 g) added. After 16 h, toluene was added and the solution evaporated in vacuo. Purification by preparative HPLC (Sunfire™, Gradient: 10-35% acetonitrile in 0.2% aqueous TFA). The fractions containing product were combined and evaporated to dryness, azeotroped with MeCN then triturated with diethyl ether to give the titled compound as solid. Yield 0.14 g.

m/z 688 (M+H)+ (APCI)

1H NMR (400 MHz, D6-DMSO) δ 10.52-10.47 (m, 2H), 8.85-8.70 (m, 2H), 8.22 (s, 1H), 8.15 (d, J=9.6 Hz, 1H), 7.49-7.43 (m, 1H), 7.21-7.12 (m, 1H), 7.15 (d, J=6.9 Hz, 1H), 6.99 (d, J=8.1 Hz, 1H), 6.58 (d, J=10.6 Hz, 1H), 6.24-6.17 (m, 1H), 5.33 (d, J=8.9 Hz, 1H), 4.66-4.51 (m, 2H), 3.44-2.91 (m, 10H), 2.15-2.03 (m, 2H), 1.95-1.77 (m, 2H), 1.35 (d, J=6.9 Hz, 6H). 6 protons obscured by solvent peaks.

EXAMPLE 52

(R)-7-(2-(3-Chloro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

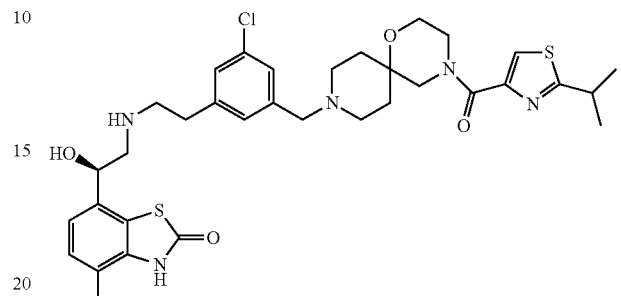

a) 2-(3-(Bromomethyl)-5-chlorophenyl)acetic acid

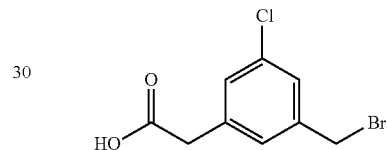

Benzoyl peroxide (0.112 g) was added to a suspension of 2-(3-chloro-5-methylphenyl)acetic acid (0.752 g) and N-bromosuccinimide (0.801 g) in DCM (15 mL), and the resulting mixture was heated at 50° C. under nitrogen overnight. The mixture was concentrated in vacuo to remove the dichloromethane and the residue was dissolved in ethyl acetate (10 mL). The solution was heated at 85° C. under nitrogen for 4 hours, then cooled. The solution was washed three times with water and once with brine, then dried over anhydrous magnesium sulphate and purified by flash chromatography on silica eluted with 1:20:79 acetic acid:ethyl acetate:isohexane to afford the crude subtitled compound as a pale yellow solid. Yield 0.735 g.

1H NMR (400 MHz, CDCl3) δ 7.33-7.31 (m, 1H), 7.24-7.22 (m, 1H), 7.21-7.18 (m, 1H), 4.41 (s, 2H), 3.64 (s, 2H). One exchangeable proton not observed.

b) 2-(3-(Bromomethyl)-5-chlorophenyl)ethanol

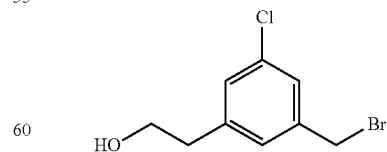

A solution of borane-methyl sulfide complex (2 M in THF, 2.8 mL) was added portionwise over 5 minutes to a solution of 2-(3-(bromomethyl)-5-chlorophenyl)acetic acid (example 52, step a) (0.73 g) in dry THF (10 mL) at room temperature. The resulting effervescing solution was stirred for 1 hour, then cooled in ice-water and quenched by the portionwise addition of methanol (3 mL) over 5 minutes. The solution was stirred at room temperature for a further 20 minutes and then concentrated in vacuo. The residue was purified by flash chromatography on silica eluted with 25% ethyl acetate in isohexane to afford the crude subtitled compound as a white solid. Yield 0.46 g.

$^1$H NMR (400 MHz, CDCl$_3$) δ 7.29-7.24 (m, 1H), 7.19-7.13 (m, 2H), 4.41 (s, 2H), 3.87 (t, J=6.5 Hz, 2H), 2.84 (t, J=6.4 Hz, 2H). One exchangeable proton not observed.

c) (9-(3-Chloro-5-(2-hydroxyethyl)benzyl)-1-oxa-4,9-diazaspiro[5.5]undecan-4-yl)(2-isopropylthiazol-4-yl)methanone

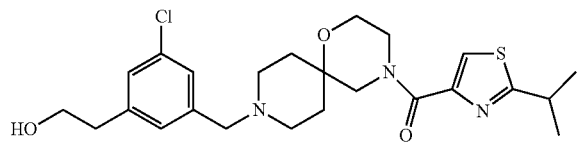 [SMILES: CC(C)c1nc(C(=O)N2CCOC3(CCN(Cc4cc(Cl)cc(CCO)c4)CC3)C2)cs1]

Triethylamine (0.18 mL) was added to a suspension of (2-isopropylthiazol-4-yl)(1-oxa-4,9-diazaspiro[5.5]undecan-4-yl)methanone trifluoroacetate (example 22, step b) (0.217 g) and 2-(3-(bromomethyl)-5-chlorophenyl)ethanol (example 52, step b) (0.160 g) in acetonitrile (5 mL) and the resulting solution was stirred at room temperature overnight. The solution was then purified by flash chromatography on silica eluted with 1:5:94 triethylamine:methanol:dichloromethane to afford a gum. The gum was dissolved in dichloromethane and the solution was washed three times with water, dried over anhydrous magnesium sulphate and concentrated in vacuo to afford the subtitled compound as a pale yellow foam. Yield 0.254 g.

$^1$H NMR (400 MHz, D$_6$-DMSO, 90° C.) δ 7.90 (s, 1H), 7.21-6.92 (m, 3H), 4.31 (t, J=5.3 Hz, 1H), 3.79-3.49 (m, 8H), 3.42 (s, 2H), 3.31 (septet, J=6.8 Hz, 1H), 2.71 (t, J=6.7 Hz, 2H), 2.43-2.22 (m, 4H), 1.77-1.65 (m, 2H), 1.60-1.48 (m, 2H), 1.36 (d, J=6.9 Hz, 6H).

d) 2-(3-Chloro-5-((4-(2-isopropylthiazole-4-carbonyl)-1-oxa-4,9-diazaspiro[5.5]undecan-9-yl)methyl)phenyl)acetaldehyde

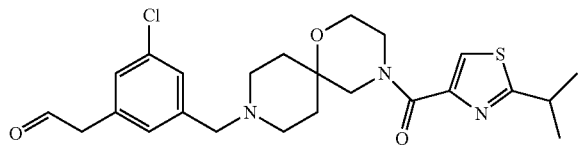 [SMILES: CC(C)c1nc(C(=O)N2CCOC3(CCN(Cc4cc(Cl)cc(CC=O)c4)CC3)C2)cs1]

A solution of (9-(3-chloro-5-(2-hydroxyethyl)benzyl)-1-oxa-4,9-diazaspiro[5.5]undecan-4-yl)(2-isopropylthiazol-4-yl)methanone (example 52, step c) (0.242 g) in DCM (5 mL) was cooled in ice-water, treated with trifluoroacetic acid (0.059 mL) and stirred for 5 minutes. Dess-Martin periodinane (0.323 g) was added, then the mixture was removed from the cooling bath and stirred at room temperature for 30 minutes. The solution was diluted with saturated sodium thiosulphate solution (5 mL), saturated sodium bicarbonate solution (5 mL) and ethyl acetate (5 mL) and the resulting mixture was stirred vigorously for 10 minutes. The mixture was then extracted twice with ethyl acetate, the combined organic phases were washed with brine, acidified with acetic acid (0.1 mL), dried over anhydrous magnesium sulphate and concentrated in vacuo to give the crude subtitled compound as a yellow foam. Yield 0.297 g.

m/z 476 (M+H)$^+$ (APCI)

e) (R)-7-(2-(3-Chloro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

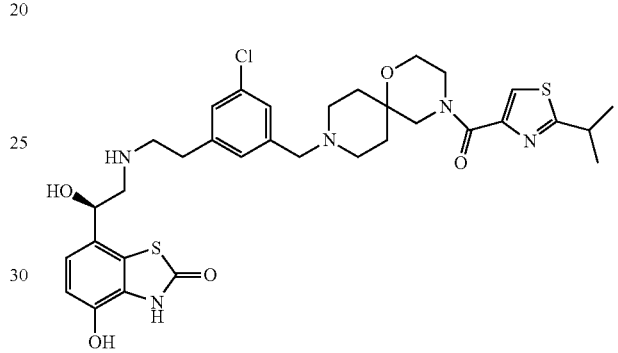

A solution of (R)-7-(2-amino-1-hydroxyethyl)-4-hydroxybenzo[d]thiazol-2(3H)-one hydrochloride (WO2007027134, example 1, step d) (0.220 g) in methanol (3 mL) was treated with acetic acid (0.047 mL) and stirred for 5 minutes. A solution of 2-(3-chloro-5-((4-(2-isopropylthiazole-4-carbonyl)-1-oxa-4,9-diazaspiro[5.5]undecan-9-yl)methyl)phenyl)acetaldehyde (example 52, step d) (0.296 g) in methanol (4 mL) was then added, and the resulting mixture was stirred at room temperature for 5 minutes, before cooling in ice-water and treating with sodium triacetoxyborohydride (0.181 g). The mixture was stirred in ice-water for 10 minutes and then at room temperature for 45 minutes, before cooling in ice-water and treating with more sodium triacetoxyborohydride (0.533 g). The mixture was then stirred overnight, allowing it to slowly warm to room temperature. The following morning the mixture was concentrated in vacuo. The residue was dissolved in a mixture of methanol (1.5 mL), acetonitrile (1.5 mL) and water (1.5 mL) and purified by preparative HPLC (Sunfire™, Gradient: 5-50% acetonitrile in 0.2% aqueous TFA). Fractions containing product were concentrated in vacuo and co-evaporated from acetonitrile three times to give a colourless residue. The residue was triturated with diethyl ether to give a solid, which was removed by filtration, washed with diethyl ether and dried in vacuo at room temperature to afford the titled compound as a white solid. Yield 0.092 g.

m/z 686 (M+H)$^+$ (APCI)

$^1$H NMR (400 MHz, D$_6$-DMSO, 90° C.) δ 7.94 (s, 1H), 7.50-7.44 (m, 1H), 7.44-7.37 (m, 1H), 7.34-7.26 (m, 1H), 6.93 (d, J=8.5 Hz, 1H), 6.77 (d, J=8.2 Hz, 1H), 4.90 (dd, J=7.9, 5.4 Hz, 1H), 4.26-4.08 (m, 2H), 3.77-3.59 (m, 6H), 3.35-3.21 (m, 3H), 3.16-2.91 (m, 8H), 2.06-1.90 (m, 2H), 1.81-1.63 (m, 2H), 1.35 (d, J=6.9 Hz, 6H). Six exchangeable protons not observed.

EXAMPLE 53

(R)-7-(2-(3-Fluoro-5-((4-(4-isopropylthiazole-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

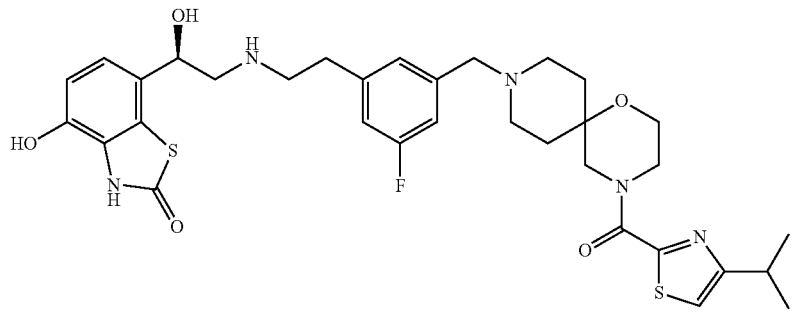 [SMILES: CC(C)c1csc(C(=O)N2CCOC3(CCN(Cc4cc(F)cc(CCNC[C@H](O)c5ccc(O)c6[nH]c(=O)sc56)c4)CC3)C2)n1]

a) Ethyl 4-isopropylthiazole-2-carboxylate

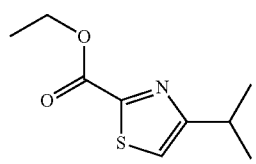

1-Bromo-3-methylbutan-2-one (3.72 g) in ethanol (15 mL) was added dropwise over 15 minutes to a refluxing solution of ethyl 2-amino-2-thioxoacetate (3 g) in ethanol (120 mL). The mixture was heated at reflux for 2 hours and then cooled to room temperature. The solvent was evaporated down under reduced pressure to a volume of 30 mL, this solution was added to ice/water (200 mL) and the mixture neutralised by dropwise addition of '880' concentrated aqueous ammonia. The mixture was extracted twice with ethyl acetate, the combined organics were washed with brine, dried over sodium sulphate, filtered and the solvent evaporated under reduced pressure. The crude product was purified by flash silica chromatography eluting with 20% ethyl acetate in isohexane. Pure fractions were evaporated to dryness to afford the subtitled compound. Yield 2.2 g.

m/z 200 (M+H)$^+$ (APCI)

b) 4-Isopropylthiazole-2-carboxylic acid

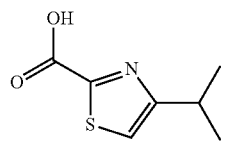

A solution of ethyl 4-isopropylthiazole-2-carboxylate (example 53, step a) (2.2 g) in a mixture of methanol (10 mL) and THF (20 mL) was treated with a solution of lithium hydroxide (0.264 g) in water (20 mL). The reaction mixture was stirred at 20° C. for 24 hours. The organic solvent was removed under reduced pressure and the remaining aqueous mixture was partitioned between ethyl acetate and water. The aqueous layer was acidified with 2M hydrochloric acid and extracted twice with ethyl acetate, the combined organics were washed with brine, dried over sodium sulphate, filtered and the solvent evaporated under reduced pressure. The crude product was triturated with cyclohexane to afford the subtitled compound. Yield 0.93 g.

m/z 170 (M–H)$^-$ (APCI)

$^1$H NMR (400 MHz, D$_6$-DMSO) δ 7.67 (s, 1H), 3.16-3.05 (m, 1H), 1.26 (d, 6H). One exchangeable proton not observed.

c) (9-(3-Fluoro-5-(2-hydroxyethyl)benzyl)-1-oxa-4,9-diazaspiro[5.5]undecan-4-yl)(4-isopropylthiazol-2-yl)methanone

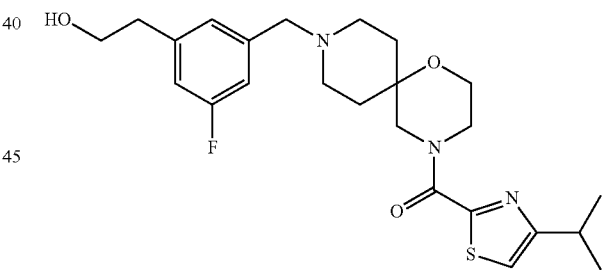

A solution of 2,2,2-trifluoro-1-(9-(3-fluoro-5-(2-hydroxyethyl)benzyl)-1-oxa-4,9-diazaspiro[5.5]undecan-4-yl)ethanone (example 41, step d) (0.21 g) in methanol (3 mL) was added to ammonia (35% aqueous solution, 15 mL) and the reaction mixture stirred at 20° C. for 1 hour. The mixture was evaporated to dryness under reduced pressure and the residue azeotroped three times with acetonitrile. The residue was dissolved in DMF (7 mL) and treated with 4-isopropylthiazole-2-carboxylic acid (example 53, step b) (0.089 g) followed by triethylamine (0.290 mL) and then HATU (0.257 g) and the resultant mixture stirred at 20° C. for 1 hour. The mixture was partitioned between ethyl acetate and brine, the organic layer was washed twice with brine, dried over sodium sulphate, filtered and the solvent evaporated under reduced pressure to afford the subtitled compound. Yield 0.325 g.

m/z 462 (M+H)$^+$ (APCI)

d) (R)-7-(2-(3-Fluoro-5-((4-(4-isopropylthiazole-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

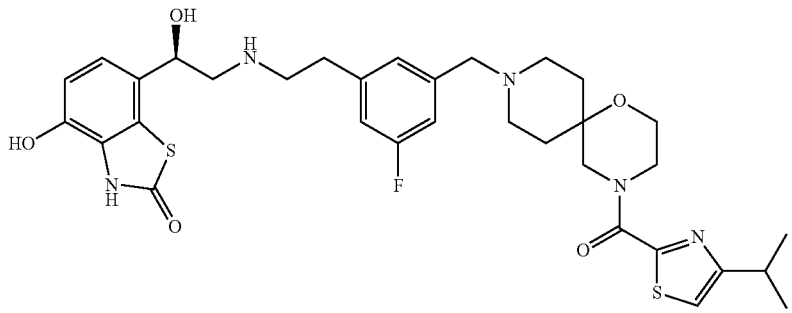 [SMILES: CC(C)c1csc(C(=O)N2CCOC3(CCN(Cc4cc(F)cc(CCNC[C@H](O)c5ccc(O)c6[nH]c(=O)sc56)c4)CC3)C2)n1]

A solution of (9-(3-fluoro-5-(2-hydroxyethyl)benzyl)-1-oxa-4,9-diazaspiro[5.5]undecan-4-yl)(4-isopropylthiazol-2-yl)methanone (example 53, step c) (0.23 g) in DCM (20 mL) was treated with trifluoroacetic acid (0.038 mL) followed by Dess-Martin periodinane (0.275 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.029 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.196 g) and acetic acid (0.029 mL) in methanol (15 mL). The mixture was cooled in an ice bath and treated with sodium cyanoborohydride (0.063 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.140 g.

m/z 670 (M+H)+ (APCI)
$^1$H NMR (400 MHz, D$_6$-DMSO, 90° C.) δ 11.27 (s, 1H), 7.51 (s, 1H), 7.28-7.16 (m, 3H), 6.93 (d, J=8.2 Hz, 1H), 6.77 (d, J=8.2 Hz, 1H), 4.95-4.88 (m, 1H), 4.26 (s, 2H), 4.19-3.82 (m, 4H), 3.80-3.74 (m, 2H), 3.27 (t, J=7.9 Hz, 2H), 3.19-2.98 (m, 9H), 2.09-1.98 (m, 2H), 1.85-1.73 (m, 2H), 1.27 (d, J=7.1 Hz, 6H). Five exchangeable protons not observed.

EXAMPLE 54

(R)-7-(2-(3-Fluoro-5-((4-(5-isopropylthiazole-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

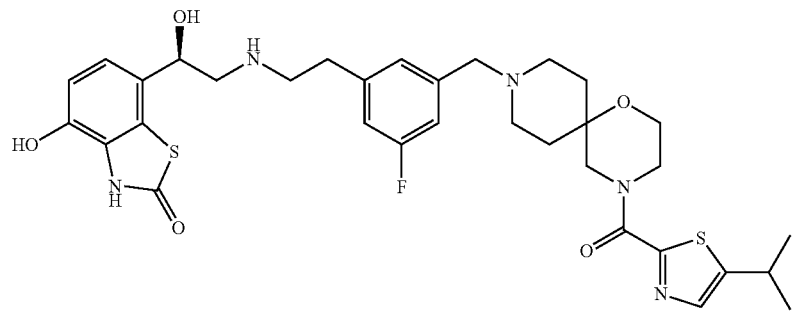 [SMILES: CC(C)c1cnc(C(=O)N2CCOC3(CCN(Cc4cc(F)cc(CCNC[C@H](O)c5ccc(O)c6[nH]c(=O)sc56)c4)CC3)C2)s1]

a) Ethyl 5-isopropylthiazole-2-carboxylate

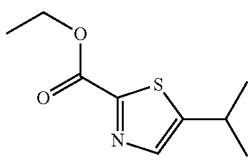

A solution of bromine (0.162 mL) in a mixture of DCM (1.2 mL) and dioxane (0.3 mL) was added slowly dropwise, to a cooled solution at 0° C. of 3-methylbutanal (0.272 g) in a mixture of DCM (1.6 mL) and dioxane (0.4 mL). The mixture was stirred at 5° C. for 2 hours. The reaction mixture was cooled to 0° C. and the solvents were removed under a stream of nitrogen gas. The residue, still at 0° C. was treated portionwise with ethyl 2-amino-2-thioxoacetate (0.42 g). The resultant mixture was heated under nitrogen from 0° C. to 70° C. over a period of 15 minutes. At the end of this time the mixture was cooled in an ice bath and treated with ethyl acetate and saturated sodium bicarbonate solution, the organic layer was dried over sodium sulphate, filtered and the solvent removed under reduced pressure. The crude product was purified by flash silica chromatography using 30% ethyl acetate in isohexane as solvent. Pure fractions were evaporated to dryness to afford the subtitled compound. Yield 0.105 g.

m/z 200 (M+H)$^+$ (APCI)

b) 5-Isopropylthiazole-2-carboxylic acid

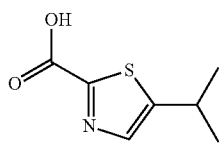

A solution of ethyl 5-isopropylthiazole-2-carboxylate (example 54, step a) (0.105 g) in methanol (5 mL) was treated with a solution of lithium hydroxide (0.025 g) in water (3 mL) and the resultant mixture was stirred vigorously at 20° C. for 2 hours. The methanol was evaporated off under reduced pressure and the residual aqueous solution was diluted with brine (10 mL). The aqueous layer was washed with ether, then cooled in an ice bath and acidified by dropwise addition of concentrated aqueous hydrochloric acid. The mixture was extracted twice with ethyl acetate. The combined ethyl acetate layers were washed with brine, dried over sodium sulphate, filtered and the solvent evaporated under reduced pressure to afford the subtitled compound. Yield 0.048 g.

$^1$H NMR (400 MHz, D$_6$-DMSO) δ 7.84 (s, 1H), 3.34-3.26 (m, 1H), 1.31 (d, J=6.9 Hz, 6H). One exchangeable proton not observed.

c) (9-(3-Fluoro-5-(2-hydroxyethyl)benzyl)-1-oxa-4,9-diazaspiro[5.5]undecan-4-yl)(5-isopropylthiazol-2-yl)methanone

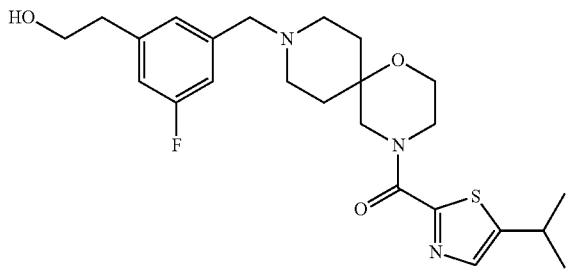 [SMILES: CC(C)c1cnc(C(=O)N2CCOC3(CCN(Cc4cc(F)cc(CCO)c4)CC3)C2)s1]

A solution of 2,2,2-trifluoro-1-(9-(3-fluoro-5-(2-hydroxyethyl)benzyl)-1-oxa-4,9-diazaspiro[5.5]undecan-4-yl)ethanone (example 41, step d) (0.113 g) in methanol (3 mL) was added to ammonia (35% aqueous solution, 15 mL) and the reaction mixture stirred at 20° C. for 1 hour. The mixture was evaporated to dryness under reduced pressure and the residue azeotroped three times with acetonitrile. The residue was dissolved in DMF (7 mL) and treated with 5-isopropylthiazole-2-carboxylic acid (example 54, step b) (0.048 g) followed by triethylamine (0.156 mL) and then HATU (0.139 g) and the resultant mixture stirred at 20° C. for 1 hour. The mixture was partitioned between ethyl acetate and brine, the organic layer was washed twice with brine, dried over sodium sulphate, filtered and the solvent evaporated under reduced pressure. The crude product was purified by flash silica chromatography using 2.5% methanol in dichloromethane with 1% triethylamine as solvent.

Pure fractions were evaporated to dryness to afford the subtitled compound. Yield 104 mg.

m/z 462 (M+H)$^+$ (APCI)

d) (R)-7-(2-(3-Fluoro-5-((4-(5-isopropylthiazole-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

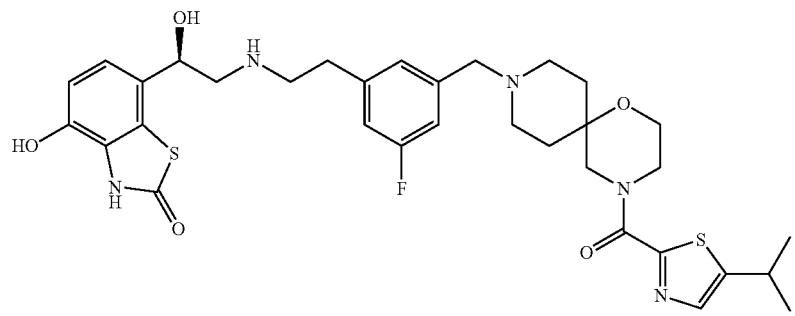 [SMILES: CC(C)c1cnc(C(=O)N2CCOC3(CCN(Cc4cc(F)cc(CCNC[C@H](O)c5ccc(O)c6[nH]c(=O)sc56)c4)CC3)C2)s1]

A solution of (9-(3-fluoro-5-(2-hydroxyethyl)benzyl)-1-oxa-4,9-diazaspiro[5.5]undecan-4-yl)(5-isopropylthiazol-2-yl)methanone (example 54, step c) (0.104 g) in DCM (20 mL) was treated with trifluoroacetic acid (0.017 mL) followed by Dess-Martin periodinane (0.124 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.013 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.089 g) and acetic acid (0.013 mL) in methanol (15 mL). The mixture was cooled in an ice bath and treated with sodium cyanoborohydride (0.028 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.045 mg.

m/z 670 (M+H)$^+$ (APCI)

$^1$H NMR (400 MHz, D$_6$-DMSO, 90° C.) δ 7.67 (s, 1H), 7.28-7.16 (m, 3H), 6.93 (d, J=8.5 Hz, 1H), 6.77 (d, J=8.5 Hz, 1H), 4.94-4.89 (m, 1H), 4.26 (s, 2H), 4.11-3.79 (m, 4H), 3.78-3.73 (m, 2H), 3.31-3.24 (m, 2H), 3.18-2.99 (m, 9H), 2.06-1.97 (m, 2H), 1.85-1.74 (m, 2H), 1.31 (d, J=7.0 Hz, 6H). Six exchangeable protons not observed.

EXAMPLE 55

(R)-7-(2-(3-Fluoro-5-((4-(2-isopropylthiazole-5-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

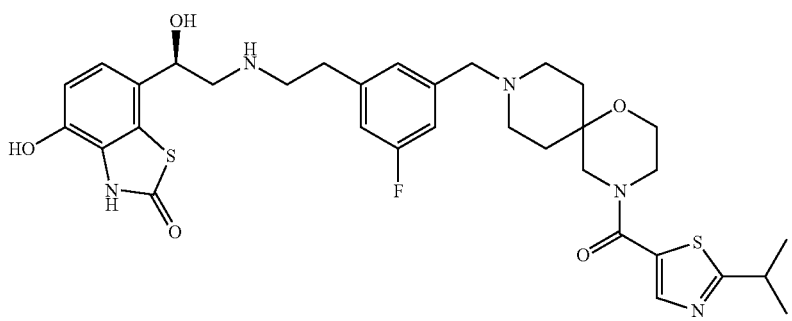 [SMILES: CC(C)c1ncc(C(=O)N2CCOC3(CCN(Cc4cc(F)cc(CCNC[C@H](O)c5ccc(O)c6[nH]c(=O)sc56)c4)CC3)C2)s1]

a) Ethyl 2-isopropylthiazole-5-carboxylate

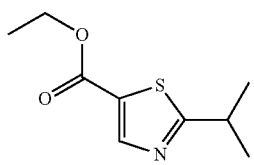

A mixture of 2-methylpropanethioamide (3.3 g) and ethyl 2-chloro-3-oxopropanoate (4.82 g) in acetone (50 mL) was heated at reflux under nitrogen for 3 hours. The mixture was cooled to room temperature and the solvent removed under reduced pressure. The crude product was purified by flash silica chromatography using 12% ethyl acetate in isohexane as solvent. Pure fractions were evaporated to dryness to afford the subtitled compound. Yield 1.6 g.

m/z 200 (M+H)$^+$ (APCI)

b) 2-Isopropylthiazole-5-carboxylic acid

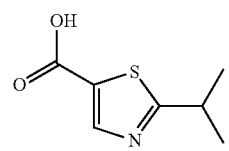

A solution of ethyl 2-isopropylthiazole-5-carboxylate (example 55, step a) (0.33 g) in methanol (6 mL) was treated with a solution of lithium hydroxide (0.079 g) in water (3 mL) and the resultant mixture stirred for 2 hours at 20° C. The methanol was evaporated off under reduced pressure and the residue partitioned between ether and brine. The aqueous layer was acidified by dropwise addition of dilute hydrochloric acid and the mixture extracted with ethyl acetate. The organic layer was washed with brine, dried over sodium sulphate, filtered and the solvent evaporated under reduced pressure to afford the subtitled compound. Yield 0.185 g.

m/z 172 (M+H)$^+$ (APCI)

$^1$H NMR (400 MHz, D$_6$-DMSO) δ 13.38 (s, 1H), 8.22 (s, 1H), 3.35-3.26 (m, 1H), 1.34 (d, J=6.8 Hz, 6H).

c) 2-(3-(1-Oxa-4,9-diazaspiro[5.5]undecan-9-ylmethyl)-5-fluorophenyl)ethanol

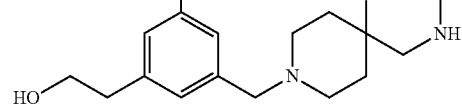

'880' Ammonia solution (5 mL) was added to a solution of 2,2,2-trifluoro-1-(9-(3-fluoro-5-(2-hydroxyethyl)benzyl)-1- oxa-4,9-diazaspiro[5.5]undecan-4-yl)ethanone (example 41, step d) (2.2 g) in methanol (25 mL). The resulting mixture was stirred for 90 min and the solvent evaporated. The residue was azeotroped three times with acetonitrile and concentrated to give the subtitled compound as a clear gum. Yield 1.96 g.

m/z 309 (M+H)+ (APCI)

$^1$H NMR (300 MHz, D$_6$-DMSO) δ 6.97 (s, 1H), 6.94 (s, 1H), 6.91 (s, 1H), 3.65-3.56 (m, 4H), 3.49-3.39 (m, 2H), 2.85-2.78 (m, 2H), 2.76-2.68 (m, 4H), 2.48-2.39 (m, 2H), 2.32-2.21 (m, 2H), 1.89-1.77 (m, 2H), 1.58-1.44 (m, 2H). Two exchangeable protons not observed.

d) (9-(3-Fluoro-5-(2-hydroxyethyl)benzyl)-1-oxa-4,9-diazaspiro[5.5]undecan-4-yl)(2-isopropylthiazol-5-yl)methanone

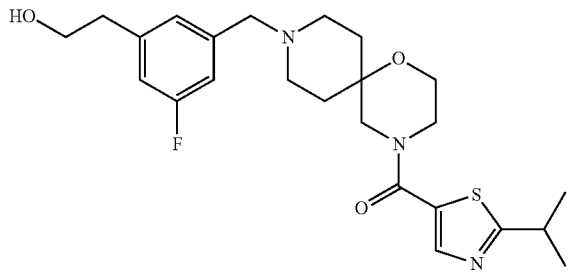 [SMILES: CC(C)c1ncc(C(=O)N2CCOC3(CCN(Cc4cc(F)cc(CCO)c4)CC3)C2)s1]

A solution of 2-(3-(1-oxa-4,9-diazaspiro[5.5]undecan-9-ylmethyl)-5-fluorophenyl)ethanol (example 55, step c) (0.153 g) in DMF (7 mL) was treated with triethylamine (0.208 mL) followed by 2-isopropylthiazole-5-carboxylic acid (example 55, step b) (0.085 g). The mixture was cooled to 0° C. and HATU (0.245 g) was added. The reaction mixture was stirred for 2 hours at 20° C. The mixture was partitioned between ethyl acetate and brine, the organic layer was washed twice with brine, dried over sodium sulphate, filtered and the solvent evaporated under reduced pressure. The crude product was purified by flash silica chromatography using 2.5% methanol in dichloromethane with 1% triethylamine as solvent. Pure fractions were evaporated to dryness to afford the subtitled compound. Yield 0.130 g.

m/z 462 (M+H)+ (APCI)

e) (R)-7-(2-(3-Fluoro-5-((4-(2-isopropylthiazole-5-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate A solution of (9-(3-fluoro-5-(2-hydroxyethyl)benzyl)-1-oxa-4,9-diazaspiro[5.5]undecan-4-yl)(2-isopropylthiazol-5-yl)methanone (example 55, step d) (0.13 g) in DCM (20 mL) was treated with trifluoroacetic acid (0.022 mL) followed by Dess-Martin periodinane (0.155 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.016 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.111 g) and acetic acid (0.016 mL) in methanol (15 mL). The mixture was cooled in an ice bath and treated with sodium cyanoborohydride (0.035 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.1 g.

m/z 670 (M+H)+ (APCI)

$^1$H NMR (400 MHz, D$_6$-DMSO, 90° C.) δ 11.27 (s, 1H), 7.92 (s, 1H), 7.30-7.18 (m, 3H), 6.93 (d, J=8.2 Hz, 1H), 6.77 (d, J=8.2 Hz, 1H), 4.95-4.89 (m, 1H), 4.30 (s, 2H), 3.75-3.70 (m, 2H), 3.68-3.63 (m, 2H), 3.54 (s, 2H), 3.33-3.24 (m, 3H), 3.22-3.00 (m, 8H), 2.07-1.98 (m, 2H), 1.84-1.72 (m, 2H), 1.35 (d, J=6.9 Hz, 6H). Five exchangeable protons not observed.

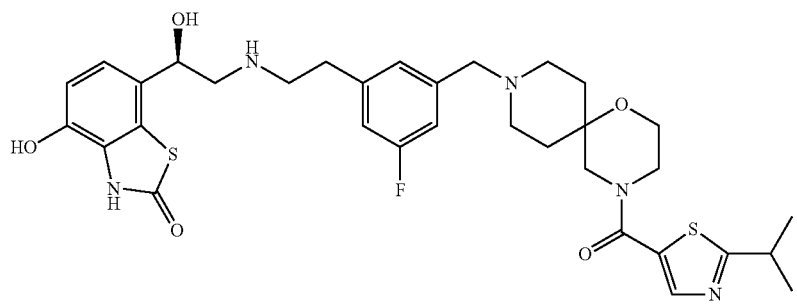 [SMILES: CC(C)c1ncc(C(=O)N2CCOC3(CCN(Cc4cc(F)cc(CCNC[C@H](O)c5ccc(O)c6[nH]c(=O)sc56)c4)CC3)C2)s1]

EXAMPLE 56

(R)-7-(2-(3-Fluoro-5-((4-(2-propylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

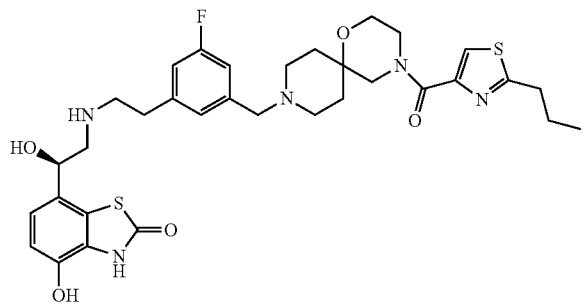 [SMILES: CCCc1nc(C(=O)N2CCOC3(CCN(Cc4cc(F)cc(CCNC[C@H](O)c5ccc(O)c6[nH]c(=O)sc56)c4)CC3)C2)cs1]

a) Ethyl 2-butyramido-3-mercaptopropanoate

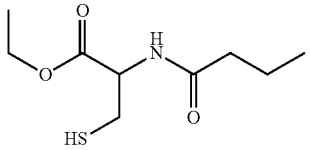

Triethylamine (4.5 mL) was added to a suspension of ethyl 2-amino-3-mercaptopropanoate hydrochloride (5 g) in DCM (50 mL). The resulting mixture was cooled in an ice/salt bath and butyryl chloride (3.3 mL) was added dropwise. The resulting mixture was allowed to warm to RT and stirred overnight. The reaction was quenched with saturated sodium bicarbonate solution (50 mL) and the layers separated. The aqueous phase was extracted with DCM (2×100 mL). The combined organic solutions were washed with brine (100 mL), dried over sodium sulphate, filtered and evaporated. The resulting white solid was purified by silica gel chromatography eluting with 4:1 to 1:1 isohexane:ethyl acetate gradient. The fractions containing product were combined and evaporated to give the subtitled compound as a white solid. Yield 3 g.

$^1$H NMR (400 MHz, D$_6$-DMSO) δ 8.21 (d, J=7.7 Hz, 1H), 4.43-4.37 (m, 1H), 4.13-4.06 (m, 2H), 2.88-2.80 (m, 1H), 2.78-2.69 (m, 1H), 2.12 (t, J=7.2 Hz, 2H), 1.60-1.47 (m, 2H), 1.22-1.14 (m, 3H), 0.90-0.81 (m, 3H). One exchangeable proton not observed.
m/z 218 (M−H)⁻ (APCI)

b) Ethyl 2-propylthiazole-4-carboxylate

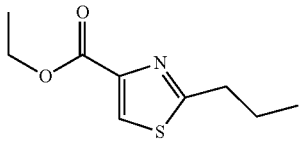

A solution of HCl (4M in 1,4-dioxane, 20 mL) was added to a solution of ethyl 2-butyramido-3-mercaptopropanoate (example 56, step a) (3 g) in ethanol (20 mL) and the resulting mixture stirred overnight. The solvent was evaporated and the residue azeotroped twice with toluene. The residue was redissolved in acetonitrile (50 mL), manganese dioxide (11.9 g) was added and the mixture heated at reflux overnight. The reaction was filtered through a pad of Celite. The filter pad was washed with MeCN (3×100 mL). The combined filtrate and washings were evaporated and the residue was purified by silica gel chromatography eluting with 9:1 isohexane:ethyl acetate. The product containing fractions were combined and evaporated to give the subtitled compound as a clear oil. Yield 0.24 g.

$^1$H NMR (400 MHz, CDCl$_3$) δ 8.05 (s, 1H), 4.42 (q, J=7.1 Hz, 2H), 3.04 (t, J=7.7 Hz, 2H), 1.89-1.77 (m, 2H), 1.40 (t, J=7.0 Hz, 3H), 1.02 (t, J=7.4 Hz, 3H).

c) 2-Propylthiazole-4-carboxylic acid

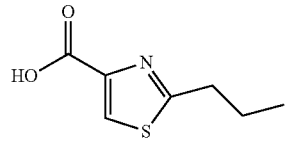

Lithium hydroxide monohydrate (0.2 g) was added to a solution of ethyl 2-propylthiazole-4-carboxylate (example 56, step b) (0.24 g) in a mixture of THF (4 mL) and water (1 mL). The resulting suspension was stirred overnight at RT. The reaction was acidified with aqueous HCl solution (2M, 3 mL) and evaporated. The residue was partitioned between brine (5 mL) and ethyl acetate (20 mL). The layers were separated and the aqueous phase extracted with ethyl acetate (2×20 mL). The combined organic solutions were dried over sodium sulphate, filtered and evaporated to give the subtitled compound as a white solid. Yield 0.17 g.

$^1$H NMR (400 MHz, D$_6$-DMSO) δ 12.91 (s, 1H), 8.31 (s, 1H), 2.96 (t, J=7.4 Hz, 2H), 1.79-1.68 (m, 2H), 0.95 (t, J=7.4 Hz, 3H).

d) (9-(3-Fluoro-5-(2-hydroxyethyl)benzyl)-1-oxa-4,9-diazaspiro[5.5]undecan-4-yl)(2-propylthiazol-4-yl)methanone

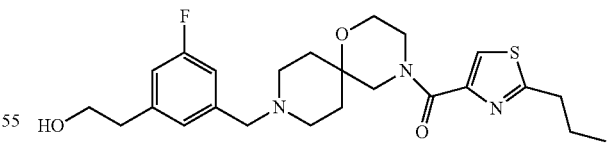

O-(7-Azabenzotriazol-1-yl)-N,N,N',N'-tetramethyluronium hexafluorophosphate (0.25 g) was added to a solution of 2-(3-(1-oxa-4,9-diazaspiro[5.5]undecan-9-ylmethyl)-5-fluorophenyl)ethanol (example 55, step c) (0.16 g), 2-propylthiazole-4-carboxylic acid (example 56, step c) (0.09 g) and triethylamine (0.29 mL) in DMF (7 mL) and the resulting yellow solution was stirred for 30 min. The mixture was partitioned between ethyl acetate (100 mL) and brine (100 mL). The organic phase was separated, washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added, and the mixture evaporated to give the subtitled compound as a clear gum. Yield 0.14 g.

m/z 462 (M+H)⁺ (APCI)

¹H NMR (400 MHz, D$_6$-DMSO, 90° C.) δ 7.89 (s, 1H), 6.95 (s, 1H), 6.89 (s, 1H), 6.86 (s, 1H), 4.31 (t, J=4.7 Hz, 1H), 3.69-3.59 (m, 8H), 3.44 (s, 2H), 2.98 (t, J=7.2 Hz, 2H), 2.72 (t, J=6.8 Hz, 2H), 2.43-2.28 (m, 4H), 1.82-1.66 (m, 4H), 1.59-1.50 (m, 2H), 0.97 (t, J=7.3 Hz, 3H).

e) (R)-7-(2-(3-Fluoro-5-((4-(2-propylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

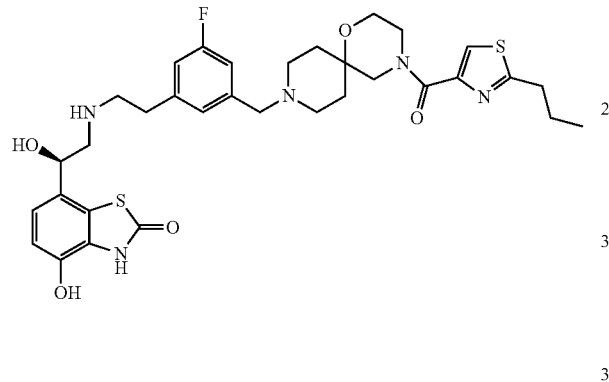

TFA (0.023 mL) was added to a (9-(3-fluoro-5-(2-hydroxyethyl)benzyl)-1-oxa-4,9-diazaspiro[5.5]undecan-4-yl)(2-propylthiazol-4-yl)methanone (example 56, step d) (0.14 g) in DCM (5 mL) at 0° C. The mixture was stirred for 5 min then Dess-Martin periodinane (0.19 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.017 mL) and (R)-7-(2-amino-1-hydroxyethyl)-4-hydroxybenzo[d]thiazol-2(3H)-one hydrochloride (WO2007027134, example 1, step d) (0.12 g) were then added and the mixture stirred for 5 min before cooling in an ice bath. Sodium cyanoborohydride (0.029 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethylether to give the titled compound as a white solid. Yield 0.077 g.

m/z 670 (M+H)⁺ (APCI)

¹H NMR (400 MHz, D$_6$-DMSO, 90° C.) δ 11.27 (s, 1H), 7.93 (s, 1H), 7.29-7.15 (m, 3H), 6.93 (d, J=8.2 Hz, 1H), 6.77 (d, J=8.5 Hz, 1H), 4.95-4.88 (m, 1H), 4.28-4.21 (m, 2H), 3.73-3.61 (m, 6H), 3.27 (t, J=7.9 Hz, 2H), 3.16-2.93 (m, 10H), 2.05-1.95 (m, 2H), 1.83-1.70 (m, 4H), 0.96 (t, J=7.3 Hz, 3H). Five exchangeable protons not observed.

EXAMPLE 57

(R)-7-(2-(3-((4-(2-Cyclopropylthiazole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

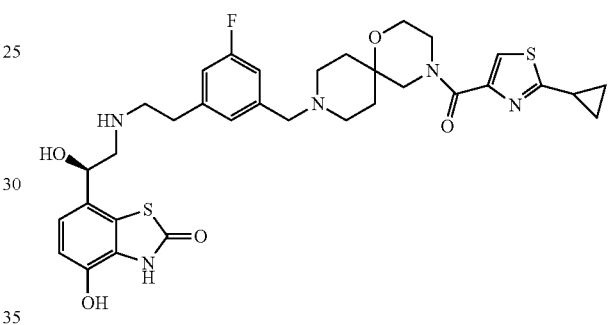

a) Ethyl 2-(cyclopropanecarboxamido)-3-mercaptopropanoate

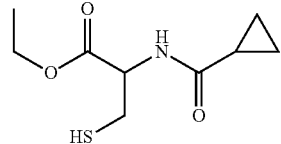

Cyclopropanecarbonyl chloride (3.1 mL) was added to a suspension of triethylamine (4.68 mL) and ethyl 2-amino-3-mercaptopropanoate hydrochloride (5.2 g) in DCM (200 mL) at 0° C. The resulting mixture was allowed to warm to RT and stirred overnight. The reaction was quenched with ethanol and the solvent evaporated. The residue was suspended in ethyl acetate (200 mL) and washed with saturated sodium bicarbonate solution (2×150 mL), aqueous HCl solution (2M, 2×150 mL) and brine (150 mL), then dried over magnesium sulphate, filtered and evaporated. The resulting white solid was purified by silica gel chromatography eluting with 4:1 isohexane:ethyl acetate to give the subtitled compound as a white solid. Yield 5 g.

¹H NMR (300 MHz, D$_6$-DMSO) δ 8.51 (d, J=7.7 Hz, 1H), 4.44 (td, J=7.5, 5.3 Hz, 1H), 4.17-4.05 (m, 2H), 2.91-2.67 (m, 2H), 2.53-2.52 (m, 1H), 1.78-1.60 (m, 1H), 1.19 (t, J=6.8 Hz, 3H), 0.71-0.66 (m, 4H).

b) Ethyl 2-cyclopropylthiazole-4-carboxylate

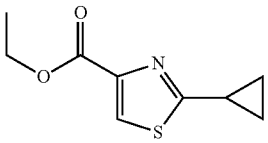

A solution of ethyl 2-(cyclopropanecarboxamido)-3-mercaptopropanoate (example 57, step a) (5 g) and tosic acid (0.875 g) in toluene (100 mL) was heated at reflux under Dean and Stark conditions overnight. The reaction was allowed to cool and the toluene solution was washed with saturated sodium hydrogen carbonate solution (3×100 mL) dried over sodium sulphate, filtered and evaporated. The resulting brown gum was redissolved in acetonitrile (100 mL). Manganese dioxide (40 g) was added and the mixture heated at reflux overnight. The reaction was filtered through Celite and the filter pad washed with MeCN (3×100 mL). The combined filtrate and washings were evaporated and the residue purified by silica gel chromatography eluting with 9:1 to 4:1 isohexane:ethyl acetate gradient. The fractions containing product were combined and evaporated to give the subtitled compound as a clear oil. Yield 0.15 g.

$^1$H NMR (400 MHz, CDCl$_3$) δ 7.94 (s, 1H), 4.40 (q, J=7.1 Hz, 2H), 2.45-2.37 (m, 1H), 1.39 (t, J=7.2 Hz, 3H), 1.20-1.04 (m, 4H).

c) 2-Cyclopropylthiazole-4-carboxylic acid

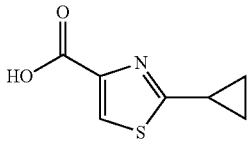 [SMILES: O=C(O)c1csc(C2CC2)n1]

Lithium hydroxide monohydrate (0.13 g) was added to a solution of ethyl 2-cyclopropylthiazole-4-carboxylate (example 57, step b) (0.15 g) in a mixture of THF (8 mL) and water (2 mL) and the resulting mixture was stirred overnight. The reaction was acidified with aqueous HCl (2M, 3 mL) and the solvent evaporated. The residue was partitioned between brine (20 mL) and ethyl acetate (30 mL). The layers were separated and the aqueous phase extracted with ethyl acetate (2×30 mL). The combined organic solutions were dried over sodium sulphate, filtered and evaporated to give the subtitled compound as an off white solid. Yield 0.12 g.

$^1$H NMR (300 MHz, D$_6$-DMSO) δ 12.88 (s, 1H), 8.19 (s, 1H), 2.48-2.37 (m, 1H), 1.18-1.09 (m, 2H), 1.01-0.94 (m, 2H).

d) (2-Cyclopropylthiazol-4-yl)(9-(3-fluoro-5-(2-hydroxyethyl)benzyl)-1-oxa-4,9-diazaspiro[5.5]undecan-4-yl)methanone

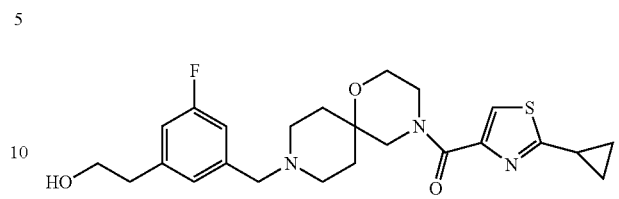

O-(7-Azabenzotriazol-1-yl)-N,N,N',N'-tetramethyluronium hexafluorophosphate (0.34 g) was added to a solution of 2-(3-(1-oxa-4,9-diazaspiro[5.5]undecan-9-ylmethyl)-5-fluorophenyl)ethanol (example 55, step c) (0.21 g), 2-cyclpropylthiazole-4-carboxylic acid (example 57, step c) (0.12 g) and triethylamine (0.38 mL) in DMF (7 mL) and the resulting yellow solution was stirred for 30 min. The mixture was partitioned between ethyl acetate and brine (100 mL), the organic layer was washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added and the solvent evaporated under reduced pressure to give the subtitled compound as a clear gum. Yield 0.15 g.

m/z 460 (M+H)$^+$ (APCI)

$^1$H NMR (400 MHz, D$_6$-DMSO, 90° C.) δ 7.79 (s, 1H), 6.96 (s, 1H), 6.90 (s, 1H), 6.86 (s, 1H), 4.35 (s, 1H), 3.67-3.56 (m, 8H), 3.44 (s, 2H), 2.72 (t, J=6.7 Hz, 2H), 2.46-2.30 (m, 5H), 1.75-1.66 (m, 2H), 1.58-1.47 (m, 2H), 1.17-1.10 (m, 2H), 1.01-0.94 (m, 2H).

e) (R)-7-(2-(3-((4-(2-Cyclopropylthiazole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

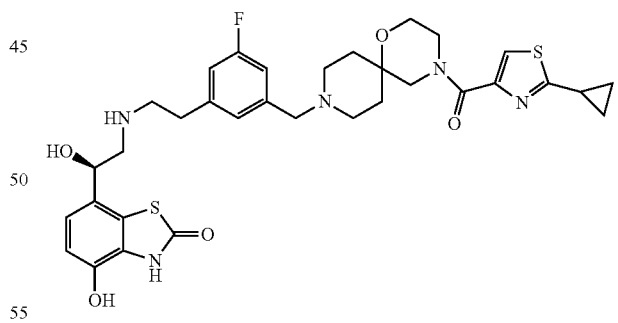

Trifluoroacetic acid (0.025 mL) was added to (2-cyclopropylthiazol-4-yl)(9-(3-fluoro-5-(2-hydroxyethyl)benzyl)-1-oxa-4,9-diazaspiro[5.5]undecan-4-yl)methanone (example 57, step d) (0.15 g) in DCM (5 mL) at 0° C. The mixture was stirred for 5 min then Dess-Martin periodinane (0.21 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL).

The combined organic solutions were washed with brine (20 mL), acidified with a few drops of acetic acid, dried over sodium sulfate, filtered and evaporated in vacuo. The residue was dissolved in methanol (5 mL), acetic acid (0.019 mL) and (R)-7-(2-amino-1-hydroxyethyl)-4-hydroxybenzo[d]thiazol-2(3H)-one hydrochloride (WO2007027134, example 1, step d) (0.13 g) were then added and the mixture stirred for 5 min before cooling in an ice bath. Sodium cyanoborohydride (0.031 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethylether to give the titled compound as a white solid. Yield 0.085 g.

m/z 668 (M+H)$^+$ (APCI)

$^1$H NMR (400 MHz, D$_6$-DMSO, 90° C.) δ 7.81 (s, 1H), 7.28-7.16 (m, 3H), 6.93 (d, J=8.5 Hz, 1H), 6.77 (d, J=8.2 Hz, 1H), 4.97-4.86 (m, 1H), 4.26 (s, 2H), 3.72-3.58 (m, 6H), 3.31-2.99 (m, 10H), 2.06-1.92 (m, 2H), 1.82-1.68 (m, 2H), 1.19-0.90 (m, 4H). One proton obscured by DMSO and six exchangeable protons not observed.

EXAMPLE 58

(R)-7-(2-(3-((4-(2-Cyclobutylthiazole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

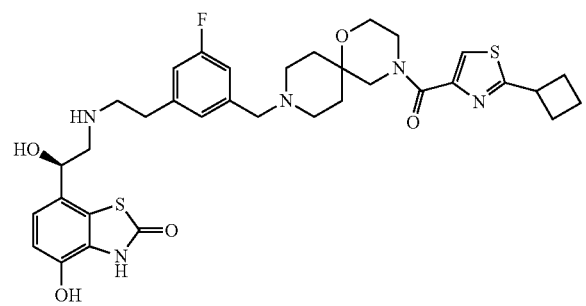 [SMILES: O=C(c1csc(C2CCC2)n1)N1CCOC2(CCN(Cc3cc(F)cc(CCNC[C@H](O)c4ccc(O)c5[nH]c(=O)sc45)c3)CC2)C1]

a) Ethyl 2-(cyclobutanecarboxamido)-3-mercaptopropanoate

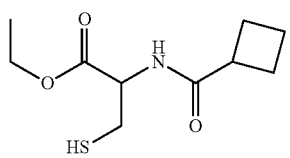

Triethylamine (15 mL) was added to a suspension of cyclobutanecarboxylic acid (2.57 mL) and ethyl 2-amino-3-mercaptopropanoate hydrochloride (5 g) in DMF (40 mL). The resulting mixture was cooled in an ice bath and a solution of T3P (1.57M in THF, 20.6 mL) was added dropwise. The resulting mixture was allowed to warm to RT and stirred overnight. The reaction was quenched with saturated sodium bicarbonate solution (50 mL) and the layers separated. The aqueous phase was extracted with DCM (2×100 mL). The combined organic solutions were washed with brine (100 mL), dried over sodium sulphate, filtered and evaporated. The resulting white solid was purified by silica gel chromatography eluting with 4:1 to 1:1 isohexane:ethyl acetate gradient. The fractions containing product were combined and evaporated to give the subtitled compound as a clear oil. Yield 3.20 g.

m/z 230 (M−H)$^-$ (APCI)

$^1$H NMR (400 MHz, D$_6$-DMSO) δ 8.05 (d, J=7.9 Hz, 1H), 4.41-4.32 (m, 1H), 4.14-4.05 (m, 2H), 2.89-2.68 (m, 2H), 2.21-1.70 (m, 7H), 1.18 (t, J=7.1 Hz, 3H). One exchangeable proton not observed.

b) Ethyl 2-cyclobutylthiazole-4-carboxylate

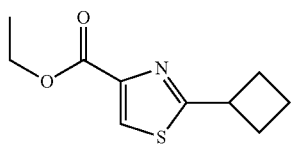

A solution of HCl (4M in 1,4-dioxane, 3.46 mL) was added to a solution of ethyl 2-(cyclobutanecarboxamido)-3-mercaptopropanoate (example 58, step a) (3.2 g) in ethanol (20 mL) and the resulting mixture stirred overnight. The solvent was evaporated and the residue azeotroped twice with toluene. The residue was redissolved in acetonitrile (50 mL), manganese dioxide (12 g) was added and the mixture heated at reflux overnight. The reaction was filtered through a pad of Celite which was then washed with MeCN (3×100 mL). The combined filtrate and washings were evaporated and the residue was purified by silica gel chromatography eluting with 9:1 isohexane:ethyl acetate. The fractions containing product were combined and evaporated to give the subtitled compound as a clear oil. Yield 0.48 g.

$^1$H NMR (400 MHz, CDCl$_3$) δ 8.06 (s, 1H), 4.42 (q, J=7.1 Hz, 2H), 4.00-3.89 (m, 1H), 2.56-2.45 (m, 2H), 2.41-2.29 (m, 2H), 2.16-1.90 (m, 2H), 1.40 (t, J=7.0 Hz, 3H).

c) 2-Cyclobutylthiazole-4-carboxylic acid

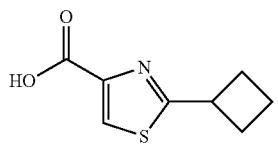 [SMILES: O=C(O)c1csc(C2CCC2)n1]

Lithium hydroxide monohydrate (0.38 g) was added to a solution of ethyl 2-cyclobutylthiazole-4-carboxylate (example 58, step b) (0.48 g) in a mixture of THF (8 mL) and water (2 mL). The resulting suspension was stirred overnight at RT. The reaction was acidified with aqueous HCl solution (2M, 5 mL) and evaporated to dryness. The residue was partitioned between brine (5 mL) and ethyl acetate (20 mL). The layers were separated and the aqueous phase extracted with ethyl acetate (2×20 mL). The combined organic solutions were dried over sodium sulphate, filtered and evaporated to give the subtitled compound as a white solid. Yield 0.38 g.

$^1$H NMR (400 MHz, D$_6$-DMSO) δ 12.91 (s, 1H), 8.32 (s, 1H), 3.94-3.83 (m, 1H), 2.46-2.35 (m, 2H), 2.32-2.21 (m, 2H), 2.09-1.97 (m, 1H), 1.94-1.81 (m, 1H).

d) (2-Cyclobutylthiazol-4-yl)(9-(3-fluoro-5-(2-hydroxyethyl)benzyl)-1-oxa-4,9-diazaspiro[5.5]undecan-4-yl)methanone

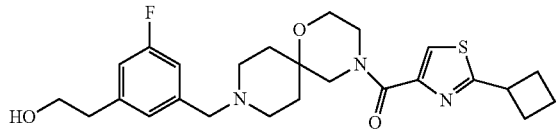 [SMILES: O=C(c1csc(C2CCC2)n1)N1CCOC2(CCN(Cc3cc(F)cc(CCO)c3)CC2)C1]

O-(7-Azabenzotriazol-1-yl)-N,N,N',N'-tetramethyluronium hexafluorophosphate (0.32 g) was added to a solution of 2-(3-(1-oxa-4,9-diazaspiro[5.5]undecan-9-ylmethyl)-5-fluorophenyl)ethanol (example 55, step c) (0.2 g), 2-cyclobutylthiazole-4-carboxylic acid (example 58, step c) (0.12 g) and triethylamine (0.36 mL) in DMF (7 mL) and the resulting yellow solution was stirred for 30 min. The mixture was partitioned between ethyl acetate and brine (100 mL) and the layers separated. The organic phase was washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added and the solvent evaporated to give the subtitled compound as a clear oil. Yield 0.18 g.

$^1$H NMR (400 MHz, D$_6$-DMSO, 90° C.) δ 7.91 (s, 1H), 6.95 (s, 1H), 6.89 (s, 1H), 6.86 (s, 1H), 4.36-4.25 (m, 1H), 3.87 (q, J=8.3 Hz, 1H), 3.70-3.57 (m, 8H), 3.43 (s, 2H), 2.72 (t, J=6.7 Hz, 2H), 2.46-2.26 (m, 8H), 2.11-1.91 (m, 2H), 1.76-1.66 (m, 2H), 1.60-1.51 (m, 2H).

e) (R)-7-(2-(3-((4-(2-Cyclobutylthiazole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

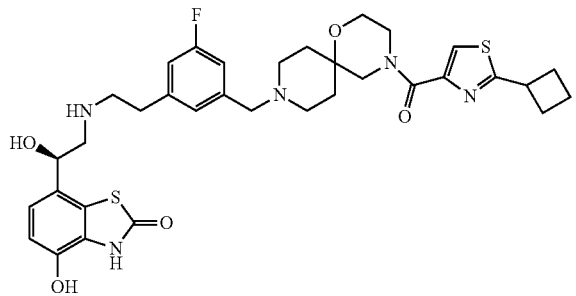 [SMILES: O=C(c1csc(C2CCC2)n1)N1CCOC2(CCN(Cc3cc(F)cc(CCNC[C@H](O)c4ccc(O)c5[nH]c(=O)sc45)c3)CC2)C1]

TFA (0.026 mL) was added to a solution of (2-cyclobutylthiazol-4-yl)(9-(3-fluoro-5-(2-hydroxyethyl)benzyl)-1-oxa-4,9-diazaspiro[5.5]undecan-4-yl)methanone (example 58, step d) (0.16 g) in DCM (5 mL) at 0° C. The mixture was stirred for 5 min then Dess-Martin periodinane (0.22 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.019 mL) and (R)-7-(2-amino-1-hydroxyethyl)-4-hydroxybenzo[d]thiazol-2(3H)-one hydrochloride (WO2007027134, example 1, step d) (0.13 g) were then added and the mixture stirred for 5 min before cooling in an ice bath. Sodium cyanoborohydride (0.032 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethylether to give the titled compound as a white solid. Yield 0.12 g.

m/z 682 (M+H)$^+$ (APCI)

$^1$H NMR (400 MHz, D$_6$-DMSO, 90° C.) δ 11.26 (s, 1H), 7.94 (s, 1H), 7.30-7.17 (m, 3H), 6.93 (d, J=8.2 Hz, 1H), 6.78 (d, J=8.2 Hz, 1H), 4.99-4.89 (m, 1H), 4.35-4.25 (m, 2H), 3.93-3.81 (m, 1H), 3.75-3.62 (m, 6H), 3.32-2.99 (m, 10H), 2.47-2.39 (m, 2H), 2.31-2.20 (m, 2H), 2.10-1.72 (m, 6H). Five exchangeable protons not observed.

EXAMPLE 59

(R)-7-(2-(3-((4-(2-Cyclopentylthiazole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

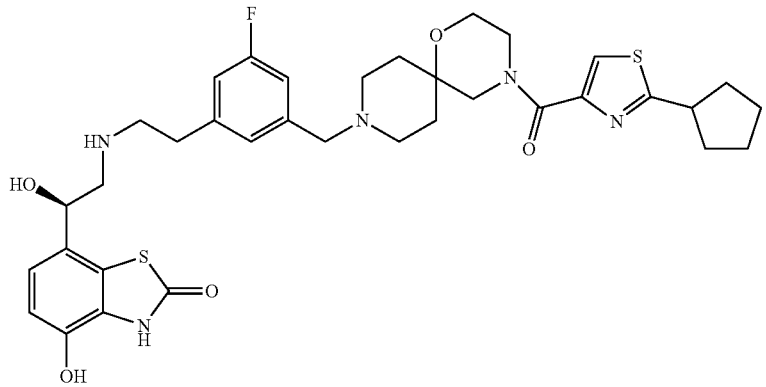 [SMILES: O=C(c1csc(C2CCCC2)n1)N1CCOC2(CCN(Cc3cc(F)cc(CCNC[C@H](O)c4ccc(O)c5[nH]c(=O)sc45)c3)CC2)C1]

a) Ethyl 2-(cyclopentanecarboxamido)-3-mercaptopropanoate

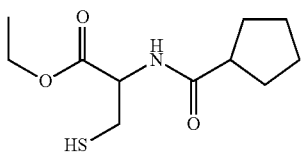

CDI (8.5 g) was added to a solution of cyclopentanecarboxylic acid (5.2 mL) in DMF (40 mL). The resulting mixture was stirred for 1 h and cooled in an ice bath. Ethyl 2-amino-3-mercaptopropanoate hydrochloride (8.88 g) was added, followed by triethylamine (10 mL). The resulting mixture was allowed to warm to RT and stirred overnight. The reaction was quenched with saturated sodium bicarbonate solution (50 mL) and the layers separated. The aqueous was extracted with DCM (2×100 mL). The combined organic solutions were washed with brine (100 mL), dried over sodium sulphate, filtered and evaporated. The resulting solid was purified by silica gel chromatography eluting with 4:1 to 1:1 isohexane:ethyl acetate gradient. The fractions containing product were combined and evaporated to give the subtitled compound as a white solid. Yield 7.7 g.

$^1$H NMR (400 MHz, D$_6$-DMSO) δ 8.15 (d, J=7.7 Hz, 1H), 4.41-4.34 (m, 1H), 4.14-4.05 (m, 2H), 2.89-2.61 (m, 3H), 1.81-1.45 (m, 9H), 1.18 (t, J=7.0 Hz, 3H).

b) Ethyl 2-cyclopentyl-4,5-dihydrothiazole-4-carboxylate

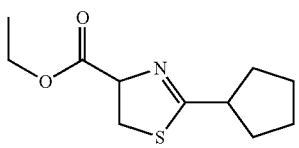

Tosic acid monohydrate (0.78 g) was added to a solution of ethyl 2-(cyclopentanecarboxamido)-3-mercaptopropanoate (example 59, step a) (5 g) in toluene (40 mL). The resulting mixture was heated at reflux under Dean and Stark conditions for 6 h. The reaction was allowed to cool, then the toluene solution was washed with saturated sodium bicarbonate solution (20 mL) and the solvent evaporated. The residue was azeotroped with toluene. The resulting white solid was purified by silica gel chromatography eluting with 9:1 isohexane:ethyl acetate. The fractions containing product were combined and evaporated to give the subtitled compound as a clear oil. Yield 3.2 g.

$^1$H NMR (400 MHz, CDCl$_3$) δ 5.08-4.99 (m, 1H), 4.26 (q, J=7.2 Hz, 2H), 3.56-3.44 (m, 2H), 3.08-2.99 (m, 1H), 2.03-1.93 (m, 2H), 1.83-1.70 (m, 4H), 1.64-1.59 (m, 2H), 1.31 (t, J=7.2 Hz, 3H).

c) Ethyl 2-cyclopentylthiazole-4-carboxylate

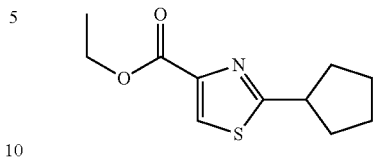

Manganese dioxide (24 g) was added to a solution of ethyl 2-cyclopentyl-4,5-dihydrothiazole-4-carboxylate (example 59, step b) (3.2 g) in acetonitrile (100 mL) and the resulting mixture heated at reflux overnight. The reaction was allowed to cool and filtered through a pad of Celite. The filter pad was washed with acetonitrile (2×100 mL) and the combined filtrate and washings evaporated. The residue was purified by silica gel chromatography eluting with 9:1 isohexane:ethyl acetate. The fractions containing product were combined, evaporated and redissolved in ethanol (20 mL). A slurry of palladium on carbon (5%, 0.66 g) in water (0.5 mL) was added and the resulting suspension stirred under an atmosphere of hydrogen at 5 bar pressure for 2 h. The mixture was filtered through a pad of Celite which was washed with ethanol (3×50 mL). The combined filtrate and washings were evaporated to give the subtitled compound as a clear oil. Yield 0.9 g.

$^1$H NMR (400 MHz, CDCl$_3$) δ 8.04 (s, 1H), 4.41 (q, J=7.2 Hz, 2H), 3.60-3.48 (m, 1H), 2.29-2.18 (m, 2H), 1.89-1.67 (m, 6H), 1.40 (t, J=7.0 Hz, 3H).

d) 2-Cyclopentylthiazole-4-carboxylic acid

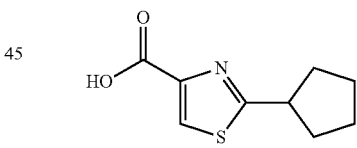

Lithium hydroxide monohydrate (0.67 g) was added to solution of ethyl 2-cyclopentylthiazole-4-carboxylate (example 59, step c) (0.9 g) in a mixture of THF (40 mL) and water (10 mL). The resulting mixture was stirred overnight. The reaction was acidified with aqueous HCl solution (2M, mL) and the solvent evaporated. The residue was partitioned between brine (50 mL) and ethyl acetate (50 mL) and the layers separated. The aqueous phase was extracted with ethyl acetate (2×50 mL). The combined organic solutions were dried over sodium sulphate, filtered and evaporated to give the subtitled compound as a pale yellow solid. Yield 0.77 g.

$^1$H NMR (400 MHz, D$_6$-DMSO) δ 12.89 (s, 1H), 8.30 (s, 1H), 3.51-3.41 (m, 1H), 2.17-2.07 (m, 2H), 1.82-1.59 (m, 6H).

e) (2-Cyclopentylthiazol-4-yl)(9-(3-fluoro-5-(2-hydroxyethyl)benzyl)-1-oxa-4,9-diazaspiro[5.5]undecan-4-yl)methanone

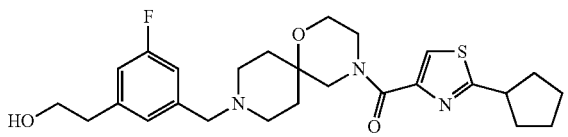 [SMILES: O=C(c1csc(C2CCCC2)n1)N1CCOC2(CCN(Cc3cc(F)cc(CCO)c3)CC2)C1]

O-(7-Azabenzotriazol-1-yl)-N,N,N',N'-tetramethyluronium hexafluorophosphate (0.33 g) was added to a solution of 2-(3-(1-oxa-4,9-diazaspiro[5.5]undecan-9-ylmethyl)-5-fluorophenyl)ethanol (example 55, step c) (0.21 g), 2-cyclopentylthiazole-4-carboxylic acid (example 59, step d) (0.13 g) and triethylamine (0.38 mL) in DMF (7 mL) and the resulting yellow solution was stirred for 30 min. The mixture was partitioned between ethyl acetate and brine (100 mL), the organic phase was washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added and the solvent evaporated under reduced pressure to give the subtitled compound as a clear gum. Yield 0.19 g.

$^1$H NMR (400 MHz, D$_6$-DMSO, 90° C.) δ 7.89 (s, 1H), 6.95 (s, 1H), 6.88 (s, 1H), 6.86 (s, 1H), 4.30 (t, J=5.1 Hz, 1H), 3.69-3.61 (m, 8H), 3.43 (s, 2H), 2.76-2.69 (m, 3H), 2.42-2.28 (m, 4H), 2.18-2.06 (m, 2H), 1.86-1.64 (m, 8H), 1.60-1.49 (m, 2H).

f) (R)-7-(2-(3-((4-(2-Cyclopentylthiazole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate Trifluoroacetinc acid (0.028 mL) was added to a solution of (2-cyclopentylthiazol-4-yl)(9-(3-fluoro-5-(2-hydroxyethyl)benzyl)-1-oxa-4,9-diazaspiro[5.5]undecan-4-yl)methanone (example 59, step e) (0.18 g) in DCM (5 mL) at 0° C. The mixture was stirred for 5 min then Dess-Martin periodinane (0.23 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.021 mL) and (R)-7-(2-amino-1-hydroxyethyl)-4-hydroxybenzo[d]thiazol-2(3H)-one hydrochloride (WO2007027134, example 1, step d) (0.14 g) were then added and the mixture stirred for 5 min before cooling in an ice bath. Sodium cyanoborohydride (0.034 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethylether to give the titled compound as a white solid. Yield 0.7 g.

m/z 696 (M+H)$^+$ (APCI)

$^1$H NMR (400 MHz, D$_6$-DMSO, 90° C.) δ 7.92 (s, 1H), 7.28-7.15 (m, 3H), 6.93 (d, J=8.5 Hz, 1H), 6.77 (d, J=8.2 Hz, 1H), 4.97-4.86 (m, 1H), 4.30-4.20 (m, 2H), 3.74-3.58 (m, 6H), 3.52-3.42 (m, 1H), 3.27 (t, J=7.9 Hz, 2H), 3.19-2.96 (m, 8H), 2.18-1.93 (m, 4H), 1.84-1.59 (m, 8H). Six exchangeable protons not observed.

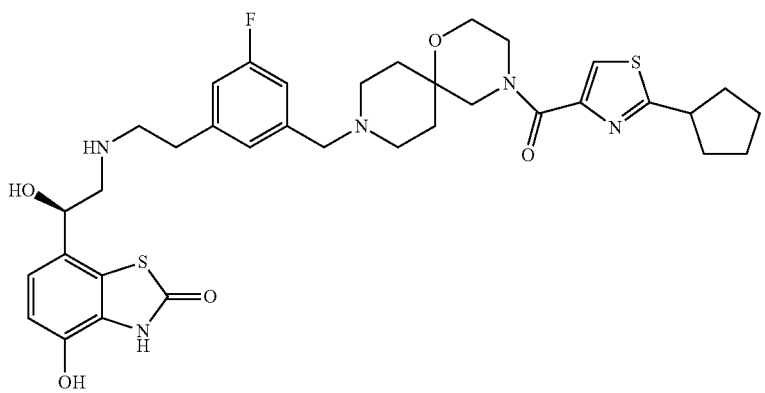 [SMILES: O=C(c1csc(C2CCCC2)n1)N1CCOC2(CCN(Cc3cc(F)cc(CCNC[C@H](O)c4ccc(O)c5[nH]c(=O)sc45)c3)CC2)C1]

EXAMPLE 60

(R)-7-(2-(3-Fluoro-5-((4-(4-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

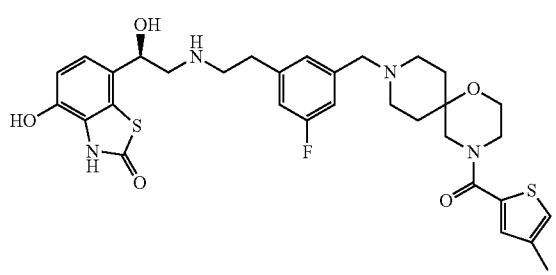 [SMILES: Cc1csc(C(=O)N2CCOC3(CCN(Cc4cc(F)cc(CCNC[C@H](O)c5ccc(O)c6[nH]c(=O)sc56)c4)CC3)C2)c1]

a) (9-(3-Fluoro-5-(2-hydroxyethyl)benzyl)-1-oxa-4,9-diazaspiro[5.5]undecan-4-yl)(4-methylthiophen-2-yl)methanone

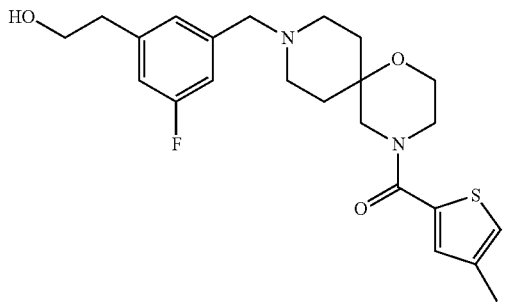 [SMILES: Cc1csc(C(=O)N2CCOC3(CCN(Cc4cc(F)cc(CCO)c4)CC3)C2)c1]

A solution of 2,2,2-trifluoro-1-(9-(3-fluoro-5-(2-hydroxyethyl)benzyl)-1-oxa-4,9-diazaspiro[5.5]undecan-4-yl)ethanone (example 41, step d) (0.17 g) in methanol (3 mL) was added to ammonia (35% aqueous solution, 15 mL) and the reaction mixture stirred at 20° C. for 1 hour. The mixture was evaporated to dryness under reduced pressure and the residue azeotroped three times with acetonitrile. The residue was dissolved in DMF (6 mL) and treated with 4-methylthiophene-2-carboxylic acid (0.060 g) followed by triethylamine (0.176 mL) and then HATU (0.208 g) and the resultant mixture stirred at 20° C. for 1 hour. The mixture was partitioned between ethyl acetate and brine, the organic layer was washed twice with brine, dried over sodium sulphate, filtered and the solvent evaporated under reduced pressure. The crude product was purified by flash silica chromatography using 2.5% methanol in dichloromethane with 1% triethylamine as solvent. Pure fractions were evaporated to dryness to afford the subtitled compound. Yield 0.120 g.

m/z 433 (M+H)+ (APCI)

b) (R)-7-(2-(3-Fluoro-5-((4-(4-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

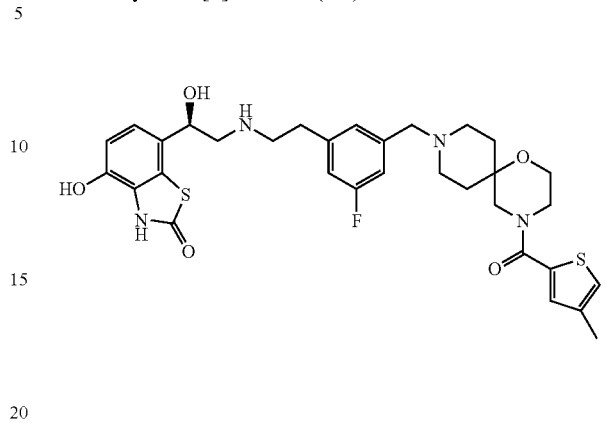

A solution of (9-(3-fluoro-5-(2-hydroxyethyl)benzyl)-1-oxa-4,9-diazaspiro[5.5]undecan-4-yl)(4-methylthiophen-2-yl)methanone (example 60, step a) (0.120 g) in DCM (20 mL) was treated with trifluoroacetic acid (0.021 ml) followed by Dess Martin periodinane (0.153 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.016 ml) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.109 g) and acetic acid (0.016 ml) in methanol (15 mL). The mixture was cooled in an ice bath and treated with sodium cyanoborohydride (0.035 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.075 g.

m/z 641 (M+H)+ (APCI)

$^1$H NMR (400 MHz, D$_6$-DMSO, 90° C.) δ 7.30-7.17 (m, 5H), 6.93 (d, J=8.2 Hz, 1H), 6.77 (d, J=8.5 Hz, 1H), 4.94-4.89 (m, 1H), 4.27 (s, 2H), 3.73-3.69 (m, 2H), 3.67-3.63 (m, 2H), 3.54 (s, 2H), 3.27 (t, J=7.9 Hz, 2H), 3.19-2.99 (m, 8H), 2.22 (s, 3H), 2.05-1.97 (m, 2H), 1.82-1.71 (m, 2H). Six exchangeable protons not observed.

EXAMPLE 61

(R)-7-(2-(4-Chloro-3-((4-(2-isopropylthiazazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

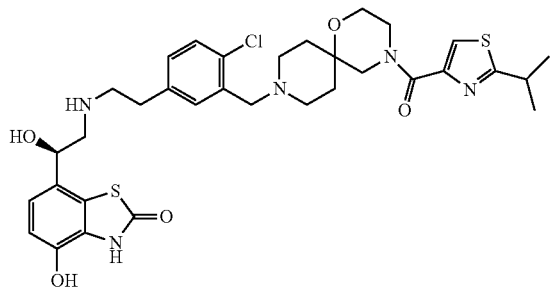 [SMILES: CC(C)c1nc(C(=O)N2CCOC3(CCN(Cc4cc(CCNC[C@H](O)c5ccc(O)c6[nH]c(=O)sc56)ccc4Cl)CC3)C2)cs1]

a) 5-(Carboxymethyl)-2-chlorobenzoic acid

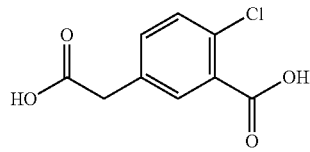 [SMILES: O=C(O)Cc1ccc(Cl)c(C(=O)O)c1]

Potassium hydroxide (0.969 g) in water (10 mL) was added to a solution of 2-chloro-5-(cyanomethyl)benzoic acid (1.25 g) in ethanol (10 mL) and the resulting mixture was heated at reflux for 2.25 hours, then allowed to cool. The mixture was concentrated in vacuo to remove the ethanol and then diluted with water and washed twice with ethyl acetate. The organic phases were discarded, whilst the aqueous phase was acidified to pH 1 with concentrated hydrochloric acid and extracted twice with ethyl acetate. The combined extracts were dried over anhydrous magnesium sulphate and concentrated in vacuo to afford the subtitled compound as a brown gum. Yield 1.38 g.

$^1$H NMR (400 MHz, D$_6$-DMSO) δ 12.93 (br s, 2H), 7.69 (d, J=2.1 Hz, 1H), 7.48 (d, J=8.3 Hz, 1H), 7.42 (dd, J=8.3, 2.2 Hz, 1H), 3.66 (s, 2H).

b) 2-(4-Chloro-3-(hydroxymethyl)phenyl)ethanol

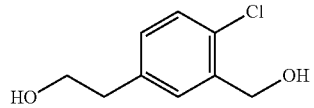

A solution of borane-methyl sulfide complex (2M in THF, 6.50 mL) was added portionwise over 5 minutes to a solution of 5-(carboxymethyl)-2-chlorobenzoic acid (example 61, step a) (1.37 g) in dry THF (20 mL) at room temperature. The resulting effervescing solution was stirred at room temperature for 1.5 hours, then heated to reflux for 1 hour. The cooled mixture was quenched by the portionwise addition of methanol (5 mL) over 5 minutes. The solution was stirred at room temperature for 2 hours and then purified by flash chromatography on silica eluted with 5% methanol in dichloromethane to afford the subtitled compound as a colourless oil. Yield 0.933 g.

$^1$H NMR (400 MHz, CDCl$_3$) δ 7.36 (d, J=2.1 Hz, 1H), 7.30 (d, J=7.9 Hz, 1H), 7.11 (dd, J=8.1, 2.2 Hz, 1H), 4.77 (s, 2H), 3.87 (t, J=6.5 Hz, 2H), 2.86 (t, J=6.5 Hz, 2H). Two exchangeable protons not observed.

c) 2-Chloro-5-(2-hydroxyethyl)benzaldehyde

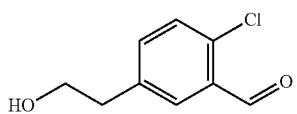

Manganese (IV) dioxide (1.00 g) was added to a solution of 2-(4-chloro-3-(hydroxymethyl)phenyl)ethanol (example 61, step b) (0.200 g) in DCM (5 mL), and the resulting suspension was stirred at room temperature overnight. The mixture was then filtered through Celite, washing the residue well with DCM. The filtrate and washings were concentrated in vacuo to afford the subtitled compound as a colourless oil. Yield 0.197 g.

$^1$H NMR (400 MHz, CDCl$_3$) δ 10.47 (s, 1H), 7.80 (d, J=2.1 Hz, 1H), 7.42 (d, J=2.1 Hz, 1H), 7.41 (s, 1H), 3.89 (br t, J=5.9 Hz, 2H), 2.90 (t, J=6.4 Hz, 2H), 1.42 (br s, 1H).

d) (9-(2-Chloro-5-(2-hydroxyethyl)benzyl)-1-oxa-4,9-diazaspiro[5.5]undecan-4-yl)(2-isopropylthiazol-4-yl)methanone

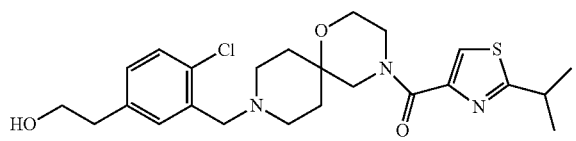 [SMILES: CC(C)c1nc(C(=O)N2CCOC3(CCN(Cc4cc(CCO)ccc4Cl)CC3)C2)cs1]

A solution of (2-isopropylthiazol-4-yl)(1-oxa-4,9-diazaspiro[5.5]undecan-4-yl)methanone trifluoroacetate (example 22, step b) (0.294 g) in NMP (2 mL) was treated with acetic acid (0.039 mL) and stirred for 5 minutes. A solution of 2-chloro-5-(2-hydroxyethyl)benzaldehyde (example 61, step c) (0.189 g) in NMP (3 mL) was then added, the resulting solution was stirred for 1 hour and was then treated with sodium triacetoxyborohydride (0.217 g). The mixture was stirred overnight at room temperature, then poured into saturated sodium bicarbonate and extracted twice with ethyl acetate. The combined extracts were washed three times with water, once with brine, then dried over anhydrous magnesium sulphate and purified by flash chromatography on silica eluted with 1:2:97 triethylamine:methanol:dichloromethane to afford the subtitled compound as a colourless gum. Yield 0.238 g.

$^1$H NMR (400 MHz, D$_6$-DMSO, 90° C.) δ 7.91 (s, 1H), 7.29 (d, J=1.8 Hz, 1H), 7.25 (d, J=8.2 Hz, 1H), 7.09 (dd, J=8.2, 2.1 Hz, 1H), 4.29 (t, J=5.1 Hz, 1H), 3.70-3.59 (m, 8H), 3.51 (s, 2H), 3.32 (septet, J=6.9 Hz, 1H), 2.71 (t, J=6.8 Hz, 2H), 2.45-2.29 (m, 4H), 1.75-1.66 (m, 2H), 1.60-1.51 (m, 2H), 1.36 (d, J=6.7 Hz, 6H).

e) 2-(4-Chloro-3-((4-(2-isopropylthiazole-4-carbonyl)-1-oxa-4,9-diazaspiro[5.5]undecan-9-yl)methyl)phenyl)acetaldehyde

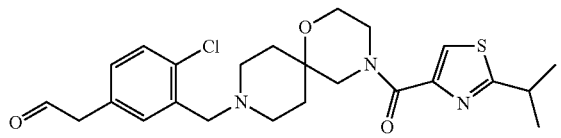 [SMILES: CC(C)c1nc(C(=O)N2CCOC3(CCN(Cc4cc(CC=O)ccc4Cl)CC3)C2)cs1]

A solution of (9-(2-chloro-5-(2-hydroxyethyl)benzyl)-1-oxa-4,9-diazaspiro[5.5]undecan-4-yl)(2-isopropylthiazol-4-yl)methanone (example 61, step d) (0.230 g) in DCM (5 mL) was cooled in ice-water, treated with trifluoroacetic acid (0.074 mL) and stirred for 5 minutes. Dess-Martin periodinane (0.313 g) was added, then the mixture was removed from the cooling bath and stirred at room temperature for 40 minutes. The solution was diluted with saturated sodium thiosulphate solution (5 mL), saturated sodium bicarbonate solution (5 mL) and ethyl acetate (5 mL) and the resulting mixture was stirred vigorously for 10 minutes. The mixture was then extracted twice with ethyl acetate, the combined organic phases were washed with brine, acidified with acetic acid (0.1 mL), dried over anhydrous magnesium sulphate and concentrated in vacuo to give the crude subtitled compound as a yellow foam. Yield 0.274 g.

m/z 476 (M+H)$^+$ (APCI)

f) (R)-7-(2-(4-Chloro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

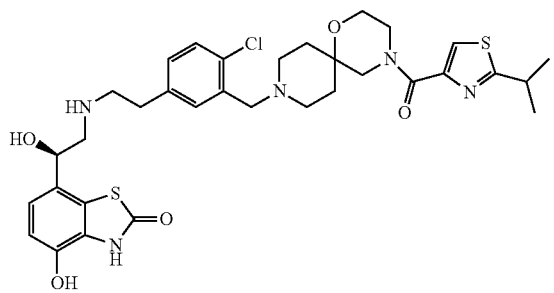 [SMILES: CC(C)c1nc(C(=O)N2CCOC3(CCN(Cc4cc(CCNC[C@H](O)c5ccc(O)c6[nH]c(=O)sc56)ccc4Cl)CC3)C2)cs1]

A solution of (R)-7-(2-amino-1-hydroxyethyl)-4-hydroxybenzo[d]thiazol-2(3H)-one hydrochloride (WO2007027134, example 1, step d) (0.225 g) in methanol (3 mL) was treated with acetic acid (0.029 mL) and stirred for 5 minutes. A solution of 2-(4-chloro-3-((4-(2-isopropylthiazole-4-carbonyl)-1-oxa-4,9-diazaspiro[5.5]undecan-9-yl)methyl)phenyl)acetaldehyde (example 61, step e) (0.274 g) in methanol (4 mL) was then added, and the resulting mixture was stirred at room temperature for 5 minutes, before cooling in ice-water and treating with sodium cyanoborohydride (0.051 g). The cooling bath was removed and the mixture was stirred at room temperature for 140 minutes, before treating with more sodium cyanoborohydride (0.055 g). The mixture was then stirred overnight. The following morning the mixture was concentrated in vacuo. The residue was dissolved in a mixture of methanol (1.5 mL), acetonitrile (1.5 mL) and water (1.5 mL) and purified by preparative HPLC (Sunfire™, Gradient: 5-50% acetonitrile in 0.2% aqueous TFA). Fractions containing product were concentrated in vacuo and co-evaporated from acetonitrile three times to give a colourless residue. The residue was triturated with diethyl ether to give a solid, which was collected by filtration, washed with diethyl ether and dried in vacuo at room temperature to afford the titled compound as a white solid. Yield 0.062 g.

m/z 686 (M+H)$^+$ (APCI)

$^1$H NMR (400 MHz, D$_6$-DMSO, 90° C.) δ 7.93 (s, 1H), 7.52-7.43 (m, 2H), 7.35-7.26 (m, 1H), 6.93 (d, J=8.5 Hz, 1H), 6.77 (d, J=8.5 Hz, 1H), 4.89 (dd, J=7.8, 5.5 Hz, 1H), 3.76-3.60 (m, 6H), 3.36-3.16 (m, 3H), 3.15-2.83 (m, 8H), 2.02-1.84 (m, 2H), 1.80-1.63 (m, 2H), 1.35 (d, J=6.9 Hz, 6H). One methylene (two protons) very broad and six exchangeable protons not observed.

EXAMPLE 62

(R)-4-Hydroxy-7-(1-hydroxy-2-((5-((4-(2-isopropylthiazole-4-carbonyl)-1-oxa-4,9-diazaspiro[5.5]undecan-9-yl)methyl)naphthalen-1-yl)methylamino)ethyl)benzo[d]thiazol-2(3H)-one ditrifluoroacetate

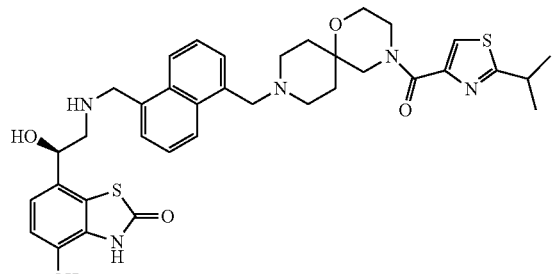

a) (9-((5-(Bromomethyl)naphthalen-1-yl)methyl)-1-oxa-4,9-diazaspiro[5.5]undecan-4-yl)(2-isopropylthiazol-4-yl)methanone

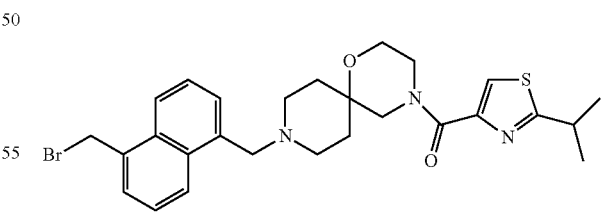

Triethylamine (0.185 mL) was added to a suspension of (2-isopropylthiazol-4-yl)(1-oxa-4,9-diazaspiro[5.5]undecan-4-yl)methanone trifluoroacetate (example 22, step b) (0.225 g) in acetonitrile (5 mL) to give a colourless solution that was stirred at room temperature overnight, then concentrated in vacuo. The residue was dissolved in NMP (5 mL) and treated with more triethylamine (0.111 mL). Meanwhile, a suspension of 1,5-bis(bromomethyl)naphthalene (0.500 g) in acetonitrile (5 mL) and NMP (5 mL) was stirred at room temperature overnight, then concentrated in vacuo to remove the acetonitrile to give a solution. The solution of amine from above was then added dropwise over 35 minutes, completing the addition with more NMP (1 mL). The resulting solution was stirred for 75 minutes, then poured into water and extracted three times with diethyl ether. The combined extracts were washed three times with water, and once with brine, then dried over anhydrous magnesium sulphate and purified by flash chromatography on silica eluted with triethylamine:dichloromethane:ethyl acetate (1:49:50) to afford the subtitled compound as a white foam. Yield 0.132 g.

m/z 542/544 (M+H)⁺ (APCI)

b) (R)-4-Hydroxy-7-(1-hydroxy-2-((5-((4-(2-isopropylthiazole-4-carbonyl)-1-oxa-4,9-diazaspiro[5.5]undecan-9-yl)methyl)naphthalen-1-yl)methylamino)ethyl)benzo[d]thiazol-2(3H)-one ditrifluoroacetate

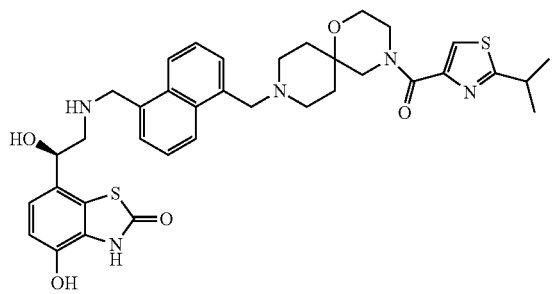 [SMILES: CC(C)c1nc(C(=O)N2CCOC3(CCN(Cc4cccc5c(CNC[C@H](O)c6ccc(O)c7[nH]c(=O)sc67)cccc45)CC3)C2)cs1]

Triethylamine (0.16 mL) was added to a solution of (R)-7-(2-amino-1-hydroxyethyl)-4-hydroxybenzo[d]thiazol-2(3H)-one hydrochloride (WO2007027134, example 1, step d) (0.188 g) in methanol (5 mL) to give a suspension, which was concentrated in vacuo and re-dissolved in NMP (4 mL). More triethylamine (0.16 mL) was added, together with a solution of (9-((5-(bromomethyl)naphthalen-1-yl)methyl)-1-oxa-4,9-diazaspiro[5.5]undecan-4-yl)(2-isopropylthiazol-4-yl)methanone (example 62, step a) (0.126 g) in NMP (3 mL), added dropwise over 30 minutes, completing the addition with more NMP (1 mL). The resulting solution was stirred at room temperature overnight. The solution was then filtered, acidified with trifluoroacetic acid (0.27 mL) and purified by preparative HPLC (Sunfire™, Gradient: 5-50% acetonitrile in 0.2% aqueous TFA). Fractions containing product were concentrated in vacuo and co-evaporated from acetonitrile once and methanol twice. The residue was triturated with diethyl ether to give a solid, which was removed by filtration, washed with diethyl ether and dried in vacuo at room temperature to afford the titled compound as a pale yellow solid. Yield 0.056 g.

m/z 688 (M+H)⁺ (APCI)

¹H NMR (400 MHz, D₆-DMSO, 90° C.) δ 8.42 (d, J=8.2 Hz, 1H), 8.31 (br d, J=8.4 Hz, 1H), 7.93 (s, 1H), 7.87-7.61 (m, 4H), 6.93 (d, J=8.5 Hz, 1H), 6.76 (d, J=8.2 Hz, 1H), 5.00-4.94 (m, 1H), 4.75 (dd, J=23.6, 14.1 Hz, 2H), 3.80-3.56 (m, 6H), 3.45-2.99 (m, 9H), 2.08-1.87 (m, 2H), 1.81-1.58 (m, 2H), 1.35 (d, J=6.9 Hz, 6H). Six exchangeable protons not observed.

EXAMPLE 63

(R)-7-(2-(3-Fluoro-5-((4-(5-methylthiophen-2-ylsulfonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

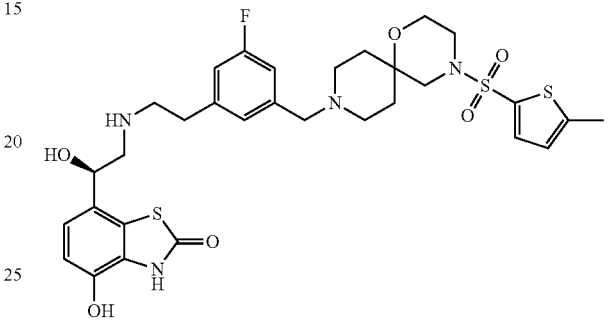

a) 2-(3-Fluoro-5-((4-(5-methylthiophen-2-ylsulfonyl)-1-oxa-4,9-diazaspiro[5.5]undecan-9-yl)methyl)phenyl)ethanol

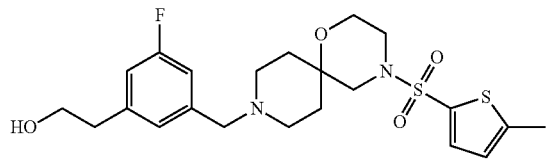 [SMILES: Cc1ccc(S(=O)(=O)N2CCOC3(CCN(Cc4cc(F)cc(CCO)c4)CC3)C2)s1]

A solution of 5-methylthiophene-2-sulfonyl chloride (0.15 g) in DCM (3 mL) was added dropwise to a solution of 2-(3-(1-oxa-4,9-diazaspiro[5.5]undecan-9-ylmethyl)-5-fluorophenyl)ethanol (example 55, step c) (0.21 g) and N-ethyl-N-isopropylpropan-2-amine (0.14 mL) in DCM (20 mL). The resulting mixture was stirred for 1 h and the solvent evaporated. The residue was partitioned between ethyl acetate (50 mL) and saturated sodium hydrogen carbonate solution (50 mL). The layers were separated and the aqueous extracted with ethyl acetate (2×50 mL). The combined organics were washed with brine (50 mL), dried over sodium sulphate, filtered and evaporated. The residue was purified by silica gel chromatography eluting with 47.5:47.5:5 ethyl acetate:isohexane:triethylamine to 95:5 ethyl acetate:triethylamine gradient. The fractions containing product were combined and evaporated to give the subtitled compound as a yellow gum. Yield 0.21 g.

¹H NMR (400 MHz, D₆-DMSO, 90° C.) δ 7.46 (d, J=3.6 Hz, 1H), 7.02 (dd, J=3.6, 1.0 Hz, 1H), 6.97 (s, 1H), 6.94 (s, 1H), 6.91 (s, 1H), 4.64 (t, J=5.1 Hz, 1H), 3.73-3.67 (m, 2H), 3.63-3.57 (m, 2H), 3.44 (s, 2H), 2.88-2.83 (m, 2H), 2.74-2.69 (m, 4H), 2.53 (s, 3H), 2.44-2.35 (m, 2H), 2.31-2.22 (m, 2H), 1.80-1.72 (m, 2H), 1.60-1.51 (m, 2H)

b) (R)-7-(2-(3-Fluoro-5-((4-(5-methylthiophen-2-ylsulfonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

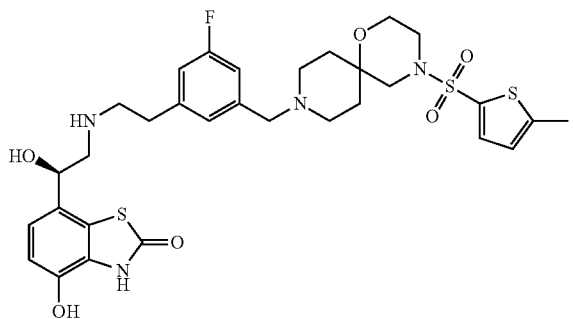 [SMILES: Cc1ccc(S(=O)(=O)N2CCOC3(CCN(Cc4cc(F)cc(CCNC[C@H](O)c5ccc(O)c6[nH]c(=O)sc56)c4)CC3)C2)s1]

TFA (0.033 mL) was added to a solution of 2-(3-fluoro-5-((4-(5-methylthiophen-2-ylsulfonyl)-1-oxa-4,9-diazaspiro[5.5]undecan-9-yl)methyl)phenyl)ethanol (example 63, step a) (0.2 g) in DCM (5 mL) at 0° C. The mixture was stirred for 5 min then Dess-Martin periodinane (0.27 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.024 mL) and (R)-7-(2-amino-1-hydroxyethyl)-4-hydroxybenzo[d]thiazol-2(3H)-one hydrochloride (WO2007027134, example 1, step d) (0.17 g) were then added and the mixture stirred for 5 min before cooling in an ice bath. Sodium cyanoborohydride (0.04 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethylether to give the titled compound as a white solid. Yield 0.7 g.

m/z 677 (M+H)$^+$ (APCI)

$^1$H NMR (400 MHz, D$_6$-DMSO, 90° C.) δ 7.43 (d, J=3.7 Hz, 1H), 7.30-7.16 (m, 3H), 7.00-6.96 (m, 1H), 6.93 (d, J=8.5 Hz, 1H), 6.78 (d, J=8.3 Hz, 1H), 4.92 (dd, J=7.9, 5.4 Hz, 1H), 4.29 (s, 2H), 3.79-3.71 (m, 2H), 3.32-3.23 (m, 2H), 3.17-2.93 (m, 10H), 2.85 (s, 2H), 2.53 (s, 3H), 2.13-2.02 (m, 2H), 1.90-1.74 (m, 2H). Six exchangeable protons not observed.

EXAMPLE 64

(R)-4-Hydroxy-7-(1-hydroxy-2-(2-(3-((4-(2-isopropylthiazole-4-carbonyl)-1-oxa-4,9-diazaspiro[5.5]undecan-9-yl)methyl)phenoxy)ethylamino)ethyl)benzo[d]thiazol-2(3H)-one ditrifluoroacetate

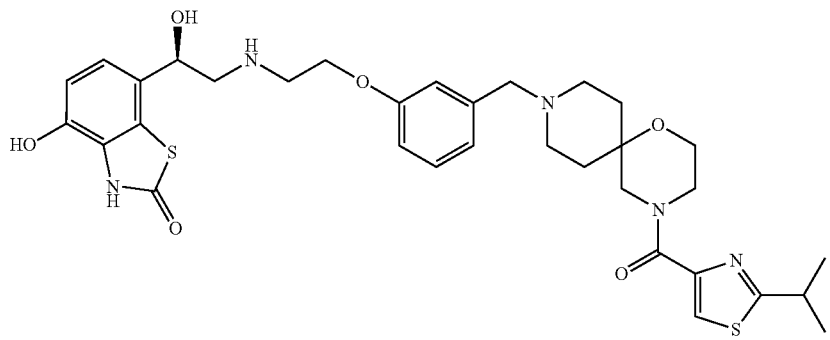 [SMILES: CC(C)c1nc(C(=O)N2CCOC3(CCN(Cc4cccc(OCCNC[C@H](O)c5ccc(O)c6[nH]c(=O)sc56)c4)CC3)C2)cs1]

a) (9-(3-(2,2-Diethoxyethoxy)benzyl)-1-oxa-4,9-diazaspiro[5.5]undecan-4-yl)(2-isopropylthiazol-4-yl)methanone

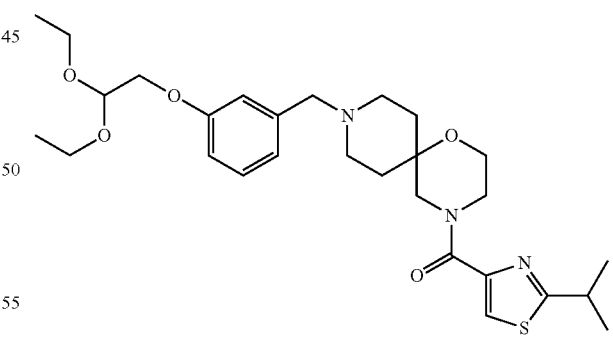

Methanesulfonyl chloride (0.110 mL) was added dropwise to a stirred solution at 0° C. of (3-(2,2-diethoxyethoxy)phenyl)methanol (example 38, step a) (0.307 g) and triethylamine (0.196 mL) in DCM (30 mL). The resultant mixture was stirred at 20° C. for 1 hour. The mixture was washed with water and the organic layer was dried over sodium sulphate, filtered and the solvent evaporated under reduced pressure. The residue was dissolved in acetonitrile (30 mL) and treated with triethylamine (1 mL) followed by (2-isopropylthiazol- 4-yl)(1-oxa-4,9-diazaspiro[5.5]undecan-4-yl)methanone trifluoroacetate (example 22, step b) (0.400 g). The mixture was stirred at 20° C. for 2 hours. The solvent was removed under reduced pressure and the residue partitioned between ethyl acetate and brine. The organic layer was dried over sodium sulphate, filtered and the solvent removed under reduced pressure. The crude product was purified by flash silica chromatography using 2.5% methanol in dichloromethane with 1% triethylamine as solvent. Pure fractions were evaporated to dryness to afford the subtitled compound. Yield 0.360 g.

m/z 532 (M+H)+ (APCI)

b) 2-(3-((4-(2-Isopropylthiazole-4-carbonyl)-1-oxa-4,9-diazaspiro[5.5]undecan-9-yl)methyl)phenoxy)acetaldehyde

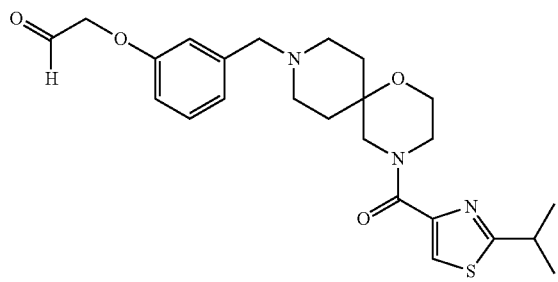 [SMILES: CC(C)c1nc(C(=O)N2CCOC3(CCN(Cc4cccc(OCC=O)c4)CC3)C2)cs1]

A solution of (9-(3-(2,2-diethoxyethoxy)benzyl)-1-oxa-4,9-diazaspiro[5.5]undecan-4-yl)(2-isopropylthiazol-4-yl)methanone (example 64, step a) (0.36 g) in acetic acid (20 mL) was treated with water (20 mL) and the reaction mixture then heated at 65° C. for 18 hours under nitrogen. The solvents were evaporated under reduced pressure and the residue was azeotroped with toluene to afford the subtitled compound. Yield 0.31 g. Used directly.

c) (R)-4-Hydroxy-7-(1-hydroxy-2-(2-(3-((4-(2-isopropylthiazole-4-carbonyl)-1-oxa-4,9-diazaspiro[5.5]undecan-9-yl)methyl)phenoxy)ethylamino)ethyl)benzo[d]thiazol-2(3H)-one ditrifluoroacetate A solution of 2-(3-((4-(2-isopropylthiazole-4-carbonyl)-1-oxa-4,9-diazaspiro[5.5]undecan-9-yl)methyl)phenoxy)acetaldehyde (example 64, step b) (0.31 g) in methanol (10 mL) was treated with (R)-7-(2-amino-1-hydroxyethyl)-4-hydroxybenzo[d]thiazol-2(3H)-one hydrochloride (WO2007027134, example 1, step d) (0.267 g) followed by acetic acid (0.039 mL) and the mixture cooled in an ice bath. Sodium cyanoborohydride (0.085 g) was added and the mixture stirred at room temperature for 4 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.2 g.

m/z 668 (M+H)+ (APCI)

$^1$H NMR (400 MHz, D$_6$-DMSO, 90° C.) δ 11.27 (s, 1H), 7.94 (s, 1H), 7.39 (t, J=8.0 Hz, 1H), 7.16-7.13 (m, 2H), 7.09-7.05 (m, 1H), 6.94 (d, J=8.5 Hz, 1H), 6.78 (d, J=8.2 Hz, 1H), 4.98-4.93 (m, 1H), 4.36-4.28 (m, 4H), 3.70 (s, 4H), 3.65 (s, 2H), 3.47-3.42 (m, 2H), 3.34-3.26 (m, 1H), 3.23-3.05 (m, 6H), 2.09-1.98 (m, 2H), 1.84-1.71 (m, 2H), 1.35 (d, J=7.1 Hz, 6H). Five exchangeable protons not observed.

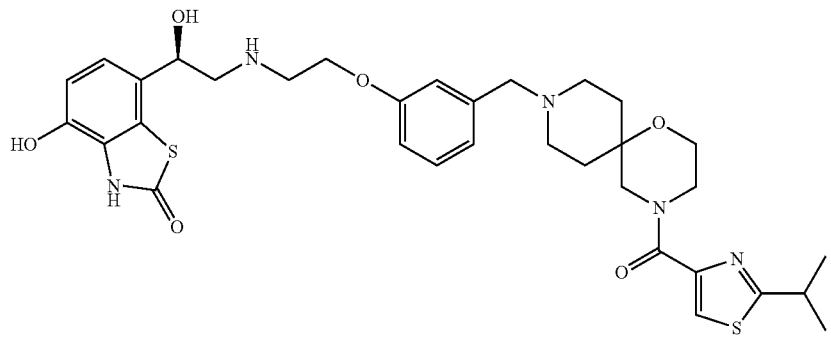 [SMILES: CC(C)c1nc(C(=O)N2CCOC3(CCN(Cc4cccc(OCCNC[C@H](O)c5ccc(O)c6[nH]c(=O)sc56)c4)CC3)C2)cs1]

EXAMPLE 65

(R)-4-Hydroxy-7-(1-hydroxy-2-(2-(3-((4-(2-isopropylthiazole-4-carbonyl)-1-oxa-4,9-diazaspiro[5.5]undecan-9-yl)methyl)phenylthio)ethylamino)ethyl)benzo[d]thiazol-2(3H)-one ditrifluoroacetate

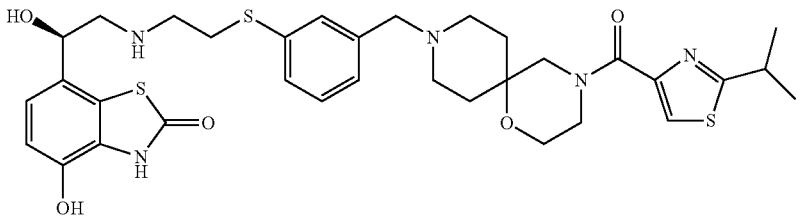 [SMILES: CC(C)c1nc(C(=O)N2CCOC3(CCN(Cc4cccc(SCCNC[C@H](O)c5ccc(O)c6[nH]c(=O)sc56)c4)CC3)C2)cs1]

a) 3-(2-(tert-Butyldimethylsilyloxy)ethylthio)benzoic acid

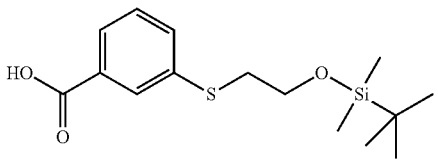 [SMILES: CC(C)(C)[Si](C)(C)OCCSc1cccc(C(=O)O)c1]

(2-Bromoethoxy)(tert-butyl)dimethylsilane (1.48 mL) was added dropwise to a suspension of 3-mercaptobenzoic acid (1.07 g) and potassium carbonate (1.91 g) in DMF (15 mL). The resulting suspension was stirred for 2 h. The reaction was carefully acidified by dropwise addition of aqueous HCl solution (2M, 10 mL) and poured into water (100 mL). The resulting aqueous was extracted with ethyl acetate (3×100 mL). The combined organics were washed with brine (50 mL), dried over sodium sulphate, filtered and evaporated to give the subtitled compound as a clear oil. Yield 2.8 g.

$^1$H NMR (400 MHz, D$_6$-DMSO) δ 13.11 (s, 1H), 7.89 (t, J=1.7 Hz, 1H), 7.79-7.74 (m, 1H), 7.66-7.61 (m, 1H), 7.47 (t, J=7.7 Hz, 1H), 3.82 (t, J=6.4 Hz, 2H), 3.19 (t, J=6.4 Hz, 2H), 0.87 (s, 9H), 0.05 (s, 6H).

b) 2-(3-(Hydroxymethyl)phenylthio)ethanol

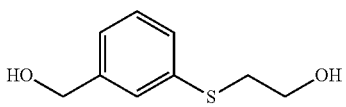

Borane dimethyl sulfide complex (2M in THF, 17.3 mL) was added dropwise to an ice cold solution of 3-(2-(tert-butyldimethylsilyloxy)ethylthio)benzoic acid (example 65, step a) (2.16 g) in THF (50 mL). The reaction was allowed to warm to RT, then heated at reflux for 2 h. The reaction was cooled in an ice bath and aqueous HCl solution (2M, 50 mL) was added dropwise. The resulting mixture was stirred overnight. The reaction was concentrated to half its original volume and the resulting aqueous extracted with DCM (3×100 mL). The combined organics were washed with brine (100 mL), dried over sodium sulphate, filtered and evaporated. The residue was purified by silica gel chromatography eluting with 4:1 isohexane:ethyl acetate to 100% ethyl acetate gradient. The fractions containing product were combined and evaporated to give the subtitled compound as a clear oil. Yield 0.77 g.

$^1$H NMR (400 MHz, D$_6$-DMSO) δ 7.29-7.23 (m, 2H), 7.21-7.17 (m, 1H), 7.13-7.09 (m, 1H), 5.20 (t, J=5.8 Hz, 1H), 4.92 (t, J=5.6 Hz, 1H), 4.47 (d, J=5.9 Hz, 2H), 3.59-3.53 (m, 2H), 3.02 (t, J=6.9 Hz, 2H).

c) 3-(2-Hydroxyethylthio)benzaldehyde

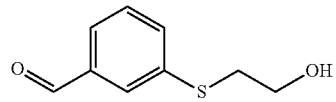 [SMILES: O=Cc1cccc(SCCO)c1]

Manganese dioxide (1.36 g) was added to a solution of 2-(3-(hydroxymethyl)phenylthio)ethanol (example 65, step b) (0.29 g) in DCM (10 mL). The resulting mixture was heated at reflux for 4 h, cooled and filtered through Celite. The filter pad was washed with DCM (3×20 mL). The filtrate and washing were combined and evaporated to give the subtitled compound as a yellow gum. Yield 0.2 g.

$^1$H NMR (400 MHz, D$_6$-DMSO) δ 9.99 (s, 1H), 7.84 (s, 1H), 7.71-7.64 (m, 2H), 7.54 (t, J=7.7 Hz, 1H), 4.99 (t, J=5.6 Hz, 1H), 3.64-3.57 (m, 2H), 3.13 (t, J=6.7 Hz, 2H).

d) (9-(3-(2-hydroxyethylthio)benzyl)-1-oxa-4,9-diazaspiro[5.5]undecan-4-yl)(2-isopropylthiazol-4-yl)methanone

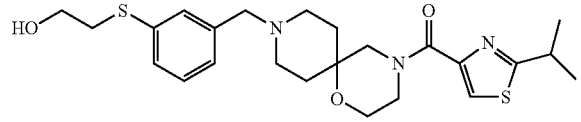 [SMILES: CC(C)c1nc(C(=O)N2CCOC3(CCN(Cc4cccc(SCCO)c4)CC3)C2)cs1]

3-(2-Hydroxyethylthio)benzaldehyde (example 65, step c) (0.16 g) was added to a solution of (2-isopropylthiazol-4-yl)

(1-oxa-4,9-diazaspiro[5.5]undecan-4-yl)methanone trifluoroacetate (example 22, step b) (0.25 g) and acetic acid (0.046 mL) in N-methyl-2-pyrrolidinone (5 mL) and the resulting mixture was stirred for 1 h and cooled in an ice bath. Sodium triacetoxyborohydride (0.26 g) was then added and the mixture allowed to warm to RT and stirred overnight. The reaction was poured into a mixture of sodium bicarbonate solution (20 mL) and water (80 mL). The aqueous phase was extracted with ether (3×100 mL). The combined organic solutions were washed with brine (100 mL), dried over sodium sulphate, filtered and evaporated. The crude product was purified by silica gel chromatography eluting with 95:5 ethyl acetate:triethylamine. The fractions containing product were combined and evaporated to give the subtitled compound as a yellow oil. Yield 0.22 g.

$^1$H NMR (400 MHz, D$_6$-DMSO, 90° C.) δ 7.94-7.83 (m, 1H), 7.28-7.18 (m, 3H), 7.12-7.05 (m, 1H), 4.61-4.53 (m, 1H), 3.70-3.54 (m, 8H), 3.47-3.39 (m, 2H), 3.37-3.27 (m, 1H), 3.06-2.96 (m, 2H), 2.42-2.25 (m, 4H), 1.75-1.65 (m, 2H), 1.59-1.50 (m, 2H), 1.41-1.32 (m, 6H).

e) (R)-4-Hydroxy-7-(1-hydroxy-2-(2-(3-((4-(2-isopropylthiazole-4-carbonyl)-1-oxa-4,9-diazaspiro[5.5]undecan-9-yl)methyl)phenylthio)ethylamino)ethyl)benzo[d]thiazol-2(3H)-one ditrifluoroacetate

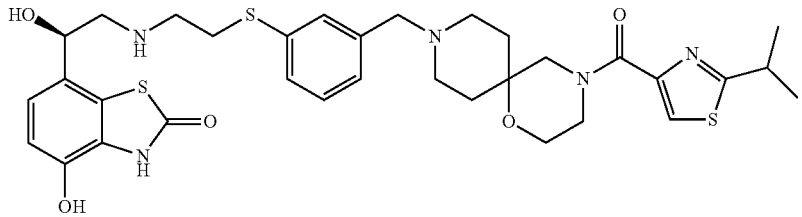 [SMILES: CC(C)c1nc(C(=O)N2CCOC3(CCN(Cc4cccc(SCCNC[C@H](O)c5ccc(O)c6[nH]c(=O)sc56)c4)CC3)C2)cs1]

Trifluoroacetic acid (0.033 mL) was added to a solution of (9-(3-(2-hydroxyethylthio)benzyl)-1-oxa-4,9-diazaspiro[5.5]undecan-4-yl)(2-isopropylthiazol-4-yl)methanone (example 65, step d) (0.22 g) in DCM (5 mL) at 0° C. The mixture was stirred for 5 min then Dess-Martin periodinane (0.29 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.026 mL) and (R)-7-(2-amino-1-hydroxyethyl)-4-hydroxybenzo[d]thiazol-2(3H)-one hydrochloride (WO2007027134, example 1, step d) (0.15 g) were then added and the mixture stirred for 5 min before cooling in an ice bath. Sodium cyanoborohydride (0.044 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 5-30% acetonitrile in 0.2% aqueous TFA). The fractions containing product were combined, evaporated in vacuo and the residue triturated with diethylether to give the titled compound as a white solid. Yield 0.54 g.

m/z 684 (M+H)$^+$ (APCI)

$^1$H NMR (400 MHz, D$_6$-DMSO, 90° C.) δ 7.94 (s, 1H), 7.54-7.34 (m, 4H), 6.91 (d, J=8.2 Hz, 1H), 6.76 (d, J=8.2 Hz, 1H), 4.88 (dd, J=8.7, 4.6 Hz, 1H), 4.24 (s, 2H), 3.74-3.61 (m, 6H), 3.38-2.95 (m, 11H), 2.08-1.94 (m, 2H), 1.82-1.68 (m, 2H), 1.35 (d, J=6.9 Hz, 6H). Six exchangeable protons not observed.

EXAMPLE 66

(R)-4-Hydroxy-7-(1-hydroxy-2-(3-((4-(4-isopropylthiazole-2-carbonyl)-1-oxa-4,9-diazaspiro[5.5]undecan-9-yl)methyl)phenethylamino)ethyl)benzo[d]thiazol-2(3H)-one ditrifluoroacetate

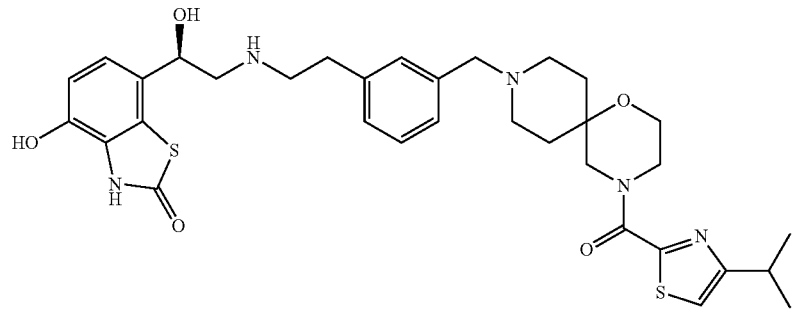 [SMILES: CC(C)c1csc(C(=O)N2CCOC3(CCN(Cc4cccc(CCNC[C@H](O)c5ccc(O)c6[nH]c(=O)sc56)c4)CC3)C2)n1]

251 a) tert-Butyl 4-(4-isopropylthiazole-2-carbonyl)-1-oxa-4,9-diazaspiro[5.5]undecane-9-carboxylate

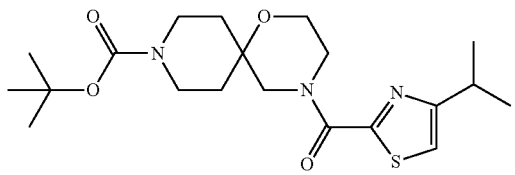 [SMILES: CC(C)c1csc(C(=O)N2CCOC3(CCN(C(=O)OC(C)(C)C)CC3)C2)n1]

HATU (0.924 g) was added in one portion to a stirred solution at 0° C. of 4-isopropylthiazole-2-carboxylic acid (0.32 g) and tert-butyl 1-oxa-4,9-diazaspiro[5.5]undecane-9-carboxylate (example 12, step b) (0.547 g) and triethylamine (0.781 mL) in DMF (12 mL). The reaction mixture was stirred at room temperature for 2 hours. The mixture was partitioned between ethyl acetate and brine, the organic layer was washed twice with brine, dried over sodium sulphate, filtered and the solvent evaporated under reduced pressure. The crude product was purified by flash silica chromatography using 30% ethyl acetate in isohexane as solvent. Pure fractions were evaporated to dryness to afford the subtitled compound. Yield 0.54 g.

$^1$H NMR (400 MHz, D$_6$-DMSO, 90° C.) δ 7.50 (s, 1H), 3.77-3.72 (m, 2H), 3.52-3.45 (m, 2H), 3.21-3.13 (m, 2H), 3.12-3.04 (m, 1H), 3.00 (s, 4H), 1.74-1.67 (m, 2H), 1.52-1.43 (m, 2H), 1.39 (s, 9H), 1.26 (d, J=6.8 Hz, 6H).

b) (4-Isopropylthiazol-2-yl)(1-oxa-4,9-diazaspiro[5.5]undecan-4-yl)methanone

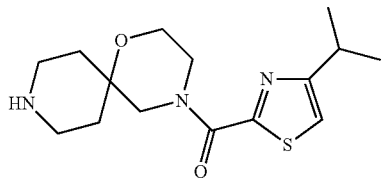 [SMILES: CC(C)c1csc(C(=O)N2CCOC3(CCNCC3)C2)n1]

252

A solution of tert-butyl 4-(4-isopropylthiazole-2-carbonyl)-1-oxa-4,9-diazaspiro[5.5]undecane-9-carboxylate (example 66, step a) (0.54 g) in DCM (20 mL) was treated with trifluoroacetic acid (5 mL) and the reaction mixture allowed to stand at 20° C. for 20 minutes. Toluene (40 mL) was added and the solvents removed under reduced pressure. The residue was azeotroped twice with acetonitrile to afford the subtitled compound. Yield 0.56 g.

m/z 310 (M+H)$^+$ (APCI)

c) (9-(3-(2-Hydroxyethyl)benzyl)-1-oxa-4,9-diazaspiro[5.5]undecan-4-yl)(4-isopropylthiazol-2-yl)methanone

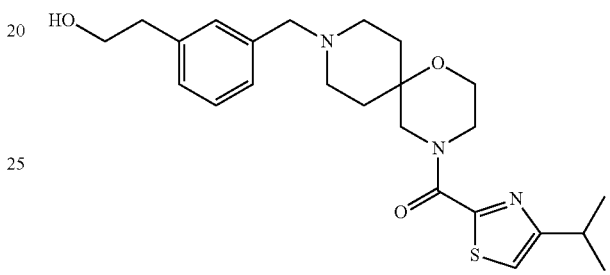

A solution of (4-isopropylthiazol-2-yl)(1-oxa-4,9-diazaspiro[5.5]undecan-4-yl)methanone (example 66, step b) (0.28 g) and 2-(3-(bromomethyl)phenyl)ethanol (example 6, step a) (0.171 g) in acetonitrile (20 mL) was treated with triethylamine (0.276 mL) and the reaction mixture stirred for 2 hours at 20° C. The solvent was evaporated under reduced pressure and the residue partitioned between ethyl acetate and saturated sodium bicarbonate solution. The organic layer was dried over sodium sulphate, filtered and the solvent removed under reduced pressure. The crude product was purified by flash silica chromatography using 2.5% methanol in dichloromethane with 1% triethylamine as solvent to afford the subtitled compound. Yield 0.25 g.

m/z 444 (M+H)$^+$ (APCI)

d) (R)-4-Hydroxy-7-(1-hydroxy-2-(3-((4-(4-isopropylthiazole-2-carbonyl)-1-oxa-4,9-diazaspiro[5.5]undecan-9-yl)methyl)phenethylamino)ethyl)benzo[d]thiazol-2(3H)-one ditrifluoroacetate

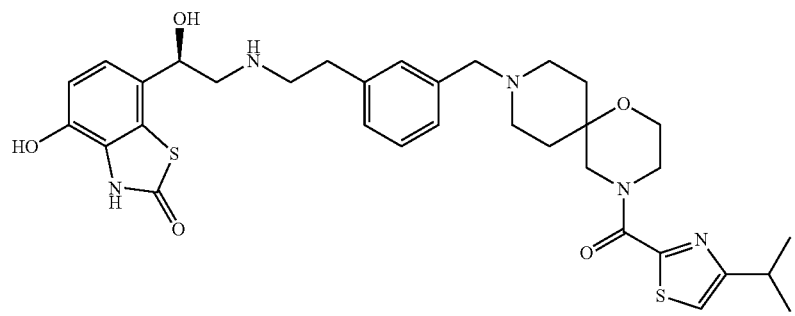 [SMILES: CC(C)c1csc(C(=O)N2CCOC3(CCN(Cc4cccc(CCNC[C@H](O)c5ccc(O)c6[nH]c(=O)sc56)c4)CC3)C2)n1]

A solution of (9-(3-(2-hydroxyethyl)benzyl)-1-oxa-4,9-diazaspiro[5.5]undecan-4-yl)(4-isopropylthiazol-2-yl)methanone (example 66, step c) (0.25 g) in DCM (20 mL) was treated with trifluoroacetic acid (0.043 mL) followed by Dess-Martin periodinane (0.311 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.032 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.222 g) and acetic acid (0.032 mL) in methanol (20 mL). The mixture was cooled in an ice bath and treated with sodium cyanoborohydride (0.071 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired product were evaporated to dryness to afford the titled compound. Yield 0.18 g m/z 652 (M+H)$^+$ (APCI)

$^1$H NMR (300 MHz, D$_6$-DMSO, 90° C.) δ 11.35 (s, 1H), 7.53 (s, 1H), 7.43-7.32 (m, 4H), 6.93 (d, J=8.3 Hz, 1H), 6.78 (d, J=8.5 Hz, 1H), 4.97-4.89 (m, 1H), 4.29 (s, 2H), 3.76 (s, 2H), 4.17-3.30 (m, 4H), 3.28-3.15 (m, 4H), 3.14-2.98 (m, 7H), 2.10-1.97 (m, 2H), 1.87-1.70 (m, 2H), 1.26 (d, J=7.1 Hz, 6H). Five exchangeable protons not observed.

EXAMPLE 67

(R)-7-(2-(2-Fluoro-3-((4-(2-(2,2,2-trifluoroethyl)thiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate a) 3,3,3-Trifluoropropanamide

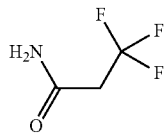

A solution of 3,3,3-trifluoropropanoic acid (4 g) in ether (150 mL) at 0° C. was treated in one portion to with phosphorus pentachloride (6.06 g). The mixture was heated at reflux under nitrogen for 2.5 hours. The reaction mixture was cooled to room temperature. Further ether (100 mL) was added and the mixture cooled in an ice bath. Ammonia gas was bubbled through the stirred mixture for 30 minutes. The solvent was removed under reduced pressure and the residue was partitioned between saturated sodium bicarbonate solution and ethyl acetate. The aqueous layer was re-extracted twice with ethyl acetate, the combined organics were dried over sodium sulphate, filtered and the solvent was removed under reduced pressure to afford the subtitled compound. Yield 3.9 g. Used directly.

b) 3,3,3-Trifluoropropanethioamide

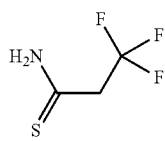

Phosphorus pentasulfide (1.603 g) was added in one portion to a solution of 3,3,3-trifluoropropanamide (example 67, step a) (3.9 g) in MTBE (150 mL). The reaction mixture was stirred at 20° C. for 20 hours. The mixture was filtered and the solvent was evaporated under reduced pressure to afford the subtitled compound. Yield 4 g. The product was used directly in the next step.

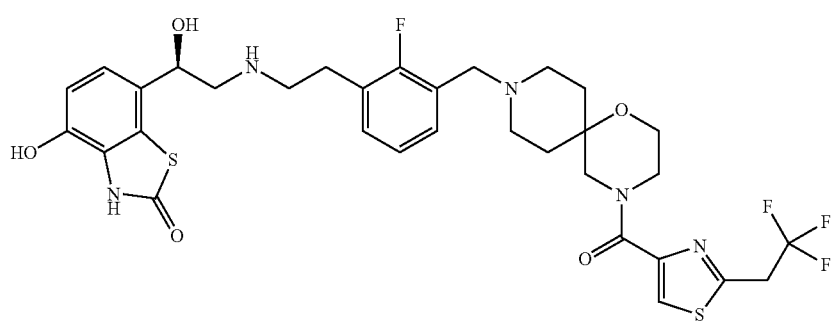 [SMILES: O=C(c1csc(CC(F)(F)F)n1)N1CCOC2(CCN(Cc3cccc(CCNC[C@H](O)c4ccc(O)c5[nH]c(=O)sc45)c3F)CC2)C1]

c) Ethyl 2-(2,2,2-trifluoroethyl)thiazole-4-carboxylate

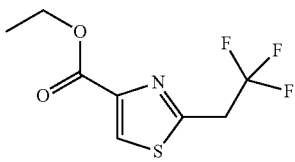

A solution of 3,3,3-trifluoropropanethioamide (example 67, step b) (4 g) and ethyl 3-bromo-2-oxopropanoate (5.45 g) in THF (120 mL) was heated at reflux for 2 hours. The solvent was removed under reduced pressure and the residue was partitioned between ethyl acetate and saturated sodium bicarbonate solution. The organic layer was dried over sodium sulphate, filtered and the solvent evaporated under reduced pressure. The crude product was purified by flash silica chromatography using 17% ethyl acetate in isohexane as solvent. Pure fractions were evaporated to dryness to afford the subtitled compound. Yield 1.9 g.

m/z 240 (M+H)$^+$ (APCI)

$^1$H NMR (400 MHz, CDCl$_3$) δ 8.23 (s, 1H), 4.45 (q, J=7.1 Hz, 2H), 3.94 (q, J=10.2 Hz, 2H), 1.42 (t, J=7.0 Hz, 3H).

d) 2-(2,2,2-Trifluoroethyl)thiazole-4-carboxylic acid

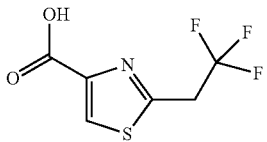 [SMILES: O=C(O)c1csc(CC(F)(F)F)n1]

A mixture of ethyl 2-(2,2,2-trifluoroethyl)thiazole-4-carboxylate (example 67, step c) (0.3 g) in concentrated hydrochloric acid (7 mL) and water (7 mL) was heated at 80° C. for 5 hours under nitrogen. The solvent was evaporated under a stream of nitrogen and the residue partitioned between ethyl acetate (40 mL) and brine (3 mL). The organic layer was dried over sodium sulphate, filtered and the solvent evaporated under reduced pressure to afford the subtitled compound. Yield 0.23 g.

m/z 210 (M−H)$^−$ (APCI)

$^1$H NMR (300 MHz, CDCl$_3$) δ 8.36 (s, 1H), 3.95 (q, J=10.0 Hz, 2H). One exchangeable proton not observed.

e) 2,2,2-Trifluoro-1-(9-(2-fluoro-3-(2-hydroxyethyl)benzyl)-1-oxa-4,9-diazaspiro[5.5]undecan-4-yl)ethanone

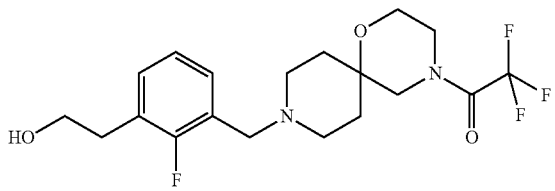 [SMILES: O=C(N1CCOC2(CCN(Cc3cccc(CCO)c3F)CC2)C1)C(F)(F)F]

2-Fluoro-3-(2-hydroxyethyl)benzaldehyde (example 48, step a) (1.05 g) was added to a solution of 2,2,2-trifluoro-1-(1-oxa-4,9-diazaspiro[5.5]undecan-4-yl)ethanone trifluoroacetate (example 12, step d) (2.08 g) and acetic acid (0.33 mL) in N-methyl-2-pyrrolidinone (10 mL). The resulting mixture was stirred for 15 min then cooled in an ice bath. Sodium triacetoxyborohydride (1.81 g) was then added and the mixture stirred overnight. The reaction was poured into a mixture of saturated sodium hydrogen carbonate solution (20 mL) and water (100 mL). The aqueous was extracted with ethyl acetate (3×100 mL). The combined organics were washed with water (50 mL) and brine (100 mL), dried over sodium sulphate, filtered and evaporated. The residue was purified by silica gel chromatography eluting with 4:1 isohexane:ethyl acetate+5% triethylamine to ethyl acetate+5% triethylamine gradient. The fractions containing product were combined and evaporated to give the subtitled compound as a clear oil. Yield 1.9 g. Used immediately.

f) 2-(3-(1-Oxa-4,9-diazaspiro[5.5]undecan-9-ylmethyl)-2-fluorophenyl)ethanol

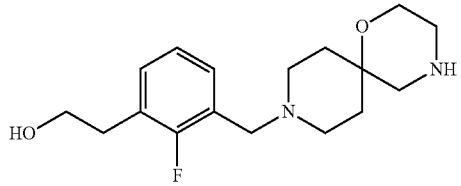 [SMILES: OCCc1cccc(CN2CCC3(CC2)CNCCO3)c1F]

'880' Aqueous ammonia solution (5 mL) was added to a solution of 2,2,2-trifluoro-1-(9-(2-fluoro-3-(2-hydroxyethyl)benzyl)-1-oxa-4,9-diazaspiro[5.5]undecan-4-yl)ethanone (example 67, step e) (1.9 g) in methanol (25 mL). The resulting mixture was stirred for 90 min and the solvent evaporated. The residue was purified by silica gel chromatography eluting with 94.5:5:0.5 to 89:10:1 DCM:methanol:'880' ammonia gradient. The fractions containing product were combined and evaporated to give a gum that solidified on standing. The white solid was triturated with isohexane and dried over sodium sulphate to give the subtitled compound as a white solid. Yield 1 g.

m/z 309 (M+H)$^+$ (APCI)

$^1$H NMR (400 MHz, D$_6$-DMSO) δ 7.24-7.15 (m, 2H), 7.06 (t, J=7.6 Hz, 1H), 4.69 (t, J=5.3 Hz, 1H), 3.64-3.54 (m, 2H), 3.53-3.43 (m, 4H), 2.74 (t, J=7.0 Hz, 2H), 2.60 (t, J=4.9 Hz, 2H), 2.45-2.35 (m, 2H), 2.34-2.24 (m, 2H), 1.83-1.74 (m, 2H), 1.47-1.36 (m, 2H). Two protons obscured by solvent peaks and one exchangeable proton not observed.

g) (9-(2-Fluoro-3-(2-hydroxyethyl)benzyl)-1-oxa-4, 9-diazaspiro[5.5]undecan-4-yl)(2-(2,2,2-trifluoroethyl)thiazol-4-yl)methanone

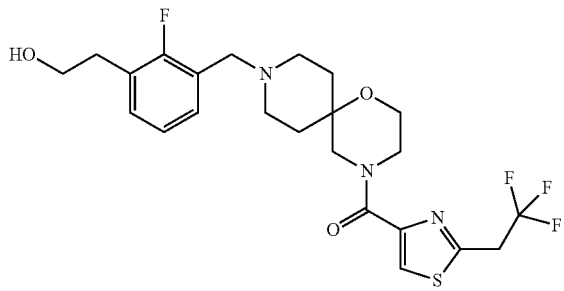 [SMILES: O=C(c1csc(CC(F)(F)F)n1)N1CCOC2(CCN(Cc3cccc(CCO)c3F)CC2)C1]

HATU (0.181 g) was added in one portion to a stirred solution at 0° C. of 2-(2,2,2-trifluoroethyl)thiazole-4-carboxylic acid (example 67, step d) (0.077 g) and 2-(3-(1-oxa-4,9-diazaspiro[5.5]undecan-9-ylmethyl)-2-fluorophenyl)ethanol (example 67, step f) (0.113 g) and triethylamine (0.153 mL) in DMF (5 mL). The reaction mixture was stirred at room temperature for 2 hours. The mixture was partitioned between ethyl acetate and brine, the organic layer was washed twice with brine, dried over sodium sulphate, filtered and the solvent evaporated under reduced pressure to afford the sub-titled compound. Yield 0.180 g.

m/z 502 (M+H)+ (APCI)

h) (R)-7-(2-(2-Fluoro-3-((4-(2-(2,2,2-trifluoroethyl)thiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate A solution of (9-(2-fluoro-3-(2-hydroxyethyl)benzyl)-1-oxa-4,9-diazaspiro[5.5]undecan-4-yl)(2-(2,2,2-trifluoroethyl)thiazol-4-yl)methanone (example 67, step g) (0.18 g) in DCM (15 mL) was treated with trifluoroacetic acid (0.028 mL) followed by Dess-Martin periodinane (0.198 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.021 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.141 g) and acetic acid (0.021 mL) in methanol (15.0 mL). The mixture was cooled in an ice bath and treated with sodium cyanoborohydride (0.045 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.091 g.

m/z 710 (M+H)+ (APCI)

$^1$H NMR (400 MHz, D$_6$-DMSO, 90° C.) δ 8.15 (s, 1H), 7.52-7.40 (m, 2H), 7.25 (t, J=7.6 Hz, 1H), 6.94 (d, J=8.2 Hz, 1H), 6.77 (d, J=8.2 Hz, 1H), 4.94-4.89 (m, 1H), 4.29 (s, 2H), 4.20 (q, J=11.0 Hz, 2H), 3.74-3.61 (m, 6H), 3.28-3.02 (m, 10H), 2.06-1.96 (m, 2H), 1.85-1.72 (m, 2H). Six exchangeable protons not observed.

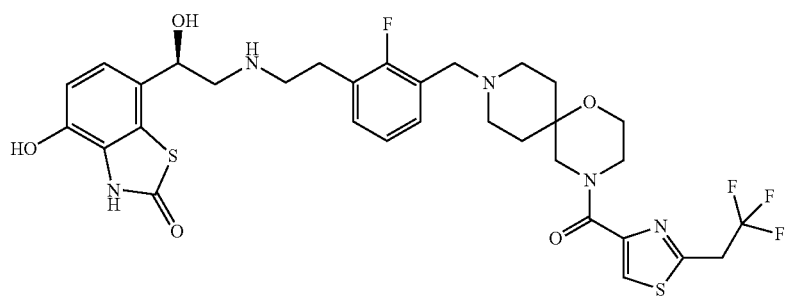 [SMILES: O=C(c1csc(CC(F)(F)F)n1)N1CCOC2(CCN(Cc3cccc(CCNC[C@H](O)c4ccc(O)c5[nH]c(=O)sc45)c3F)CC2)C1]

EXAMPLE 68

(R)-7-(2-(3-((4-(Benzo[b]thiophene-5-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

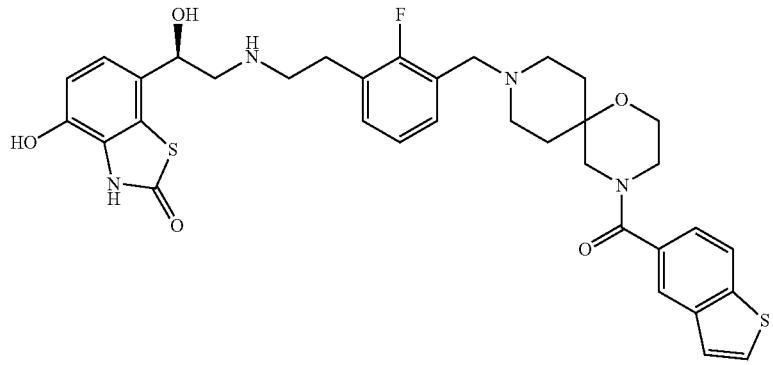 [SMILES: O=C(c1ccc2sccc2c1)N1CCOC2(CCN(Cc3cccc(CCNC[C@H](O)c4ccc(O)c5[nH]c(=O)sc45)c3F)CC2)C1]

a) Benzo[b]thiophen-5-yl(9-(2-fluoro-3-(2-hydroxyethyl)benzyl)-1-oxa-4,9-diazaspiro[5.5]undecan-4-yl)methanone

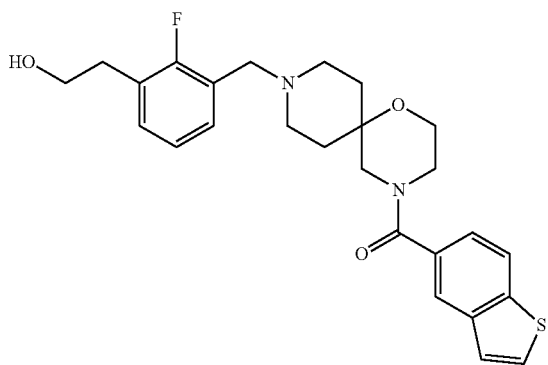 [SMILES: O=C(c1ccc2sccc2c1)N1CCOC2(CCN(Cc3cccc(CCO)c3F)CC2)C1]

HATU (0.181 g) was added in one portion to a stirred solution at 0° C. of benzo[b]thiophene-5-carboxylic acid (0.065 g) and 2-(3-(1-oxa-4,9-diazaspiro[5.5]undecan-9-yl-methyl)-2-fluorophenyl)ethanol (example 67, step f) (0.113 g) and triethylamine (0.153 mL) in DMF (5 mL). The reaction mixture was stirred at room temperature for 2 hours. The mixture was partitioned between ethyl acetate and brine, the organic layer was washed twice with brine, dried over sodium sulphate, filtered and the solvent evaporated under reduced pressure to afford the subtitled compound. Yield 0.160 g.

m/z 469 (M+H)$^+$ (APCI)

b) (R)-7-(2-(3-((4-(Benzo[b]thiophene-5-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

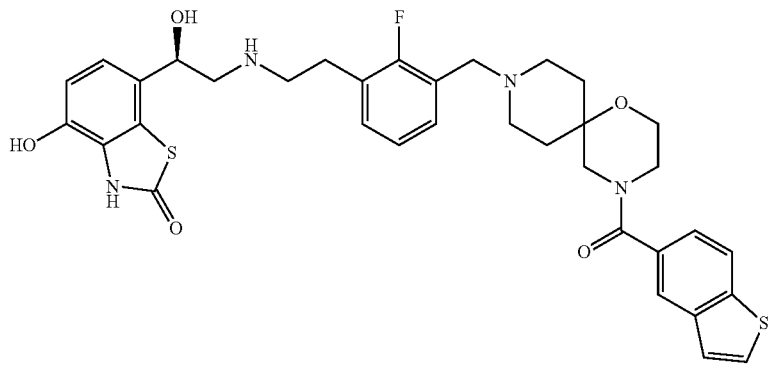 [SMILES: O=C(c1ccc2sccc2c1)N1CCOC2(CCN(Cc3cccc(CCNC[C@H](O)c4ccc(O)c5[nH]c(=O)sc45)c3F)CC2)C1]

A solution of benzo[b]thiophen-5-yl(9-(2-fluoro-3-(2-hydroxyethyl)benzyl)-1-oxa-4,9-diazaspiro[5.5]undecan-4-yl)methanone (example 68, step a) (0.160 g) in DCM (15 mL) was treated with trifluoroacetic acid (0.026 mL) followed by Dess-Martin periodinane (0.188 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.02 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.135 g) and acetic acid (0.02 mL) in methanol (15 mL). The mixture was cooled in an ice bath and treated with sodium cyanoborohydride (0.043 mg). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.116 g.

m/z 677 (M+H)$^+$ (APCI)

$^1$H NMR (400 MHz, D$_6$-DMSO, 90° C.) δ 11.28 (s, 1H), 8.04 (d, J=8.2 Hz, 1H), 7.91 (s, 1H), 7.80 (d, J=5.4 Hz, 1H), 7.52-7.42 (m, 3H), 7.38-7.35 (m, 1H), 7.25 (t, J=7.7 Hz, 1H), 6.94 (d, J=8.5 Hz, 1H), 6.78 (t, J=4.1 Hz, 1H), 4.95-4.90 (m, 1H), 4.35 (s, 2H), 3.69 (t, J=5.0 Hz, 2H), 3.53-3.44 (m, 4H), 3.28-3.19 (m, 4H), 3.16-3.04 (m, 6H), 2.11-2.03 (m, 2H), 1.80-1.68 (m, 2H). Five exchangeable protons not observed.

EXAMPLE 69

(R)-7-(2-(2-Fluoro-3-((4-(2-isopropyl-5-methylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate a) Methyl 2-isopropyl-5-methylthiazole-4-carboxylate

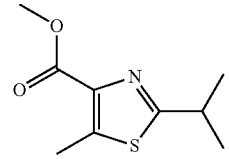

A mixture of methyl 3-bromo-2-oxobutanoate (4.6 g) and 2-methylpropanethioamide (2.5 g) in THF (100 mL) was heated at reflux for 18 hours. The solvent was evaporated under reduced pressure. The residue was partitioned between ethyl acetate and saturated sodium bicarbonate solution and the organic layer was dried over sodium sulphate, filtered and the solvent evaporated under reduced pressure. The residue was purified by flash silica chromatography using 17% ethyl acetate in isohexane as solvent. Pure fractions were evaporated to dryness to afford the subtitled compound. Yield 1.7 g.

m/z 200 (M+H)$^+$ (APCI)

b) 2-Isopropyl-5-methylthiazole-4-carboxylic acid

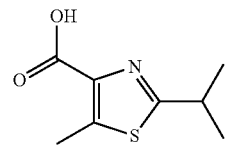

A solution of lithium hydroxide monohydrate (0.2 g) in water (3 mL) was added to a solution of methyl 2-isopropyl-5-methylthiazole-4-carboxylate (example 69, step a) (0.5 g) in methanol (7 mL) and the reaction mixture was stirred at 20° C. for 3 hours. The methanol was removed under reduced pressure and the remaining aqueous solution was washed with ethyl acetate. The aqueous layer was acidified by dropwise addition of concentrated aqueous HCl and this mixture was extracted with ethyl acetate. The organic layer was dried over sodium sulphate, filtered and the solvent was removed under reduced pressure. The resultant gum crystallised on standing. Trituration with a mixture of isohexane (4 mL) and ether (1 mL) afforded the subtitled compound. Yield 0.160 g.

$^1$H NMR (400 MHz, CDCl$_3$) δ 3.29-3.18 (m, 1H), 2.78 (s, 3H), 1.38 (d, J=7.1 Hz, 6H). One exchangeable proton not observed.

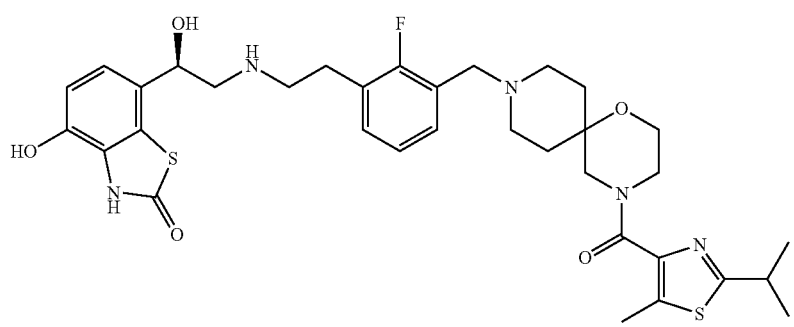

c) (9-(2-Fluoro-3-(2-hydroxyethyl)benzyl)-1-oxa-4,9-diazaspiro[5.5]undecan-4-yl)(2-isopropyl-5-methylthiazol-4-yl)methanone

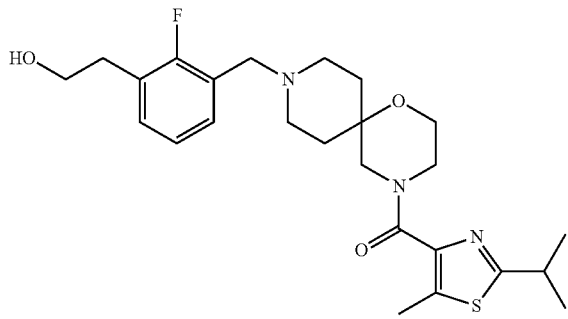 [SMILES: Cc1sc(C(C)C)nc1C(=O)N1CCOC2(CCN(Cc3cccc(CCO)c3F)CC2)C1]

HATU (0.175 g) was added in one portion to a stirred solution at 0° C. of 2-isopropyl-5-methylthiazole-4-carboxylic acid (example 69, step b) (0.066 mg) and 2-(3-(1-oxa-4,9-diazaspiro[5.5]undecan-9-ylmethyl)-2-fluorophenyl)ethanol (example 67, step f) (0.109 g) and triethylamine (0.148 mL) in DMF (5 mL). The reaction mixture was stirred at room temperature for 2 hours. The mixture was partitioned between ethyl acetate and brine, the organic layer was washed twice with brine, dried over sodium sulphate, filtered and the solvent evaporated under reduced pressure to afford the subtitled compound. Yield 0.155 mg.

m/z 476 (M+H)+ (APCI)

d) (R)-7-(2-(2-Fluoro-3-((4-(2-isopropyl-5-methylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate A solution of (9-(2-fluoro-3-(2-hydroxyethyl)benzyl)-1-oxa-4,9-diazaspiro[5.5]undecan-4-yl)(2-isopropyl-5-methylthiazol-4-yl)methanone (example 69, step c) (0.155 g) in DCM (15 mL) was treated with trifluoroacetic acid (0.025 mL) followed by Dess-Martin periodinane (0.180 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.019 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.128 g) and acetic acid (0.019 mL) in methanol (15.00 mL). The mixture was cooled in an ice bath and treated with sodium cyanoborohydride (41 mg). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.12 g.

m/z 684 (M+H)+ (APCI)

1H NMR (400 MHz, D6-DMSO, 90° C.) δ 11.28 (s, 1H), 7.50-7.39 (m, 2H), 7.28-7.22 (m, 1H), 6.93 (d, J=24.1 Hz, 1H), 6.77 (d, J=26.1 Hz, 1H), 4.93-4.88 (m, 1H), 4.26 (s, 2H), 3.67 (s, 2H), 3.58-3.43 (m, 4H), 3.26-3.00 (m, 11H), 2.43 (s, 3H), 2.03-1.94 (m, 2H), 1.81-1.65 (m, 2H), 1.30 (d, J=6.8 Hz, 6H). Five exchangeable protons not observed.

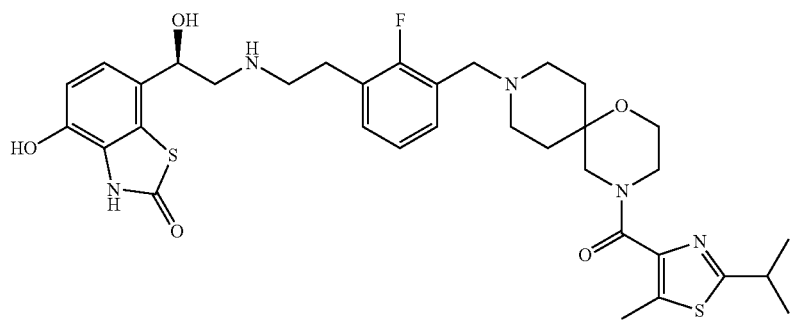 [SMILES: Cc1sc(C(C)C)nc1C(=O)N1CCOC2(CCN(Cc3cccc(CCNC[C@H](O)c4ccc(O)c5[nH]c(=O)sc45)c3F)CC2)C1]

EXAMPLE 70

(R)-7-(2-(2-Fluoro-3-((4-(5-isopropylthiophene-3-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

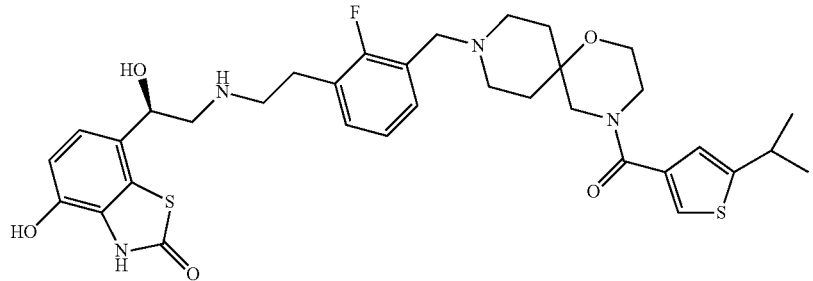 [SMILES: CC(C)c1cc(C(=O)N2CCOC3(CCN(Cc4cccc(CCNC[C@H](O)c5ccc(O)c6[nH]c(=O)sc56)c4F)CC3)C2)cs1]

a) (9-(2-Fluoro-3-(2-hydroxyethyl)benzyl)-1-oxa-4,9-diazaspiro[5.5]undecan-4-yl)(5-isopropylthiophen-3-yl)methanone

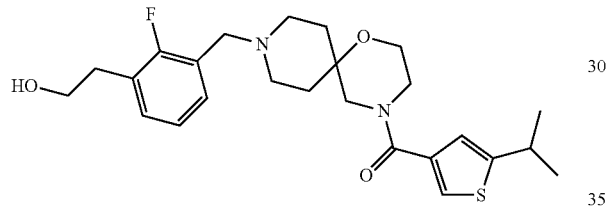

HATU (0.183 g) was added in one portion to a stirred solution at 0° C. of 5-isopropylthiophene-3-carboxylic acid (0.063 g) and 2-(3-(1-oxa-4,9-diazaspiro[5.5]undecan-9-ylmethyl)-2-fluorophenyl)ethanol (example 67, step f) (0.114 g) and triethylamine (0.155 mL) in DMF (5 mL). The reaction mixture was stirred at room temperature for 2 hours. The mixture was partitioned between ethyl acetate and brine, the organic layer was washed twice with brine, dried over sodium sulphate, filtered and the solvent evaporated under reduced pressure. The crude product was purified by flash silica chromatography using 2.5% methanol in dichloromethane with 1% triethylamine as solvent. Pure fractions were evaporated to dryness to afford the subtitled compound. Yield 0.100 g.

m/z 461 (M+H)+ (APCI)

b) (R)-7-(2-(2-Fluoro-3-((4-(5-isopropylthiophene-3-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

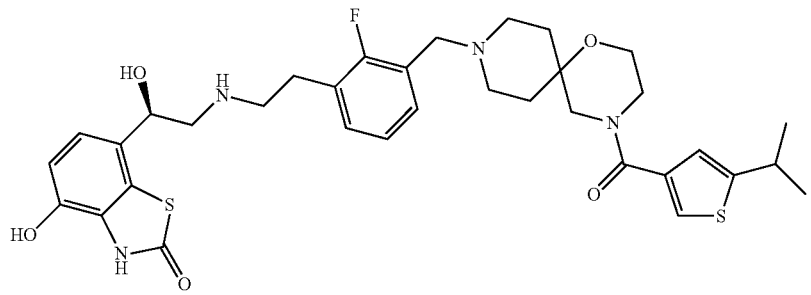 [SMILES: CC(C)c1cc(C(=O)N2CCOC3(CCN(Cc4cccc(CCNC[C@H](O)c5ccc(O)c6[nH]c(=O)sc56)c4F)CC3)C2)cs1]

A solution of (9-(2-fluoro-3-(2-hydroxyethyl)benzyl)-1-oxa-4,9-diazaspiro[5.5]undecan-4-yl)(5-isopropylthiophen-3-yl)methanone (example 70, step a) (0.100 g) in DCM (15 mL) was treated with trifluoroacetic acid (0.017 mL) followed by Dess-Martin periodinane (0.120 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.012 mL) was added to this solution and the solvent then removed under reduced pressure. The residue was dissolved in methanol (3 mL) and added to a solution of (R)-7-

(2-amino-1-hydroxyethyl)-4-hydroxybenzo[d]thiazol-2(3H)-one hydrochloride (WO2007027134, example 1, step d) (0.086 g) and acetic acid (0.012 mL) in methanol (15.00 mL). The mixture was cooled in an ice bath and treated with sodium cyanoborohydride (0.027 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.052 mg.

m/z 669 (M+H)+ (APCI)

$^1$H NMR (400 MHz, D$_6$-DMSO, 90° C.) δ 7.51-7.46 (m, 2H), 7.43 (t, J=7.5 Hz, 1H), 7.25 (t, J=7.7 Hz, 1H), 6.95-6.89 (m, 2H), 6.77 (d, J=8.2 Hz, 1H), 4.95-4.90 (m, 1H), 4.30 (s, 2H), 3.69-3.65 (m, 2H), 3.55-3.51 (m, 2H), 3.45 (s, 2H), 3.24 (t, J=8.1 Hz, 2H), 3.20-3.03 (m, 9H), 2.05-1.97 (m, 2H), 1.79-1.69 (m, 2H), 1.28 (d, J=6.8 Hz, 6H). Six exchangeable protons not observed.

EXAMPLE 71

(R)-7-(2-(2-Fluoro-3-((4-(2-(pentan-3-yl)thiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

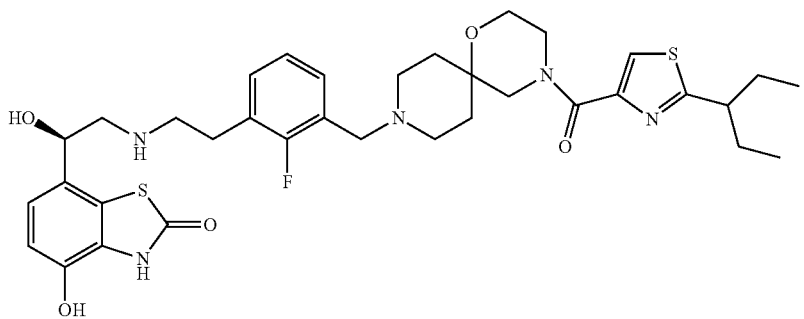 [SMILES: CCC(CC)c1nc(C(=O)N2CCOC3(CCN(Cc4cccc(CCNC[C@H](O)c5ccc(O)c6[nH]c(=O)sc56)c4F)CC3)C2)cs1]

a) 2-Ethylbutanamide P

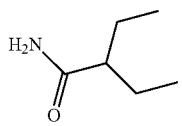

2-Ethylbutanoyl chloride (5 g) was cautiously added dropwise to ice cold 35% aqueous ammonia (50 mL) and the resulting suspension stirred for 1 h. The reaction mixture was extracted with DCM (3×100 mL). The combined organics were washed with brine (100 mL), dried over sodium sulphate, filtered and evaporated to give the subtitled compound as a white solid. Yield 3.4 g.

$^1$H NMR (400 MHz, D$_6$-DMSO) δ 7.23 (s, 1H), 6.71 (s, 1H), 1.98-1.88 (m, 1H), 1.50-1.27 (m, 4H), 0.81 (t, J=7.4 Hz, 6H).

b) 2-Ethylbutanethioamide

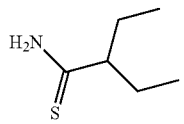

Phosphorus pentasulfide (1.54 g) was added to a solution of 2-ethylbutanamide (example 71, step a) (3.4 g) in MTBE (300 mL) and the resulting mixture stirred for 3 h. The reaction was filtered through Celite and the filter pad washed with MTBE (100 mL). The combined filtrate and washings were evaporated to give the subtitled compound as a yellow oil. Yield 3.8 g. Used directly.

c) Ethyl 2-(pentan-3-yl)thiazole-4-carboxylate

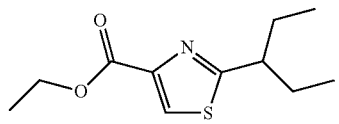

Ethyl 3-bromo-2-oxopropanoate (2.5 mL) was added dropwise to a solution of 2-ethylbutanethioamide (example 71, step b) (3.8 g) in ethanol (100 mL) and the resulting mixture heated at reflux overnight. The solvent was evaporated and the residue partitioned between ethyl acetate (100 mL) and saturated sodium hydrogen carbonate solution (100 mL). The layers were separated and the aqueous phase extracted with ethyl acetate (2×100 mL). The combined organic solutions were washed with brine (100 mL), dried over sodium sulphate, filtered and evaporated. The residue was purified by silica gel chromatography eluting with 20:1 isohexane:ethyl acetate. The fractions containing product were combined and evaporated to give the subtitled compound as a yellow oil. Yield 2.8 g.

$^1$H NMR (400 MHz, D$_6$-DMSO) δ 8.42 (s, 1H), 4.29 (q, J=7.1 Hz, 2H), 2.99-2.89 (m, 1H), 1.82-1.58 (m, 4H), 1.30 (t, J=7.0 Hz, 3H), 0.81 (t, J=7.4 Hz, 6H).

d) 2-(Pentan-3-yl)thiazole-4-carboxylic acid

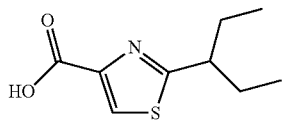

Lithium hydroxide monohydrate (2.07 g) was added to a solution of ethyl 2-(pentan-3-yl)thiazole-4-carboxylate (example 71, step c) (2.8 g) in a mixture of THF (80 mL) and water (20 mL). The resulting mixture was stirred overnight. The reaction was acidified with concentrated hydrochloric acid (6 mL) and the volatiles evaporated. The resulting aqueous mixture was saturated with sodium chloride and extracted with ethyl acetate (3×100 mL). The combined organic solutions were dried over sodium sulphate, filtered and evaporated to give the subtitled compound as a white solid. Yield 2.3 g $^1$H NMR (300 MHz, D$_6$-DMSO) δ 12.91 (s, 1H), 8.34 (s, 1H), 2.98-2.86 (m, 1H), 1.84-1.56 (m, 4H), 0.81 (t, J=7.3 Hz, 6H).

e) (9-(2-Fluoro-3-(2-hydroxyethyl)benzyl)-1-oxa-4, 9-diazaspiro[5.5]undecan-4-yl)(2-(pentan-3-yl)thiazol-4-yl)methanone

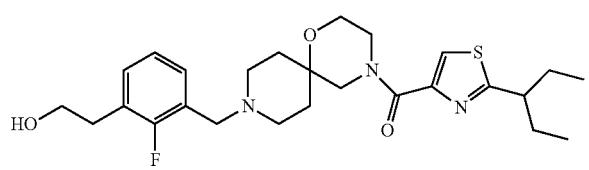 [SMILES: CCC(CC)c1nc(C(=O)N2CCOC3(CCN(Cc4cccc(CCO)c4F)CC3)C2)cs1]

O-(7-Azabenzotriazol-1-yl)-N,N,N',N'-tetramethyluronium hexafluorophosphate (0.2 g) was added to a solution of 2-(3-(1-oxa-4,9-diazaspiro[5.5]undecan-9-ylmethyl)-2-fluorophenyl)ethanol (example 67, step f) (0.13 g), 2-(pentan-3-yl)thiazole-4-carboxylic acid (example 71, step d) (0.081 g) and triethylamine (0.23 mL) in DMF (7 mL) at 0° C. The resulting yellow solution was allowed to warm to RT and was stirred for 2 h. The mixture was partitioned between ethyl acetate and brine (100 mL), the organic phase was washed with brine (2×100 mL), dried over sodium sulphate, filtered and then evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added, and the solvent evaporated under reduced pressure to give the subtitled compound a as clear gum. Yield 0.25 g.

m/z 490 (M+H)$^+$ (APCI)

$^1$H NMR (400 MHz, D$_6$-DMSO, 90° C.) δ 7.93 (s, 1H), 7.22-7.14 (m, 2H), 7.03 (t, J=7.6 Hz, 1H), 4.39-4.32 (m, 1H), 3.69-3.58 (m, 6H), 3.52-3.46 (m, 2H), 2.97-2.90 (m, 1H), 2.75 (t, J=7.3 Hz, 2H), 2.70 (s, 2H), 2.46-2.29 (m, 4H), 1.82-1.66 (m, 6H), 1.58-1.47 (m, 2H), 0.85 (t, J=7.3 Hz, 6H).

f) (R)-7-(2-(2-Fluoro-3-((4-(2-(pentan-3-yl)thiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

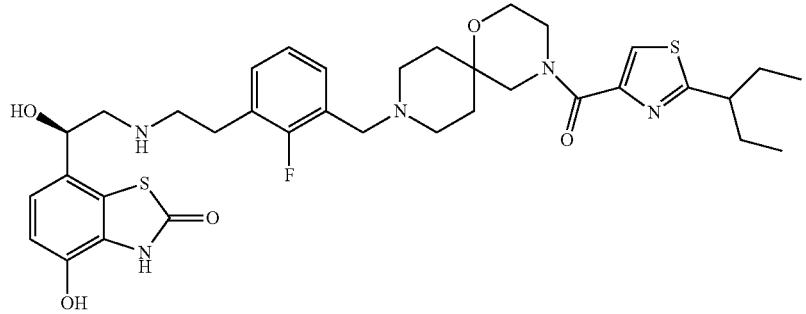 [SMILES: CCC(CC)c1nc(C(=O)N2CCOC3(CCN(Cc4cccc(CCNC[C@H](O)c5ccc(O)c6[nH]c(=O)sc56)c4F)CC3)C2)cs1]

Trifluoroacetic acid (0.031 mL) was added to a solution of (9-(2-fluoro-3-(2-hydroxyethyl)benzyl)-1-oxa-4,9-diazaspiro[5.5]undecan-4-yl)(2-(pentan-3-yl)thiazol-4-yl)methanone (example 71, step e) (0.2 g) in DCM (5 mL) at 0° C. The mixture was stirred for 5 min then Dess-Martin periodinane (0.25 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.023 mL) and (R)-7-(2-amino-1-hydroxyethyl)-4-hydroxybenzo[d]thiazol-2(3H)-one hydrochloride (WO2007027134, example 1, step d) (0.13 g) were then added and the mixture stirred for 5 min before cooling in an ice bath. Sodium cyanoborohydride (0.038 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-35% acetonitrile in 0.2% aqueous TFA). The fractions containing product were combined, evaporated in vacuo and the residue triturated with diethylether to give the titled compound as a white solid. Yield 0.17 g.

m/z 698 (M+H)$^+$ (APCI)

$^1$H NMR (400 MHz, D$_6$-DMSO, 90° C.) δ 11.26 (s, 1H), 8.01-7.83 (m, 1H), 7.56-7.38 (m, 2H), 7.30-7.19 (m, 1H), 7.01-6.89 (m, 1H), 6.83-6.71 (m, 1H), 4.99-4.88 (m, 1H), 4.38-4.23 (m, 2H), 3.78-3.57 (m, 6H), 3.33-2.86 (m, 11H), 2.10-1.97 (m, 2H), 1.87-1.61 (m, 6H), 0.91-0.76 (m, 6H). Five exchangeable protons not observed.

EXAMPLE 72

(R)-7-(2-(2-Fluoro-3-((4-(2-isobutylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

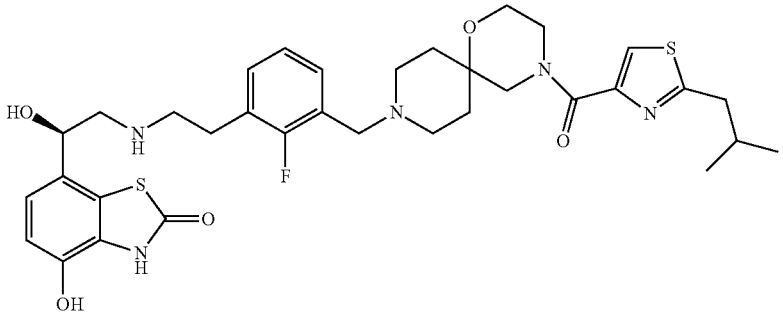 [SMILES: CC(C)Cc1nc(C(=O)N2CCOC3(CCN(Cc4cccc(CCNC[C@H](O)c5ccc(O)c6[nH]c(=O)sc56)c4F)CC3)C2)cs1]

a) 3-Methylbutanamide

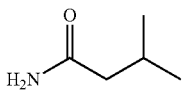

3-Methylbutanoyl chloride (10 mL) was cautiously added dropwise to ice cold 35% aqueous ammonia (50 mL) and the resulting suspension stirred for 1 h. The reaction mixture was extracted with DCM (3×100 mL). The combined organic solutions were washed with brine (100 mL), dried over sodium sulphate, filtered and evaporated to give the subtitled compound as a white solid. Yield 5.6 g.

$^1$H NMR (300 MHz, D$_6$-DMSO) δ 7.20 (s, 1H), 6.67 (s, 1H), 1.99-1.88 (m, 3H), 0.87 (d, J=6.4 Hz, 6H).

b) 3-Methylbutanethioamide

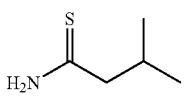

Phosphorous pentasulfide (2.9 g) was added to a suspension of 3-methylbutanamide (example 72, step a) (5.6 g) in MTBE (300 mL) and the resulting mixture stirred for 3 h. The reaction was filtered through Celite and the filter pad washed with MTBE (100 mL). The combined filtrate and washings were evaporated to give the subtitled compound as a yellow oil. Yield 5.6 g.

$^1$H NMR (300 MHz, D$_6$-DMSO) δ 9.32 (s, 1H), 9.10 (s, 1H), 2.33 (d, J=7.3 Hz, 2H), 2.22-2.07 (m, 1H), 0.88 (d, J=6.4 Hz, 6H).

c) Ethyl 2-isobutylthiazole-4-carboxylate

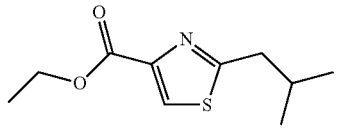

To a solution of 3-methylbutanethioamide (example 72, step b) (5.6 g) in ethanol (100 mL) was added ethyl 3-bromo-2-oxopropanoate (6.7 mL). The resulting mixture was stirred overnight at RT, then heated at reflux for 5 h. The solvent was evaporated and the residue was partitioned between ethyl acetate (250 mL) and saturated sodium hydrogen carbonate solution (100 mL). The layers were separated and the organic phase was washed with brine (100 mL), dried over magnesium sulphate, filtered and evaporated. The residue was purified by silica gel chromatography eluting with 20:1 to 10:1 isohexane:ethyl acetate gradient. The fractions containing product were combined and evaporated to give the subtitled compound as a yellow oil. Yield 5.2 g.

$^1$H NMR (400 MHz, D$_6$-DMSO) δ 8.39 (s, 1H), 4.29 (q, J=7.1 Hz, 2H), 2.88 (d, J=7.2 Hz, 2H), 2.10-1.97 (m, 1H), 1.30 (t, J=7.2 Hz, 3H), 0.93 (d, J=6.7 Hz, 6H).

d) 2-Isobutylthiazole-4-carboxylic acid

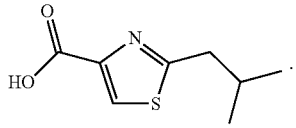

Lithium hydroxide monohydrate (4.1 g) was added to a solution of ethyl 2-isobutylthiazole-4-carboxylate (example 72, step c) (5.2 g) in a mixture of THF (80 mL) and water (20 mL). The resulting mixture was stirred overnight. The reaction was carefully acidified with concentrated hydrochloric acid (10 mL) and the volatiles evaporated. The resulting aqueous mixture was poured into brine (50 mL) and extracted with ethyl acetate (3×100 mL). The combined organic solutions were washed with brine (50 mL), dried over sodium sulphate, filtered and evaporated to give the subtitled compound as a white solid. Yield 3.8 g.

$^1$H NMR (300 MHz, D$_6$-DMSO) δ 12.90 (s, 1H), 8.32 (s, 1H), 2.87 (d, J=7.1 Hz, 2H), 2.11-1.96 (m, 1H), 0.94 (d, J=6.7 Hz, 6H).

e) (9-(2-Fluoro-3-(2-hydroxyethyl)benzyl)-1-oxa-4,9-diazaspiro[5.5]undecan-4-yl)(2-isobutylthiazole-4-yl)methanone

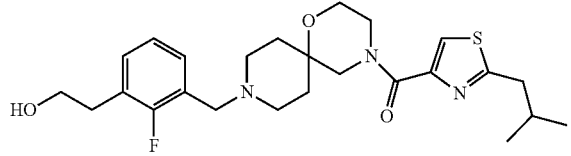 [SMILES: CC(C)Cc1nc(C(=O)N2CCOC3(CCN(Cc4cccc(CCO)c4F)CC3)C2)cs1]

O-(7-Azabenzotriazol-1-yl)-N,N,N',N'-tetramethyluronium hexafluorophosphate (0.2 g) was added to a solution of 2-(3-(1-oxa-4,9-diazaspiro[5.5]undecan-9-ylmethyl)-2-fluorophenyl)ethanol (example 67, step f) (0.13 g), 2-isobutylthiazole-4-carboxylic acid (example 72, step d) (0.08 g) and triethylamine (0.23 mL) in DMF (7 mL) at 0° C. and the resulting yellow solution allowed to warm to RT and was stirred for 2 h. The mixture was partitioned between ethyl acetate and brine (100 mL), the organic phase was washed with brine (2×100 mL), dried over sodium sulphate, filtered and then evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added, and the solvent evaporated under reduced pressure to give the subtitled compound as a clear gum. Yield 0.24 g.

m/z 476 (M+H)⁺ (APCI)
¹H NMR (400 MHz, D₆-DMSO, 90° C.) δ 7.90 (s, 1H), 7.22-7.14 (m, 2H), 7.03 (t, J=7.4 Hz, 1H), 4.35 (t, J=4.7 Hz, 1H), 3.68-3.57 (m, 6H), 3.52-3.42 (m, 2H), 2.89 (d, J=6.9 Hz, 2H), 2.76 (t, J=7.5 Hz, 2H), 2.70 (s, 2H), 2.45-2.28 (m, 4H), 2.12-2.03 (m, 1H), 1.74-1.65 (m, 2H), 1.57-1.48 (m, 2H), 0.96 (d, J=6.7 Hz, 6H).

f) (R)-7-(2-(2-Fluoro-3-((4-(2-isobutylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate Trifluoroacetic acid (0.031 mL) was added to a solution of (9-(2-fluoro-3-(2-hydroxyethyl)benzyl)-1-oxa-4,9-diazaspiro[5.5]undecan-4-yl)(2-isobutylthiazol-4-yl)methanone (example 72, step e) (0.19 g) in DCM (5 mL) at 0° C. The mixture was stirred for 5 min then Dess-Martin periodinane (0.25 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.023 mL) and (R)-7-(2-amino-1-hydroxyethyl)-4-hydroxybenzo[d]thiazol-2(3H)-one hydrochloride (WO2007027134, example 1, step d) (0.13 g) were then added and the mixture stirred for 5 min before cooling in an ice bath. Sodium cyanoborohydride (0.038 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-35% acetonitrile in 0.2% aqueous TFA). The fractions containing product were combined, evaporated in vacuo and the residue triturated with diethyl-ether to give the titled compound as a white solid. Yield 0.10 g.

m/z 684 (M+H)⁺ (APCI)
¹H NMR (400 MHz, D₆-DMSO, 90° C.) δ 11.39-11.19 (m, 1H), 7.94 (s, 1H), 7.53-7.40 (m, 2H), 7.25 (t, J=7.7 Hz, 1H), 6.93 (d, J=8.2 Hz, 1H), 6.77 (d, J=8.2 Hz, 1H), 4.92 (dd, J=8.5, 4.9 Hz, 1H), 4.33-4.26 (m, 2H), 3.72-3.59 (m, 6H), 3.28-3.01 (m, 10H), 2.88 (d, J=6.9 Hz, 2H), 2.11-1.95 (m, 3H), 1.84-1.69 (m, 2H), 0.95 (d, J=6.7 Hz, 6H). Five exchangeable protons not observed.

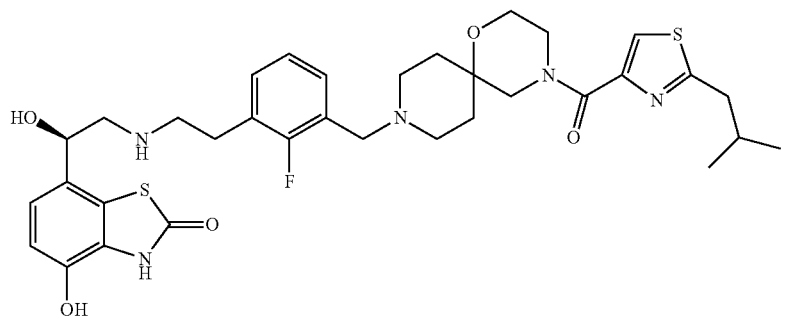 [SMILES: CC(C)Cc1nc(C(=O)N2CCOC3(CCN(Cc4cccc(CCNC[C@H](O)c5ccc(O)c6[nH]c(=O)sc56)c4F)CC3)C2)cs1]

EXAMPLE 73

(R)-7-(2-(2-Fluoro-3-((4-(5-isopropylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

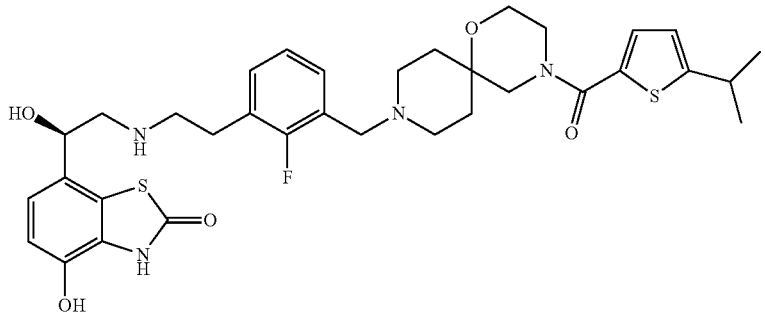 [SMILES: CC(C)c1ccc(C(=O)N2CCOC3(CCN(Cc4cccc(CCNC[C@H](O)c5ccc(O)c6[nH]c(=O)sc56)c4F)CC3)C2)s1]

a) (9-(2-Fluoro-3-(2-hydroxyethyl)benzyl)-1-oxa-4,9-diazaspiro[5.5]undecan-4-yl)(5-isopropylthiophen-2-yl)methanone

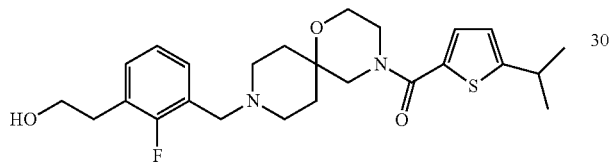

b) (R)-7-(2-(2-Fluoro-3-((4-(5-isopropylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

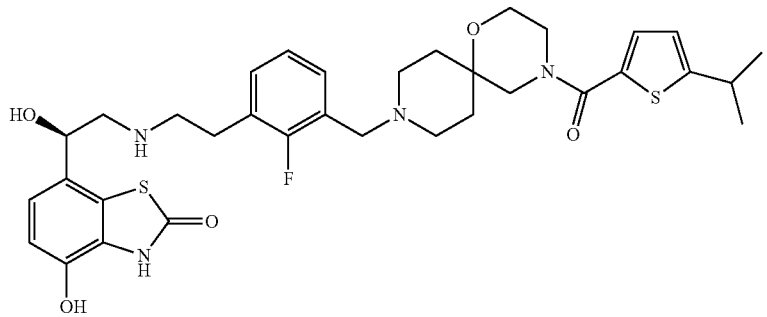 [SMILES: CC(C)c1ccc(C(=O)N2CCOC3(CCN(Cc4cccc(CCNC[C@H](O)c5ccc(O)c6[nH]c(=O)sc56)c4F)CC3)C2)s1]

O-(7-Azabenzotriazol-1-yl)-N,N,N',N'-tetramethyluronium hexafluorophosphate (0.2 g) was added to a solution of 2-(3-(1-oxa-4,9-diazaspiro[5.5]undecan-9-ylmethyl)-2-fluorophenyl)ethanol (example 67, step f) (0.13 g), 5-isopropylthiophene-2-carboxylic acid (0.07 g) and triethylamine (0.23 mL) in DMF (7 mL) at 0° C. The resulting yellow solution was allowed to warm to RT and was stirred for 2 h. The mixture was partitioned between ethyl acetate (100 mL) and brine (100 mL), the organic phase was washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added, and the solvent evaporated to give the subtitled compound as a clear gum. Yield 0.23 g.

m/z 461 (M+H)$^+$ (APCI)

$^1$H NMR (400 MHz, D$_6$-DMSO, 90° C.) δ 7.22-7.15 (m, 3H), 7.03 (t, J=7.4 Hz, 1H), 6.83 (d, J=3.6 Hz, 1H), 4.35 (t, J=5.0 Hz, 1H), 3.69-3.58 (m, 6H), 3.49 (s, 2H), 3.21-3.13 (m, 1H), 2.76 (t, J=8.4 Hz, 2H), 2.70 (s, 2H), 2.42-2.36 (m, 4H), 1.75-1.68 (m, 2H), 1.56-1.46 (m, 2H), 1.29 (d, J=6.7 Hz, 6H)

Trifluoroacetic acid (0.031 mL) was added to a solution of (9-(2-fluoro-3-(2-hydroxyethyl)benzyl)-1-oxa-4,9-diazaspiro[5.5]undecan-4-yl)(5-isopropylthiophen-2-yl)methanone (example 73, step a) (0.18 g) in DCM (5 mL) at 0° C. The mixture was stirred for 5 min then Dess-Martin periodinane (0.25 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.023 mL) and (R)-7-(2-amino-1-hydroxyethyl)-4-hydroxybenzo[d]thiazol-2(3H)-one hydrochloride (WO2007027134, example 1, step d) (0.13 g) were then added and the mixture stirred for 5 min before cooling in an ice bath. Sodium cyanoborohydride (0.025 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-40% acetonitrile in 0.2% aqueous TFA). The fractions containing product were combined, evaporated in vacuo and the residue triturated with dielthylether to give the titled compound as a white solid. Yield 0.12 g.

m/z 669 (M+H)+ (APCI)

$^1$H NMR (400 MHz, D$_6$-DMSO, 90° C.) δ 11.26 (s, 1H), 7.54-7.40 (m, 2H), 7.28-7.21 (m, 2H), 6.94 (d, J=8.5 Hz, 1H), 6.84 (dd, J=3.6, 0.8 Hz, 1H), 6.78 (d, J=8.2 Hz, 1H), 4.93 (dd, J=8.5, 4.9 Hz, 1H), 4.34 (s, 2H), 3.73-3.64 (m, 4H), 3.54 (s, 2H), 3.29-3.03 (m, 11H), 2.07-1.98 (m, 2H), 1.85-1.73 (m, 2H), 1.29 (d, J=6.9 Hz, 6H). Five exchangeable protons not observed.

EXAMPLE 74

(R)-7-(2-(2-Fluoro-3-((4-(4-isopropylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

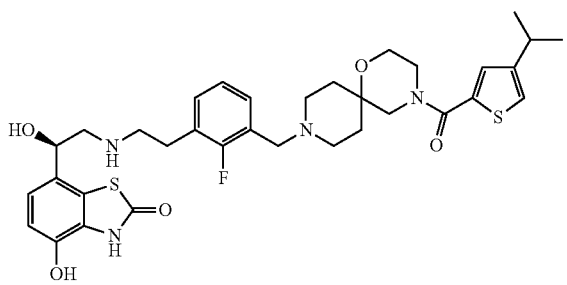 [SMILES: CC(C)c1csc(C(=O)N2CCOC3(CCN(Cc4cccc(CCNC[C@H](O)c5ccc(O)c6[nH]c(=O)sc56)c4F)CC3)C2)c1]

a) 1-(4-Isopropylthiophen-2-yl)ethanone

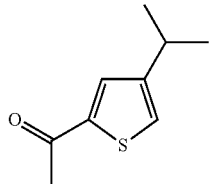

1-(Thiophen-2-yl)ethanone (5.4 mL) was added to an ice cold suspension of aluminum chloride (33 g), in dry chloroform (100 mL). 2-Bromopropane (5.2 mL) was then added dropwise over 5 min. The reaction was allowed to warm to RT and stirred overnight. The dark suspension was cautiously poured onto ice and the mixture stirred for 10 min. The layers were separated and the aqueous phase extracted with DCM (100 mL). The combined organic layers were washed with sodium hydroxide solution (2M, 200 mL) and water (200 mL), dried over sodium sulphate, filtered and evaporated. The residue was purified by silica gel chromatography eluting with 2% ethyl acetate in isohexane. The fractions containing product were combined and evaporated to give the subtitled compound as a light yellow oil. Yield 5.4 g.

$^1$H NMR (400 MHz, CDCl$_3$) δ 7.58 (d, J=1.3 Hz, 1H), 3.01-2.92 (m, 1H), 2.55 (s, 3H), 1.27 (d, J=6.9 Hz, 6H). One thiophene proton obscured by CDCl$_3$ signal ~7.26.

b) 4-Isopropylthiophene-2-carboxylic acid

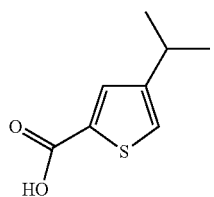

A solution of 1-(4-isopropylthiophen-2-yl)ethanone (example 74, step a) (1 g) in 1,4-dioxane (10 mL) was cautiously added to a solution of sodium hydroxide (1.19 g) in aqueous sodium hypochlorite (8%, 50 mL) at 60° C. The resulting mixture was heated to 75° C. and stirred for 1 h. The reaction was allowed to cool and the aqueous phase washed with DCM (50 mL). The aqueous phase was treated with aqueous sodium bisulphite solution (10%, 20 mL) and carefully acidified with concentrated hydrochloric acid. The resulting mixture was extracted with DCM (3×50 mL). The combined organic solutions were dried over sodium sulphate, filtered and evaporated to give a yellow oil. Purification was by preparative HPLC (Sunfire™, Gradient: 5-95% acetonitrile in 0.2% aqueous TFA). The fractions containing product were combined, evaporated and dried under high vacuum to give the subtitled compound as a white solid. Yield 0.5 g.

$^1$H NMR (300 MHz, D$_6$-DMSO) δ 12.95 (s, 1H), 7.65 (d, J=1.5 Hz, 1H), 7.51-7.49 (m, 1H), 2.94 (septet, J=6.9 Hz, 1H), 1.20 (d, J=6.9 Hz, 6H).

c) (9-(2-Fluoro-3-(2-hydroxyethyl)benzyl)-1-oxa-4,9-diazaspiro[5.5]undecan-4-yl)(4-isopropylthiophen-2-yl)methanone

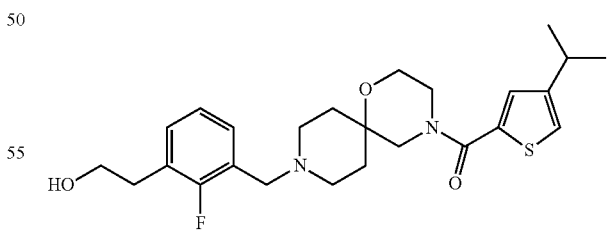

O-(7-Azabenzotriazol-1-yl)-N,N,N',N'-tetramethyluronium hexafluorophosphate (0.2 g) was added to a solution of 2-(3-(1-oxa-4,9-diazaspiro[5.5]undecan-9-ylmethyl)-2-fluorophenyl)ethanol (example 67, step f) (0.13 g), 4-isopropylthiophene-2-carboxylic acid (example 74, step b) (0.07 g) and triethylamine (0.23 mL) in DMF (7 mL) at 0° C. The resulting yellow solution was allowed to warm to RT and was stirred for 2 h. The mixture was partitioned between ethyl acetate (100 mL) and brine (100 mL), the organic layer was washed with brine (2×100 mL), dried over sodium sulphate, filtered and evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added, and the solvent evaporated under reduced pressure to give the subtitled compound as a clear gum. Yield 0.23 g.

m/z 461 (M+H)+ (APCI)

1H NMR (400 MHz, D6-DMSO, 90° C.) δ 7.30-7.14 (m, 4H), 7.05-7.00 (m, 1H), 4.35 (s, 1H), 3.68-3.58 (m, 6H), 3.51-3.47 (m, 2H), 2.98-2.92 (m, 1H), 2.75 (t, J=7.3 Hz, 2H), 2.70 (s, 2H), 2.41-2.34 (m, 4H), 1.75-1.68 (m, 2H), 1.56-1.47 (m, 2H), 1.21 (d, J=6.9 Hz, 6H).

d) (R)-7-(2-(2-Fluoro-3-((4-(4-isopropylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

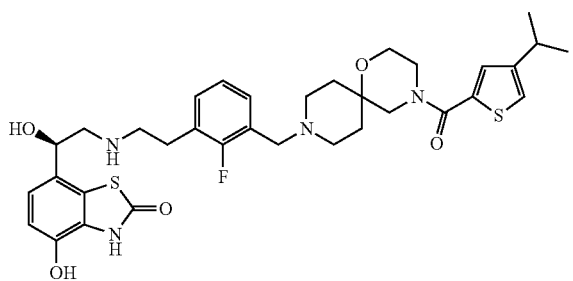 [SMILES: CC(C)c1csc(C(=O)N2CCOC3(CCN(Cc4cccc(CCNC[C@H](O)c5ccc(O)c6[nH]c(=O)sc56)c4F)CC3)C2)c1]

Trifluoroacetic acid (0.031 mL) was added to a solution of (9-(2-fluoro-3-(2-hydroxyethyl)benzyl)-1-oxa-4,9-diazaspiro[5.5]undecan-4-yl)(4-isopropylthiophen-2-yl)methanone (example 74, step c) (0.18 g) in DCM (5 mL) at 0° C. The mixture was stirred for 5 min then Dess-Martin periodinane (0.25 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.023 mL) and (R)-7-(2-amino-1-hydroxyethyl)-4-hydroxybenzo[d]thiazol-2(3H)-one hydrochloride (WO2007027134, example 1, step d) (0.13 g) were then added and the mixture stirred for 5 min before cooling in an ice bath. Sodium cyanoborohydride (0.025 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-40% acetonitrile in 0.2% aqueous TFA). The fractions containing product were combined, evaporated in vacuo and the residue triturated with diethylether to give the titled compound as a white solid. Yield 0.13 g.

m/z 669 (M+H)+ (APCI)

1H NMR (400 MHz, D6-DMSO, 90° C.) δ 11.26 (s, 1H), 7.53-7.47 (m, 1H), 7.47-7.41 (m, 1H), 7.31 (s, 1H), 7.29 (s, 1H), 7.25 (t, J=7.6 Hz, 1H), 6.94 (d, J=8.5 Hz, 1H), 6.78 (d, J=8.2 Hz, 1H), 4.93 (dd, J=8.3, 4.7 Hz, 1H), 4.35-4.31 (m, 2H), 3.73-3.62 (m, 4H), 3.54 (s, 2H), 3.26-3.03 (m, 10H), 2.94 (septet, J=7 Hz, 1H), 2.08-1.98 (m, 2H), 1.85-1.71 (m, 2H), 1.21 (d, J=6.9 Hz, 6H). Five exchangeable protons not observed.

EXAMPLE 75

(R)-7-(2-(2-Chloro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

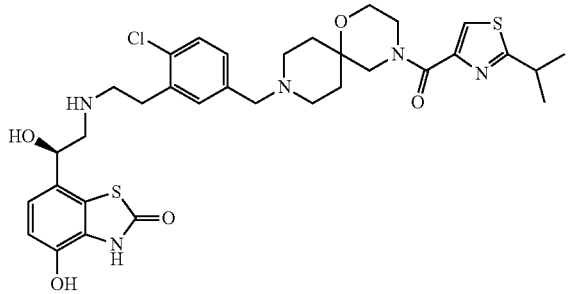 [SMILES: CC(C)c1nc(C(=O)N2CCOC3(CCN(Cc4ccc(Cl)c(CCNC[C@H](O)c5ccc(O)c6[nH]c(=O)sc56)c4)CC3)C2)cs1]

a) 3-(Carboxymethyl)-4-chlorobenzoic acid

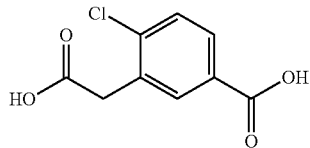 [SMILES: O=C(O)Cc1cc(C(=O)O)ccc1Cl]

Potassium hydroxide (1.549 g) in water (15 mL) was added to a suspension of 4-chloro-3-(cyanomethyl)benzoic acid (2.07 g) in ethanol (15 mL) and the resulting solution was heated at reflux for 4 hours, then allowed to cool. The mixture was concentrated in vacuo to remove the ethanol and then diluted with water and washed twice with ethyl acetate. The organic phases were discarded, whilst the aqueous phase was acidified to pH 1 with concentrated hydrochloric acid and extracted twice with ethyl acetate. The combined extracts were washed with brine, dried over anhydrous magnesium sulphate and concentrated in vacuo to afford the subtitled compound as a pale brown solid. Yield 2.06 g.

m/z 214 (M+) (EI)

b) 2-(2-Chloro-5-(hydroxymethyl)phenyl)ethanol

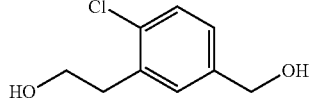

A solution of borane-methyl sulfide complex (2M in THF, 12.0 mL) was added portionwise over 3 minutes to a suspension of 3-(carboxymethyl)-4-chlorobenzoic acid (example 75, step a) (2.06 g) in dry THF (30 mL) at room temperature. The resulting effervescing dense suspension was stirred at room temperature for 1 hour, then heated to reflux for 1 hour. The cooled mixture was quenched by the portionwise addition of methanol (10 mL) over 2 minutes. The solution was stirred at room temperature for 30 minutes and then concentrated onto silica and purified by flash chromatography on silica eluted with 5% methanol in dichloromethane to afford the subtitled compound as a white solid. Yield 0.983 g.

$^1$H NMR (400 MHz, CDCl$_3$) δ 7.35 (d, J=8.2 Hz, 1H), 7.28 (d, J=2.1 Hz, 1H), 7.18 (dd, J=8.2, 2.1 Hz, 1H), 4.65 (s, 2H), 3.89 (t, J=6.7 Hz, 2H), 3.02 (t, J=6.5 Hz, 2H). Two exchangeable protons not observed.

c) 4-Chloro-3-(2-hydroxyethyl)benzaldehyde

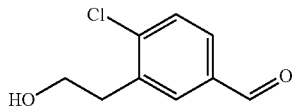

Manganese (IV) dioxide (1.00 g) was added to a solution of 2-(2-chloro-5-(hydroxymethyl)phenyl)ethanol (example 75, step b) (0.205 g) in DCM (10 mL), and the resulting suspension was stirred at room temperature overnight. The mixture was then filtered through Celite, washing the filter pad well with DCM. The filtrate and washings were concentrated in vacuo to afford the subtitled compound as a colourless oil. Yield 0.159 g.

$^1$H NMR (400 MHz, CDCl$_3$) δ 9.97 (s, 1H), 7.81 (d, J=2.0, 1H), 7.70 (dd, J=2.0, 8.2, 1H), 7.53 (t, J=6.7, 1H), 3.94 (dd, J=6.4, 11.6, 2H), 3.10 (t, J=6.6, 2H), 1.46 (t, J=5.2, 1H).

d) (9-(4-Chloro-3-(2-hydroxyethyl)benzyl)-1-oxa-4,9-diazaspiro[5.5]undecan-4-yl)(2-isopropylthiazol-4-yl)methanone

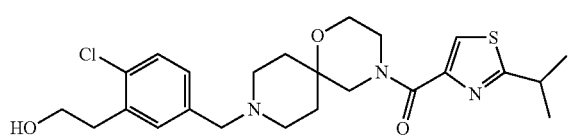 [SMILES: CC(C)c1nc(C(=O)N2CCOC3(CCN(Cc4ccc(Cl)c(CCO)c4)CC3)C2)cs1]

A solution of (2-isopropylthiazol-4-yl)(1-oxa-4,9-diazaspiro[5.5]undecan-4-yl)methanone trifluoroacetate (example 22, step b) (0.178 g) in NMP (2 mL) was treated with acetic acid (0.032 mL) and stirred for 5 minutes. A solution of 4-chloro-3-(2-hydroxyethyl)benzaldehyde (example 75, step c) (0.154 g) in NMP (3 mL) was then added, the resulting solution was stirred for 1 hour and was then treated with sodium triacetoxyborohydride (0.181 g) and stirred overnight at room temperature. More sodium triacetoxyborohydride (0.404 g) was added and the mixture was stirred for an additional 6 hours, then poured into saturated sodium bicarbonate and extracted twice with ethyl acetate. The combined extracts were washed three times with water, once with brine, then dried over anhydrous magnesium sulphate and purified by flash chromatography on silica eluted with 1:2:97 triethylamine:methanol:dichloromethane to afford the subtitled compound as a colourless gum. Yield 0.157 g.

$^1$H NMR (400 MHz, D$_6$-DMSO, 90° C.) δ 7.90 (s, 1H), 7.29 (d, J=8.2 Hz, 1H), 7.24 (d, J=1.4 Hz, 1H), 7.11 (dd, J=8.2, 1.8 Hz, 1H), 4.37 (t, J=5.3 Hz, 1H), 3.73-3.56 (m, 8H), 3.41 (s, 2H), 3.35-3.28 (m, 1H), 2.85 (t, J=6.9 Hz, 2H), 2.41-2.10 (m, 4H), 1.75-1.62 (m, 2H), 1.60-1.46 (m, 2H), 1.36 (d, J=6.7 Hz, 6H).

e) 2-(2-Chloro-5-((4-(2-isopropylthiazole-4-carbonyl)-1-oxa-4,9-diazaspiro[5.5]undecan-9-yl)methyl)phenyl)acetaldehyde

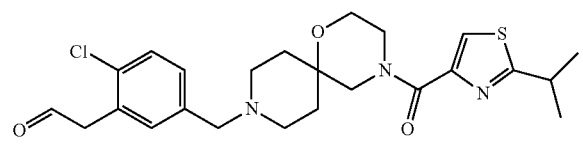 [SMILES: CC(C)c1nc(C(=O)N2CCOC3(CCN(Cc4ccc(Cl)c(CC=O)c4)CC3)C2)cs1]

A solution of (9-(4-chloro-3-(2-hydroxyethyl)benzyl)-1-oxa-4,9-diazaspiro[5.5]undecan-4-yl)(2-isopropylthiazol-4-yl)methanone (example 75, step d) (0.152 g) in DCM (5 mL) was cooled in ice-water, treated with trifluoroacetic acid (0.049 mL) and stirred for 5 minutes. Dess-Martin periodinane (0.205 g) was added, then the mixture was removed from the cooling bath and stirred at room temperature for 30 minutes. The solution was diluted with saturated sodium thiosulphate solution (5 mL), saturated sodium bicarbonate solution (5 mL) and ethyl acetate (5 mL) and the resulting mixture was stirred vigorously for 10 minutes. The mixture was then extracted twice with ethyl acetate, the combined organic phases were washed with brine, acidified with acetic acid (0.1 mL), dried over anhydrous magnesium sulphate and concentrated in vacuo to give the crude subtitled compound as a yellow gum. Yield 0.197 g.

m/z 476 (M+H)$^+$ (APCI)

f) (R)-7-(2-(2-Chloro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

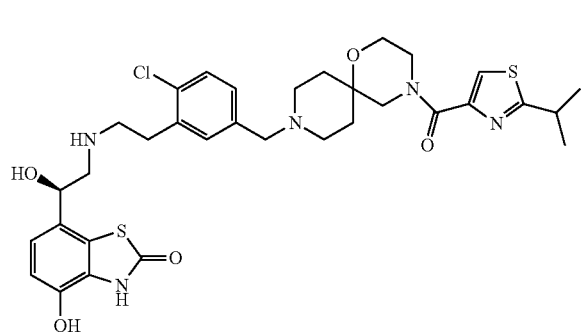 [SMILES: CC(C)c1nc(C(=O)N2CCOC3(CCN(Cc4ccc(Cl)c(CCNC[C@H](O)c5ccc(O)c6[nH]c(=O)sc56)c4)CC3)C2)cs1]

A solution of (R)-7-(2-amino-1-hydroxyethyl)-4-hydroxybenzo[d]thiazol-2(3H)-one hydrochloride (WO2007027134, example 1, step d) (0.145 g) in methanol (2 mL) was treated with acetic acid (0.024 mL) and stirred for 5 minutes. A solution of 2-(2-chloro-5-((4-(2-isopropylthiazole-4-carbonyl)-1-oxa-4,9-diazaspiro[5.5]undecan-9-yl)methyl)phenyl)acetaldehyde (example 75, step e) (0.197 g) in methanol (3 mL) was then added, and the resulting mixture was stirred at room temperature for 5 minutes, before cooling in ice-water and treating with sodium cyanoborohydride (0.039 g). The cooling bath was removed and the mixture was stirred at room temperature for 140 minutes, before treating with more sodium cyanoborohydride (0.040 g). The mixture was then stirred overnight. The following morning, the mixture was quenched with a drop of water and the solution was filtered and purified by preparative HPLC (Sunfire™, Gradient: 15-35% acetonitrile in 0.2% aqueous TFA). Fractions containing product were concentrated in vacuo and co-evaporated from acetonitrile three times to give a colourless residue. The residue was triturated with diethyl ether to give a solid, which was collected by filtration, washed with diethyl ether and dried in vacuo at room temperature to afford the titled compound as a white solid. Yield 0.077 g.

m/z 686/688 (M+H)$^+$ (APCI)

$^1$H NMR (400 MHz, D$_6$-DMSO, 90° C.) δ 7.94 (s, 1H), 7.53 (d, J=8.2 Hz, 1H), 7.48-7.39 (m, 2H), 6.94 (d, J=8.2 Hz, 1H), 6.77 (d, J=8.5 Hz, 1H), 4.91 (dd, J=8.5, 4.9 Hz, 1H), 4.22 (s, 2H), 3.75-3.60 (m, 6H), 3.52-2.96 (m, 11H), 2.09-1.90 (m, 2H), 1.83-1.62 (m, 2H), 1.35 (d, J=6.9 Hz, 6H). Six exchangeable protons not observed.

EXAMPLE 76

(R)-8-Hydroxy-5-(1-hydroxy-2-(3-((4-(4-isopropylthiazole-2-carbonyl)-1-oxa-4,9-diazaspiro[5.5]undecan-9-yl)methyl)phenethylamino)ethyl)quinolin-2 (1H)-one ditrifluoroacetate A solution of (9-(3-(2-hydroxyethyl)benzyl)-1-oxa-4,9-diazaspiro[5.5]undecan-4-yl)(4-isopropylthiazol-2-yl) methanone (example 66, step c) (0.195 g) in DCM (20 mL) was treated with trifluoroacetic acid (0.034 ml) followed by Dess-Martin periodinane (0.242 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.025 ml) was added to this solution and the solvent then removed under reduced pressure. The residue was dissolved in methanol (3 mL) and added to a solution of (R)-5-(2-amino-1-(tert-butyldimethylsilyloxy)ethyl)-8-hydroxyquinolin-2(1H)-one (WO2004106333) (191 mg) in methanol (15 mL). The mixture was cooled to 0° C. and sodium triacetoxyborohydride (0.140 g) was added in one portion. The reaction mixture was stirred at 20° C. for 3 hours. The solvent was removed under reduced pressure and the residue partitioned between ethyl acetate and saturated sodium bicarbonate solution. The organic layer was dried over sodium sulphate, filtered and the solvent removed under reduced

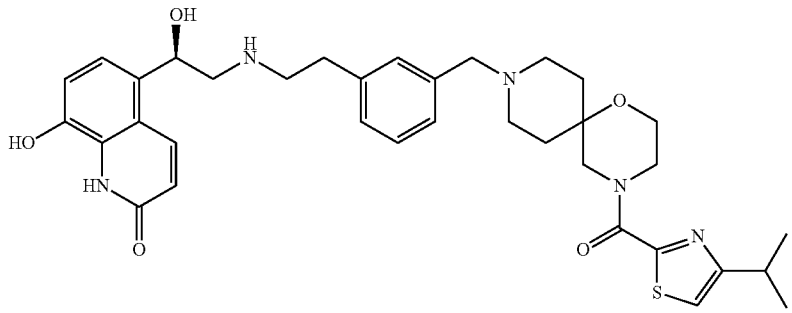 [SMILES: CC(C)c1csc(C(=O)N2CCOC3(CCN(Cc4cccc(CCNC[C@H](O)c5ccc(O)c6[nH]c(=O)ccc56)c4)CC3)C2)n1]

a) (R)-5-(1-(tert-Butyldimethylsilyloxy)-2-(3-((4-(4-isopropylthiazole-2-carbonyl)-1-oxa-4,9-diazaspiro [5.5]undecan-9-yl)methyl)phenethylamino)ethyl)-8-hydroxyquinolin-2(1H)-one

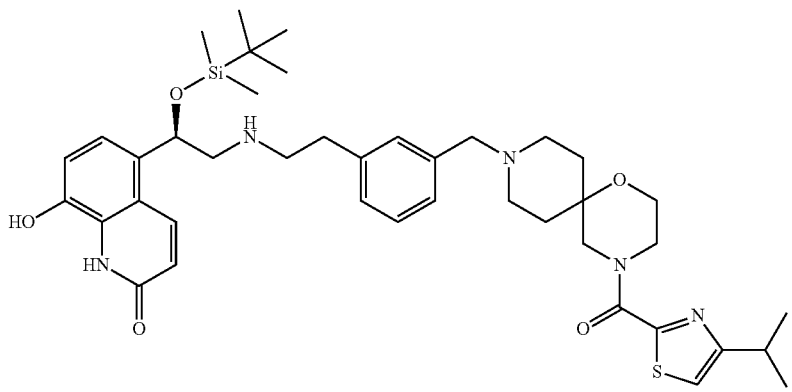 [SMILES: CC(C)c1csc(C(=O)N2CCOC3(CCN(Cc4cccc(CCNC[C@H](O[Si](C)(C)C(C)(C)C)c5ccc(O)c6[nH]c(=O)ccc56)c4)CC3)C2)n1]

pressure. The crude product was purified by flash silica chromatography using 9% methanol in dichloromethane with 1% '880' aqueous ammonia as solvent. Pure fractions were evaporated to dryness to afford the subtitled compound. Yield 0.133 g.

m/z 760 (M+H)+ (APCI)

b) (R)-8-Hydroxy-5-(1-hydroxy-2-(3-((4-(4-isopropylthiazole-2-carbonyl)-1-oxa-4,9-diazaspiro[5.5]undecan-9-yl)methyl)phenethylamino)ethyl)quinolin-2(1H)-one ditrifluoroacetate

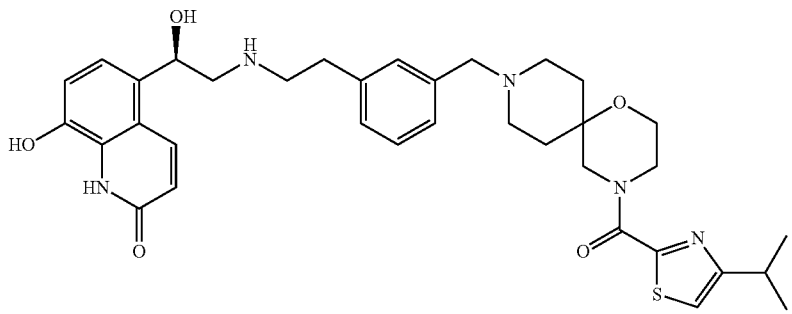 [SMILES: CC(C)c1csc(C(=O)N2CCOC3(CCN(Cc4cccc(CCNC[C@H](O)c5ccc(O)c6[nH]c(=O)ccc56)c4)CC3)C2)n1]

Triethylamine trihydrofluoride (0.034 mL) in methanol (1 mL) was added to a solution of (R)-5-(1-(tert-butyldimethylsilyloxy)-2-(3-((4-(4-isopropylthiazole-2-carbonyl)-1-oxa-4,9-diazaspiro[5.5]undecan-9-yl)methyl)phenethylamino)ethyl)-8-hydroxyquinolin-2(1H)-one (example 76, step a) (0.133 g) in THF (4 mL) and the reaction mixture allowed to stand at 20° C. for 18 hours. The solvent was removed under reduced pressure and the crude product was purified by preparative HPLC (Sunfire™, Gradient: 10-40% acetonitrile in 0.2% aqueous TFA). The fractions containing the desired compound were evaporated to dryness to afford the titled compound. Yield 0.090 g.

m/z 646 (M+H)+ (APCI)
$^1$H NMR (400 MHz, $D_6$-DMSO, 90° C.) δ 8.17 (d, J=10.0 Hz, 1H), 7.51 (s, 1H), 7.44-7.33 (m, 4H), 7.14 (d, J=8.2 Hz, 1H), 7.00 (d, J=8.2 Hz, 1H), 6.54 (d, J=10.0 Hz, 1H), 5.38-5.33 (m, 1H), 4.28 (s, 2H), 3.78-3.74 (m, 2H), 4.13-3.47 (m, 4H), 3.28 (t, J=8.2 Hz, 2H), 3.21-3.00 (m, 9H), 2.09-1.99 (m, 2H), 1.84-1.72 (m, 2H), 1.26 (d, J=6.8 Hz, 6H). Six exchangeable protons not observed.

EXAMPLE 77

(R)-5-(2-(2,3-Difluoro-4-(2-(4-(2-isopropylthiazole-4-carbonyl)-1-oxa-4,9-diazaspiro[5.5]undecan-9-yl)ethoxy)phenethylamino)-1-hydroxyethyl)-8-hydroxyquinolin-2(1H)-one ditrifluoroacetate

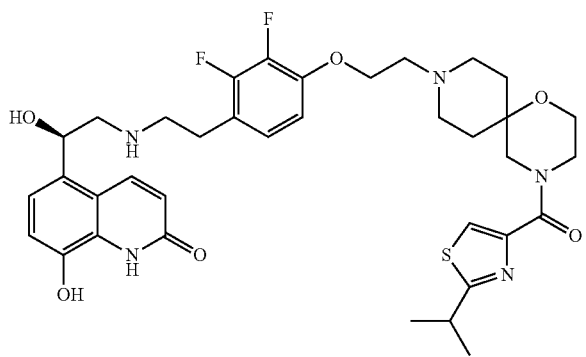 [SMILES: CC(C)c1nc(C(=O)N2CCOC3(CCN(CCOc4ccc(CCNC[C@H](O)c5ccc(O)c6[nH]c(=O)ccc56)c(F)c4F)CC3)C2)cs1]

a) 2-(2,3-Difluoro-4-hydroxyphenyl)acetic acid

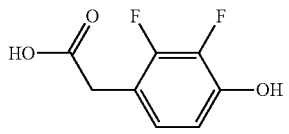

A solution of boron tribromide (1M in DCM, 13.4 mL) was added dropwise to suspension of 2-(2,3-difluoro-4-methoxyphenyl)acetic acid (1.18 g) in DCM (5 mL) at −78° C. The reaction was allowed to warm to RT and stirred overnight. The reaction was cooled to −78° C. and a solution of boron tribromide (1M in DCM, 13.4 mL) was added. The reaction was allowed to warm to RT and stirred for 1 h. The reaction was poured onto ice. The resulting aqueous solution was extracted with DCM (5×50 mL). The aqueous phase was then extracted with ethyl acetate (3×100 mL). The organic solutions were combined, washed with brine (50 mL), dried over magnesium sulphate, filtered and evaporated to give the subtitled compound as a tan solid. Yield 1.09 g.

$^1$H NMR (400 MHz, D$_6$-DMSO) δ 12.43 (s, 1H), 10.24 (s, 1H), 6.91 (td, J=8.3, 2.1 Hz, 1H), 6.72 (td, J=8.3, 1.8 Hz, 1H), 3.54 (s, 2H).

b) 2,3-Difluoro-4-(2-hydroxyethyl)phenol


A solution of borane dimethylsulfide complex (2M in THF, 14.4 mL) was added dropwise to a solution of 2-(2,3-difluoro-4-hydroxyphenyl)acetic acid (example 77, step a) (1.08 g) in tetrahydrofuran (25 mL) at 0° C. and the resulting mixture was allowed to warm to RT and stirred overnight. The reaction was quenched with methanol and when bubbling had ceased the solvent evaporated. The residue was purified by silica gel chromatography eluting with 4:1 isohexane:ethyl acetate to ethyl acetate gradient. The fractions containing product were combined and evaporated to give the subtitled compound as white solid. Yield 0.95 g.

$^1$H NMR (300 MHz, D$_6$-DMSO) δ 10.08 (s, 1H), 6.87 (td, J=8.3, 2.2 Hz, 1H), 6.69 (td, J=8.4, 1.9 Hz, 1H), 4.68 (t, J=5.3 Hz, 1H), 3.58-3.49 (m, 2H), 2.66 (t, J=7.0 Hz, 2H).

c) 2-(4-(2,2-Diethoxyethoxy)-2,3-difluorophenyl)ethanol

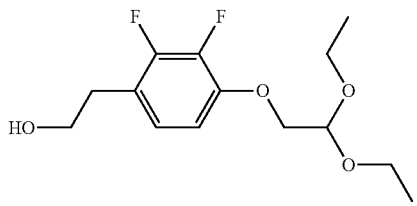 [SMILES: CCOC(COc1ccc(CCO)c(F)c1F)OCC]

Cesium carbonate (0.99 g) was added to a solution of 2,3-difluoro-4-(2-hydroxyethyl)phenol (example 77, step b) (0.44 g) and 2-bromo-1,1-diethoxyethane (0.4 mL) in DMF (10 mL). The resulting suspension was heated at 90° C. for 18 h. The reaction was allowed to cool and poured into water (100 mL). The aqueous mixture was extracted with diethyl-ether (3×100 mL). The combined organic solutions were washed with water (200 mL) and brine (200 mL), dried over magnesium sulfate, filtered and evaporated. The crude material was purified by silica gel chromatography eluting with isohexane to 1:1 ethyl acetate:isohexane gradient. The fractions containing product were combined and evaporated to give the subtitled compound as a yellow oil. Yield 0.49 g.

$^1$H NMR (400 MHz, D$_6$-DMSO) δ 7.06-6.93 (m, 2H), 4.81 (t, J=5.1 Hz, 1H), 4.70 (t, J=5.3 Hz, 1H), 4.02 (d, J=5.4 Hz, 2H), 3.73-3.62 (m, 2H), 3.61-3.50 (m, 4H), 2.71 (t, J=6.9 Hz, 2H), 1.13 (t, J=7.0 Hz, 6H).

d) 2-(2,3-Difluoro-4-(2-hydroxyethyl)phenoxy)acetaldehyde

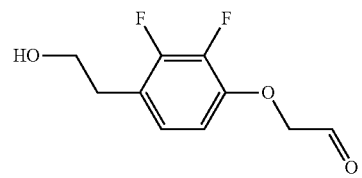 [SMILES: O=CCOc1ccc(CCO)c(F)c1F]

Concentrated hydrochloric acid (5 mL) was added to a solution of 2-(4-(2,2-diethoxyethoxy)-2,3-difluorophenyl)ethanol (example 77, step c) (0.49 g) in 1,4-dioxane (10 mL) and the resulting mixture was stirred for 1 h. The mixture was carefully diluted with water (50 mL) and extracted with ethyl acetate (3×50 mL). The combined organics were washed with water (50 mL) and brine (50 mL), dried over sodium sulphate, filtered and evaporated to give the subtitled compound, which was used directly. Yield 0.31 g.

e) (9-(2-(2,3-Difluoro-4-(2-hydroxyethyl)phenoxy)ethyl)-1-oxa-4,9-diazaspiro[5.5]undecan-4-yl)(2-isopropylthiazol-4-yl)methanone

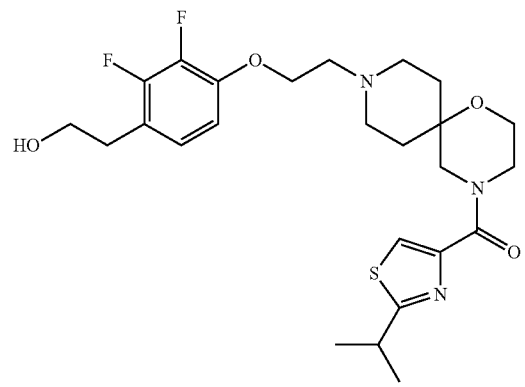 [SMILES: CC(C)c1nc(C(=O)N2CCOC3(CCN(CCOc4ccc(CCO)c(F)c4F)CC3)C2)cs1]

(2-Isopropylthiazol-4-yl)(1-oxa-4,9-diazaspiro[5.5]undecan-4-yl)methanone trifluoroacetate (example 22, step b) (0.5 g) was added to a solution of 2-(2,3-difluoro-4-(2-hydroxyethyl)phenoxy)acetaldehyde (example 77, step d) (0.31 g) in N-methyl-2-pyrrolidinone (10 mL) and acetic acid (0.07 mL). The resulting mixture was stirred for 30 min then cooled in an ice bath. Sodium triacetoxyborohydride (0.38 g) was then added and the reaction was allowed to warm to RT and stirred overnight. The reaction mixture was partitioned between ethyl acetate (100 mL) and water (100 mL). The aqueous phase was basified with saturated sodium hydrogen carbonate solution and the layers separated. The aqueous phase was extracted with ethyl acetate (2×100 mL). The combined organic solutions were washed with water (100 mL) and brine (100 mL), dried over sodium sulphate, filtered and evaporated.

The residue was purified by silica gel chromatography, eluting with 47.5:47.5:5 isohexane:ethylacetate:triethylamine to 5% triethylamine in ethyl acetate. The fractions containing product were combined and evaporated to give the subtitled compound as a clear gum. Yield 0.41 g.

m/z 510 (M+H)+ (APCI)

$^1$H NMR (400 MHz, D$_6$-DMSO, 90° C.) δ 7.93 (s, 1H), 7.06-6.85 (m, 2H), 4.58-4.36 (m, 1H), 4.13 (t, J=5.7 Hz, 2H), 3.73-3.51 (m, 8H), 3.36-3.23 (m, 1H), 2.76-2.63 (m, 4H), 1.76-1.45 (m, 4H), 1.35 (d, J=6.9 Hz, 6H)+4 protons obscured by DMSO peak.

f) (R)-5-(2-(2,3-Difluoro-4-(2-(4-(2-isopropylthiazole-4-carbonyl)-1-oxa-4,9-diazaspiro[5.5]undecan-9-yl)ethoxy)phenethylamino)-1-hydroxyethyl)-8-hydroxyquinolin-2(1H)-one ditrifluoroacetate

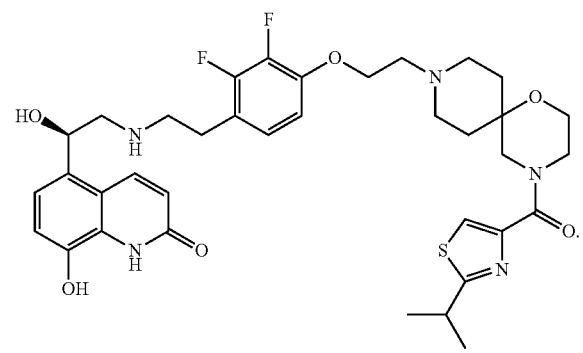 [SMILES: CC(C)c1nc(C(=O)N2CCOC3(CCN(CCOc4ccc(CCNC[C@H](O)c5ccc(O)c6[nH]c(=O)ccc56)c(F)c4F)CC3)C2)cs1]

Trifluoroacetic acid (0.03 mL) was added to a solution of (9-(2-(2,3-difluoro-4-(2-hydroxyethyl)phenoxy)ethyl)-1-oxa-4,9-diazaspiro[5.5]undecan-4-yl)(2-isopropylthiazol-4-yl)methanone (example 77, step e) (0.18 g) in DCM (5 mL) at 0° C. The reaction was stirred for 5 min then Dess-Martin periodinane (0.225 g) was added. The mixture was allowed to warm to RT and stirred for 1 h. Saturated sodium thiosulphate solution (5 mL), saturated sodium bicarbonate solution (5 mL) and ethyl acetate (20 mL) were added and the mixture stirred vigorously for 5 min. The layers were separated and the aqueous extracted with ethyl acetate (20 mL). The combined organics were washed with brine (20 mL), acidified with a few drops of acetic acid, dried over sodium sulphate, filtered and evaporated. The residue was redissolved in methanol (5 mL), acetic acid (0.02 mL) and (R)-5-(2-amino-1-(tert-butyldimethylsilyloxy)ethyl)-8-hydroxyquinolin-2 (1H)-one (WO2004106333) (0.12 g) were added, the mixture was stirred for 5 min and cooled in an ice bath. Sodium cyanoborohydride (0.033 g) was then added, the reaction was allowed to warm to RT and stirred overnight. The reaction was concentrated and purified by silica gel chromatography eluting with 94.5:5:0.5 to 89:10:1 DCM:methanol:'880' ammonia gradient. The fractions containing product were combined and evaporated. The residue was dissolved in THF (5 mL), triethylamine trihydrofluoride (0.17 mL) was added and the mixture stirred overnight. The solvent was evaporated and the residue azeotroped twice with toluene. Purification was by preparative HPLC (Sunfire™, Gradient: 10-30% acetonitrile in 0.2% aqueous TFA). The fractions containing product were combined, evaporated and triturated with ether to give the titled compound as a white solid. Yield 0.11 g.

m/z 712 (M+H)+ (APCI)

$^1$H NMR (400 MHz, D$_6$-DMSO, 90° C.) δ 8.18 (d, J=9.7 Hz, 1H), 7.96 (s, 1H), 7.18-6.96 (m, 4H), 6.54 (d, J=10.0 Hz, 1H), 5.36 (dd, J=8.7, 4.1 Hz, 1H), 4.50-4.42 (m, 2H), 3.76-3.65 (m, 6H), 3.62-3.54 (m, 2H), 3.44-2.98 (m, 11H), 2.12-2.01 (m, 2H), 1.90-1.75 (m, 2H), 1.35 (d, J=6.7 Hz, 6H). Six exchangeable protons not observed.

EXAMPLE 78

(R)-7-(2-(3-((4-(2-Butylthiazole-4-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

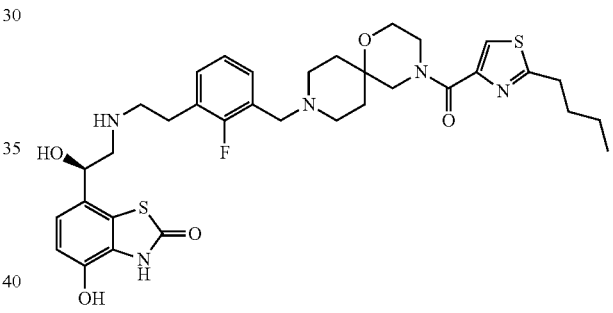

a) tert-Butyl(2-fluorophenethoxy)dimethylsilane

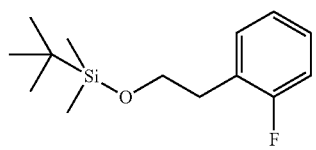 [SMILES: CC(C)(C)[Si](C)(C)OCCc1ccccc1F]

tert-Butyldimethylsilyl chloride (6.45 g) was added to a stirred solution of 2-(2-fluorophenyl)ethanol (5.00 g) and 1H-imidazole (7.29 g) in dry DMF (30 mL) cooled in an ice bath. After 45 min, the reaction mixture was diluted with ethyl acetate, washed three times with water and evaporated in vacuo. The resulting gum was dissolved in isohexane and applied to a silica gel column eluting with isohexane followed by 1:3 ethyl acetate:isohexane to collect the product as an oil. Yield 9.0 g.

$^1$H NMR (400 MHz, CDCl$_3$) δ 7.28-7.18 (m, 2H), 7.13-7.00 (m, 2H), 3.84 (t, J=6.8 Hz, 2H), 2.89 (t, J=7.2 Hz, 2H), 0.89 (s, 9H), 0.008 (s, 6H).

b) 3-(2-(tert-Butyldimethylsilyloxy)ethyl)-2-fluorobenzaldehyde

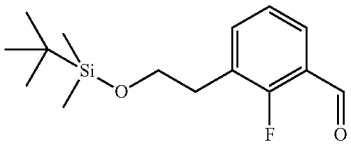 [SMILES: CC(C)(C)[Si](C)(C)OCCc1cccc(C=O)c1F]

tert-Butyl(2-fluorophenethoxy)dimethylsilane (example 78, step a) (5.00 g) was added over 5 minutes to a stirred solution of sec-butyllithium (1.4 molar solution in cyclohexane, 14.0 mL) and N1-(2-(dimethylamino)ethyl)-N1,N2,N2-trimethylethane-1,2-diamine (4.10 mL) in THF (25 mL) cooled to −78° C. After 2 h, N,N-dimethylformamide (10.06 g) was added, the reaction mixture was stirred at −78° C. for 1 h, and then the cooling bath was removed. After a further 0.5 h, the reaction was quenched with water. Ethyl acetate (300 mL) was added and the reaction mixture washed with water (3×150 mL), 2M HCl (2×50 mL), water (2×50 mL), brine then dried over sodium sulphate, filtered and evaporated in vacuo to give the subtitled compound as an oil. Yield 5.3 g.

$^1$H NMR (400 MHz, CDCl$_3$) δ 10.40 (s, 1H), 7.76 (dt, J=2.0 and 6.8 Hz, 1H), 7.54 (dt, J=1.6 and 7.2 Hz, 1H), 7.21 (t, J=7.2 Hz, 1H), 3.88 (t, J=5.2 Hz, 2H), 2.95 (dt, J=1.2 and 6.4 Hz, 2H), 0.88 (s, 9H), 0.008 (s, 6H).

c) 1-(9-(3-(2-(tert-Butyldimethylsilyloxy)ethyl)-2-fluorobenzyl)-1-oxa-4,9-diazaspiro[5.5]undecan-4-yl)-2,2,2-trifluoroethanone

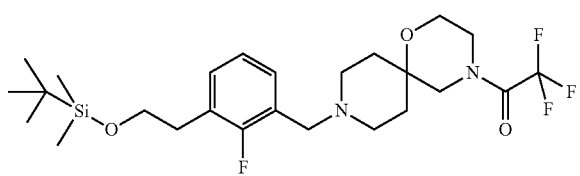 [SMILES: CC(C)(C)[Si](C)(C)OCCc1cccc(CN2CCC3(CC2)CN(C(=O)C(F)(F)F)CCO3)c1F]

3-(2-(tert-Butyldimethylsilyloxy)ethyl)-2-fluorobenzaldehyde (example 78, step b) (2.159 g) was added to stirred solution of 2,2,2-trifluoro-1-(1-oxa-4,9-diazaspiro[5.5]undecan-4-yl)ethanone trifluoroacetate (example 12, step d) (2.80 g) and acetic acid (0.438 mL) in NMP (25 mL). After 5 minutes, sodium triacetoxyborohydride (3.24 g) was added. After 16 h, water was added and the mixture partitioned between water (250 mL) and ethyl acetate (250 mL). The ethyl acetate solution was washed with water (3×250 mL) and brine, then evaporated to dryness. Purification by silica gel chromatography eluting with 20:1:1, isohexane:ethyl acetate:triethylamine gave the subtitled compound as a gum. Yield 2.5 g.

$^1$H NMR (400 MHz, CDCl$_3$) δ 7.27-7.20 (m, 1H), 7.20-7.13 (m, 1H), 7.08-7.01 (m, 1H), 3.84 (t, J=7.2 Hz, 3H), 3.80-3.77 (m, 2H), 3.71-3.67 (m, 1H), 3.64-3.58 (m, 3H), 3.56 (s, 1H), 3.41 (s, 1H), 2.90 (q, J=6.4 Hz, 2H), 2.69-2.62 (m, 1H), 2.52-2.44 (m, 1H), 2.43-2.35 (m, 1H), 1.92-1.80 (m, 2H), 1.72-1.60 (m, 2H), 0.89 (s, 9H), 0.00 (s, 6H).

d) 9-(3-(2-(tert-Butyldimethylsilyloxy)ethyl)-2-fluorobenzyl)-1-oxa-4,9-diazaspiro[5.5]undecane

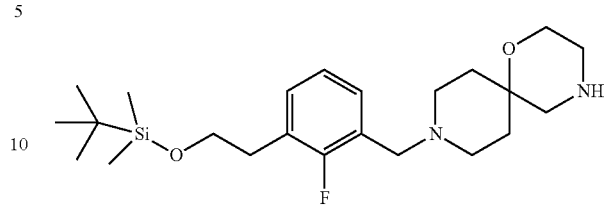

'880' Aqueous ammonia (3.0 mL) was added to stirred solution of 1-(9-(3-(2-(tert-butyldimethylsilyloxy)ethyl)-2-fluorobenzyl)-1-oxa-4,9-diazaspiro[5.5]undecan-4-yl)-2,2,2-trifluoroethanone (example 78, step c) (2.5 g) in MeOH (10 mL). After 1 h, the reaction mixture was evaporated to dryness. Acetonitrile was added, the solution was evaporated to dryness in vacuo, and the process repeated three times to give the subtitled compound as an oil. Yield 2.07 g. Used directly.

m/z 423 (M+H)$^+$ (APCI)

e) Pentanethioamide

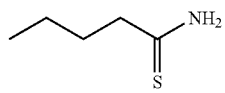

Phosphorus pentasulfide (5.56 g) was added to a stirred suspension of pentanamide (10.0 g) in methyl tert-butyl ether (300 mL). After 16 h, the mixture was filtered through Celite and evaporated in vacuo to give the subtitled compound as a yellow oil. Yield 11.4 g.

$^1$H NMR (400 MHz, D$_6$-DMSO) δ 9.35-9.23 (br s, 1H), 9.15-9.05 (br s, 1H), 2.52-2.42 (m, 2H), 1.68-1.55 (m, 2H), 1.35-1.22 (m, 2H), 0.87 (t, J=7.6 Hz, 3H).

f) Ethyl 2-butylthiazole-4-carboxylate

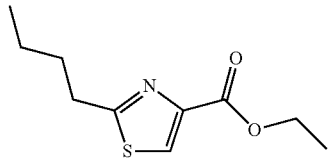

Ethyl 3-bromo-2-oxopropanoate (6.76 mL) was added very carefully to a stirred solution of pentanethioamide (example 78, step e) (6.30 g) in ethanol (100 mL). The solution was then heated at reflux for 16 h. After cooling, the reaction mixture was diluted with ethyl acetate, washed with saturated sodium bicarbonate solution and evaporated in vacuo. Purification by silica gel chromatography eluting with 1:6 ethyl acetate: isohexane gave the subtitled compound as a yellow oil. Yield 6.5 g.

$^1$H NMR (400 MHz, CDCl$_3$) δ 8.05 (s, 1H), 4.42 (q, J=7.1 Hz, 2H), 3.02-3.05 (m, 2H), 1.85-1.75 (m, 2H), 1.50-1.38 (m, 5H), 0.95 (t, J=7.1 Hz, 3H).

g) 2-Butylthiazole-4-carboxylic acid

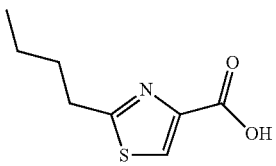

Lithium hydroxide (5.00 g) was added to a stirred mixture of ethyl 2-butylthiazole-4-carboxylate (example 78, step f) (6.50 g) in THF (80 mL) and water (20 mL). After 16 h, concentrated hydrochloric acid (10 mL) was added and the solution concentrated to ~40 mL. The reaction mixture was partitioned between ethyl acetate and brine. The aqueous layer was extracted three times with ethyl acetate. The combined organic layers were dried over magnesium sulphate, filtered and evaporated in vacuo to give the subtitled compound as an off white solid. Yield 4.6 g.

$^1$H NMR (300 MHz, CDCl$_3$) δ 8.18 (s, 1H), 3.11-3.03 (m, 2H), 1.88-1.78 (m, 2H), 1.52-1.38 (m, 2H), 0.97 (t, J=7.2 Hz, 3H). One exchangeable proton not observed.

h) (9-(3-(2-(tert-Butyldimethylsilyloxy)ethyl)-2-fluorobenzyl)-1-oxa-4,9-diazaspiro[5.5]undecan-4-yl)(2-butylthiazol-4-yl)methanone

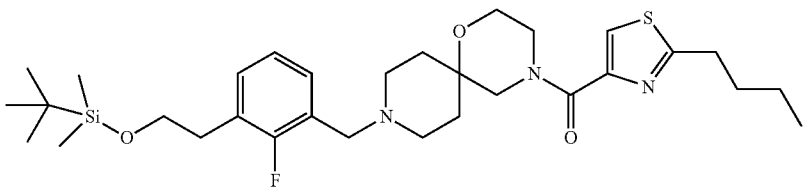 [SMILES: CCCCc1nc(C(=O)N2CCOC3(CCN(Cc4cccc(CCO[Si](C)(C)C(C)(C)C)c4F)CC3)C2)cs1]

2-(3H-[1,2,3]Triazolo[4,5-b]pyridin-3-yl)-1,1,3,3-tetramethylisouronium hexafluorophosphate(V) (0.378 g) was added to a stirred solution of 2-butylthiazole-4-carboxylic acid (example 78, step g) (0.193 g), 9-(3-(2-(tert-butyldimethylsilyloxy)ethyl)-2-fluorobenzyl)-1-oxa-4,9-diazaspiro[5.5]undecane (example 78, step d) (0.4 g), and triethylamine (0.383 g) in DMF (4 mL). After 1 h, the reaction mixture was partitioned between water and ethyl acetate. The ethyl acetate layer was washed twice with water and brine, dried over magnesium sulphate, filtered and evaporated in vacuo. Purification by silica gel chromatography eluting with 7:1:0.5, isohexane:ethyl acetate:triethylamine gave the subtitled compound as a gum. Yield 0.35 g.

$^1$H NMR (400 MHz, D$_6$-DMSO, 90° C.) δ 7.94 (s, 1H), 7.30-7.16 (m, 2H), 7.13-7.05 (m, 1H), 3.88-3.80 (m, 2H), 3.74-3.62 (m, 6H), 3.55-3.49 (m, 2H), 3.09-3.00 (m, 2H under water peak), 2.87-2.79 (m, 2H), 2.49-2.32 (m, 4H), 1.84-1.68 (m, 4H), 1.62-1.51 (m, 2H), 1.50-1.39 (m, 2H), 0.97 (t, J=7.9 Hz, 3H), 0.87 (s, 9H), 0.00 (s, 6H).

i) (2-Butylthiazol-4-yl)(9-(2-fluoro-3-(2-hydroxyethyl)benzyl)-1-oxa-4,9-diazaspiro[5.5]undecan-4-yl)methanone

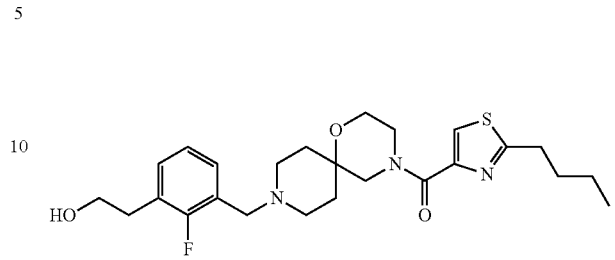

TBAF (1M solution in THF, 2.0 mL) was added to a solution of (9-(3-(2-(tert-butyldimethylsilyloxy)ethyl)-2-fluorobenzyl)-1-oxa-4,9-diazaspiro[5.5]undecan-4-yl)(2-butylthiazol-4-yl)methanone (example 78, step h) (0.350 g) in THF (4 mL). After 0.5 h, the solution was concentrated. Purification by silica gel chromatography eluting with 10:1 ethyl acetate; triethylamine gave the subtitled compound as a gum. Yield 0.24 g.

$^1$H NMR (400 MHz, D$_6$-DMSO, 90° C.) δ 7.88 (s, 1H), 7.22-7.13 (m, 2H), 7.03 (t, J=7.6 Hz, 1H), 4.35 (t, J=5.2 Hz, 1H), 3.68-3.56 (m, 12H), 3.48 (s, 2H), 3.00 (t, J=7.5 Hz, 2H), 2.75 (t, J=7.5 Hz, 2H), 2.44-2.28 (m, 4H), 1.78-1.65 (m, 2H), 1.45-1.33 (m, 2H), 0.91 (t, J=7.5 Hz, 3H).

j) 2-(3-((4-(2-Butylthiazole-4-carbonyl)-1-oxa-4,9-diazaspiro[5.5]undecan-9-yl)methyl)-2-fluorophenyl)acetaldehyde

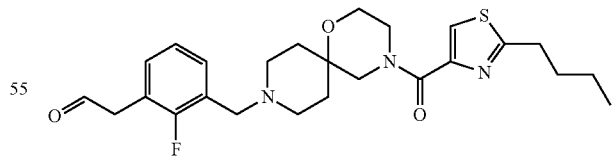

Dess-Martin periodinane (0.278 g) was added to a stirred solution of (2-butylthiazol-4-yl)(9-(2-fluoro-3-(2-hydroxyethyl)benzyl)-1-oxa-4,9-diazaspiro[5.5]undecan-4-yl)methanone (example 78, step i) (0.240 g) and trifluoroacetic acid (0.058 mL) in DCM (5 mL). After 1 h, ethyl acetate (30 k) (R)-7-(2-(3-((4-(2-Butylthiazole-4-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

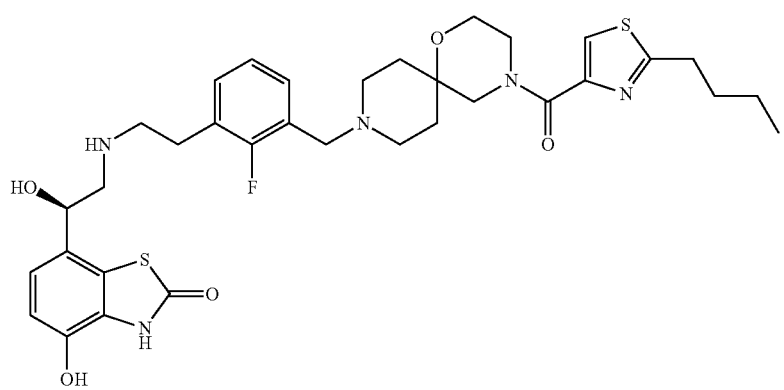 [SMILES: CCCCc1nc(C(=O)N2CCOC3(CCN(Cc4cccc(CCNC[C@H](O)c5ccc(O)c6[nH]c(=O)sc56)c4F)CC3)C2)cs1]

Acetic acid (0.044 mL) was added to a stirred solution of (R)-7-(2-amino-1-hydroxyethyl)-4-hydroxybenzo[d]thiazol-2(3H)-one hydrochloride (WO2007027134, example 1, step d) (0.200 g) and 2-(3-((4-(2-butylthiazole-4-carbonyl)-1-oxa-4,9-diazaspiro[5.5]undecan-9-yl)methyl)-2-fluorophenyl)acetaldehyde (example 78, step j) (0.240 g) in MeOH (10 mL). After 1 min, sodium cyanoborohydride (0.064 g) was added. After 1.5 h, the reaction mixture was filtered and purified by preparative HPLC (Sunfire™, Gradient: 10-40% acetonitrile in 0.2% aqueous TFA). The fractions containing the pure product were combined and evaporated in vacuo. Acetonitrile (200 mL) was added and the solution was evaporated in vacuo to a gum. This process was repeated twice. Diethyl ether was added and the titled compound collected as a solid. Yield 0.15 g.

m/z 684 (M+H)+ (APCI)

$^1$H NMR (400 MHz, D$_6$-DMSO, 90° C.) δ 11.28 (br s, 1H), 7.92 (s, 1H), 7.52-7.37 (m, 2H), 7.25 (t, J=8.4 Hz, 1H), 6.93 (d, J=8.3 Hz, 1H), 6.77 (d, J=8.3 Hz, 1H), 4.94-4.87 (m, 1H), 4.30 (s, 2H), 3.70 (br s, 6H), 3.63 (s, 2H), 3.28-2.92 (m, 10H), 2.06-1.94 (m, 2H), 1.82-1.66 (m, 4H), 1.43-1.31 (m, 2H), 0.90 (t, J=7.6 Hz, 3H). Five exchangeable protons not observed.

EXAMPLE 79

(R)-7-(2-(3-((4-(Benzo[b]thiophene-2-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

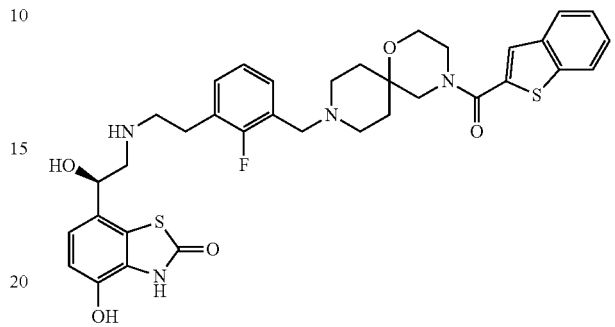

mL) was added followed by a mixture of saturated sodium thiosulphate solution (5 mL) and saturated sodium bicarbonate solution (5 mL). The reaction mixture was shaken well and separated. The ethyl acetate solution was washed with saturated sodium bicarbonate solution, water and brine. Acetic acid (0.08 mL) was added, the solution was dried over sodium sulphate, filtered and evaporated in vacuo (bath temperature ~30° C.) to give the subtitled compound as a gum. Yield 0.24 g. Used directly.

m/z 474 (M+H)+ (APCI)

a) Benzo[b]thiophen-2-yl(9-(3-(2-(tert-butyldimethylsilyloxy)ethyl)-2-fluorobenzyl)-1-oxa-4,9-diazaspiro[5.5]undecan-4-yl)methanone

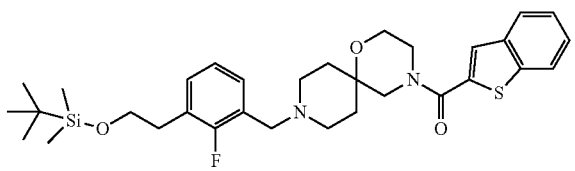 [SMILES: CC(C)(C)[Si](C)(C)OCCc1cccc(CN2CCC3(CC2)CN(C(=O)c2cc4ccccc4s2)CCO3)c1F]

2-(3H-[1,2,3]Triazolo[4,5-b]pyridin-3-yl)-1,1,3,3-tetramethylisouronium hexafluorophosphate(V) (0.378 g) was added to a stirred solution of benzo[b]thiophene-2-carboxylic acid (0.186 g), 9-(3-(2-(tert-butyldimethylsilyloxy)ethyl)-2-fluorobenzyl)-1-oxa-4,9-diazaspiro[5.5]undecane (example 78, step d) (0.40 g), and triethylamine (0.383 g) in DMF (4 mL). After 1 h, the reaction mixture was partitioned between water and ethyl acetate. The ethyl acetate layer was washed twice with water and once with brine, dried over magnesium sulphate, filtered and evaporated in vacuo. Purification by silica gel chromatography eluting with 7:1:0.5, isohexane:ethyl acetate:triethylamine gave the subtitled compound as a gum. Yield 0.38 g.

¹H NMR (400 MHz, D₆-DMSO) δ 8.14-8.08 (m, 1H), 8.05-7.99 (m, 1H), 7.82 (s, 1H), 7.57-7.51 (m, 2H), 7.33-7.23 (m, 2H), 7.14 (t, J=8.1 Hz, 1H), 3.86 (t, J=7.3 Hz, 2H), 3.81-3.72 (m, 4H), 3.63 (s, 2H), 3.56 (s, 2H), 3.38 (s, 2H), 2.86 (t, J=7.4 Hz, 2H), 2.46-2.34 (m, 2H), 1.89-1.81 (m, 2H), 1.66-1.52 (m, 2H), 0.88 (s, 9H), 0.00 (s, 6H).

b) Benzo[b]thiophen-2-yl(9-(2-fluoro-3-(2-hydroxyethyl)benzyl)-1-oxa-4,9-diazaspiro[5.5]undecan-4-yl)methanone

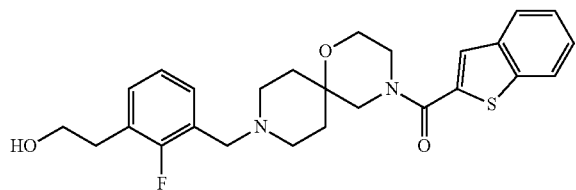 [SMILES: O=C(c1cc2ccccc2s1)N1CCOC2(CCN(Cc3cccc(CCO)c3F)CC2)C1]

TBAF (1M solution in THF, 2 mL) was added to a solution of benzo[b]thiophen-2-yl(9-(3-(2-(tert-butyldimethylsilyloxy)ethyl)-2-fluorobenzyl)-1-oxa-4,9-diazaspiro[5.5]undecan-4-yl)methanone (example 79, step a) (0.370 g) in THF (4 mL). After 0.5 h, the solution was concentrated. Purification by silica gel chromatography eluting with 10:1 ethyl acetate: triethylamine gave the subtitled compound as a gum. Yield 0.26 g.

¹H NMR (400 MHz, D₆-DMSO, 90° C.) δ 7.99-7.95 (m, 1H), 7.93-7.88 (m, 1H), 7.67 (s, 1H), 7.46-7.39 (m, 2H), 7.17 (q, J=7.5 Hz, 2H), 7.01 (t, J=8.0 Hz, 1H), 4.39-4.33 (m, 1H), 3.72-3.57 (m, 4H), 3.54 (s, 2H), 3.48 (s, 2H), 2.99 (s, 2H), 2.75 (t, J=7.6 Hz, 2H), 2.46-2.32 (m, 4H), 1.80-1.71 (m, 2H), 1.58-1.48 (m, 2H).

c) 2-(3-((4-(Benzo[b]thiophene-2-carbonyl)-1-oxa-4,9-diazaspiro[5.5]undecan-9-yl)methyl)-2-fluorophenyl)acetaldehyde

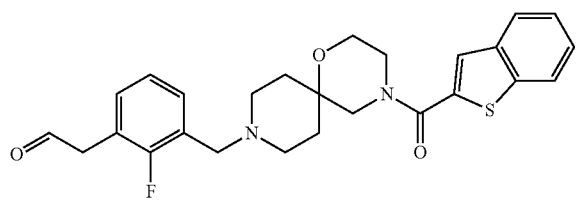 [SMILES: O=CCc1cccc(CN2CCC3(CC2)CN(C(=O)c2cc4ccccc4s2)CCO3)c1F]

Dess-Martin periodinane (0.282 g) was added to a stirred solution of benzo[b]thiophen-2-yl(9-(2-fluoro-3-(2-hydroxyethyl)benzyl)-1-oxa-4,9-diazaspiro[5.5]undecan-4-yl)methanone (example 79, step b) (0.240 g) and trifluoroacetic acid (0.059 mL) in DCM (5 mL). After 1 h, ethyl acetate (30 mL) was added followed by a mixture of saturated sodium thiosulphate solution (5 mL) and saturated sodium bicarbonate solution (5 mL). The reaction mixture was shaken well and separated. The ethyl acetate solution was washed with saturated sodium bicarbonate solution, water and brine. Acetic acid (0.08 mL) was added, then the solution was dried over sodium sulphate, filtered and evaporated in vacuo (bath temperature ~30° C.) to give the subtitled compound as a gum. Yield 0.24 g. Used directly.

m/z 467 (M+H)⁺ (APCI)

d) (R)-7-(2-(3-((4-(Benzo[b]thiophene-2-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

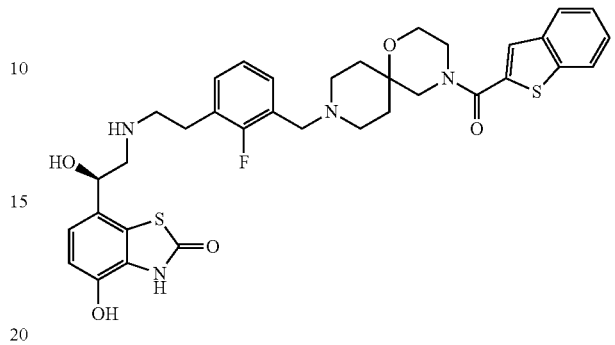

Acetic acid (0.044 mL) was added to a stirred solution of (R)-7-(2-amino-1-hydroxyethyl)-4-hydroxybenzo[d]thiazol-2(3H)-one hydrochloride (WO2007027134, example 1, step d) (0.203 g) and 2-(3-((4-(benzo[b]thiophene-2-carbonyl)-1-oxa-4,9-diazaspiro[5.5]undecan-9-yl)methyl)-2-fluorophenyl)acetaldehyde (example 79, step c) (0.240 g) in MeOH (10 mL). After 1 min, sodium cyanoborohydride (0.081 g) was added. After 1.5 h, the reaction mixture was filtered and purified by preparative HPLC (Sunfire™, Gradient: 10-40% acetonitrile in 0.2% aqueous TFA). The fractions containing the pure product were combined and evaporated in vacuo. Acetonitrile (200 mL) was added and the solution was evaporated in vacuo to a gum. This process was repeated twice. Diethyl ether was added and the titled compound collected as a solid. Yield 0.19 g.

m/z 677 (M+H)⁺ (APCI)

¹H NMR (400 MHz, D₆-DMSO, 90° C.) δ 11.28 (s, 1H), 8.00-7.95 (m, 1H), 7.92-7.88 (m, 1H), 7.69 (s, 1H), 7.50-7.38 (m, 4H), 7.25 (t, J=7.5 Hz, 1H), 6.94 (d, J=8.4 Hz, 1H), 6.77 (d, J=8.4 Hz, 1H), 4.90 (dd, J=4.2 and 8.56 Hz, 1H), 4.35-4.19 (m, 2H), 3.76-3.68 (m, 4H), 3.59 (s, 2H), 3.27-2.99 (m, 10H), 2.09-1.99 (m, 2H), 1.82-1.70 (m, 2H). Five exchangeable protons not observed.

EXAMPLE 80

(R)-7-(2-(2-Chloro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

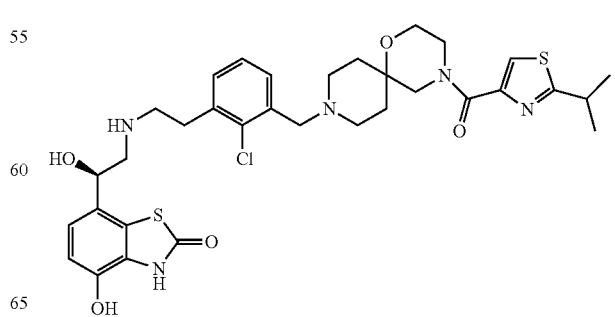

a) 2-Chloro-3-(cyanomethyl)benzoic acid

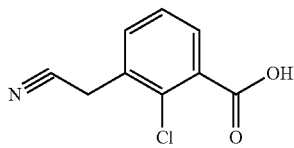 [SMILES: N#CCc1cccc(C(=O)O)c1Cl]

A solution of 3-(bromomethyl)-2-chlorobenzoic acid (6.39 g) in DMF (75 mL) was treated with a solution of potassium cyanide (3.34 g) in water (25 mL) and the resulting solution was stirred at room temperature overnight. The mixture was diluted with water and extracted twice with ethyl acetate. The organic phases were discarded, whilst the aqueous phase was carefully acidified with concentrated hydrochloric acid (25 mL), venting any liberated HCN through a bleach solution via a stream of nitrogen. After being stirred for 2 hours, the aqueous phase was extracted twice more with ethyl acetate. The combined organic phases were washed three times with water, once with brine, then dried over anhydrous magnesium sulphate and concentrated in vacuo to afford the crude subtitled compound as a pale brown solid. Yield 4.12 g.

$^1$H NMR (400 MHz, D$_6$-DMSO) δ 7.73 (dd, J=7.7, 1.5 Hz, 1H), 7.69 (dd, J=7.8, 1.7 Hz, 1H), 7.48 (t, J=7.7 Hz, 1H), 4.16 (s, 2H)+1 exchangeable proton not observed.

b) 3-(Carboxymethyl)-2-chlorobenzoic acid

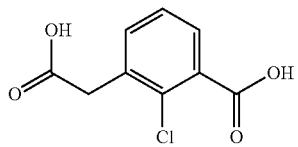 [SMILES: O=C(O)Cc1cccc(C(=O)O)c1Cl]

Potassium hydroxide (2.976 g) in water (30 mL) was added to a suspension of 2-chloro-3-(cyanomethyl)benzoic acid (example 80, step a) (4.12 g) in ethanol (30 mL) and the resulting solution was heated at reflux for 2 hours, then allowed to cool overnight. The mixture was concentrated in vacuo to remove the ethanol and then diluted with water and washed twice with ethyl acetate. The organic phases were discarded, whilst the aqueous phase was acidified to pH 1 with concentrated hydrochloric acid and extracted three times with ethyl acetate. The combined extracts were dried over anhydrous magnesium sulphate and concentrated in vacuo to afford the crude subtitled compound as a yellow solid. Yield 4.11 g. Used directly.

c) 2-(2-Chloro-3-(hydroxymethyl)phenyl)ethanol

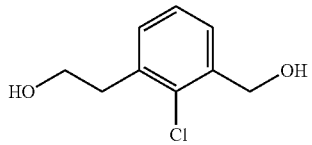 [SMILES: OCCc1cccc(CO)c1Cl]

A solution of borane-methyl sulfide complex (2M in THF, 20 mL) was added portionwise over 5 minutes to a suspension of 3-(carboxymethyl)-2-chlorobenzoic acid (example 80, step b) (4.11 g) in dry THF (100 mL) at room temperature. The resulting effervescing suspension was stirred at room temperature for 30 minutes, then heated to reflux for 60 minutes, and allowed to cool to room temperature overnight. The mixture was quenched by the portionwise addition of methanol (15 mL) over 15 minutes. The mixture was diluted further with methanol to give a solution, which was then concentrated in vacuo to give a syrup. The syrup was purified by flash chromatography on silica eluted with 2% methanol in dichloromethane to the afford the crude subtitled compound as a white solid. Yield 1.44 g.

m/z 186 (M$^+$) (EI)

d) 2-Chloro-3-(2-hydroxyethyl)benzaldehyde

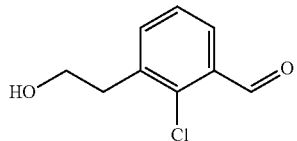 [SMILES: O=Cc1cccc(CCO)c1Cl]

Manganese (IV) dioxide (1.599 g) was added to a solution of 2-(2-chloro-3-(hydroxymethyl)phenyl)ethanol (example 80, step c) (0.342 g) in DCM (20 mL), and the resulting suspension was stirred at room temperature overnight. The mixture was then concentrated onto silica and purified by flash chromatography on silica eluted with 25% ethyl acetate in isohexane to afford the subtitled compound as a white crystalline solid. Yield 0.223 g.

$^1$H NMR (400 MHz, CDCl$_3$) δ 10.54 (d, J=0.8 Hz, 1H), 7.83 (dd, J=7.7, 1.5 Hz, 1H), 7.55 (dd, J=7.7, 1.8 Hz, 1H), 7.35 (t, J=7.6 Hz, 1H), 3.94 (dd, J=11.0, 6.4 Hz, 2H), 3.11 (t, J=6.6 Hz, 2H), 1.46 (t, J=4.9 Hz, 1H).

e) (9-(2-Chloro-3-(2-hydroxyethyl)benzyl)-1-oxa-4,9-diazaspiro[5.5]undecan-4-yl)(2-isopropylthiazol-4-yl)methanone

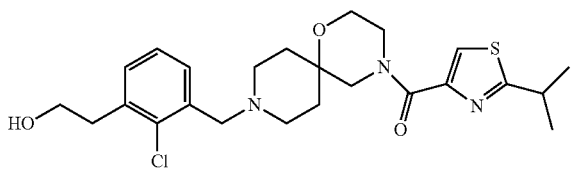 [SMILES: CC(C)c1nc(C(=O)N2CCOC3(CCN(Cc4cccc(CCO)c4Cl)CC3)C2)cs1]

A solution of (2-isopropylthiazol-4-yl)(1-oxa-4,9-diazaspiro[5.5]undecan-4-yl)methanone trifluoroacetate (example 22, step b) (0.325 g) in NMP (3 mL) was treated with acetic acid (0.067 mL) and stirred for 5 minutes. A solution of 2-chloro-3-(2-hydroxyethyl)benzaldehyde (example 80, step d) (0.217 g) in NMP (4 mL) was then added, the resulting solution was stirred for 1 hour and then treated with sodium triacetoxyborohydride (1.025 g). The mixture was stirred overnight at room temperature, then poured into saturated sodium bicarbonate and extracted twice with ethyl acetate. The combined extracts were washed three times with water, once with brine, then dried over anhydrous magnesium sulphate and purified by flash chromatography on silica eluted with 1:2:97 triethylamine:methanol:dichloromethane to afford the subtitled compound as a colourless gum. Yield 0.411 g.

¹H NMR (400 MHz, D₆-DMSO, 90° C.) δ 7.91 (d, J=1.3 Hz, 1H), 7.30 (d, J=7.2 Hz, 1H), 7.24-7.16 (m, 2H), 4.36 (t, J=5.1 Hz, 1H), 3.73-3.59 (m, 8H), 3.55 (s, 2H), 3.32 (septet, J=6.8 Hz, 1H), 2.89 (t, J=7.0 Hz, 2H), 2.46-2.40 (m, 1H), 2.40-2.28 (m, 1H), 2.17 (t, J=8.1 Hz, 1H), 1.91 (quintet, J=7.5 Hz, 1H), 1.77-1.65 (m, 2H), 1.62-1.50 (m, 2H), 1.36 (d, J=6.5 Hz, 6H).

f) 2-(2-Chloro-3-((4-(2-isopropylthiazole-4-carbonyl)-1-oxa-4,9-diazaspiro[5.5]undecan-9-yl)methyl)phenyl)acetaldehyde

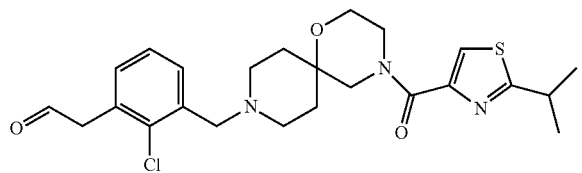 [SMILES: CC(C)c1nc(C(=O)N2CCOC3(CCN(Cc4cccc(CC=O)c4Cl)CC3)C2)cs1]

A solution of (9-(2-chloro-3-(2-hydroxyethyl)benzyl)-1-oxa-4,9-diazaspiro[5.5]undecan-4-yl)(2-isopropylthiazol-4-yl)methanone (example 80, step e) (0.386 g) in DCM (5 mL) was cooled in ice-water, treated with trifluoroacetic acid (0.125 mL) and stirred for 5 minutes. Dess-Martin periodinane (0.519 g) was added, then the mixture was removed from the cooling bath and stirred at room temperature for 35 minutes. The solution was diluted with saturated sodium thiosulphate solution (5 mL), saturated sodium bicarbonate solution (5 mL) and ethyl acetate (5 mL) and the resulting mixture was stirred vigorously for 10 minutes. The mixture was then extracted twice with ethyl acetate, the combined organic phases were washed with brine, acidified with acetic acid (0.1 mL), dried over anhydrous magnesium sulphate and concentrated in vacuo to give the crude subtitled compound as a pale yellow gum. Yield 0.494 g.

m/z 476 (M+H)⁺ (APCI)

g) (R)-7-(2-(2-Chloro-3-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate A solution of (R)-7-(2-amino-1-hydroxyethyl)-4-hydroxybenzo[d]thiazol-2(3H)-one hydrochloride (WO2007027134, example 1, step d) (0.181 g) in methanol (2 mL) was treated with acetic acid (0.030 mL) and stirred for 10 minutes. A solution of 2-(2-chloro-3-((4-(2-isopropylthiazole-4-carbonyl)-1-oxa-4,9-diazaspiro[5.5]undecan-9-yl)methyl)phenyl)acetaldehyde (example 80, step f) (0.247 g) in methanol (3 mL) was then added, and the resulting mixture was stirred at room temperature for 10 minutes, before cooling in ice-water and treating with sodium cyanoborohydride (0.102 g). The cooling bath was removed and the mixture was stirred at room temperature overnight. The next day, more sodium cyanoborohydride (0.099 g) was added, and the mixture was stirred for an additional 4 hours. The solution was quenched by the addition of a drop of water, filtered, and purified by preparative HPLC (Sunfire™, Gradient: 5-50% acetonitrile in 0.2% aqueous TFA). Fractions containing product were concentrated in vacuo and co-evaporated from acetonitrile three times to give a colourless residue. The residue was triturated with diethyl ether to give a solid, which was collected by filtration, washed with diethyl ether and dried in vacuo at room temperature to afford the titled compound as a white solid. Yield 0.053 g.

m/z 686/688 (M+H)⁺ (APCI)

¹H NMR (400 MHz, D₆-DMSO) δ 11.68 (s, 1H), 10.23 (s, 1H), 8.91 (br d, J=26.7 Hz, 2H), 8.03 (s, 1H), 7.68-7.56 (m, 1H), 7.54-7.40 (m, 2H), 6.93 (d, J=8.5 Hz, 1H), 6.78 (d, J=8.2 Hz, 1H), 6.56-6.43 (m, 1H), 4.91 (br d, J=8.5 Hz, 1H), 4.57-4.43 (m, 2H), 3.90-3.42 (m, 6H), 3.38-3.25 (m, 4H), 3.24-3.02 (m, 7H), 2.08 (br d, J=13.3 Hz, 2H), 1.92-1.54 (m, 2H), 1.34 (d, J=6.7 Hz, 6H). One exchangeable proton not observed.

EXAMPLE 81

(R)-5-(2-(2-Chloro-3-((4-(2-isopropylthiazole-4-carbonyl)-1-oxa-4,9-diazaspiro[5.5]undecan-9-yl)methyl)phenethylamino)-1-hydroxyethyl)-8-hydroxyquinolin-2(1H)-one ditrifluoroacetate

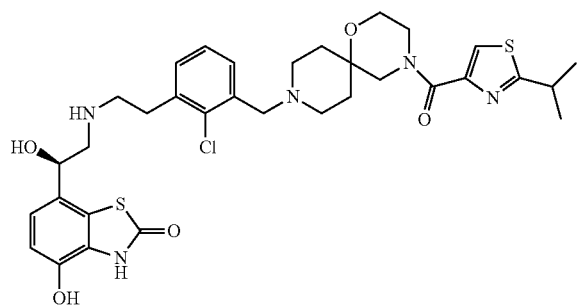 [SMILES: CC(C)c1nc(C(=O)N2CCOC3(CCN(Cc4cccc(CCNC[C@H](O)c5ccc(O)c6[nH]c(=O)sc56)c4Cl)CC3)C2)cs1]

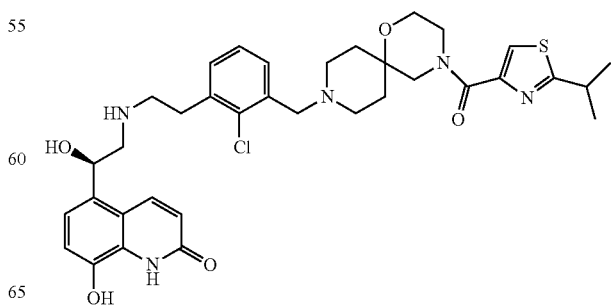

a) (R)-5-(1-(tert-Butyldimethylsilyloxy)-2-(2-chloro-3-((4-(2-isopropylthiazole-4-carbonyl)-1-oxa-4,9-diazaspiro[5.5]undecan-9-yl)methyl)phenethylamino)ethyl)-8-hydroxyquinolin-2(1H)-one

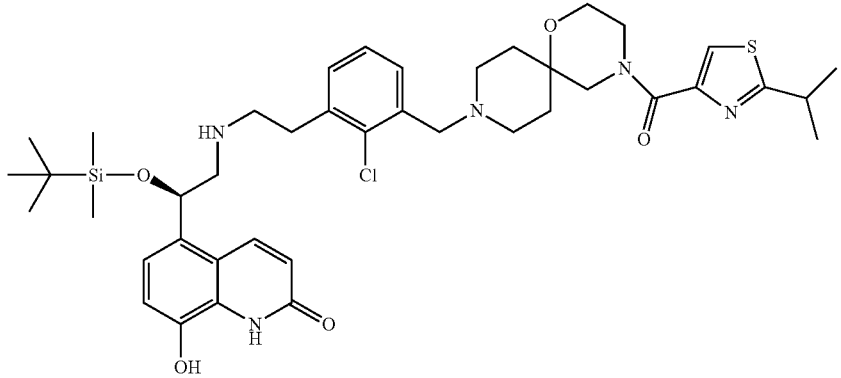 [SMILES: CC(C)c1nc(C(=O)N2CCOC3(CCN(Cc4cccc(CCNC[C@H](O[Si](C)(C)C(C)(C)C)c5ccc(O)c6[nH]c(=O)ccc56)c4Cl)CC3)C2)cs1]

A solution of (R)-5-(2-amino-1-(tert-butyldimethylsilyloxy)ethyl)-8-hydroxyquinolin-2(1H)-one (WO2004106333) (0.261 g) in methanol (2 mL) was treated with acetic acid (0.030 mL) and stirred for 10 minutes. A solution of 2-(2-chloro-3-((4-(2-isopropylthiazole-4-carbonyl)-1-oxa-4,9-diazaspiro[5.5]undecan-9-yl)methyl)phenyl)acetaldehyde (example 80, step f) (0.247 g) in methanol (3 mL) was then added, and the resulting mixture was stirred at room temperature for 10 minutes, before cooling in ice-water and treating with sodium cyanoborohydride (0.102 g). The cooling bath was removed and the mixture was stirred at room temperature overnight. More sodium cyanoborohydride (0.101 g) was added, and the mixture was stirred over a second night. The solution was then concentrated onto flash silica in vacuo, and the resulting powder was purified by flash chromatography on silica eluted with 1:3:96 to 1:5:94 triethylamine:methanol:dichloromethane to afford the subtitled compound as a yellow oil. Yield 0.130 g.

$^1$H NMR (400 MHz, D$_6$-DMSO, 90° C.) δ 8.40 (d, J=9.7 Hz, 1H), 8.10 (s, 1H), 7.48 (dd, J=7.3, 2.1 Hz, 1H), 7.38-7.30 (m, 2H), 7.17 (d, J=8.2 Hz, 1H), 7.09 (d, J=8.2 Hz, 1H), 6.65 (d, J=9.7 Hz, 1H), 5.26 (dd, J=7.6, 5.0 Hz, 1H), 3.91-3.78 (m, 6H), 3.72 (s, 2H), 3.55-3.46 (m, 1H), 3.10-3.03 (m, 1H), 2.99 (s, 4H), 2.93-2.86 (m, 1H), 2.68-2.47 (m, 4H), 1.94-1.84 (m, 2H), 1.80-1.68 (m, 2H), 1.55 (d, J=7.0 Hz, 6H), 0.99 (s, 9H), 0.18 (d, J=4.6 Hz, 6H). Three exchangeable protons not observed.

b) (R)-5-(2-(2-Chloro-3-((4-(2-isopropylthiazole-4-carbonyl)-1-oxa-4,9-diazaspiro[5.5]undecan-9-yl)methyl)phenylamino)-1-hydroxyethyl)-8-hydroxyquinolin-2(1H)-one ditrifluoroacetate A solution of (R)-5-(1-(tert-butyldimethylsilyloxy)-2-(2-chloro-3-((4-(2-isopropylthiazole-4-carbonyl)-1-oxa-4,9-diazaspiro[5.5]undecan-9-yl)methyl)phenethylamino)ethyl)-8-hydroxyquinolin-2(1H)-one (example 81, step a) (0.124 g) and triethylamine trihydrofluoride (0.051 mL) in THF (5 mL) was stirred at room temperature overnight then concentrated in vacuo. The residue was dissolved in methanol (4 mL) and the resulting solution was filtered and purified by preparative HPLC (Sunfire™, Gradient: 10-30% acetonitrile in 0.2% aqueous TFA). Fractions containing product were concentrated in vacuo and co-evaporated from acetonitrile three times to give a colourless residue. The residue was triturated with diethyl ether to give a solid, which was collected by filtration, washed with diethyl ether and dried in vacuo at room temperature to afford the titled compound as a white powder. Yield 0.076 g.

m/z 680/682 (M+H)$^+$ (APCI)

$^1$H NMR (400 MHz, D$_6$-DMSO, 90° C.) δ 8.17 (d, J=10.0 Hz, 1H), 7.94 (s, 1H), 7.55 (d, J=7.2 Hz, 1H), 7.47-7.34 (m, 2H), 7.14 (d, J=8.2 Hz, 1H), 6.99 (d, J=8.2 Hz, 1H), 6.55 (d, J=10.0 Hz, 1H), 5.34 (dd, J=9.1, 4.0 Hz, 1H), 4.33-4.09 (br m, 2H), 3.77-3.60 (m, 6H), 3.44-2.87 (m, 11H), 2.02-1.87 (m, 2H), 1.81-1.65 (m, 2H), 1.35 (d, J=6.9 Hz, 6H). Six exchangeable protons not observed.

EXAMPLE 82

(R)-4-Hydroxy-7-(1-hydroxy-2-(3-((4-(5-isopropylthiophene-3-carbonyl)-1-oxa-4,9-diazaspiro[5.5]undecan-9-yl)methyl)phenethylamino)ethyl)benzo[d]thiazol-2(3H)-one ditrifluoroacetate

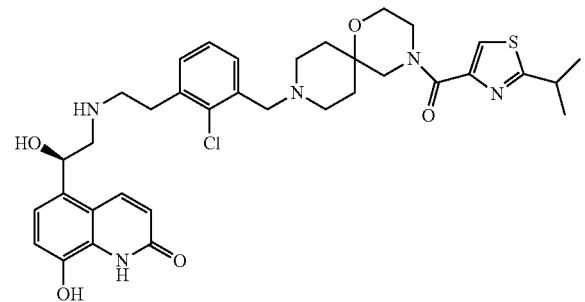 [SMILES: CC(C)c1nc(C(=O)N2CCOC3(CCN(Cc4cccc(CCNC[C@H](O)c5ccc(O)c6[nH]c(=O)ccc56)c4Cl)CC3)C2)cs1]

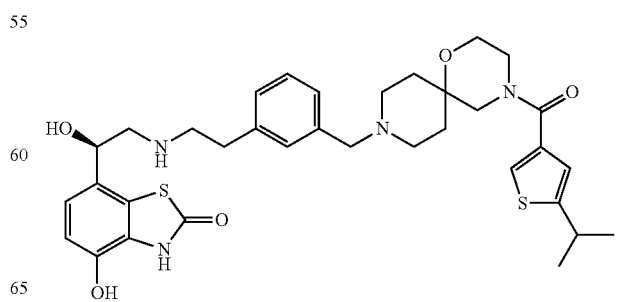

a) 2-(3-(1-Oxa-4,9-diazaspiro[5.5]undecan-9-ylmethyl)phenyl)ethanol

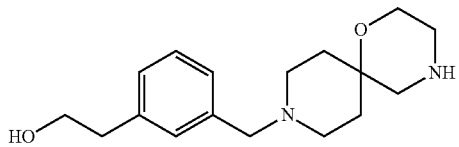 [SMILES: OCCc1cccc(CN2CCC3(CC2)CNCCO3)c1]

'880' Ammonia solution (5 mL) was added to a solution of 2,2,2-trifluoro-1-(9-(3-(2-hydroxyethyl)benzyl)-1-oxa-4,9-diazaspiro[5.5]undecan-4-yl)ethanone (example 12, step e) (2.02 g) in methanol (25 mL). The resulting mixture was stirred for 90 min and the solvent evaporated. The residue was purified by silica gel chromatography eluting with 94.5:5:0.5 to 89:10:1 DCM:methanol:'880' aqueous ammonia gradient. The fractions containing product were combined and evaporated to give the subtitled compound as a clear oil. Yield 1.44 g.

m/z 291 (M+H)$^+$ (APCI)

$^1$H NMR (400 MHz, D$_6$-DMSO, 90° C.) δ 7.18 (t, J=7.4 Hz, 1H), 7.13-7.02 (m, 3H), 4.34 (s, 1H), 3.61 (t, J=6.9 Hz, 2H), 3.51-3.45 (m, 2H), 3.41 (s, 2H), 2.71 (t, J=6.9 Hz, 2H), 2.62 (t, J=4.9 Hz, 2H), 2.52 (s, 2H), 2.42-2.23 (m, 4H), 1.82-1.72 (m, 2H), 1.53-1.38 (m, 2H). One exchangeable proton not observed.

b) (9-(3-(2-Hydroxyethyl)benzyl)-1-oxa-4,9-diazaspiro[5.5]undecan-4-yl)(5-isopropylthiophen-3-yl)methanone

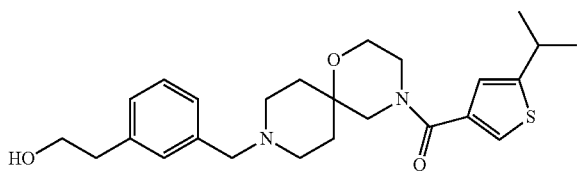 [SMILES: CC(C)c1cc(C(=O)N2CCOC3(CCN(Cc4cccc(CCO)c4)CC3)C2)cs1]

O-(7-Azabenzotriazol-1-yl)-N,N,N',N'-tetramethyluronium hexafluorophosphate (0.55 g) was added to a solution of 2-(3-(1-oxa-4,9-diazaspiro[5.5]undecan-9-ylmethyl)phenyl)ethanol (example 82, step a) (0.32 g), 5-isopropylthiophene-3-carboxylic acid (0.19 g) and triethylamine (0.61 mL) in DMF (7 mL) at 0° C. The resulting yellow solution was allowed to warm to RT and was stirred for 2 h. The mixture was partitioned between ethyl acetate (100 mL) and brine (100 mL), the organic phase was washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added, and the solvent evaporated under reduced pressure to give the subtitled compound as a clear gum. Yield 0.4 g.

m/z 443 (M+H)$^+$ (APCI)

c) (R)-4-Hydroxy-7-(1-hydroxy-2-(3-((4-(5-isopropylthiophene-3-carbonyl)-1-oxa-4,9-diazaspiro[5.5]undecan-9-yl)methyl)phenethylamino)ethyl)benzo[d]thiazol-2(3H)-one ditrifluoroacetate

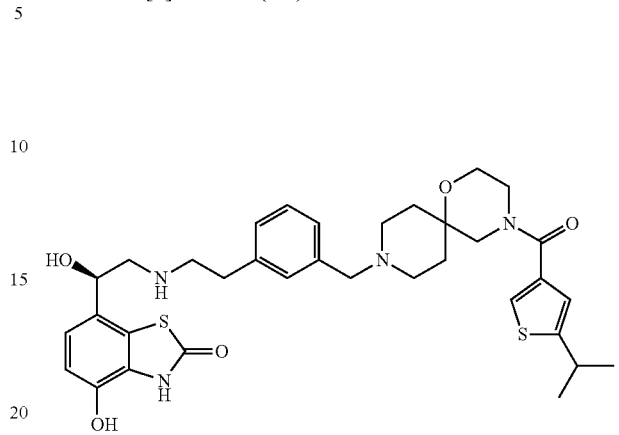

Trifluoroacetic acid (0.035 mL) was added to a solution (9-(3-(2-hydroxyethyl)benzyl)-1-oxa-4,9-diazaspiro[5.5]undecan-4-yl)(5-isopropylthiophen-3-yl)methanone (example 82, step b) (0.2 g) in DCM (5 mL) at 0° C. The mixture was stirred for 5 min then Dess-Martin periodinane (0.29 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.026 mL) and (R)-7-(2-amino-1-hydroxyethyl)-4-hydroxybenzo[d]thiazol-2(3H)-one hydrochloride (WO2007027134, example 1, step d) (0.14 g) were then added and the mixture stirred for 5 min before cooling in an ice bath. Sodium cyanoborohydride (0.043 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-40% acetonitrile in 0.2% aqueous TFA). The fractions containing product were combined, evaporated in vacuo and the residue triturated with diethylether to give the titled compound as a white solid. Yield 0.07 g.

m/z 651 (M+H)$^+$ (APCI)

$^1$H NMR (400 MHz, D$_6$-DMSO, 90° C.) δ 7.50-7.32 (m, 5H), 6.96-6.88 (m, 2H), 6.77 (d, J=8.2 Hz, 1H), 4.98-4.88 (m, 1H), 4.28 (s, 2H), 3.72-3.63 (m, 2H), 3.59-3.34 (m, 4H), 3.29-2.97 (m, 11H), 2.11-1.93 (m, 2H), 1.86-1.68 (m, 2H), 1.28 (d, J=6.7 Hz, 6H). Six exchangeable protons not observed.

EXAMPLE 83

(R)-8-Hydroxy-5-(1-hydroxy-2-(3-((4-(5-isopropylthiophene-3-carbonyl)-1-oxa-4,9-diazaspiro[5.5]undecan-9-yl)methyl)phenethylamino)ethyl)quinolin-2(1H)-one ditrifluoroacetate

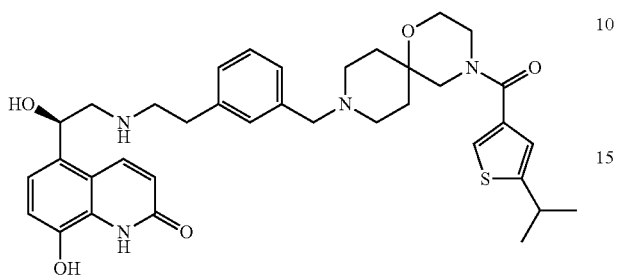

TFA (0.04 mL) was added to a solution (9-(3-(2-hydroxyethyl)benzyl)-1-oxa-4,9-diazaspiro[5.5]undecan-4-yl)(5-isopropylthiophen-3-yl)methanone (example 82, step b) (0.2 g) in DCM (5 mL) at 0° C. The reaction was stirred for 5 min then Dess-Martin periodinane (0.29 g) was added. The mixture was allowed to warm to RT and stirred for 1 h. Saturated sodium thiosulphate solution (5 mL), saturated sodium bicarbonate solution (5 mL) and ethyl acetate (20 mL) were added and the mixture stirred vigorously for 5 min. The layers were separated and the aqueous extracted with ethyl acetate (20 mL). The combined organics were washed with brine (20 mL), acidified with a few drops of acetic acid, dried over sodium sulphate, filtered and evaporated. The residue was redissolved in methanol (5 mL), acetic acid (0.03 mL) and (R)-5-(2-amino-1-(tert-butyldimethylsilyloxy)ethyl)-8-hydroxyquinolin-2(1H)-one (WO2004106333) (0.15 g) were added, then the mixture was stirred for 5 min and cooled in an ice bath. Sodium cyanoborohydride (0.043 g) was then added, the reaction was allowed to warm to RT and stirred overnight. The reaction was concentrated and purified by silica gel chromatography eluting with 94.5:5:0.5 to 89:10:1 DCM:methanol:'880' ammonia gradient. The fractions containing product were combined and evaporated. The residue was dissolved in THF (5 mL), triethylamine trihydrofluoride (0.22 mL) was added and the mixture stirred overnight. The solvent was evaporated and the residue azeotroped twice with toluene. Purification was by preparative HPLC (Sunfire™, Gradient: 10-30% acetonitrile in 0.2% aqueous TFA). The fractions containing product were combined, evaporated and triturated with dielthylether to give the titled compound as a white solid. Yield 0.06 g.

m/z 645 (M+H)$^+$ (APCI)

$^1$H NMR (400 MHz, D$_6$-DMSO, 90° C.) δ 8.17 (d, J=9.7 Hz, 1H), 7.48 (s, 1H), 7.45-7.33 (m, 4H), 7.14 (d, J=8.2 Hz, 1H), 7.00 (d, J=8.2 Hz, 1H), 6.90 (s, 1H), 6.54 (d, J=10.0 Hz, 1H), 5.36 (dd, J=8.5, 4.1 Hz, 1H), 4.29 (s, 2H), 3.72-3.63 (m, 2H), 3.57-3.38 (m, 4H), 3.28 (t, J=8.1 Hz, 2H), 3.22-2.98 (m, 9H), 2.10-1.95 (m, 2H), 1.81-1.62 (m, 2H), 1.28 (d, J=6.7 Hz, 6H). Six exchangeable protons not observed.

EXAMPLE 84

(R)-4-Hydroxy-7-(1-hydroxy-2-(3-((4-(2-isobutylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

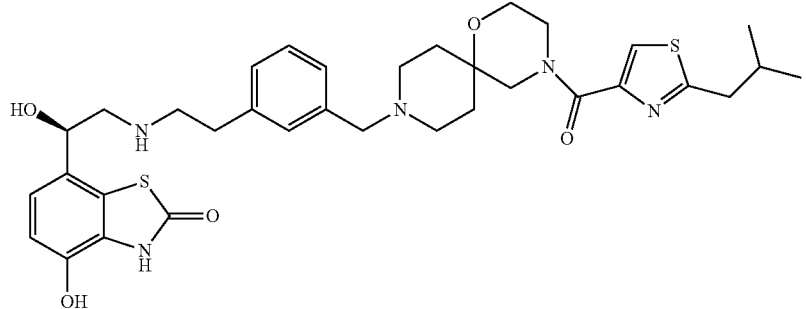 [SMILES: CC(C)Cc1nc(C(=O)N2CCOC3(CCN(Cc4cccc(CCNC[C@H](O)c5ccc(O)c6[nH]c(=O)sc56)c4)CC3)C2)cs1]

a) (9-(3-(2-Hydroxyethyl)benzyl)-1-oxa-4,9-diazaspiro[5.5]undecan-4-yl)(2-isobutylthiazol-4-yl)methanone

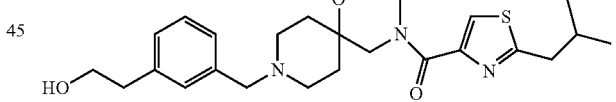

O-(7-Azabenzotriazol-1-yl)-N,N,N',N'-tetramethyluronium hexafluorophosphate (0.34 g) was added to a solution of 2-(3-(1-oxa-4,9-diazaspiro[5.5]undecan-9-ylmethyl)phenyl)ethanol (example 82, step a) (0.2 g), 2-isobutylthiazole-4-carboxylic acid (0.13 g) and triethylamine (0.38 mL) in DMF (7 mL) at 0° C. The resulting yellow solution was allowed to warm to RT and was stirred for 2 h. The mixture was partitioned between ethyl acetate (100 mL) and brine (100 mL), the organic phase was washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added, and the solvent evaporated under reduced pressure to give the subtitled compound as a clear gum. Yield 0.2 g.

m/z 458 (M+H)$^+$ (APCI)

$^1$H NMR (400 MHz, D$_6$-DMSO, 90° C.) δ 7.99 (s, 1H), 7.26-7.03 (m, 4H), 4.60 (t, J=5.3 Hz, 1H), 3.72-3.50 (m, 8H), 3.46-3.34 (m, 2H), 2.94-2.84 (m, 2H), 2.71 (t, J=7.1 Hz, 2H), 2.43-2.01 (m, 5H), 1.74-1.37 (m, 4H), 1.01-0.90 (m, 6H)

b) (R)-4-Hydroxy-7-(1-hydroxy-2-(3-((4-(2-isobutylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

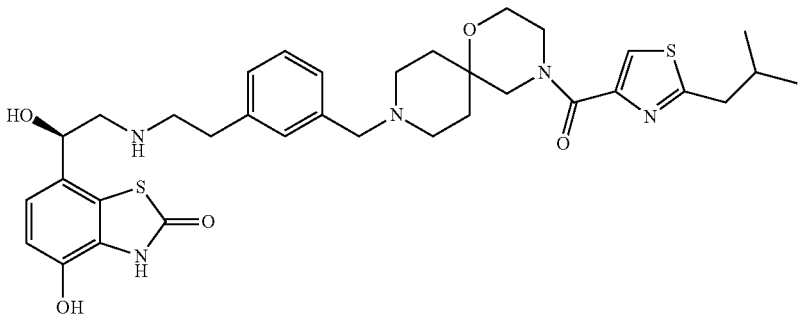 [SMILES: CC(C)Cc1nc(C(=O)N2CCOC3(CCN(Cc4cccc(CCNC[C@H](O)c5ccc(O)c6[nH]c(=O)sc56)c4)CC3)C2)cs1]

Trifluoroacetic acid (0.032 mL) was added to a of (9-(3-(2-hydroxyethyl)benzyl)-1-oxa-4,9-diazaspiro[5.5]undecan-4-yl)(2-isobutylthiazol-4-yl)methanone (example 84, step a) (0.19 g) in DCM (5 mL) at 0° C. The mixture was stirred for 5 min then Dess-Martin periodinane (0.26 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.024 mL) and (R)-7-(2-amino-1-hydroxyethyl)-4-hydroxybenzo[d]thiazol-2(3H)-one hydrochloride (WO2007027134, example 1, step d) (0.11 g) were then added and the mixture was stirred for 5 min before cooling in an ice bath. Sodium cyanoborohydride (0.04 g) was then added, the mixture was allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-35% acetonitrile in 0.2% aqueous TFA). The fractions containing product were combined, evaporated in vacuo and the residue triturated with diethylether to give the titled compound as a white solid. Yield 0.1 g.

m/z 666 (M+H)$^+$ (APCI)

$^1$H NMR (400 MHz, D$_6$-DMSO, 90° C.) δ 11.27 (s, 1H), 7.93 (s, 1H), 7.44-7.33 (m, 4H), 6.93 (d, J=8.5 Hz, 1H), 6.77 (d, J=8.2 Hz, 1H), 4.92 (dd, J=7.9, 5.1 Hz, 1H), 4.34-4.21 (m, 2H), 3.73-3.60 (m, 6H), 3.28-2.96 (m, 10H), 2.88 (d, J=6.9 Hz, 2H), 2.11-1.95 (m, 3H), 1.84-1.64 (m, 2H), 0.95 (d, J=6.7 Hz, 6H). Five exchangeable protons not observed.

EXAMPLE 85

(R)-7-(2-(2-Fluoro-3-((4-(6-isopropylpicolinoyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

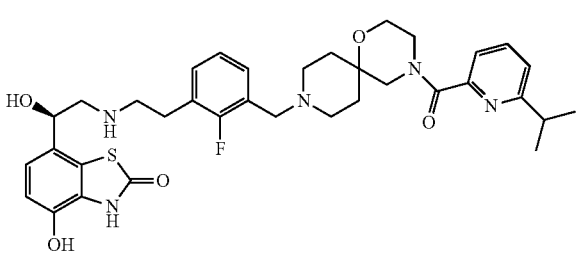 [SMILES: CC(C)c1cccc(C(=O)N2CCOC3(CCN(Cc4cccc(CCNC[C@H](O)c5ccc(O)c6[nH]c(=O)sc56)c4F)CC3)C2)n1]

a) 2-Isopropylpyridine

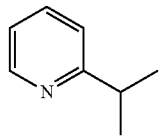

A solution of butyllithium (1.6M in hexanes, 50 mL) was added dropwise over 20 min to a solution of 2-ethylpyridine (9.34 mL) in tetrahydrofuran (50 mL) at −70° C. The mixture was stirred for 2 h then methyl iodide (5 mL) was added dropwise over 15 min. The resulting orange slurry was allowed to warm to RT and stirred overnight. The solvent was evaporated and the residue diluted with diethylether (100 mL). The organic layer was washed with water (2×100 mL) and brine (100 mL), then dried over sodium sulphate, filtered and evaporated to give the subtitled compound as a yellow oil. Yield 9.1 g.

m/z 122 (M+H)$^+$ (APCI)

¹H NMR (300 MHz, CDCl₃) δ 8.56-8.52 (m, 1H), 7.60 (td, J=7.7, 2.1 Hz, 1H), 7.19-7.15 (m, 1H), 7.09 (ddd, J=7.4, 4.9, 1.2 Hz, 1H), 3.06 (septet, J=6.9 Hz, 1H), 1.31 (d, J=6.9 Hz, 6H).

b) 2-Isopropylpyridine 1-oxide

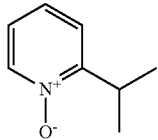

MCPBA (22.0 g) was added to a solution of 2-isopropylpyridine (example 85, step a) (9.1 g) in DCM (250 mL) and the resulting mixture stirred for 3 h. The reaction mixture was washed with saturated sodium bicarbonate solution (4×100 mL) and brine (100 mL), then dried over sodium sulphate, filtered and evaporated. Purification was by silica gel chromatography eluting with ethyl acetate to 10% methanol in ethyl acetate gradient. The fractions containing product were combined and evaporated to give the subtitled compound as a yellow oil. Yield 3.9 g.

m/z 138 (M+H)⁺ (APCI)

¹H NMR (400 MHz, D₆-DMSO) δ 8.23 (dd, J=6.2, 1.5 Hz, 1H), 7.41 (dd, J=7.7, 2.3 Hz, 1H), 7.35-7.24 (m, 2H), 3.56 (septet, J=7 Hz, 1H), 1.20 (d, J=7 Hz, 6H).

c) 6-Isopropylpicolinonitrile

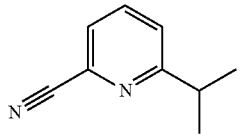

Trimethylsilyl cyanide (1.53 mL) was added to a solution of 2-isopropylpyridine 1-oxide (example 85, step b) (1.3 g) in DCM (40 mL) and the resulting mixture was stirred for 5 min. Diethylcarbamoyl chloride (1.2 mL) was added and the mixture stirred for 3 days. An aqueous solution of potassium carbonate (10%, 40 mL) was added and the mixture stirred for 10 min. The layers were separated and the aqueous phase extracted with DCM (2×40 mL). The combined organic solutions were washed with brine (40 mL), dried over sodium sulphate, filtered and evaporated. Purification was by silica gel chromatography eluting with 3:1 isohexane:ethyl acetate. The fractions containing product were combined and evaporated to give the subtitled compound as a clear oil. Yield 1.23 g.

m/z 147 (M+H)⁺ (APCI)

¹H NMR (300 MHz, CDCl₃) δ 7.74 (t, J=7.8 Hz, 1H), 7.51 (dd, J=7.6, 0.9 Hz, 1H), 7.39 (dd, J=8.1, 0.9 Hz, 1H), 3.11 (septet, J=6.7 Hz, 1H), 1.31 (d, J=6.7 Hz, 6H).

d) 6-Isopropylpicolinic acid

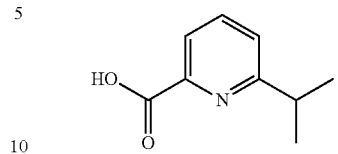

Concentrated hydrochloric acid (15 mL) was added to a solution of 6-isopropylpicolinonitrile (example 85, step c) (1.23 g) in methanol (30 mL). The resulting mixture was heated at reflux for 17 h and allowed to cool to RT. The mixture was cautiously poured into sodium hydroxide solution (10M, 50 mL) and stirred at RT overnight. The reaction was concentrated and the pH adjusted to 5 using 2M HCl solution. The aqeuous mixture was extracted with chloroform (3×100 mL). The organic solutions were combined, washed with brine (100 mL), dried over sodium sulphate, filtered and evaporated to give the subtitled compound as a yellow oil. Yield 0.94 g.

m/z 166 (M+H)⁺ (APCI)

¹H NMR (400 MHz, D₆-DMSO) δ 7.89-7.81 (m, 2H), 7.48 (dd, J=7.2, 1.3 Hz, 1H), 3.05 (septet, J=6.9 Hz, 1H), 1.22 (d, J=6.9 Hz, 6H). One exchangeable proton not observed.

e) (9-(2-Fluoro-3-(2-hydroxyethyl)benzyl)-1-oxa-4,9-diazaspiro[5.5]undecan-4-yl)(6-isopropylpyridin-2-yl)methanone

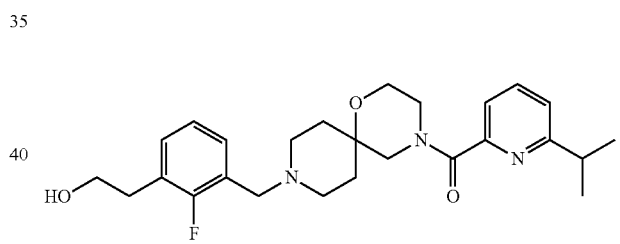

O-(7-Azabenzotriazol-1-yl)-N,N,N',N'-tetramethyluronium hexafluorophosphate (0.20 g) was added to a solution of 9-(3-(2-(tert-butyldimethylsilyloxy)ethyl)-2-fluorobenzyl)-1-oxa-4,9-diazaspiro[5.5]undecane (example 78, step d) (0.17 g), 6-isopropylpicolinic acid (example 85, step d) (0.07 g) and triethylamine (0.22 mL) in DMF (7 mL) at 0° C. The resulting yellow solution was allowed to warm to RT and was stirred for 2 h. The mixture was partitioned between ethyl acetate (100 mL) and brine (100 mL). The organic phase was separated, washed with brine (2×100 mL), dried over sodium sulphate, filtered and the solvent evaporated. The residue was dissolved in THF (10 mL) and a solution of TBAF in THF (1M, 0.8 mL) was added. The resulting mixture was stirred for 2 h and the solvent evaporated. Purification was by silica gel chromatography eluting with 47.5:47.5:5 isohexane:ethyl acetate:triethylamine to 95:5 ethyl acetate:triethylamine gradient. The fractions containing product were combined, toluene (50 mL) was added and the solvent evaporated under reduced pressure to give the subtitled compound as a clear gum. Yield 0.2 g.

m/z 456 (M+H)⁺ (APCI)

313 f) (R)-7-(2-(2-Fluoro-3-((4-(6-isopropylpicolinoyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

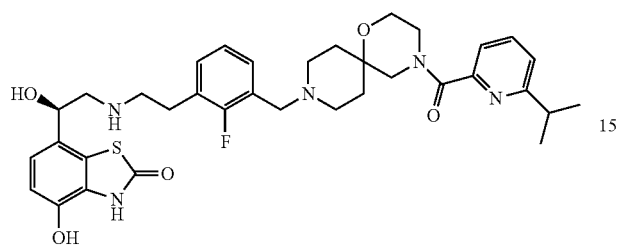

TFA (0.034 mL) was added to a solution of (9-(2-fluoro-3-(2-hydroxyethyl)benzyl)-1-oxa-4,9-diazaspiro[5.5]undecan-4-yl)(6-isopropylpyridin-2-yl)methanone (example 85, step e) (0.2 g) in DCM (5 mL) at 0° C. The mixture was stirred for 5 min then Dess-Martin periodinane (0.28 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.025 mL) and (R)-7-(2-amino-1-hydroxyethyl)-4-hydroxybenzo[d]thiazol-2(3H)-one hydrochloride (WO2007027134, example 1, step d) (0.12 g) were then added and the mixture stirred for 5 min before cooling in an ice bath. Sodium cyanoborohydride (0.04 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-35% acetonitrile in 0.2% aqueous TFA). The fractions containing product were combined, evaporated in vacuo and the residue triturated with diethylether to give the titled compound as a white solid. Yield 0.057 g.

m/z 664 (M+H)⁺ (APCI)

$^1$H NMR (400 MHz, D$_6$-DMSO, 90° C.) δ 11.27 (s, 1H), 7.81 (t, J=7.7 Hz, 1H), 7.54-7.21 (m, 5H), 6.94 (d, J=8.2 Hz, 1H), 6.77 (d, J=8.5 Hz, 1H), 4.97-4.82 (m, 1H), 4.40-4.25 (m, 2H), 3.77-3.47 (m, 6H), 3.29-2.99 (m, 11H), 2.11-1.62 (m, 4H), 1.24 (d, J=6.9 Hz, 6H). Five exchangeable protons not observed.

314

EXAMPLE 86

(R)-7-(2-(3-((4-(5-Ethylthiophene-3-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

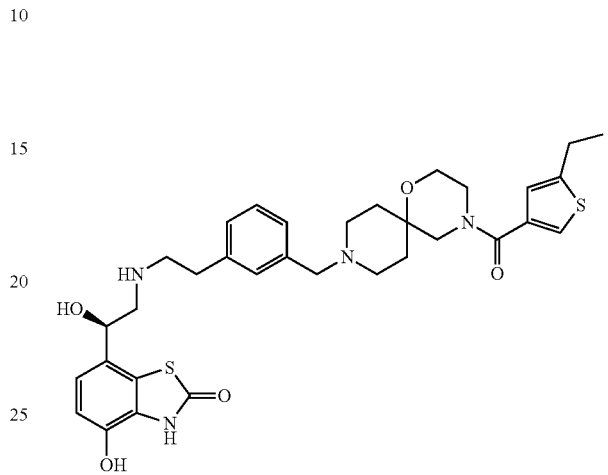

a) (5-Ethylthiophen-3-yl)(9-(3-(2-hydroxyethyl)benzyl)-1-oxa-4,9-diazaspiro[5.5]undecan-4-yl)methanone

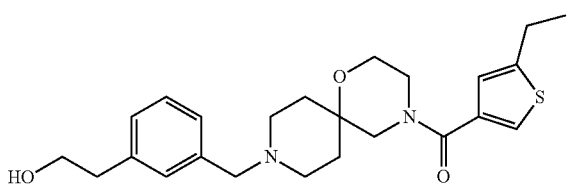 [SMILES: CCc1cc(C(=O)N2CCOC3(CCN(Cc4cccc(CCO)c4)CC3)C2)cs1]

HATU (0.209 g) was added to a stirred solution of 5-ethylthiophene-3-carboxylic acid (0.086 g), 2-(3-(1-oxa-4,9-diazaspiro[5.5]undecan-9-ylmethyl)phenyl)ethanol (example 82, step a) (0.160 g), and triethylamine (0.3 mL) in DMF (2 mL). After 1 h, the reaction mixture was diluted with ethyl acetate (25 mL) and washed with brine (2×25 mL). The ethyl acetate layer was evaporated in vacuo. Purification by silica gel chromatography eluting with 10:1, ethyl acetate:triethylamine gave the subtitled compound as a gum. Yield 0.18 g.

¹H NMR (400 MHz, D₆-DMSO, 90° C.) δ 7.52 (s, 1H), 7.20 (t, J=7.4 Hz, 1H), 7.13-7.05 (m, 3H), 6.90 (s, 1H), 4.60 (t, J=5.3 Hz, 1H), 3.64-3.55 (m, 4H), 3.53-3.46 (m, 2H), 3.31 (s, 4H), 2.81 (q, J=7.3 Hz, 2H), 2.74-2.66 (m, 2H), 2.37-2.23 (m, 4H), 1.75-1.65 (m, 2H), 1.56-1.35 (m, 2H), 1.24 (t, J=7.7 Hz, 3H).

b) 2-(3-((4-(5-Ethylthiophene-3-carbonyl)-1-oxa-4,9-diazaspiro[5.5]undecan-9-yl)methyl)phenyl)acetaldehyde

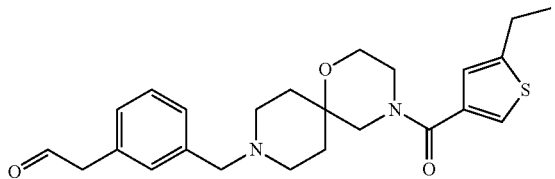 [SMILES: CCc1cc(C(=O)N2CCOC3(CCN(Cc4cccc(CC=O)c4)CC3)C2)cs1]

Dess-Martin periodinane (0.232 g) was added to a stirred solution of (5-ethylthiophen-3-yl)(9-(3-(2-hydroxyethyl)benzyl)-1-oxa-4,9-diazaspiro[5.5]undecan-4-yl)methanone (example 86, step a) (0.180 g) and trifluoroacetic acid (0.042 mL) in DCM (5 mL). After 1 h, ethyl acetate (30 mL) was added followed by a mixture of saturated sodium thiosulphate solution (5 mL) and saturated sodium bicarbonate solution (5 mL). The reaction mixture was shaken well and separated. The ethyl acetate solution was washed with saturated sodium bicarbonate solution, water and brine. Acetic acid (0.08 mL) was added, the solution was dried over sodium sulphate, filtered and evaporated in vacuo (bath temperature ~30° C.) to give the subtitled compound as a gum. Yield 0.17 g. Used directly.

m/z 427 (M+H)⁺ (APCI)

c) (R)-7-(2-(3-((4-(5-Ethylthiophene-3-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

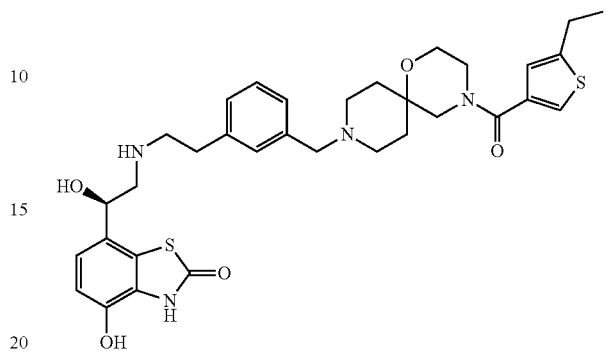

Acetic acid (0.036 mL) was added to a stirred solution of (R)-7-(2-amino-1-hydroxyethyl)-4-hydroxybenzo[d]thiazol-2(3H)-one hydrochloride (WO2007027134, example 1, step d) (0.166 g) and 2-(3-((4-(5-ethylthiophene-3-carbonyl)-1-oxa-4,9-diazaspiro[5.5]undecan-9-yl)methyl)phenyl)acetaldehyde (example 86, step b) (0.180 g) in methanol (8 mL). After 1 min, sodium cyanoborohydride (0.080 g) was added. After 1.5 h, the reaction mixture was filtered and purified by preparative HPLC (Sunfire™, Gradient: 10-40% acetonitrile in 0.2% aqueous TFA. The fractions containing the pure product were combined and evaporated in vacuo. Acetonitrile (200 mL) was added and the solution was evaporated in vacuo to give a gum. This process was repeated twice. Diethyl ether was added and the titled compound collected as a white solid. Yield 0.13 g.

m/z 637 (M+H)⁺ (APCI)

¹H NMR (300 MHz, D₆-DMSO, 90° C.) δ 11.37 (s, 1H), 7.51-7.30 (m, 5H), 6.93 (d, J=8.1 Hz, 1H), 6.77 (d, J=8.1 Hz, 1H), 6.91-6.86 (m, 1H), 4.94-4.86 (m, 1H), 4.29 (s, 2H), 3.71-3.31 (m, 8H), 3.29-2.93 (m, 8H), 2.81 (q, J=7.9 Hz, 2H), 2.15-1.91 (m, 2H), 1.75-1.51 (m, 2H), 1.25 (t, J=7.6 Hz, 3H). 5 exchangeable protons not observed.

EXAMPLE 87

(R)-4-Hydroxy-7-(1-hydroxy-2-(3-((4-(2-propylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

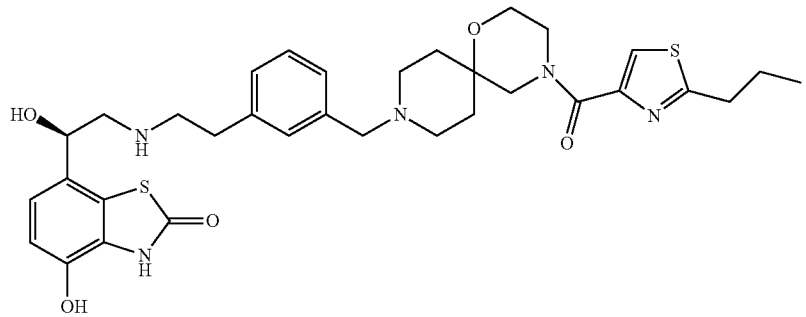

a) Butanethioamide

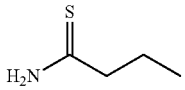

Phosphorous pentasulfide (3 g) was added to a suspension of butyramide (5 g) in MTBE (300 mL) and the resulting mixture stirred for 3 h. The reaction was filtered through Celite and the filter pad washed with MTBE (100 mL). The combined filtrate and washings were evaporated to give the subtitled compound as a yellow oil. Yield 5.2 g.

$^1$H NMR (300 MHz, D$_6$-DMSO) δ 9.32 (s, 1H), 9.12 (s, 1H), 2.43 (t, J=7.4 Hz, 2H), 1.72-1.59 (m, 2H), 0.86 (t, J=7.4 Hz, 3H).

b) Ethyl 2-propylthiazole-4-carboxylate

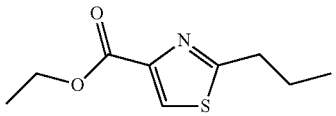

Ethyl 3-bromo-2-oxopropanoate (6.32 mL) was added to a solution of butanethioamide (example 87, step a) (5.2 g) in ethanol (100 mL) and the resulting mixture heated at reflux overnight. The solvent was evaporated and the residue partitioned between ethyl acetate (100 mL) and saturated sodium hydrogen carbonate solution (100 mL). The layers were separated and the aqueous phase extracted with ethyl acetate (2×100 mL). The combined organic solutions were washed with brine (100 mL) dried over sodium sulphate, filtered and evaporated. Purification was by silica gel chromatography eluting with 10:1 isohexane:ethyl acetate. The fractions containing product were combined and evaporated to give the subtitled compound as a yellow oil. Yield 5.24 g.

m/z 200 (M+H)$^+$ (APCI)

$^1$H NMR (400 MHz, CDCl$_3$) δ 8.05 (s, 1H), 4.42 (q, J=7.2 Hz, 2H), 3.04 (t, J=7.7 Hz, 2H), 1.89-1.78 (m, 2H), 1.40 (t, J=7.2 Hz, 3H), 1.02 (t, J=7.2 Hz, 3H).

c) 2-Propylthiazole-4-carboxylic acid

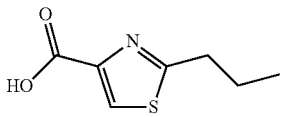

Lithium hydroxide monohydrate (4.4 g) was added to a solution of ethyl 2-propylthiazole-4-carboxylate (example 87, step b) (5.24 g) in a mixture of THF (80 mL) and water (20 mL). The resulting mixture was stirred overnight. The reaction was acidified with concentrated hydrochloric acid and the volatiles evaporated. The resulting aqueous mixture was saturated with sodium chloride and extracted with ethyl acetate (3×100 mL). The combined organic solutions were dried over sodium sulphate, filtered and evaporated to give the subtitled compound as a white solid. Yield 2.5 g.

$^1$H NMR (300 MHz, D$_6$-DMSO) δ 12.91 (s, 1H), 8.31 (s, 1H), 2.97 (t, J=7.5 Hz, 2H), 1.81-1.67 (m, 2H), 0.95 (t, J=7.3 Hz, 3H).

d) (9-(3-(2-Hydroxyethyl)benzyl)-1-oxa-4,9-diazaspiro[5.5]undecan-4-yl)(2-propylthiazol-4-yl)methanone

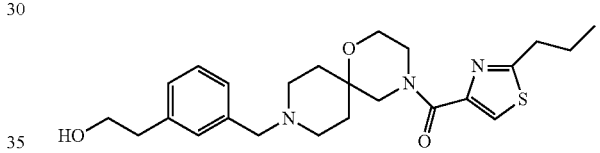

O-(7-Azabenzotriazol-1-yl)-N,N,N',N'-tetramethyluronium hexafluorophosphate (0.24 g) was added to a solution of 2-(3-(1-oxa-4,9-diazaspiro[5.5]undecan-9-ylmethyl)phenyl)ethanol (example 82, step a) (0.14 g), 2-propylthiazole-4-carboxylic acid (example 87, step c) (0.084 g) and triethylamine (0.27 mL) in DMF (7 mL) at 0° C. The resulting yellow solution was allowed to warm to RT and was stirred for 2 h. The mixture was partitioned between ethyl acetate (100 mL) and brine (100 mL), the organic phase was washed with brine (2×100 mL), dried over sodium sulphate, filtered and the solvent evaporated. The resulting gum was purified by silica gel chromatography eluting with 47.5:47.5:5 isohexane:ethyl acetate:triethylamine to 95:5 ethyl acetate:triethylamine gradient. The fractions containing product were combined, toluene (200 mL) was added and the solvent evaporated under reduced pressure to give the subtitled compound as a clear gum. Yield 0.14 g.

m/z 444 (M+H)$^+$ (APCI)

$^1$H NMR (400 MHz, D$_6$-DMSO, 90° C.) δ 7.91 (s, 1H), 7.18 (t, J=7.4 Hz, 1H), 7.12-7.04 (m, 3H), 4.37-4.30 (m, 1H), 3.69-3.57 (m, 8H), 3.41 (s, 2H), 2.98 (t, J=7.3 Hz, 2H), 2.71 (t, J=7.1 Hz, 2H), 2.40-2.23 (m, 4H), 1.82-1.64 (m, 4H), 1.59-1.46 (m, 2H), 0.97 (t, J=7.4 Hz, 3H).

e) (R)-4-Hydroxy-7-(1-hydroxy-2-(3-((4-(2-propylthiazole-4-carbonyl)-1-oxa-4,9-diazaspiro[5.5]undecan-9-yl)methyl)phenethylamino)ethyl)benzo[d]thiazol-2(3H)-one ditrifluoroacetate

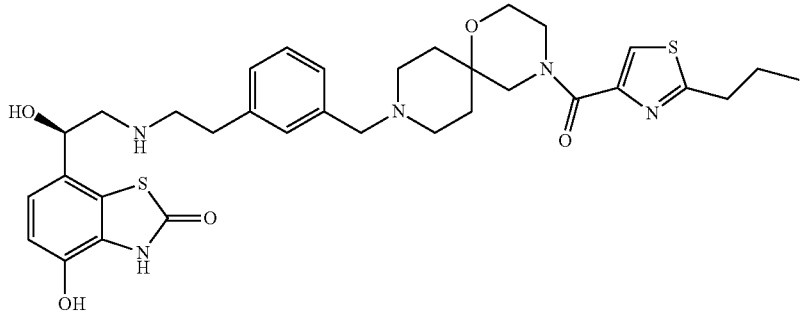

TFA (0.023 mL) was added to a solution of (9-(3-(2-hydroxyethyl)benzyl)-1-oxa-4,9-diazaspiro[5.5]undecan-4-yl)(2-propylthiazol-4-yl)methanone (example 87, step d) (0.13 g) in DCM (5 mL) at 0° C. The mixture was stirred for 5 min then Dess-Martin periodinane (0.19 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.017 mL) and (R)-7-(2-amino-1-hydroxyethyl)-4-hydroxybenzo[d]thiazol-2(3H)-one hydrochloride (WO2007027134, example 1, step d) (0.077 g) were then added and the mixture stirred for 5 min before cooling in an ice bath. Sodium cyanoborohydride (0.028 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined, evaporated in vacuo. Further purification was by preparative HPLC (Sunfire™, Gradient: 10-35% acetonitrile in 0.2% aqueous TFA). The fractions containing product were combined, evaporated in vacuo and the residue triturated with diethylether to give the titled compound as a white solid. Yield 0.09 g.

m/z 652 (M+H)⁺ (APCI)
$^1$H NMR (400 MHz, D$_6$-DMSO, 90° C.) δ 11.29 (s, 1H), 7.96-7.92 (m, 1H), 7.46-7.32 (m, 4H), 6.98-6.92 (m, 1H), 6.81-6.75 (m, 1H), 4.98-4.90 (m, 1H), 4.34-4.27 (m, 2H), 3.76-3.62 (m, 6H), 3.30-2.94 (m, 12H), 2.08-1.98 (m, 2H), 1.85-1.70 (m, 4H), 1.01-0.92 (m, 3H). Five exchangeable protons not observed.

EXAMPLE 88

(R)-7-(2-(3-(2-Fluoro-3-((4-(2-isopropylthiazole-4-carbonyl)-1-oxa-4,9-diazaspiro[5.5]undecan-9-yl)methyl)phenyl)propylamino)-1-hydroxyethyl)-4-hydroxybenzo[d]thiazol-2(3H)-one ditrifluoroacetate

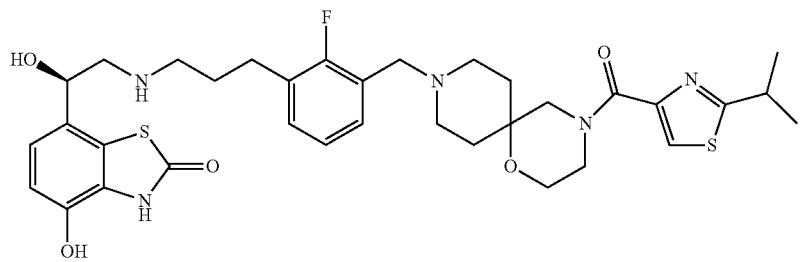

a) 3-(2-Fluorophenyl)propan-1-ol

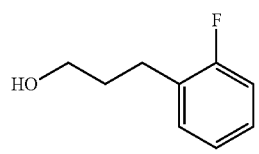 [SMILES: OCCCc1ccccc1F]

A solution of borane dimethylsulfide complex (2M in THF, 27.6 mL) was added dropwise to a solution of 3-(2-fluorophenyl)propanoic acid (3.09 g) in tetrahydrofuran (25 mL) and the resulting mixture was allowed to warm to RT and stirred overnight. The reaction was quenched with methanol and, when bubbling had ceased, evaporated. Purification was by silica gel chromatography eluting with 4:1 to 1:1 isohexane:ethyl acetate gradient. The fractions containing product were combined and evaporated in vacuo to give the subtitled compound as a clear oil. Yield 2.72 g.
$^1$H NMR (300 MHz, CDCl$_3$) δ 7.24-7.13 (m, 2H), 7.09-6.97 (m, 2H), 3.67 (t, J=6.3 Hz, 2H), 2.74 (t, J=7.6 Hz, 2H), 1.95-1.83 (m, 2H). One exchangeable proton not observed.

b) tert-Butyl(3-(2-fluorophenyl)propoxy)dimethylsilane

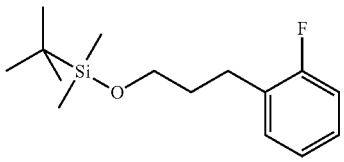 [SMILES: CC(C)(C)[Si](C)(C)OCCCc1ccccc1F]

tert-Butyldimethylsilyl chloride (3.19 g) was added to a solution of imidazole (3.6 g) and 3-(2-fluorophenyl)propan-1-ol (example 88, step a) (2.72 g) in dry DMF (30 mL) cooled in an ice bath. After 45 min, the reaction mixture was diluted with ethyl acetate (100 mL), washed with water (3×100 mL) and evaporated. The resulting gum was purified by silica gel chromatography eluting with isohexane. The fractions containing product were combined and evaporated to give the subtitled compound as a clear oil. Yield 4.4 g.

$^1$H NMR (300 MHz, CDCl$_3$) δ 7.23-7.09 (m, 2H), 7.09-6.94 (m, 2H), 3.64 (t, J=6.3 Hz, 2H), 2.75-2.66 (m, 2H), 1.89-1.76 (m, 2H), 0.91 (s, 9H), 0.05 (s, 6H).

c) 3-(3-(tert-Butyldimethylsilyloxy)propyl)-2-fluorobenzaldehyde

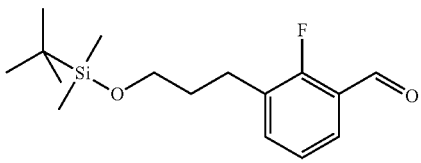 [SMILES: CC(C)(C)[Si](C)(C)OCCCc1cccc(C=O)c1F]

tert-Butyl(3-(2-fluorophenyl)propoxy)dimethylsilane (example 88, step b) (4.4 g) was added dropwise over 5 min to a solution of sec-butyllithium (1.4M in cyclohexane, 11.7 mL) and 1,1,4,7,7-pentamethyldiethylenetriamine (3.4 mL) in THF (25 mL) at −78° C. The resulting mixture was stirred for 2 h, then DMF (6.4 mL) was cautiously added and the resulting mixture allowed to warm to RT and stirred overnight. The reaction was quenched with water (100 mL) and then ethyl acetate (250 mL) was added. The phases were separated and the organic phase washed with water (2×100 mL), 2M HCl solution (2×50 mL), and brine (100 mL), then dried over magnesium sulphate, filtered and evaporated. Purification was by silica gel chromatography eluting with isohexane to 10% ether in isohexane gradient. The product containing fractions were combined and evaporated to give the subtitled compound as a clear oil. Yield 1 g.

$^1$H NMR (400 MHz, CDCl$_3$) δ 10.38 (s, 1H), 7.73-7.67 (m, 1H), 7.48 (td, J=7.4, 1.8 Hz, 1H), 7.18 (t, J=7.7 Hz, 1H), 3.66 (t, J=6.0 Hz, 2H), 2.82-2.75 (m, 2H), 1.90-1.80 (m, 2H), 0.91 (s, 9H), 0.06 (s, 6H).

d) (9-(2-Fluoro-3-(3-hydroxypropyl)benzyl)-1-oxa-4,9-diazaspiro[5.5]undecan-4-yl)(2-isopropylthiazol-4-yl)methanone

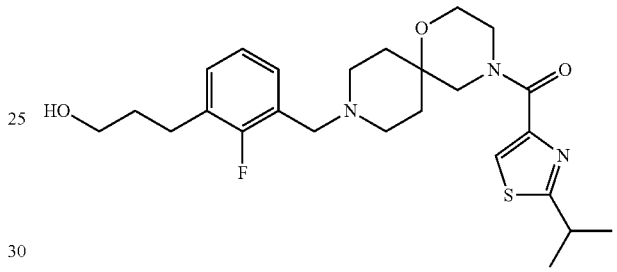

3-(3-(tert-Butyldimethylsilyloxy)propyl)-2-fluorobenzaldehyde (example 88, step c) (0.15 g) was added to a solution of (2-isopropylthiazol-4-yl)(1-oxa-4,9-diazaspiro[5.5]undecan-4-yl)methanone trifluoroacetate (example 22, step b) (0.19 g) and acetic acid (0.03 mL) in N-methyl-2-pyrrolidinone (10 mL). The resulting mixture was stirred for 15 min then cooled in an ice bath. Sodium triacetoxyborohydride (0.16 g) was then added and the mixture stirred overnight. The reaction was poured into a mixture of saturated sodium hydrogen carbonate solution (20 mL) and water (100 mL). The aqueous was extracted with ethyl acetate (3×100 mL). The combined organics were washed with water (50 mL) and brine (100 mL), dried over sodium sulphate, filtered and evaporated. The residue was redissolved in THF (10 mL) and a solution of TBAF (1M in THF, 1.52 mL) was added. The resulting mixture was stirred for 2 h and the solvent evaporated. The residue was purified by column chromatography eluting with 4:1 isohexane:ethyl acetate+5% triethylamine to ethyl acetate+5% triethylamine gradient. The fractions containing product were combined and evaporated to give the subtitled compound as a clear oil. Yield 0.22 g.

m/z 476 (M+H)$^+$ (APCI)

$^1$H NMR (400 MHz, D$_6$-DMSO, 90° C.) δ 7.99 (s, 1H), 7.24-7.12 (m, 2H), 7.08-7.01 (m, 1H), 4.48 (t, J=5.1 Hz, 1H), 3.74-3.38 (m, 10H), 2.62 (t, J=7.7 Hz, 2H), 2.46-2.13 (m, 4H), 1.74-1.44 (m, 6H), 1.35 (d, J=6.4 Hz, 6H). One proton obscured by water peak.

e) (R)-7-(2-(3-(2-Fluoro-3-((4-(2-isopropylthiazole-4-carbonyl)-1-oxa-4,9-diazaspiro[5.5]undecan-9-yl)methyl)phenyl)propylamino)-1-hydroxyethyl)-4-hydroxybenzo[d]thiazol-2(3H)-one ditrifluoroacetate

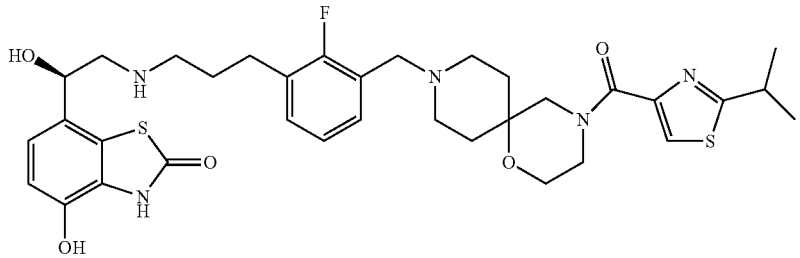 [SMILES: CC(C)c1nc(C(=O)N2CCOC3(CCN(Cc4cccc(CCCNC[C@H](O)c5ccc(O)c6[nH]c(=O)sc56)c4F)CC3)C2)cs1]

Trifluoroaceticacid (0.032 mL) was added to a solution of (9-(2-fluoro-3-(3-hydroxypropyl)benzyl)-1-oxa-4,9-diazaspiro[5.5]undecan-4-yl)(2-isopropylthiazol-4-yl)methanone (example 88, step d) (0.2 g) in DCM (5 mL) at 0° C. The mixture was stirred for 5 min then Dess-Martin periodinane (0.27 g) was added. The resulting yellow solution was allowed to warm to RT and stirred for 1 h. A mixture of saturated sodium thiosulphate solution (5 mL), saturated sodium bicarbonate solution (5 mL) and ethyl acetate (20 mL) was then added and the resulting mixture stirred vigorously for 10 min. The aqueous phase was separated and extracted with ethyl acetate (20 mL). The combined organic solutions were washed with brine (20 mL), acidified with a few drops of acetic acid, dried over sodium sulfate, filtered and evaporated in vacuo. The residue was dissolved in methanol (5 mL), acetic acid (0.024 mL) and (R)-7-(2-amino-1-hydroxyethyl)-4-hydroxybenzo[d]thiazol-2(3H)-one hydrochloride (WO2007027134, example 1, step d) (0.11 g) were then added and the mixture stirred for 5 min before cooling in an ice bath. Sodium cyanoborohydride (0.040 g) was then added, the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-35% acetonitrile in 0.2% aqueous TFA). The fractions containing product were combined, evaporated in vacuo and the residue triturated with diethylether to give the titled compound as a white solid. Yield 0.14 g.

m/z 684 (M+H)⁺ (APCI)
4.39-4.24 (m, 2H), 3.77-3.58 (m, 6H), 3.34-2.94 (m, 9H),
$^{1}$H NMR (400 MHz, D$_6$-DMSO, 90° C.) δ 11.25 (s, 1H), 7.98-7.89 (m, 1H), 7.52-7.35 (m, 2H), 7.28-7.16 (m, 1H), 6.98-6.86 (m, 1H), 6.82-6.70 (m, 1H), 4.96-4.84 (m, 1H), 4.39-4.24 (m, 2H), 3.77-3.58 (m, 6H), 3.34-2.94 (m, 9H), 2.80-2.66 (m, 2H), 2.10-1.70 (m, 6H), 1.41-1.27 (m, 6H) and 5 exchangables not observed

EXAMPLE 89

(R)-4-Hydroxy-7-(1-hydroxy-2-(3-((10-(2-methylthiazole-4-carbonyl)-7-oxa-3,10-diazaspiro[5.6]dodecan-3-yl)methyl)phenethylamino)ethyl)benzo[d]thiazol-2(3H)-one ditrifluoroacetate

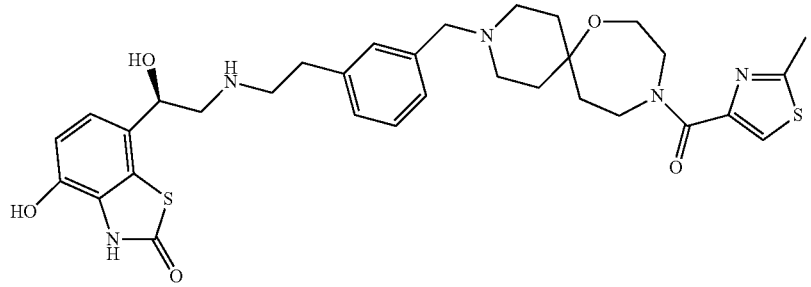 [SMILES: Cc1nc(C(=O)N2CCOC3(CCN(Cc4cccc(CCNC[C@H](O)c5ccc(O)c6[nH]c(=O)sc56)c4)CC3)CC2)cs1]

a) tert-Butyl 4-(cyanomethyl)-4-hydroxypiperidine-1-carboxylate

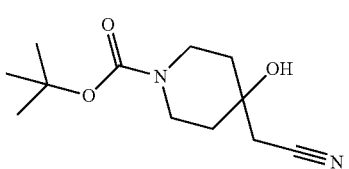 [SMILES: CC(C)(C)OC(=O)N1CCC(O)(CC#N)CC1]

A solution of tert-butyl 1-oxa-6-azaspiro[2.5]octane-6-carboxylate (2 g) in DMF (20 mL) was treated with potassium cyanide (0.672 g) and the resultant mixture stirred at 20° C. for 4 days. The mixture was partitioned between ethyl acetate and brine, the organic layer was washed twice with brine, dried over sodium sulphate, filtered and the solvent evaporated under reduced pressure. The crude product was purified by flash silica chromatography using 60% ethyl acetate in isohexane as solvent. Pure fractions were evaporated to dryness to afford the subtitled compound. Yield 1.18 g.

$^1$H NMR (400 MHz, CDCl$_3$) δ 3.95-3.85 (m, 2H), 3.19-3.10 (m, 2H), 2.54 (s, 2H), 1.86 (s, 1H), 1.76-1.61 (m, 4H), 1.46 (s, 9H).

b) tert-Butyl 4-(2-aminoethyl)-4-hydroxypiperidine-1-carboxylate

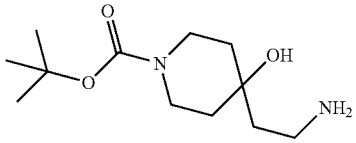 [SMILES: CC(C)(C)OC(=O)N1CCC(O)(CCN)CC1]

A solution of tert-butyl 4-(cyanomethyl)-4-hydroxypiperidine-1-carboxylate (example 89, step a) (1.4 g) in a mixture of ethanol (20 mL) and acetic acid (20 mL) was hydrogenated at 4 atmospheres pressure of hydrogen in the presence of platinum(IV) oxide (0.25 g) for 4 hours. The catalyst was filtered off and the solvents removed under reduced pressure. The residue was partitioned between dilute aqueous NaOH and ethyl acetate and the organic layer dried over sodium sulphate, filtered and the solvent evaporated under reduced pressure to afford the subtitled compound. Yield 1.1 g. Used directly.

c) tert-Butyl 4-(2-(2-chloroacetamido)ethyl)-4-hydroxypiperidine-1-carboxylate

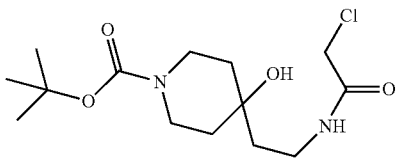 [SMILES: CC(C)(C)OC(=O)N1CCC(O)(CCNC(=O)CCl)CC1]

Chloroacetyl chloride (0.483 mL) was added dropwise over 10 minutes to a vigorously stirred mixture at 0° C. of tert-butyl 4-(2-aminoethyl)-4-hydroxypiperidine-1-carboxylate (example 89, step b) (1.1 g) in ethyl acetate (25 mL) and potassium carbonate (1.77 g) dissolved in water (20 mL). The mixture was then stirred at 0° C. for 45 minutes before being extracted with ethyl acetate. The organic layer was dried over sodium sulphate, filtered and the solvent evaporated under reduced pressure. The crude product was purified by flash silica chromatography eluting with ethyl acetate. Pure fractions were evaporated to dryness to afford the subtitled compound. Yield 0.9 g.
m/z 319 (M−H)$^−$ (APCI)

d) tert-Butyl 9-oxo-7-oxa-3,10-diazaspiro[5.6]dodecane-3-carboxylate

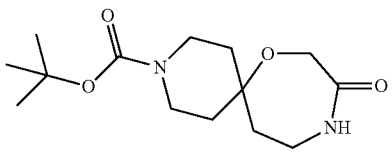 [SMILES: CC(C)(C)OC(=O)N1CCC2(CCNC(=O)CO2)CC1]

A solution of tert-butyl 4-(2-(2-chloroacetamido)ethyl)-4-hydroxypiperidine-1-carboxylate (example 89, step c) (0.3 g) in dry THF (18 mL) was added dropwise over 6 hours to a refluxing mixture of potassium tert-butoxide (1M in tert-butanol, 3 mL) and dry THF (60 mL). At the end of the addition the mixture was heated at reflux for a further 15 minutes and then cooled to room temperature. The mixture was partitioned between ethyl acetate and brine. The organic layer was dried over sodium sulphate, filtered and the solvent evaporated under reduced pressure. Trituration with diethyl-ether afforded the subtitled compound. Yield 0.117 g.
$^1$H NMR (400 MHz, D$_6$-DMSO) δ 7.67 (s, 1H), 4.01 (s, 2H), 3.57 (d, J=13.1 Hz, 2H), 3.11 (dd, J=9.6, 4.2 Hz, 2H), 3.05-2.95 (m, 2H), 1.85-1.76 (m, 4H), 1.38 (s, 9H), 1.37-1.32 (m, 2H).

e) tert-Butyl 7-oxa-3,10-diazaspiro[5.6]dodecane-3-carboxylate

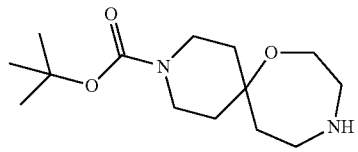 [SMILES: CC(C)(C)OC(=O)N1CCC2(CCNCCO2)CC1]

Borane-methyl sulfide complex (2M in THF, 2.88 mL) was added to a solution of tert-butyl 9-oxo-7-oxa-3,10-diazaspiro[5.6]dodecane-3-carboxylate (example 89, step d) (0.41 g) in dry THF (40 mL) and the reaction mixture then heated at 70° C. for 30 minutes under nitrogen. The mixture was cooled to room temperature and quenched with methanol. The solvents were removed under reduced pressure and the residue dissolved in methanol (100 mL). N1,N2-dimethylethane-1,2-diamine (1.0 g) was added and the mixture heated at reflux under nitrogen for 16 h. Further N1,N2-dimethylethane-1,2-diamine (1.0 g) was added and refluxing continued for 16 h. The solvents were evaporated under reduced pressure and the residue azeotroped with toluene. The crude product was purified by flash silica chromatography using 6% methanol in dichloromethane with 1% triethylamine as solvent. Pure fractions were evaporated to dryness to afford the subtitled compound. Yield 0.176 g.
m/z 271 (M+H)$^+$ (APCI)

f) tert-Butyl 10-(2-methylthiazole-4-carbonyl)-7-oxa-3,10-diazaspiro[5.6]dodecane-3-carboxylate

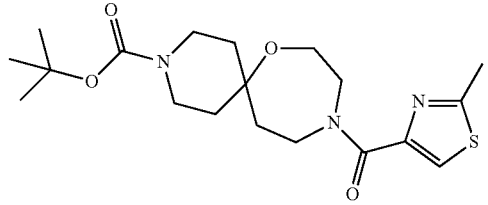 [SMILES: Cc1nc(C(=O)N2CCOC3(CCN(C(=O)OC(C)(C)C)CC3)CC2)cs1]

HATU (0.322 g) was added in one portion to a solution at 0° C. of tert-butyl 7-oxa-3,10-diazaspiro[5.6]dodecane-3-carboxylate (example 89, step e) (0.176 g) and 2-methylthiazole-4-carboxylic acid (0.093 g) and triethylamine (0.36 mL) in DMF (10 mL). The mixture was then stirred at 20° C. for 1 hour. The reaction mixture was partitioned between ethyl acetate and brine. The organic layer was washed twice with brine, dried over sodium sulphate, filtered and the solvent evaporated under reduced pressure. The crude product was purified by flash silica chromatography eluting with ethyl acetate. Pure fractions were evaporated to dryness to afford the subtitled compound. Yield 210 mg.

$^1$H NMR (400 MHz, D$_6$-DMSO, 90° C.) δ 7.78 (s, 1H), 3.69 (s, 4H), 3.65-3.62 (m, 2H), 3.59-3.53 (m, 2H), 3.11-3.03 (m, 2H), 2.66 (s, 3H), 1.85-1.81 (m, 2H), 1.74-1.67 (m, 2H), 1.39 (s, 9H), 1.38-1.33 (m, 2H).

g) (2-Methylthiazol-4-yl)(7-oxa-3,10-diazaspiro[5.6]dodecan-10-yl)methanone trifluoroacetate

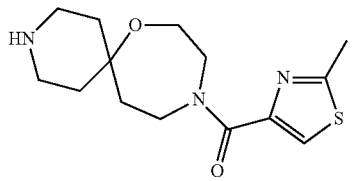 [SMILES: Cc1nc(C(=O)N2CCOC3(CCNCC3)CC2)cs1]

A solution of tert-butyl 10-(2-methylthiazole-4-carbonyl)-7-oxa-3,10-diazaspiro[5.6]dodecane-3-carboxylate (example 89, step f) (0.21 g) in DCM (10 mL) was treated with trifluoroacetic acid (10 mL) and the solution allowed to stand at 20° C. for 25 minutes. Toluene (40 mL) was added and the solvents evaporated under reduced pressure. The residue was azeotroped with acetonitrile to afford the subtitled compound. Yield 0.21 g.

m/z 296 (M+H)$^+$ (APCI)

h) (3-(3-(2-Hydroxyethyl)benzyl)-7-oxa-3,10-diazaspiro[5.6]dodecan-10-yl)(2-methylthiazol-4-yl)methanone

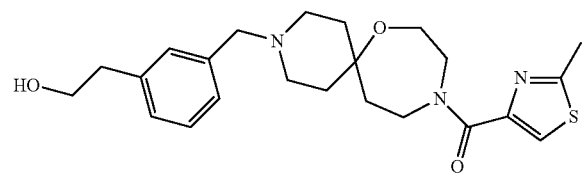 [SMILES: Cc1nc(C(=O)N2CCOC3(CCN(Cc4cccc(CCO)c4)CC3)CC2)cs1]

A solution of (2-methylthiazol-4-yl)(7-oxa-3,10-diazaspiro[5.6]dodecan-10-yl)methanone trifluoroacetate (example 89, step g) (0.21 g) in acetonitrile (15 mL) was treated with triethylamine (0.214 mL) followed by 2-(3-(bromomethyl)phenyl)ethanol (example 6, step a) (0.121 g). The reaction mixture was stirred for 3 hours at 20° C. The solvent was evaporated under reduced pressure and the residue was partitioned between DCM and saturated sodium bicarbonate solution. The aqueous layer was re-extracted twice with DCM and the combined organics were dried over sodium sulphate, filtered and the solvent removed under reduced pressure. The crude product was purified by flash silica chromatography using 6% methanol in dichloromethane with 1% triethylamine as solvent. Pure fractions were evaporated to dryness to afford the subtitled compound. Yield 0.21 g.

m/z 430 (M+H)$^+$ (APCI)

i) (R)-4-Hydroxy-7-(1-hydroxy-2-(3-((10-(2-methylthiazole-4-carbonyl)-7-oxa-3,10-diazaspiro[5.6]dodecan-3-yl)methyl)phenethylamino)ethyl)benzo[d]thiazol-2(3H)-one ditrifluoroacetate

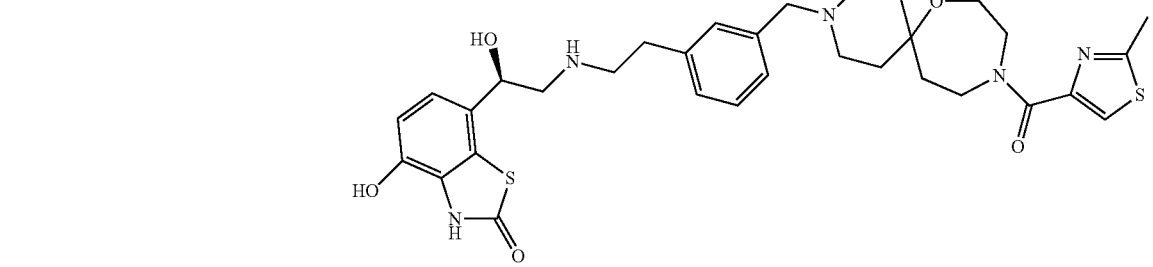

A solution of (3-(3-(2-hydroxyethyl)benzyl)-7-oxa-3,10-diazaspiro[5.6]dodecan-10-yl)(2-methylthiazol-4-yl)methanone (example 89, step h) (0.21 g) in DCM (15 mL) was treated with trifluoroacetic acid (0.038 mL) followed by Dess-Martin periodinane (0.311 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.028 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.193 g) and acetic acid (0.028 mL) in methanol (15 mL). The mixture was cooled in an ice bath and treated with sodium cyanoborohydride (0.061 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.145 g.

m/z 638 (M+H)$^+$ (APCI)

$^1$H NMR (400 MHz, D$_6$-DMSO, 90° C.) δ 11.27 (s, 1H), 7.79 (s, 1H), 7.44-7.32 (m, 4H), 6.93 (d, J=8.5 Hz, 1H), 6.77 (d, J=8.5 Hz, 1H), 4.94-4.89 (m, 1H), 4.28 (s, 2H), 3.71 (s, 4H), 3.68-3.64 (m, 2H), 3.25 (t, J=8.1 Hz, 2H), 3.20-2.99 (m, 8H), 2.66 (s, 3H), 2.04-1.95 (m, 2H), 1.91-1.83 (m, 2H), 1.78-1.67 (m, 2H). Five exchangeable protons not observed.

EXAMPLE 90

(R)-7-(2-(2-(2-Fluoro-3-((4-(2-isopropylthiazole-4-carbonyl)-1-oxa-4,9-diazaspiro[5.5]undecan-9-yl)methyl)phenyl)-2-methylpropylamino)-1-hydroxy-ethyl)-4-hydroxybenzo[d]thiazol-2(3H)-one ditrifluoroacetate

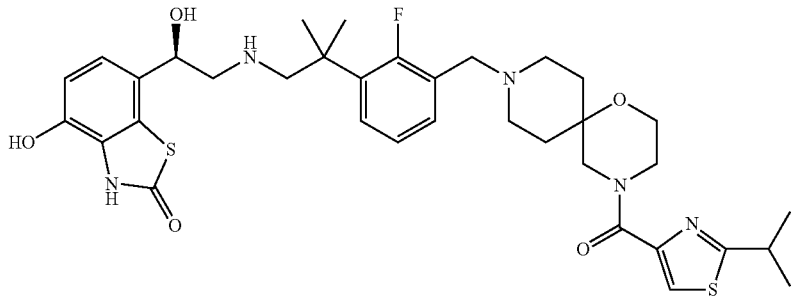 [SMILES: CC(C)c1nc(C(=O)N2CCOC3(CCN(Cc4cccc(C(C)(C)CNC[C@H](O)c5ccc(O)c6[nH]c(=O)sc56)c4F)CC3)C2)cs1]

a) Methyl 2-(2-fluorophenyl)acetate

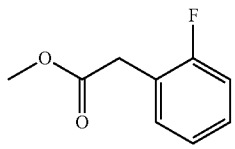

A solution of 2-(2-fluorophenyl)acetic acid (9.6 g) in methanol (200 mL) was treated with trimethylsilyl chloride (10 mL) and the mixture heated at reflux for 2 hours. The solvent was removed under reduced pressure and the residue partitioned between ethyl acetate and saturated sodium bicarbonate solution, the organic layer was dried over sodium sulphate, filtered and the solvent removed under reduced pressure to afford the subtitled compound. Yield 9.7 g.

$^1$H NMR (400 MHz, CDCl$_3$) δ 7.29-7.23 (m, 2H), 7.13-7.03 (m, 2H), 3.71 (s, 3H), 3.68 (s, 2H).

b) Methyl 2-(2-fluorophenyl)-2-methylpropanoate

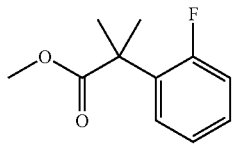

To a solution of iodomethane (3.2 mL) in dry DMF (80 mL) at 0° C. was added sodium hydride (60% suspension, 2 g) followed by methyl 2-(2-fluorophenyl)acetate (example 90, step a) (2.75 g). The mixture was allowed to slowly warm to room temperature and then stirred at room temp for 5 hours. The reaction was quenched by careful addition of saturated aqueous ammonium chloride (120 mL). The mixture was extracted three times with ethyl acetate, the combined organics were washed with brine, dried over sodium sulphate, filtered and the solvent removed under reduced pressure. The crude product was purified by flash silica chromatography using 8% ethyl acetate in isohexane as solvent. Pure fractions were evaporated to dryness to afford the subtitled compound. Yield 2.6 g.

$^1$H NMR (400 MHz, D$_6$-DMSO) δ 7.46-7.40 (m, 1H), 7.35-7.29 (m, 1H), 7.22-7.11 (m, 2H), 3.58 (s, 3H), 1.48 (s, 6H).

c) 2-(2-Fluorophenyl)-2-methylpropanoic acid

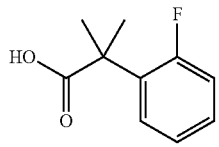

A solution of sodium hydroxide (1 g) in water (50 mL) was added to a solution of methyl 2-(2-fluorophenyl)-2-methyl-propanoate (example 90, step b) (2.6 g) in methanol (50 mL) and THF (50 mL). The reaction mixture was heated at 40° C. for 40 hours. The organics were removed under reduced pressure and the remaining aqueous solution washed with ethyl acetate. The aqueous layer was cooled and acidified by addition of concentrated HCl. The mixture was extracted with ethyl acetate and the organic layer washed with brine before being dried over sodium sulphate, filtered and the solvent removed under reduced pressure to afford the subtitled compound. Yield 1.5 g.

m/z 181 (M−H)$^-$ (APCI)

d) 2-(2-Fluorophenyl)-2-methylpropan-1-ol

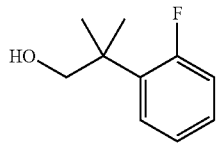

Borane-methyl sulfide (2M in THF, 12.35 mL) was added dropwise to a solution of 2-(2-fluorophenyl)-2-methylpropanoic acid (example 90, step c) (1.5 g) in THF (30 mL). The reaction mixture was stirred at 20° C. for 8 hours. The mixture was quenched by careful addition of methanol until evolution of gas ceased. The solvents were removed under reduced pressure and the residue azeotroped with toluene. The crude product was purified by flash silica chromatography using 30% ethyl acetate in isohexane as solvent. Pure fractions were evaporated to dryness to afford the subtitled compound. Yield 1.3 g.

$^1$H NMR (400 MHz, CDCl$_3$) δ 7.36-7.31 (m, 1H), 7.25-7.19 (m, 1H), 7.13-7.08 (m, 1H), 7.04-6.99 (m, 1H), 3.79 (dd, J=6.4, 1.0 Hz, 2H), 1.39 (d, J=1.0 Hz, 6H). One exchangeable proton not observed.

e) tert-Butyl(2-(2-fluorophenyl)-2-methylpropoxy)dimethylsilane

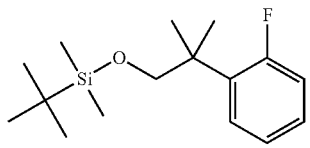 [SMILES: CC(C)(CO[Si](C)(C)C(C)(C)C)c1ccccc1F]

tert-Butyldimethylsilyl chloride (1.4 g) was added portionwise to a stirred solution of 2-(2-fluorophenyl)-2-methylpropan-1-ol (example 90, step d) (1.3 g) and imidazole (0.631 g) in DMF (7 mL) at 20° C. The reaction mixture was stirred for 3 hours at room temperature and then partitioned between ethyl acetate and brine. The organic layer was washed twice with brine, dried over sodium sulphate, filtered and the solvent evaporated under reduced pressure. The crude product was purified by flash silica chromatography, elution gradient 100% isohexane to 1% diethyl ether in isohexane. Pure fractions were evaporated to dryness to afford the subtitled compound. Yield 1.4 g.

$^1$H NMR (400 MHz, CDCl$_3$) δ 7.34-7.29 (m, 1H), 7.20-7.14 (m, 1H), 7.08-7.03 (m, 1H), 7.00-6.94 (m, 1H), 3.71 (s, 2H), 1.35 (s, 6H), 0.80 (s, 9H), −0.06 (s, 6H).

f) 3-(1-(tert-Butyldimethylsilyloxy)-2-methylpropan-2-yl)-2-fluorobenzaldehyde

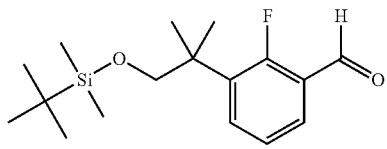 [SMILES: CC(C)(CO[Si](C)(C)C(C)(C)C)c1cccc(C=O)c1F]

sec-Butyllithium (1.4M in cyclohexane, 3.54 mL) was added to dry tetrahydrofuran (10 mL) under nitrogen and the solution cooled to −78° C. N1-(2-(dimethylamino)ethyl)-N1,N2,N2-trimethylethane-1,2-diamine (0.859 g) was added slowly dropwise. A solution of tert-butyl(2-(2-fluorophenyl)-2-methylpropoxy)dimethylsilane (example 90, step e) (1.4 g) in dry tetrahydrofuran (3 mL) was then added dropwise over 5 minutes. The reaction mixture was stirred for 2 hours at −78° C. DMF (2.69 mL) was added dropwise over 5 minutes and the mixture stirred at −78° C. for 1 hour followed by room temperature for 45 minutes. The reaction mixture was quenched by addition of water. Ethyl acetate (200 mL) was added and the organic washed three times with water followed by twice with 2M HCl and twice with water, then brine and dried over sodium sulphate, filtered and the solvent evaporated under reduced pressure. The crude product was purified by flash silica chromatography, elution gradient 1 to 5% ethyl acetate in isohexane. Pure fractions were evaporated to dryness to afford the subtitled compound. Yield 0.98 g.

$^1$H NMR (400 MHz, CDCl$_3$) δ 10.39 (s, 1H), 7.75-7.70 (m, 1H), 7.63-7.58 (m, 1H), 7.19 (t, J=7.8 Hz, 1H), 3.74 (s, 2H), 1.39 (d, J=1.3 Hz, 6H), 0.79 (s, 9H), −0.05 (s, 6H).

g) (9-(2-Fluoro-3-(1-hydroxy-2-methylpropan-2-yl)benzyl)-1-oxa-4,9-diazaspiro[5.5]undecan-4-yl)(2-isopropylthiazol-4-yl)methanone

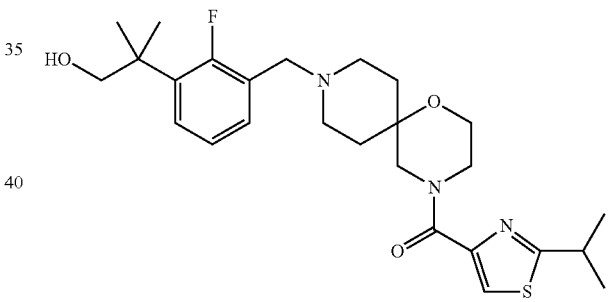

Sodium triacetoxyborohydride (0.502 g) was added to a stirred solution at 0° C. of (2-isopropylthiazol-4-yl)(1-oxa-4,9-diazaspiro[5.5]undecan-4-yl)methanone trifluoroacetate (example 22, step b) (0.668 g) and 3-(1-(tert-butyldimethylsilyloxy)-2-methylpropan-2-yl)-2-fluorobenzaldehyde (example 90, step f) (0.49 g) and acetic acid (0.090 mL) in NMP (20 mL). The reaction mixture was then stirred at 20° C. for 18 hours. The mixture was partitioned between ethyl acetate and saturated sodium bicarbonate solution, the organic layer was washed twice with brine, dried over sodium sulphate, filtered and the solvent evaporated under reduced pressure. The resultant gum was dissolved in THF (20 mL) and treated with tetrabutylammonium fluoride (1M in THF, 3.16 mL). The solution was allowed to stand at 20° C. for 8 hours. The solvent was evaporated under reduced pressure and the crude product was purified by flash silica chromatography, elution gradient 0 to 1% methanol in dichloromethane with 1% triethylamine. Pure fractions were evaporated to dryness to afford the subtitled compound. Yield 0.63 g.

m/z 490 (M+H)$^+$ (APCI)

h) (R)-7-(2-(2-(2-Fluoro-3-((4-(2-isopropylthiazole-4-carbonyl)-1-oxa-4,9-diazaspiro[5.5]undecan-9-yl)methyl)phenyl)-2-methylpropylamino)-1-hydroxyethyl)-4-hydroxybenzo[d]thiazol-2(3H)-one ditrifluoroacetate

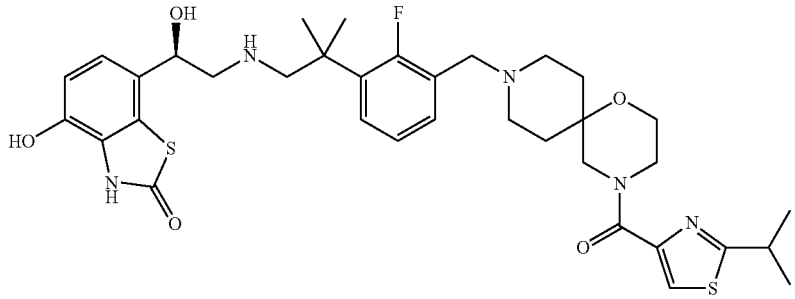 [SMILES: CC(C)c1nc(C(=O)N2CCOC3(CCN(Cc4cccc(C(C)(C)CNC[C@H](O)c5ccc(O)c6[nH]c(=O)sc56)c4F)CC3)C2)cs1]

A solution of (9-(2-fluoro-3-(1-hydroxy-2-methylpropan-2-yl)benzyl)-1-oxa-4,9-diazaspiro[5.5]undecan-4-yl)(2-isopropylthiazol-4-yl)methanone (example 90, step g) (0.21 g) in DCM (15 mL) was treated with trifluoroacetic acid (0.033 mL) followed by Dess-Martin periodinane (0.273 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.025 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.169 g) and acetic acid (0.025 mL) in methanol (15 mL). The mixture was cooled in an ice bath and treated with sodium cyanoborohydride (0.054 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.125 g.

m/z 698 (M+H)+ (APCI)
1H NMR (400 MHz, D6-DMSO, 90° C.) δ 11.25 (s, 1H), 7.93 (s, 1H), 7.56-7.46 (m, 2H), 7.31-7.25 (m, 1H), 6.89 (d, J=8.5 Hz, 1H), 6.75 (d, J=8.5 Hz, 1H), 4.97-4.91 (m, 1H), 4.31 (s, 2H), 3.70 (s, 4H), 3.65 (s, 2H), 3.50-3.37 (m, 2H), 3.33-3.26 (m, 1H), 3.23-3.15 (m, 2H), 3.12-3.02 (m, 4H), 2.06-1.97 (m, 2H), 1.83-1.72 (m, 2H), 1.50 (s, 6H), 1.34 (d, J=6.8 Hz, 6H). Five exchangeable protons not observed.

EXAMPLE 91

(R)-7-(2-(3-((4-(5-Ethylthiophene-3-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

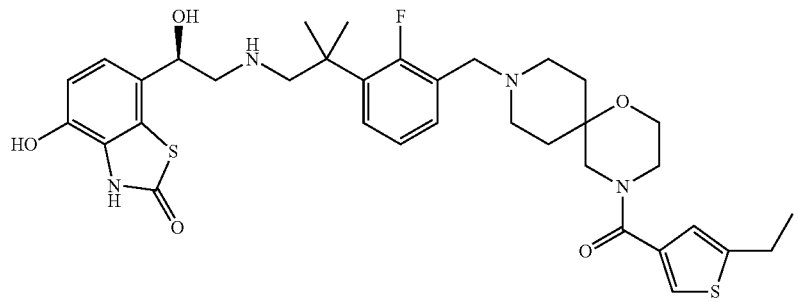 [SMILES: CCc1cc(C(=O)N2CCOC3(CCN(Cc4cccc(C(C)(C)CNC[C@H](O)c5ccc(O)c6[nH]c(=O)sc56)c4F)CC3)C2)cs1]

a) (5-Ethylthiophen-3-yl)(9-(2-fluoro-3-(2-hydroxyethyl)benzyl)-1-oxa-4,9-diazaspiro[5.5]undecan-4-yl)methanone

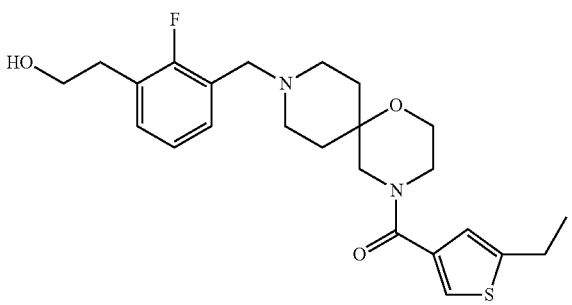 [SMILES: CCc1cc(C(=O)N2CCOC3(CCN(Cc4cccc(CCO)c4F)CC3)C2)cs1]

HATU (0.316 g) was added in one portion to a solution at 0° C. of 9-(3-(2-(tert-butyldimethylsilyloxy)ethyl)-2-fluorobenzyl)-1-oxa-4,9-diazaspiro[5.5]undecane (example 78, step d) (0.271 g) and 5-ethylthiophene-3-carboxylic acid (0.1 g) and triethylamine (0.36 mL) in DMF (10 mL). The mixture was then stirred at 20° C. for 1 hour. The reaction mixture was partitioned between ethyl acetate and brine, the organic layer was washed twice with brine, dried over sodium sulphate, filtered and the solvent evaporated under reduced pressure. The residue was dissolved in THF (20 mL) and treated with tetrabutylammonium fluoride (1M in THF, 1.921 mL). The reaction mixture was allowed to stand at 20° C. for 18 hours and the solvent was then removed under reduced pressure. The crude product was purified by flash silica chromatography using 2% methanol in dichloromethane with 1% triethylamine as solvent. Pure fractions were evaporated to dryness to afford the subtitled compound. Yield 0.12 g.

m/z 447 (M+H)$^+$ (APCI)

b) (R)-7-(2-(3-((4-(5-Ethylthiophene-3-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

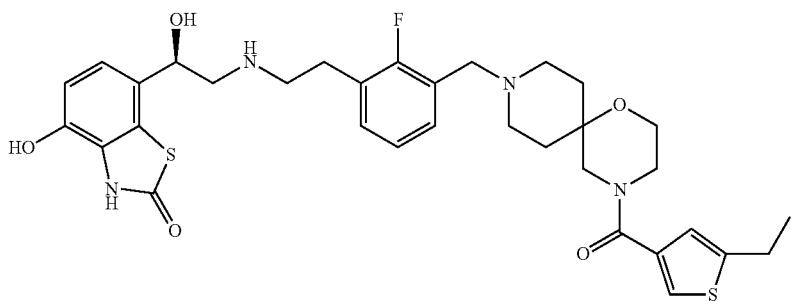 [SMILES: CCc1cc(C(=O)N2CCOC3(CCN(Cc4cccc(CCNC[C@H](O)c5ccc(O)c6[nH]c(=O)sc56)c4F)CC3)C2)cs1]

A solution of (5-ethylthiophen-3-yl)(9-(2-fluoro-3-(2-hydroxyethyl)benzyl)-1-oxa-4,9-diazaspiro[5.5]undecan-4-yl)methanone (example 91, step a) (0.12 g) in DCM (15 mL) was treated with trifluoroacetic acid (0.021 mL) followed by Dess-Martin periodinane (0.171 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.015 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.106 g) and acetic acid (0.015 mL) in methanol (15 mL). The mixture was cooled in an ice bath and treated with sodium cyanoborohydride (0.034 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.095 g.

m/z 655 (M+H)$^+$ (APCI)

$^1$H NMR (400 MHz, D$_6$-DMSO, 90° C.) δ 11.27 (s, 1H), 7.52-7.41 (m, 3H), 7.25 (t, J=7.7 Hz, 1H), 6.94 (d, J=8.5 Hz, 1H), 6.89 (s, 1H), 6.77 (d, J=8.2 Hz, 1H), 4.95-4.89 (m, 1H), 4.30 (s, 2H), 3.67 (t, J=5.0 Hz, 2H), 3.53 (t, J=5.0 Hz, 2H), 3.45 (s, 2H), 3.24 (t, J=7.9 Hz, 2H), 3.18-3.03 (m, 8H), 2.81 (q, J=7.5 Hz, 2H), 2.05-1.97 (m, 2H), 1.79-1.68 (m, 2H), 1.25 (t, J=7.6 Hz, 3H). Five exchangeable protons not observed.

EXAMPLE 92

(R)-5-(2-(2-(2-Fluoro-3-((4-(2-isopropylthiazole-4-carbonyl)-1-oxa-4,9-diazaspiro[5.5]undecan-9-yl)methyl)phenyl)-2-methylpropylamino)-1-hydroxyethyl)-8-hydroxyquinolin-2(1H)-one ditrifluoroacetate

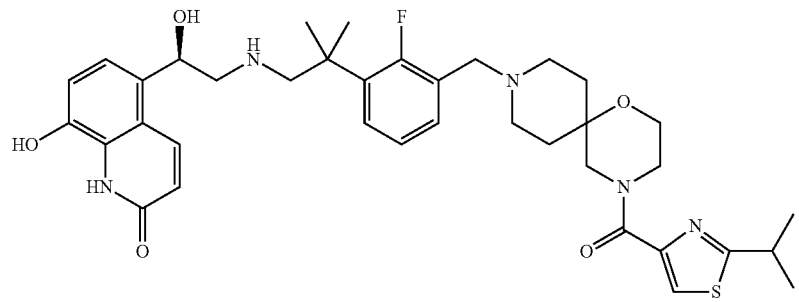 [SMILES: CC(C)c1nc(C(=O)N2CCOC3(CCN(Cc4cccc(C(C)(C)CNC[C@H](O)c5ccc(O)c6[nH]c(=O)ccc56)c4F)CC3)C2)cs1]

a) (R)-5-(1-(tert-Butyldimethylsilyloxy)-2-(2-(2-fluoro-3-((4-(2-isopropylthiazole-4-carbonyl)-1-oxa-4,9-diazaspiro[5.5]undecan-9-yl)methyl)phenyl)-2-methylpropylamino)ethyl)-8-hydroxyquinolin-2(1H)-one

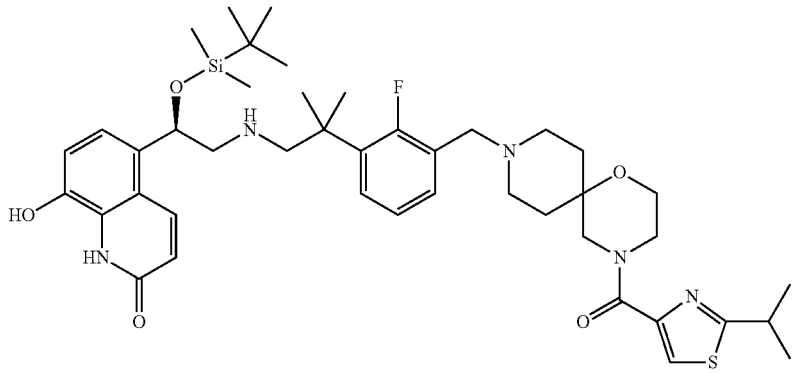 [SMILES: CC(C)c1nc(C(=O)N2CCOC3(CCN(Cc4cccc(C(C)(C)CNC[C@H](O[Si](C)(C)C(C)(C)C)c5ccc(O)c6[nH]c(=O)ccc56)c4F)CC3)C2)cs1]

A solution of (9-(2-fluoro-3-(1-hydroxy-2-methylpropan-2-yl)benzyl)-1-oxa-4,9-diazaspiro[5.5]undecan-4-yl)(2-isopropylthiazol-4-yl)methanone (example 90, step g) (0.21 g) in DCM (20 mL) was treated with trifluoroacetic acid (0.033 mL) followed by Dess-Martin periodinane (0.236 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.025 ml) was added to this solution and the solvent then removed under reduced pressure. The residue was dissolved in methanol (3 mL) and added to a solution of (R)-5-(2-amino-1-(tert-butyldimethylsilyloxy)ethyl)-8-hydroxyquinolin-2(1H)-one (WO2004106333) (0.186 g) in methanol (15 mL). The mixture was cooled to 0° C. and sodium triacetoxyborohydride (0.136 g) was added in one portion. The reaction mixture was stirred at 20° C. for 3 hours. The solvent was removed under reduced pressure and the residue partitioned between ethyl acetate and saturated sodium bicarbonate solution, the organic layer was dried over sodium sulphate, filtered and the solvent removed under reduced pressure. The crude product was purified by flash silica chromatography using 9% methanol in dichloromethane with 1% '880' aqueous ammonia as solvent. Pure fractions were evaporated to dryness to afford the subtitled compound. Yield 0.28 g.

m/z 806 (M+H)$^+$ (APCI)

b) (R)-5-(2-(2-(2-Fluoro-3-((4-(2-isopropylthiazole-4-carbonyl)-1-oxa-4,9-diazaspiro[5.5]undecan-9-yl)methyl)phenyl)-2-methylpropylamino)-1-hydroxyethyl)-8-hydroxyquinolin-2(1H)-one ditrifluoroacetate

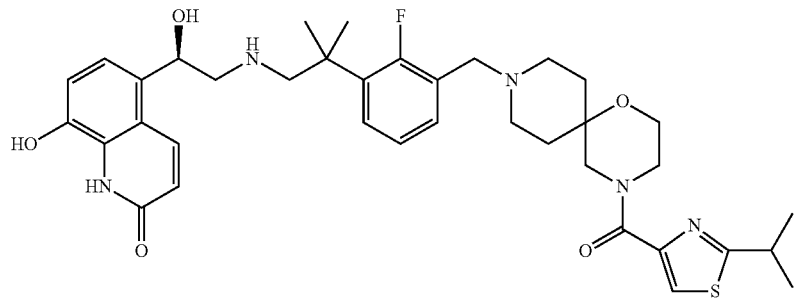 [SMILES: CC(C)c1nc(C(=O)N2CCOC3(CCN(Cc4cccc(C(C)(C)CNC[C@H](O)c5ccc(O)c6[nH]c(=O)ccc56)c4F)CC3)C2)cs1]

Triethylamine trihydrofluoride (0.074 mL) in methanol (2 mL) was added to a solution of (R)-5-(1-(tert-butyldimethylsilyloxy)-2-(2-(2-fluoro-3-((4-(2-isopropylthiazole-4-carbonyl)-1-oxa-4,9-diazaspiro[5.5]undecan-9-yl)methyl)phenyl)-2-methylpropylamino)ethyl)-8-hydroxyquinolin-2(1H)-one (example 92, step a) (0.28 g) in THF (8 mL) and the reaction mixture allowed to stand at 20° C. for 18 hours. The solvents were removed under reduced pressure and the crude product was purified by preparative HPLC (Sunfire™, Gradient: 10-40% acetonitrile in 0.2% aqueous TFA). The fractions containing the desired compound were evaporated to dryness to afford the titled compound. Yield 0.175 g.

m/z 692 (M+H)$^+$ (APCI)

$^1$H NMR (400 MHz, D$_6$-DMSO, 90° C.) δ 8.14 (d, J=10.0 Hz, 1H), 7.93 (s, 1H), 7.57-7.50 (m, 2H), 7.29 (t, J=7.8 Hz, 1H), 7.08 (d, J=8.2 Hz, 1H), 6.98 (d, J=8.2 Hz, 1H), 6.52 (d, J=10.0 Hz, 1H), 5.40-5.34 (m, 1H), 4.34 (s, 2H), 3.69 (s, 4H), 3.65 (s, 2H), 3.56-3.43 (m, 2H), 3.33-3.18 (m, 3H), 3.15-3.06

(m, 4H), 2.06-1.98 (m, 2H), 1.83-1.72 (m, 2H), 1.52 (s, 6H), 1.34 (d, J=7.8 Hz, 6H). Six exchangeable protons not observed.

EXAMPLE 93

(R)-7-(2-(3-((4-(5-Ethylthiophene-3-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

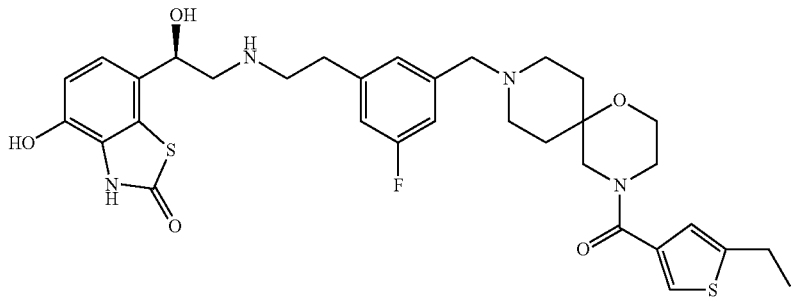 [SMILES: CCc1cc(C(=O)N2CCOC3(CCN(Cc4cc(F)cc(CCNC[C@H](O)c5ccc(O)c6[nH]c(=O)sc56)c4)CC3)C2)cs1]

a) (5-Ethylthiophen-3-yl)(9-(3-fluoro-5-(2-hydroxyethyl)benzyl)-1-oxa-4,9-diazaspiro[5.5]undecan-4-yl)methanone

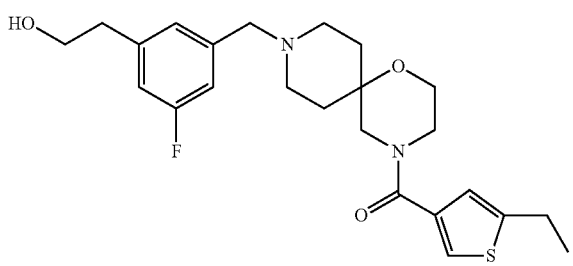 [SMILES: CCc1cc(C(=O)N2CCOC3(CCN(Cc4cc(F)cc(CCO)c4)CC3)C2)cs1]

HATU (0.449 g) was added in one portion to a solution at 0° C. of 2-(3-(1-oxa-4,9-diazaspiro[5.5]undecan-9-ylmethyl)-5-fluorophenyl)ethanol (example 55, step c) (0.28 g) and 5-ethylthiophene-3-carboxylic acid (0.142 g) and triethylamine (0.506 mL) in DMF (10 mL). The mixture was then stirred at 20° C. for 1 hour. The reaction mixture was partitioned between ethyl acetate and brine, the organic layer was washed twice with brine, dried over sodium sulphate, filtered and the solvent evaporated under reduced pressure. The crude product was purified by flash silica chromatography using 2% methanol in dichloromethane with 1% triethylamine as solvent. Pure fractions were evaporated to dryness to afford the subtitled compound. Yield 0.21 g.

m/z 447 (M+H)$^+$ (APCI)

b) (R)-7-(2-(3-((4-(5-Ethylthiophene-3-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one ditrifluoroacetate

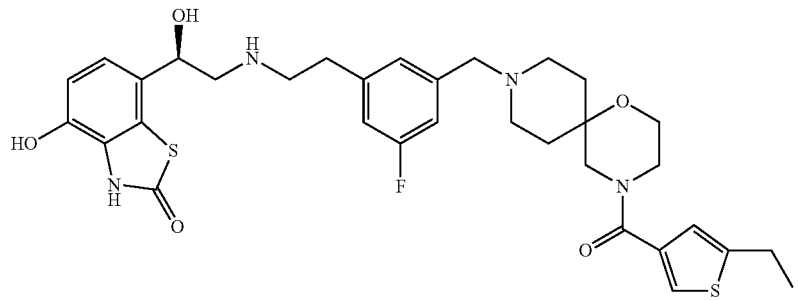 [SMILES: CCc1cc(C(=O)N2CCOC3(CCN(Cc4cc(F)cc(CCNC[C@H](O)c5ccc(O)c6[nH]c(=O)sc56)c4)CC3)C2)cs1]

A solution of (5-ethylthiophen-3-yl)(9-(3-fluoro-5-(2-hydroxyethyl)benzyl)-1-oxa-4,9-diazaspiro[5.5]undecan-4-yl)methanone (example 93, step a) (0.21 g) in DCM (15 mL) was treated with trifluoroacetic acid (0.036 mL) followed by Dess-Martin periodinane (0.299 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.027 mL) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d)

(0.185 g) and acetic acid (0.027 mL) in methanol (15 mL). The mixture was cooled in an ice bath and treated with sodium cyanoborohydride (0.059 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.115 g.

m/z 655 (M+H)⁺ (APCI)

¹H NMR (400 MHz, D₆-DMSO, 90° C.) δ 11.26 (s, 1H), 7.47 (s, 1H), 7.28-7.17 (m, 3H), 6.93 (d, J=8.7 Hz, 1H), 6.89 (s, 1H), 6.77 (d, J=8.2 Hz, 1H), 4.95-4.90 (m, 1H), 4.28 (s, 2H), 3.67 (t, J=5.0 Hz, 2H), 3.53 (t, J=4.9 Hz, 2H), 3.45 (s, 2H), 3.27 (t, J=7.9 Hz, 2H), 3.19-3.00 (m, 8H), 2.81 (q, J=7.6 Hz, 2H), 2.07-1.99 (m, 2H), 1.80-1.68 (m, 2H), 1.25 (t, J=7.4 Hz, 3H). Five exchangeable protons not observed.

EXAMPLE 94

(R)-8-Hydroxy-5-(1-hydroxy-2-(3-(2-(4-(2-methylthiazole-4-carbonyl)-1-oxa-4,9-diazaspiro[5.5]undecan-9-yl)ethoxy)benzylamino)ethyl)quinolin-2(1H)-one ditrifluoroacetate

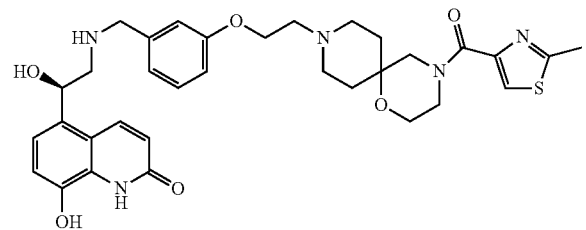 [SMILES: Cc1nc(C(=O)N2CCOC3(CCN(CCOc4cccc(CNC[C@H](O)c5ccc(O)c6[nH]c(=O)ccc56)c4)CC3)C2)cs1]

3-(2-(4-(2-Methylthiazole-4-carbonyl)-1-oxa-4,9-diazaspiro[5.5]undecan-9-yl)ethoxy)benzaldehyde (example 10, step b) (0.24 g) was added to a mixture of (R)-5-(2-amino-1-(tert-butyldimethylsilyloxy)ethyl)-8-hydroxyquinolin-2(1H)-one (WO2004106333) (0.187 g) and acetic acid (0.032 mL) in methanol (2 mL). The mixture was stirred for 30 min then cooled in an ice bath. Sodium triacetoxyborohydride (0.178 g) was then added and the mixture stirred for 2 h and concentrated in vacuo. The residue was partitioned between ethyl acetate (50 mL) and pH 7.2 buffer (50 mL). The aqueous was separated and extracted with ethyl acetate (2×50 mL). The combined organic solutions were washed with brine (20 mL), dried over sodium sulphate, filtered and evaporated. Purification was by silica gel chromatography eluting with 95:5:0.5 to 92:8:0.8 DCM:methanol:'880' aqueous ammonia gradient. The fractions containing product were combined, evaporated in vacuo and dissolved in tetrahydrofuran (5 mL). Triethylamine trihydrofluoride (0.091 mL) was added and the mixture stirred overnight. The solvent was evaporated in vacuo and residue dissolved in a mixture of acetonitrile and water (1:1, 5 mL). Purification was by preparative HPLC (Sunfire™, Gradient: 5-50% acetonitrile in 0.2% aqueous TFA). The fractions containing product were combined evaporated in vacuo and the residue triturated with diethylether to give the titled compounds as a white solid. Yield 0.15 g.

m/z 634 (M+H)⁺ (APCI)

¹H NMR (300 MHz, D₆-DMSO, 90° C.) δ 8.09 (d, J=10.0 Hz, 1H), 7.92 (s, 1H), 7.37 (t, J=7.8 Hz, 1H), 7.20-6.94 (m, 5H), 6.50 (d, J=10.0 Hz, 1H), 5.37 (dd, J=8.2, 4.5 Hz, 1H), 4.37 (t, J=5.0 Hz, 2H), 4.30-4.16 (m, 2H), 3.76-3.62 (m, 6H), 3.61-3.54 (m, 2H), 3.46-3.35 (m, 2H), 3.31-3.17 (m, 2H), 3.11-3.01 (m, 2H), 2.68 (s, 3H), 2.11-1.98 (m, 2H), 1.94-1.78 (m, 2H). Six exchangeable protons not observed.

EXAMPLE 95

(R)-8-Hydroxy-5-(1-hydroxy-2-(3-(3-(4-(2-methylthiazole-4-carbonyl)-1-oxa-4,9-diazaspiro[5.5]undecan-9-yl)propoxy)benzylamino)ethyl)quinolin-2(1H)-one ditrifluoroacetate

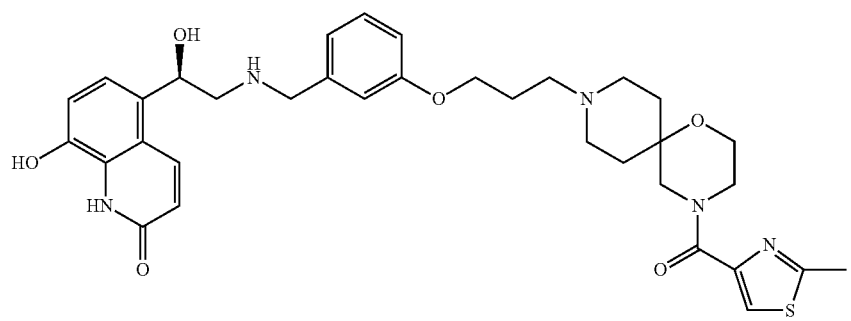 [SMILES: Cc1nc(C(=O)N2CCOC3(CCN(CCCOc4cccc(CNC[C@H](O)c5ccc(O)c6[nH]c(=O)ccc56)c4)CC3)C2)cs1]

a) 3-(3-Formylphenoxy)propyl methanesulfonate

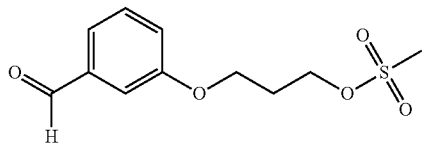 [SMILES: CS(=O)(=O)OCCCOc1cccc(C=O)c1]

3-Bromo-1-propanol (3.94 mL) and potassium carbonate (6.22 g) were added to 3-hydroxybenzaldehyde (5 g) in acetonitrile (100 mL). The resulting mixture was stirred at reflux for 5 hours under nitrogen. The reaction mixture was cooled to room temperature and partitioned between ethyl acetate and ice-cold, dilute aqueous sodium hydroxide. The organic layer was washed with brine, dried over sodium sulphate, filtered and the solvent removed under reduced pressure. The residue was dissolved in DCM (30 mL) and treated with triethylamine (5.7 mL). The solution was cooled to 0° C. and treated dropwise with methanesulfonyl chloride (3.2 mL). The reaction mixture was stirred at 0° C. for 10 minutes and then at room temperature for 1 hour. The mixture was washed twice with brine, dried over sodium sulphate, filtered and the solvent evaporated under reduced pressure. The crude product was purified by flash silica chromatography using 33% ethyl acetate in isohexane as solvent. Pure fractions were evaporated to dryness to afford the subtitled compound. Yield 5.20 g.

¹H NMR (400 MHz, CDCl₃) δ 9.98 (s, 1H), 7.50-7.43 (m, 2H), 7.40-7.39 (m, 1H), 7.20-7.16 (m, 1H), 4.46 (t, J=6.2 Hz, 2H), 4.17 (t, J=5.9 Hz, 2H), 3.01 (s, 3H), 2.30-2.23 (m, 2H).

b) 3-(3-(4-(2-Methylthiazole-4-carbonyl)-1-oxa-4,9-diazaspiro[5.5]undecan-9-yl)propoxy)benzaldehyde

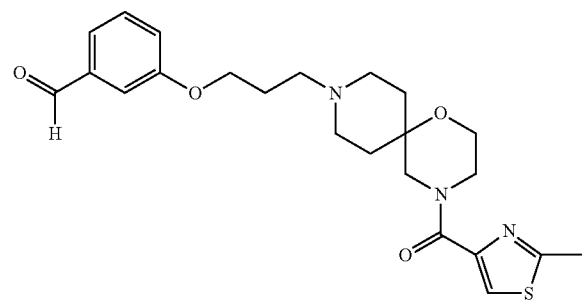 [SMILES: Cc1nc(C(=O)N2CCOC3(CCN(CCCOc4cccc(C=O)c4)CC3)C2)cs1]

A solution of 3-(3-formylphenoxy)propyl methanesulfonate (example 95, step a) (0.209 g) and (2-methylthiazol-4-yl)(1-oxa-4,9-diazaspiro[5.5]undecan-4-yl)methanone trifluoroacetate (example 4, step h) (0.32 g) and triethylamine (0.282 mL) in acetonitrile (10 mL) were heated at 65° C. for 18 hours. The solvent was evaporated off under reduced pressure and the residue partitioned between ethyl acetate and brine. The organic layer was dried over sodium sulphate, filtered and the solvent evaporated under reduced pressure. The crude product was purified by flash silica chromatography using 2% methanol and 1% triethylamine in dichloromethane. Pure fractions were evaporated to dryness to afford the subtitled compound. Yield 0.157 g.

m/z 444 (M+H)⁺ (APCI)

c) (R)-5-(1-(tert-Butyldimethylsilyloxy)-2-(3-(3-(4-(2-methylthiazole-4-carbonyl)-1-oxa-4,9-diazaspiro[5.5]undecan-9-yl)propoxy)benzylamino)ethyl)-8-hydroxyquinolin-2(1H)-one

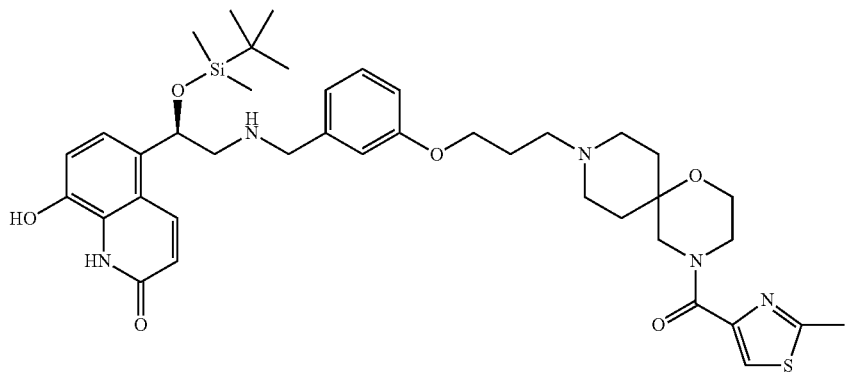 [SMILES: Cc1nc(C(=O)N2CCOC3(CCN(CCCOc4cccc(CNC[C@H](O[Si](C)(C)C(C)(C)C)c5ccc(O)c6[nH]c(=O)ccc56)c4)CC3)C2)cs1]

Sodium triacetoxyborohydride (0.113 g) was added in one portion to a stirred solution at 0° C. of 3-(3-(4-(2-methylthiazole-4-carbonyl)-1-oxa-4,9-diazaspiro[5.5]undecan-9-yl)propoxy)benzaldehyde (example 95, step b) (0.157 g), (R)-5-(2-amino-1-(tert-butyldimethylsilyloxy)ethyl)-8-hydroxyquinolin-2(1H)-one (WO2004106333) (0.118 g) and acetic acid (0.020 mL) in methanol (7 mL). The resulting mixture was stirred at 20° C. for 2 hours. Most of the methanol was evaporated under reduced pressure and the residue was partitioned between ethyl acetate and aqueous phosphate buffer (pH=7.2), the organic layer was dried over sodium sulphate, filtered and the solvent evaporated under reduced pressure. The crude product was purified by flash silica chromatography using 8% methanol and 1% '880' aqueous ammonia in dichloromethane as solvent. Pure fractions were evaporated to dryness to afford the subtitled compound. Yield 0.160 g.

m/z 762 (M+H)⁺ (APCI)

d) (R)-8-Hydroxy-5-(1-hydroxy-2-(3-(3-(4-(2-methylthiazole-4-carbonyl)-1-oxa-4,9-diazaspiro[5.5]undecan-9-yl)propoxy)benzylamino)ethyl)quinolin-2(1H)-one ditrifluoroacetate

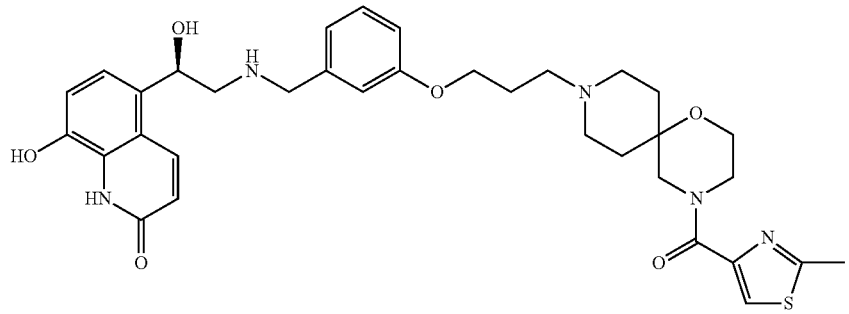 [SMILES: Cc1nc(C(=O)N2CCOC3(CCN(CCCOc4cccc(CNC[C@H](O)c5ccc(O)c6[nH]c(=O)ccc56)c4)CC3)C2)cs1]

A solution of (R)-5-(1-(tert-butyldimethylsilyloxy)-2-(3-(3-(4-(2-methylthiazole-4-carbonyl)-1-oxa-4,9-diazaspiro[5.5]undecan-9-yl)propoxy)benzylamino)ethyl)-8-hydroxyquinolin-2(1H)-one (example 95, step c) (0.160 g) in THF (2 mL) was treated with triethylamine trihydrofluoride (0.041 mL) and the resultant mixture stirred for 18 hours at 20° C. The solvent was evaporated off and the crude product was purified by preparative HPLC (Sunfire™, Gradient: 5-35% acetonitrile in 0.2% aqueous TFA). The fractions containing the desired compound were evaporated to dryness to afford the titled compound. Yield 0.081 mg.

m/z 648 (M+H)$^+$ (APCI)

$^1$H NMR (400 MHz, D$_6$-DMSO) δ 10.75-10.43 (m, 2H), 10.00-9.74 (m, 1H), 9.30 (s, 1H), 9.10 (s, 1H), 8.07 (d, J=9.7 Hz, 1H), 8.01 (s, 1H), 7.36 (t, J=7.9 Hz, 1H), 7.16-7.09 (m, 3H), 7.01-6.94 (m, 2H), 6.54 (d, J=9.7 Hz, 1H), 5.35 (d, J=9.5 Hz, 1H), 4.21 (s, 2H), 4.07-4.00 (m, 2H), 3.83-3.16 (m, 10H), 3.08-2.90 (m, 4H), 2.70 (s, 3H), 2.18-2.04 (m, 4H), 1.83-1.66 (m, 2H). One exchangeable proton not observed.

EXAMPLE 96

(R)-8-Hydroxy-5-(1-hydroxy-2-(3-((4-(2-methylthiazole-4-carbonyl)-1-oxa-4,9-diazaspiro[5.5]undecan-9-yl)methyl)benzylamino)ethyl)quinolin-2(1H)-one ditrifluoroacetate

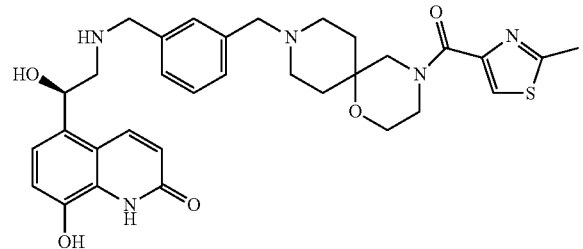 [SMILES: Cc1nc(C(=O)N2CCOC3(CCN(Cc4cccc(CNC[C@H](O)c5ccc(O)c6[nH]c(=O)ccc56)c4)CC3)C2)cs1]

a) 3-((4-(2-Methylthiazole-4-carbonyl)-1-oxa-4,9-diazaspiro[5.5]undecan-9-yl)methyl)benzaldehyde

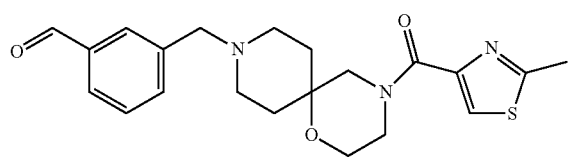 [SMILES: Cc1nc(C(=O)N2CCOC3(CCN(Cc4cccc(C=O)c4)CC3)C2)cs1]

A solution of (2-methylthiazol-4-yl)(1-oxa-4,9-diazaspiro[5.5]undecan-4-yl)methanone trifluoroacetate (example 4, step h) (0.408 g), 3-(bromomethyl)benzaldehyde (0.205 g) and triethylamine (0.36 mL) in acetonitrile (10 mL) was stirred at room temperature overnight. The solution was concentrated in vacuo and the residue partitioned between ethyl acetate and saturated sodium bicarbonate. The organic phase was washed twice with water, once with brine, then dried over anhydrous magnesium sulphate and purified by flash chromatography on silica eluted with 5% methanol in dichloromethane to afford the subtitled compound as a yellow gum. Yield 0.325 g.

$^1$H NMR (400 MHz, D$_6$-DMSO, 90° C.) δ 10.01 (s, 1H), 7.85 (d, J=0.8 Hz, 1H), 7.80 (s, 1H), 7.76 (d, J=7.4 Hz, 1H), 7.61 (d, J=7.4 Hz, 1H), 7.52 (t, J=7.4 Hz, 1H), 3.71-3.46 (m, 8H), 2.68 (s, 3H), 2.44-2.29 (m, 4H), 1.78-1.65 (m, 2H), 1.61-1.46 (m, 2H).

b) (R)-5-(1-(tert-Butyldimethylsilyloxy)-2-(3-((4-(2-methylthiazole-4-carbonyl)-1-oxa-4,9-diazaspiro[5.5]undecan-9-yl)methyl)benzylamino)ethyl)-8-hydroxyquinolin-2(1H)-one

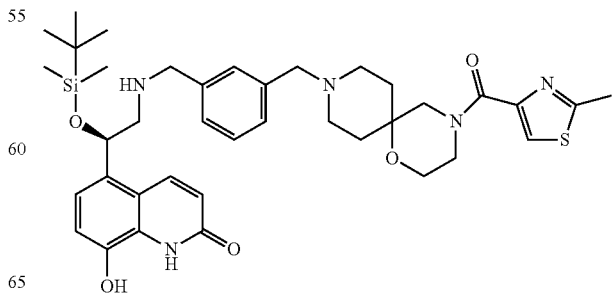

A solution of 3-((4-(2-methylthiazole-4-carbonyl)-1-oxa-4,9-diazaspiro[5.5]undecan-9-yl)methyl)benzaldehyde (example 96, step a) (0.303 g), (R)-5-(2-amino-1-(tert-butyldimethylsilyloxy)ethyl)-8-hydroxyquinolin-2(1H)-one (WO2004106333) (0.330 g) and acetic acid (0.043 mL) in methanol (5 mL) was stirred at room temperature for 30 minutes, then cooled in an ice-water bath under nitrogen and treated with sodium triacetoxyborohydride (0.243 g) in one portion. The mixture was stirred in ice-water for 2 hours, then concentrated in vacuo. The residue was partitioned between ethyl acetate and saturated sodium bicarbonate solution, the phases were separated, and the aqueous phase was extracted twice more with ethyl acetate. Any insoluble gummy residues were dissolved in methanol. The combined ethyl acetate phases were washed with brine, dried over magnesium sulphate and combined with the methanol solution. The whole was purified by flash chromatography on silica eluted with 1:7:92 triethylamine:methanol:dichloromethane to afford the slightly impure subtitled product as a yellow foam. Yield 0.324 g.

$^1$H NMR (400 MHz, D$_6$-DMSO, 90° C.) δ 8.35 (d, J=10.0 Hz, 1H), 8.01 (s, 1H), 7.40-7.30 (m, 2H), 7.30-7.23 (m, 2H), 7.17 (d, J=8.2 Hz, 1H), 7.08 (d, J=8.2 Hz, 1H), 6.59 (d, J=10.0 Hz, 1H), 5.30 (dd, J=7.3, 4.7 Hz, 1H), 3.91-3.70 (m, 8H), 3.57 (s, 2H), 3.02 (dd, J=12.3, 7.4 Hz, 1H), 2.91-2.77 (m, 4H), 2.56-2.43 (m, 4H), 1.90-1.80 (m, 2H), 1.74-1.62 (m, 2H), 0.99 (s, 9H), 0.19 (s, 3H), 0.00 (s, 3H). Three exchangeable protons not observed.

c) (R)-8-Hydroxy-5-(1-hydroxy-2-(3-((4-(2-methylthiazole-4-carbonyl)-1-oxa-4,9-diazaspiro[5.5]undecan-9-yl)methyl)benzylamino)ethyl)quinolin-2(1H)-one ditrifluoroacetate

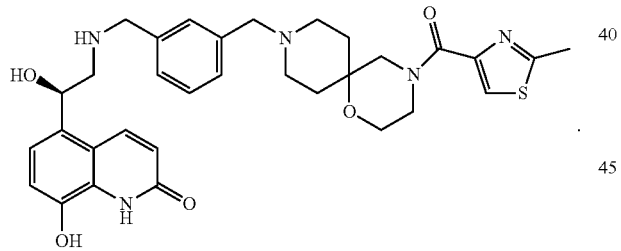

A solution of (R)-5-(1-(tert-butyldimethylsilyloxy)-2-(3-((4-(2-methylthiazole-4-carbonyl)-1-oxa-4,9-diazaspiro[5.5]undecan-9-yl)methyl)benzylamino)ethyl)-8-hydroxyquinolin-2(1H)-one (example 96, step b) (0.320 g) and triethylamine trihydrofluoride (0.15 mL) in THF (5 mL) was stirred at room temperature overnight then concentrated in-vacuo. The residue was dissolved in a mixture of acetonitrile (3 ml) and water (1 ml) and the resulting solution purified by preparative HPLC (Sunfire™, Gradient: 5-50% acetonitrile in 0.2% aqueous TFA). Fractions containing product were concentrated in vacuo and co-evaporated from acetonitrile three times to give a white foam. The foam was triturated with diethyl ether to give a solid, which was removed by filtration, washed with diethyl ether and dried in-vacuo at room temperature to afford the titled compound as a white powder. Yield 0.264 g.

m/z 604 (M+H)$^+$ (APCI)

$^1$H NMR (400 MHz, D$_6$-DMSO, 90° C.) δ 8.08 (d, J=9.7 Hz, 1H), 7.90 (s, 1H), 7.65-7.49 (m, 4H), 7.10 (d, J=7.9 Hz, 1H), 6.97 (d, J=8.2 Hz, 1H), 6.52 (d, J=10.0 Hz, 1H), 5.35 (dd, J=8.6, 4.2 Hz, 1H), 4.35-4.21 (m, 4H), 3.74-3.57 (m, 6H), 3.23-2.98 (m, 6H), 2.67 (s, 3H), 2.06-1.91 (m, 2H), 1.85-1.65 (m, 2H). Six exchangeable protons not observed.

EXAMPLE 97

(R)-5-(2-(2,5-Dimethyl-4-(2-(4-(2-methylthiazole-4-carbonyl)-1-oxa-4,9-diazaspiro[5.5]undecan-9-yl)ethoxy)benzylamino)-1-hydroxyethyl)-8-hydroxyquinolin-2(1H)-one ditrifluoroacetate

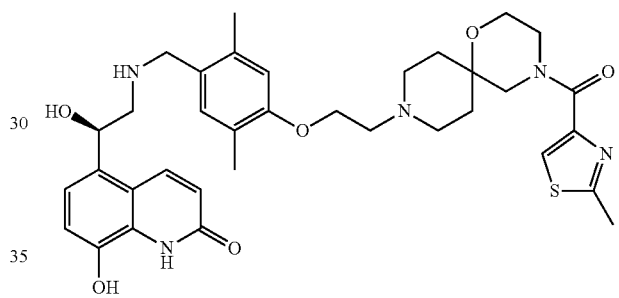

2,5-Dimethyl-4-(2-(4-(2-methylthiazole-4-carbonyl)-1-oxa-4,9-diazaspiro[5.5]undecan-9-yl)ethoxy)benzaldehyde (example 18, step f) (0.08 g) was added to a mixture of (R)-5-(2-amino-1-(tert-butyldimethylsilyloxy)ethyl)-8-hydroxyquinolin-2(1H)-one (WO2004106333) (0.088 g) and acetic acid (0.010 mL) in methanol (2 mL). The mixture was stirred for 30 min then cooled in an ice bath. Sodium cyanoborohydride (0.016 g) was then added and the mixture stirred for 2 h. The solvent was removed in vacuo and the residue was purified by silica gel chromatography eluting with 95:5:0.5 to 92:8:0.8 DCM:methanol:'880' aqueous ammonia gradient. The fractions containing product were combined and evaporated in vacuo. The residue was redissolved in tetrahydrofuran (5 mL), triethylamine trihydrofluoride (0.028 mL) was added and the mixture stirred overnight. The solvent was evaporated in vacuo. Purification was by preparative HPLC (Sunfire™, Gradient: 5-50% acetonitrile in 0.2% aqueous TFA). The fractions containing product were combined, evaporated in vacuo and the residue triturated with diethyl ether to give the titled compound as a white solid. Yield 0.07 g.

m/z 662 (M+H)$^+$ (APCI)

$^1$H NMR (400 MHz, D$_6$-DMSO, 90° C.) δ 8.12 (d, J=10.0 Hz, 1H), 7.92 (s, 1H), 7.27 (s, 1H), 7.12 (d, J=8.2 Hz, 1H), 6.99 (d, J=8.2 Hz, 1H), 6.86 (s, 1H), 6.51 (d, J=9.7 Hz, 1H), 5.38 (dd, J=8.2, 4.6 Hz, 1H), 4.35 (t, J=4.9 Hz, 2H), 4.25-4.13 (m, 2H), 3.76-3.64 (m, 6H), 3.61-3.53 (m, 2H), 3.46-3.36 (m, 2H), 3.33-3.20 (m, 2H), 3.19-3.10 (m, 2H), 2.68 (s, 3H), 2.33 (s, 3H), 2.15 (s, 3H), 2.12-2.01 (m, 2H), 1.95-1.79 (m, 2H). Six exchangeable protons not observed.

EXAMPLE 98

(R)-8-Hydroxy-5-(1-hydroxy-2-((5-(2-(4-(2-methylthiazole-4-carbonyl)-1-oxa-4,9-diazaspiro[5.5]undecan-9-yl)ethyl)thiophen-2-yl)methylamino)ethyl)quinolin-2(1H)-one ditrifluoroacetate

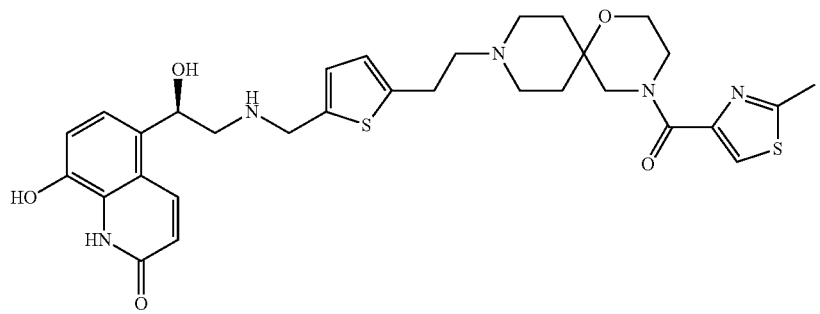 [SMILES: Cc1nc(C(=O)N2CCOC3(CCN(CCc4ccc(CNC[C@H](O)c5ccc(O)c6[nH]c(=O)ccc56)s4)CC3)C2)cs1]

a) (R)-5-(1-(tert-Butyldimethylsilyloxy)-2-((5-(2-(4-(2-methylthiazole-4-carbonyl)-1-oxa-4,9-diazaspiro[5.5]undecan-9-yl)ethyl)thiophen-2-yl)methylamino)ethyl)-8-hydroxyquinolin-2(1H)-one ditrifluoroacetate

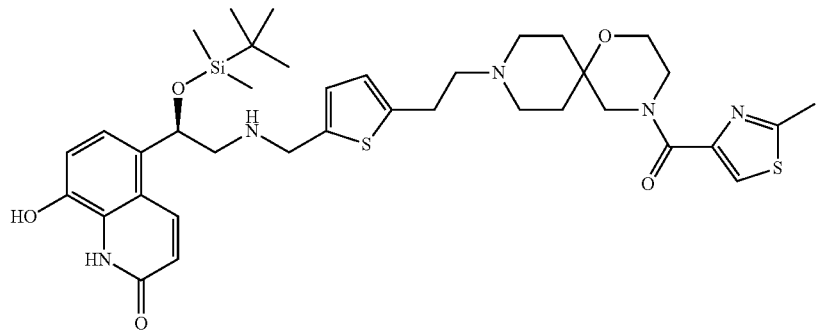 [SMILES: Cc1nc(C(=O)N2CCOC3(CCN(CCc4ccc(CNC[C@H](O[Si](C)(C)C(C)(C)C)c5ccc(O)c6[nH]c(=O)ccc56)s4)CC3)C2)cs1]

A solution of 5-(2-(4-(2-methylthiazole-4-carbonyl)-1-oxa-4,9-diazaspiro[5.5]undecan-9-yl)ethyl)thiophene-2-carbaldehyde (example 21, step c) (0.188 g) and (R)-5-(2-amino-1-(tert-butyldimethylsilyloxy)ethyl)-8-hydroxyquinolin-2(1H)-one (WO2004106333) (0.150 g) in methanol (10 mL) was treated with acetic acid (0.026 mL) followed by sodium triacetoxyborohydride (0.143 g). The mixture was stirred at 20° C. for 18 hours. Further sodium triacetoxyborohydride (0.143 g) was added and stirring at 20° C. was continued for 2 hours. Further sodium triacetoxyborohydride (143 mg) was added and stirring continued for 2 hours. The methanol was removed under reduced pressure and the residue was partitioned between saturated sodium bicarbonate solution and ethyl acetate. The organic layer was dried over sodium sulphate, filtered and the solvent removed under reduced pressure. The crude product was purified by flash silica chromatography using 1% concentrated aqueous ammonia and 8% methanol in dichloromethane as solvent. Pure fractions were evaporated to dryness to afford the subtitled compound. Yield 0.122 g.

m/z 738 (M+H)$^+$ (APCI)

b) (R)-8-Hydroxy-5-(1-hydroxy-2-((5-(2-(4-(2-methylthiazole-4-carbonyl)-1-oxa-4,9-diazaspiro[5.5]undecan-9-yl)ethyl)thiophen-2-yl)methylamino)ethyl)quinolin-2(1H)-one ditrifluoroacetate

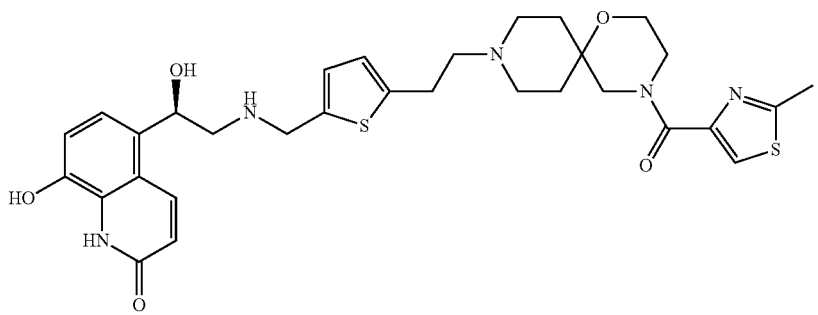 [SMILES: Cc1nc(C(=O)N2CCOC3(CCN(CCc4ccc(CNC[C@H](O)c5ccc(O)c6[nH]c(=O)ccc56)s4)CC3)C2)cs1]

A solution of (R)-5-(1-(tert-butyldimethylsilyloxy)-2-((5-(2-(4-(2-methylthiazole-4-carbonyl)-1-oxa-4,9-diazaspiro[5.5]undecan-9-yl)ethyl)thiophen-2-yl)methylamino)ethyl)-8-hydroxyquinolin-2(1H)-one (example 98, step a) (0.122 g) in THF (4 mL) was treated with a solution of triethylamine trihydrofluoride (0.035 mL) in methanol (1 mL) and the resultant mixture was allowed to stand at 20° C. for 18 hours. The solvents were removed under reduced pressure and the crude product was purified by preparative HPLC (Sunfire™, Gradient: 10-40% acetonitrile in 0.2% aqueous TFA). The fractions containing the desired compound were evaporated to dryness to afford the titled compound. Yield 0.085 g.

m/z 624 (M+H)$^+$ (APCI)

$^1$H NMR (400 MHz, D$_6$-DMSO, 90° C.) δ 8.10 (d, J=31.8 Hz, 1H), 7.93 (s, 1H), 7.15 (d, J=12.5 Hz, 1H), 7.10 (d, J=15.7 Hz, 1H), 6.98 (d, J=22.6 Hz, 1H), 6.92 (d, J=11.2 Hz, 1H), 6.53 (d, J=30.4 Hz, 1H), 5.37-5.31 (m, 1H), 4.41 (dd, J=17.7, 14.4 Hz, 2H), 3.71 (s, 4H), 3.66 (s, 2H), 3.42-3.33 (m, 4H), 3.27-3.06 (m, 6H), 2.68 (s, 3H), 2.10-1.98 (m, 2H), 1.88-1.75 (m, 2H). Six exchangeable protons not observed.

EXAMPLE 99

(R)-7-(2-(5-((4-(5-Ethylthiophene-3-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

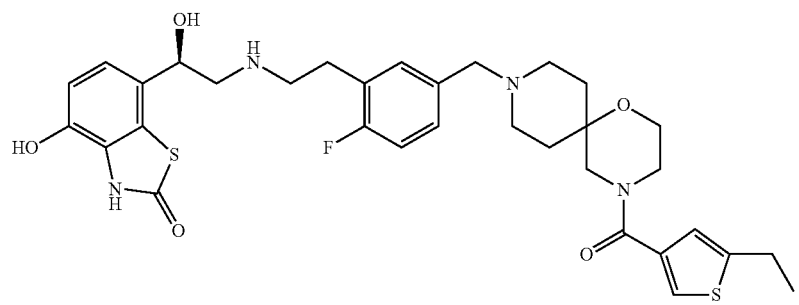 [SMILES: CCc1cc(C(=O)N2CCOC3(CCN(Cc4ccc(F)c(CCNC[C@H](O)c5ccc(O)c6[nH]c(=O)sc56)c4)CC3)C2)cs1]

a) (5-Ethylthiophen-3-yl)(1-oxa-4,9-diazaspiro[5.5]undecan-4-yl)methanone trifluoroacetate

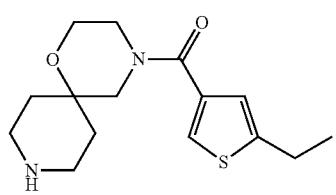 [SMILES: CCc1cc(C(=O)N2CCOC3(CCNCC3)C2)cs1]

HATU (1.15 g) was added in one portion to a solution at 0° C. of tert-butyl 1-oxa-4,9-diazaspiro[5.5]undecane-9-carboxylate hydrochloride (WuXi PharmaTech) (0.682 g) and 5-ethylthiophene-3-carboxylic acid (0.364 g) and triethylamine (1.3 mL) in DMF (10 mL). The mixture was then stirred at 20° C. for 1 hour. The reaction mixture was partitioned between ethyl acetate and brine, the organic layer was washed twice with brine, dried over sodium sulphate, filtered and the solvent evaporated under reduced pressure. The crude product was purified by flash silica chromatography using 50% ethyl acetate in isohexane. Pure fractions were evaporated to dryness to afford the 'BOC' protected intermediate. DCM (10 mL) was added followed by trifluoroacetic acid (10 mL) and the resultant solution allowed to stand at 20° C. for 25 minutes. Toluene (30 mL) was added and the solvents evaporated under reduced pressure. The residue was azeotroped twice with acetonitrile to yield the subtitled compound. Yield 0.950 g.

m/z 295 (M+H)$^+$ (APCI)

acetate and saturated sodium bicarbonate solution. The organic layer was dried over sodium sulphate, filtered and the solvent evaporated under reduced pressure. The crude product was purified by flash silica chromatography using 1% triethylamine and 2% methanol in dichloromethane as solvent. Pure fractions were evaporated to dryness to afford the subtitled compound. Yield 0.2 g.

m/z 447 (M+H)$^+$ (APCI)

c) (R)-7-(2-(5-((4-(5-Ethylthiophene-3-carbonyl)-1-oxa-4,9-diazaspiro[5.5]undecan-9-yl)methyl)-2-fluorophenethylamino)-1-hydroxyethyl)-4-hydroxybenzo[d]thiazol-2(3H)-one ditrifluoroacetate

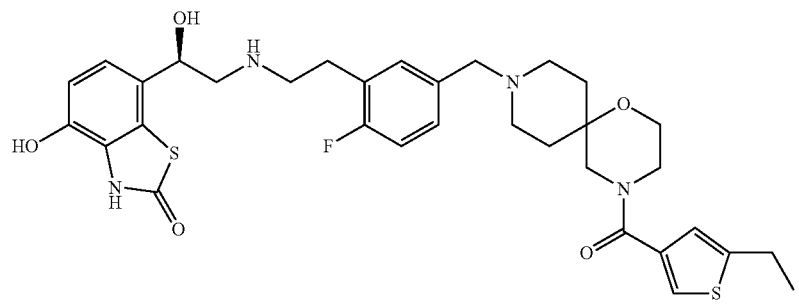

b) (5-Ethylthiophen-3-yl)(9-(4-fluoro-3-(2-hydroxyethyl)benzyl)-1-oxa-4,9-diazaspiro[5.5]undecan-4-yl)methanone

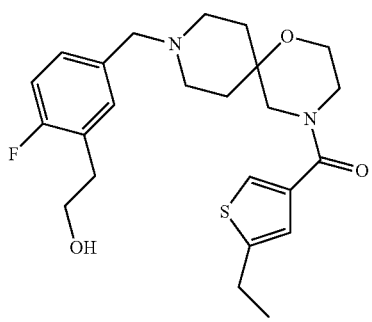 [SMILES: CCc1cc(C(=O)N2CCOC3(CCN(Cc4ccc(F)c(CCO)c4)CC3)C2)cs1]

2-(5-(Bromomethyl)-2-fluorophenyl)ethanol (example 47, step a) (0.171 g) was added to a solution of (5-ethylthiophen-3-yl)(1-oxa-4,9-diazaspiro[5.5]undecan-4-yl)methanone trifluoroacetate (example 99, step a) (0.3 g) and triethylamine (0.410 ml) in acetonitrile (15 mL) and the mixture stirred at 20° C. for 2 hours. The solvent was evaporated under reduced pressure and the residue partitioned between ethyl A solution of (5-ethylthiophen-3-yl)(9-(4-fluoro-3-(2-hydroxyethyl)benzyl)-1-oxa-4,9-diazaspiro[5.5]undecan-4-yl)methanone (example 99, step b) (0.2 g) in DCM (15 mL) was treated with trifluoroacetic acid (0.035 ml) followed by Dess-Martin periodinane (0.285 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.026 ml) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.176 g) and acetic acid (0.026 ml) in methanol (15 mL). The mixture was cooled in an ice bath and treated with sodium cyanoborohydride (0.056 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.14 g.

(M+H)$^+$ 655 (APCI)

$^1$H NMR (400 MHz, D$_6$-DMSO, 90° C.) δ 11.27 (s, 1H), 7.49-7.44 (m, 3H), 7.29-7.23 (m, 1H), 6.94 (d, J=7.2 Hz, 1H), 6.89 (s, 1H), 6.77 (d, J=8.2 Hz, 1H), 4.94-4.89 (m, 1H), 4.26 (s, 2H), 3.67 (t, J=5.0 Hz, 2H), 3.53 (t, J=5.0 Hz, 2H), 3.45 (s,

2H), 3.24 (t, J=8.1 Hz, 2H), 3.18-3.02 (m, 8H), 2.81 (q, J=7.5 Hz, 2H), 2.07-1.98 (m, 2H), 1.79-1.67 (m, 2H), 1.25 (t, J=7.4 Hz, 3H). Five exchangeable protons not observed.

EXAMPLE 100

(R)-7-(2-(3-((4-(5-Ethylthiophene-3-carbonyl)-1-oxa-4,9-diazaspiro[5.5]undecan-9-yl)methyl)-4-fluorophenethylamino)-1-hydroxyethyl)-4-hydroxybenzo[d]thiazol-2(3H)-one ditrifluoroacetate

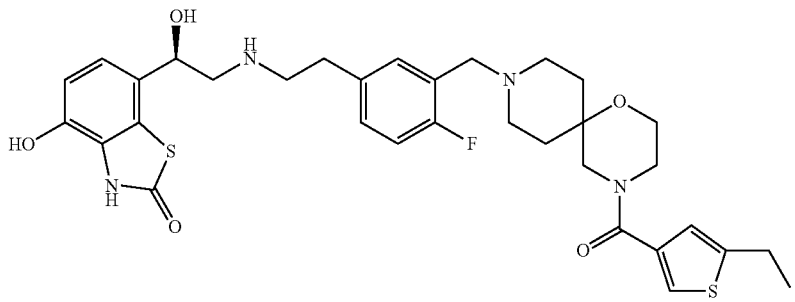 [SMILES: CCc1cc(C(=O)N2CCOC3(CCN(Cc4cc(CCNC[C@H](O)c5ccc(O)c6[nH]c(=O)sc56)ccc4F)CC3)C2)cs1]

a) tert-Butyl(4-fluorophenethoxy)dimethylsilane

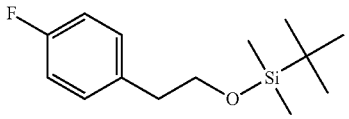

tert-Butyldimethylsilyl chloride (0.903 g) was added portionwise to a stirred solution of 2-(4-fluorophenyl)ethanol (0.7 g) and imidazole (0.408 g) in DMF (20 mL) at 20° C. The reaction mixture was stirred for 3 hours at room temperature and then partitioned between ethyl acetate and brine. The organic layer was washed twice with brine, dried over sodium sulphate, filtered and the solvent evaporated under reduced pressure. The crude product was purified by flash silica chromatography using 2% ethyl acetate in isohexane as solvent. Pure fractions were evaporated to dryness to afford the subtitled compound. Yield 0.99 g.

$^1$H NMR (400 MHz, CDCl$_3$) δ 7.18-7.13 (m, 2H), 6.99-6.93 (m, 2H), 3.77 (t, J=6.9 Hz, 2H), 2.78 (t, J=6.8 Hz, 2H), 0.86 (s, 9H), −0.03 (s, 6H)

b) 5-(2-(tert-Butyldimethylsilyloxy)ethyl)-2-fluorobenzaldehyde

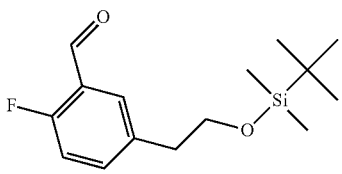 [SMILES: CC(C)(C)[Si](C)(C)OCCc1ccc(F)c(C=O)c1]

sec-Butyllithium (1.4M in cyclohexane, 2.78 ml) was added to dry tetrahydrofuran (10 mL) under nitrogen and the solution cooled to −78° C. N1-(2-(dimethylamino)ethyl)-N1,N2,N2-trimethylethane-1,2-diamine (0.674 g) was added slowly dropwise. A solution of tert-butyl(4-fluorophenethoxy)dimethylsilane (example 100, step a) (0.99 g) in dry tetrahydrofuran (3 mL) was then added dropwise over 5 minutes. Reaction mixture stirred for 2 hours at −78° C. DMF (2.1 ml) was added dropwise over 5 minutes and the mixture stirred at −78° C. for 1 hour followed by room temperature for 45 minutes. The reaction mixture was quenched by addition of water. Ethyl acetate (200 mL) was added and the organic washed three times with water, followed by twice with 2M HCl and then twice with water. The organic solution was washed with brine, dried over sodium sulphate, filtered and evaporated under reduced pressure. The crude product was purified by flash silica chromatography using 2% ethyl acetate in isohexane as solvent. Pure fractions were evaporated to dryness to afford the subtitled compound. Yield 0.5 g.

$^1$H NMR (400 MHz, CDCl$_3$) δ 10.36 (s, 1H), 7.72-7.69 (m, 1H), 7.48-7.43 (m, 1H), 7.11-7.06 (m, 1H), 3.80 (t, J=6.5 Hz, 2H), 2.83 (t, J=6.4 Hz, 2H), 0.85 (s, 9H), 0.04 (s, 6H).

c) (5-Ethylthiophen-3-yl)(9-(2-fluoro-5-(2-hydroxyethyl)benzyl)-1-oxa-4,9-diazaspiro[5.5]undecan-4-yl)methanone

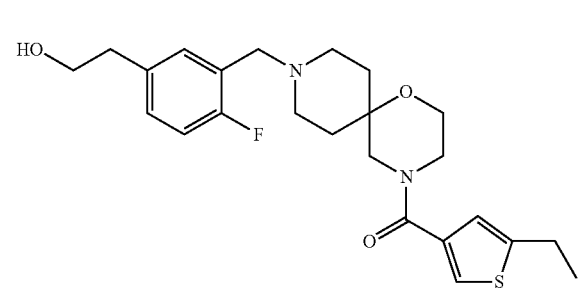 [SMILES: CCc1cc(C(=O)N2CCOC3(CCN(Cc4cc(CCO)ccc4F)CC3)C2)cs1]

Sodium triacetoxyborohydride (0.225 g) was added to a stirred solution at 0° C. of (5-ethylthiophen-3-yl)(1-oxa-4,9-diazaspiro[5.5]undecan-4-yl)methanone trifluoroacetate (example 99, step a) (0.289 g) and 5-(2-(tert-butyldimethylsilyloxy)ethyl)-2-fluorobenzaldehyde (example 100, step b) (0.2 g) and acetic acid (0.041 ml) in NMP (20 mL). The reaction mixture was then stirred at 20° C. for 18 hours. Further sodium triacetoxyborohydride (0.150 g) was added and stirring continued for 4 hours. The mixture was partitioned between ethyl acetate and saturated sodium bicarbonate solution, the organic layer was washed twice with brine, dried over sodium sulphate, filtered and the solvent evaporated under reduced pressure. The resultant gum was dissolved in THF (20 mL) and treated with TBAF (1M in THF, 1.4 ml). The solution was allowed to stand at 20° C. for 8 hours. The solvent was evaporated under reduced pressure and the crude product was purified by flash silica chromatography using 2% methanol in dichloromethane with 1% triethylamine as solvent. Pure fractions were evaporated to dryness to afford the subtitled compound. Yield 0.18 g.

m/z 447 (M+H)⁺ (APCI)

d) (R)-7-(2-(3-((4-(5-Ethylthiophene-3-carbonyl)-1-oxa-4,9-diazaspiro[5.5]undecan-9-yl)methyl)-4-fluorophenethylamino)-1-hydroxyethyl)-4-hydroxybenzo[d]thiazol-2(3H)-one ditrifluoroacetate

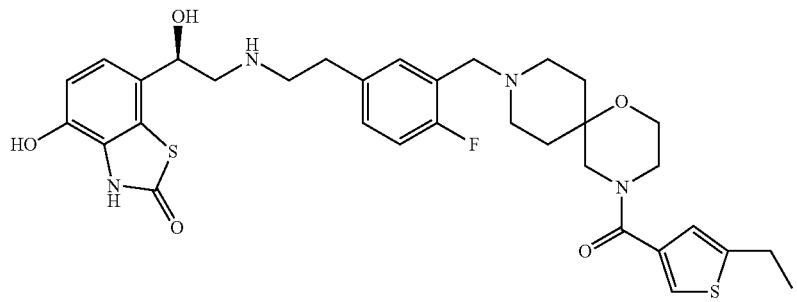 [SMILES: CCc1cc(C(=O)N2CCOC3(CCN(Cc4cc(CCNC[C@H](O)c5ccc(O)c6[nH]c(=O)sc56)ccc4F)CC3)C2)cs1]

A solution of (5-ethylthiophen-3-yl)(9-(2-fluoro-5-(2-hydroxyethyl)benzyl)-1-oxa-4,9-diazaspiro[5.5]undecan-4-yl)methanone (example 100, step c) (0.18 g) in DCM (15 mL) was treated with trifluoroacetic acid (0.031 ml) followed by Dess-Martin periodinane (0.256 g) and the resultant mixture stirred at 20° C. for 40 minutes. The reaction mixture was treated with saturated sodium thiosulphate solution (20 mL) and saturated sodium bicarbonate solution (20 mL) and ethyl acetate (30 mL) and stirred vigorously for 5 minutes. The mixture was extracted twice with ethyl acetate, the combined organics were washed with saturated sodium bicarbonate solution, dried over sodium sulphate and filtered. Acetic acid (0.023 ml) was added to this solution and the solvent then removed under reduced pressure. The residue was dissolved in methanol (3 mL) and added to a solution of (R)-7-(2-amino-1-hydroxyethyl)-4-hydroxybenzo[d]thiazol-2(3H)-one hydrochloride (WO2007027134, example 1, step d) (0.159 g) and acetic acid (0.023 ml) in methanol (15 mL). The mixture was cooled in an ice bath and treated with sodium cyanoborohydride (0.051 g). The cooling bath was removed and the mixture stirred at 20° C. for 3 hours. The solvent was evaporated down to a volume of 3 mL under reduced pressure and THF (20 mL) was added. The mixture was washed with a mixture of saturated brine (10 mL) and saturated sodium bicarbonate solution (1 mL). The organic layer was dried over sodium sulphate, filtered and the solvent removed under reduced pressure. The residue was azeotroped twice with acetonitrile. The crude product was purified by preparative HPLC (Sunfire™, Gradient: 10-40% acetonitrile in 0.2% aqueous TFA). The fractions containing the desired compound were evaporated to dryness to afford the titled compound. Yield 0.14 g.

m/z 655 (M+H)⁺ (APCI)

¹H NMR (400 MHz, D₆-DMSO, 90° C.) δ 11.27 (s, 1H), 7.48-7.43 (m, 2H), 7.42-7.37 (m, 1H), 7.25 (t, J=9.1 Hz, 1H), 6.93 (d, J=8.1 Hz, 1H), 6.89 (s, 1H), 6.77 (d, J=8.5 Hz, 1H), 4.94-4.88 (m, 1H), 4.27 (s, 2H), 3.67 (t, J=5.0 Hz, 2H), 3.53 (t, J=5.0 Hz, 2H), 3.45 (s, 2H), 3.23 (t, J=8.2 Hz, 2H), 3.18-2.97 (m, 8H), 2.81 (q, J=7.8 Hz, 2H), 2.04-1.98 (m, 2H), 1.79-1.69 (m, 2H), 1.25 (t, J=7.6 Hz, 3H). Five exchangeable protons not observed.

EXAMPLE 101

(R)-4-Hydroxy-7-(1-hydroxy-2-(2-(6-(4-(2-isopropylthiazole-4-carbonyl)-1-oxa-4,9-diazaspiro[5.5]undecan-9-yl)hexylthio)ethylamino)ethyl)benzo[d]thiazol-2(3H)-one formate

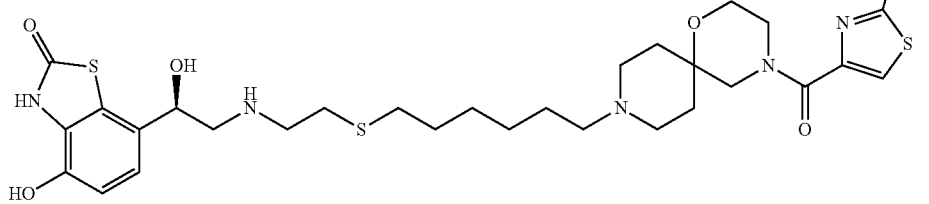

a) 6-(2,2-Dimethoxyethylthio)hexan-1-ol

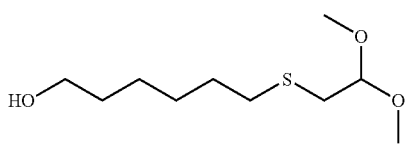

To a solution of 6-mercapto-hexan-1-ol (2.5 mL) in MeCN (30 mL) at 0° C. was added sodium hydride (60% suspension in mineral oil, 0.81 g). The mixture was stirred at 0° C. for 1 h then 2-bromo-1,1-dimethoxy-ethane (2.4 mL) was added.

The resulting mixture was stirred at RT for 20 h, then was quenched by addition of saturated sodium bicarbonate solution. The mixture was extracted with ethyl acetate (×3), then the combined organics were washed with saturated sodium bicarbonate solution, then with brine, dried over sodium sulfate, filtered and evaporated in vacuo. Purification was by silica gel chromatography eluting with 25% ethyl acetate in cyclohexane to give the subtitled compound as a colourless liquid. Yield 1.85 g.

$^1$H NMR (400 MHz, D$_4$-MeOH) δ 4.49 (t, J=5.5 Hz, 1H), 3.64 (t, J=6.6 Hz, 2H), 3.37 (s, 6H), 2.69 (d, J=5.5 Hz, 2H), 2.59 (t, J=7.4 Hz, 2H), 1.66-1.52 (m, 4H), 1.46-1.32 (m, 4H). One exchangeable proton not observed.

b) 2-(6-Bromohexylthio)acetaldehyde

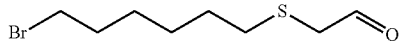 [SMILES: O=CCSCCCCCCBr]

To a solution of 6-(2,2-dimethoxyethylthio)hexan-1-ol (example 101, step a) (1.85 g) in DCM (75 mL) at 0° C. under N$_2$ was added carbon tetrabromide (3.31 g) followed by triphenylphosphine (2.62 g) portionwise. The resultant mixture was stirred at RT for 1.25 h then concentrated in vacuo. Purification was by silica gel chromatography eluting with 0-50% ethyl acetate in cyclohexane to give the subtitled compound as a yellow liquid. Yield 1.31 g.

$^1$H NMR (400 MHz, CDCl$_3$) δ 9.47 (t, J=3.5 Hz, 1H), 3.43-3.36 (m, 2H), 3.18 (d, J=3.5 Hz, 2H), 2.44 (t, J=7.3 Hz, 2H), 1.91-1.81 (m, 2H), 1.64-1.53 (m, 2H), 1.49-1.36 (m, 4H).

c) (R)-tert-Butyl 2-(6-Bromohexylthio)ethyl(2-hydroxy-2-(4-hydroxy-2-oxo-2,3-dihydrobenzo[d]thiazol-7-yl)ethyl)carbamate

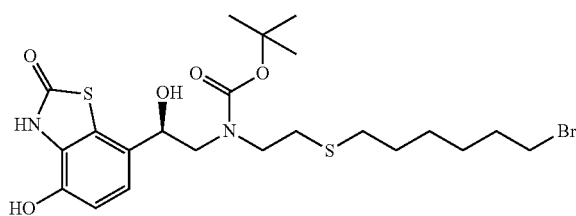 [SMILES: CC(C)(C)OC(=O)N(CCSCCCCCCBr)C[C@H](O)c1ccc(O)c2[nH]c(=O)sc12]

To a solution of 2-(6-bromohexylthio)acetaldehyde (example 101, step b) (1.2 g) in DMF (20 mL) with acetic acid (0.287 mL) and 3 Å molecular sieves at 0° C. under N$_2$ was added (R)-7-(2-amino-1-hydroxyethyl)-4-hydroxybenzo[d]thiazol-2(3H)-one hydrochloride (WO2007027134, example 1, step d) (1.45 g). The resultant mixture was stirred at 0° C. for 1 h, then sodium triacetoxyborohydride (1.6 g) was added and the mixture stirred at RT for 2 h. Di-tert-butyl dicarbonate (1.1 g) was added and stirring was continued for 20 h. The reaction mixture was quenched by addition of saturated sodium bicarbonate solution (40 mL), then the solution was extracted with ethyl acetate (×3). The combined organic solutions were washed with brine, dried over sodium sulfate, filtered and evaporated in vacuo. Purification was by silica gel chromatography eluting with 0-100% ethyl acetate in cyclohexane to give the subtitled compound as a yellow oil. Yield 0.56 g.

$^1$H NMR (300 MHz, D$_4$-MeOH) δ 6.89 (dd, J=18.6, 8.3 Hz, 1H), 6.72 (d, J=8.2 Hz, 1H), 4.87 (s, 1H), 3.59-3.39 (m, 4H), 3.33-3.29 (m, 2H), 2.64-2.41 (m, 4H), 1.89-1.80 (m, 2H), 1.66-1.32 (m, 15H). Three exchangeable protons not observed.

d) tert-Butyl 4-(2,2,2-trifluoroacetyl)-1-oxa-4,9-diazaspiro[5.5]undecane-9-carboxylate

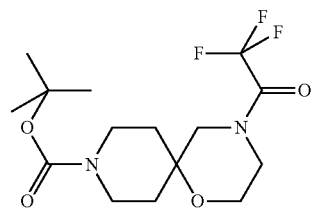 [SMILES: CC(C)(C)OC(=O)N1CCC2(CC1)CN(C(=O)C(F)(F)F)CCO2]

A solution of trifluoroacetic anhydride (2.2 mL) in DCM (14 mL) was added dropwise over 20 min to a solution of tert-butyl 1-oxa-4,9-diazaspiro[5.5]undecane-9-carboxylate hydrochloride (WuXi PharmaTech) (4.7 g) and triethylamine (4.9 mL) in DCM (90 mL) at 0° C. The mixture was stirred at 0° C. for 45 min and then at RT for 2 h. Water (90 mL) was added and the mixture was vigorously stirred for 10 min. The layers were separated and the aqueous layer was extracted with DCM (50 mL). The combined organic layers were dried over sodium sulfate and evaporated in vacuo. The residue was purified by silica gel chromatography eluting with 40-50% EtOAc in petroleum ether (40-60° C.) to give the subtitled compound as a yellow oil. Yield 2.73 g.

$^1$H NMR (400 MHz, CDCl$_3$) δ 3.86 (d, J=13.3 Hz, 1H), 3.77 (t, J=4.9 Hz, 2H), 3.74-3.64 (m, 2H), 3.61 (t, J=4.8 Hz, 1H), 3.52 (s, 1H), 3.23-3.15 (m, 1H), 3.07 (t, J=11.4 Hz, 1H), 1.85 (d, J=13.8 Hz, 1H), 1.77 (d, J=13.9 Hz, 1H), 1.52-1.37 (m, 12H).

e) 2,2,2-Trifluoro-1-(1-oxa-4,9-diazaspiro[5.5]undecan-4-yl)ethanone trifluoroacetate

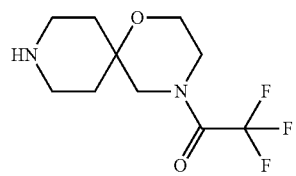 [SMILES: O=C(N1CCOC2(CCNCC2)C1)C(F)(F)F]

Trifluoroacetic acid (66 mL) was added to a solution of tert-butyl 4-(2,2,2-trifluoroacetyl)-1-oxa-4,9-diazaspiro[5.5]undecane-9-carboxylate (example 101, step d) (4.33 g) in DCM (66 mL) and the resulting mixture was stirred at RT for 20 min. Toluene (50 mL) was added and the mixture was evaporated in vacuo (×3) to give the subtitled compound. Yield 5.52 g.

$^1$H NMR (400 MHz, CDCl$_3$) δ 8.73 (br s, 2H), 3.77 (d, J=5.1 Hz, 2H), 3.72 (d, J=5.3 Hz, 1H), 3.65 (d, J=5.0 Hz, 1H), 3.58 (s, 1H), 3.48 (s, 1H), 3.33 (s, 2H), 3.24 (s, 2H), 2.08 (t, J=14.6 Hz, 2H), 1.93-1.75 (m, 2H).

f) (R)-tert-Butyl 2-hydroxy-2-(4-hydroxy-2-oxo-2,3-dihydrobenzo[d]thiazol-7-yl)ethyl(2-(6-(4-(2,2,2-trifluoroacetyl)-1-oxa-4,9-diazaspiro[5.5]undecan-9-yl)hexylthio)ethyl)carbamate

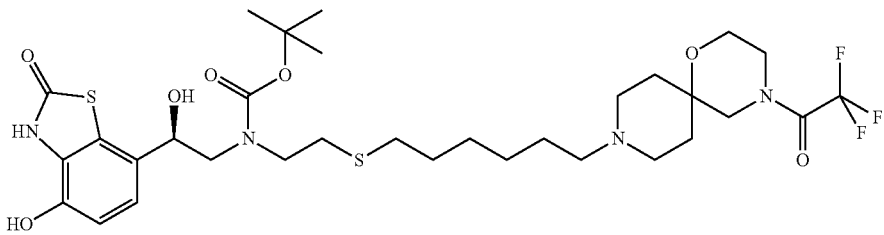 [SMILES: CC(C)(C)OC(=O)N(CCSCCCCCCN1CCC2(CC1)CN(C(=O)C(F)(F)F)CCO2)C[C@H](O)c1ccc(O)c2[nH]c(=O)sc12]

(R)-tert-Butyl 2-(6-bromohexylthio)ethyl(2-hydroxy-2-(4-hydroxy-2-oxo-2,3-dihydrobenzo[d]thiazol-7-yl)ethyl)carbamate (example 101, step c) (0.55 g) was combined with 2,2,2-trifluoro-1-(1-oxa-4,9-diaza-spiro[5.5]undec-4-yl)-ethanone trifluoroacetic acid salt (example 101, step e) (0.25 g) and triethylamine (0.26 mL) in acetonitrile (20 mL) and heated at 80° C. for 48 h. The volatiles were evaporated in vacuo. Purification was achieved by silica gel chromatography eluting with 10% MeOH in DCM to give the subtitled compound as a yellow gum. Yield 0.10 g and 0.074 g (less pure).

m/z 721 (M+H)$^+$ $^1$H NMR (400 MHz, D$_4$-MeOH) δ 6.81 (s, 1H), 6.69 (d, J=8.21 Hz, 1H), 3.80-3.74 (m, 2H), 3.65 (s, 2H), 3.58-3.54 (m, 1H), 3.52-3.47 (m, 1H), 3.11-2.94 (m, 4H), 2.51-2.41 (m, 6H), 2.05-1.95 (m, 2H), 1.80-1.59 (m, 8H), 1.50 (s, 9H), 1.46-1.25 (m, 6H). One proton obscured by solvent peak and three exchangeable protons not observed.

g) (R)-tert-Butyl 2-(6-(1-oxa-4,9-diazaspiro[5.5]undecan-9-yl)hexylthio)ethyl(2-hydroxy-2-(4-hydroxy-2-oxo-2,3-dihydrobenzo[d]thiazol-7-yl)ethyl)carbamate

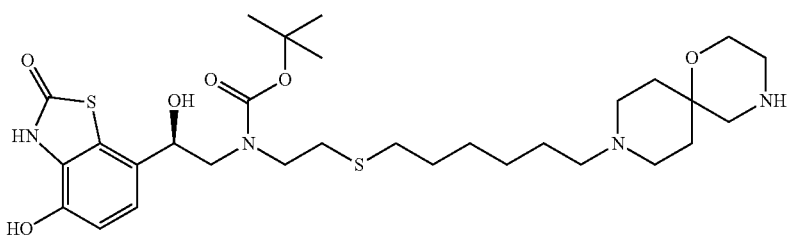 [SMILES: CC(C)(C)OC(=O)N(CCSCCCCCCN1CCC2(CC1)CNCCO2)C[C@H](O)c1ccc(O)c2[nH]c(=O)sc12]

To a stirring solution of (R)-tert-butyl 2-hydroxy-2-(4-hydroxy-2-oxo-2,3-dihydrobenzo[d]thiazol-7-yl)ethyl(2-(6-(4-(2,2,2-trifluoroacetyl)-1-oxa-4,9-diazaspiro[5.5]undecan-9-yl)hexylthio)ethyl)carbamate (example 101, step f) (0.18 g) in methanol (10 mL) was added a solution of potassium carbonate (0.06 g) in water (10 mL). The mixture was stirred at RT for 17 h then the methanol was removed under a stream of nitrogen. The solution was diluted with brine, extracted with ethyl acetate (×3) and dried over sodium sulfate, filtered and evaporated in vacuo. The residue was dissolved in methanol and evaporated in vacuo to give the subtitled compound as a brown glass. Yield 0.15 g.

m/z 625 (M+H)$^+$ $^1$H NMR (300 MHz, D$_4$-MeOH) δ 6.94-6.82 (m, 1H), 6.73 (d, J=2.0 Hz, 1H), 3.66-3.59 (m, 2H), 3.51-3.40 (m, 2H), 2.80-2.69 (m, 4H), 2.66-2.62 (m, 2H), 2.55-2.40 (m, 8H), 2.04-1.94 (m, 2H), 1.62-1.56 (m, 8H), 1.55-1.21 (m, 13H). One proton obscured by solvent peak and four exchangeable protons not observed.

h) (R)-4-Hydroxy-7-(1-hydroxy-2-(2-(6-(4-(2-isopropylthiazole-4-carbonyl)-1-oxa-4,9-diazaspiro[5.5]undecan-9-yl)hexylthio)ethylamino)ethyl)benzo[d]thiazol-2(3H)-one formate m/z 678 (M+H)$^+$ $^1$H NMR (400 MHz, D$_6$-DMSO, 80° C.) δ 8.18 (s, 1H), 7.91 (d, J=0.7 Hz, 1H), 6.90 (d, J=8.3 Hz, 1H), 6.72 (d, J=8.3 Hz, 1H), 4.64-4.58 (m, 1H), 3.72-3.62 (m, 2H), 3.62-3.58 (m, 6H), 3.38-3.28 (m, 1H), 2.84-2.74 (m, 6H), 2.62-2.58 (m, 2H), 2.47-2.31 (m, 6H), 1.78-1.69 (m, 2H), 1.60-1.50 (m, 4H), 1.45-1.41 (m, 2H), 1.38 (d, J=6.6 Hz, 6H), 1.32-1.26 (m, 2H). Five exchangeable protons not observed.

EXAMPLE 102

(R)-4-Hydroxy-7-(1-hydroxy-2-(7-(4-(2-isopropylthiazole-4-carbonyl)-1-oxa-4,9-diazaspiro[5.5]undecan-9-yl)-2,2-dimethylheptylamino)ethyl)benzo[d]thiazol-2(3H)-one formate

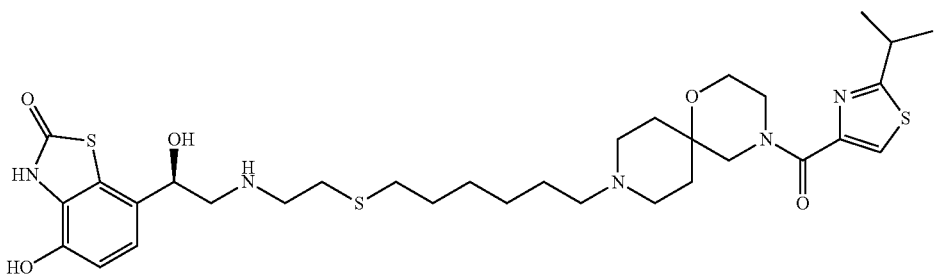 [SMILES: CC(C)c1nc(C(=O)N2CCOC3(CCN(CCCCCCSCCNC[C@H](O)c4ccc(O)c5[nH]c(=O)sc45)CC3)C2)cs1]

To a solution (R)-tert-butyl 2-(6-(1-oxa-4,9-diazaspiro[5.5]undecan-9-yl)hexylthio)ethyl(2-hydroxy-2-(4-hydroxy-2-oxo-2,3-dihydrobenzo[d]thiazol-7-yl)ethyl)carbamate (example 101, step g) (0.093 g) in DMF (3 mL) was added triethylamine (0.062 mL) and 2-isopropyl-thiazole-4-carboxylic acid (0.025 g) followed by O-(7-azabenzotriazol-1-yl)-N,N,N',N'-tetramethyluronium hexafluorophosphate (0.079 g). The resultant mixture was stirred at RT for 4 h then 4 drops of '880' aqueous ammonia were added and the mixture was stirred for 15 min. Brine and ethyl acetate were added to the solution and the phases were separated, then the organic phase was extracted with ethyl acetate (×2). The combined organic phase was dried over sodium sulphate, filtered and evaporated in vacuo. The residue was dissolved in DCM (2 mL) then trifluoroacetic acid (1 mL) was added. The solution was left to stand at RT for 40 min then toluene (20 mL) was added and the mixture was concentrated in vacuo. A further amount of toluene was added and the mixture concentrated again before the material was azeotroped with acetonitrile. Purification was by preparative HPLC (Phenomenex Gemini®, Gradient: 10-40% acetonitrile in 0.1% aqueous formic acid). The fractions containing product were combined and freeze dried to give the titled compound as a colourless solid. Yield 0.016 g.

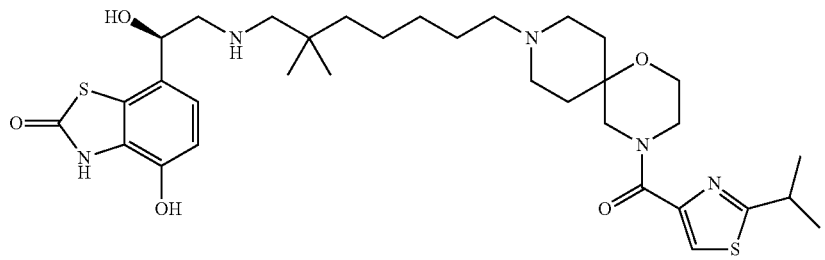 [SMILES: CC(C)c1nc(C(=O)N2CCOC3(CCN(CCCCCC(C)(C)CNC[C@H](O)c4ccc(O)c5[nH]c(=O)sc45)CC3)C2)cs1]

a) Ethyl 7-bromo-2,2-dimethylheptanoate

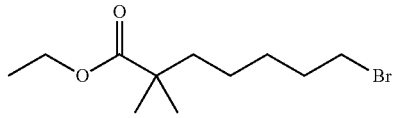

To a solution of diisopropylamine (5.82 mL) in THF (30 mL) was added n-butyllithium (2.5M in hexanes, 16.4 mL) at 0° C. and the mixture was stirred for 30 min at this temperature before being cooled to −78° C. Ethyl isobutyrate (5 mL) was added dropwise and the resultant mixture was stirred at −78° C. for 1 h before addition of 1,5-dibromopentane (5.61 mL). The reaction mixture was stirred at −78° C. for 1 h then at RT for 2.5 h before being poured into saturated ammonium chloride solution. The solution was extracted with ethyl acetate (×2), then the combined organics were washed with water and dried over sodium sulphate, filtered and evaporated in vacuo. Purification was by silica gel chromatography eluting with 0-25% ethyl acetate in cyclohexane to give the subtitled compound as a yellow liquid. Yield 4.45 g.

¹H NMR (400 MHz, CDCl₃) δ 4.08 (q, J=7.1 Hz, 2H), 3.41-3.33 (m, 2H), 1.91-1.77 (m, 2H), 1.61-1.44 (m, 2H), 1.52-1.24 (m, 2H), 1.21 (t, J=7.1 Hz, 5H), 1.12 (s, 6H).

b) 7-Bromo-2,2-dimethylheptan-1-ol

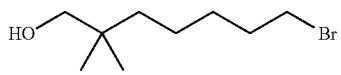

To a solution of ethyl 7-bromo-2,2-dimethylheptanoate (example 102, step a) (1.5 g) in dry diethyl ether (50 mL) at 0° C. under N₂ was added diisobutylaluminium hydride (1M in toluene, 12.5 mL) dropwise. The reaction mixture was stirred at 0° C. for 1 h then quenched by addition of saturated potassium sodium tartrate (150 mL). The mixture was stirred for 1 h then extracted with ethyl acetate (×3). The combined organics were washed with brine and dried over sodium sulphate, filtered and evaporated in vacuo. Purification was by silica gel chromatography eluting with 0-25% ethyl acetate in cyclohexane to give the subtitled compound as a colourless liquid. Yield 1.16 g.

¹H NMR (400 MHz, CDCl₃) δ 3.41 (t, J=6.8 Hz, 2H), 3.32 (d, J=5.8 Hz, 2H), 1.93-1.82 (m, 2H), 1.47-1.37 (m, 2H), 1.35-1.20 (m, 4H), 0.91-0.81 (m, 6H). One exchangeable proton not observed.

c) (9-(7-Hydroxy-6,6-dimethylheptyl)-1-oxa-4,9-diazaspiro[5.5]undecan-4-yl)(2-isopropylthiazol-4-yl)methanone

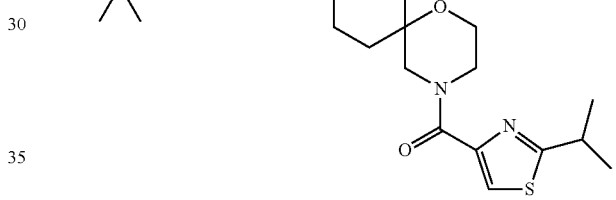

(2-Isopropylthiazol-4-yl)(1-oxa-4,9-diazaspiro[5.5]undecan-4-yl)methanone trifluoroacetate (example 22, step b) (0.5 g) was dissolved in methanol and applied to a SCX cartridge pre-wetted with methanol. The cartridge was washed with methanol and eluted with 2M ammonia in methanol solution. The eluent was evaporated in vacuo to afford the material as the free base (0.29 g). To this material was added 7-bromo-2,2-dimethylheptan-1-ol (example 102, step b) (0.26 g) in acetonitrile (10 mL), then triethylamine (0.27 mL), and the resultant mixture was heated at 60° C. for 17 h. The volatiles were evaporated in vacuo and the crude product was purified by silica gel chromatography eluting with 0% then 5% then 10% methanol in DCM to afford the subtitled compound as a colourless gum. Yield 0.29 g.

m/z 452 (M+H)⁺

¹H NMR (400 MHz, CDCl₃) δ 7.87 (s, 1H), 4.01-3.95 (m, 2H), 3.80-3.62 (m, 2H), 3.49 (s, 1H), 3.34-3.28 (m, 2H), 3.16-3.09 (m, 1H), 2.98-2.75 (m, 3H), 2.42-2.20 (m, 2H), 2.09 (br m, 2H), 1.95-1.82 (m, 2H), 1.47-1.40 (m, 8H), 1.34-1.21 (m, 8H), 0.85 (s, 6H). One exchangeable proton not observed.

d) 7-(4-(2-Isopropylthiazole-4-carbonyl)-1-oxa-4,9-diazaspiro[5.5]undecan-9-yl)-2,2-dimethylheptanal

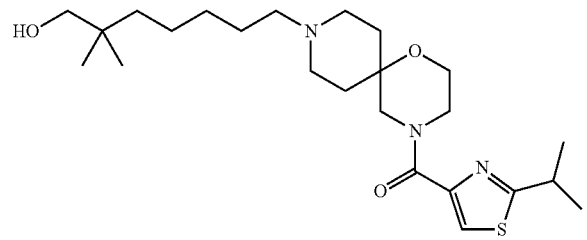 [SMILES: CC(C)c1nc(C(=O)N2CCOC3(CCN(CCCCCC(C)(C)CO)CC3)C2)cs1]

Trifluoroacetic acid (0.048 mL) was added to a solution of (9-(7-hydroxy-6,6-dimethylheptyl)-1-oxa-4,9-diazaspiro[5.5]undecan-4-yl)(2-isopropylthiazol-4-yl)methanone (example 102, step c) (0.28 g) in DCM (15 mL) at 0° C. under argon and the mixture stirred for 5 min before addition of Dess-Martin periodinane (0.39 g). The reaction mixture was stirred at RT for 1 h then was quenched by addition of saturated sodium bisulfite solution (10 mL) and saturated sodium bicarbonate solution (10 mL) then ethyl acetate was added and the mixture stirred for 5 min. The layers were separated and the aqueous solution was extracted with ethyl acetate (×2). The combined organic solutions were washed with saturated sodium bicarbonate solution. Acetic acid (0.053 mL) was added to the organic phase which was then dried over sodium sulphate, filtered and evaporated in vacuo to afford the crude subtitled compound as a yellow oil. Yield 0.33 g.

m/z 450 (M+H)

¹H NMR (300 MHz, CDCl₃) δ 9.43 (s, 1H), 7.86 (s, 1H), 4.02-3.86 (m, 3H), 3.82-3.67 (m, 4H), 3.36-3.26 (m, 2H), 3.24-2.97 (m, 2H), 2.85-2.66 (m, 4H), 2.03 (d, J=8.4 Hz, 2H), 1.79-1.60 (s, 2H), 1.48-1.35 (m, 8H), 1.34-1.19 (m, 4H), 1.06 (s, 6H).

e) (R)-4-Hydroxy-7-(1-hydroxy-2-(7-(4-(2-isopropylthiazole-4-carbonyl)-1-oxa-4,9-diazaspiro[5.5]undecan-9-yl)-2,2-dimethylheptylamino)ethyl)benzo[d]thiazol-2(3H)-one formate

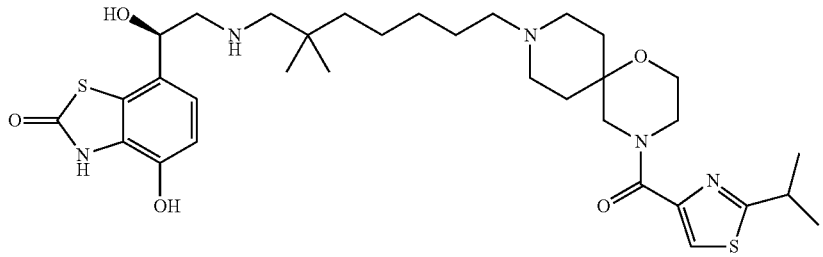

Acetic acid (0.053 mL) was added to a mixture of 7-(4-(2-isopropylthiazole-4-carbonyl)-1-oxa-4,9-diazaspiro[5.5]undecan-9-yl)-2,2-dimethylheptanal (example 102, step d) (0.33 g) and (R)-7-(2-amino-1-hydroxyethyl)-4-hydroxybenzo[d]thiazol-2(3H)-one hydrochloride (WO2007027134, example 1, step d) (0.25 g) with 3 Å molecular sieves in anhydrous methanol (10 mL). The mixture was stirred for 5 min then cooled to 0° C. Sodium triacetoxyborohydride (0.13 g) was added and the resulting mixture stirred at RT for 16.5 h. The solution was filtered then concentrated in vacuo. The residue was dissolved in a mixture of acetonitrile and water and purified by preparative HPLC (Phenomenex Gemini®, Gradient: 10-40% acetonitrile in 0.1% aqueous formic acid). The fractions containing product were combined and freeze-dried to give the titled compound as a white solid. Yield 0.1 g.

m/z 660 (M+H)$^+$ $^1$H NMR (400 MHz, D$_4$-MeOH) δ 8.50 (s, 1H), 7.89 (s, 1H), 6.93 (d, J=8.3 Hz, 1H), 6.71 (d, J=8.3 Hz, 1H), 4.93 (dd, J=9.5, 4.1 Hz, 1H), 3.92-3.56 (m, 6H), 3.37-3.26 (m, 1H), 3.10-2.66 (m, 10H), 2.11-1.96 (m, 2H), 1.84-1.57 (m, 4H), 1.38 (d, J=6.9 Hz, 6H), 1.29 (s, 6H), 0.96 (s, 6H). Five exchangeable protons not observed.

EXAMPLE 103

(R)-4-Hydroxy-7-(1-hydroxy-2-(9-(4-(2-isopropylthiazole-4-carbonyl)-1-oxa-4,9-diazaspiro[5.5]undecan-9-yl)-2,2-dimethylnonylamino)ethyl)benzo[d]thiazol-2(3H)-one formate

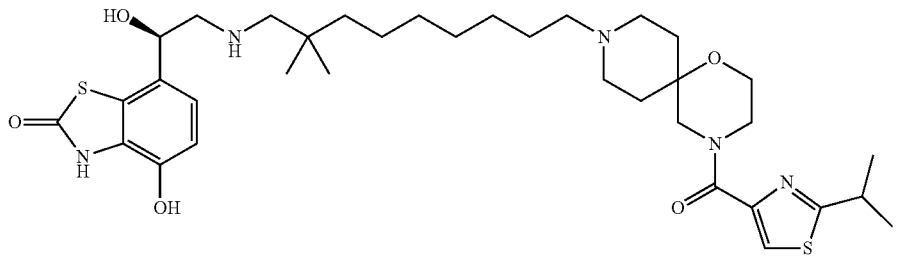 [SMILES: CC(C)c1nc(C(=O)N2CCOC3(CCN(CCCCCCCC(C)(C)CNC[C@H](O)c4ccc(O)c5[nH]c(=O)sc45)CC3)C2)cs1]

a) Ethyl 9-bromo-2,2-dimethylnonanoate

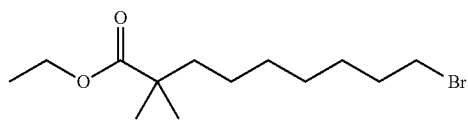 [SMILES: CCOC(=O)C(C)(C)CCCCCCCBr]

To a solution of diisopropylamine (5.82 mL) in THF (30 mL) was added n-butyllithium (2.5M in hexanes, 16.4 mL) at 0° C. and the mixture was stirred for 30 min at this temperature before being cooled to −78° C. Ethyl isobutyrate (5 mL) was added dropwise and the resultant mixture was stirred at −78° C. for 1 h before addition of 1,7-dibromoheptane (6.4 mL). The reaction mixture was stirred at −78° C. for 1 h then at RT for 2 h before being poured into saturated ammonium chloride solution. The solution was extracted with ethyl acetate (×2) then the combined organics were washed with brine, dried over sodium sulphate, filtered and evaporated in vacuo. Purification was by silica gel chromatography eluting with 0-10% ethyl acetate in cyclohexane to give the subtitled compound as a colourless liquid. Yield 1.27 g.

$^1$H NMR (400 MHz, CDCl$_3$) δ 4.11 (q, J=7.1 Hz, 2H), 3.43-3.37 (m, 2H), 1.91-1.80 (m, 2H), 1.56-1.36 (m, 4H), 1.39-1.21 (m, 9H), 1.15 (s, 6H).

b) 9-Bromo-2,2-dimethylnonan-1-ol

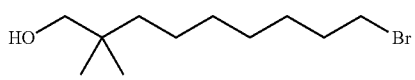

To a solution of ethyl 9-bromo-2,2-dimethylnonanoate (example 103, step a) (1.27 g) in dry diethyl ether (40 mL) at 0° C. under $N_2$ was added diisobutylaluminium hydride (1M in toluene, 9.5 mL) dropwise. The reaction mixture was stirred at 0° C. for 1.25 h then quenched by addition of saturated potassium sodium tartrate solution (150 mL). The mixture was stirred for 15 min then extracted with ethyl acetate (×3) then the combined organics were washed with brine, dried over sodium sulphate, filtered and evaporated in vacuo. Purification was by silica gel chromatography eluting with 0-25% ethyl acetate in cyclohexane to give the subtitled compound as a colourless liquid. Yield 0.56 g.

$^1$H NMR (400 MHz, CDCl$_3$) δ 3.41 (t, J=6.9 Hz, 2H), 3.31 (d, J=5.2 Hz, 2H), 1.91-1.79 (m, 2H), 1.47-1.39 (m, 2H), 1.34-1.21 (m, 8H), 0.86 (s, 6H). One exchangeable proton not observed.

c) (9-(9-Hydroxy-8,8-dimethylnonyl)-1-oxa-4,9-diazaspiro[5.5]undecan-4-yl)(2-isopropylthiazol-4-yl)methanone

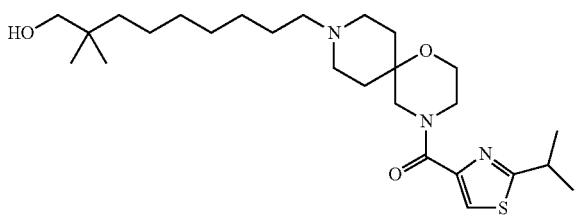 [SMILES: CC(C)c1nc(C(=O)N2CCOC3(CCN(CCCCCCCC(C)(C)CO)CC3)C2)cs1]

2-Isopropylthiazol-4-yl)(1-oxa-4,9-diazaspiro[5.5]undecan-4-yl)methanone trifluoroacetate (example 22, step b) (0.5 g) was dissolved in methanol and applied to a SCX cartridge pre-wetted with methanol. The cartridge was washed with methanol and eluted with 2M ammonia in methanol solution. The eluent was evaporated in vacuo to afford the material as the free base (0.26 g). To this material was added 9-bromo-2,2-dimethylnonan-1-ol (example 103, step b) (0.25 g) in acetonitrile (10 mL) and triethylamine (0.23 mL) and the resultant mixture was heated at 60° C. for 15 h. The volatiles were evaporated in vacuo and the crude product purified by silica gel chromatography eluting with 0-10% methanol in DCM to afford impure subtitled compound as a colourless gum which was repurified by silica gel chromatography eluting with 0-10% methanol in DCM to afford the subtitled compound as an off-white solid. Yield 0.37 g.

m/z 480 (M+H)$^+$ $^1$H NMR (400 MHz, CDCl$_3$) δ 7.87 (s, 1H), 4.08-3.91 (m, 1H), 3.80-3.75 (m, 3H), 3.45-3.32 (m, 2H), 3.35-3.30 (m, 2H), 3.06-2.84 (m, 3H), 2.48-2.31 (m, 2H), 2.17-2.03 (m, 2H), 1.96-1.83 (m, 2H), 1.66-1.51 (m, 4H), 1.43 (d, J=6.9 Hz, 6H), 1.39-1.31 (m, 4H), 1.30-1.16 (m, 6H), 0.86 (s, 6H). One exchangeable proton not observed.

d) 9-(4-(2-Isopropylthiazole-4-carbonyl)-1-oxa-4,9-diazaspiro[5.5]undecan-9-yl)-2,2-dimethylnonanal

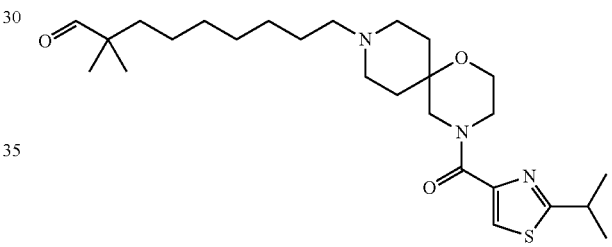

Trifluoroacetic acid (0.059 mL) was added to a solution of (9-(9-hydroxy-8,8-dimethylnonyl)-1-oxa-4,9-diazaspiro[5.5]undecan-4-yl)(2-isopropylthiazol-4-yl)methanone (example 103, step c) (0.37 g) in DCM (20 mL) at 0° C. under argon and the mixture stirred for 5 min before addition of Dess-Martin periodinane (0.49 g). The reaction mixture was stirred at RT for 1.25 h then was quenched by addition of saturated sodium thiosulfate solution (20 mL) and saturated sodium bicarbonate solution (20 mL) then ethyl acetate was added and the mixture stirred for 5 min. The phases were separated and the aqueous layer was extracted with ethyl acetate (×2). The combined organic solutions were washed with saturated sodium bicarbonate solution. Acetic acid (0.066 mL) was added to the organic phase which was then dried over sodium sulphate, filtered and evaporated in vacuo to afford the crude subtitled compound as a yellow oil. Yield 0.40 g.

m/z 478 (M+H)$^+$ $^1$H NMR (400 MHz, CDCl$_3$) δ 9.46-9.41 (s, 1H), 7.87 (s, 1H), 4.05-3.89 (m, 3H), 3.82-3.67 (m, 5H), 3.36-3.26 (m, 3H), 2.87-2.79 (m, 4H), 2.09-2.02 (m, 2H), 1.77-1.65 (m, 2H), 1.47-1.36 (m, 10H), 1.32-1.13 (m, 6H), 1.03 (s, 6H).

e) (R)-4-Hydroxy-7-(1-hydroxy-2-(9-(4-(2-isopropylthiazole-4-carbonyl)-1-oxa-4,9-diazaspiro[5.5]undecan-9-yl)-2,2-dimethylnonylamino)ethyl)benzo[d]thiazol-2(3H)-one formate

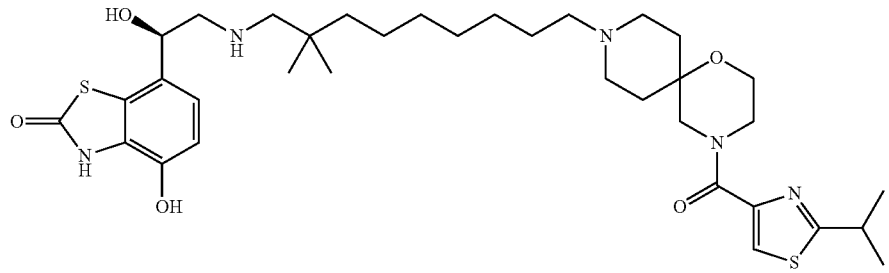 [SMILES: CC(C)c1nc(C(=O)N2CCOC3(CCN(CCCCCCCC(C)(C)CNC[C@H](O)c4ccc(O)c5[nH]c(=O)sc45)CC3)C2)cs1]

Acetic acid (0.066 mL) was added to a mixture of 9-(4-(2-isopropylthiazole-4-carbonyl)-1-oxa-4,9-diazaspiro[5.5]undecan-9-yl)-2,2-dimethylnonanal (example 103, step d) (0.4 g) and (R)-7-(2-amino-1-hydroxyethyl)-4-hydroxybenzo[d]thiazol-2(3H)-one hydrochloride (WO2007027134, example 1, step d) (0.3 g) with 3 Å molecular sieves in anhydrous methanol (10 mL). The mixture was stirred for 5 min then cooled to 0° C. Sodium triacetoxyborohydride (0.16 g) was added and the resulting mixture stirred at RT for 16.5 h. The solution was filtered then concentrated in vacuo. The residue was dissolved in a mixture of acetonitrile and water and purified by preparative HPLC (Phenomenex Gemini®, Gradient: 10-40% acetonitrile in 0.1% aqueous formic acid). The fractions containing product were combined and freeze-dried to give the titled compound as a white solid. Yield 0.10 g.

m/z 688 (M+H)$^+$ $^1$H NMR (400 MHz, D$_4$-MeOH) δ 8.51 (s, 1H), 7.88 (s, 1H), 6.92 (d, J=8.3 Hz, 1H), 6.70 (d, J=8.3 Hz, 1H), 4.93-4.88 (m, 1H), 3.92-3.53 (m, 6H), 3.32-3.25 (m, 1H), 3.11-2.52 (m, 10H), 1.98 (s, 2H), 1.82-1.48 (br m, 3H), 1.37 (d, J=6.9 Hz, 6H), 1.38-1.31 (m, 5H), 1.30-1.22 (m, 6H), 0.91 (s, 6H). Five exchangeable protons not observed.

EXAMPLE 104

(R)-4-Hydroxy-7-(1-hydroxy-2-(4-(2-(4-(5-methylthiophene-3-carbonyl)-1-oxa-4,9-diazaspiro[5.5]undecan-9-yl)ethoxy)benzylamino)ethyl)benzo[d]thiazol-2(3H)-one formate a) tert-Butyl 4-(5-methylthiophene-3-carbonyl)-1-oxa-4,9-diazaspiro[5.5]undecane-9-carboxylate

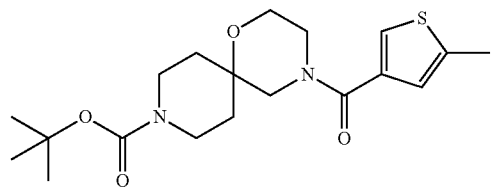

O-(7-Azabenzotriazol-1-yl)-N,N,N',N'-tetramethyluronium hexafluorophosphate (0.91 g) was added to a solution of tert-butyl 1-oxa-4,9-diazaspiro[5.5]undecane-9-carboxylate hydrochloride (WuXi PharmaTech) (0.5 g), 5-methylthiophene-3-carboxylic acid (0.243 g) and triethylamine (0.95 mL) in DMF (10 mL) and the resulting mixture stirred for 16 h. The reaction mixture was poured into brine (40 mL) and extracted with ethyl acetate (3×50 mL). The combined organic solutions were washed with water (150 mL), brine (150 mL), dried over sodium sulphate, filtered and evaporated in vacuo. Purification was by silica gel chromatography eluting with 0-10% methanol in dichloromethane to give the subtitled compound as a clear oil. Yield 0.34 g.

$^1$H NMR (400 MHz, CDCl$_3$) δ 7.23 (s, 1H), 6.81 (s, 1H), 3.72 (s, 6H), 3.46 (s, 3H), 3.15 (s, 3H), 2.49 (d, J=1.1 Hz, 3H), 1.82 (br d, J=13.5 Hz, 2H), 1.45 (s, 9H).

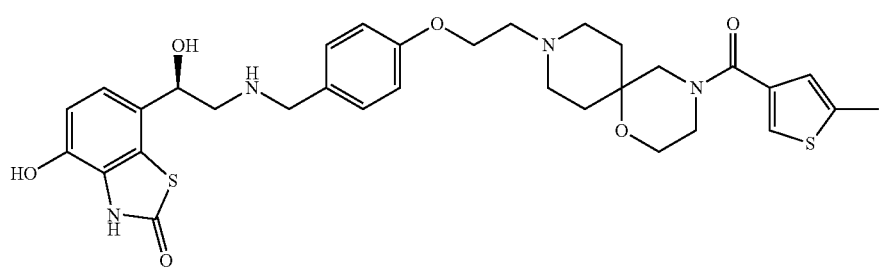 [SMILES: Cc1cc(C(=O)N2CCOC3(CCN(CCOc4ccc(CNC[C@H](O)c5ccc(O)c6[nH]c(=O)sc56)cc4)CC3)C2)cs1]

b) (5-Methylthiophen-3-yl)(1-oxa-4,9-diazaspiro [5.5]undecan-4-yl)methanone

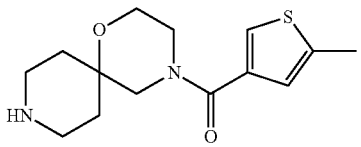 [SMILES: Cc1cc(C(=O)N2CCOC3(CCNCC3)C2)cs1]

Trifluoroacetic acid (2.5 mL) was added to a solution of tert-butyl 4-(5-methylthiophene-3-carbonyl)-1-oxa-4,9-diazaspiro[5.5]undecane-9-carboxylate (example 104, step a) (0.34 g) in DCM (10 mL) and the resulting mixture was stirred for 45 minutes and allowed to stand overnight. The solvent was evaporated in vacuo. Toluene (3×25 mL) was added and the mixture evaporated in vacuo. The residue was dissolved in methanol (20 mL) and applied to a SCX cartridge pre-wetted with methanol. The cartridge was washed with methanol (40 mL) and eluted with 2M ammonia in methanol solution (20 mL). The eluent was evaporated in vacuo to give the subtitled compound as a colourless oil. Yield 0.25 g.

$^1$H NMR (400 MHz, D$_6$-DMSO) δ 7.50 (s, 1H), 6.88 (s, 1H), 3.67-3.57 (m, 2H), 3.49 (s, 2H), 3.38 (s, 4H), 2.68 (s, 2H), 2.45 (d, J=1.1 Hz, 3H), 1.57 (s, 2H), 1.37 (s, 2H). One exchangeable proton not observed.

c) (R)-tert-Butyl 2-hydroxy-2-(4-hydroxy-2-oxo-2,3-dihydrobenzo[d]thiazol-7-yl)ethyl(4-(2-(4-(5-methylthiophene-3-carbonyl)-1-oxa-4,9-diazaspiro[5.5] undecan-9-yl)ethoxy)benzyl)carbamate

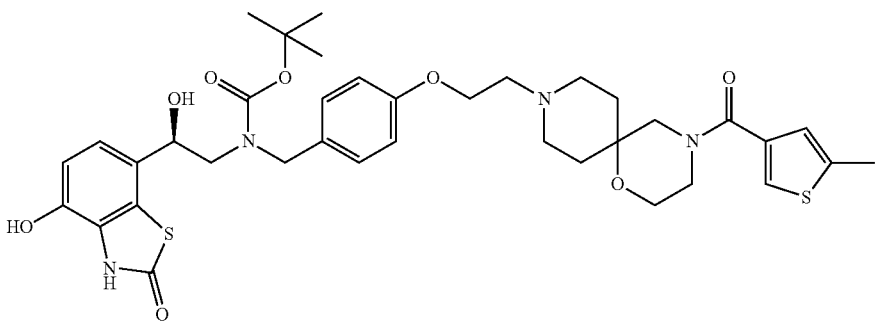 [SMILES: Cc1cc(C(=O)N2CCOC3(CCN(CCOc4ccc(CN(C[C@H](O)c5ccc(O)c6[nH]c(=O)sc56)C(=O)OC(C)(C)C)cc4)CC3)C2)cs1]

Triethylamine (0.25 mL) was added to a solution of (5-methylthiophen-3-yl)(1-oxa-4,9-diazaspiro[5.5]undecan-4-yl)methanone (example 104, step b) (0.195 g) (0.195 g) in acetonitrile (2.5 mL). This solution was added to a solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 108, step c) (0.5 g) in acetonitrile (2.5 mL). The resulting mixture was heated at 80° C. for 48 hours. The reaction mixture was evaporated in vacuo. Purification was by silica gel chromatography eluting with 0-10% methanol in dichloromethane to give the subtitled compound as a cream solid. Yield 0.33 g.

$^1$H NMR (300 MHz, D$_4$-MeOH) δ 7.42 (s, 1H), 7.07 (d, J=6.7 Hz, 2H), 6.85 (d, J=13.0 Hz, 4H), 6.70 (d, J=8.2 Hz, 1H), 4.28 (s, 1H), 4.12 (s, 2H), 3.71 (s, 2H), 3.66-3.48 (m, 5H), 3.38-3.29 (m, 5H), 2.90 (s, 2H), 2.80-2.55 (m, 4H), 2.48 (s, 3H), 1.94-1.89 (m, 1H), 1.44 (s, 4H), 1.37 (s, 6H). Three exchangeable protons not observed.

d) (R)-4-Hydroxy-7-(1-hydroxy-2-(4-(2-(4-(5-methylthiophene-3-carbonyl)-1-oxa-4,9-diazaspiro[5.5] undecan-9-yl)ethoxy)benzylamino)ethyl)benzo[d] thiazol-2(3H)-one formate

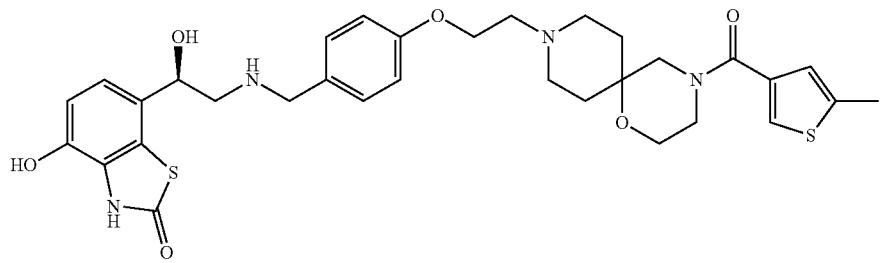 [SMILES: Cc1cc(C(=O)N2CCOC3(CCN(CCOc4ccc(CNC[C@H](O)c5ccc(O)c6[nH]c(=O)sc56)cc4)CC3)C2)cs1]

Trifluoroacetic acid (1.2 mL) was added to a solution of (R)-tert-butyl 2-hydroxy-2-(4-hydroxy-2-oxo-2,3-dihydrobenzo[d]thiazol-7-yl)ethyl(4-(2-(4-(5-methylthiophene-3-carbonyl)-1-oxa-4,9-diazaspiro[5.5]undecan-9-yl)ethoxy)benzyl)carbamate (example 104, step c) (0.33 g) in DCM (5 mL) and the resulting mixture stirred for 10 minutes. Toluene (20 mL) was added and the mixture was evaporated in vacuo. The residue was azeotroped with toluene (3×20 mL). Purification was by preparative HPLC (Phenomenex Gemini®, Gradient: 5-40% acetonitrile in 0.1% aqueous formic acid). The fractions containing product were combined and freeze-dried to give the titled compound as a white solid. Yield 0.12 g.

m/z 639 (M+H)$^+$ $^1$H NMR (400 MHz, D$_6$-DMSO) δ 8.13 (s, 1H), 7.45 (s, 1H), 7.22 (d, J=8.34 Hz, 2H), 6.88-6.78 (m, 4H), 6.66 (d, J=8.27 Hz, 1H), 4.65 (m, 1H), 4.09-4.00 (m, 2H), 3.85-3.77

(m, 3H), 3.67-3.60 (m, 4H), 3.56-3.47 (m, 2H), 2.81-2.63 (m, 5H), 2.49-2.36 (m, 5H), 1.77-1.67 (m, 2H), 1.59-1.37 (m, 2H). Five exchangeable protons not observed.

EXAMPLE 105

(R)-4-Hydroxy-7-(1-hydroxy-2-(9-(4-(5-methylthiophene-3-carbonyl)-1-oxa-4,9-diazaspiro[5.5]undecan-9-yl)nonylamino)ethyl)benzo[d]thiazol-2(3H)-one formate

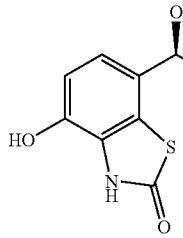
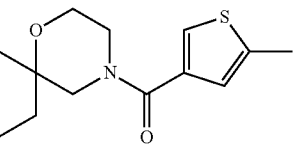

ample 104, step b) (0.28 g) and triethylamine (0.278 mL) in acetonitrile (7 mL). The resulting mixture was stirred at 60° C. overnight. The reaction mixture was evaporated in vacuo and the residue was taken up into DCM (30 mL), washed with brine (2×15 mL), dried over sodium sulphate, filtered and evaporated in vacuo. Purification was by silica gel chromatography eluting with 0-10% methanol in dichloromethane to give the subtitled compound as a white solid. Yield 0.3 g.

$^1$H NMR (400 MHz, D$_6$-DMSO) δ 7.54 (s, 1H), 6.91 (s, 1H), 4.32 (t, J=5.1 Hz, 1H), 3.66 (s, 2H), 3.52 (s, 2H), 3.41-3.33 (m, 3H), 2.95 (s, 4H), 2.45 (d, J=1.1 Hz, 3H), 2.02 (s, 3H), 1.64 (s, 4H), 1.40 (t, J=6.8 Hz, 2H), 1.26 (s, 11H). One exchangeable proton not observed.

b) (R)-4-Hydroxy-7-(1-hydroxy-2-(9-(4-(5-methylthiophene-3-carbonyl)-1-oxa-4,9-diazaspiro[5.5]undecan-9-yl)nonylamino)ethyl)benzo[d]thiazol-2(3H)-one formate

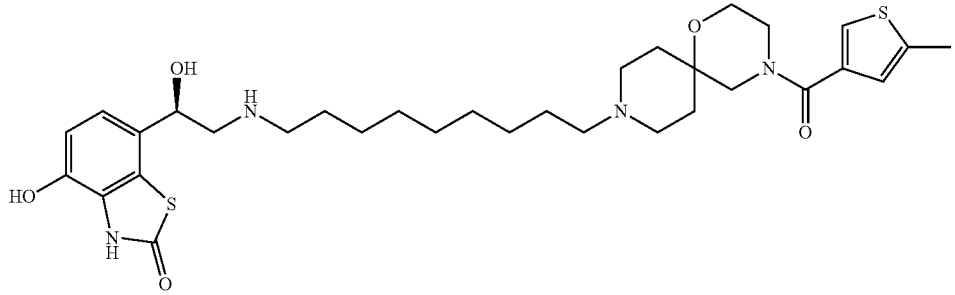 [SMILES: Cc1cc(C(=O)N2CCOC3(CCN(CCCCCCCCCNC[C@H](O)c4ccc(O)c5[nH]c(=O)sc45)CC3)C2)cs1]

a) (9-(9-Hydroxynonyl)-1-oxa-4,9-diazaspiro[5.5]undecan-4-yl)(5-methylthiophen-3-yl)methanone

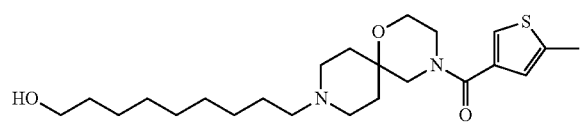 [SMILES: Cc1cc(C(=O)N2CCOC3(CCN(CCCCCCCCCO)CC3)C2)cs1]

A solution of 9-bromo-1-nonanol (0.335 g) in acetonitrile (3 mL) was added to a solution of (5-methylthiophen-3-yl)(1-oxa-4,9-diazaspiro[5.5]undecan-4-yl)methanone (ex- Trifluoroacetic acid (0.055 mL) was added to a solution of (9-(9-hydroxynonyl)-1-oxa-4,9-diazaspiro[5.5]undecan-4-yl)(5-methylthiophen-3-yl)methanone (example 105, step a) (0.3 g) in DCM (15 mL) at 0° C. under argon. The resulting mixture was stirred for 5 min and then Dess-Martin periodinane (0.45 g) was added. The mixture was stirred at room temperature for 1 h then quenched by addition of saturated sodium thiosulfate solution (14 mL) and saturated sodium bicarbonate solution (14 mL) then ethyl acetate (30 mL) was added and the mixture stirred for 5 min. The layers were separated and the aqueous layer was extracted with ethyl acetate (2×40 mL). Acetic acid (0.159 mL) was added to the combined organic layers which were dried over magnesium sulphate, filtered and evaporated in vacuo. The yellow oil was dissolved in dry methanol (15 mL). (R)-7-(2-Amino-1-hydroxyethyl)-4-hydroxybenzo[d]thiazol-2(3H)-one hydrochloride (WO2007027134, example 1, step d) (0.28 g) was added, followed by acetic acid (0.061 mL) and 3 Å molecular sieves. After stirring for min at room temperature, the reaction mixture was cooled to 0° C. Sodium triacetoxyborohydride (0.15 g) was added and the mixture stirred at room temperature for 18 h. The reaction mixture was filtered and the solvent was evaporated in vacuo. The residue was purified by preparative HPLC (Phenomenex Gemini®, Gradient: 5-40% acetonitrile in 0.1% aqueous formic acid). The fractions containing product were combined and freeze-dried to give the titled compound as a white solid. Yield 0.07 g.

m/z 631 (M+H)+

$^1$H NMR (400 MHz, D$_6$-DMSO) δ 8.24 (s, 1H), 7.45 (s, 1H), 6.85-6.80 (m, 2H), 6.67 (d, J=8.3 Hz, 1H), 4.67 (t, J=6.5 Hz, 1H), 3.63-3.21 (m, 6H), 2.75 (d, J=6.5 Hz, 2H), 2.63 (t, J=7.3 Hz, 2H), 2.40 (d, J=1.1 Hz, 3H), 2.38-2.16 (m, 6H), 1.70-1.61 (m, 2H), 1.47-1.29 (m, 6H), 1.19 (s, 10H). Five exchangeable protons not observed.

EXAMPLE 106

(R)-7-(2-(4-(2-(4-(Benzo[d]thiazole-2-carbonyl)-1-oxa-4,9-diazaspiro[5.5]undecan-9-yl)ethoxy)benzylamino)-1-hydroxyethyl)-4-hydroxybenzo[d]thiazol-2(3H)-one formate

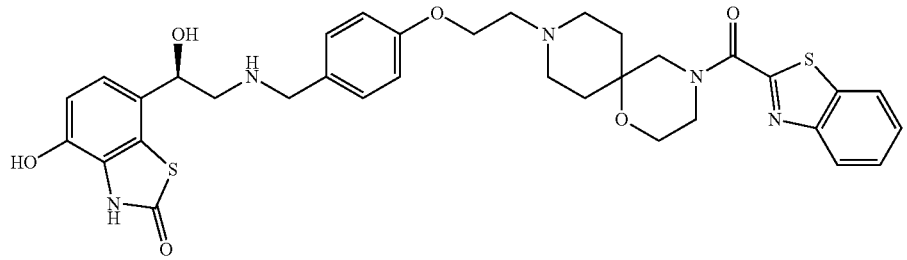 [SMILES: O=C(c1nc2ccccc2s1)N1CCOC2(CCN(CCOc3ccc(CNC[C@H](O)c4ccc(O)c5[nH]c(=O)sc45)cc3)CC2)C1]

a) tert-Butyl 4-(benzo[d]thiazole-2-carbonyl)-1-oxa-4,9-diazaspiro[5.5]undecane-9-carboxylate

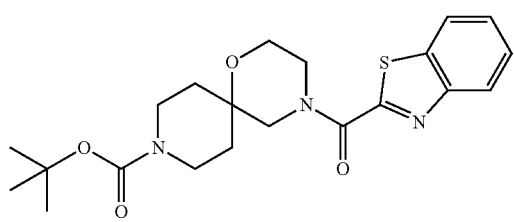 [SMILES: CC(C)(C)OC(=O)N1CCC2(CC1)CN(C(=O)c1nc3ccccc3s1)CCO2]

O-(7-Azabenzotriazol-1-yl)-N,N,N',N'-tetramethyluronium hexafluorophosphate (1.45 g) was added to a solution of tert-butyl 1-oxa-4,9-diazaspiro[5.5]undecane-9-carboxylate hydrochloride (WuXi PharmaTech) (0.8 g), 1,3-benzothiazol-2-carboxylic acid (0.588 g) and triethylamine (1.51 mL) in DMF (15 mL) and the resulting mixture stirred for 16 h.

The volume of DMF was reduced in vacuo and the reaction mixture was partitioned between water (30 mL) and ethyl acetate (30 mL). The organic layer was washed with water (30 mL) and brine (30 mL), dried over magnesium sulphate, filtered and evaporated in vacuo. Purification was by silica gel chromatography eluting with 0-10% methanol in dichloromethane to give the subtitled compound as a yellow oil. Yield 0.83 g.

$^1$H NMR (400 MHz, D$_6$-DMSO) δ 8.23-8.09 (m, 2H), 7.63-7.52 (m, 2H), 4.34 (s, 1H), 4.20 (s, 1H), 3.78 (s, 2H), 3.71 (s, 1H), 3.64-3.51 (m, 3H), 3.08 (s, 2H), 1.76 (d, J=13.7 Hz, 2H), 1.55-1.34 (m, 11H).

b) Benzo[d]thiazol-2-yl(1-oxa-4,9-diazaspiro[5.5]undecan-4-yl)methanone

Trifluoroacetic acid (5 mL) was added to a solution of tert-butyl 4-(benzo[d]thiazole-2-carbonyl)-1-oxa-4,9-diazaspiro[5.5]undecane-9-carboxylate (example 106, step a) (0.83 g) in DCM (15 mL) and the resulting mixture was stirred for 25 minutes. The solvent was evaporated in vacuo. The residue was dissolved in DCM:methanol (1:1) (5 mL) and applied to a SCX cartridge pre-wetted with DCM:methanol (1:1). The cartridge was washed with methanol (60 mL) and eluted with 2M ammonia in methanol solution (40 mL). The eluent was evaporated in vacuo to give the subtitled compound as a colourless oil. Yield 0.57 g.

$^1$H NMR (400 MHz, D$_6$-DMSO) δ 8.18-8.13 (m, 1H), 8.10-8.07 (m, 1H), 7.60-7.50 (m, 2H), 4.25 (t, J=4.8 Hz, 1H), 4.17 (s, 1H), 4.04 (s, 1H), 3.70 (s, 2H), 3.65 (d, J=5.5 Hz, 1H), 3.56 (s, 1H), 2.73-2.46 (m, 4H), 1.62-1.54 (m, 2H), 1.50-1.36 (m, 2H).

c) (R)-tert-Butyl 4-(2-(4-(benzo[d]thiazole-2-carbonyl)-1-oxa-4,9-diazaspiro[5.5]undecan-9-yl)ethoxy)benzyl(2-hydroxy-2-(4-hydroxy-2-oxo-2,3-dihydrobenzo[d]thiazol-7-yl)ethyl)carbamate

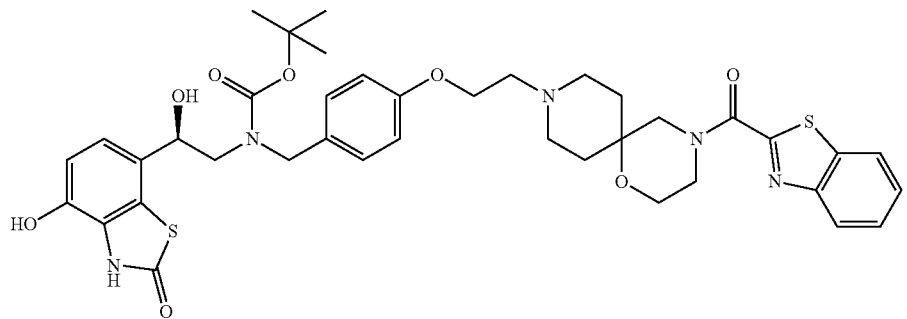 [SMILES: CC(C)(C)OC(=O)N(Cc1ccc(OCCN2CCC3(CC2)CN(C(=O)c2nc4ccccc4s2)CCO3)cc1)C[C@H](O)c1ccc(O)c2[nH]c(=O)sc12]

Triethylamine (0.25 mL) was added to a solution of benzo[d]thiazol-2-yl(1-oxa-4,9-diazaspiro[5.5]undecan-4-yl)methanone (example 106, step b) (0.22 g) in acetonitrile (2.5 mL). This solution was added to a solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 108, step c) (0.5 g) in acetonitrile (2.5 mL). The resulting mixture was heated at 80° C. for 48 hours. The reaction mixture was evaporated in vacuo. Purification was by silica gel chromatography eluting with 0-10% methanol in dichloromethane to give the subtitled compound as a cream foam. Yield 0.34 g.

$^1$H NMR (400 MHz, D$_6$-DMSO) δ 11.49 (s, 1H), 9.93 (s, 1H), 8.21 (d, J=7.5 Hz, 1H), 8.14 (d, J=7.7 Hz, 1H), 7.64-7.56 (m, 2H), 7.07 (s, 2H), 6.93-6.79 (m, 2H), 6.78-6.67 (m, 2H), 5.68 (s, 1H), 4.73 (s, 1H), 4.35-4.22 (m, 3H), 4.07 (s, 4H), 3.76 (s, 2H), 3.70 (s, 1H), 3.62 (s, 1H), 3.17 (s, 6H), 2.67 (s, 2H), 1.77 (s, 1H), 1.62 (s, 1H), 1.35 (s, 3H), 1.27 (s, 6H). One exchangeable proton not observed.

d) (R)-7-(2-(4-(2-(4-(Benzo[d]thiazole-2-carbonyl)-1-oxa-4,9-diazaspiro[5.5]undecan-9-yl)ethoxy)benzylamino)-1-hydroxyethyl)-4-hydroxybenzo[d]thiazol-2(3H)-one formate Trifluoroacetic acid (1.25 mL) was added to a solution of (R)-tert-butyl 4-(2-(4-(benzo[d]thiazole-2-carbonyl)-1-oxa-4,9-diazaspiro[5.5]undecan-9-yl)ethoxy)benzyl(2-hydroxy-2-(4-hydroxy-2-oxo-2,3-dihydrobenzo[d]thiazol-7-yl)ethyl)carbamate (example 106, step c) (0.33 g) in DCM (4 mL) and the resulting mixture stirred for 10 minutes. Toluene (20 mL) was added and the mixture was evaporated in vacuo. The residue was azeotroped with toluene (3×20 mL). Purification was by preparative HPLC (Phenomenex Gemini®, Gradient: 5-40% acetonitrile in 0.1% aqueous formic acid). The fractions containing product were combined and freeze-dried to give the titled compound as a white solid. Yield 0.096 g.

m/z 676 (M+H)$^+$ $^1$H NMR (400 MHz, D$_4$-MeOH) δ 8.44 (s, 1H); 8.09-8.00 (m, 2H); 7.58-7.48 (m, 2H); 7.37 (t, J=6.6 Hz, 2H); 7.00 (t, J=9.4 Hz, 2H); 6.91 (d, J=8.3 Hz, 1H); 6.71 (d, J=8.3 Hz, 1H); 4.93-4.88 (m, 1H); 4.43-3.38 (m, 1H); 4.37-4.34 (s, 1H); 4.27-4.20 (m, 2H); 4.14 (s, 2H); 3.87-3.82 (m, 2H); 3.81-3.76 (m, 1H); 3.71 (s, 1H); 3.20-3.11 (m, 2H); 3.12-3.01 (m, 4H); 2.96-2.82 (m, 2H); 2.10-2.01 (m, 2H); 1.88-1.76 (m, 2H). Five exchangeable protons not observed.

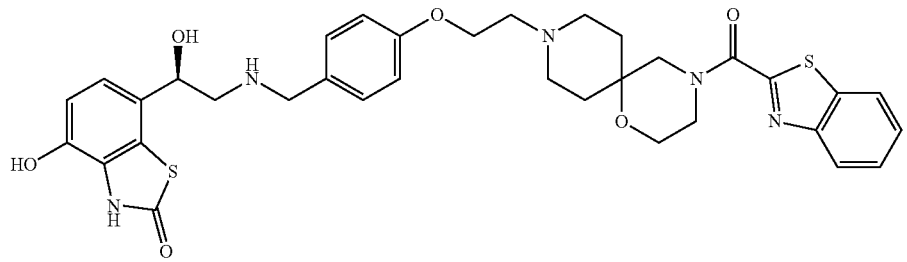 [SMILES: O=C(c1nc2ccccc2s1)N1CCOC2(CCN(CCOc3ccc(CNC[C@H](O)c4ccc(O)c5[nH]c(=O)sc45)cc3)CC2)C1]

EXAMPLE 107

(R)-7-(2-(9-(4-(Benzo[d]thiazole-2-carbonyl)-1-oxa-4,9-diazaspiro[5.5]undecan-9-yl)nonylamino)-1-hydroxyethyl)-4-hydroxybenzo[d]thiazol-2(3H)-one formate

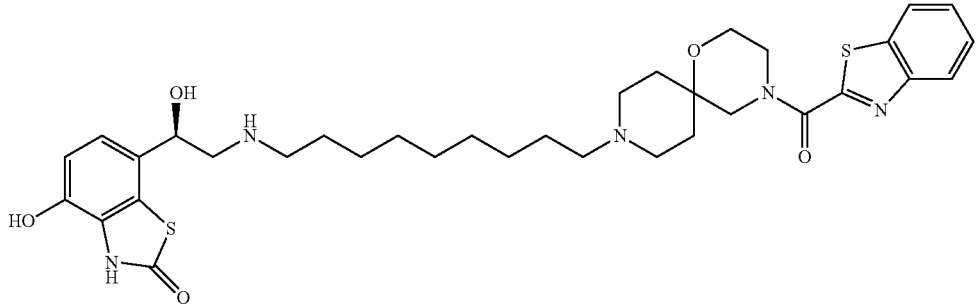 [SMILES: O=C(c1nc2ccccc2s1)N1CCOC2(CCN(CCCCCCCCCNC[C@H](O)c3ccc(O)c4[nH]c(=O)sc34)CC2)C1]

a) Benzo[d]thiazol-2-yl(9-(9-hydroxynonyl)-1-oxa-4,9-diaza spiro[5.5]undecan-4-yl)methanone

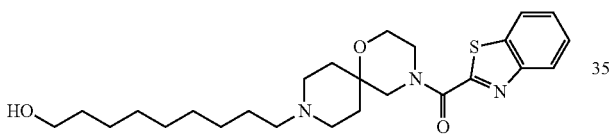

A solution of 9-bromo-1-nonanol (0.335 g) in acetonitrile (3 mL) was added to a solution of benzo[d]thiazol-2-yl(1-oxa-4,9-diazaspiro[5.5]undecan-4-yl)methanone (example 106, step b) (0.34 g) and triethylamine (0.278 mL) in acetonitrile (7 mL). The resulting mixture was stirred at 60° C. overnight. The reaction mixture was evaporated in vacuo and the residue was taken up into DCM (30 mL), washed with brine (2×15 mL), dried over sodium sulphate, filtered and evaporated in vacuo. Purification was by silica gel chromatography eluting with 0-10% methanol in dichloromethane to give the subtitled compound as a white solid. Yield 0.34 g.

$^1$H NMR (400 MHz, D$_6$-DMSO) δ 8.22 (d, J=7.7 Hz, 1H), 8.14 (d, J=7.9 Hz, 1H), 7.65-7.56 (m, 2H), 4.37 (s, 1H), 4.31 (t, J=5.1 Hz, 1H), 4.27 (s, 1H), 3.80 (s, 2H), 3.72 (s, 1H), 3.63 (s, 1H), 3.41-3.33 (m, 2H), 2.99 (s, 4H), 2.10 (s, 2H), 1.86 (s, 2H), 1.64 (s, 2H), 1.40 (s, 3H), 1.27 (s, 11H).

b) (R)-7-(2-(9-(4-(Benzo[d]thiazole-2-carbonyl)-1-oxa-4,9-diazaspiro[5.5]undecan-9-yl)nonylamino)-1-hydroxyethyl)-4-hydroxybenzo[d]thiazol-2(3H)-one formate

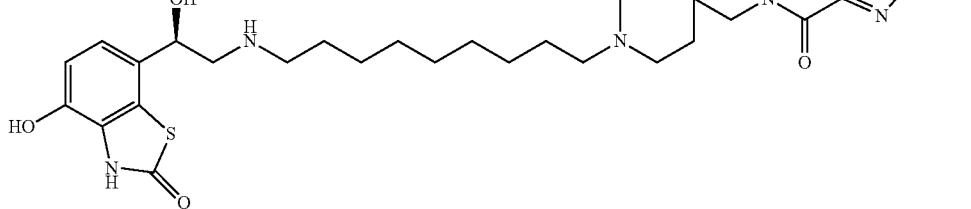

Trifluoroacetic acid (0.056 mL) was added to a solution of benzo[d]thiazol-2-yl(9-(9-hydroxynonyl)-1-oxa-4,9-diazaspiro[5.5]undecan-4-yl)methanone (example 107, step a) (0.33 g) in DCM (15 mL) at 0° C. under argon. The resulting mixture was stirred for 5 min and then Dess-Martin periodinane (0.46 g) was added. The mixture was stirred at room temperature for 1 h. Saturated sodium thiosulfate solution (14 mL), saturated sodium bicarbonate solution (14 mL) and EtOAc (30 mL) were added and the mixture was stirred for 5 min. The layers were separated and the aqueous layer was extracted with EtOAc (2×40 mL). Acetic acid (0.159 mL) was added to the combined organic layers, which were dried over magnesium sulfate, filtered and evaporated in vacuo. The yellow oil was dissolved in dry MeOH (15 mL). (R)-7-(2-amino-1-hydroxyethyl)-4-hydroxybenzo[d]thiazol-2(3H)-one hydrochloride (WO2007027134, example 1, step d) (0.28 g) was added, followed by acetic acid (0.062 mL) and 3 Å molecular sieves. After stirring for 5 min at room temperature, the reaction mixture was cooled to 0° C. Sodium triacetoxyborohydride (0.15 g) was added and the mixture was stirred at room temperature for 18 h. The reaction mixture was filtered and the solvent was evaporated in vacuo. The residue was purified by preparative HPLC (Phenomenex Gemini®, Gradient: 5-40% acetonitrile in 0.1% aqueous formic acid). The fractions containing product were combined and freeze-dried to give the subtitled compound as a white solid. Yield 0.14 g.

m/z 668 (M+H)$^+$ $^1$H NMR (400 MHz, D$_6$-DMSO) δ 8.23 (s, 1H), 8.17-8.14 (m, 1H), 8.09 (d, J=7.9 Hz, 1H), 7.60-7.49 (m, 2H), 6.84 (d, J=8.3 Hz, 1H), 6.68 (d, J=8.29 Hz, 1H), 4.74-4.64 (m, 1H), 4.29-4.24 (m, 1H), 4.20 (s, 1H), 3.72-3.62 (m, 3H), 3.56 (s, 1H), 2.79 (d, J=5.5 Hz, 2H), 2.69-2.62 (m, 2H), 2.42-2.13 (m, 6H), 1.74-1.64 (m, 2H), 1.63-1.30 (m, 6H), 1.19 (d, J=9.6 Hz, 10H). Five exchangeable protons not observed.

EXAMPLE 108

(R)-4-Hydroxy-7-(1-hydroxy-2-(4-(2-(4-(2-isopropylthiazole-4-carbonyl)-1-oxa-4,9-diazaspiro[5.5]undecan-9-yl)ethoxy)benzylamino)ethyl)benzo[d]thiazol-2(3H)-one formate

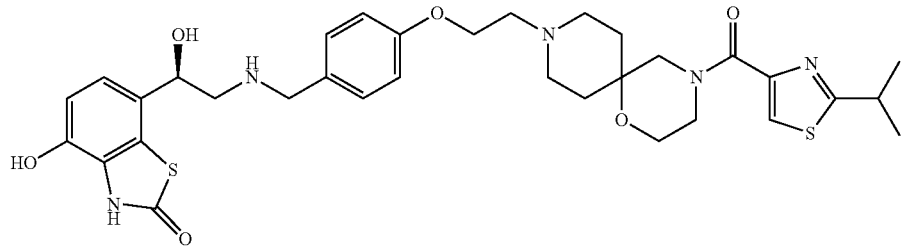 [SMILES: CC(C)c1nc(C(=O)N2CCOC3(CCN(CCOc4ccc(CNC[C@H](O)c5ccc(O)c6[nH]c(=O)sc56)cc4)CC3)C2)cs1]

a) 4-(2-Hydroxyethoxy)benzaldehyde

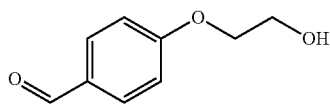 [SMILES: O=Cc1ccc(OCCO)cc1]

2-Bromoethanol (5.8 mL) and potassium carbonate (11.3 g) were successively added to a solution of 4-hydroxybenzaldehyde (5.0 g) in MeCN (100 mL). The resulting mixture was stirred and heated at reflux for 3 days under argon. The reaction mixture was cooled to RT and partitioned between EtOAc (100 mL) and 1M aqueous NaOH solution (100 mL). The organic layer was washed with brine (100 mL). The aqueous layers were combined and extracted with EtOAc (50 mL). The organic layers were combined, dried over sodium sulphate, filtered and evaporated in vacuo to give the subtitled compound as a yellow oil. Yield 6.4 g.

$^1$H NMR (400 MHz, CDCl$_3$) δ 9.90 (s, 1H), 7.87-7.81 (m, 2H), 7.06-6.98 (m, 2H), 4.18 (dd, J=5.0, 4.0 Hz, 2H), 4.04-3.97 (m, 2H), 2.18-1.96 (m, 1H).

b) 2-(4-Formylphenoxy)ethyl methanesulfonate

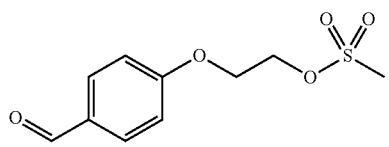 [SMILES: CS(=O)(=O)OCCOc1ccc(C=O)cc1]

Methanesulfonylchloride (3.3 mL) was added dropwise over 5 min to a solution of 4-(2-hydroxyethoxy)benzaldehyde (example 108, step a) (6.4 g) and triethylamine (6.4 mL) in DCM (30 mL) at 0° C. under argon. The resulting mixture was stirred at 0° C. for 10 min and then at RT for 1 h. The reaction mixture was washed with brine (2×30 mL), dried over sodium sulphate, filtered and evaporated in vacuo. The residue was purified by silica gel chromatography eluting with 40-50% EtOAc in petroleum ether (40-60° C.) to give the subtitled compound as a viscous yellow oil. Yield 8.87 g.

$^1$H NMR (400 MHz, CDCl$_3$) δ 9.92-9.87 (m, 1H), 7.89-7.81 (m, 2H), 7.05-6.98 (m, 2H), 4.62-4.58 (m, 2H), 4.36-4.32 (m, 2H), 3.10 (s, 3H).

c) (R)-2-(4-((tert-Butoxycarbonyl(2-hydroxy-2-(4-hydroxy-2-oxo-2,3-dihydrobenzo[d]thiazol-7-yl)ethyl)amino)methyl)phenoxy)ethyl methanesulfonate

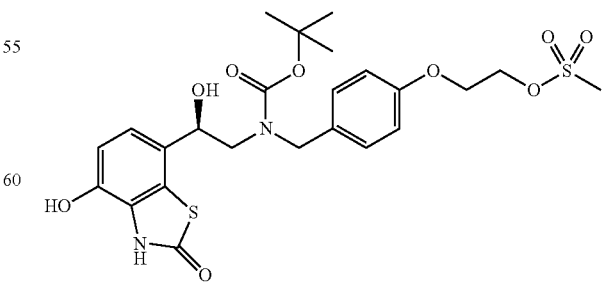

A mixture of 2-(4-formylphenoxy)ethyl methanesulfonate (example 108, step b) (1.7 g), (R)-7-(2-amino-1-hydroxyethyl)-4-hydroxybenzo[d]thiazol-2(3H)-one hydrochloride (WO2007027134, example 1, step d) (2.0 g) and acetic acid (0.44 mL) in dry DMF (40 mL) was stirred at RT for 15 min in the presence of 4 Å molecular sieves. The reaction mixture was cooled to 0° C. and sodium triacetoxyborohydride (2.2 g) was added in 4 portions at 2 min intervals. The resulting mixture was stirred at RT for 1 h. Di-tert-butyl dicarbonate (1.8 g) was added to the reaction mixture which was stirred for 2 h. Saturated sodium bicarbonate solution (100 mL) and EtOAc (100 mL) were added and the mixture was stirred for 5 min. The layers were separated and the aqueous layer was extracted with EtOAc (×4). The combined organic layers washed with brine (×2), dried over sodium sulphate, filtered and evaporated in vacuo. The yellow solid was purified by silica gel chromatography eluting with 0-5% MeOH in DCM to give the subtitled compound as a green solid. Yield 0.135 g.

m/z 768 (M+H)$^+$ $^1$H NMR (400 MHz, CDCl$_3$) δ 7.86 (s, 1H), 6.83 (br s, 2H), 6.71-6.46 (m, 4H), 4.78 (br s, 1H), 4.46-2.51 (m, 19H), 1.90 (br s, 4H), 1.53 (s, 9H), 1.39 (s, 3H), 1.29 (s, 3H). Three exchangeable protons not observed.

e) (R)-4-Hydroxy-7-(1-hydroxy-2-(4-(2-(4-(2-iso-propylthiazole-4-carbonyl)-1-oxa-4,9-diazaspiro[5.5]undecan-9-yl)ethoxy)benzylamino)ethyl)benzo[d]thiazol-2(3H)-one formate

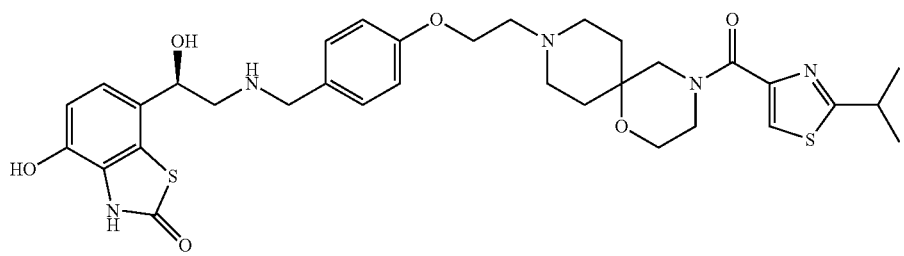

were dried over sodium sulphate, filtered and evaporated in vacuo. The residue was purified by silica gel chromatography eluting with 0-80% EtOAc in petroleum ether (40-60° C.) to give the subtitled compound as a yellow oil. Yield 2.25 g.

$^1$H NMR (400 MHz, CDCl$_3$) δ 7.05 (d, J=7.6 Hz, 2H), 6.80 (d, J=8.0 Hz, 3H), 6.70 (d, J=8.0 Hz, 1H), 4.81 (bs, 1H), 4.54 (t, J=4.3 Hz, 2H), 4.34-4.26 (m, 1H), 4.24-4.08 (m, 3H), 3.57-3.42 (m, 1H), 3.33-3.23 (m, 1H), 3.07 (s, 3H), 1.49 (s, 9H). Three exchangeable protons not observed.

d) (R)-tert-Butyl 2-hydroxy-2-(4-hydroxy-2-oxo-2,3-dihydrobenzo[d]thiazol-7-yl)ethyl(4-(2-(4-(2-isopropylthiazole-4-carbonyl)-1-oxa-4,9-diazaspiro[5.5]undecan-9-yl)ethoxy)benzyl)carbamate Trifluoroacetic acid (0.7 mL) was added to a solution of (R)-tert-butyl 2-hydroxy-2-(4-hydroxy-2-oxo-2,3-dihydrobenzo[d]thiazol-7-yl)ethyl(4-(2-(4-(2-isopropylthiazole-4-carbonyl)-1-oxa-4,9-diazaspiro[5.5]undecan-9-yl)ethoxy)benzyl)carbamate (example 108, step d) (0.122 g) in DCM (1.5 mL). The resulting mixture was stirred at RT for 10 min. Toluene (15 mL) was added and the reaction mixture was evaporated in vacuo. The residue was azeotroped twice with MeCN. The viscous yellow residue was purified by HPLC (Phenomenex Gemini, Gradient: 5-40% acetonitrile in 0.1% aqueous formic acid). The fractions containing product were combined and freeze dried to give the titled compound as a white solid. Yield 0.052 g.

m/z 668 (M+H)$^+$

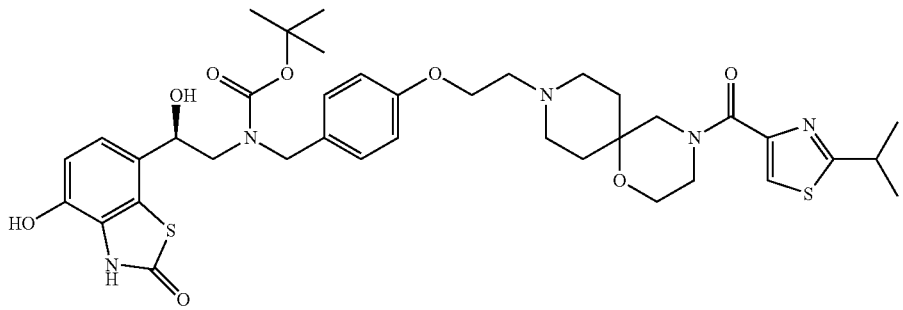 [SMILES: CC(C)c1nc(C(=O)N2CCOC3(CCN(CCOc4ccc(CN(C[C@H](O)c5ccc(O)c6[nH]c(=O)sc56)C(=O)OC(C)(C)C)cc4)CC3)C2)cs1]

A solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 108, step c) (0.295 g) in MeCN (1.1 mL) was added dropwise to a solution of (2-isopropylthiazol-4-yl)(1-oxa-4,9-diazaspiro[5.5]undecan-4-yl)methanone trifluoroacetate (example 22, step b) (0.150 g) and triethylamine (0.11 mL) in MeCN (1.1 mL) at RT under argon. The resulting mixture was stirred at 60° C. under argon for 34 h. After cooling to RT the solvent was removed in vacuo. The residue was taken up in DCM, $^1$H NMR (400 MHz, D$_4$-MeOH) δ 8.47 (s, 1H), 7.87 (s, 1H), 7.36 (d, J=8.19 Hz, 2H), 6.98 (s, 2H), 6.91 (d, J=8.36 Hz, 1H), 6.71 (d, J=8.30 Hz, 1H), 4.90 (dd, J=9.4, 4.1 Hz, 1H), 4.18 (s, 2H), 4.11 (s, 2H), 3.75 (s, 5H), 3.63 (s, 1H), 3.40 (m, 1H), 3.19-2.80 (m, 8H), 1.95 (s, 2H), 1.75 (s, 1H), 1.65 (s, 1H), 1.38 (d, J=6.9 Hz, 6H). Five exchangeable protons not observed.

EXAMPLE 109

(R)-4-Hydroxy-7-(1-hydroxy-2-(9-(4-(2-isopropy-lthiazole-4-carbonyl)-1-oxa-4,9-diazaspiro[5.5]unde-can-9-yl)nonylamino)ethyl)benzo[d]thiazol-2(3H)-one formate

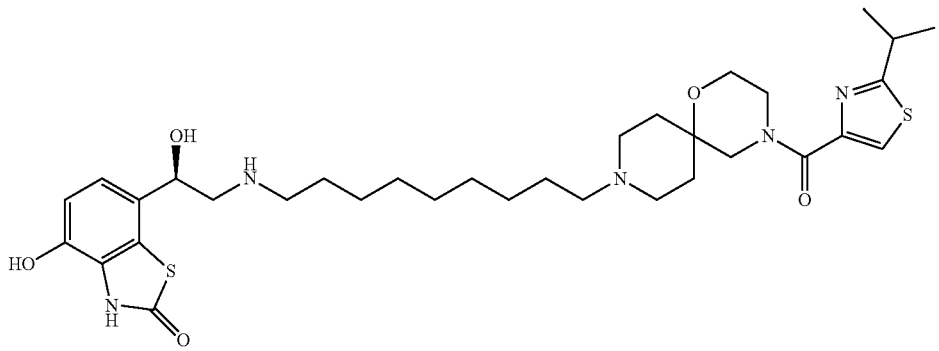 [SMILES: CC(C)c1nc(C(=O)N2CCOC3(CCN(CCCCCCCCCNC[C@H](O)c4ccc(O)c5[nH]c(=O)sc45)CC3)C2)cs1]

a) (9-(9-Hydroxynonyl)-1-oxa-4,9-diazaspiro[5.5]undecan-4-yl)(2-isopropylthiazol-4-yl)methanone

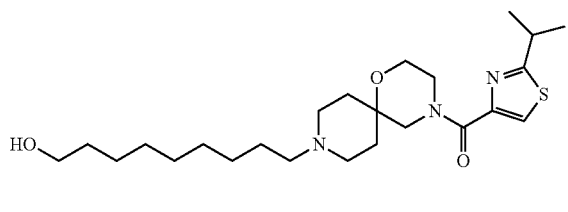 [SMILES: CC(C)c1nc(C(=O)N2CCOC3(CCN(CCCCCCCCCO)CC3)C2)cs1]

b) (R)-4-Hydroxy-7-(1-hydroxy-2-(9-(4-(2-isopropy-lthiazole-4-carbonyl)-1-oxa-4,9-diazaspiro[5.5]unde-can-9-yl)nonylamino)ethyl)benzo[d]thiazol-2(3H)-one formate

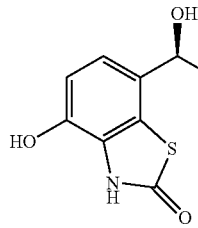

A solution of 9-bromo-1-nonanol (0.316 g) in MeCN (3 mL) was added to solution of (2-isopropylthiazol-4-yl)(1-oxa-4,9-diazaspiro[5.5]undecan-4-yl)methanone trifluoroacetate (example 22, step b) (0.40 g) and triethylamine (0.395 mL) in MeCN (7 mL). The resulting mixture was stirred at 60° C. under argon for 16 h. After cooling to RT the solvent was removed in vacuo. The residue was taken up in DCM, washed with brine (×2), dried over sodium sulphate, filtered and evaporated in vacuo. The orange solid was purified by silica gel chromatography eluting with 0-10% MeOH in DCM to give the subtitled compound as an off-white solid. Yield 0.325 g.

$^1$H NMR (400 MHz, CDCl$_3$) δ 7.87 (s, 1H), 3.97 (s, 2H), 3.76 (s, 3H), 3.63 (t, J=6.6 Hz, 2H), 3.36 (s, 3H), 2.92 (s, 4H), 2.25 (s, 2H), 2.14-2.03 (m, 2H), 1.84 (s, 2H), 1.63 (s, 2H), 1.60-1.50 (m, 2H), 1.42 (d, J=6.8 Hz, 6H), 1.42-1.21 (m, 10H).

Trifluoroacetic acid (0.027 mL) was added to a solution of (9-(9-hydroxynonyl)-1-oxa-4,9-diazaspiro[5.5]undecan-4-yl)(2-isopropylthiazol-4-yl)methanone (example 109, step a) (0.16 g) in DCM (6.3 mL) at 0° C. The resulting mixture was stirred for 5 min and then Dess-Martin periodinane (0.225 g) was added. The mixture was stirred at RT for 45 min. Saturated sodium thiosulfate solution (6 mL), saturated sodium bicarbonate solution (6 mL) and EtOAc (36 mL) were added and the mixture was stirred for 5 min. The layers were separated and the aqueous layer was extracted with EtOAc (2×40 mL). The combined organic layers were washed with saturated sodium bicarbonate solution (40 mL), treated with acetic acid (0.067 mL), dried over sodium sulphate, filtered and evaporated in vacuo. The viscous orange oil was dissolved in dry MeOH (6.6 mL) and (R)-7-(2-amino-1-hydroxyethyl)-4-hydroxybenzo[d]thiazol-2(3H)-one hydrochloride (WO2007027134, example 1, step d) (0.138 g) was added, followed by acetic acid (0.03 mL) and 3 Å molecular sieves. After stirring for 5 min at RT, the reaction mixture was cooled to 0° C. and sodium triacetoxyborohydride (0.075 g) was added. The mixture was stirred at RT for 1 h then another portion of sodium triacetoxyborohydride (0.075 g) was added and the mixture was stirred at RT for another 16 h. The reaction mixture was filtered and the solvent was evaporated in vacuo. The residue was purified by HPLC (Phenomenex Gemini®, Gradient: 5-40% acetonitrile in 0.1% aqueous formic acid). The fractions containing product were combined and freeze-dried to give the titled compound as a white solid. Yield 0.060 g.

m/z 660 (M+H)$^+$ $^1$H NMR (400 MHz, D$_4$-MeOH) δ 8.52 (s, 1H), 7.86 (s, 1H), 6.94 (d, J=8.4 Hz, 1H), 6.52 (d, J=8.3 Hz, 1H), 4.98-4.89 (m, 1H), 3.90-3.58 (m, 6H), 3.37-3.25 (m, 1H), 3.15-3.02 (m, 3H), 3.01-2.93 (m, 3H), 2.91-2.65 (m, 4H), 2.10-1.96 (m, 2H), 1.83-1.54 (m, 6H), 1.41-1.28 (m, 16H). Five exchangeable protons not observed.

A solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 108, step c) (0.426 g) in MeCN (2 mL) was added dropwise to a solution of (5-methylthiophen-2-yl)(1-oxa-4,9-diazaspiro[5.5]undecan-4-yl)methanone trifluoroacetate (example 9, step b) (0.154 g) and triethylamine (0.15 mL) in MeCN (5 mL) at RT under argon. The resulting mixture was stirred at 60° C. under argon for 16 h, and then at 80° C. for an additional 3 h. After cooling to RT the solvent was removed in vacuo. The residue was taken up in DCM, washed with brine and water (×2), dried over sodium sulphate, filtered and evaporated in vacuo. The brown solid was purified by silica gel chromatography eluting with 0-10% MeOH in DCM to give the subtitled compound as a yellow solid. Yield 0.246 g.

$^1$H NMR (400 MHz, CDCl$_3$) δ 7.11 (d, J=3.6 Hz, 1H), 6.89 (s, 2H), 6.70-6.59 (m, 4H), 6.51 (d, J=8.2 Hz, 1H), 4.76 (s, 1H), 4.20-4.10 (m, 4H), 3.74 (s, 4H), 3.59-3.44 (m, 4H), 2.93-2.77 (m, 4H), 2.61 (s, 2H), 2.47 (s, 3H), 1.93-1.84 (m, 2H), 1.74-1.60 (m, 2H), 1.52 (s, 9H). Three exchangeable protons not observed.

EXAMPLE 110

(R)-4-Hydroxy-7-(1-hydroxy-2-(4-(2-(4-(5-methylthiophene-2-carbonyl)-1-oxa-4,9-diazaspiro[5.5]undecan-9-yl)ethoxy)benzylamino)ethyl)benzo[d]thiazol-2(3H)-one formate

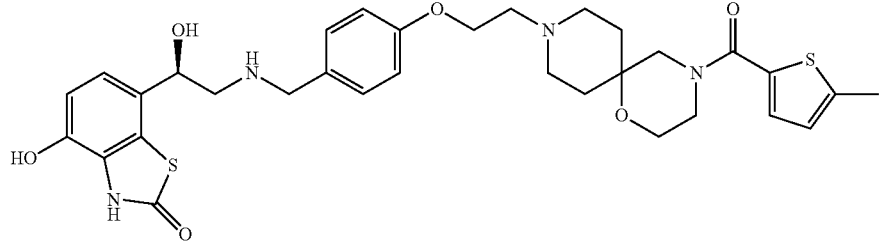 [SMILES: Cc1ccc(C(=O)N2CCOC3(CCN(CCOc4ccc(CNC[C@H](O)c5ccc(O)c6[nH]c(=O)sc56)cc4)CC3)C2)s1]

a) (R)-tert-Butyl 2-hydroxy-2-(4-hydroxy-2-oxo-2,3-dihydrobenzo[d]thiazol-7-yl)ethyl(4-(2-(4-(5-methylthiophene-2-carbonyl)-1-oxa-4,9-diazaspiro[5.5]undecan-9-yl)ethoxy)benzyl)carbamate

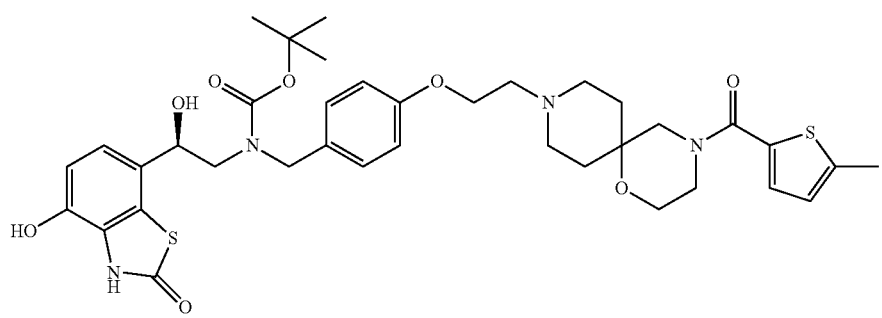 [SMILES: Cc1ccc(C(=O)N2CCOC3(CCN(CCOc4ccc(CN(C[C@H](O)c5ccc(O)c6[nH]c(=O)sc56)C(=O)OC(C)(C)C)cc4)CC3)C2)s1]

b) (R)-4-Hydroxy-7-(1-hydroxy-2-(4-(2-(4-(5-methylthiophene-2-carbonyl)-1-oxa-4,9-diazaspiro[5.5]undecan-9-yl)ethoxy)benzylamino)ethyl)benzo[d]thiazol-2(3H)-one formate

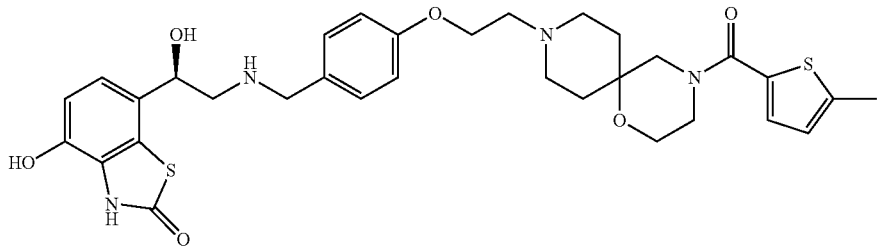 [SMILES: Cc1ccc(C(=O)N2CCOC3(CCN(CCOc4ccc(CNC[C@H](O)c5ccc(O)c6[nH]c(=O)sc56)cc4)CC3)C2)s1]

Trifluoroacetic acid (0.75 mL) was added to a solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 110, step a) (0.243 g) in DCM (3 mL). The resulting mixture was stirred at RT for 10 min. Toluene (30 mL) was added and the reaction mixture was evaporated in vacuo (x 3). The residue was purified by HPLC (Phenomenex Gemini®, Gradient: 5-40% acetonitrile in 0.1% aqueous formic acid). The fractions containing product were combined, and freeze dried to give the titled compound as a white solid. Yield 0.65 g.

m/z 639 (M+H)$^+$ $^1$H NMR (400 MHz, D$_4$-MeOH) δ 8.44 (s, 1H), 7.40-7.35 (m, 2H), 7.19 (d, J=3.7 Hz, 1H), 7.02-6.97 (m, 2H), 6.92 (d, J=8.36 Hz, 1H), 6.78-6.76 (m, 1H), 6.71 (d, J=8.30 Hz, 1H), 4.93-4.88 (m, 1H), 4.21 (t, J=5.17 Hz, 2H), 4.13 (s, 2H), 3.76-3.70 (m, 4H), 3.61 (s, 2H), 3.11-3.07 (m, 2H), 3.07-3.01 (m, 2H), 3.03-2.91 (m, 2H), 2.88-2.76 (m, 2H), 2.47 (d, J=1.0 Hz, 3H), 2.02-1.93 (m, 2H), 1.74-1.61 (m, 2H). Five exchangeable protons not observed.

EXAMPLE 111

(R)-4-Hydroxy-7-(1-hydroxy-2-(9-(4-(5-methylthiophene-2-carbonyl)-1-oxa-4,9-diazaspiro[5.5]undecan-9-yl)nonylamino)ethyl)benzo[d]thiazol-2(3H)-one formate a) (9-(9-Hydroxynonyl)-1-oxa-4,9-diazaspiro[5.5]undecan-4-yl)(5-methylthiophen-2-yl)methanone

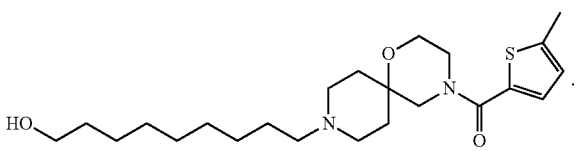 [SMILES: Cc1ccc(C(=O)N2CCOC3(CCN(CCCCCCCCCO)CC3)C2)s1]

A solution of 9-bromo-1-nonanol (0.314 g) in MeCN (3 mL) was added to solution of (5-methylthiophen-2-yl)(1-oxa-4,9-diazaspiro[5.5]undecan-4-yl)methanone trifluoroacetate (example 9, step b) (0.263 g) and triethylamine (0.261 mL) in MeCN (7 mL). The resulting mixture was stirred at 60° C. under argon for 16 h. After cooling to RT the solvent was removed in vacuo. The residue was taken up in DCM, washed with brine (×2), dried over sodium sulphate, filtered and evaporated in vacuo. The white solid was purified by silica gel chromatography eluting with 0-10% MeOH in DCM to give the subtitled compound as a white solid. Yield 0.352 g.

$^1$H NMR (400 MHz, CDCl$_3$) δ 7.10 (d, J=3.6 Hz, 1H), 6.71 (dd, J=3.6, 1.2 Hz, 1H), 3.73 (s, 4H), 3.66-3.60 (m, 4H), 3.22 (s, 2H), 2.84 (s, 3H), 2.50 (d, J=1.0 Hz, 3H), 2.15 (s, 1H), 2.11-1.97 (m, 2H), 1.83 (s, 2H), 1.61-1.50 (m, 3H), 1.32 (s, 11H). One exchangeable proton not observed.

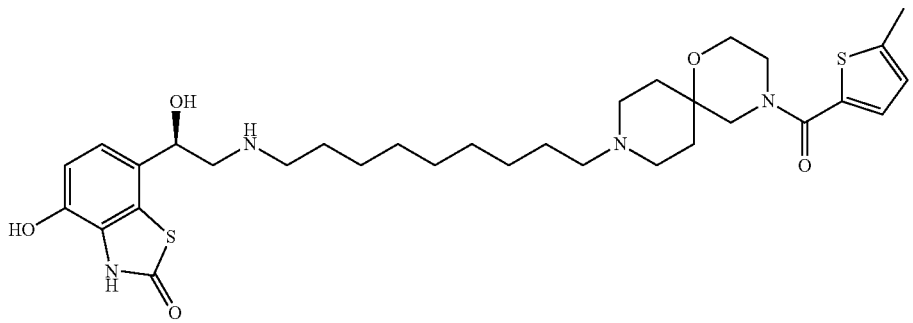 [SMILES: Cc1ccc(C(=O)N2CCOC3(CCN(CCCCCCCCCNC[C@H](O)c4ccc(O)c5[nH]c(=O)sc45)CC3)C2)s1]

b) (R)-4-Hydroxy-7-(1-hydroxy-2-(9-(4-(5-methylthiophene-2-carbonyl)-1-oxa-4,9-diazaspiro[5.5]undecan-9-yl)nonylamino)ethyl)benzo[d]thiazol-2(3H)-one formate

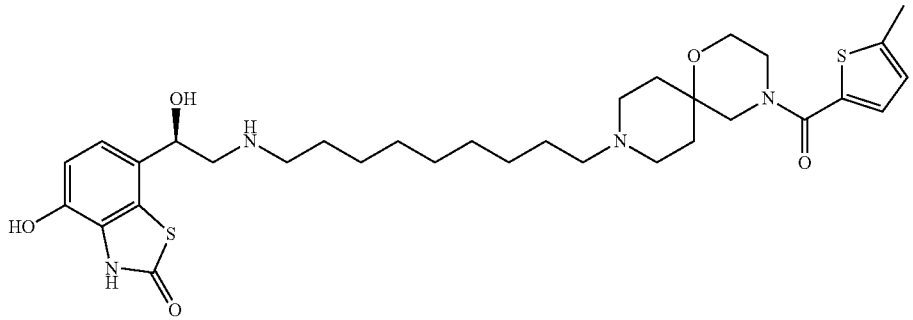

Trifluoroacetic acid (0.064 mL) was added to a solution of (9-(9-hydroxynonyl)-1-oxa-4,9-diazaspiro[5.5]undecan-4-yl)(5-methylthiophen-2-yl)methanone (example 111, step a) (0.350 g) in DCM (15 mL) at 0° C. The resulting mixture was stirred for 5 min and then Dess-Martin periodinane (0.527 g) was added. The mixture was stirred at RT for 1 h. Saturated sodium thiosulphate solution (14 mL), saturated sodium bicarbonate solution (14 mL) and EtOAc (30 mL) was added and the mixture was stirred for 5 min. The layers were separated and the aqueous layer was extracted with EtOAc (2×40 mL). The combined organic layers were washed with saturated sodium bicarbonate solution (40 mL), treated with acetic acid (0.159 mL), dried over sodium sulphate, filtered and evaporated in vacuo. The yellow oil was dissolved in dry MeOH (15.6 mL) and (R)-7-(2-amino-1-hydroxyethyl)-4-hydroxybenzo[d]thiazol-2(3H)-one hydrochloride (WO2007027134, example 1, step d) (0.327 g) was added, followed by acetic acid (0.071 mL) and 3 Å molecular sieves. After stirring for 5 min at RT, the reaction mixture was cooled to 0° C. and sodium triacetoxyborohydride (0.176 g) was added and the mixture was stirred at RT for 1 h. Another portion of sodium triacetoxyborohydride (0.075 g) was added and the mixture was stirred at RT for 17 h. The reaction mixture was filtered and the solvent was evaporated in vacuo. The residue was purified by HPLC (Phenomenex Gemini®, Gradient: 5-40% acetonitrile in 0.1% aqueous formic acid). The fractions containing product were combined and freeze-dried to give the titled compound as a white solid. Yield 0.127 g.

m/z 631 (M+H)⁺

¹H NMR (400 MHz, D₄-MeOH) δ 8.49 (s, 1H), 7.20 (d, J=3.7 Hz, 1H), 6.95 (d, J=8.3 Hz, 1H), 6.79-6.76 (m, 1H), 6.73 (d, J=8.3 Hz, 1H), 4.97-4.91 (m, 1H), 3.76-3.72 (m, 4H), 3.62 (s, 2H), 3.20-3.04 (m, 4H), 3.03-2.93 (m, 3H), 2.95-2.84 (m, 3H), 2.47 (d, J=1.0 Hz, 3H), 2.11-2.01 (m, 2H), 1.80-1.62 (m, 6H), 1.40-1.31 (m, 10H). Five exchangeable protons not observed.

EXAMPLE 112

(R)-4-Hydroxy-7-(1-hydroxy-2-(4-(2-(4-(2-phenylthiazole-4-carbonyl)-1-oxa-4,9-diazaspiro[5.5]undecan-9-yl)ethoxy)benzylamino)ethyl)benzo[d]thiazol-2(3H)-one ditrifluoroacetate

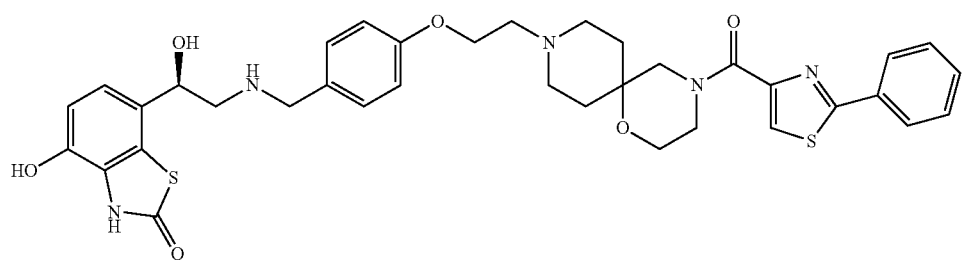 [SMILES: O=C(c1csc(-c2ccccc2)n1)N1CCOC2(CCN(CCOc3ccc(CNC[C@H](O)c4ccc(O)c5[nH]c(=O)sc45)cc3)CC2)C1]

a) tert-Butyl 4-(2-phenylthiazole-4-carbonyl)-1-oxa-4,9-diazaspiro[5.5]undecane-9-carboxylate

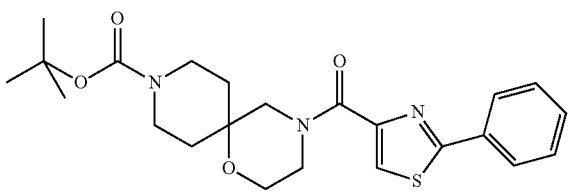 [SMILES: CC(C)(C)OC(=O)N1CCC2(CC1)CN(C(=O)c1csc(-c3ccccc3)n1)CCO2]

A solution of tert-butyl 1-oxa-4,9-diazaspiro[5.5]undecane-9-carboxylate hydrochloride (WuXi PharmaTech) (0.60 g) in DMF (11 mL) was treated with triethylamine (1.1 mL), followed by 2-phenyl-1,3-thiazole-4-carboxylic acid (0.421 g) and then O-(7-azabenzotriazol-1-yl)-N,N,N',N'-tetramethyluronium hexafluorophosphate (1.09 g). The resulting mixture was stirred at RT for 7 h. DMF was removed in vacuo. The residue was taken up in EtOAc (50 mL) and washed with saturated sodium bicarbonate solution (2×30 mL), water (30 mL) and brine (30 mL), dried over sodium sulphate, filtered and evaporated in vacuo. The brown oil was purified by silica gel chromatography eluting with 0-10% MeOH in DCM to give the subtitled compound as a brown solid. Yield 0.857 g.

$^1$H NMR (400 MHz, CDCl$_3$) δ 8.00 (s, 1H), 7.92 (s, 2H), 7.47 (d, J=4.1 Hz, 3H), 4.13-3.96 (m, 2H), 3.83 (s, 3H), 3.73 (s, 2H), 3.29-3.13 (m, 2H), 1.94-1.83 (m, 2H), 1.62-1.51 (m, 3H), 1.45 (s, 9H).

(0.85 mg) in DCM (15.2 mL). The resulting mixture was stirred at RT for 1 h. Toluene (30 mL) was added and the mixture was evaporated in vacuo. The yellow residue was dissolved in MeOH and applied to a SCX cartridge pre-wetted with MeOH. The cartridge was washed with MeOH and eluted with 2M ammonia in MeOH. The eluent was evaporated in vacuo to give the subtitled compound as a brown oil. Yield 0.629 g.

$^1$H NMR (400 MHz, CDCl$_3$) δ 7.98 (s, 1H), 7.95-7.90 (m, 2H), 7.49-7.44 (m, 3H), 4.07 (br s, 1H), 3.99 (br s, 1H), 3.88-3.79 (m, 3H), 3.70 (br s, 1H), 3.02-2.81 (m, 3H), 2.80-2.69 (m, 1H), 1.83 (d, J=13.7 Hz, 2H), 1.70-1.44 (m, 2H). One exchangeable proton not observed.

c) (R)-tert-Butyl 2-hydroxy-2-(4-hydroxy-2-oxo-2,3-dihydrobenzo[d]thiazol-7-yl)ethyl(4-(2-(4-(2-phenylthiazole-4-carbonyl)-1-oxa-4,9-diazaspiro[5.5]undecan-9-yl)ethoxy)benzyl)carbamate

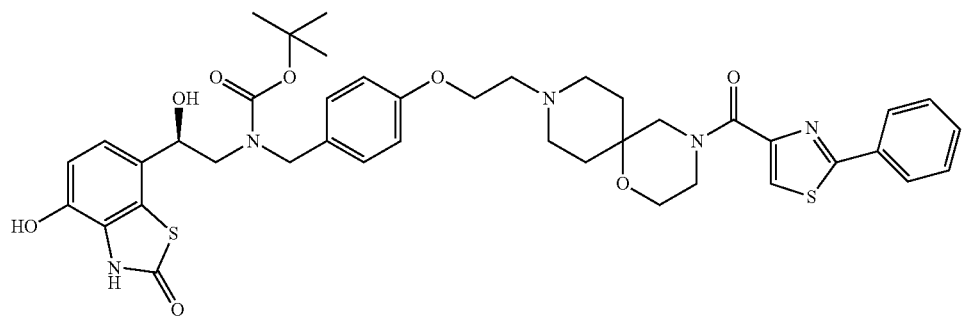

b) (2-Phenylthiazol-4-yl)(1-oxa-4,9-diazaspiro[5.5]undecan-4-yl)methanone

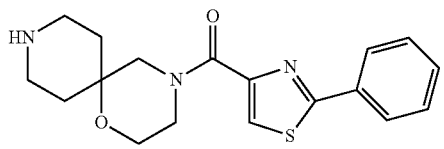 [SMILES: O=C(c1csc(-c2ccccc2)n1)N1CCOC2(CCNCC2)C1]

Trifluoroacetic acid (3.8 mL) was added to a solution of tert-butyl 4-(2-phenylthiazole-4-carbonyl)-1-oxa-4,9-diazaspiro[5.5]undecane-9-carboxylate (example 112, step a)

A solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 108, step c) (0.619 g) in MeCN (3 mL) was added dropwise to a solution of (2-phenylthiazol-4-yl)(1-oxa-4,9-diazaspiro[5.5]undecan-4-yl)methanone (example 112, step b) (0.274 g) and triethylamine (0.22 mL) in MeCN (7.3 mL) at RT under argon. The resulting mixture was stirred at 80° C. under argon for 16 h. After cooling to RT the solvent was removed in vacuo. The residue was taken up in DCM, washed with brine and water, dried over sodium sulphate, filtered and evaporated in vacuo. The residue was purified by silica gel chromatography eluting with 0-70% EtOAc in petroleum ether (40-60° C.) to give the subtitled compound as a yellow solid. Yield 0.42 g.

$^1$H NMR (400 MHz, CDCl$_3$) δ 8.04-7.95 (m, 1H), 7.94-7.79 (m, 2H), 7.50-7.41 (m, 2H), 7.40-7.28 (m, 1H), 7.02-6.81 (m, 2H), 6.70-6.37 (m, 3H), 4.84-4.70 (m, 1H), 4.25-3.92 (m, 6H), 3.87-3.75 (m, 3H), 3.74-3.58 (m, 2H), 3.57-3.36 (m, 2H), 2.99-2.77 (m, 3H), 2.76-2.43 (m, 3H), 2.01-1.86 (m, 2H), 1.84-1.58 (m, 2H), 1.52 (s, 9H). Three exchangeable protons not observed.

d) (R)-4-Hydroxy-7-(1-hydroxy-2-(4-(2-(4-(2-phenylthiazole-4-carbonyl)-1-oxa-4,9-diazaspiro[5.5]undecan-9-yl)ethoxy)benzylamino)ethyl)benzo[d]thiazol-2(3H)-one ditrifluoroacetate

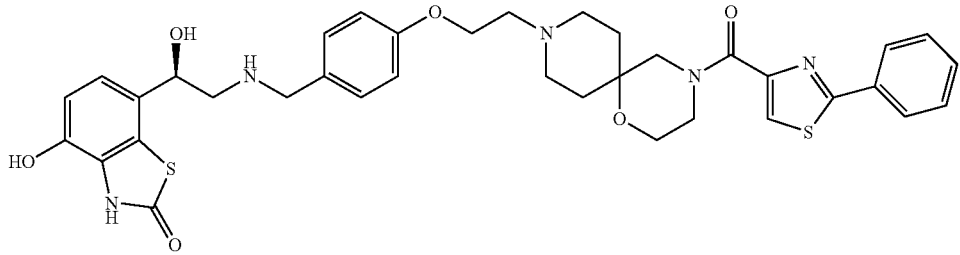 [SMILES: O=C(c1csc(-c2ccccc2)n1)N1CCOC2(CCN(CCOc3ccc(CNC[C@H](O)c4ccc(O)c5[nH]c(=O)sc45)cc3)CC2)C1]

Trifluoroacetic acid (1.2 mL) was added to a solution of (R)-tert-butyl 2-hydroxy-2-(4-hydroxy-2-oxo-2,3-dihydrobenzo[d]thiazol-7-yl)ethyl(4-(2-(4-(2-phenylthiazole-4-carbonyl)-1-oxa-4,9-diazaspiro[5.5]undecan-9-yl)ethoxy)benzyl)carbamate (example 112, step c) (0.415 g) in DCM (4.7 mL). The resulting mixture was stirred at RT for 15 min. Toluene (40 mL) was added and the reaction mixture was evaporated in vacuo (×2). The residue was purified by HPLC (Phenomenex Gemini®, Gradient: 5-40% acetonitrile in 0.1% aqueous formic acid). The fractions containing product were combined, and freeze dried to give the titled compound as a white solid. Yield 0.176 g.

m/z 702 (M+H)$^+$ $^1$H NMR (400 MHz, D$_4$-MeOH) δ 8.07 (s, 1H), 7.94 (br s, 2H), 7.51-7.39 (m, 5H), 7.06 (br s, 2H), 6.93 (d, J=8.4 Hz, 1H), 6.71 (d, J=8.4 Hz, 1H), 4.92-4.88 (m, 1H), 4.38 (br s, 2H), 4.24-4.14 (m, 2H), 4.03-3.49 (m, 10H), 3.38-3.28 (m, 2H), 3.08-3.00 (m, 2H), 2.33-2.22 (m, 2H), 1.87 (br s, 2H). Six exchangeable protons not observed.

EXAMPLE 113

(R)-4-Hydroxy-7-(1-hydroxy-2-(9-(4-(2-phenylthiazole-4-carbonyl)-1-oxa-4,9-diazaspiro[5.5]undecan-9-yl)nonylamino)ethyl)benzo[d]thiazol-2(3H)-one formate a) (9-(9-Hydroxynonyl)-1-oxa-4,9-diazaspiro[5.5]undecan-4-yl)(2-phenylthiazol-4-yl)methanone

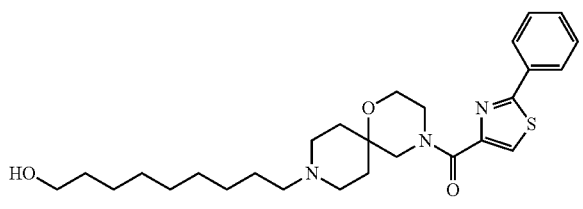 [SMILES: O=C(c1csc(-c2ccccc2)n1)N1CCOC2(CCN(CCCCCCCCCO)CC2)C1]

A solution of 9-bromo-1-nonanol (0.346 g) in MeCN (3 mL) was added to solution of (2-phenylthiazol-4-yl)(1-oxa-4,9-diazaspiro[5.5]undecan-4-yl)methanone (example 112, step b) (0.355 g) and triethylamine (0.288 mL) in MeCN (7 mL). The resulting mixture was stirred at 60° C. under argon for 17 h. After cooling to RT the solvent was removed in vacuo. The residue was taken up in DCM, washed with brine (×2), dried over sodium sulphate, filtered and evaporated in vacuo. The yellow oil was purified by silica gel chromatography eluting with 0-7% MeOH in DCM to give the subtitled compound as a white solid. Yield 0.378 g.

$^1$H NMR (400 MHz, CDCl$_3$) δ 8.02 (s, 1H), 8.00-7.87 (m, 2H), 7.57 (s, 1H), 7.49-7.42 (m, 2H), 4.16-4.08 (m, 2H), 3.81 (s, 4H), 3.72 (br s, 1H), 3.63 (t, J=6.6 Hz, 2H), 3.33-2.64 (m, 6H), 2.25-2.04 (m, 3H), 1.79 (s, 3H), 1.61-1.50 (m, 3H), 1.39-1.25 (m, 9H).

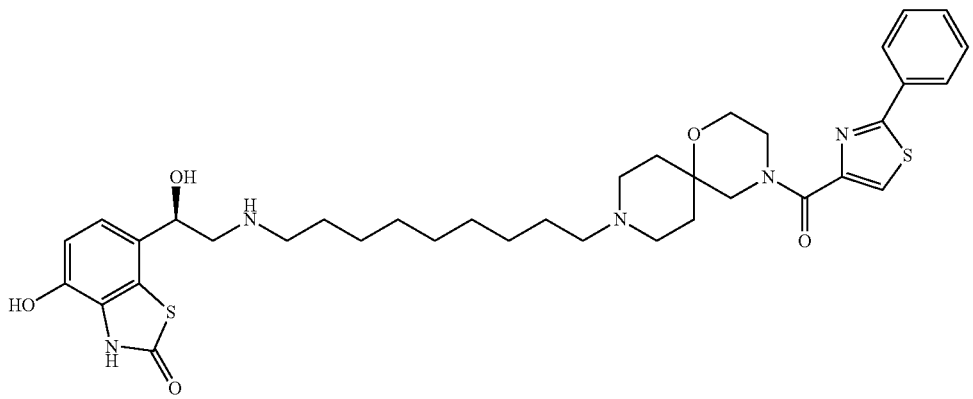 [SMILES: O=C(c1csc(-c2ccccc2)n1)N1CCOC2(CCN(CCCCCCCCCNC[C@H](O)c3ccc(O)c4[nH]c(=O)sc34)CC2)C1]

b) (R)-4-Hydroxy-7-(1-hydroxy-2-(9-(4-(2-phenylthiazole-4-carbonyl)-1-oxa-4,9-diazaspiro[5.5]undecan-9-yl)nonylamino)ethyl)benzo[d]thiazol-2(3H)-one formate

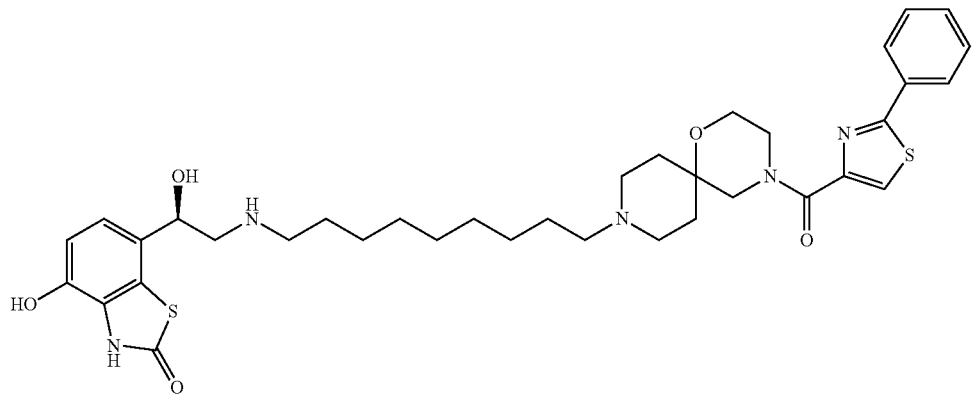

Trifluoroacetic acid (0.059 mL) was added to a solution of (9-(9-hydroxynonyl)-1-oxa-4,9-diazaspiro[5.5]undecan-4-yl)(2-phenylthiazol-4-yl)methanone (example 113, step a) (0.373 g) in DCM (14 mL) at 0° C. The resulting mixture was stirred for 5 min and then Dess-Martin periodinane (0.489 g) was added. The mixture was stirred at RT for 1 h. Saturated sodium thiosulfate solution (14 mL), saturated sodium bicarbonate solution (14 mL) and EtOAc (30 mL) were added and the mixture was stirred for 5 min. The layers were separated and the aqueous layer was extracted with EtOAc (2×30 mL). The combined organic layers were treated with acetic acid (0.148 mL), dried over sodium sulphate, filtered and evaporated in vacuo. The yellow oil was dissolved in dry MeOH (15 mL) and (R)-7-(2-amino-1-hydroxyethyl)-4-hydroxybenzo[d]thiazol-2(3H)-one hydrochloride (WO2007027134, example 1, step d) (0.303 g) was added, followed by acetic acid (0.066 mL) and 3 Å molecular sieves. After stirring for 5 min at RT, the reaction mixture was cooled to 0° C. and sodium triacetoxyborohydride (0.163 g) was added and the mixture was stirred at RT for 18 h. The reaction mixture was filtered and the solvent was evaporated in vacuo. The residue was purified by HPLC (Phenomenex Gemini®, Gradient: 5-40% acetonitrile in 0.1% aqueous formic acid). The fractions containing product were combined and freeze-dried to give the titled compound as a white solid. Yield 0.118 g.

m/z 694 (M+H)$^+$ $^1$H NMR (400 MHz, D$_4$-MeOH) δ 8.31 (s, 1H), 7.97 (br s, 1H), 7.99-7.91 (m, 2H), 7.51-7.44 (m, 3H), 6.95 (d, J=8.4 Hz, 1H), 6.72 (d, J=8.4 Hz, 1H), 4.97-4.89 (m, 1H), 3.99-3.86 (m, 2H), 3.85-3.63 (m, 4H), 3.14-3.01 (m, 2H), 3.00-2.91 (m, 3H), 2.90-2.56 (m, 4H), 2.12-1.97 (m, 2H), 1.85-1.47 (m, 6H), 1.43-1.22 (m, 10H). One protons obscured by solvent and five exchangeable protons not observed.

EXAMPLE 114

(R)-4-Hydroxy-7-(1-hydroxy-2-(4-(2-(4-(2-isopropylthiazole-5-carbonyl)-1-oxa-4,9-diazaspiro[5.5]undecan-9-yl)ethoxy)benzylamino)ethyl)benzo[d]thiazol-2(3H)-one ditrifluoracetate

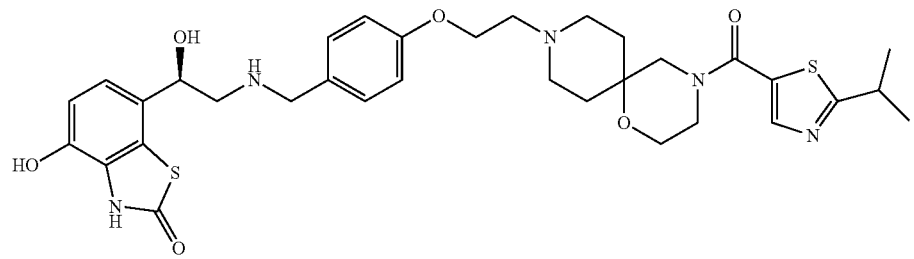 [SMILES: CC(C)c1ncc(C(=O)N2CCOC3(CCN(CCOc4ccc(CNC[C@H](O)c5ccc(O)c6[nH]c(=O)sc56)cc4)CC3)C2)s1]

a) tert-Butyl 4-(2-isopropylthiazole-5-carbonyl)-1-oxa-4,9-diazaspiro[5.5]undecane-9-carboxylate

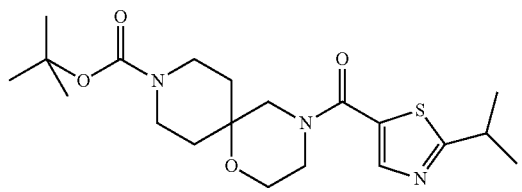 [SMILES: CC(C)c1ncc(C(=O)N2CCOC3(CCN(C(=O)OC(C)(C)C)CC3)C2)s1]

A solution of tert-butyl 1-oxa-4,9-diazaspiro[5.5]undecane-9-carboxylate hydrochloride (WuXi PharmaTech) (0.694 g) in DMF (13 mL) was treated with triethylamine (1.3 mL), followed by 2-isopropylthiazole-5-carboxylic acid (example 55, step b) (0.406 g) and then O-(7-azabenzotriazol-1-yl)-N,N,N',N'-tetramethyluronium hexafluorophosphate (1.26 g). The resulting mixture was stirred at RT for 16 h. DMF was removed in vacuo. The residue was taken up in EtOAc (40 mL) and washed with saturated sodium bicarbonate solution (2×40 mL), water (40 mL) and brine (40 mL), dried over sodium sulphate, filtered and evaporated in vacuo. The viscous orange oil was purified by silica gel chromatography eluting with 0-7% MeOH in DCM to give the subtitled compound as a viscous orange oil. Yield 0.765 g.

$^1$H NMR (400 MHz, CDCl$_3$) δ 7.80 (s, 1H), 3.75 (d, J=3.2 Hz, 6H), 3.55 (d, J=4.3 Hz, 2H), 3.36-3.28 (m, 1H), 3.15 (s, 2H), 1.89-1.78 (m, 2H), 1.58 (s, 2H), 1.45 (s, 9H), 1.42 (d, J=6.9 Hz, 6H).

b) (2-Isopropylthiazol-5-yl)(1-oxa-4,9-diazaspiro[5.5]undecan-4-yl)methanone

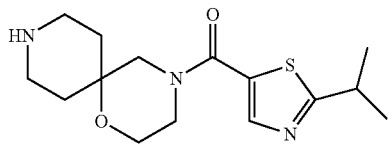 [SMILES: CC(C)c1ncc(C(=O)N2CCOC3(CCNCC3)C2)s1]

Trifluoroacetic acid (3.9 mL) was added to a solution of tert-butyl 4-(2-isopropylthiazole-5-carbonyl)-1-oxa-4,9-diazaspiro[5.5]undecane-9-carboxylate (example 113, step a) (0.765 g) in DCM (14.8 mL). The resulting mixture was stirred at RT for 1 h. Toluene (30 mL) was added and the mixture was evaporated in vacuo. The yellow residue was dissolved in MeOH and applied to a SCX cartridge pre-wetted with MeOH. The cartridge was washed with MeOH and eluted with 2M ammonia in MeOH. The eluent was evaporated in vacuo to give the subtitled compound as a yellow oil. Yield 0.552 g.

$^1$H NMR (400 MHz, CDCl$_3$) δ 7.81 (s, 1H), 3.79-3.71 (m, 4H), 3.64-3.44 (m, 2H), 3.36-3.26 (m, 1H), 2.96-2.87 (m, 2H), 2.85-2.73 (m, 2H), 1.86-1.75 (m, 2H), 1.59 (s, 2H), 1.42 (d, J=6.9 Hz, 6H). One exchangeable proton not observed.

c) (R)-tert-Butyl 2-hydroxy-2-(4-hydroxy-2-oxo-2,3-dihydrobenzo[d]thiazol-7-yl)ethyl(4-(2-(4-(2-isopropylthiazole-5-carbonyl)-1-oxa-4,9-diazaspiro[5.5]undecan-9-yl)ethoxy)benzyl)carbamate

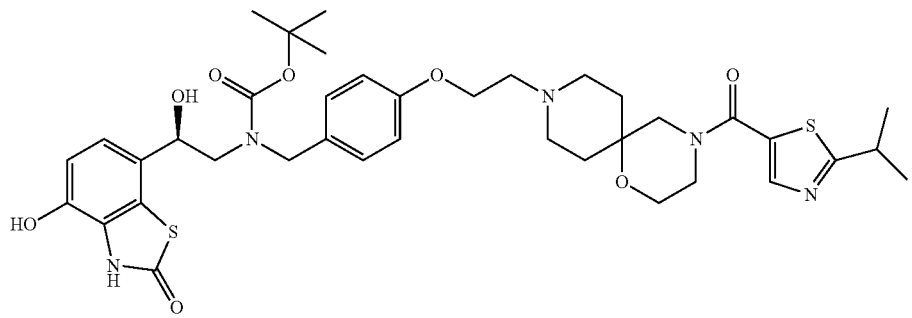 [SMILES: CC(C)c1ncc(C(=O)N2CCOC3(CCN(CCOc4ccc(CN(C[C@H](O)c5ccc(O)c6[nH]c(=O)sc56)C(=O)OC(C)(C)C)cc4)CC3)C2)s1]

A solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 108, step c) (0.575 g) in MeCN (3 mL) was added dropwise to a solution of (2-isopropylthiazol-5-yl)(1-oxa-4,9-diazaspiro[5.5]undecan-4-yl)methanone (example 114, step b) (0.229 g) and triethylamine (0.21 mL) in MeCN (7.3 mL) at RT under argon. The resulting mixture was stirred at 80° C. under argon for 16 h. After cooling to RT the solvent was removed in vacuo. The residue was taken up in DCM (25 mL), washed with brine (20 mL) and water (20 mL), dried over sodium sulphate, filtered and evaporated in vacuo. The residue was purified by silica gel chromatography eluting with 0-8% MeOH in DCM to give the subtitled compound as a yellow solid. Yield 0.395 g.

$^1$H NMR (400 MHz, CDCl$_3$) δ 7.69 (s, 1H), 7.01-6.83 (s, 2H), 6.70-6.62 (m, 3H), 6.57-6.47 (m, 1H), 4.79 (s, 1H), 4.25-4.06 (m, 3H), 3.77-3.63 (m, 4H), 3.57-3.39 (m, 4H), 3.34-3.26 (m, 2H), 2.90 (s, 4H), 2.61 (s, 2H), 1.95-1.85 (m, 2H), 1.63 (s, 2H), 1.51 (s, 9H), 1.45-1.37 (m, 6H). Three exchangeable protons not observed.

d) (R)-4-Hydroxy-7-(1-hydroxy-2-(4-(2-(4-(2-iso-propylthiazole-5-carbonyl)-1-oxa-4,9-diazaspiro[5.5]undecan-9-yl)ethoxy)benzylamino)ethyl)benzo[d]thiazol-2(3H)-one ditrifluoracetate

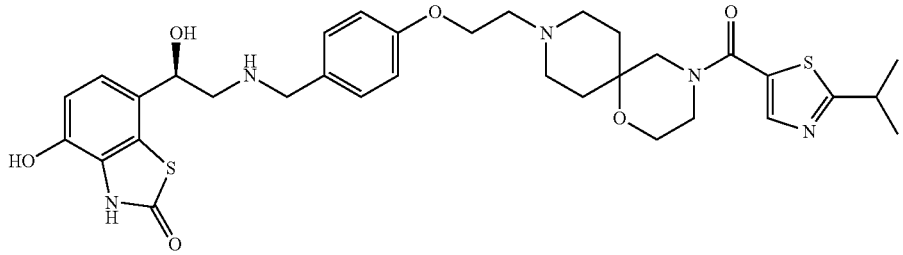 [SMILES: CC(C)c1ncc(C(=O)N2CCOC3(CCN(CCOc4ccc(CNC[C@H](O)c5ccc(O)c6[nH]c(=O)sc56)cc4)CC3)C2)s1]

Trifluoroacetic acid (1.2 mL) was added to a solution of (R)-tert-butyl 2-hydroxy-2-(4-hydroxy-2-oxo-2,3-dihydrobenzo[d]thiazol-7-yl)ethyl(4-(2-(4-(2-isopropylthiazole-5-carbonyl)-1-oxa-4,9-diazaspiro[5.5]undecan-9-yl)ethoxy)benzyl)carbamate (example 114, step c) (0.39 g) in DCM (4.7 mL). The resulting mixture was stirred at RT for 15 min. Toluene (30 mL) was added and the reaction mixture was evaporated in vacuo (×3). The residue was purified by HPLC (Phenomenex Gemini®, Gradient: 5-40% acetonitrile in 0.1% aqueous trifluoroacetic acid). The fractions containing product were combined, and freeze dried to give the titled compound as a white solid. Yield 0.201 g.
m/z 668 (M+H)+
$^1$H NMR (400 MHz, D$_4$-MeOH) δ 7.91 (s, 1H), 7.42 (d, J=8.6 Hz, 2H), 7.06 (d, J=8.6 Hz, 2H), 6.93 (d, J=8.3 Hz, 1H), 6.71 (d, J=8.3 Hz, 1H), 4.91-4.88 (m, 1H), 4.38 (t, J=4.9 Hz, 2H), 4.24-4.15 (m, 2H), 3.82-3.71 (m, 5H), 3.66-3.57 (m, 4H), 3.56-3.48 (m, 2H), 3.38-3.25 (m, 1H), 3.08-3.00 (m, 2H), 2.29-2.17 (m, 2H), 2.12-1.93 (br s, 1H), 1.88-1.73 (m, 2H), 1.38 (d, J=6.7 Hz, 6H). Six exchangeable protons not observed.

EXAMPLE 115

(R)-4-Hydroxy-7-(1-hydroxy-2-(9-(4-(2-isopropylthiazole-5-carbonyl)-1-oxa-4,9-diazaspiro[5.5]undecan-9-yl)nonylamino)ethyl)benzo[d]thiazol-2(3H)-one formate a) (9-(9-Hydroxynonyl)-1-oxa-4,9-diazaspiro[5.5]undecan-4-yl)(2-isopropylthiazol-5-yl)methanone

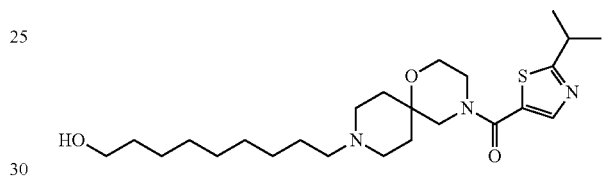

A solution of 9-bromo-1-nonanol (0.446 g) in MeCN (3.9 mL) was added to solution of (2-isopropylthiazol-5-yl)(1-oxa-4,9-diazaspiro[5.5]undecan-4-yl)methanone (example 114, step b) (0.395 g) and triethylamine (0.36 mL) in MeCN (8.6 mL). The resulting mixture was stirred at 60° C. under argon for 16 h. After cooling to RT the solvent was removed in vacuo. The residue was taken up in DCM (25 mL), washed with brine (20 mL) and water (20 mL), dried over sodium sulphate, filtered and evaporated in vacuo. The residue was purified by silica gel chromatography eluting with 0-10% MeOH in DCM to give the subtitled compound as a white solid. Yield 0.329 g.
$^1$H NMR (400 MHz, CDCl$_3$) δ 7.81 (s, 1H), 3.74 (s, 4H), 3.63 (t, J=6.6 Hz, 2H), 3.59 (s, 2H), 3.36-3.26 (m, 1H), 3.10-2.49 (m, 5H), 2.03-1.91 (m, 3H), 1.68 (s, 2H), 1.61-1.50 (m, 3H), 1.43 (d, J=6.9 Hz, 6H), 1.36-1.29 (m, 11H). One exchangeable proton not observed.

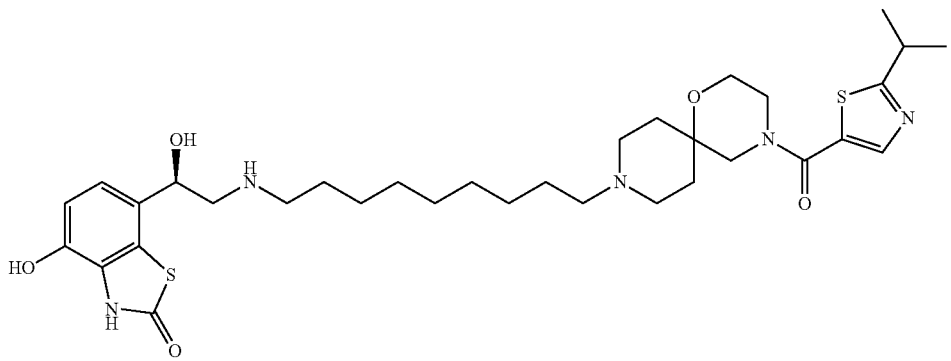 [SMILES: CC(C)c1ncc(C(=O)N2CCOC3(CCN(CCCCCCCCCNC[C@H](O)c4ccc(O)c5[nH]c(=O)sc45)CC3)C2)s1]

b) (R)-4-Hydroxy-7-(1-hydroxy-2-(9-(4-(2-isopropy-lthiazole-5-carbonyl)-1-oxa-4,9-diazaspiro[5.5]undecan-9-yl)nonylamino)ethyl)benzo[d]thiazol-2(3H)-one formate

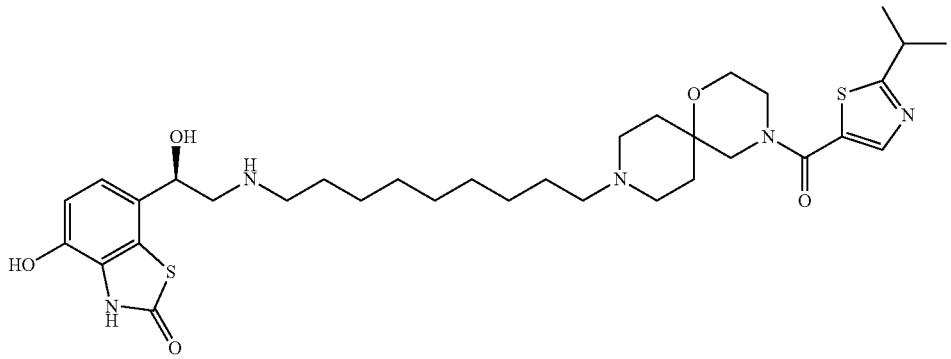 [SMILES: CC(C)c1ncc(C(=O)N2CCOC3(CCN(CCCCCCCCCNC[C@H](O)c4ccc(O)c5[nH]c(=O)sc45)CC3)C2)s1]

Trifluoroacetic acid (0.055 mL) was added to a solution of (9-(9-hydroxynonyl)-1-oxa-4,9-diazaspiro[5.5]undecan-4-yl)(2-isopropylthiazol-5-yl)methanone (example 115, step a) (0.325 g) in DCM (13 mL) at 0° C. under argon. The resulting mixture was stirred for 5 min and then Dess-Martin periodinane (0.458 g) was added. The mixture was stirred at RT for 1.5 h. Saturated sodium thiosulfate solution (14 mL), saturated sodium bicarbonate solution (14 mL) and EtOAc (28 mL) were added and the mixture was stirred for 10 min. The layers were separated and the aqueous layer was extracted with EtOAc (2×20 mL). The combined organic layer was treated with acetic acid (0.16 mL), dried over sodium sulphate, filtered and evaporated in vacuo. The yellow oil was dissolved in dry MeOH (15 mL) and (R)-7-(2-amino-1-hydroxyethyl)-4-hydroxybenzo[d]thiazol-2(3H)-one hydrochloride (WO2007027134, example 1, step d) (0.284 g) was added, followed by acetic acid (0.062 mL) and 3 Å molecular sieves. After stirring for 5 min at RT, the reaction mixture was cooled 0° C. and sodium triacetoxyborohydride (0.153 g) was added and the mixture was stirred at RT for 16 h. The reaction mixture was filtered and the solvent was evaporated in vacuo. The residue was purified by HPLC (Phenomenex Gemini®, Gradient: 5-40% acetonitrile in 0.1% aqueous formic acid). The fractions containing product were combined and freeze-dried to give the titled compound as a white solid. Yield 0.090 mg.

m/z 660 (M+H)$^+$ $^1$H NMR (400 MHz, D$_4$-MeOH) δ 8.50 (s, 1H), 7.90 (s, 1H), 6.95 (d, J=8.5 Hz, 1H), 6.73 (d, J=8.5 Hz, 1H), 4.96-4.90 (m, 1H), 3.79-3.68 (m, 4H), 3.64-3.55 (m, 2H), 3.38-3.26 (m, 1H), 3.11-3.05 (m, 2H), 3.04-2.92 (m, 4H), 2.86-2.69 (m, 4H), 2.07-2.04 (m, 2H), 1.76-1.55 (m, 6H), 1.39-1.36 (m, 7H), 1.36-1.31 (m, 9H). Five exchangeable protons not observed.

pEC$_{50}$ and Intrinsic Activity. Intrinsic Activity is expressed as a fraction relative to the maximum activity determined for formoterol in each experiment.

EXAMPLES 116-182

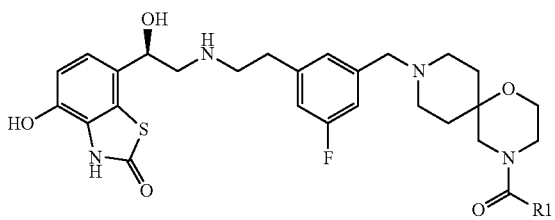

a) (R)-tert-Butyl 3-fluoro-5-((4-(2,2,2-trifluoro-acetyl)-1-oxa-4,9-diazaspiro[5.5]undecan-9-yl)methyl)phenethyl(2-hydroxy-2-(4-hydroxy-2-oxo-2,3-dihydrobenzo[d]thiazol-7-yl)ethyl)carbamate

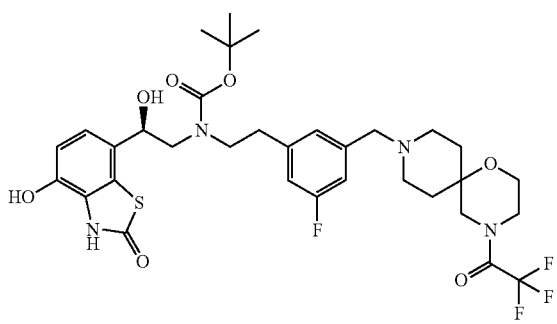 [SMILES: CC(C)(C)OC(=O)N(CCc1cc(F)cc(CN2CCC3(CC2)CN(C(=O)C(F)(F)F)CCO3)c1)C[C@H](O)c1ccc(O)c2[nH]c(=O)sc12]

A solution of 2,2,2-trifluoro-1-(9-(3-fluoro-5-(2-hydroxyethyl)benzyl)-1-oxa-4,9-diazaspiro[5.5]undecan-4-yl)ethanone (example 41, step c) (0.8 g) in dichloromethane (50 mL)

at 20° C. was treated with trifluoroacetic acid (0.152 mL) followed by Dess-Martin Periodinane (1.091 g) and the resultant mixture stirred at 20° C. for 40 minutes. The reaction mixture was treated with saturated aq sodium thiosulphate (20 mL), saturated aqueous sodium bicarbonate (20 mL) and ethyl acetate (30 mL) and stirred vigorously for 5 minutes. The mixture was extracted with ethyl acetate (×2), the combined organics were washed with aqueous sodium bicarbonate, dried over sodium sulphate, filtered, and the solvent removed under reduced pressure. The residue was dissolved in methanol (3 mL) and added to a solution of (R)-7-(2-amino-1-hydroxyethyl)-4-hydroxybenzo[d]thiazol-2(3H)-one, HCl (WO2007027134, example 1, step d) (0.780 g) in methanol (20 mL) with acetic acid (0.113 mL). This mixture was treated with sodium cyanoborohydride (0.186 g) and stirred for 2 hours at 20° C. Triethylamine (0.69 mL) was added followed by di-tert butyldicarbonate (0.689 mL) and stirring continued for 2 hours at 20° C. The solvent was removed under reduced pressure and the residue partitioned between ethyl acetate and brine. The organic layer was dried over sodium sulphate, filtered and the solvent removed under reduced pressure. The crude product was purified by silica gel chromatography eluting with 10% methanol in dichloromethane with 1% concentrated aq ammonia. Pure fractions were evaporated to dryness to afford the subtitled compound. Yield 0.7 g.

m/z 713.3 (M+H)+ b) (R)-tert-Butyl 3-(1-oxa-4,9-diazaspiro[5.5]undecan-9-ylmethyl)-5-fluorophenethyl(2-hydroxy-2-(4-hydroxy-2-oxo-2,3-dihydrobenzo[d]thiazol-7-yl)ethyl)carbamate

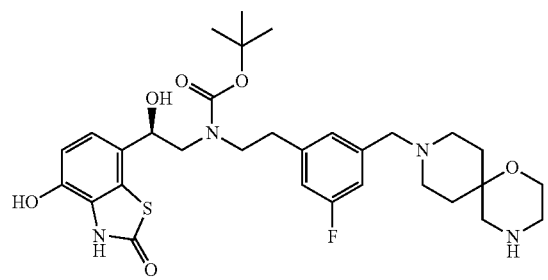 [SMILES: CC(C)(C)OC(=O)N(CCc1cc(F)cc(CN2CCC3(CC2)CNCCO3)c1)C[C@H](O)c1ccc(O)c2[nH]c(=O)sc12]

A solution of (R)-tert-butyl 3-fluoro-5-((4-(2,2,2-trifluoroacetyl)-1-oxa-4,9-diazaspiro[5.5]undecan-9-yl)methyl)phenethyl(2-hydroxy-2-(4-hydroxy-2-oxo-2,3-dihydrobenzo[d]thiazol-7-yl)ethyl)carbamate (examples 116-182, step a) (0.7 g) in 35% aqueous ammonia solution (15 mL) was allowed to stand at 20° C. for 40 minutes. The reaction mixture was evaporated to half the initial volume under reduced pressure. Water (10 mL) was added and this solution was passed through a 10 g C18 silica cartridge which had been pre-wetted with water. The column was flushed with water (20 mL). The column was then flushed with methanol (50 mL) to bring off the product. The solvent was evaporated under reduced pressure and the residue was azeotroped with acetonitrile (×2) to afford the subtitled compound. Yield 0.580 g.

m/z 617 (M+H)+ c) Parallel Synthesis

Preparation of Examples 116-182

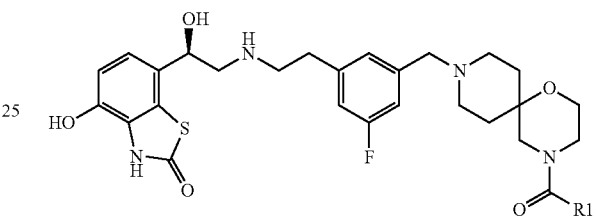

A solution of (R)-tert-butyl 3-(1-oxa-4,9-diazaspiro[5.5]undecan-9-ylmethyl)-5-fluorophenethyl(2-hydroxy-2-(4-hydroxy-2-oxo-2,3-dihydrobenzo[d]thiazol-7-yl)ethyl)carbamate (examples 116-182, step b) (496 mg) and triethylamine (244 mg) in NMP (2.4 mL) was dispensed as aliquots of 30 uL total volume. To each aliquot was added a solution of the appropriate acid (0.01 mmol) in NMP (80 uL) followed by a solution of HATU (4.9 mg) in NMP (30 uL). The reaction mixture was allowed to stand at room temperature for 18 hours. Acetonitrile (800 uL) was added and the solution passed through 'Tosic-65' resin (350 mg). The resin was washed with acetonitrile (800 uL) and the combined washings collected and again passed through the 'Tosic-65' resin. The resin was then washed with acetonitrile (3 mL). A solution of ammonia in methanol (2.5 mL of a 3.5M solution) was passed through the resin and the resultant washings evaporated under a stream of nitrogen gas. The residue was dissolved in formic acid (250 uL) and the mixture allowed to stand at room temperature for 18 hours. Acetonitrile (600 uL) was added and the solution passed through 'Tosic-65' resin (350 mg). The resin was washed with acetonitrile (800 uL) and the combined washings collected and again passed through the 'Tosic-65' resin. The resin was then washed with acetonitrile (3 mL). A solution of ammonia in methanol (2.5 mL of a 3.5M solution) was passed through the resin and the resultant washings evaporated under a stream of nitrogen gas. DMSO (200 uL) was added to the residue and the resultant solution passed through a 'Sunfire' prep C18 column (19×50 mm) using a focus gradient elution of acetonitrile vs aqueous 0.1% TFA for purification. The fractions containing product were evaporated to yield the title compounds.

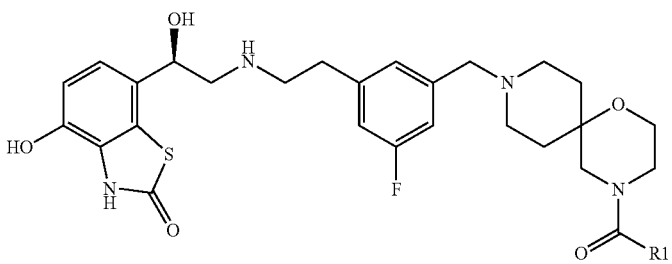

| Example no. | NAME | *—C(=O)—R1 | Observed MWt + 1 | Retention time* (min) |
|---|---|---|---|---|
| 116 | (R)-7-(2-(3-((4-(3-(1H-benzo[d]imidazol-2-yl)propanoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one |  | 689.4 | 0.97 |
| 117 | (R)-7-(2-(3-fluoro-5-((4-(2-(2-methoxyphenyl)acetyl)-1-oxa-4,9-diazaspiro[5.5]undecan-9-yl)methyl)phenethylamino)-1-hydroxyethyl)-4-hydroxybenzo[d]thiazol-2(3H)-one | 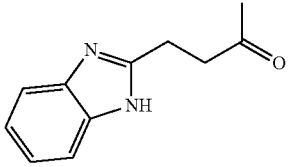 | 665.3 | 1.14 |
| 118 | (R)-7-(2-(3-fluoro-5-((4-(5-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | 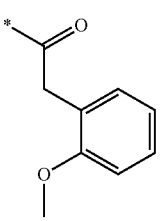 [SMILES: *C(=O)Cc1ccccc1OC] | 641.3 | 1.1 |
| 119 | (R)-7-(2-(3-fluoro-5-((4-(quinoline-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | 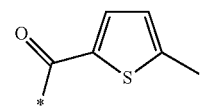 [SMILES: *C(=O)c1ccc(C)s1] | 672.3 | 1.11 |
| 120 | (R)-7-(2-(3-((4-(1H-indole-2-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 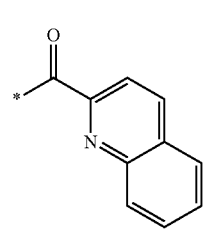 [SMILES: *C(=O)c1ccc2ccccc2n1] | 660.3 | 1.19 |
| 121 | (R)-7-(2-(3-fluoro-5-((4-(2-methylbenzoyl)-1-oxa-4,9-diazaspiro[5.5]undecan-9-yl)methyl)phenethylamino)-1-hydroxyethyl)-4-hydroxybenzo[d]thiazol-2(3H)-one |  | 635.3 | 1.07 |

-continued

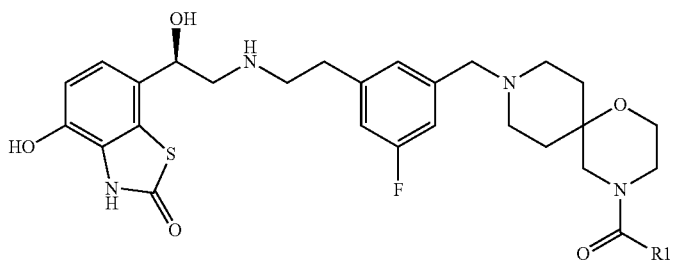

| Example no. | NAME | *—C(O)—R1 | Observed MWt + 1 | Retention time* (min) |
|---|---|---|---|---|
| 122 | (R)-7-(2-(3-fluoro-5-((4-(3-methylbenzoyl)-1-oxa-4,9-diazaspiro[5.5]undecan-9-yl)methyl)phenethylamino)-1-hydroxyethyl)-4-hydroxybenzo[d]thiazol-2(3H)-one | 3-methylbenzoyl | 635.3 | 1.1 |
| 123 | (R)-7-(2-(3-((4-(2-(biphenyl-4-yl)acetyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 2-(biphenyl-4-yl)acetyl | 711.4 | 1.25 |
| 124 | (R)-7-(2-(3-((4-(5-chlorothiophene-2-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 5-chlorothiophene-2-carbonyl | 661.2 | 1.16 |
| 125 | (R)-7-(2-(3-fluoro-5-((4-(3-methylthiophene-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | 3-methylthiophene-2-carbonyl | 641.3 | 1 |
| 126 | (R)-7-(2-(3-fluoro-5-((4-(2-(thiophen-3-yl)acetyl)-1-oxa-4,9-diazaspiro[5.5]undecan-9-yl)methyl)phenethylamino)-1-hydroxyethyl)-4-hydroxybenzo[d]thiazol-2(3H)-one | 2-(thiophen-3-yl)acetyl | 641.3 | 0.98 |
| 127 | (R)-7-(2-(3-fluoro-5-((4-(3-methylfuran-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | 3-methylfuran-2-carbonyl | 625.3 | 1.1 |

-continued

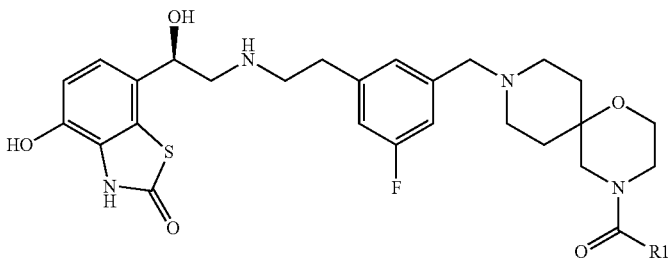

| Example no. | NAME | * ‖ R1 (O) | Observed MWt + 1 | Retention time* (min) |
|---|---|---|---|---|
| 128 | (R)-7-(2-(3-((4-(3-(1H-indol-3-yl)propanoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 688.4 | 1.03 |
| 129 | (R)-7-(2-(3-fluoro-5-((4-(1-phenylcyclopentanecarbonyl)-1-oxa-4,9-diazaspiro[5.5]undecan-9-yl)methyl)phenethylamino)-1-hydroxyethyl)-4-hydroxybenzo[d]thiazol-2(3H)-one | | 689.5 | 1.1 |
| 130 | (R)-7-(2-(3-((4-(3,3-dimethylbutanoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 615.4 | 1.1 |
| 131 | (R)-7-(2-(3-fluoro-5-((4-(2-methylfuran-3-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 625.3 | 1.1 |
| 132 | (R)-7-(2-(3-((4-(benzo[d]thiazole-6-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 678.3 | 1.02 |
| 133 | (R)-7-(2-(3-fluoro-5-((4-(5-methylimidazo[1,2-a]pyridine-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 675.3 | 0.98 |

-continued

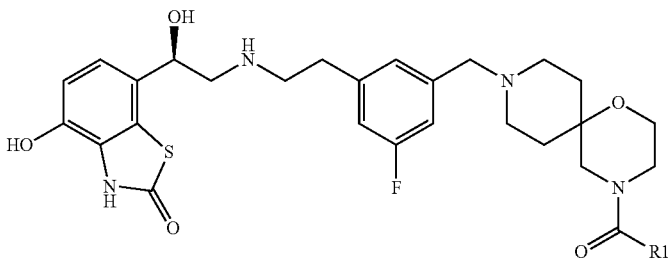

| Example no. | NAME | *—C(O)—R1 | Observed MWt + 1 | Retention time* (min) |
|---|---|---|---|---|
| 134 | (R)-7-(2-(3-fluoro-5-((4-(2-(3-methyl-1H-1,2,4-triazol-5-yl)acetyl)-1-oxa-4,9-diazaspiro[5.5]undecan-9-yl)methyl)phenethylamino)-1-hydroxyethyl)-4-hydroxybenzo[d]thiazol-2(3H)-one | | 640.4 | 0.9 |
| 135 | (R)-7-(2-(3-((4-(2-(3-ethyl-2-oxo-2,3-dihydro-1H-benzo[d]imidazol-1-yl)acetyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 719.4 | 1.16 |
| 136 | (R)-7-(2-(3-((4-(2,5-dimethoxybenzoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 681.3 | 1.11 |
| 137 | (R)-7-(2-(3-((4-(1H-indole-3-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 660.3 | 1.09 |
| 138 | (R)-7-(2-(3-((4-(1H-indole-5-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 660.3 | 1.05 |
| 139 | (R)-7-(2-(3-fluoro-5-((4-(1-methyl-1H-indole-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 674.3 | 1.09 |

-continued

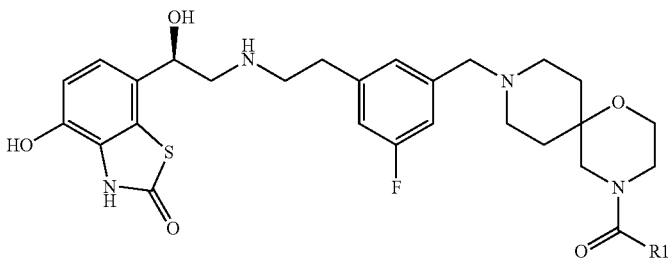

| Example no. | NAME | *─C(O)─R1 | Observed MWt + 1 | Retention time* (min) |
|---|---|---|---|---|
| 140 | (R)-7-(2-(3-((4-(1H-indole-6-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 6-indolyl carbonyl | 660.3 | 1.11 |
| 141 | (R)-7-(2-(3-((4-(1H-indole-7-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 7-indolyl carbonyl | 660.3 | 1.13 |
| 142 | (R)-7-(2-(3-fluoro-5-((4-(1-isopropyl-1H-benzo[d][1,2,3]triazole-5-carbonyl)-1-oxa-4,9-diazaspiro[5.5]undecan-9-yl)methyl)phenethylamino)-1-hydroxyethyl)-4-hydroxybenzo[d]thiazol-2(3H)-one | 1-isopropyl-benzotriazole-5-carbonyl | 704.4 | 1.04 |
| 143 | (R)-7-(2-(3-((4-(2,6-dimethylimidazo[1,2-a]pyridine-3-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 2,6-dimethylimidazo[1,2-a]pyridine-3-carbonyl | 689.4 | 0.82 |
| 144 | (R)-7-(2-(3-((4-(2-(benzo[d]isoxazol-3-yl)acetyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | benzo[d]isoxazol-3-yl acetyl | 676.3 | 1.01 |
| 145 | (R)-7-(2-(3-((4-(biphenylcarbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | biphenyl-2-carbonyl | 697.4 | 1.3 |

-continued

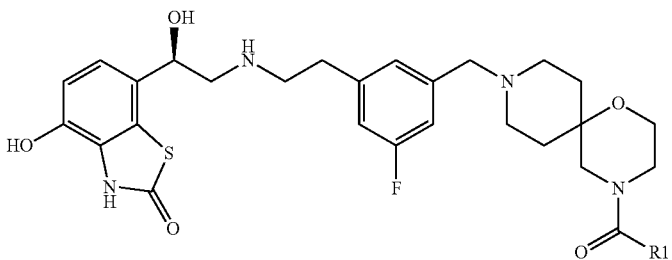

| Example no. | NAME | R1 (acyl) | Observed MWt + 1 | Retention time* (min) |
|---|---|---|---|---|
| 146 | (R)-7-(2-(3-fluoro-5-((4-(4,5,6,7-tetrahydro-2H-indazole-3-carbonyl)-1-oxa-4,9-diazaspiro[5.5]undecan-9-yl)methyl)phenethylamino)-1-hydroxyethyl)-4-hydroxybenzo[d]thiazol-2(3H)-one | 4,5,6,7-tetrahydro-2H-indazole-3-carbonyl | 665.3 | 1.13 |
| 147 | (R)-7-(2-(3-fluoro-5-((4-(2-methylthiophene-3-carbonyl)-1-oxa-4,9-diazaspiro[5.5]undecan-9-yl)methyl)phenethylamino)-1-hydroxyethyl)-4-hydroxybenzo[d]thiazol-2(3H)-one | 2-methylthiophene-3-carbonyl | 641.3 | 1.11 |
| 148 | (R)-7-(2-(3-((4-(4-(1H-pyrazol-3-yl)benzoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 4-(1H-pyrazol-3-yl)benzoyl | 687.4 | 1.07 |
| 149 | (R)-7-(2-(3-((4-(2,3-dihydrobenzofuran-5-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 2,3-dihydrobenzofuran-5-carbonyl | 663.3 | 1.07 |
| 150 | (R)-7-(2-(3-((4-(2,5-dimethylthiophene-3-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 2,5-dimethylthiophene-3-carbonyl | 655.3 | 1.15 |
| 151 | (R)-7-(2-(3-fluoro-5-((4-(4-methyl-1,2,5-oxadiazole-3-carbonyl)-1-oxa-4,9-diazaspiro[5.5]undecan-9-yl)methyl)phenethylamino)-1-hydroxyethyl)-4-hydroxybenzo[d]thiazol-2(3H)-one | 4-methyl-1,2,5-oxadiazole-3-carbonyl | 627.3 | 1.05 |

-continued

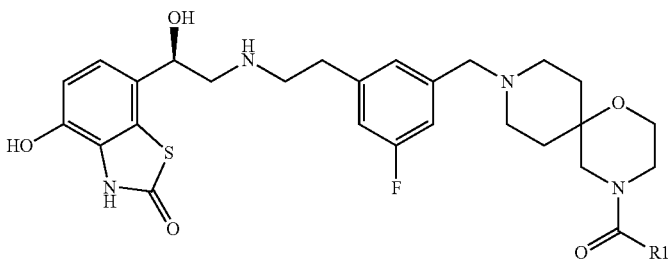

| Example no. | NAME | *—C(O)—R1 | Observed MWt + 1 | Retention time* (min) |
|---|---|---|---|---|
| 152 | (R)-7-(2-(3-fluoro-5-((4-(2-methylimidazo[1,2-a]pyridine-3-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 675.4 | 0.88 |
| 153 | (R)-7-(2-(3-fluoro-5-((4-(2-(3-methyl-1H-pyrazol-1-yl)acetyl)-1-oxa-4,9-diazaspiro[5.5]undecan-9-yl)methyl)phenethylamino)-1-hydroxyethyl)-4-hydroxybenzo[d]thiazol-2(3H)-one | | 639.3 | 0.97 |
| 154 | (R)-7-(2-(3-((4-(5-ethoxy-2-hydroxybenzoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 681.4 | 1.03 |
| 155 | (R)-7-(2-(3-fluoro-5-((4-(3-phenyl-1H-pyrazole-5-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 687.3 | 1.11 |
| 156 | (R)-7-(2-(3-((4-(4-(1H-imidazol-1-yl)benzoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 687.4 | 0.81 |
| 157 | (R)-7-(2-(3-fluoro-5-((4-(5-methyl-1H-indole-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 674.4 | 1.14 |

-continued

| Example no. | NAME |  | Observed MWt + 1 | Retention time* (min) |
|---|---|---|---|---|
| 158 | 7-((R)-2-(3-fluoro-5-((4-((S)-tetrahydrofuran-2-carbonyl)-1-oxa-4,9-diazaspiro[5.5]undecan-9-yl)methyl)phenethylamino)-1-hydroxyethyl)-4-hydroxybenzo[d]thiazol-2(3H)-one | 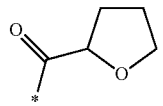 [SMILES: *C(=O)C1CCCO1] | 615.3 | 0.84 |
| 159 | (R)-7-(2-(3-fluoro-5-((4-(4-(oxazol-5-yl)benzoyl)-1-oxa-4,9-diazaspiro[5.5]undecan-9-yl)methyl)phenethylamino)-1-hydroxyethyl)-4-hydroxybenzo[d]thiazol-2(3H)-one |  | 688.3 | 0.97 |
| 160 | (R)-7-(2-(3-fluoro-5-((4-(1-phenyl-1H-pyrazole-5-carbonyl)-1-oxa-4,9-diazaspiro[5.5]undecan-9-yl)methyl)phenethylamino)-1-hydroxyethyl)-4-hydroxybenzo[d]thiazol-2(3H)-one | 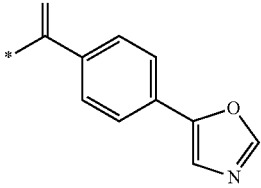 | 687.3 | 1.16 |
| 161 | 7-((1R)-2-(3-fluoro-5-((4-(3-(3-methyl-5-oxo-4,5-dihydro-1H-pyrazol-4-yl)propanoyl)-1-oxa-4,9-diazaspiro[5.5]undecan-9-yl)methyl)phenethylamino)-1-hydroxyethyl)-4-hydroxybenzo[d]thiazol-2(3H)-one |  | 669.4 | 0.97 |
| 162 | (R)-7-(2-(3-((4-(1,2-dimethyl-1H-benzo[d]imidazole-5-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 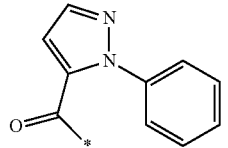 [SMILES: *C(=O)c1ccnn1-c1ccccc1] | 689.4 | 0.92 |
| 163 | (R)-7-(2-(3-fluoro-5-((4-(2-(4-methyl-1,2,5-oxadiazol-3-yl)acetyl)-1-oxa-4,9-diazaspiro[5.5]undecan-9-yl)methyl)phenethylamino)-1-hydroxyethyl)-4-hydroxybenzo[d]thiazol-2(3H)-one |  | 641.3 | 1.02 |
| 164 | (R)-7-(2-(3-((4-(3-(1H-1,2,4-triazol-1-yl)propanoyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 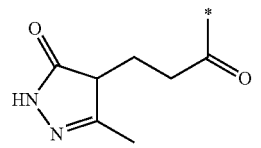 [SMILES: *C(=O)CCC1C(=O)NN=C1C] | 640.3 | 0.88 |

-continued

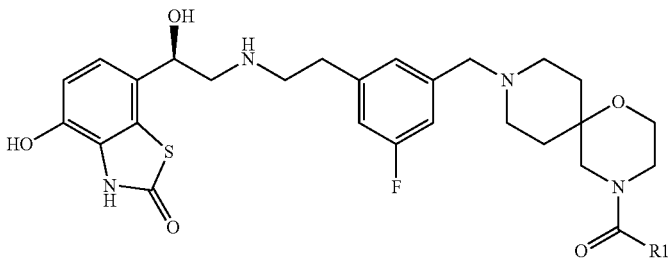

| Example no. | NAME | 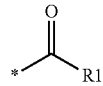 *—C(O)—R1 | Observed MWt + 1 | Retention time* (min) |
|---|---|---|---|---|
| 165 | (R)-7-(2-(3-((4-(1H-indole-4-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | indole-4-carbonyl | 660.4 | 1.03 |
| 166 | (R)-7-(2-(3-fluoro-5-((4-(2-(2-methylthiazol-4-yl)acetyl)-1-oxa-4,9-diazaspiro[5.5]undecan-9-yl)methyl)phenethylamino)-1-hydroxyethyl)-4-hydroxybenzo[d]thiazol-2(3H)-one | 2-(2-methylthiazol-4-yl)acetyl | 656.3 | 0.93 |
| 167 | (R)-7-(2-(3-((4-(2-(3,5-dimethylisoxazol-4-yl)acetyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 2-(3,5-dimethylisoxazol-4-yl)acetyl | 654.3 | 0.93 |
| 168 | (R)-7-(2-(3-((4-(2-(7-chloro-1H-indol-1-yl)acetyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 2-(7-chloro-1H-indol-1-yl)acetyl | 708.3 | 1.12 |
| 169 | (R)-7-(2-(3-((4-(biphenylcarbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | biphenylcarbonyl | 697.4 | 1.18 |
| 170 | (R)-7-(2-(3-fluoro-5-((4-(5-methyl-2-phenyl-2H-1,2,3-triazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one | 5-methyl-2-phenyl-2H-1,2,3-triazole-4-carbonyl | 702.3 | 1.13 |

-continued

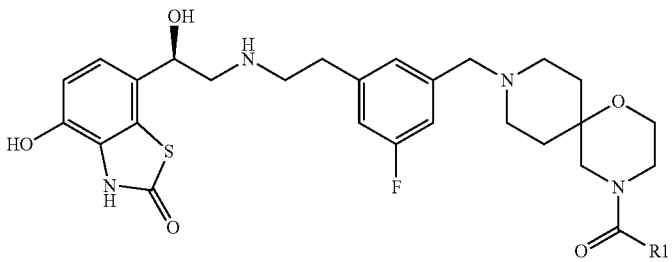

| Example no. | NAME | *—C(O)—R1 | Observed MWt + 1 | Retention time* (min) |
|---|---|---|---|---|
| 171 | (R)-7-(2-(3-((4-(biphenylcarbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | 3-biphenylcarbonyl | 697.4 | 1.34 |
| 172 | (R)-7-(2-(3-fluoro-5-((4-(quinoline-3-carbonyl)-1-oxa-4,9-diazaspiro[5.5]undecan-9-yl)methyl)phenethylamino)-1-hydroxyethyl)-4-hydroxybenzo[d]thiazol-2(3H)-one | quinoline-3-carbonyl | 672.3 | 1.05 |
| 173 | (R)-7-(2-(3-((4-(benzofuran-5-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | benzofuran-5-carbonyl | 661.3 | 1.12 |
| 174 | (R)-7-(2-(3-fluoro-5-((4-(2-phenethoxyacetyl)-1-oxa-4,9-diazaspiro[5.5]undecan-9-yl)methyl)phenethylamino)-1-hydroxyethyl)-4-hydroxybenzo[d]thiazol-2(3H)-one | 2-phenethoxyacetyl | 679.4 | 1.22 |
| 175 | (R)-7-(2-(3-fluoro-5-((4-(2-phenyl-1H-imidazole-5-carbonyl)-1-oxa-4,9-diazaspiro[5.5]undecan-9-yl)methyl)phenethylamino)-1-hydroxyethyl)-4-hydroxybenzo[d]thiazol-2(3H)-one | 2-phenyl-1H-imidazole-5-carbonyl | 687.4 | 1 |
| 176 | (R)-7-(2-(3-fluoro-5-((4-(2-methyl-2-phenylpropanoyl)-1-oxa-4,9-diazaspiro[5.5]undecan-9-yl)methyl)phenethylamino)-1-hydroxyethyl)-4-hydroxybenzo[d]thiazol-2(3H)-one | 2-methyl-2-phenylpropanoyl | 663.4 | 1.23 |

-continued

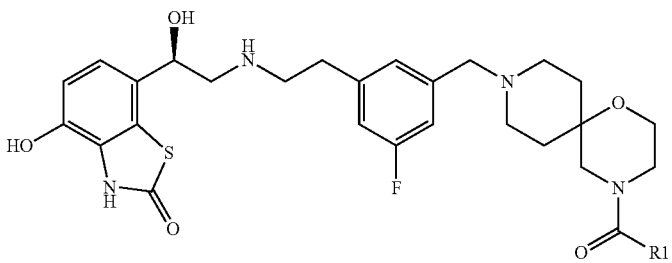

| Example no. | NAME | *—C(O)—R1 | Observed MWt + 1 | Retention time* (min) |
|---|---|---|---|---|
| 177 | (R)-7-(2-(3-fluoro-5-((4-(2-(2-(trifluoromethyl)-1H-benzo[d]imidazol-1-yl)acetyl)-1-oxa-4,9-diazaspiro[5.5]undecan-9-yl)methyl)phenethylamino)-1-hydroxyethyl)-4-hydroxybenzo[d]thiazol-2(3H)-one | | 743.3 | 1.14 |
| 178 | (R)-7-(2-(3-fluoro-5-((4-(quinoline-7-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 672.3 | 0.93 |
| 179 | (R)-7-(2-(3-fluoro-5-((4-(5-isopropylisoxazole-3-carbonyl)-1-oxa-4,9-diazaspiro[5.5]undecan-9-yl)methyl)phenethylamino)-1-hydroxyethyl)-4-hydroxybenzo[d]thiazol-2(3H)-one | | 654.4 | 1.13 |
| 180 | (R)-7-(2-(3-((4-(4,5-dimethylfuran-2-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 639.3 | 1.07 |
| 181 | (R)-7-(2-(3-fluoro-5-((4-(2-(4-hydroxyphenoxy)acetyl)-1-oxa-4,9-diazaspiro[5.5]undecan-9-yl)methyl)phenethylamino)-1-hydroxyethyl)-4-hydroxybenzo[d]thiazol-2(3H)-one | | 667.3 | 0.92 |
| 182 | (R)-7-(2-(3-((4-(5-chlorobenzofuran-2-carbonyl)-1-oxa-4,9-diazaspiro[5.5]undecan-9-yl)methyl)-5-fluorophenethylamino)-1-hydroxyethyl)-4-hydroxybenzo[d]thiazol-2(3H)-one | | 695.3 | 1.12 |

Analytical HPLC conditions: SunFire ™ C18 2.5 μm 4.6 × 30 mm column (Waters Corporation), MeCN/0.1% aq TFA, gradient 5-95% MeCN).

| Time (min) | % aqueous | % MeCN | Flow (ml/min) |
|---|---|---|---|
| 0.3 | 95 | 5 | 2.5 |
| 2.7 | 5 | 95 | 2.5 |
| 2.8 | 5 | 95 | 2.5 |
| 2.9 | 95 | 5 | 2.5 |

EXAMPLES 183-222

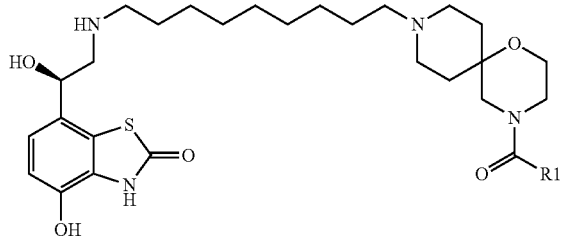

a) 9-Bromononanal

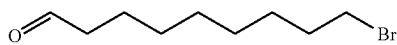 [SMILES: O=CCCCCCCCCBr]

N-Ethyldiisopropylamine (23 mL) and DMSO (9.7 mL) were added to a solution of 9-bromo-1-nonanol (10.0 g) in dry DCM (230 mL) at RT under argon. The mixture was cooled to −15° C. and sulfur trioxide-pyridine complex (21.4 g) was added in 4 portions at 5 min intervals. The mixture was stirred for 15 min after completion of the addition then water (200 mL) was added and the layers were separated. The organic layer was washed with 1M aqueous sodium bisulfate solution (4×250 mL), saturated aqueous potassium carbonate (250 mL) and brine (2×200 mL), dried over sodium sulphate, filtered and evaporated in vacuo to give the subtitled compound as an orange oil. Yield 9.02 g.

$^1$H NMR (400 MHz, CDCl$_3$): δ 9.77 (t, J=1.8 Hz, 1H), 3.40 (t, J=6.8 Hz, 2H), 2.42 (td, J=7.3, 1.8 Hz, 2H), 1.89-1.80 (m, 2H), 1.66-1.57 (m, 2H), 1.58-1.26 (m, 8H).

b) (R)-tert-Butyl 9-bromononyl(2-hydroxy-2-(4-hydroxy-2-oxo-2,3-dihydrobenzo[d]thiazol-7-yl)ethyl)carbamate

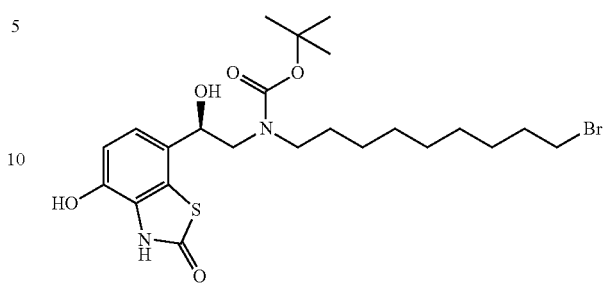

A solution of 9-bromononanal (example 183-222, step a) (3.48 g), (R)-7-(2-amino-1-hydroxyethyl)-4-hydroxybenzo[d]thiazol-2(3H)-one hydrochloride (WO2007027134, example 1 part d) (4.54 g) and acetic acid (0.99 mL) in dry DMF (91 mL) was stirred at RT for 30 min. The reaction mixture was cooled to 0° C. and sodium triacetoxyborohydride (5.00 g) was added in 4 portions at 2 min intervals. The resulting mixture was stirred at 0° C. for 5 min and then at RT for 1 h. Di-tert-butyl dicarbonate (4.12 g) was added to the reaction mixture which was stirred for 1.5 h then cooled to 0° C. and quenched with saturated aqueous sodium bicarbonate (220 mL). Ethyl acetate (200 mL) was added and the mixture was stirred vigorously for 15 min. The layers were separated and the aqueous layer was extracted with ethyl acetate (3×150 mL). The combined organic layers were dried over sodium sulphate, filtered and evaporated in vacuo. The residue was purified by silica gel chromatography eluting with 0-70% EtOAc/petroleum ether (40/60° C.) to give the subtitled compound as a yellow oil. Yield 1.68 g.

m/z 532 (M+H)$^+$ $^1$H NMR (400 MHz, CDCl$_3$): δ 7.02-6.90 (m, 1H); 6.78 (d, J=8.4 Hz, 1H), 4.92-4.87 (m, 1H), 3.63-3.27 (m, 5H), 3.20-3.04 (m, 1H), 1.89-1.79 (m, 2H), 1.71-1.17 (m, 21H)+3 exchangeable protons not observed.

c) (R)-tert-Butyl 2-hydroxy-2-(4-hydroxy-2-oxo-2,3-dihydrobenzo[d]thiazol-7-yl)ethyl(9-(4-(2,2,2-trifluoroacetyl)-1-oxa-4,9-diazaspiro[5.5]undecan-9-yl)nonyl)carbamate

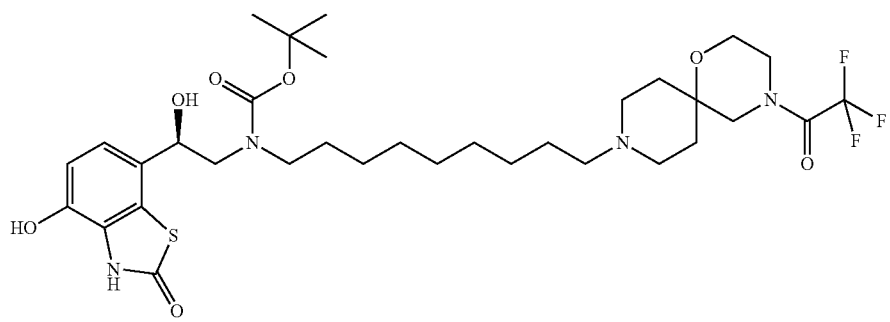 [SMILES: CC(C)(C)OC(=O)N(CCCCCCCCCN1CCC2(CC1)CN(C(=O)C(F)(F)F)CCO2)C[C@H](O)c1ccc(O)c2[nH]c(=O)sc12]

A solution of (R)-tert-butyl 9-bromononyl(2-hydroxy-2-(4-hydroxy-2-oxo-2,3-dihydrobenzo[d]thiazol-7-yl)ethyl)carbamate (example 183-222, step b) (1.68 g) in MeCN (8 mL) was added dropwise to a solution of 2,2,2-trifluoro-1-(1-oxa-4,9-diazaspiro[5.5]undecan-4-yl)ethanone trifluoroacetate (example 12, step d) (1.18 g) and triethylamine (0.81 mL) in MeCN (8 mL). The resulting mixture was stirred at 80° C. for 18 h. The reaction was allowed to cool to RT and the solvent was removed in vacuo. The brown residue was taken up in DCM and the organic layer was washed with water (×2) and brine, dried over sodium sulphate, filtered and evaporated in vacuo. The brown foam was purified by silica gel chromatography eluting with 0-10% MeOH/DCM to give the subtitled compound as a white solid. Yield 500 mg.

$^1$H NMR (400 MHz, CDCl$_3$): δ 6.95 (s, 1H), 6.80 (dd, J=8.3, 4.0 Hz, 1H), 4.93 (s, 1H), 3.79-3.26 (m, 10H), 3.03-2.64 (m, 6H), 2.10-1.98 (m, 4H), 1.78-1.70 (m, 2H), 1.48 (s, 9H), 1.36-0.96 (m, 12H) plus 3 exchangeables not observed.

d) (R)-tert-Butyl 9-(1-oxa-4,9-diazaspiro[5.5]undecan-9-yl)nonyl(2-hydroxy-2-(4-hydroxy-2-oxo-2,3-dihydrobenzo[d]thiazol-7-yl)ethyl)carbamate

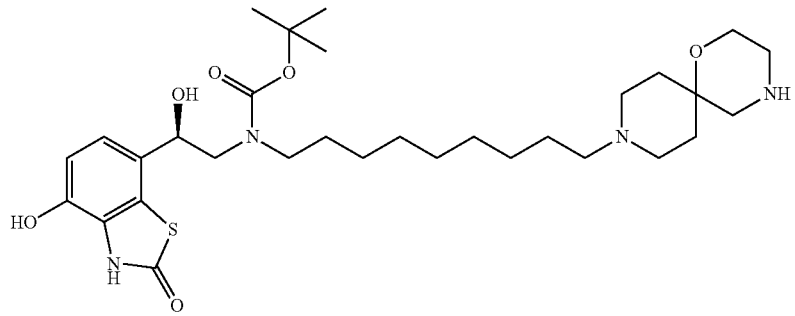 [SMILES: CC(C)(C)OC(=O)N(CCCCCCCCCN1CCC2(CC1)CNCCO2)C[C@H](O)c1ccc(O)c2[nH]c(=O)sc12]

A solution of potassium carbonate (165 mg) in water (24 mL) was added to a solution of (R)-tert-butyl 2-hydroxy-2-(4-hydroxy-2-oxo-2,3-dihydrobenzo[d]thiazol-7-yl)ethyl(9-(4-(2,2,2-trifluoroacetyl)-1-oxa-4,9-diazaspiro[5.5]undecan-9-yl)nonyl)carbamate (example 183-222, step c) (495 mg) in MeOH (24 mL). The resulting mixture was stirred at RT for 4 h. Methanol was removed by evaporation under a stream of nitrogen keeping the reaction mixture at 30° C. Water (20 mL) and brine (80 mL) were added and the mixture was extracted with EtOAc (5×60 mL). The combined organic layers were dried over sodium sulphate, filtered and evaporated in vacuo. The brown solid residue was purified by silica gel chromatography eluting with 0-20% (2M NH$_3$ in MeOH)/DCM to give the subtitled compound as a yellow solid. Yield 323 mg.

m/z 607 (M+H)$^+$ $^1$H NMR (400 MHz, DMSO): δ 6.80-6.68 (m, 1H), 6.65 (d, J=8.2 Hz, 1H), 5.58 (br s, 1H), 4.69-4.56 (m, 1H), 3.44 (t, J=3.9 Hz, 2H), 3.20-3.11 (m, 2H), 3.05-2.94 (m, 2H), 2.57 (t, J=5.2 Hz, 2H), 2.50-2.46 (m, 2H), 2.40-2.31 (m, 2H), 2.25-2.13 (m, 4H), 1.77-1.68 (m, 2H), 1.45-1.02 (m, 25H)+3 exchangeable protons not observed.

e) Parallel Chemistry

Preparation of Examples 183-222

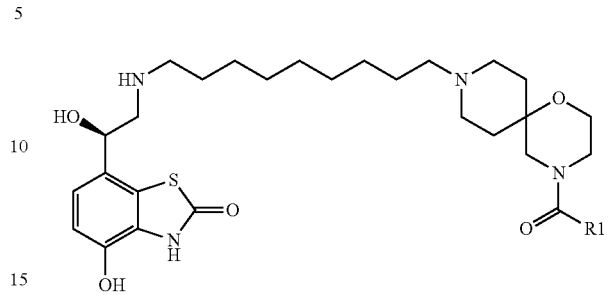

A solution of (R)-tert-butyl 9-(1-oxa-4,9-diazaspiro[5.5]undecan-9-yl)nonyl(2-hydroxy-2-(4-hydroxy-2-oxo-2,3-dihydrobenzo[d]thiazol-7-yl)ethyl)carbamate (292 mg) and triethylamine (examples 183-222, step d) (0.20 mL) in NMP (1.14 mL) was dispensed as aliquots of 30 uL total volume. To each aliquot was added a solution of the appropriate acid (0.01 mmol) in NMP (80 uL) followed by a solution of HATU (4.0 mg) in NMP (30 uL). The reaction mixture was allowed to stand at room temperature overnight. Acetonitrile (800 uL) was added and the solution passed through 'Tosic-65' resin (350 mg). The resin was washed with acetonitrile (800 uL) and the combined washings collected and again passed through the 'Tosic-65' resin. The resin was then washed with acetonitrile (3 mL). Ammonia (3.5M in methanol, 2.4 mL) was passed through the resin and the resultant washings evaporated under a stream of nitrogen gas. The residue was dissolved in formic acid (250 uL) and the mixture allowed to stand at room temperature overnight. Acetonitrile (600 uL) was added and the solution passed through 'Tosic-65' resin (350 mg). The resin was washed with acetonitrile (800 uL) and the combined washings collected and again passed through the 'Tosic-65' resin. The resin was then washed with acetonitrile (3 mL). Ammonia (3.5M in methanol, 2.4 mL) was passed through the resin and the resultant washings evaporated under a stream of nitrogen gas. DMSO (360 uL) was added to the residue and the resultant solution passed through a 'Sunfire' prep C18 column (19×50 mm) using a focus gradient elution of acetonitrile vs aq 0.1% TFA for purification. The fractions containing product were evaporated to yield the title compounds.

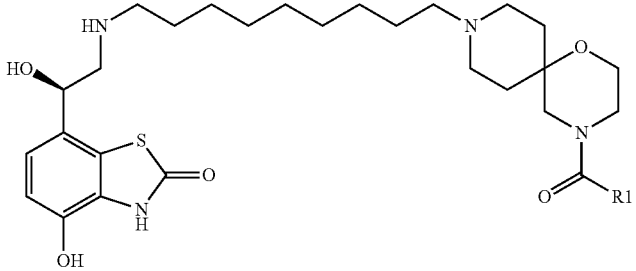

| Example no. | NAME | *—C(O)—R1 | Observed MWt + 1 | Retention time* (min) |
|---|---|---|---|---|
| 183 | (R)-4-hydroxy-7-(1-hydroxy-2-(9-(4-(4-(thiophen-2-yl)butanoyl)-1-oxa-4,9-diazaspiro[5.5]undecan-9-yl)nonylamino)ethyl)benzo[d]thiazol-2(3H)-one | | 659.4 | 1.24 |
| 184 | (R)-4-hydroxy-7-(1-hydroxy-2-(9-(4-(1-methyl-1H-pyrrole-2-carbonyl)-1-oxa-4,9-diazaspiro[5.5]undecan-9-yl)nonylamino)ethyl)benzo[d]thiazol-2(3H)-one | | 614.4 | 1.11 |
| 185 | (R)-4-hydroxy-7-(1-hydroxy-2-(9-(4-(2-(thiophen-2-yl)acetyl)-1-oxa-4,9-diazaspiro[5.5]undecan-9-yl)nonylamino)ethyl)benzo[d]thiazol-2(3H)-one | | 631.3 | 1.11 |
| 186 | (R)-4-hydroxy-7-(1-hydroxy-2-(9-(4-(2-phenylacetyl)-1-oxa-4,9-diazaspiro[5.5]undecan-9-yl)nonylamino)ethyl)benzo[d]thiazol-2(3H)-one | | 625.4 | 1.16 |
| 187 | (R)-4-hydroxy-7-(1-hydroxy-2-(9-(4-(3-phenylpropanoyl)-1-oxa-4,9-diazaspiro[5.5]undecan-9-yl)nonylamino)ethyl)benzo[d]thiazol-2(3H)-one | | 639.4 | 1.2 |
| 188 | (R)-4-hydroxy-7-(1-hydroxy-2-(9-(4-(4-phenylbutanoyl)-1-oxa-4,9-diazaspiro[5.5]undecan-9-yl)nonylamino)ethyl)benzo[d]thiazol-2(3H)-one | | 653.4 | 1.25 |
| 189 | (R)-4-hydroxy-7-(1-hydroxy-2-(9-(4-(2-methyl-2-phenylpropanoyl)-1-oxa-4,9-diazaspiro[5.5]undecan-9-yl)nonylamino)ethyl)benzo[d]thiazol-2(3H)-one | | 653.4 | 1.25 |

-continued

| Example no. | NAME | 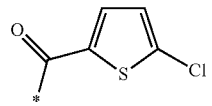 *—R1 | Observed MWt + 1 | Retention time* (min) |
|---|---|---|---|---|
| 190 | (R)-7-(2-(9-(4-(5-chlorothiophene-2-carbonyl)-1-oxa-4,9-diazaspiro[5.5]undecan-9-yl)nonylamino)-1-hydroxyethyl)-4-hydroxybenzo[d]thiazol-2(3H)-one | 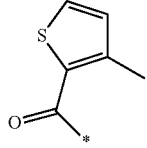 [SMILES: *C(=O)c1sccc1C] | 651.3 | 1.21 |
| 191 | (R)-4-hydroxy-7-(1-hydroxy-2-(9-(4-(3-methylthiophene-2-carbonyl)-1-oxa-4,9-diazaspiro[5.5]undecan-9-yl)nonylamino)ethyl)benzo[d]thiazol-2(3H)-one | 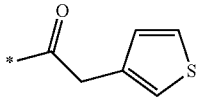 [SMILES: *C(=O)Cc1ccsc1] | 631.4 | 1.05 |
| 192 | (R)-4-hydroxy-7-(1-hydroxy-2-(9-(4-(2-(thiophen-3-yl)acetyl)-1-oxa-4,9-diazaspiro[5.5]undecan-9-yl)nonylamino)ethyl)benzo[d]thiazol-2(3H)-one | | 631.3 | 1.14 |
| 193 | (R)-4-hydroxy-7-(1-hydroxy-2-(9-(4-(3-methylfuran-2-carbonyl)-1-oxa-4,9-diazaspiro[5.5]undecan-9-yl)nonylamino)ethyl)benzo[d]thiazol-2(3H)-one | 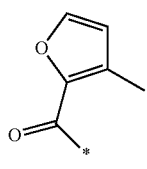 [SMILES: *C(=O)c1occc1C] | 615.4 | 1.12 |
| 194 | (R)-7-(2-(9-(4-(benzo[b]thiophene-2-carbonyl)-1-oxa-4,9-diazaspiro[5.5]undecan-9-yl)nonylamino)-1-hydroxyethyl)-4-hydroxybenzo[d]thiazol-2(3H)-one | 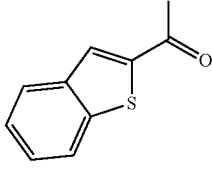 | 667.4 | 1.16 |
| 195 | (R)-7-(2-(9-(4-(4,5-dimethylfuran-2-carbonyl)-1-oxa-4,9-diazaspiro[5.5]undecan-9-yl)nonylamino)-1-hydroxyethyl)-4-hydroxybenzo[d]thiazol-2(3H)-one | 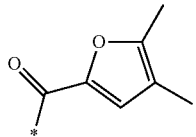 [SMILES: *C(=O)c1cc(C)c(C)o1] | 629.4 | 1.17 |
| 196 | (R)-4-hydroxy-7-(1-hydroxy-2-(9-(4-(6-methylpicolinoyl)-1-oxa-4,9-diazaspiro[5.5]undecan-9-yl)nonylamino)ethyl)benzo[d]thiazol-2(3H)-one | 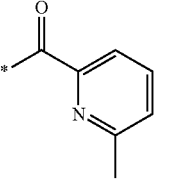 | 626.4 | 1.04 |

-continued

| Example no. | NAME | 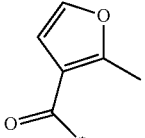 *—C(O)—R1 | Observed MWt + 1 | Retention time* (min) |
|---|---|---|---|---|
| 197 | (R)-4-hydroxy-7-(1-hydroxy-2-(9-(4-(2-methylfuran-3-carbonyl)-1-oxa-4,9-diazaspiro[5.5]undecan-9-yl)nonylamino)ethyl)benzo[d]thiazol-2(3H)-one | 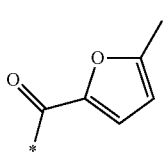 [SMILES: *C(=O)c1ccc(C)o1] | 615.4 | 1.1 |
| 198 | (R)-4-hydroxy-7-(1-hydroxy-2-(9-(4-(5-methylfuran-2-carbonyl)-1-oxa-4,9-diazaspiro[5.5]undecan-9-yl)nonylamino)ethyl)benzo[d]thiazol-2(3H)-one | 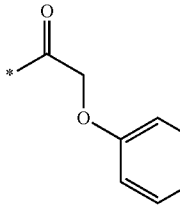 | 615.4 | 1.11 |
| 199 | (R)-4-hydroxy-7-(1-hydroxy-2-(9-(4-(2-phenoxyacetyl)-1-oxa-4,9-diazaspiro[5.5]undecan-9-yl)nonylamino)ethyl)benzo[d]thiazol-2(3H)-one | 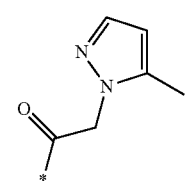 [SMILES: *C(=O)Cn1nccc1C] | 641.4 | 1.15 |
| 200 | (R)-4-hydroxy-7-(1-hydroxy-2-(9-(4-(2-(5-methyl-1H-pyrazol-1-yl)acetyl)-1-oxa-4,9-diazaspiro[5.5]undecan-9-yl)nonylamino)ethyl)benzo[d]thiazol-2(3H)-one | 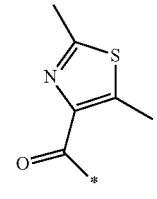 [SMILES: *C(=O)c1nc(C)sc1C] | 629.4 | 0.96 |
| 201 | (R)-7-(2-(9-(4-(2,5-dimethylthiazole-4-carbonyl)-1-oxa-4,9-diazaspiro[5.5]undecan-9-yl)nonylamino)-1-hydroxyethyl)-4-hydroxybenzo[d]thiazol-2(3H)-one | 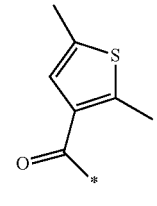 [SMILES: *C(=O)c1cc(C)sc1C] | 646.4 | 1.08 |
| 202 | (R)-7-(2-(9-(4-(2,5-dimethylthiophene-3-carbonyl)-1-oxa-4,9-diazaspiro[5.5]undecan-9-yl)nonylamino)-1-hydroxyethyl)-4-hydroxybenzo[d]thiazol-2(3H)-one | | 645.4 | 1.13 |

-continued

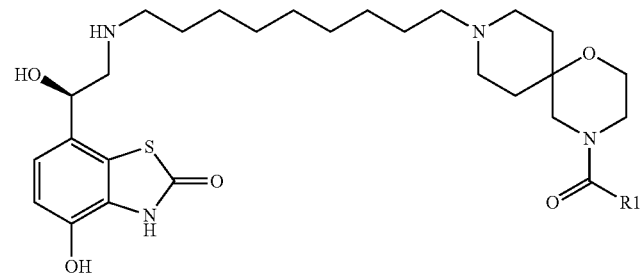

| Example no. | NAME | *—C(O)—R1 | Observed MWt + 1 | Retention time* (min) |
|---|---|---|---|---|
| 203 | (R)-7-(2-(9-(4-(2-(benzyloxy)acetyl)-1-oxa-4,9-diazaspiro[5.5]undecan-9-yl)nonylamino)-1-hydroxyethyl)-4-hydroxybenzo[d]thiazol-2(3H)-one | benzyloxyacetyl | 655.4 | 1.18 |
| 204 | (R)-4-hydroxy-7-(1-hydroxy-2-(9-(4-(2-(3-methyl-1H-pyrazol-1-yl)acetyl)-1-oxa-4,9-diazaspiro[5.5]undecan-9-yl)nonylamino)ethyl)benzo[d]thiazol-2(3H)-one | (3-methyl-1H-pyrazol-1-yl)acetyl | 629.4 | 1.04 |
| 205 | (R)-4-hydroxy-7-(1-hydroxy-2-(9-(4-(2-methylthiophene-3-carbonyl)-1-oxa-4,9-diazaspiro[5.5]undecan-9-yl)nonylamino)ethyl)benzo[d]thiazol-2(3H)-one | 2-methylthiophene-3-carbonyl | 631.4 | 1.12 |
| 206 | (R)-4-hydroxy-7-(1-hydroxy-2-(9-(4-(3-phenoxypropanoyl)-1-oxa-4,9-diazaspiro[5.5]undecan-9-yl)nonylamino)ethyl)benzo[d]thiazol-2(3H)-one | 3-phenoxypropanoyl | 655.4 | 1.22 |
| 207 | (R)-4-hydroxy-7-(1-hydroxy-2-(9-(4-(3-(thiophen-2-yl)propanoyl)-1-oxa-4,9-diazaspiro[5.5]undecan-9-yl)nonylamino)ethyl)benzo[d]thiazol-2(3H)-one | 3-(thiophen-2-yl)propanoyl | 645.4 | 1.19 |
| 208 | (R)-4-hydroxy-7-(1-hydroxy-2-(9-(4-(2-(3-methylisoxazol-5-yl)acetyl)-1-oxa-4,9-diazaspiro[5.5]undecan-9-yl)nonylamino)ethyl)benzo[d]thiazol-2(3H)-one | (3-methylisoxazol-5-yl)acetyl | 630.4 | 1.05 |
| 209 | (R)-7-(2-(9-(4-(benzofuran-5-carbonyl)-1-oxa-4,9-diazaspiro[5.5]undecan-9-yl)nonylamino)-1-hydroxyethyl)-4-hydroxybenzo[d]thiazol-2(3H)-one | benzofuran-5-carbonyl | 651.4 | 1.14 |

-continued

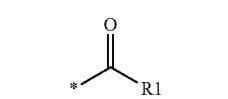

| Example no. | NAME |  | Observed MWt + 1 | Retention time* (min) |
|---|---|---|---|---|
| 210 | (R)-4-hydroxy-7-(1-hydroxy-2-(9-(4-(2 (2-methylthiazol-4-yl)acetyl)-1-oxa-4,9-diazaspiro[5.5]undecan-9-yl)nonylamino)ethyl)benzo[d]thiazol-2(3H)-one | 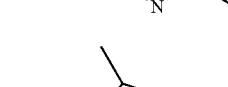 | 646.4 | 1.05 |
| 211 | (R)-7-(2-(9-(4-(2-(2,4-dimethylthiazol-5-yl)acetyl)-1-oxa-4,9-diazaspiro[5.5]undecan-9-yl)nonylamino)-1-hydroxyethyl)-4-hydroxybenzo[d]thiazol-2(3H)-one | 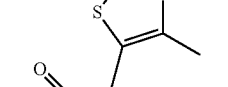 | 660.4 | 0.97 |
| 212 | (R)-7-(2-(9-(4-(2-chlorothiophene-3-carbonyl)-1-oxa-4,9-diazaspiro[5.5]undecan-9-yl)nonylamino)-1-hydroxyethyl)-4-hydroxybenzo[d]thiazol-2(3H)-one | 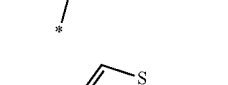 | 651.3 | 1.14 |
| 213 | (R)-4-hydroxy-7-(1-hydroxy-2-(9-(4-(4-methylthiophene-2-carbonyl)-1-oxa-4,9-diazaspiro[5.5]undecan-9-yl)nonylamino)ethyl)benzo[d]thiazol-2(3H)-one | 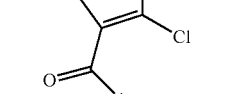 | 631.4 | 1.15 |
| 214 | (R)-4-hydroxy-7-(1-hydroxy-2-(9-(4-(5-isopropylisoxazole-3-carbonyl)-1-oxa-4,9-diazaspiro[5.5]undecan-9-yl)nonylamino)ethyl)benzo[d]thiazol-2(3H)-one |  | 644.4 | 1.3 |
| 215 | (R)-4-hydroxy-7-(1-hydroxy-2-(9-(4-(2-methylbenzo[d]thiazole-5-carbonyl)-1-oxa-4,9-diazaspiro[5.5]undecan-9-yl)nonylamino)ethyl)benzo[d]thiazol-2(3H)-one | 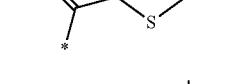 | 682.4 | 1.13 |
| 216 | (R)-7-(2-(9-(4-(2-tert-butylthiazole-4-carbonyl)-1-oxa-4,9-diazaspiro[5.5]undecan-9-yl)nonylamino)-1-hydroxyethyl)-4-hydroxybenzo[d]thiazol-2(3H)-one | | 674.4 | 1.26 |

-continued

| Example no. | NAME | *—C(O)—R1 | Observed MWt + 1 | Retention time* (min) |
|---|---|---|---|---|
| 217 | (R)-4-hydroxy-7-(1-hydroxy-2-(9-(4-(2-(trifluoromethyl)thiazole-4-carbonyl)-1-oxa-4,9-diazaspiro[5.5]undecan-9-yl)nonylamino)ethyl)benzo[d]thiazol-2(3H)-one | 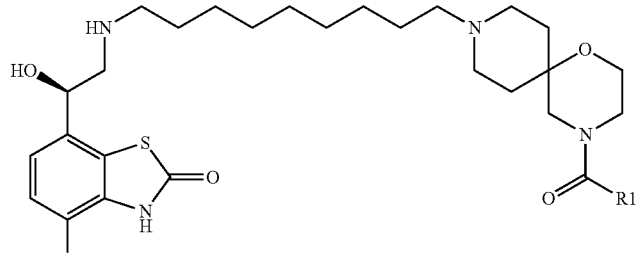 | 686.3 | 1.18 |
| 218 | (R)-7-(2-(9-(4-(2-cyclopropylthiazole-4-carbonyl)-1-oxa-4,9-diazaspiro[5.5]undecan-9-yl)nonylamino)-1-hydroxyethyl)-4-hydroxybenzo[d]thiazol-2(3H)-one | 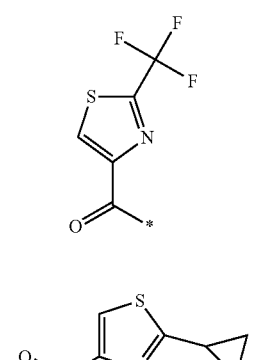 | 658.4 | 1.16 |
| 219 | (R)-4-hydroxy-7-(1-hydroxy-2-(9-(4-(2-propylthiazole-4-carbonyl)-1-oxa-4,9-diazaspiro[5.5]undecan-9-yl)nonylamino)ethyl)benzo[d]thiazol-2(3H)-one | 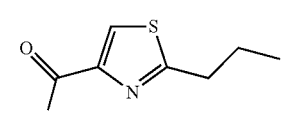 | 660.4 | 1.16 |
| 220 | (R)-7-(2-(9-(4-(2-cyclobutylthiazole-4-carbonyl)-1-oxa-4,9-diazaspiro[5.5]undecan-9-yl)nonylamino)-1-hydroxyethyl)-4-hydroxybenzo[d]thiazol-2(3H)-one | 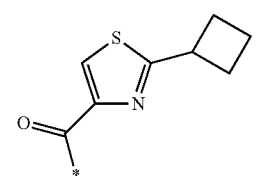 [SMILES: *C(=O)c1csc(C2CCC2)n1] | 672.4 | 1.17 |
| 221 | (R)-7-(2-(9-(4-(2-cyclopentylthiazole-4-carbonyl)-1-oxa-4,9-diazaspiro[5.5]undecan-9-yl)nonylamino)-1-hydroxyethyl)-4-hydroxybenzo[d]thiazol-2(3H)-one | 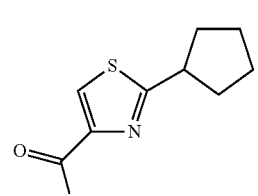 | 686.4 | 1.23 |
| 222 | (R)-7-(2-(9-(4-(4,5-dimethylthiophene-2-carbonyl)-1-oxa-4,9-diazaspiro[5.5]undecan-9-yl)nonylamino)-1-hydroxyethyl)-4-hydroxybenzo[d]thiazol-2(3H)-one | 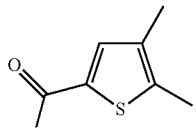 | 645.4 | 1.29 |

*Analytical HPLC conditions: SunFire ™ C18 2.5 µm 4.6 × 30 mm column (Waters Corporation), MeCN/0.1% aq TFA, gradient 5-95% MeCN).

| Time (min) | % aqueous | % MeCN | Flow (ml/min) |
| --- | --- | --- | --- |
| 0.3 | 95 | 5 | 2.5 |
| 2.7 | 5 | 95 | 2.5 |
| 2.8 | 5 | 95 | 2.5 |
| 2.9 | 95 | 5 | 2.5 |

$^1$H NMR (400 MHz, CDCl$_3$): δ 6.88-6.50 (m, 6H), 4.86-4.64 (br s, 1H), 4.34-4.15 (br s, 3H), 4.11-3.87 (m, 2H), 3.70-3.01 (m, 11H), 2.95-2.73 (br s, 2H), 2.04-1.81 (m, 2H), 1.56-1.37 (m, 11H) plus 3 exchangeables not observed.

b) (R)-tert-Butyl 4-(2-(1-oxa-4,9-diazaspiro[5.5]undecan-9-yl)ethoxy)benzyl(2-hydroxy-2-(4-hydroxy-2-oxo-2,3-dihydrobenzo[d]thiazol-7-yl)ethyl)carbamate

EXAMPLES 223-263

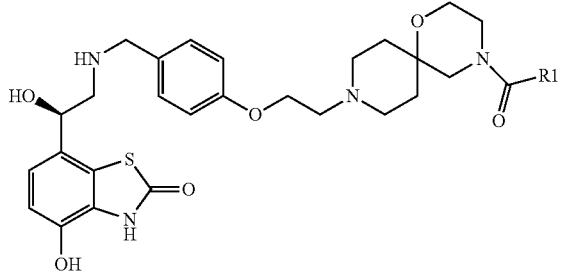

a) (R)-tert-Butyl 2-hydroxy-2-(4-hydroxy-2-oxo-2,3-dihydrobenzo[d]thiazol-7-yl)ethyl(4-(2-(4-(2,2,2-trifluoroacetyl)-1-oxa-4,9-diazaspiro[5.5]undecan-9-yl)ethoxy)benzyl)carba mate

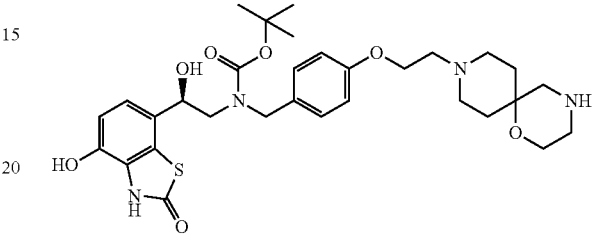

A solution of potassium carbonate (240 mg) in water (35 mL) was added to a solution of (R)-tert-butyl 2-hydroxy-2-(4-hydroxy-2-oxo-2,3-dihydrobenzo[d]thiazol-7-yl)ethyl(4-(2-(4-(2,2,2-trifluoroacetyl)-1-oxa-4,9-diazaspiro[5.5]undecan-9-yl)ethoxy)benzyl)carbamate (examples 223-263, step a) (725 mg) in MeOH (35 mL). The resulting mixture was stirred at RT for 5 h. Methanol was removed by evaporation under a stream of nitrogen keeping the reaction mixture at 25°

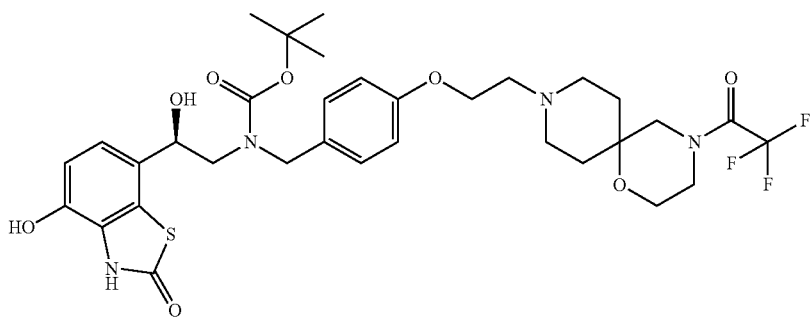 [SMILES: CC(C)(C)OC(=O)N(Cc1ccc(OCCN2CCC3(CC2)CN(C(=O)C(F)(F)F)CCO3)cc1)C[C@H](O)c1ccc(O)c2[nH]c(=O)sc12]

A solution of (R)-2-(4-((tert-butoxycarbonyl(2-hydroxy-2-(4-hydroxy-2-oxo-2,3-dihydrobenzo[d]thiazol-7-yl)ethyl)amino)methyl)phenoxy)ethyl methanesulfonate (example 108, step c) (2.20 g) in MeCN (8.5 mL) was added dropwise to a solution of 2,2,2-trifluoro-1-(1-oxa-4,9-diazaspiro[5.5]undecan-4-yl)ethanone trifluoroacetate (example 12, step d) (1.18 g) and triethylamine (0.81 mL) in MeCN (8.5 mL) at RT under argon. The resulting mixture was stirred at 60° C. under argon for 25 h. After cooling to RT the solvent was removed in vacuo. The brown residue was taken up in DCM (35 mL), washed with water (2×35 mL), dried over sodium sulphate, filtered and evaporated in vacuo. The yellow solid was purified by silica gel chromatography eluting with 0-10% MeOH/DCM to give the subtitle compound as a yellow solid. Yield 729 mg.

C. Water (20 mL) and brine (30 mL) were added and the mixture was extracted with ethyl acetate (7×30 mL). The combined organic layers were dried over sodium sulphate, filtered and evaporated in vacuo. The residue was purified by silica gel chromatography eluting with 0-20% (2M NH$_3$ in MeOH)/DCM to give the subtitled compound as a white solid. Yield 385 mg.

$^1$H NMR (400 MHz, D$_6$-DMSO): δ 7.06-6.97 (m, 2H), 6.83 (d, J=8.6 Hz, 2H), 6.78-6.62 (m, 2H), 5.64 (s, 1H), 4.68 (br s, 1H), 4.24 (s, 2H), 3.98 (t, J=5.6 Hz, 2H), 3.50 (t, 2H), 3.24-3.02 (m, 2H), 2.68-2.60 (m, 4H), 2.57 (s, 2H), 2.52-2.47 (m, 2H), 2.32 (td, J=11.9, 3.0 Hz, 2H), 1.76 (d, J=13.0 Hz, 2H), 1.43 (td, J=10.8, 3.7 Hz, 2H), 1.31 (s, 3H), 1.22 (s, 6H) plus 3 exchangeables not observed.

c) Parallel Chemistry

Preparation of Examples 223-263

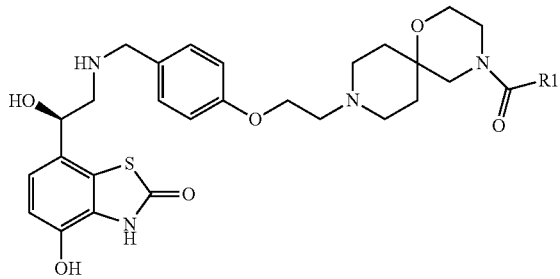

A solution of (R)-tert-butyl 4-(2-(1-oxa-4,9-diazaspiro[5.5]undecan-9-yl)ethoxy)benzyl(2-hydroxy-2-(4-hydroxy-2-oxo-2,3-dihydrobenzo[d]thiazol-7-yl)ethyl)carbamate (example 223-263, step b) (297 mg) and triethylamine (0.20 mL) in NMP (1.24 mL) was dispensed as aliquots of 30 uL total volume. To each aliquot was added a solution of the appropriate acid (0.01 mmol) in NMP (80 uL) followed by a solution of HATU (4.0 mg) in NMP (30 uL). The reaction mixture was allowed to stand at RT overnight. Acetonitrile (800 uL) was added and the solution passed through 'Tosic-65' resin (350 mg). The resin was washed with acetonitrile (800 uL) and the combined washings collected and again passed through the 'Tosic-65' resin. The resin was then washed with acetonitrile (3 mL). Ammonia (3.5M in methanol, 2.4 mL) was passed through the resin and the resultant washings evaporated under a stream of nitrogen gas. The residue was dissolved in formic acid (250 uL) and the mixture allowed to stand at room temperature overnight. Acetonitrile (600 uL) was added and the solution passed through 'Tosic-65' resin (350 mg). The resin was washed with acetonitrile (800 uL) and the combined washings collected and again passed through the 'Tosic-65' resin. The resin was then washed with acetonitrile (3 mL). Ammonia (3.5M in methanol, 2.4 mL) was passed through the resin and the resultant washings evaporated under a stream of nitrogen gas. DMSO (360 uL) was added to the residue and the resultant solution passed through a 'Sunfire' prep C18 column (19×50 mm) using a focus gradient elution of acetonitrile vs aq 0.1% TFA for purification. The fractions containing product were evaporated to yield the title compounds.

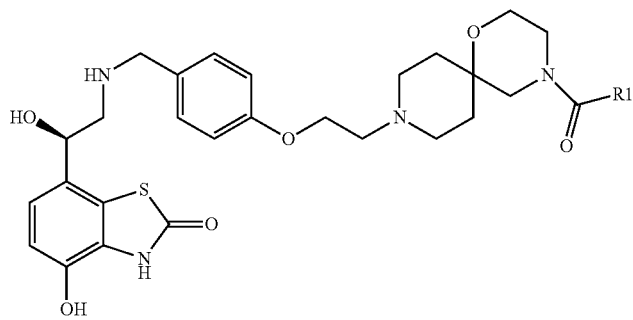

| Example no. | NAME | *⟶R1 | Observed MWt + 1 | Retention time* (min) |
|---|---|---|---|---|
| 223 | (R)-7-(2-(4-(2-(4-benzoyl-1-oxa-4,9-diazaspiro[5.5]undecan-9-yl)ethoxy)benzylamino)-1-hydroxyethyl)-4-hydroxybenzo[d]thiazol-2(3H)-one | *-C(O)-Ph | 619.3 | 1.06 |
| 224 | (R)-4-hydroxy-7-(1-hydroxy-2-(4-(2-(4-(4-(thiophen-2-yl)butanoyl)-1-oxa-4,9-diazaspiro[5.5]undecan-9-yl)ethoxy)benzylamino)ethyl)benzo[d]thiazol-2(3H)-one | *-C(O)CH2CH2CH2-(thiophen-2-yl) | 667.3 | 1.15 |
| 225 | (R)-4-hydroxy-7-(1-hydroxy-2-(4-(2-(4-(1-methyl-1H-pyrrole-2-carbonyl)-1-oxa-4,9-diazaspiro[5.5]undecan-9-yl)ethoxy)benzylamino)ethyl)benzo[d]thiazol-2(3H)-one | *-C(O)-(1-methylpyrrol-2-yl) | 622.3 | 1 |
| 226 | (R)-4-hydroxy-7-(1-hydroxy-2-(4-(2-(4-(2-(thiophen-2-yl)acetyl)-1-oxa-4,9-diazaspiro[5.5]undecan-9-yl)ethoxy)benzylamino)ethyl)benzo[d]thiazol-2(3H)-one | *-C(O)CH2-(thiophen-2-yl) | 639.3 | 1.01 |

-continued

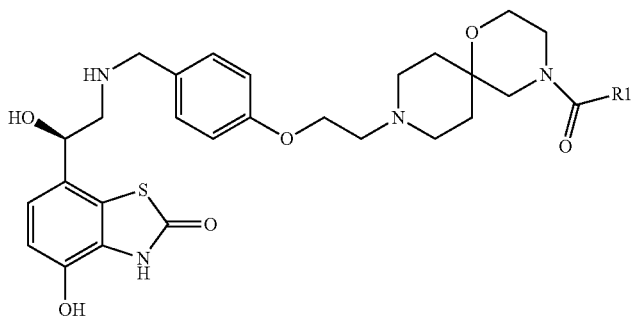

| Example no. | NAME | *−C(=O)−R1 | Observed MWt + 1 | Retention time* (min) |
|---|---|---|---|---|
| 227 | (R)-4-hydroxy-7-(1-hydroxy-2-(4-(2-(4-(2-phenylacetyl)-1-oxa-4,9-diazaspiro[5.5]undecan-9-yl)ethoxy)benzylamino)ethyl)benzo[d]thiazol-2(3H)-one | phenylacetyl | 633.3 | 1.04 |
| 228 | (R)-4-hydroxy-7-(1-hydroxy-2-(4-(2-(4-(3-phenylpropanoyl)-1-oxa-4,9-diazaspiro[5.5]undecan-9-yl)ethoxy)benzylamino)ethyl)benzo[d]thiazol-2(3H)-one | 3-phenylpropanoyl | 647.4 | 1.11 |
| 229 | (R)-4-hydroxy-7-(1-hydroxy-2-(4-(2-(4-(4-phenylbutanoyl)-1-oxa-4,9-diazaspiro[5.5]undecan-9-yl)ethoxy)benzylamino)ethyl)benzo[d]thiazol-2(3H)-one | 4-phenylbutanoyl | 661.4 | 1.17 |
| 230 | (R)-4-hydroxy-7-(1-hydroxy-2-(4-(2-(4-(2-methyl-2-phenylpropanoyl)-1-oxa-4,9-diazaspiro[5.5]undecan-9-yl)ethoxy)benzylamino)ethyl)benzo[d]thiazol-2(3H)-one | 2-methyl-2-phenylpropanoyl | 661.4 | 1.18 |
| 231 | (R)-7-(2-(4-(2-(4-(5-chlorothiophene-2-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 5-chlorothiophene-2-carbonyl | 659.2 | 1.1 |
| 232 | (R)-4-hydroxy-7-(1-hydroxy-2-(4-(2-(4-(3-methylthiophene-2-carbonyl)-1-oxa-4,9-diazaspiro[5.5]undecan-9-yl)ethoxy)benzylamino)ethyl)benzo[d]thiazol-2(3H)-one | 3-methylthiophene-2-carbonyl | 639.3 | 1.03 |
| 233 | (R)-4-hydroxy-7-(1-hydroxy-2-(4-(2-(4-(2-(thiophen-3-yl)acetyl)-1-oxa-4,9-diazaspiro[5.5]undecan-9-yl)ethoxy)benzylamino)ethyl)benzo[d]thiazol-2(3H)-one | 2-(thiophen-3-yl)acetyl | 639.3 | 1 |

-continued

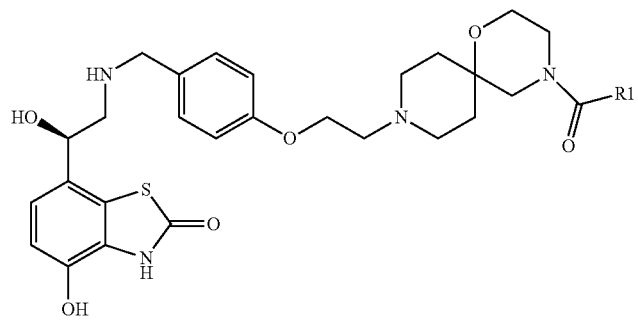

| Example no. | NAME | *—C(O)—R1 | Observed MWt + 1 | Retention time* (min) |
|---|---|---|---|---|
| 234 | (R)-4-hydroxy-7-(1-hydroxy-2-(4-(2-(4-(3-methylfuran-2-carbonyl)-1-oxa-4,9-diazaspiro[5.5]undecan-9-yl)ethoxy)benzylamino)ethyl)benzo[d]thiazol-2(3H)-one | 3-methylfuran-2-carbonyl | 623.3 | 0.97 |
| 235 | (R)-7-(2-(4-(2-(4-(benzo[b]thiophene-2-carbonyl)-1-oxa-4,9-diazaspiro[5.5]undecan-9-yl)ethoxy)benzylamino)-1-hydroxyethyl)-4-hydroxybenzo[d]thiazol-2(3H)-one | benzo[b]thiophene-2-carbonyl | 675.3 | 1.09 |
| 236 | (R)-7-(2-(4-(2-(4-(4,5-dimethylfuran-2-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 4,5-dimethylfuran-2-carbonyl | 637.3 | 0.99 |
| 237 | (R)-4-hydroxy-7-(1-hydroxy-2-(4-(2-(4-(6-methylpicolinoyl)-1-oxa-4,9-diazaspiro[5.5]undecan-9-yl)ethoxy)benzylamino)ethyl)benzo[d]thiazol-2(3H)-one | 6-methylpicolinoyl | 634.3 | 0.88 |
| 238 | (R)-4-hydroxy-7-(1-hydroxy-2-(4-(2-(4-(2-methylfuran-3-carbonyl)-1-oxa-4,9-diazaspiro[5.5]undecan-9-yl)ethoxy)benzylamino)ethyl)benzo[d]thiazol-2(3H)-one | 2-methylfuran-3-carbonyl | 623.3 | 0.91 |
| 239 | (R)-4-hydroxy-7-(1-hydroxy-2-(4-(2-(4-(5-methylfuran-2-carbonyl)-1-oxa-4,9-diazaspiro[5.5]undecan-9-yl)ethoxy)benzylamino)ethyl)benzo[d]thiazol-2(3H)-one | 5-methylfuran-2-carbonyl | 623.3 | 1.02 |

-continued

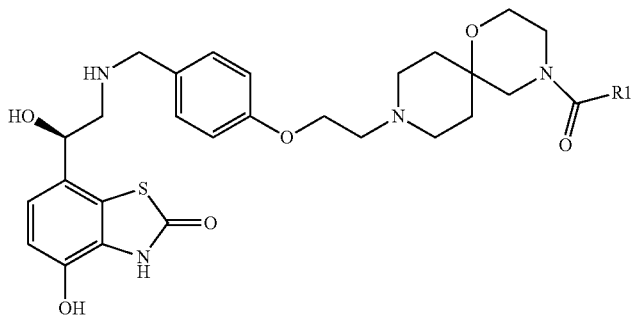

| Example no. | NAME | *⟶C(O)R1 | Observed MWt + 1 | Retention time* (min) |
|---|---|---|---|---|
| 240 | (R)-4-hydroxy-7-(1-hydroxy-2-(4-(2-(4-(2-phenoxyacetyl)-1-oxa-4,9-diazaspiro[5.5]undecan-9-yl)ethoxy)benzylamino)ethyl)benzo[d]thiazol-2(3H)-one | 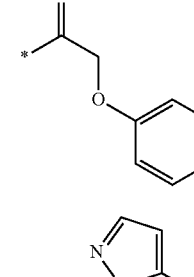 | 649.3 | 1.13 |
| 241 | (R)-4-hydroxy-7-(1-hydroxy-2-(4-(2-(4-(2-(5-methyl-1H-pyrazol-1-yl)acetyl)-1-oxa-4,9-diazaspiro[5.5]undecan-9-yl)ethoxy)benzylamino)ethyl)benzo[d]thiazol-2(3H)-one | 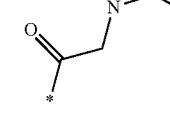 | 637.4 | 0.96 |
| 242 | (R)-7-(2-(4-(2-(4-(2,5-dimethylthiazole-4-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 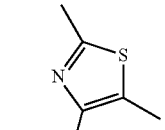 | 654.3 | 0.92 |
| 243 | (R)-7-(2-(4-(2-(4-(2,5-dimethylthiophene-3-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 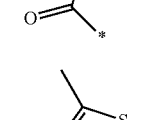 | 653.3 | 1.11 |
| 244 | (R)-7-(2-(4-(2-(4-(2-(benzyloxy)acetyl)-1-oxa-4,9-diazaspiro[5.5]undecan-9-yl)ethoxy)benzylamino)-1-hydroxyethyl)-4-hydroxybenzo[d]thiazol-2(3H)-one | 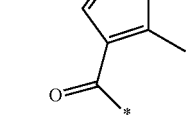 | 663.4 | 1.12 |
| 245 | (R)-4-hydroxy-7-(1-hydroxy-2-(4-(2-(4-(2-(3-methyl-1H-pyrazol-1-yl)acetyl)-1-oxa-4,9-diazaspiro[5.5]undecan-9-yl)ethoxy)benzylamino)ethyl)benzo[d]thiazol-2(3H)-one | 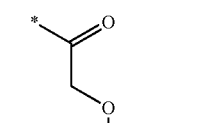 | 637.4 | 0.94 |

-continued

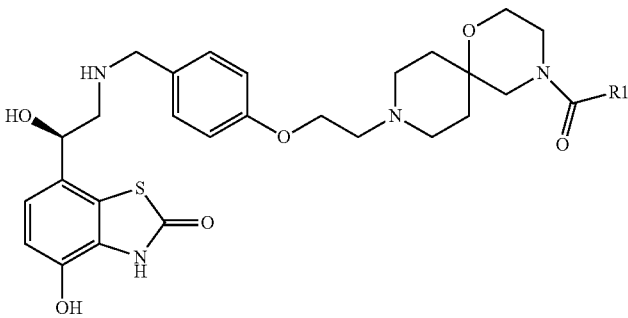

| Example no. | NAME | *―C(=O)―R1 | Observed MWt + 1 | Retention time* (min) |
|---|---|---|---|---|
| 246 | (R)-4-hydroxy-7-(1-hydroxy-2-(4-(2-(4-(2-methylthiophene-3-carbonyl)-1-oxa-4,9-diazaspiro[5.5]undecan-9-yl)ethoxy)benzylamino)ethyl)benzo[d]thiazol-2(3H)-one | | 639.3 | 1.03 |
| 247 | (R)-4-hydroxy-7-(1-hydroxy-2-(4-(2-(4-(3-phenoxypropanoyl)-1-oxa-4,9-diazaspiro[5.5]undecan-9-yl)ethoxy)benzylamino)ethyl)benzo[d]thiazol-2(3H)-one | | 663.3 | 1.11 |
| 248 | (R)-4-hydroxy-7-(1-hydroxy-2-(4-(2-(4-(3-(thiophen-2-yl)propanoyl)-1-oxa-4,9-diazaspiro[5.5]undecan-9-yl)ethoxy)benzylamino)ethyl)benzo[d]thiazol-2(3H)-one | | 653.3 | 1.04 |
| 249 | (R)-4-hydroxy-7-(1-hydroxy-2-(4-(2-(4-(2-(3-methylisoxazol-5-yl)acetyl)-1-oxa-4,9-diazaspiro[5.5]undecan-9-yl)ethoxy)benzylamino)ethyl)benzo[d]thiazol-2(3H)-one | | 638.3 | 0.9 |
| 250 | (R)-7-(2-(4-(2-(4-(benzofuran-5-carbonyl)-1-oxa-4,9-diazaspiro[5.5]undecan-9-yl)ethoxy)benzylamino)-1-hydroxyethyl)-4-hydroxybenzo[d]thiazol-2(3H)-one | | 659.3 | 1.08 |
| 251 | (R)-4-hydroxy-7-(1-hydroxy-2-(4-(2-(4-(2-(2-methylthiazol-4-yl)acetyl)-1-oxa-4,9-diazaspiro[5.5]undecan-9-yl)ethoxy)benzylamino)ethyl)benzo[d]thiazol-2(3H)-one | | 654.3 | 0.88 |

-continued

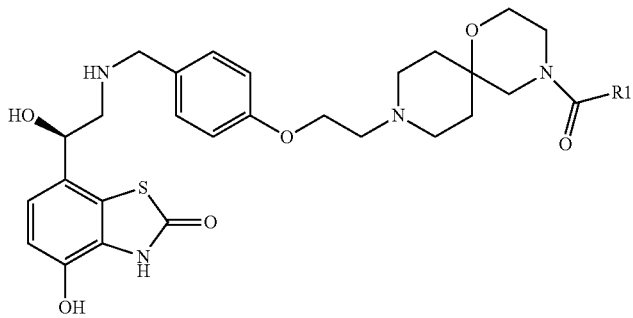

| Example no. | NAME | *─C(O)─R1 | Observed MWt + 1 | Retention time* (min) |
|---|---|---|---|---|
| 252 | (R)-7-(2-(4-(2-(4-(2-(2,4-dimethylthiazol-5-yl)acetyl)-1-oxa-4,9-diazaspiro[5.5]undecan-9-yl)ethoxy)benzylamino)-1-hydroxyethyl)-4-hydroxybenzo[d]thiazol-2(3H)-one | 2,4-dimethylthiazol-5-yl acetyl | 668.3 | 0.83 |
| 253 | (R)-7-(2-(4-(2-(4-(2-chlorothiophene-3-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 2-chlorothiophene-3-carbonyl | 659.2 | 0.96 |
| 254 | (R)-4-hydroxy-7-(1-hydroxy-2-(4-(2-(4-(4-methylthiophene-2-carbonyl)-1-oxa-4,9-diazaspiro[5.5]undecan-9-yl)ethoxy)benzylamino)ethyl)benzo[d]thiazol-2(3H)-one | 4-methylthiophene-2-carbonyl | 639.3 | 1.08 |
| 255 | (R)-4-hydroxy-7-(1-hydroxy-2-(4-(2-(4-(5-isopropylisoxazole-3-carbonyl)-1-oxa-4,9-diazaspiro[5.5]undecan-9-yl)ethoxy)benzylamino)ethyl)benzo[d]thiazol-2(3H)-one | 5-isopropylisoxazole-3-carbonyl | 652.4 | 1.02 |
| 256 | (R)-4-hydroxy-7-(1-hydroxy-2-(4-(2-(4-(2-methylbenzo[d]thiazole-5-carbonyl)-1-oxa-4,9-diazaspiro[5.5]undecan-9-yl)ethoxy)benzylamino)ethyl)benzo[d]thiazol-2(3H)-one | 2-methylbenzo[d]thiazole-5-carbonyl | 690.3 | 1.13 |
| 257 | (R)-7-(2-(4-(2-(4-(2-tert-butylthiazole-4-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 2-tert-butylthiazole-4-carbonyl | 682.4 | 1.23 |

-continued

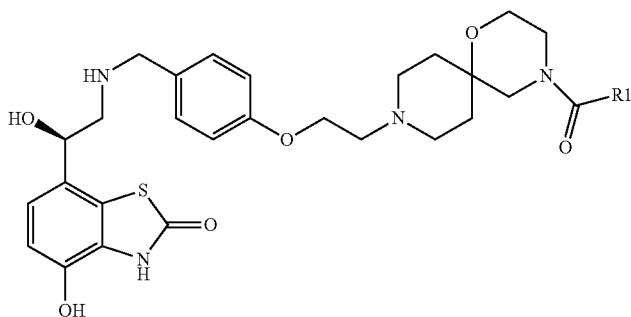

| Example no. | NAME | *—C(O)—R1 | Observed MWt + 1 | Retention time* (min) |
|---|---|---|---|---|
| 258 | (R)-4-hydroxy-7-(1-hydroxy-2-(4-(2-(4-(2-(trifluoromethyl)thiazole-4-carbonyl)-1-oxa-4,9-diazaspiro[5.5]undecan-9-yl)ethoxy)benzylamino)ethyl)benzo[d]thiazol-2(3H)-one | 2-(trifluoromethyl)thiazole-4-carbonyl | 694.3 | 1.1 |
| 259 | (R)-7-(2-(4-(2-(4-(2-cyclopropylthiazole-4-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 2-cyclopropylthiazole-4-carbonyl | 666.3 | 1.05 |
| 260 | (R)-4-hydroxy-7-(1-hydroxy-2-(4-(2-(4-(2-propylthiazole-4-carbonyl)-1-oxa-4,9-diazaspiro[5.5]undecan-9-yl)ethoxy)benzylamino)ethyl)benzo[d]thiazol-2(3H)-one | 2-propylthiazole-4-carbonyl | 668.3 | 1.08 |
| 261 | (R)-7-(2-(4-(2-(4-(2-cyclobutylthiazole-4-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 2-cyclobutylthiazole-4-carbonyl | 680.3 | 1.12 |
| 262 | (R)-7-(2-(4-(2-(4-(2-cyclopentylthiazole-4-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 2-cyclopentylthiazole-4-carbonyl | 694.4 | 1.19 |
| 263 | (R)-7-(2-(4-(2-(4-(4,5-dimethylthiophene-2-carbonyl)-1-oxa-4,9-diazaspiro[5.5]undecan-9-yl)ethoxy)benzylamino)-1-hydroxyethyl)-4-hydroxybenzo[d]thiazol-2(3H)-one | 4,5-dimethylthiophene-2-carbonyl | 653.3 | 1.18 |

*Analytical HPLC conditions: SunFire ™ C18 2.5 μm 4.6 × 30 mm column (Waters Corporation), MeCN/0.1% aq TFA, gradient 5-95% MeCN,

| Time (min) | % aqueous | % MeCN | Flow (ml/min) |
|---|---|---|---|
| 0.3 | 95 | 5 | 2.5 |
| 2.7 | 5 | 95 | 2.5 |
| 2.8 | 5 | 95 | 2.5 |
| 2.9 | 95 | 5 | 2.5 |

1 exchangeable H not observed.

EXAMPLE 264

(R)-4-Hydroxy-7-(1-hydroxy-2-(2-(5-((4-(5-isopropylthiophene-3-carbonyl)-1-oxa-4,9-diazaspiro[5.5]undecan-9-yl)methyl)thiophen-3-yl)ethylamino)ethyl)benzo[d]thiazol-2(3H)-one ditrifluoroacetate

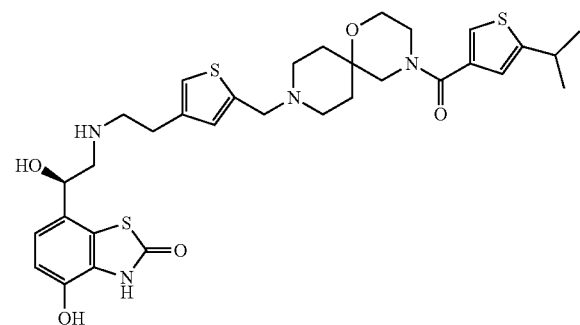 [SMILES: CC(C)c1cc(C(=O)N2CCOC3(CCN(Cc4cc(CCNC[C@H](O)c5ccc(O)c6[nH]c(=O)sc56)cs4)CC3)C2)cs1]

a) 2,2,2-Trifluoro-1-(9-((4-(2-hydroxyethyl)thiophen-2-yl)methyl)-1-oxa-4,9-diazaspiro[5.5]undecan-4-yl)ethanone

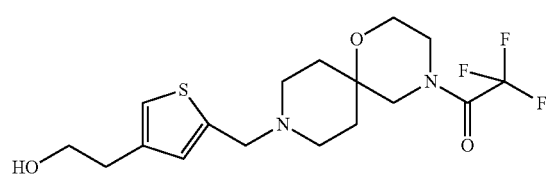 [SMILES: O=C(N1CCOC2(CCN(Cc3cc(CCO)cs3)CC2)C1)C(F)(F)F]

TBAF (1M in THF, 2.96 mL) was added to a stirred solution of 1-(9-((4-(2-(tert-butyldimethylsilyloxy)ethyl)thiophen-2-yl)methyl)-1-oxa-4,9-diazaspiro[5.5]undecan-4-yl)-2,2,2-trifluoroethanone (Example 43, step a) (1.500 g, 2.96 mmol) in THF (5 mL). After 1 h, the solution was evaporated to gum. Purification by silica gel chromatography eluting with ethyl acetate:triethylamine, 10:1 gave the subtitled compound as a gum. Yield 0.25 g.

m/z 393 (M+H)$^+$ (APCI+)

b) 2-(5-((4-(2,2,2-Trifluoroacetyl)-1-oxa-4,9-diazaspiro[5.5]undecan-9-yl)methyl)thiophen-3-yl)acetaldehyde

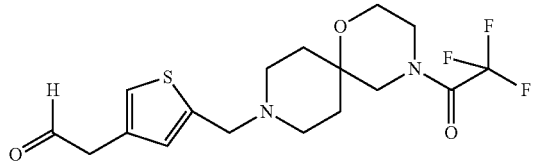 [SMILES: O=CCc1csc(CN2CCC3(CC2)CN(C(=O)C(F)(F)F)CCO3)c1]

The subtitled compound was prepared using a similar method to that described in Example 43 step (e) using 2,2,2-trifluoro-1-(9-((4-(2-hydroxyethyl)thiophen-2-yl)methyl)-1-oxa-4,9-diazaspiro[5.5]undecan-4-yl)ethanone (0.15 g) (Example 264, step a). Yield 0.15 g m/z 391 (M+H)$^+$ (APCI+)

c) (R)-tert-Butyl 2-hydroxy-2-(4-hydroxy-2-oxo-2,3-dihydrobenzo[d]thiazol-7-yl)ethyl(2-(5-((4-(2,2,2-trifluoroacetyl)-1-oxa-4,9-diazaspiro[5.5]undecan-9-yl)methyl)thiophen-3-yl)ethyl)carbamate

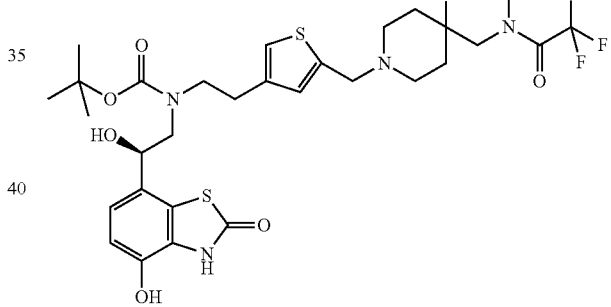

(R)-7-(2-Amino-1-hydroxyethyl)-4-hydroxybenzo[d]thiazol-2(3H)-one, HCl (1.020 g) (WO2007027134, example 1, step d) was added to a stirred solution of 2-(5-((4-(2,2,2-trifluoroacetyl)-1-oxa-4,9-diazaspiro[5.5]undecan-9-yl)methyl)thiophen-3-yl)acetaldehyde (Example 264, step b) (0.9 g) and acetic acid (0.198 mL) in MeOH (20 mL). After 2 min, sodium cyanoborohydride (0.290 g) was added. After 2 h, triethylamine (1.1 mL) and then BOC-Anhydride (0.845 g) was added. After 1 h, more BOC anhydride (0.4 g) and triethylamine (0.5 mL) was added. After 2 h, the solution was concentrated to ~5 mL then partitioned between ethyl acetate and saturated brine. The ethyl acetate layer was dried over sodium sulphate, filtered and evaporated in vacuo. Purification by silica gel chromatography eluting with methanol:dichloromethane:880 ammonia, 10:90:1 gave the subtitled compound as a gum. Yield 0.32 g m/z 701 (M+H)$^+$ (APCI+)

d) (R)-tert-Butyl 2-(5-(1-oxa-4,9-diazaspiro[5.5]
undecan-9-ylmethyl)thiophen-3-yl)ethyl(2-hydroxy-
2-(4-hydroxy-2-oxo-2,3-dihydrobenzo[d]thiazol-7-
yl)ethyl)carbamate

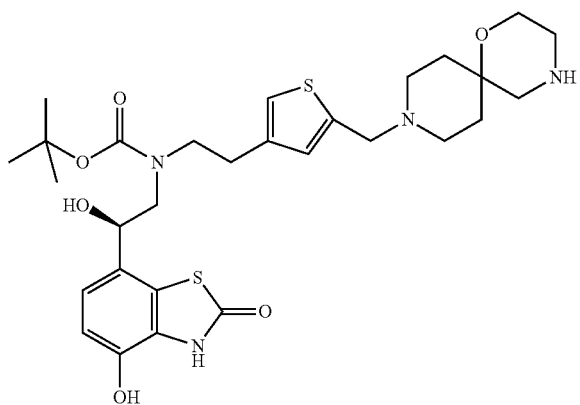 [SMILES: CC(C)(C)OC(=O)N(CCc1csc(CN2CCC3(CC2)CNCCO3)c1)C[C@H](O)c1ccc(O)c2[nH]c(=O)sc12]

35% Aqueous ammonia (5 mL) was added to (R)-tert-butyl 2-hydroxy-2-(4-hydroxy-2-oxo-2,3-dihydrobenzo[d]thiazol-7-yl)ethyl(2-(5-((4-(2,2,2-trifluoroacetyl)-1-oxa-4,9-diazaspiro[5.5]undecan-9-yl)methyl)thiophen-3-yl)ethyl)carbamate (Example 264, step c) (0.2 g). After 40 min at 20° C. the solution was concentrated to ~1 mL and the slurry added to a C18 (10 g) cartridge washing with water (20 mL), then eluting the product with methanol. The fractions containing product were combined and evaporated in vacuo. The resulting solid was dissolved in acetonitrile and evaporated in vacuo. Yield 0.11 g.
m/z 605 (M+H)+ (APCI+)

e) (R)-4-Hydroxy-7-(1-hydroxy-2-(2-(5-((4-(5-iso-
propylthiophene-3-carbonyl)-1-oxa-4,9-diazaspiro
[5.5]undecan-9-yl)methyl)thiophen-3-yl)ethylamino)
ethyl)benzo[d]thiazol-2(3H)-one ditrifluoroacetate

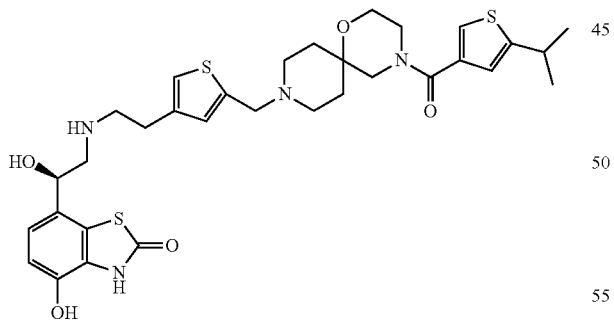

HATU (0.075 g) was added to a stirred solution (R)-tert-butyl 2-(5-(1-oxa-4,9-diazaspiro[5.5]undecan-9-ylmethyl)thiophen-3-yl)ethyl(2-hydroxy-2-(4-hydroxy-2-oxo-2,3-dihydrobenzo[d]thiazol-7-yl)ethyl)carbamate (Example 264, step d) (0.1 g), 5-isopropylthiophene-3-carboxylic acid (0.028 g) and triethylamine (0.092 mL) in DMF (2 mL). After 1 h, the reaction mixture was partitioned between water and ethyl acetate. The ethyl acetate layer was washed with water (×2) and brine, dried over sodium sulphate, filtered and evaporated in vacuo. The resulting gum was dissolved in formic acid (2 mL). After 16 h, the solution was evaporated in vacuo. Acetonitrile was added and the mixture evaporated in vacuo (×2). Toluene was added and the mixture evaporated in vacuo. The mixture was dissolved in methanol, filtered and purified by prep HPLC (Sunfire™, Gradient: 10-40% acetonitrile in 0.2% aqueous TFA). The fractions containing the pure product were combined and evaporated in vacuo. Acetonitrile (200 mL) was added and the solution was evaporated in vacuo to a gum. This process was repeated twice. Diethyl ether was added and the titled compound collected as a solid. Yield 0.05 g.
m/z 657 (M+H)+ (multimode+)
1H NMR (400 MHz, DMSO, 90° C.) δ 11.29 (s, 1H), 7.49 (s, 1H), 7.41 (s, 1H), 7.16 (s, 1H), 6.96-6.88 (m, 2H), 6.76 (d, J=10.5 Hz, 1H), 4.94-4.86 (m, 1H), 4.47 (s, 2H), 3.71-3.62 (m, 2H), 3.57-3.48 (m, 2H), 3.48-3.40 (m, 2H), 3.31-2.91 (m, 11H), 2.11-1.95 (m, 2H), 1.80-1.63 (m, 2H), 1.28 (d, J=6.6 Hz, 6H) plus 5 exchangeable protons missing.

EXAMPLE 265

(R)-4-Hydroxy-7-(1-hydroxy-2-(3-((4-(2-(pentan-3-
yl)thiazole-4-carbonyl)-1-oxa-4,9-diazaspiro[5.5]
undecan-9-yl)methyl)phenethylamino)ethyl)benzo
[d]thiazol-2(3H)-one ditrifluoroacetate

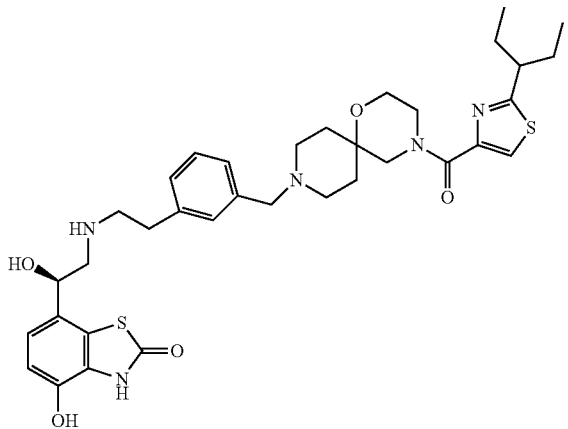 [SMILES: CCC(CC)c1nc(C(=O)N2CCOC3(CCN(Cc4cccc(CCNC[C@H](O)c5ccc(O)c6[nH]c(=O)sc56)c4)CC3)C2)cs1]

a) (9-(3-(2-Hydroxyethyl)benzyl)-1-oxa-4,9-diaza-
spiro[5.5]undecan-4-yl)(2-(pentan-3-yl)thiazol-4-yl)
methanone

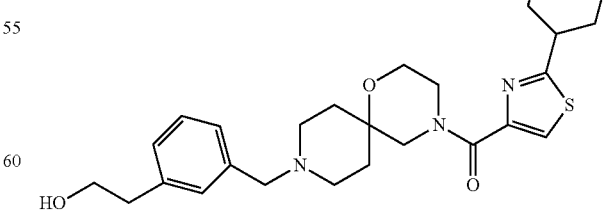

The subtitled compound was prepared using a similar method to that described in Example 82 step (b) using 2-(pentan-3-yl)thiazole-4-carboxylic acid (0.12 g) (Example 71, step d). Yield 0.18 g.

¹H NMR (400 MHz, DMSO, 90° C.) δ 7.92 (s, 1H), 7.18 (t, J=7.6 Hz, 1H), 7.11-7.04 (m, 3H), 4.24 (dd, J=5.3, 3.5 Hz, 1H), 3.72-3.57 (m, 8H), 3.41 (s, 2H), 2.71 (t, J=6.9 Hz, 2H), 2.41-2.24 (m, 4H), 1.82-1.66 (m, 4H), 1.59-1.47 (m, 2H), 0.86 (t, J=7.3 Hz, 6H)+3H obscured by water peak.

b) (R)-4-Hydroxy-7-(1-hydroxy-2-(3-((4-(2-(pentan-3-yl)thiazole-4-carbonyl)-1-oxa-4,9-diazaspiro[5.5]undecan-9-yl)methyl)phenethylamino)ethyl)benzo[d]thiazol-2(3H)-one ditrifluoroacetate

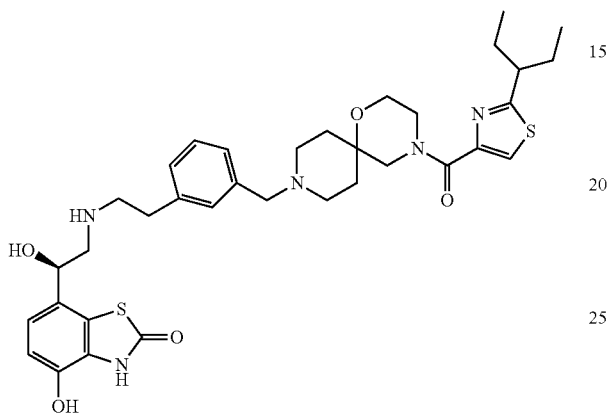

The titled compound was prepared using a similar method to that described in Example 82 step (c) using (9-(3-(2-hydroxyethyl)benzyl)-1-oxa-4,9-diazaspiro[5.5]undecan-4-yl)(2-(pentan-3-yl)thiazol-4-yl)methanone (0.18 g) (Example 265, step a). The crude aldehyde was dissolved in DCM rather than methanol. Yield 0.09 g.

m/z 680 (M+H)⁺ (Multimode+)
¹H NMR (400 MHz, DMSO, 90° C.) δ 11.36 (s, 1H), 7.98 (s, 1H), 7.44-7.32 (m, 4H), 6.93 (d, J=8.3 Hz, 1H), 6.77 (d, J=8.3 Hz, 1H), 4.94-4.86 (m, 1H), 4.34-4.24 (m, 2H), 3.75-2.88 (m, 17H), 2.13-1.96 (m, 2H), 1.79-1.59 (m, 6H), 0.83 (t, J=7.3 Hz, 6H)+5 exchangables not observed.

EXAMPLE 266

(R)-7-(2-(3-((4-(Benzofuran-5-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetic acid

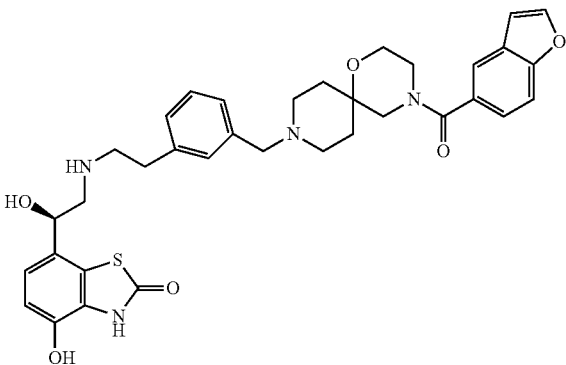 [SMILES: O=C(c1ccc2occc2c1)N1CCOC2(CCN(Cc3cccc(CCNC[C@H](O)c4ccc(O)c5[nH]c(=O)sc45)c3)CC2)C1]

a) Benzofuran-5-yl(9-(3-(2-hydroxyethyl)benzyl)-1-oxa-4,9-diazaspiro[5.5]undecan-4-yl)methanone

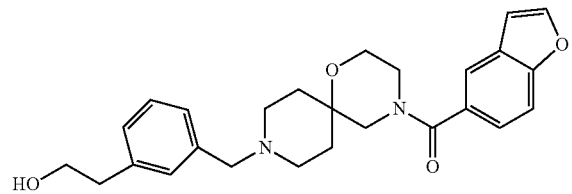 [SMILES: O=C(c1ccc2occc2c1)N1CCOC2(CCN(Cc3cccc(CCO)c3)CC2)C1]

The subtitled compound was prepared using a similar method to that described in Example 82 step (b) using benzofuran-5-carboxylic acid (0.1 g). Yield 0.16 g.
¹H NMR (400 MHz, DMSO, 90° C.) δ 7.99 (d, J=2.1 Hz, 1H), 7.67 (s, 1H), 7.60 (d, J=7.7 Hz, 1H), 7.31 (dd, J=8.6, 1.7 Hz, 1H), 7.16 (t, J=7.6 Hz, 1H), 7.10-7.02 (m, 3H), 6.97 (t, J=1.2 Hz, 1H), 4.24 (t, J=5.3 Hz, 1H), 3.68-3.58 (m, 4H), 3.52-3.34 (m, 6H), 2.70 (t, J=6.9 Hz, 2H), 2.38-2.27 (m, 4H), 1.81-1.68 (m, 2H), 1.55-1.42 (m, 2H)

b) (R)-7-(2-(3-((4-(Benzofuran-5-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetic acid

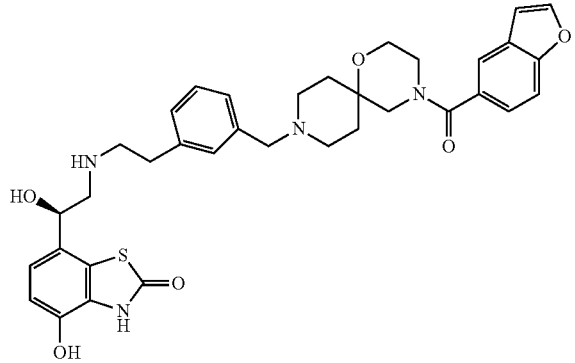 [SMILES: O=C(c1ccc2occc2c1)N1CCOC2(CCN(Cc3cccc(CCNC[C@H](O)c4ccc(O)c5[nH]c(=O)sc45)c3)CC2)C1]

The titled compound was prepared using a similar method to that described in Example 82 step (c) using benzofuran-5-yl(9-(3-(2-hydroxyethyl)benzyl)-1-oxa-4,9-diazaspiro[5.5]undecan-4-yl)methanone (0.15 g) (Example 266, step a). The crude aldehyde was dissolved in DCM rather than methanol. Yield 0.07 g.

m/z 643 (M+H)⁺ (Multimode+)
¹H NMR (300 MHz, DMSO, 90° C.) δ 11.38 (s, 1H), 8.02 (d, J=2.1 Hz, 1H), 7.71 (s, 1H), 7.63 (d, J=8.5 Hz, 1H), 7.47-7.31 (m, 5H), 6.99-6.90 (m, 2H), 6.77 (d, J=8.3 Hz, 1H), 4.95-4.86 (m, 1H), 4.33-4.25 (m, 2H), 3.72-2.94 (m, 16H), 2.14-1.98 (m, 2H), 1.77-1.53 (m, 2H)+5 exchangables not observed.

EXAMPLE 267

(R)-4-Hydroxy-7-(1-hydroxy-2-(3-((4-(5-propylthiophene-3-carbonyl)-1-oxa-4,9-diazaspiro[5.5]undecan-9-yl)methyl)phenethylamino)ethyl)benzo[d]thiazol-2(3H)-one ditrifluoroacetate

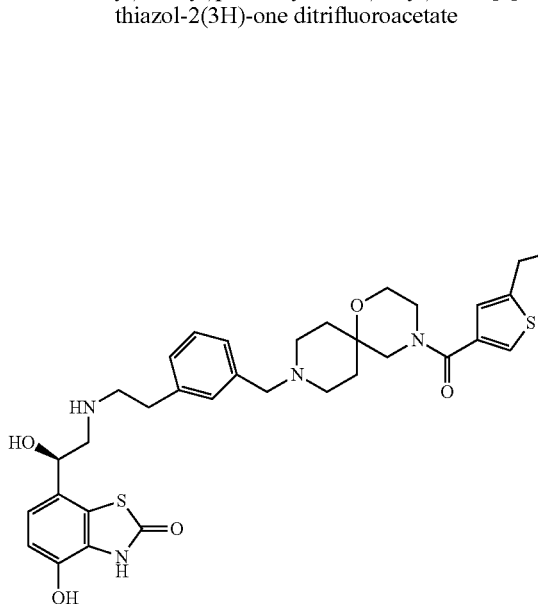

a) (9-(3-(2-Hydroxyethyl)benzyl)-1-oxa-4,9-diazaspiro[5.5]undecan-4-yl)(5-propylthiophen-3-yl)methanone

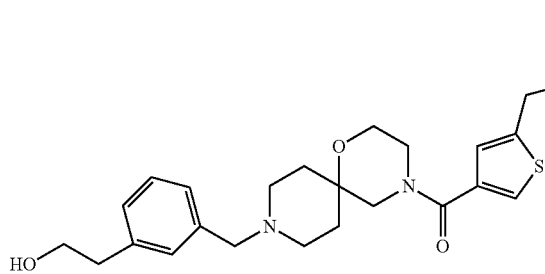

The subtitled compound was prepared using a similar method to that described in Example 82 step (b) using 5-propylthiophene-3-carboxylic acid (0.1 g). Yield 0.15 g.

¹H NMR (400 MHz, DMSO, 90° C.) δ 7.44 (d, J=1.3 Hz, 1H), 7.18 (t, J=7.4 Hz, 1H), 7.11-7.04 (m, 3H), 6.87 (d, J=1.3 Hz, 1H), 4.24 (t, J=5.1 Hz, 1H), 3.67-3.59 (m, 4H), 3.51-3.47 (m, 2H), 3.40 (s, 4H), 2.77 (dd, J=14.7, 0.9 Hz, 2H), 2.71 (t, J=7.0 Hz, 2H), 2.40-2.25 (m, 4H), 1.74-1.59 (m, 4H), 1.55-1.45 (m, 2H), 0.94 (t, J=7.3 Hz, 3H).

b) (R)-4-Hydroxy-7-(1-hydroxy-2-(3-((4-(5-propylthiophene-3-carbonyl)-1-oxa-4,9-diazaspiro[5.5]undecan-9-yl)methyl)phenethylamino)ethyl)benzo[d]thiazol-2(3H)-one ditrifluoroacetate

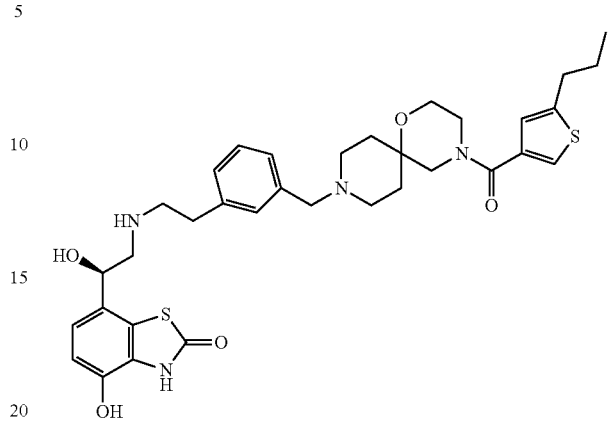

The titled compound was prepared using a similar method to that described in Example 82 step (c) using (9-(3-(2-hydroxyethyl)benzyl)-1-oxa-4,9-diazaspiro[5.5]undecan-4-yl)(5-propylthiophen-3-yl)methanone (0.15 g) (Example 267, step a). The crude aldehyde was dissolved in DCM rather than methanol. Yield 0.9 g.

m/z 651 (M+H)⁺ (Multimode+)

¹H NMR (300 MHz, DMSO, 90° C.) δ 11.38 (s, 1H), 7.51-7.32 (m, 5H), 6.96-6.87 (m, 2H), 6.77 (d, J=8.3 Hz, 1H), 4.94-4.87 (m, 1H), 4.35-4.25 (m, 2H), 3.63-2.93 (m, 16H), 2.76 (t, J=7.3 Hz, 2H), 2.14-1.98 (m, 2H), 1.72-1.56 (m, 4H), 0.93 (t, J=7.3 Hz, 3H)+5 exchangables not observed.

EXAMPLE 268

(R)-4-Hydroxy-7-(1-hydroxy-2-(3-((4-(5-isopropylthiophene-2-carbonyl)-1-oxa-4,9-diazaspiro[5.5]undecan-9-yl)methyl)phenethylamino)ethyl)benzo[d]thiazol-2(3H)-one ditrifluoroacetate

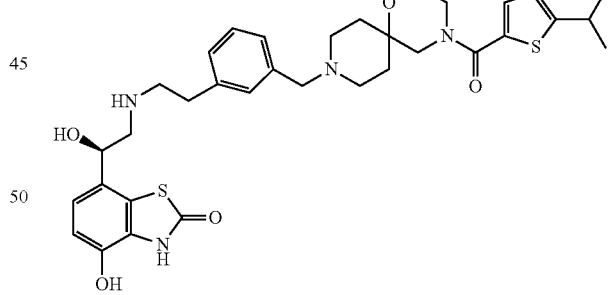

a) (9-(3-(2-Hydroxyethyl)benzyl)-1-oxa-4,9-diazaspiro[5.5]undecan-4-yl)(5-isopropylthiophen-2-yl)methanone

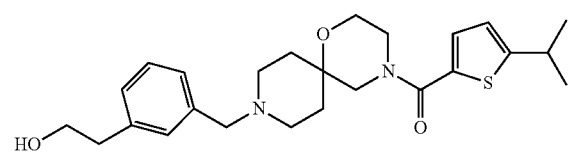 [SMILES: CC(C)c1ccc(C(=O)N2CCOC3(CCN(Cc4cccc(CCO)c4)CC3)C2)s1]

The subtitled compound was prepared using a similar method to that described in Example 82 step (b) using 5-isopropylthiophene-2-carboxylic acid (0.1 g). Yield 0.18 g.

¹H NMR (400 MHz, DMSO, 90° C.) δ 7.23-7.15 (m, 2H), 7.13-7.04 (m, 3H), 6.84 (d, J=3.6 Hz, 1H), 4.24 (t, J=4.7 Hz, 1H), 3.69-3.58 (m, 6H), 3.50 (s, 2H), 3.41 (s, 2H), 3.17 (septet, J=6.8 Hz, 1H), 2.71 (t, J=6.9 Hz, 2H), 2.39-2.30 (m, 4H), 1.75-1.67 (m, 2H), 1.56-1.47 (m, 2H), 1.29 (d, J=6.7 Hz, 6H).

b) (R)-4-Hydroxy-7-(1-hydroxy-2-(3-((4-(5-isopropylthiophene-2-carbonyl)-1-oxa-4,9-diazaspiro[5.5]undecan-9-yl)methyl)phenethylamino)ethyl)benzo[d]thiazol-2(3H)-one ditrifluoroacetate

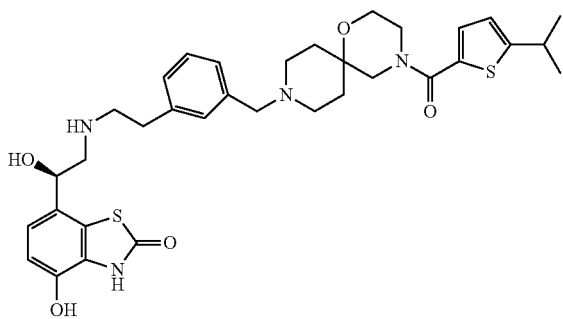 [SMILES: CC(C)c1ccc(C(=O)N2CCOC3(CCN(Cc4cccc(CCNC[C@H](O)c5ccc(O)c6[nH]c(=O)sc56)c4)CC3)C2)s1]

The titled compound was prepared using a similar method to that described in Example 82 step (c) using (9-(3-(2-hydroxyethyl)benzyl)-1-oxa-4,9-diazaspiro[5.5]undecan-4-yl)(5-isopropylthiophen-2-yl)methanone (0.18 g) (Example 268, step a). The crude aldehyde was dissolved in DCM rather than methanol. Yield 0.09 g m/z 651 (M+H)⁺ (Multimode+)

¹H NMR (300 MHz, DMSO, 90° C.) δ 11.37 (s, 1H), 7.45-7.33 (m, 4H), 7.24 (d, J=3.1 Hz, 1H), 6.93 (d, J=8.1 Hz, 1H), 6.85 (d, J=3.7 Hz, 1H), 6.77 (d, J=8.5 Hz, 1H), 4.96-4.86 (m, 1H), 4.36-4.26 (m, 2H), 3.75-3.63 (m, 4H), 3.56-3.48 (m, 2H), 3.36-2.94 (m, 11H), 2.13-1.96 (m, 2H), 1.81-1.62 (m, 2H), 1.28 (d, J=6.9 Hz, 6H)+5 exchangables not observed.

EXAMPLE 269

(R)-7-(2-(2,3-Difluoro-4-(2-(4-(2-isopropylthiazole-4-carbonyl)-1-oxa-4,9-diazaspiro[5.5]undecan-9-yl)ethoxy)phenethylamino)-1-hydroxyethyl)-4-hydroxybenzo[d]thiazol-2(3H)-one ditrifluoroacetate

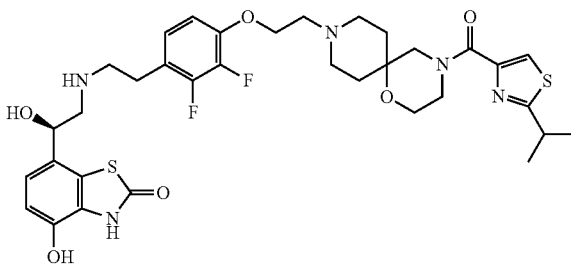 [SMILES: CC(C)c1nc(C(=O)N2CCOC3(CCN(CCOc4ccc(CCNC[C@H](O)c5ccc(O)c6[nH]c(=O)sc56)c(F)c4F)CC3)C2)cs1]

The titled compound was prepared using a similar method to that described in Example 82 step (c) using (9-(2-(2,3-difluoro-4-(2-hydroxyethyl)phenoxy)ethyl)-1-oxa-4,9-diazaspiro[5.5]undecan-4-yl)(2-isopropylthiazol-4-yl)methanone (0.22 g) (Example 77, step e). The crude aldehyde was dissolved in DCM rather than methanol. Yield 0.13 g.

m/z 718 (M+H)⁺ (Multimode+)

¹H NMR (300 MHz, DMSO, 90° C.) δ 11.36 (s, 1H), 7.98 (d, J=0.8 Hz, 1H), 7.15-7.00 (m, 2H), 6.93 (d, J=8.3 Hz, 1H), 6.77 (d, J=8.3 Hz, 1H), 4.93-4.86 (m, 1H), 4.46-4.38 (m, 2H), 3.74-2.94 (m, 19H), 2.15-1.97 (m, 2H), 1.87-1.69 (m, 2H), 1.35 (d, J=6.7H, 6H)+5 exchangables not observed.

EXAMPLE 270

(R)-4-Hydroxy-7-(1-hydroxy-2-(5-((4-(2-isopropylthiazole-4-carbonyl)-1-oxa-4,9-diazaspiro[5.5]undecan-9-yl)methyl)-2-(trifluoromethyl)phenethylamino)ethyl)benzo[d]thiazol-2(3H)-one ditrifluoroacetate

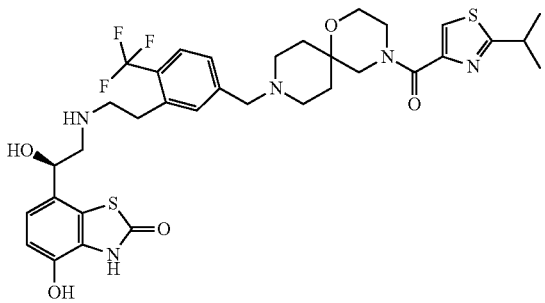 [SMILES: CC(C)c1nc(C(=O)N2CCOC3(CCN(Cc4ccc(C(F)(F)F)c(CCNC[C@H](O)c5ccc(O)c6[nH]c(=O)sc56)c4)CC3)C2)cs1]

a) 2-(5-(Bromomethyl)-2-(trifluoromethyl)phenyl)ethanol

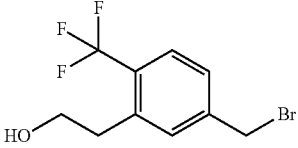 [SMILES: OCCc1cc(CBr)ccc1C(F)(F)F]

Benzoyl peroxide (0.085 g) was added to a suspension of 2-(5-methyl-2-(trifluoromethyl)phenyl)acetic acid (1.12 g) and N-bromosuccinimide (1.101 g) in chlorobenzene (18 mL), and the resulting mixture was heated at 100° C. under nitrogen for 80 minutes, then allowed to cool. The resulting mixture was diluted with ethyl acetate, washed three times with water, once with brine, then dried (MgSO₄), filtered and concentrated in vacuo to give a yellow oil. The oil was dissolved in tetrahydrofuran (11 mL) and treated with a 2 molar solution of borane-methyl sulfide complex in THF (5.1 mL), portionwise over 2 minutes. The resulting mixture was stirred at room temperature overnight, then cooled in ice-water and quenched by the addition of methanol. The effervescing mixture was removed from the cooling bath, stirred at room temperature for 70 minutes, then concentrated in vacuo. The residue was purified by flash chromatography on silica eluted with 15% ethyl acetate in isohexane to afford the crude product as a yellow oil. Yield 0.919 g.

b) (9-(3-(2-Hydroxyethyl)-4-(trifluoromethyl)benzyl)-1-oxa-4,9-diazaspiro[5.5]undecan-4-yl)(2-isopropylthiazol-4-yl)methanone

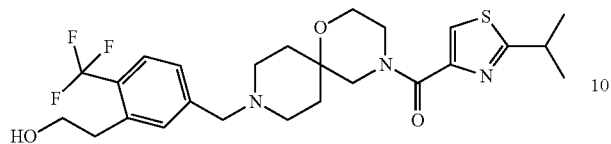

The subtitled compound was prepared using a similar method to that described in Example 6 step (b) using a solution of 2-(5-(bromomethyl)-2-(trifluoromethyl)phenyl)ethanol (0.38 g) (Example 270 step a) in acetonitrile which was added dropwise over 30 minutes to (2-isopropylthiazol-4-yl)(1-oxa-4,9-diazaspiro[5.5]undecan-4-yl)methanone trifluoroacetate (Example 22 step b). Purification was by silica gel chromatography eluting 5% triethylamine in ethyl acetate. Yield 0.32 g.

$^1$H NMR (400 MHz, DMSO, 90° C.) δ 7.90 (s, 1H), 7.56 (d, J=8.2 Hz, 1H), 7.39 (s, 1H), 7.29 (d, J=7.9 Hz, 1H), 4.44 (t, J=5.3 Hz, 1H), 3.71-3.56 (m, 6H), 3.50 (s, 2H), 3.31 (septet, J=6.9 Hz, 1H), 2.90 (t, J=6.9 Hz, 2H), 2.57-2.25 (m, 4H), 1.81-1.66 (m, 4H), 1.62-1.49 (m, 2H), 1.36 (d, J=6.9 Hz, 6H).

c) 2-(5-((4-(2-Isopropylthiazole-4-carbonyl)-1-oxa-4,9-diazaspiro[5.5]undecan-9-yl)methyl)-2-(trifluoromethyl)phenyl)acetaldehyde

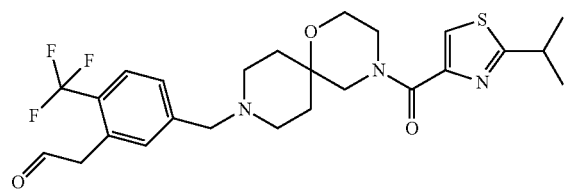 [SMILES: CC(C)c1nc(C(=O)N2CCOC3(CCN(Cc4ccc(C(F)(F)F)c(CC=O)c4)CC3)C2)cs1]

The subtitled compound was prepared using a similar method to that described in Example 16 step c) using (9-(3-(2-hydroxyethyl)-4-(trifluoromethyl)benzyl)-1-oxa-4,9-diazaspiro[5.5]undecan-4-yl)(2-isopropylthiazol-4-yl)methanone (0.32 g) (Example 270, step b). The mixture was stirred for 90 min after the addition of the Dess-Martin periodinane. Yield 0.38 g.

d) (R)-4-Hydroxy-7-(1-hydroxy-2-(5-((4-(2-isopropylthiazole-4-carbonyl)-1-oxa-4,9-diazaspiro[5.5]undecan-9-yl)methyl)-2-(trifluoromethyl)phenethylamino)ethyl)benzo[d]thiazol-2(3H)-one ditrifluoroacetate

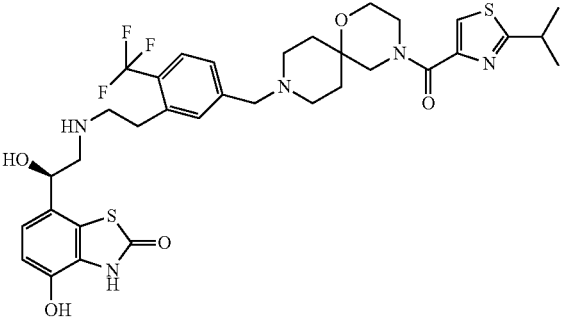 [SMILES: CC(C)c1nc(C(=O)N2CCOC3(CCN(Cc4ccc(C(F)(F)F)c(CCNC[C@H](O)c5ccc(O)c6[nH]c(=O)sc56)c4)CC3)C2)cs1]

The titled compound was prepared using a similar method to that described in Example 18 step g) using a solution of 2-(5-((4-(2-isopropylthiazole-4-carbonyl)-1-oxa-4,9-diazaspiro[5.5]undecan-9-yl)methyl)-2-(trifluoromethyl)phenyl)acetaldehyde (0.3 g) (Example 270, step c) in methanol (3 mL). After the addition of sodium cyanoborohydride the mixture was stirred at room temperature for 3.75 hours. The solution was concentrated to a volume of ~3 mL, diluted with THF and washed with a mixture of brine and saturated aqueous sodium bicarbonate. The organic phase was dried over anhydrous magnesium sulphate and concentrated in vacuo. The residue was co-evaporated twice from acetonitrile, then dissolved in acetonitrile:water (1:1), filtered and purified by preparative HPLC (Sunfire, Gradient: 5-50% acetonitrile in 0.2% aqueous TFA). The fractions containing product were combined and concentrated in vacuo and co-evaporated from acetonitrile three times to give a colourless residue. The residue was triturated with diethyl ether to give a solid, which was removed by filtration, washed with diethyl ether and dried in vacuo at room temperature to afford the product as a white solid. Yield 0.115 g.

m/z 720 (M+H)$^+$ (APCI+)

$^1$H NMR (400 MHz, DMSO, 90° C.) δ 7.93 (s, 1H), 7.77 (d, J=8.2 Hz, 1H), 7.61-7.53 (m, 2H), 6.94 (d, J=8.2 Hz, 1H), 6.77 (d, J=8.5 Hz, 1H), 4.91 (dd, J=8.6, 4.7 Hz, 1H), 4.27-4.08 (m, 2H), 3.76-3.59 (m, 6H), 3.48-2.85 (m, 11H), 2.03-1.88 (m, 2H), 1.78-1.63 (m, 2H), 1.35 (d, J=6.9 Hz, 6H). Six exchangeable protons not observed.

EXAMPLE 271

(R)-7-(2-(3-((2,2-Dimethyl-4-(2-methylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one ditrifluoroacetate

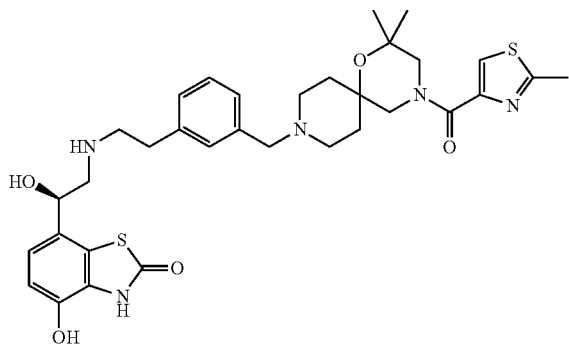 [SMILES: Cc1nc(C(=O)N2CC(C)(C)OC3(CCN(Cc4cccc(CCNC[C@H](O)c5ccc(O)c6[nH]c(=O)sc56)c4)CC3)C2)cs1]

a) 1-Benzyl-4-((2-methylallylamino)methyl)piperidin-4-ol

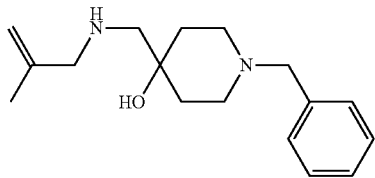 [SMILES: C=C(C)CNCC1(O)CCN(Cc2ccccc2)CC1]

A mixture of 6-benzyl-1-oxa-6-azaspiro[2.5]octane (2 g) and 2-methylprop-2-en-1-amine HCl (2 g) and Hunig's Base (3.44 mL) in ethanol (30 mL) was heated at 70° C. for 18 hours. The mixture was cooled to room temperature and the solvent evaporated under reduced pressure. The residue was partitioned between DCM and brine, the aqueous layer was re-extracted with fresh DCM and the combined organics dried over sodium sulphate, filtered and the solvent evaporated under reduced pressure to afford the subtitled compound. Yield 2.70 g.
m/z 275 (M+H)$^+$ (APCI+)

b) tert-Butyl 9-benzyl-2,2-dimethyl-1-oxa-4,9-diazaspiro[5.5]undecane-4-carboxylate

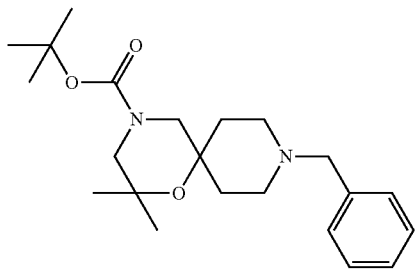 [SMILES: CC(C)(C)OC(=O)N1CC(C)(C)OC2(CCN(Cc3ccccc3)CC2)C1]

Concentrated sulfuric acid (12 ml) was added to 1-benzyl-4-((2-methylallylamino)methyl)piperidin-4-ol (Example 271, step a) (2.2 g) and the mixture was allowed to stand for 2 hours at room temperature. The reaction mixture was treated with ice/water (100 mL) followed by solid sodium bicarbonate, portionwise, until the mixture was basic. Acetonitrile (50 mL) was added followed by BOC-anhydride (1.925 g) and the reaction mixture stirred at room temperature for 18 hours. The reaction mixture was extracted with ethyl acetate (×2) and the combined organics were dried over sodium sulphate, filtered and the solvent evaporated under reduced pressure. The crude product was purified by flash silica chromatography, eluting with 1% methanol in dichloromethane switching to 1% methanol in dichloromethane with 1% triethylamine. Pure fractions were evaporated to dryness to afford the subtitled compound. Yield 0.8 g.
m/z 375 (M+H)$^+$ (APCI+)

c) tert-Butyl 2,2-dimethyl-1-oxa-4,9-diazaspiro[5.5]undecane-4-carboxylate

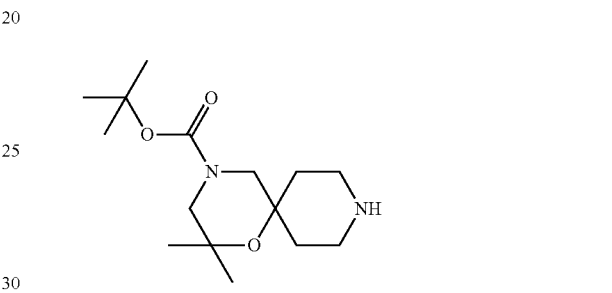

A mixture of tert-butyl 9-benzyl-2,2-dimethyl-1-oxa-4,9-diazaspiro[5.5]undecane-4-carboxylate (Example 271, step b) (0.8 g) dissolved in ethanol (50 mL) and 10% palladium on carbon (0.5 g) was treated with ammonium formate (0.8 g) and the reaction mixture heated at reflux for 30 minutes. The mixture was cooled to room temperature and filtered through diatomacious earth. The solvent was evaporated and the residue azeotroped with acetonitrile (×2) to afford the subtitled compound. Yield 0.55 g.
$^1$H NMR (400 MHz, DMSO, 90° C.) δ 3.25 (s, 2H), 3.19 (s, 2H), 2.84-2.76 (m, 2H), 2.59-2.50 (m, 2H), 1.51-1.42 (m, 4H), 1.41 (s, 9H), 1.13 (s, 6H). 1 exchangeable not observed.

d) tert-Butyl 9-(3-(2-hydroxyethyl)benzyl)-2,2-dimethyl-1-oxa-4,9-diazaspiro[5.5]undecane-4-carboxylate

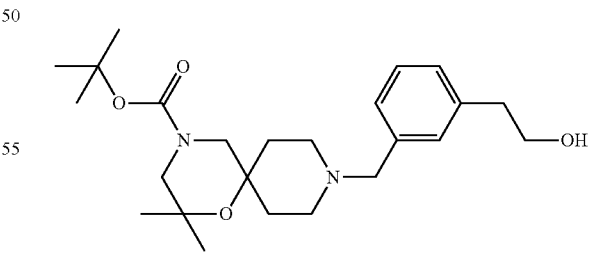

2-(3-(Bromomethyl)phenyl)ethanol (0.416 g) was added portionwise over 1 hour to a solution of tert-butyl 2,2-dimethyl-1-oxa-4,9-diazaspiro[5.5]undecane-4-carboxylate (Example 271, step c) (0.55 g) and triethylamine (0.809 mL) in acetonitrile (20 mL). The mixture was stirred for 2 hours at 20° C. The solvent was evaporated under reduced pressure and the residue partitioned between saturated sodium bicarbonate solution and DCM, the organic layer was dried over sodium sulphate, filtered and the solvent evaporated under reduced pressure. The crude product was purified by flash silica chromatography, eluting with 2% methanol in dichloromethane with 1% triethylamine to afford the subtitled compound. Yield 0.78 g.

$^1$H NMR (400 MHz, DMSO, 90° C.) δ 7.21-7.04 (m, 4H), 4.24 (t, J=5.5 Hz, 1H), 3.66-3.59 (m, 2H), 3.43 (s, 2H), 3.25 (s, 2H), 3.19 (s, 2H), 3.00 (s, 2H), 2.71 (t, J=7.0 Hz, 2H), 2.32-2.24 (m, 2H), 1.64-1.50 (m, 4H), 1.40 (s, 9H), 1.13 (s, 6H).

e) 2-(3-((2,2-Dimethyl-1-oxa-4,9-diazaspiro[5.5] undecan-9-yl)methyl)phenyl)ethanol

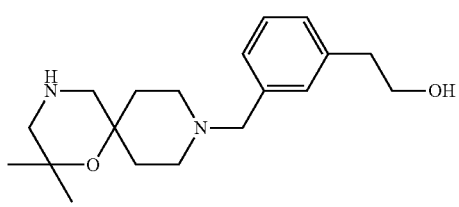 [SMILES: CC1(C)CNCC2(CCN(Cc3cccc(CCO)c3)CC2)O1]

Trifluoroacetic acid (5 mL) was added to a solution of tert-butyl 9-(3-(2-hydroxyethyl)benzyl)-2,2-dimethyl-1-oxa-4,9-diazaspiro[5.5]undecane-4-carboxylate (Example 271, step d) (0.78 g) in DCM (20 mL) and the reaction mixture allowed to stand for 30 minutes at 20° C. Toluene (40 mL) was added and the solvents evaporated under reduced pressure, the residue was azeotroped with acetonitrile (×2). The residue was dissolved in water (30 mL) and washed with ethyl acetate, the aqueous layer was basified by addition of solid sodium carbonate and stirred for 30 minutes at 20° C. The aqueous mixture was then extracted with DCM (×6), the combined DCM layers were dried over sodium sulphate, filtered and the solvent evaporated under reduced pressure to afford the subtitled compound. Yield 0.4 g.

m/z 319 (M+H)$^+$ (APCI+)

f) (9-(3-(2-Hydroxyethyl)benzyl)-2,2-dimethyl-1-oxa-4,9-diazaspiro[5.5]undecan-4-yl)(2-methylthiazol-4-yl)methanone

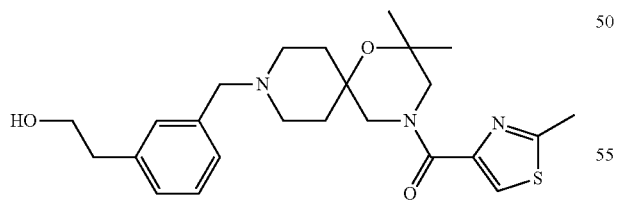

The subtitled compound was prepared using a similar method to that described in Example 22 step (a) using 2-(3-((2,2-dimethyl-1-oxa-4,9-diazaspiro[5.5]undecan-9-yl)methyl)phenyl)ethanol (0.2 g) (Example 271, step e) and 2-methylthiazole-4-carboxylic acid (0.09 g). The reaction mixture was stirred for 18 h, and the elution solvent for the chromatography was 2% methanol in dichloromethane with 1% triethylamine. Yield 0.16 g m/z 444.1 (M+H)$^+$ (APCI+)

g) (R)-7-(2-(3-((2,2-Dimethyl-4-(2-methylthiazole-4-carbonyl)-1-oxa-4,9-diazaspiro[5.5]undecan-9-yl) methyl)phenethylamino)-1-hydroxyethyl)-4-hydroxybenzo[d]thiazol-2(3H)-one ditrifluoroacetate

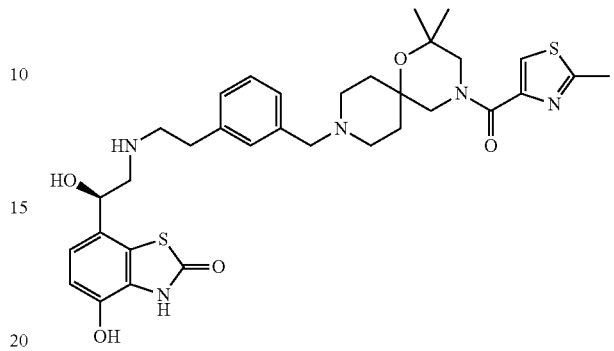

The titled compound was prepared using a similar method to that described in Example 22 step (d) using (9-(3-(2-hydroxyethyl)benzyl)-2,2-dimethyl-1-oxa-4,9-diazaspiro[5.5] undecan-4-yl)(2-methylthiazol-4-yl)methanone (0.15 g) (Example 271, step f). The mixture was stirred for 3 h after the addition of the sodium cyanoborohydride, and 2-methyltetrahydrofuran was added instead of THF. Yield 0.12 g.

m/z 652 (M+H)$^+$ (Multimode+)

$^1$H NMR (400 MHz, DMSO, 90° C.) δ 11.27 (s, 1H), 7.93 (s, 1H), 7.43-7.32 (m, 4H), 6.93 (d, J=8.5 Hz, 1H), 6.77 (d, J=8.2 Hz, 1H), 4.94-4.89 (m, 1H), 4.29 (s, 2H), 3.68 (s, 2H), 3.62 (s, 2H), 3.28-3.10 (m, 8H), 3.06-2.97 (m, 2H), 2.67 (s, 3H), 1.95-1.73 (m, 4H), 1.19 (s, 6H). 5 exchangeables not observed.

EXAMPLE 272

(R)-5-(2-(3-((4-(5-ethylthiophene-3-carbonyl)-2,2-dimethyl-1-oxa-4,9-diazaspiro[5.5]undecan-9-yl) methyl)phenethylamino)-1-hydroxyethyl)-8-hydroxyquinolin-2(1H)-one ditrifluoroacetate

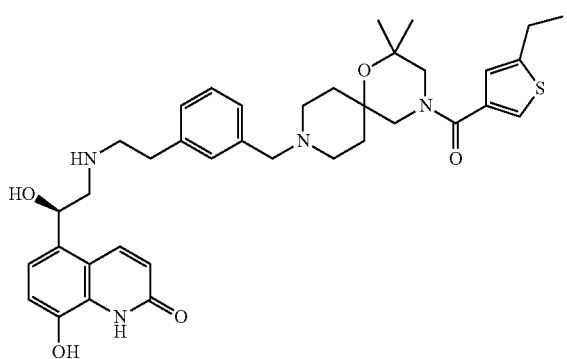 [SMILES: CCc1cc(C(=O)N2CC(C)(C)OC3(CCN(Cc4cccc(CCNC[C@H](O)c5ccc(O)c6[nH]c(=O)ccc56)c4)CC3)C2)cs1]

a) (5-Ethylthiophen-3-yl)(9-(3-(2-hydroxyethyl)benzyl)-2,2-dimethyl-1-oxa-4,9-diazaspiro[5.5]undecan-4-yl)methanone

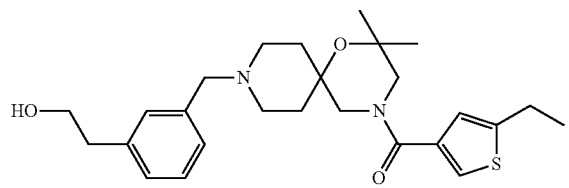 [SMILES: CCc1cc(C(=O)N2CC(C)(C)OC3(CCN(Cc4cccc(CCO)c4)CC3)C2)cs1]

The subtitled compound was prepared using a similar method to that described in Example 271 step (f) using 2-(3-((2,2-dimethyl-1-oxa-4,9-diazaspiro[5.5]undecan-9-yl)methyl)phenyl)ethanol (0.2 g) (Example 271, step e) and 5-ethylthiophene-3-carboxylic acid. Yield 0.22 g.

m/z 457.1 (M+H)$^+$ (APCI+)

b) (R)-5-(2-(3-((4-(5-ethylthiophene-3-carbonyl)-2,2-dimethyl-1-oxa-4,9-diazaspiro[5.5]undecan-9-yl)methyl)phenethylamino)-1-hydroxyethyl)-8-hydroxyquinolin-2(1H)-one ditrifluoroacetate

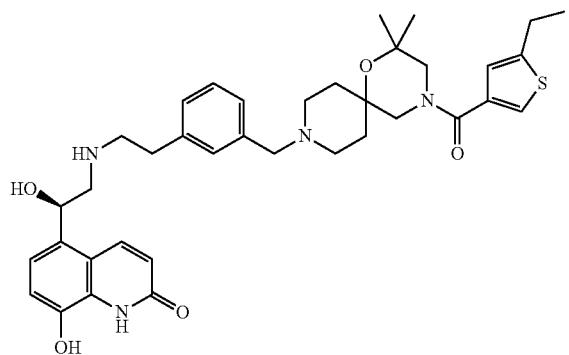 [SMILES: CCc1cc(C(=O)N2CC(C)(C)OC3(CCN(Cc4cccc(CCNC[C@H](O)c5ccc(O)c6[nH]c(=O)ccc56)c4)CC3)C2)cs1]

The titled compound was prepared using a similar method to that described in Example 23 using (5-ethylthiophen-3-yl)(9-(3-(2-hydroxyethyl)benzyl)-2,2-dimethyl-1-oxa-4,9-diazaspiro[5.5]undecan-4-yl)methanone (0.22 g) (Example 272, step a). The mixture was stirred for 3 h after the addition of sodium triacetoxyborohydride in step a). Yield 0.085 g.

m/z 659 (M+H)$^+$ (Multimode+)

$^1$H NMR (400 MHz, DMSO, 90° C.) δ 8.16 (d, J=10.0 Hz, 1H), 7.48 (d, J=1.5 Hz, 1H), 7.44-7.29 (m, 4H), 7.13 (d, J=8.2 Hz, 1H), 6.99 (d, J=8.2 Hz, 1H), 6.91 (d, J=1.0 Hz, 1H), 6.55 (d, J=10.0 Hz, 1H), 5.37-5.32 (m, 1H), 4.24 (s, 2H), 3.52-3.40 (m, 4H), 3.28 (t, J=8.3 Hz, 2H), 3.20-2.99 (m, 8H), 2.81 (q, J=7.4 Hz, 2H), 1.93-1.65 (m, 4H), 1.25 (t, J=7.4 Hz, 3H), 1.18 (s, 6H). 6 exchangeables not observed.

EXAMPLE 273

(R)-8-Hydroxy-5-(1-hydroxy-2-(5-((4-(2-isopropylthiazole-4-carbonyl)-1-oxa-4,9-diazaspiro[5.5]undecan-9-yl)methyl)-2-(trifluoromethyl)phenethylamino)ethyl)quinolin-2(1H)-one ditrifluoroacetate

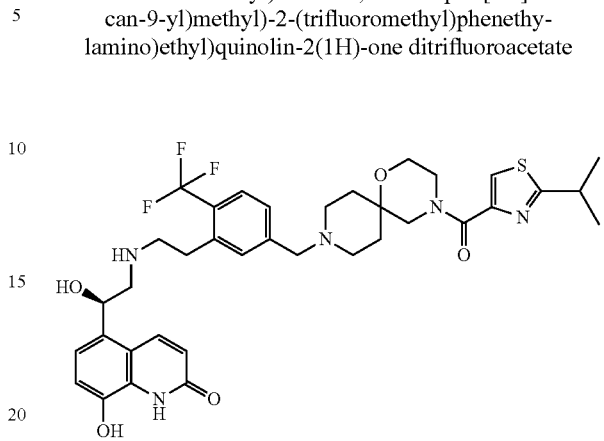

A solution of (R)-5-(2-amino-1-(tert-butyldimethylsilyloxy)ethyl)-8-hydroxyquinolin-2(1H)-one (0.15 g) (WO2004106333) in methanol (2 mL) was treated with acetic acid (0.021 mL) and stirred for 10 minutes. A solution of 2-(5-((4-(2-isopropylthiazole-4-carbonyl)-1-oxa-4,9-diazaspiro[5.5]undecan-9-yl)methyl)-2-(trifluoromethyl)phenyl)acetaldehyde (Example 270, step c) (0.190 g) in methanol (3 mL) was then added, and the resulting mixture was stirred at room temperature for 10 minutes, before cooling in ice-water and treating with sodium cyanoborohydride (0.038 g). The cooling bath was removed and the mixture was stirred at room temperature for 2.75 hours. The solution was concentrated to a volume of ~3 mL, diluted with THF (20 mL) and washed with a mixture of brine (10 mL) and saturated aqueous sodium bicarbonate (1 mL). The organic phase was dried over anhydrous magnesium sulphate and concentrated in vacuo. The residue was co-evaporated twice from acetonitrile, partially dissolved in THF (10 mL), treated with triethylamine trihydrofluoride (0.12 mL) and stirred at room temperature overnight. The mixture was concentrated in vacuo and the residue dissolved in acetonitrile:water (3:2, 10 mL), filtered and purified by preparative HPLC (Sunfire, Gradient: 5-50% acetonitrile in 0.2% aqueous TFA). Fractions containing product were concentrated in vacuo and co-evaporated from acetonitrile three times to give a colourless residue. The residue was triturated with diethyl ether to give a solid, which was collected by filtration, washed with diethyl ether and dried in vacuo at room temperature to afford the titled compound as a white solid. Yield 0.133 g.

m/z 714 (M+H)$^+$ (APCI+)

$^1$H NMR (400 MHz, DMSO, 90° C.) δ 8.17 (d, J=10.0 Hz, 1H), 7.93 (s, 1H), 7.77 (d, J=8.2 Hz, 1H), 7.62-7.53 (m, 2H), 7.14 (d, J=8.2 Hz, 1H), 7.00 (d, J=8.2 Hz, 1H), 6.55 (d, J=10.0 Hz, 1H), 5.34 (dd, J=9.1, 4.0 Hz, 1H), 4.29-4.10 (m, 2H), 3.76-3.59 (m, 6H), 3.49-2.87 (m, 11H), 2.05-1.87 (m, 2H), 1.80-1.62 (m, 2H), 1.34 (d, J=6.9 Hz, 6H). Six exchangeable protons not observed.

EXAMPLE 274

(R)-8-Hydroxy-5-(1-hydroxy-2-(3-((4-(2-(pentan-3-yl)thiazole-4-carbonyl)-1-oxa-4,9-diazaspiro[5.5]undecan-9-yl)methyl)phenethylamino)ethyl)quinolin-2(1H)-one ditrifluoroacetate

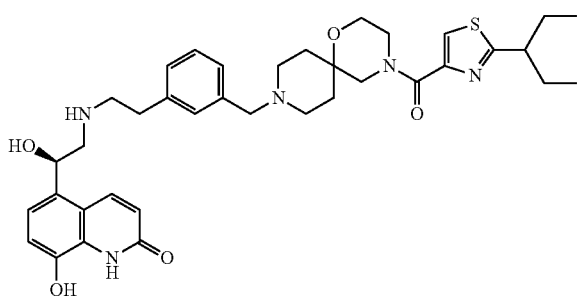 [SMILES: CCC(CC)c1nc(C(=O)N2CCOC3(CCN(Cc4cccc(CCNC[C@H](O)c5ccc(O)c6[nH]c(=O)ccc56)c4)CC3)C2)cs1]

a) 2-(3-((4-(2-(Pentan-3-yl)thiazole-4-carbonyl)-1-oxa-4,9-diazaspiro[5.5]undecan-9-yl)methyl)phenyl)acetaldehyde

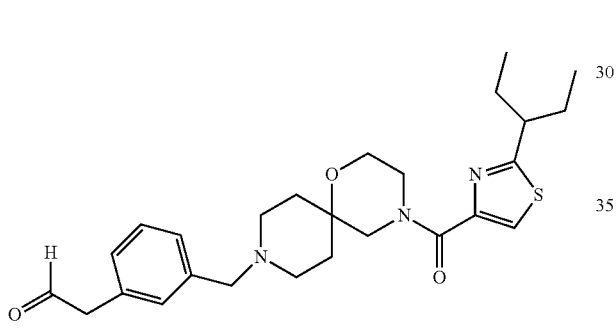

The subtitled compound was prepared using a similar method to that described in Example 16 step c) using (9-(3-(2-hydroxyethyl)benzyl)-1-oxa-4,9-diazaspiro[5.5]undecan-4-yl)(2-(pentan-3-yl)thiazol-4-yl)methanone (0.16 g) (Example 265, step a). Yield 0.24 g.

m/z 470 (M+H)+ (APCI+)

b) (R)-8-Hydroxy-5-(1-hydroxy-2-(3-((4-(2-(pentan-3-yl)thiazole-4-carbonyl)-1-oxa-4,9-diazaspiro[5.5]undecan-9-yl)methyl)phenethylamino)ethyl)quinolin-2(1H)-one ditrifluoroacetate

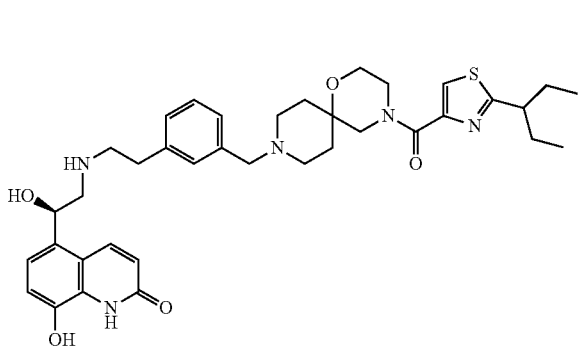 [SMILES: CCC(CC)c1nc(C(=O)N2CCOC3(CCN(Cc4cccc(CCNC[C@H](O)c5ccc(O)c6[nH]c(=O)ccc56)c4)CC3)C2)cs1]

The titled compound was prepared using a similar method to that described in Example 273 using 2-(3-((4-(2-(pentan-3-yl)thiazole-4-carbonyl)-1-oxa-4,9-diazaspiro[5.5]undecan-9-yl)methyl)phenyl)acetaldehyde (Example 274, step a). Yield 0.097 g.

m/z 674 (M+H)+ (APCI+)

¹H NMR (400 MHz, DMSO, 90° C.) δ 8.15 (d, J=10.0 Hz, 1H), 7.95 (s, 1H), 7.47-7.28 (m, 4H), 7.13 (d, J=8.2 Hz, 1H), 6.99 (d, J=7.9 Hz, 1H), 6.55 (d, J=9.7 Hz, 1H), 5.39-5.28 (m, 1H), 4.33-4.11 (m, 2H), 3.79-3.56 (m, 6H), 3.50-2.84 (m, 11H), 2.11-1.90 (m, 2H), 1.83-1.58 (m, 6H), 0.84 (t, J=7.3 Hz, 6H). Six exchangeable protons not observed.

EXAMPLE 275

(R)-8-Hydroxy-5-(1-hydroxy-2-(1-(3-((4-(5-isopropylthiophene-3-carbonyl)-1-oxa-4,9-diazaspiro[5.5]undecan-9-yl)methyl)phenyl)-2-methylpropan-2-ylamino)ethyl)quinolin-2(1H)-one ditrifluoroacetate

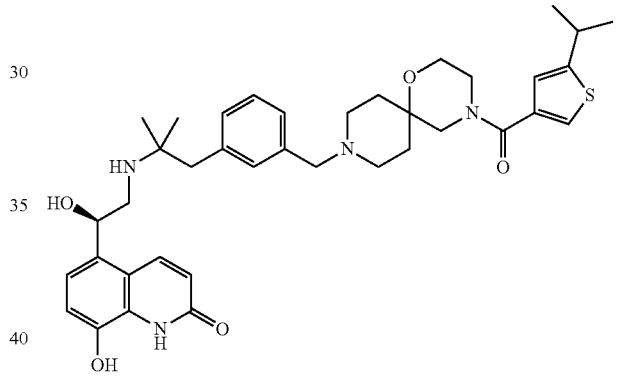

a) 3-(2-(tert-Butoxycarbonylamino)-2-methylpropyl)benzoic acid

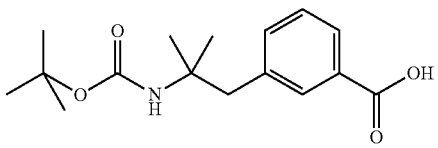 [SMILES: CC(C)(Cc1cccc(C(=O)O)c1)NC(=O)OC(C)(C)C]

The subtitled compound was prepared using a similar method to that described in Example 53, step b) using methyl 3-(2-(tert-butoxycarbonylamino)-2-methylpropyl)benzoate. The reaction mixture was stirred at 20° C. for 18 hours, then at 40° C. for 10 hours. The mixture was partitioned between water and diethyl ether, and the final trituration was not required.

m/z 292 (M−H)+ (APCI+)

b) tert-Butyl 1-(3-(hydroxymethyl)phenyl)-2-methyl-propan-2-ylcarbamate

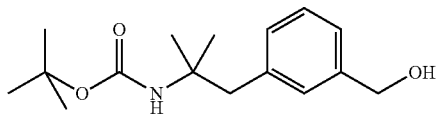 [SMILES: CC(C)(Cc1cccc(CO)c1)NC(=O)OC(C)(C)C]

The subtitled compound was prepared using a similar method to that described in Example 16, step a) using 3-(2-(tert-butoxycarbonylamino)-2-methylpropyl)benzoic acid (2.68 g). The reaction mixture was cooled in an ice bath during the addition, then stirred at 20° C. for 2 hours. Yield 2.5 g.

¹H NMR (400 MHz, DMSO)S 7.23-7.13 (m, 2H), 7.06 (s, 1H), 6.98 (d, J=7.4 Hz, 1H), 6.23 (s, 1H), 5.09 (t, J=5.6 Hz, 1H), 4.45 (d, J=5.6 Hz, 2H), 2.89 (s, 2H), 1.42 (s, 9H), 1.14 (s, 6H).

c) (3-(2-Amino-2-methylpropyl)phenyl)methanol

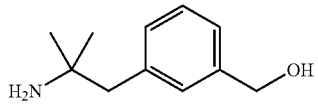

Trifluoroacetic acid (5 mL) was added to a solution of tert-butyl 1-(3-(hydroxymethyl)phenyl)-2-methylpropan-2-ylcarbamate (Example 275, step b) (0.7 g) in DCM (20 mL) and the resultant solution allowed to stand at 20° C. for 30 minutes. Toluene (40 mL) was added and the solvents evaporated under reduced pressure. The residue was partitioned between DCM and 1M aqueous sodium hydroxide, and the aqueous layer was extracted with DCM (×2). The combined organics were dried over sodium sulphate, filtered and the solvent removed under reduced pressure to afford the subtitled compound. Yield 0.440 g.

m/z 180 (M+H)⁺ (APCI+)

¹H NMR (400 MHz, DMSO) δ 7.23 (t, J=8.0 Hz, 1H), 7.19-7.12 (m, 2H), 7.04 (d, J=8.6 Hz, 1H), 4.47 (s, 2H), 2.58 (s, 2H), 0.99 (s, 6H). 3 exchangeables not observed.

d) (R)-8-(Benzyloxy)-5-(1-(tert-butyldimethylsilyloxy)-2-(1-(3-(hydroxymethyl)phenyl)-2-methylpropan-2-ylamino)ethyl)quinolin-2(1H)-one

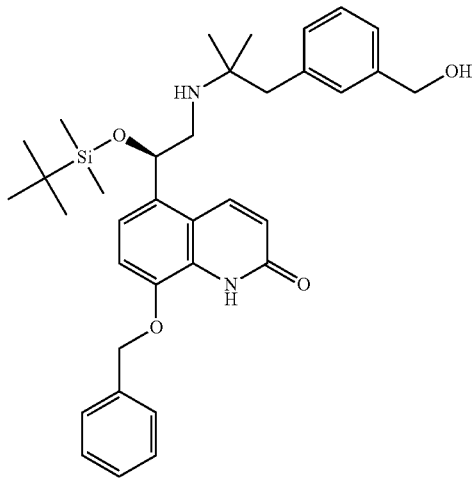 [SMILES: CC(C)(Cc1cccc(CO)c1)NC[C@H](O[Si](C)(C)C(C)(C)C)c1ccc(OCc2ccccc2)c2[nH]c(=O)ccc12]

A mixture of (R)-8-(benzyloxy)-5-(2-bromo-1-(tert-butyldimethylsilyloxy)ethyl)quinolin-2 (1H)-one (0.518 g) and (3-(2-amino-2-methylpropyl)phenyl)methanol (0.19 g) (example 275, step c) and sodium iodide (0.159 g) and Hunig's Base (0.555 mL) in acetonitrile (3 mL) was heated at reflux under nitrogen for 2 days. Further (3-(2-amino-2-methylpropyl)phenyl)methanol (0.19 g) and Hunig's Base (0.185 mL) were added and heating at reflux continued for 1 day. The reaction mixture was cooled to room temperature and partitioned between ethyl acetate and brine, the organic layer was dried over sodium sulphate, filtered and the solvent evaporated under reduced pressure. The crude product was purified by flash silica chromatography eluting with 3% methanol and 1% triethylamine in dichloromethane. Pure fractions were evaporated to dryness to afford the subtitled compound. Yield 0.44 g.

m/z 587 (M+H)⁺ (APCI+)

e) (R)-5-(1-(tert-Butyldimethylsilyloxy)-2-(1-(3-(hydroxymethyl)phenyl)-2-methylpropan-2-ylamino)ethyl)-8-hydroxyquinolin-2(1H)-one

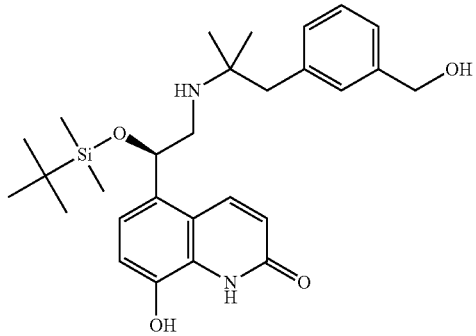 [SMILES: CC(C)(Cc1cccc(CO)c1)NC[C@H](O[Si](C)(C)C(C)(C)C)c1ccc(O)c2[nH]c(=O)ccc12]

A mixture of (R)-8-(benzyloxy)-5-(1-(tert-butyldimethylsilyloxy)-2-(1-(3-(hydroxymethyl)phenyl)-2-methylpropan-2-ylamino)ethyl)quinolin-2(1H)-one (Example 275, step d) (0.44 g) and palladium on carbon (10%) (80 mg) in ethanol (30 mL) was stirred vigorously under 5 bar pressure of hydrogen for 3 hours. The catalyst was filtered off and the solvent evaporated under reduced pressure to afford the subtitled compound. Yield 0.37 g.

m/z 497 (M+H)⁺ (APCI+)

f) (R)-tert-Butyl 5-(1-(tert-butyldimethylsilyloxy)-2-(1-(3-(hydroxymethyl)phenyl)-2-methylpropan-2-ylamino)ethyl)-2-oxo-1,2-dihydroquinolin-8-yl carbonate

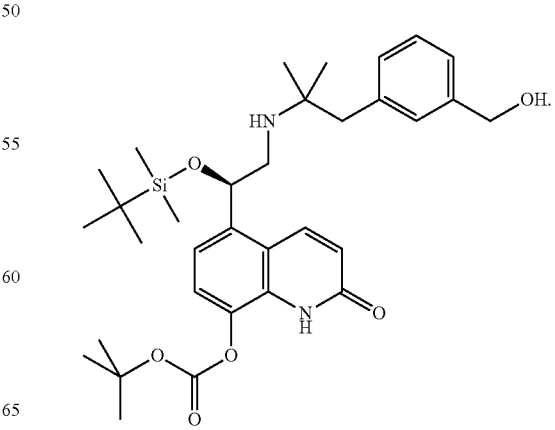

A solution of (R)-5-(1-(tert-butyldimethylsilyloxy)-2-(1-(3-(hydroxymethyl)phenyl)-2-methylpropan-2-ylamino)ethyl)-8-hydroxyquinolin-2(1H)-one (Example 275, step e) (0.37 g) and BOC-anhydride (0.163 g) and triethylamine (0.208 mL) in ethanol (20 mL) was allowed to stand at room temperature for 18 hours. The solvent was removed under reduced pressure to afford the subtitled compound. Yield 0.44 g.

m/z 597 (M+H)$^+$ (APCI+)

g) (R)-tert-Butyl 5-(1-(tert-butyldimethylsilyloxy)-2-(1-(3-formylphenyl)-2-methylpropan-2-ylamino)ethyl)-2-oxo-1,2-dihydroquinolin-8-yl carbonate

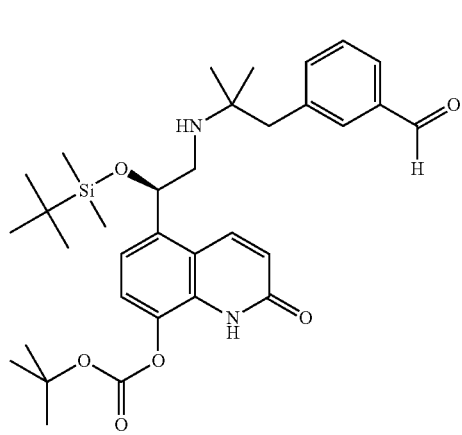 [SMILES: CC(C)(Cc1cccc(C=O)c1)NC[C@H](O[Si](C)(C)C(C)(C)C)c1ccc(OC(=O)OC(C)(C)C)c2[nH]c(=O)ccc12]

Manganese dioxide (0.6 g) was added to a solution of (R)-tert-butyl 5-(1-(tert-butyldimethylsilyloxy)-2-(1-(3-(hydroxymethyl)phenyl)-2-methylpropan-2-ylamino)ethyl)-2-oxo-1,2-dihydroquinolin-8-yl carbonate (Example 275, step f) (0.44 g) in dichloromethane (30 mL) and the mixture stirred vigorously at 20° C. for 3 hours. The reaction mixture was filtered through diatomaceous earth and the solvent removed under reduced pressure to afford the subtitled compound. Yield 0.42 g.

m/z 595 (M+H)$^+$ (APCI+)

h) (R)-3-(2-(2-(tert-Butyldimethylsilyloxy)-2-(8-hydroxy-2-oxo-1,2-dihydroquinolin-5-yl)ethylamino)-2-methylpropyl)benzaldehyde

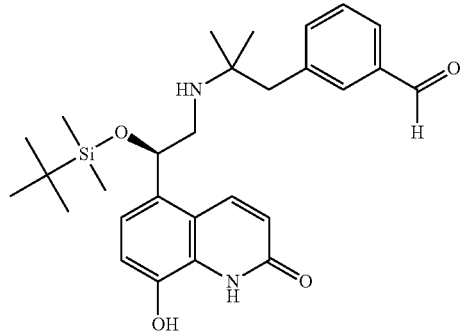 [SMILES: CC(C)(Cc1cccc(C=O)c1)NC[C@H](O[Si](C)(C)C(C)(C)C)c1ccc(O)c2[nH]c(=O)ccc12]

A solution of (R)-tert-butyl 5-(1-(tert-butyldimethylsilyloxy)-2-(1-(3-formylphenyl)-2-methylpropan-2-ylamino)ethyl)-2-oxo-1,2-dihydroquinolin-8-yl carbonate (Example 275, step g) (0.42 g) in methanol (15 mL) was treated with ammonia (35% aqueous) (2 mL). The reaction mixture was allowed to stand for 3 hours at 20° C. The solvent was removed under a stream of nitrogen and the residue was partitioned between ethyl acetate and brine. The aqueous layer was extracted with ethyl acetate and the combined organics dried over sodium sulphate, filtered and the solvent evaporated under reduced pressure to afford the subtitled compound. Yield 0.34 g.

m/z 495 (M+H)$^+$ (APCI+)

i) (5-Isopropylthiophen-3-yl)(1-oxa-4,9-diazaspiro[5.5]undecan-4-yl)methanone

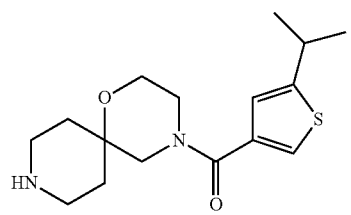 [SMILES: CC(C)c1cc(C(=O)N2CCOC3(CCNCC3)C2)cs1]

The subtitled compound was prepared using a similar method to that described in Example 22, steps a) and b) using 5-isopropylthiophene-3-carboxylic acid. In step b) the residue was not purified by chromatography. The crude product was azeotroped with acetonitrile (×2). The residue was partitioned between DCM and 1M aqueous sodium hydroxide, the aqueous layer was extracted with DCM (×3) and the combined organics dried over sodium sulphate, filtered and the solvent removed under reduced pressure to afford the subtitled compound. Yield 0.4 g.

m/z 309 (M+H)$^+$ (APCI+)

j) (R)-5-(1-(tert-Butyldimethylsilyloxy)-2-(1-(3-((4-(5-isopropylthiophene-3-carbonyl)-1-oxa-4,9-diazaspiro[5.5]undecan-9-yl)methyl)phenyl)-2-methylpropan-2-ylamino)ethyl)-8-hydroxyquinolin-2(1H)-one

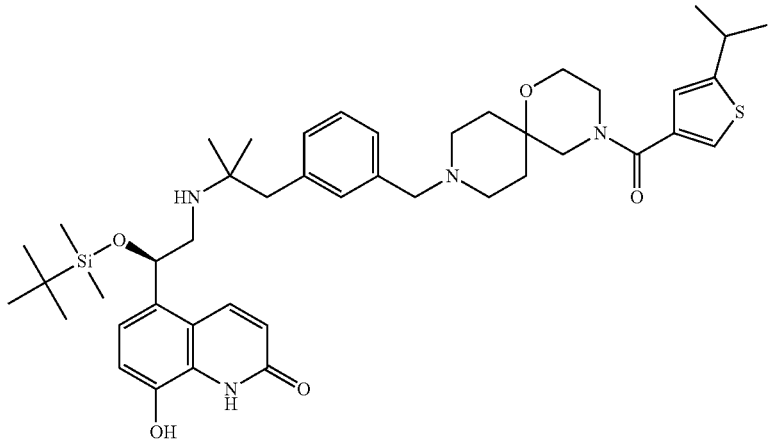 [SMILES: CC(C)c1cc(C(=O)N2CCOC3(CCN(Cc4cccc(CC(C)(C)NC[C@H](O[Si](C)(C)C(C)(C)C)c5ccc(O)c6[nH]c(=O)ccc56)c4)CC3)C2)cs1]

The subtitled compound was prepared using a similar method to that described in Example 14, step b) using (R)-3-(2-(2-(tert-butyldimethylsilyloxy)-2-(8-hydroxy-2-oxo-1,2-dihydroquinolin-5-yl)ethylamino)-2-methylpropyl)benzaldehyde (0.32 g) (Example 275, step h) and (5-isopropylthiophen-3-yl)(1-oxa-4,9-diazaspiro[5.5]undecan-4-yl)methanone (0.21 g) (Example 275, step i)). The crude product was purified by flash silica chromatography, 8% methanol in dichloromethane with 1% 880 aqueous ammonia. Pure fractions were evaporated to dryness to afford the subtitled compound. Yield 0.31 g.

m/z 787 (M+H)$^+$ (APCI+)

k) (R)-8-Hydroxy-5-(1-hydroxy-2-(1-(3-((4-(5-isopropylthiophene-3-carbonyl)-1-oxa-4,9-diazaspiro[5.5]undecan-9-yl)methyl)phenyl)-2-methylpropan-2-ylamino)ethyl)quinolin-2(1H)-one ditrifluoroacetate

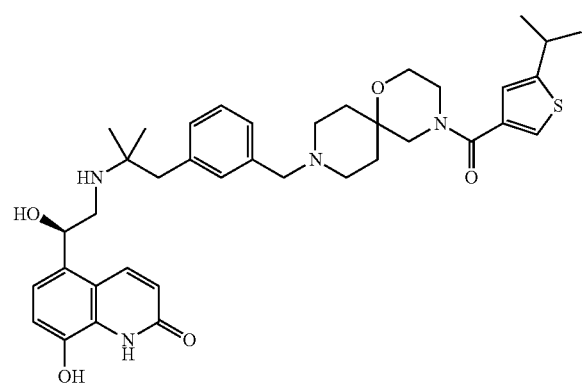 [SMILES: CC(C)c1cc(C(=O)N2CCOC3(CCN(Cc4cccc(CC(C)(C)NC[C@H](O)c5ccc(O)c6[nH]c(=O)ccc56)c4)CC3)C2)cs1]

The titled compound was prepared using a similar method to that described in Example 23, step b) using (R)-5-(1-(tert-butyldimethylsilyloxy)-2-(1-(3-((4-(5-isopropylthiophene-3-carbonyl)-1-oxa-4,9-diazaspiro[5.5]undecan-9-yl)methyl)phenyl)-2-methylpropan-2-ylamino)ethyl)-8-hydroxyquinolin-2(1H)-one (0.31 g) (Example 275, step j). Yield 0.18 g.

m/z 673 (M+H)$^+$ (multimode+)

$^1$H NMR (400 MHz, DMSO, 90° C.) δ 9.98 (s, 1H), 8.14 (d, J=10.0 Hz, 1H), 7.47 (s, 1H), 7.44-7.40 (m, 2H), 7.36-7.30 (m, 2H), 7.20 (d, J=8.2 Hz, 1H), 7.01 (d, J=8.2 Hz, 1H), 6.89 (s, 1H), 6.58 (d, J=9.7 Hz, 1H), 5.37-5.31 (m, 1H), 4.26 (s, 2H), 3.68-3.63 (m, 2H), 3.55-3.51 (m, 2H), 3.21-2.98 (m, 11H), 2.01 (s, 2H), 1.69 (s, 2H), 1.31-1.24 (m, 12H) plus 5 exchangeables not observed.

EXAMPLE 276

8-Hydroxy-5-((R)-1-hydroxy-2-((R)-1-(3-((4-(5-isopropylthiophene-3-carbonyl)-1-oxa-4,9-diazaspiro[5.5]undecan-9-yl)methyl)phenyl)propan-2-ylamino)ethyl)quinolin-2(1H)-one ditrifluoroacetate

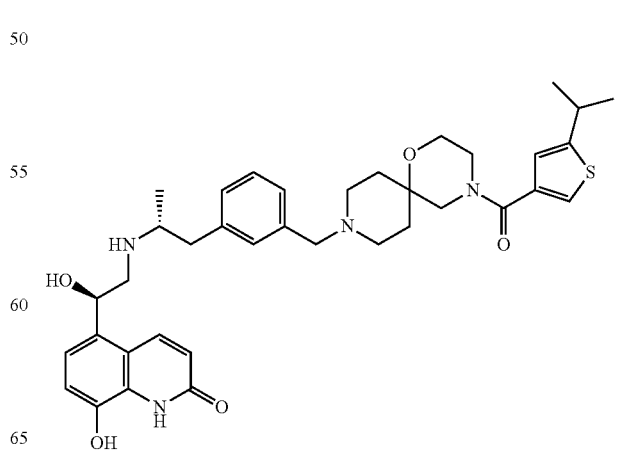

a) 1-(3-((tert-Butyldimethylsilyloxy)methyl)phenyl)propan-2-one

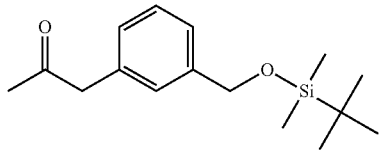 [SMILES: CC(=O)Cc1cccc(CO[Si](C)(C)C(C)(C)C)c1]

A mixture of (3-bromobenzyloxy)(tert-butyl)dimethylsilane (16.72 g), isopropenyl acetate (9.2 mL), tri-n-butyltin methoxide (24 mL), palladium(II)acetate (0.625 g) and tri(o-tolyl)phosphine (1.70 g) in anhydrous toluene (65 mL) was heated at reflux at 100° C. for 5 hours and then left to cool overnight. The mixture was diluted with ethyl acetate (130 mL) and 4 molar aqueous potassium fluoride (80 mL) and stirred vigorously for 20 minutes. Diatomaceous earth was added and the suspension was then filtered through diatomaceous earth, washing the residue well with ethyl acetate. The combined filtrate and washings were dried over anhydrous magnesium sulphate and concentrated in vacuo and purified by flash chromatography on silica eluting with isohexane, 10% dichloromethane in isohexane and 20% diethyl ether in isohexane to afford the subtitled compound as a yellow oil. Yield 13.71 g.

$^1$H NMR (400 MHz, CDCl$_3$) δ 7.30 (t, J=7.6 Hz, 1H), 7.23 (d, J=7.7 Hz, 1H), 7.16 (s, 1H), 7.09 (d, J=7.4 Hz, 1H), 4.73 (s, 2H), 3.68 (s, 2H), 2.14 (s, 3H), 0.94 (s, 9H), 0.10 (s, 6H).

b) (3-((R)-2-((R)-1-Phenylethylamino)propyl)phenyl)methanol hydrochloride

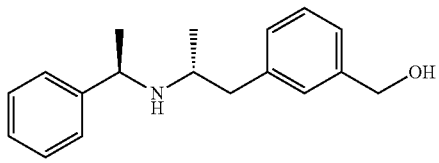 [SMILES: C[C@H](Cc1cccc(CO)c1)N[C@H](C)c1ccccc1]

A solution of 1-(3-((tert-butyldimethylsilyloxy)methyl)phenyl)propan-2-one (Example 276, step a) (6.85 g) in dichloromethane (240 mL) was treated with acetic acid (1.27 mL), (R)-(+)-1-phenylethylamine (2.83 mL) and sodium triacetoxyborohydride (7.09 g), and the resulting suspension was stirred at room temperature overnight. The mixture was quenched by the portionwise addition of saturated aqueous sodium bicarbonate (120 mL) over 5 minutes. The two-phase mixture was stirred vigorously for 1.75 hours, then separated. The aqueous phase was extracted with more dichloromethane, and the combined organic phases were dried (MgSO$_4$), filtered and concentrated to afford an oil. The oil was purified by flash silica chromatography eluting with 10% ethanol in isohexane to give the silylated alcohol as a yellow oil (7.21 g). The oil was dissolved in HCl/methanol solution (1M, 20 mL), kept at room temperature for 25 minutes, then concentrated in vacuo. The resulting gum was triturated with methanol/diethyl ether to give a crystalline slurry that was stirred for minutes. The solid was removed by filtration, washed well with diethyl ether and recrystallised three times from methanol/diethyl ether to afford the subtitled compound as white crystals. Yield 1.9 g.

m/z 270 (M+H)$^+$ (APCI+)

$^1$H NMR (400 MHz, DMSO) δ 9.84 (br s, 1H), 9.21 (br s, 1H), 7.69 (d, J=6.9 Hz, 2H), 7.53-7.40 (m, 3H), 7.23 (t, J=7.6 Hz, 1H), 7.16 (d, J=7.7 Hz, 1H), 6.98 (s, 1H), 6.88 (d, J=7.4 Hz, 1H), 5.16 (t, J=5.6 Hz, 1H), 4.69-4.55 (m, 1H), 4.43 (d, J=5.4 Hz, 2H), 3.42-3.30 (m, 1H), 3.04-2.91 (m, 1H), 2.61-2.47 (m, 1H), 1.63 (d, J=6.7 Hz, 3H), 1.10 (d, J=6.7 Hz, 3H).

c) (R)-(3-(2-Aminopropyl)phenyl)methanol

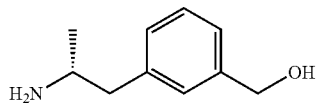

A mixture of (3-((R)-2-((R)-1-phenylethylamino)propyl)phenyl)methanol hydrochloride (Example 276, step b) (1.92 g), 20% palladium hydroxide on carbon (0.757 g) and ammonium formate (2.28 g) in ethanol (30 mL) was stirred at 75° C. for 1.5 hours, then allowed to cool. The suspension was filtered through diatomaceous earth, washing the residue well with ethanol. The combined filtrate and washings were concentrated in vacuo to afford a pale yellow gum as a mixture of desired product and des-hydroxy analogue. Yield 1.54 g. Used directly d) (R)-tert-Butyl 1-(3-(hydroxymethyl)phenyl)propan-2-ylcarbamate

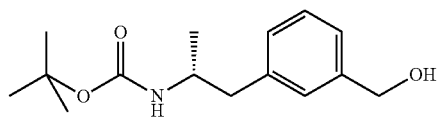 [SMILES: C[C@H](Cc1cccc(CO)c1)NC(=O)OC(C)(C)C]

A solution of di-tert-butyl dicarbonate (2.034 g) in THF (5 mL) was added dropwise over 20 minutes to a solution of the impure (R)-(3-(2-aminopropyl)phenyl)methanol (Example 276, step c) (1.54 g) in THF (10 mL) and water (10 mL). The resulting mixture was stirred at room temperature over a weekend, then triethylamine (3.90 mL) was added. More di-tert-butyl dicarbonate (2.013 g) in THF (5 mL) was added dropwise over 30 minutes. The resulting mixture was stirred at room temperature overnight, then concentrated in vacuo to remove THF. The resulting oily aqueous phase was extracted twice with ethyl acetate and the combined extracts dried (MgSO$_4$), filtered and concentrated onto flash silica in vacuo. The residue was purified by flash chromatography on silica eluting with 35% ethyl acetate in isohexane to afford the subtitled compound as a white solid. Yield 0.9 g.

$^1$H NMR (400 MHz, CDCl$_3$) δ 7.29 (t, J=7.6 Hz, 1H), 7.25-7.17 (m, 2H), 7.11 (d, J=7.4 Hz, 1H), 4.68 (s, 2H), 4.37 (br s, 1H), 3.91 (br s, 1H), 2.85 (dd, J=12.7, 5.0 Hz, 1H), 2.66 (dd, J=13.3, 7.4 Hz, 1H), 1.42 (s, 9H), 1.09 (d, J=6.7 Hz, 3H). One exchangeable proton not observed.

e) 8-(Benzyloxy)-5-((R)-1-(tert-butyldimethylsilyloxy)-2-((R)-1-(3-(hydroxymethyl)phenyl)propan-2-ylamino)ethyl)quinolin-2 (1H)-one

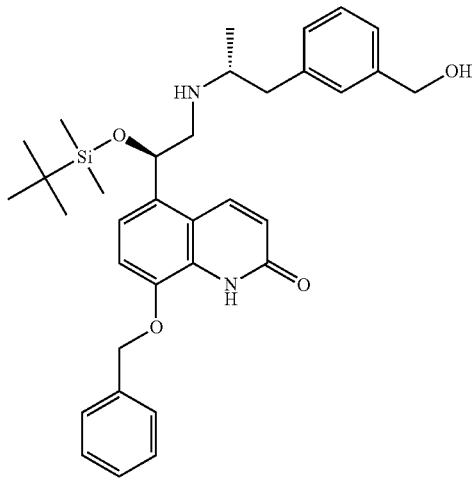 [SMILES: C[C@H](Cc1cccc(CO)c1)NC[C@H](O[Si](C)(C)C(C)(C)C)c1ccc(OCc2ccccc2)c2[nH]c(=O)ccc12]

A solution of (R)-tert-butyl 1-(3-(hydroxymethyl)phenyl)propan-2-ylcarbamate (Example 276, step d) (0.78 g) in dichloromethane (20 mL) was treated with trifluoroacetic acid (5 mL) and stirred at room temperature for 40 minutes. Toluene was added and the solution was concentrated in vacuo. The residue was partitioned between 1M aqueous NaOH and DCM and the phases separated. The aqueous phase was extracted twice more with DCM, then the combined organic extracts were dried (MgSO$_4$) and concentrated in vacuo to afford (R)-(3-(2-aminopropyl)phenyl)methanol as a colourless oil that slowly crystallised to a white solid on standing (0.442 g). A mixture of (R)-(3-(2-aminopropyl)phenyl)methanol (0.223 g), (R)-8-(benzyloxy)-5-(2-bromo-1-(tert-butyldimethylsilyloxy)ethyl)quinolin-2(1H)-one (0.72 g), sodium iodide (0.219 g) and Hunig's Base (0.77 mL) in acetonitrile (3 mL) was heated at reflux under nitrogen overnight. More (R)-(3-(2-aminopropyl)phenyl)methanol (0.219 g), Hunig's Base (0.51 mL) and acetonitrile (2 mL) were added and the mixture was heated at reflux over a second night. The cooled reaction mixture was diluted with ethyl acetate, washed twice with water, once with brine, then dried (MgSO$_4$) and concentrated onto flash silica in vacuo. The resulting powder was purified by flash chromatography on silica eluting with 5% triethylamine in ethyl acetate to afford the subtitled compound as a pale yellow foam. Yield 0.525 g.

$^1$H NMR (400 MHz, CDCl$_3$) δ 9.37 (br s, 1H), 8.46 (d, J=9.7 Hz, 1H), 7.69-7.56 (m, 5H), 7.39-7.22 (m, 4H), 7.17 (d, J=8.2 Hz, 1H), 7.12 (d, J=6.7 Hz, 1H), 6.82 (d, J=10.0 Hz, 1H), 5.37 (d, J=2.1 Hz, 2H), 5.26 (dd, J=7.4, 5.6 Hz, 1H), 4.82 (s, 2H), 3.24 (dd, J=11.4, 7.6 Hz, 1H), 3.05 (q, J=6.5 Hz, 1H), 2.93 (dd, J=11.4, 5.5 Hz, 1H), 2.84 (dd, J=13.6, 7.0 Hz, 1H), 2.74 (dd, J=13.2, 6.8 Hz, 1H), 1.25 (d, J=6.2 Hz, 3H), 1.04 (s, 9H), 0.24 (s, 3H), 0.00 (s, 3H). Two exchangeable protons not observed.

f) 5-((R)-1-(tert-Butyldimethylsilyloxy)-2-((R)-1-(3-(hydroxymethyl)phenyl)propan-2-ylamino)ethyl)-8-hydroxyquinolin-2(1H)-one

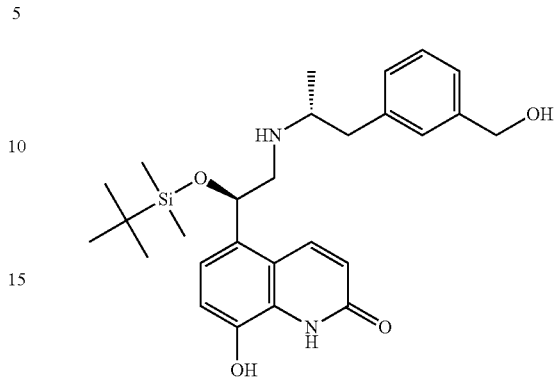

A mixture of 8-(benzyloxy)-5-((R)-1-(tert-butyldimethylsilyloxy)-2-((R)-1-(3-(hydroxymethyl)phenyl)propan-2-ylamino)ethyl)quinolin-2(1H)-one (Example 276, step e) (0.52 g) and 10% palladium on carbon catalyst (0.102 g) in ethanol (36 mL) was hydrogenated at room temperature and at 5 bar pressure of hydrogen for 1.5 hours, then hydrogenated at room temperature and at 1 bar pressure of hydrogen overnight. The mixture was filtered through diatomaceous earth, washing the catalyst well with ethanol, and the combined filtrate and washings were concentrated in vacuo to afford the subtitled compound. Yield 0.42 g. Material used immediately in the next step.

m/z 483 (M+H)$^+$ (APCI+)

g) tert-Butyl (R)-2-(8-(tert-butoxycarbonyloxy)-2-oxo-1,2-dihydroquinolin-5-yl)-2-(tert-butyldimethylsilyloxy)ethyl((R)-1-(3-(hydroxymethyl)phenyl)propan-2-yl)carbamate

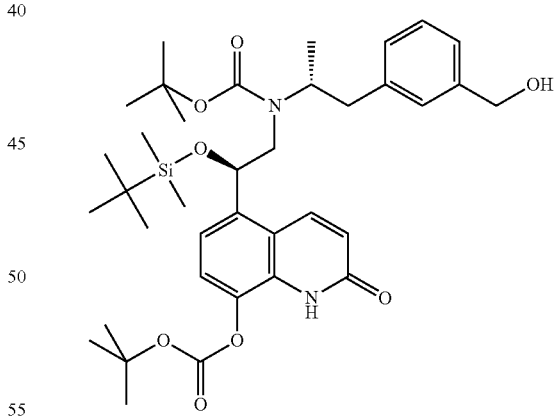

5-((R)-1-(tert-Butyldimethylsilyloxy)-2-((R)-1-(3-(hydroxymethyl)phenyl)propan-2-ylamino)ethyl)-8-hydroxyquinolin-2(1H)-one (Example 276, step f) (0.42 g) was dissolved in ethanol (25 mL), treated with triethylamine (0.26 mL) and di-tert-butyl dicarbonate (0.201 g) and stirred at room temperature for 1.5 hours. More di-tert-butyl dicarbonate (0.203 g) and triethylamine (0.13 mL) were added and the mixture was stirred at room temperature overnight, before it was concentrated in vacuo to afford the subtitled compound. Yield 0.609 g. Material used immediately in the next step.

m/z 683 (M+H)$^+$ (APCI+)

h) tert-Butyl (R)-2-(8-(tert-butoxycarbonyloxy)-2-oxo-1,2-dihydroquinolin-5-yl)-2-(tert-butyldimethylsilyloxy)ethyl((R)-1-(3-formylphenyl)propan-2-yl)carbamate

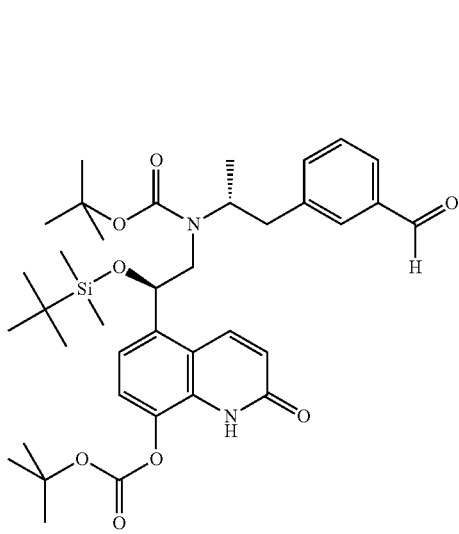 [SMILES: C[C@H](Cc1cccc(C=O)c1)N(C[C@H](O[Si](C)(C)C(C)(C)C)c1ccc(OC(=O)OC(C)(C)C)c2[nH]c(=O)ccc12)C(=O)OC(C)(C)C]

tert-Butyl (R)-2-(8-(tert-butoxycarbonyloxy)-2-oxo-1,2-dihydroquinolin-5-yl)-2-(tert-butyldimethylsilyloxy)ethyl((R)-1-(3-(hydroxymethyl)phenyl)propan-2-yl)carbamate (Example 276, step g) (0.609 g) was dissolved in dichloromethane (30 mL), treated with manganese (IV) oxide (0.791 g) and the resulting suspension stirred at room temperature over a weekend. More manganese (IV) oxide (0.801 g) was added and the suspension was stirred for a further 4 hours. The mixture was filtered through diatomaceous earth, washing the residue well with DCM, and the combined filtrate and washings were concentrated in vacuo to afford the subtitled compound. Yield 0.521 g. Material used immediately in the next step.

m/z 681 (M+H)⁺ (APCI+)

i) tert-Butyl (R)-2-(tert-butyldimethylsilyloxy)-2-(8-hydroxy-2-oxo-1,2-dihydroquinolin-5-yl)ethyl((R)-1-(3-formylphenyl)propan-2-yl)carbamate

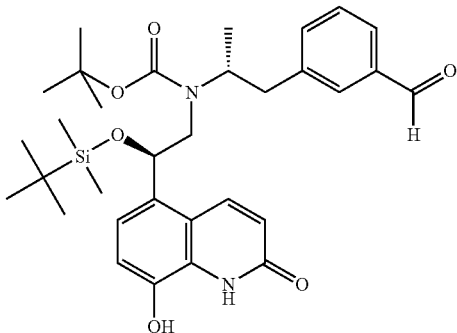 [SMILES: C[C@H](Cc1cccc(C=O)c1)N(C[C@H](O[Si](C)(C)C(C)(C)C)c1ccc(O)c2[nH]c(=O)ccc12)C(=O)OC(C)(C)C]

tert-Butyl (R)-2-(8-(tert-butoxycarbonyloxy)-2-oxo-1,2-dihydroquinolin-5-yl)-2-(tert-butyldimethylsilyloxy)ethyl ((R)-1-(3-formylphenyl)propan-2-yl)carbamate (Example 276, step h) (0.521 g) was suspended in methanol (20 mL) and treated with '880' aqueous ammonia (2.5 mL) to give a suspension that was stirred at room temperature for 3 hours. The mixture was concentrated by blowing with a stream of nitrogen, and the residue was partitioned between ethyl acetate, water and brine, and the phases separated. The aqueous phase was extracted with ethyl acetate, and the combined organic phases were washed with brine, dried (MgSO₄) and concentrated in vacuo to afford the subtitled compound. Yield 0.476 g. Material used immediately in the next step.

m/z 581 (M+H)⁺ (APCI+)

j) tert-Butyl (R)-2-(tert-butyldimethylsilyloxy)-2-(8-hydroxy-2-oxo-1,2-dihydroquinolin-5-yl)ethyl((R)-1-(3-((4-(5-isopropylthiophene-3-carbonyl)-1-oxa-4,9-diazaspiro[5.5]undecan-9-yl)methyl)phenyl)propan-2-yl)carbamate

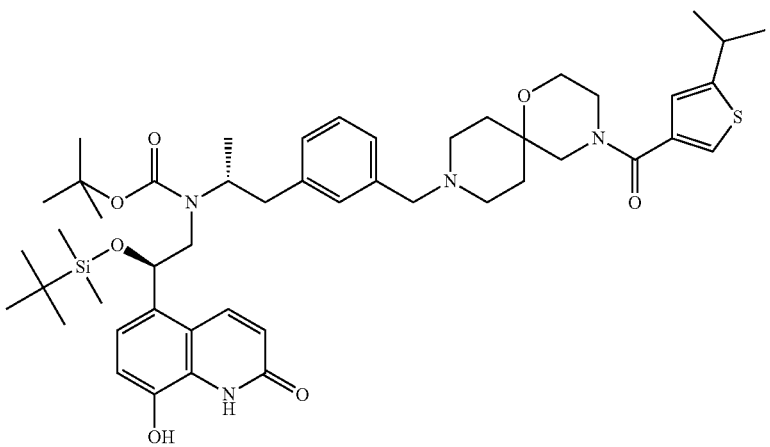 [SMILES: CC(C)c1cc(C(=O)N2CCOC3(CCN(Cc4cccc(C[C@@H](C)N(C[C@H](O[Si](C)(C)C(C)(C)C)c5ccc(O)c6[nH]c(=O)ccc56)C(=O)OC(C)(C)C)c4)CC3)C2)cs1]

tert-Butyl (R)-2-(tert-butyldimethylsilyloxy)-2-(8-hydroxy-2-oxo-1,2-dihydroquinolin-5-yl)ethyl((R)-1-(3-formylphenyl)propan-2-yl)carbamate (Example 276, step i) (0.476 g) was treated with (5-isopropylthiophen-3-yl)(1-oxa- 4,9-diazaspiro[5.5]undecan-4-yl)methanone (Example 275, step i) (0.296 g), N-methyl-2-pyrrolidinone (20 mL), acetic acid (0.052 mL) and sodium triacetoxyborohydride (0.294 g), and the mixture was stirred at room temperature overnight. The solution was poured into a mixture of saturated sodium bicarbonate solution and water and extracted three times with diethyl ether. The combined extracts were washed with water and brine, dried (MgSO₄) and concentrated in vacuo, then purified by flash chromatography on silica eluted with 1:5:94 NEt₃:MeOH:DCM to afford the subtitled compound. Yield 0.471 g.

m/z 874 (M+H)⁺ (APCI+)

k) 8-Hydroxy-5-((R)-1-hydroxy-2-((R)-1-(3-((4-(5-isopropylthiophene-3-carbonyl)-1-oxa-4,9-diazaspiro[5.5]undecan-9-yl)methyl)phenyl)propan-2-ylamino)ethyl)quinolin-2(1H)-one ditrifluoroacetate

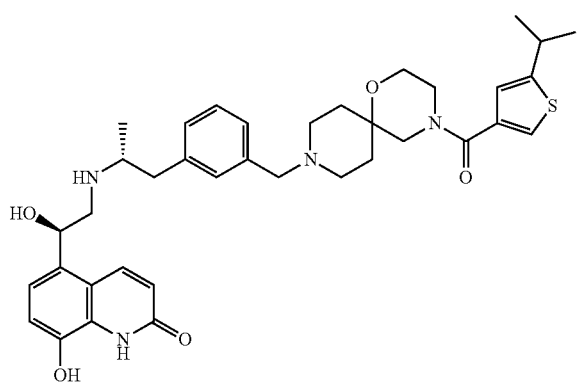

A solution of tert-butyl (R)-2-(tert-butyldimethylsilyloxy)-2-(8-hydroxy-2-oxo-1,2-dihydroquinolin-5-yl)ethyl ((R)-1-(3-((4-(5-isopropylthiophene-3-carbonyl)-1-oxa-4,9-diazaspiro[5.5]undecan-9-yl)methyl)phenyl)propan-2-yl) carbamate (Example 276, step j) (0.465 g) in formic acid (25 mL) was stirred at room temperature for 4 hours, then diluted with toluene and concentrated in vacuo. The residue was dissolved in a mixture of water and acetonitrile (11 mL), filtered, and purified by preparative HPLC (Sunfire, Gradient: 5-50% acetonitrile in 0.2% aqueous TFA). Fractions containing product were concentrated in vacuo and co-evaporated from acetonitrile three times to give a colourless residue. The residue was triturated with diethyl ether to give a solid, which was collected by filtration, washed with diethyl ether and dried in vacuo at room temperature to afford the titled compound as a white solid. Yield 0.234 g.

m/z 659 (M+H)⁺ (APCI+)

¹H NMR (400 MHz, DMSO, 90° C.) δ 8.20-8.13 (m, 1H), 7.48 (d, J=1.0 Hz, 1H), 7.46-7.31 (m, 4H), 7.20-7.13 (m, 1H), 7.00 (d, J=8.2 Hz, 1H), 6.90 (s, 1H), 6.56 (d, J=9.7 Hz, 1H), 5.37 (t, J=6.4 Hz, 1H), 4.29 (s, 2H), 3.70-3.62 (m, 2H), 3.62-3.50 (m, 3H), 3.49-3.36 (m, 2H), 3.30-2.98 (m, 8H), 2.81-2.71 (m, 1H), 2.12-1.93 (m, 2H), 1.81-1.60 (m, 2H), 1.28 (d, J=6.7 Hz, 6H), 1.20-1.13 (m, 3H). Six exchangeable protons not observed.

EXAMPLE 277

(R)—N-Cyclohexyl-N-(2-(2-hydroxy-2-(4-hydroxy-2-oxo-2,3-dihydrobenzo[d]thiazol-7-yl)ethylamino)ethyl)-3-(3-((4-(2-methylthiazole-4-carbonyl)-1-oxa-4,9-diazaspiro[5.5]undecan-9-yl)methyl)phenethoxy)propanamide ditrifluoroacetate

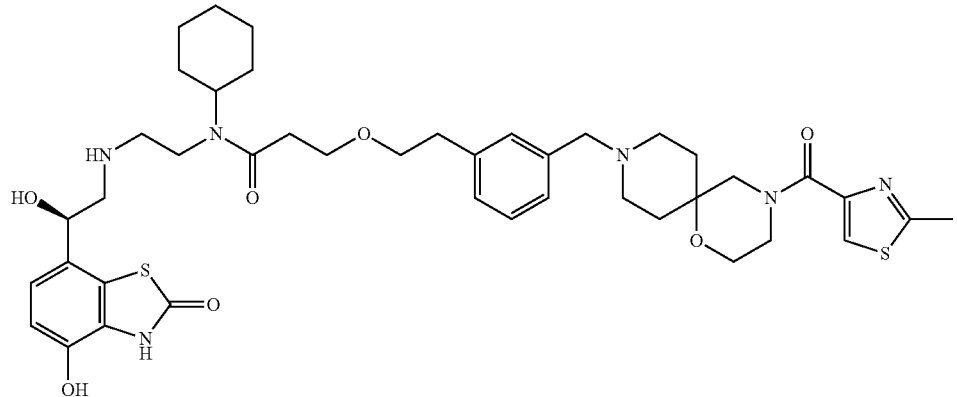 [SMILES: Cc1nc(C(=O)N2CCOC3(CCN(Cc4cccc(CCOCCC(=O)N(CCNC[C@H](O)c5ccc(O)c6[nH]c(=O)sc56)C5CCCCC5)c4)CC3)C2)cs1]

a) tert-Butyl 3-(3-((4-(2-methylthiazole-4-carbonyl)-1-oxa-4,9-diazaspiro[5.5]undecan-9-yl)methyl)phenethoxy)propanoate

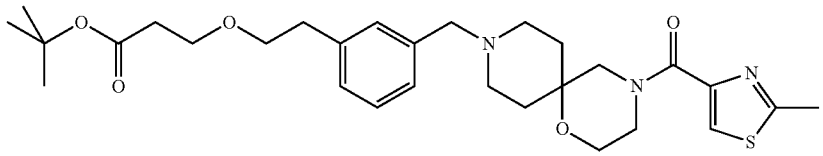 [SMILES: Cc1nc(C(=O)N2CCOC3(CCN(Cc4cccc(CCOCCC(=O)OC(C)(C)C)c4)CC3)C2)cs1]

Triton-B (0.094 mL) was added to a solution of (9-(3-(2-hydroxyethyl)benzyl)-1-oxa-4,9-diazaspiro[5.5]undecan-4-yl)(2-methylthiazol-4-yl)methanone (Example 6, step b) (1.72 g) in toluene (30 mL). The mixture was concentrated in vacuo and cooled to 0° C. tert-Butyl acrylate (0.671 mL) was added over 1 minute and the mixture was stirred at room temperature over 20 hours. The reaction was diluted with DCM (50 mL) and the organic washed with saturated sodium bicarbonate solution (50 mL), brine (50 mL), dried over sodium sulphate, filtered and evaporated to afford the subtitled compound. Material used directly in the next step.

b) 3-(3-((4-(2-Methylthiazole-4-carbonyl)-1-oxa-4,9-diazaspiro[5.5]undecan-9-yl)methyl)phenethoxy)propanoic acid

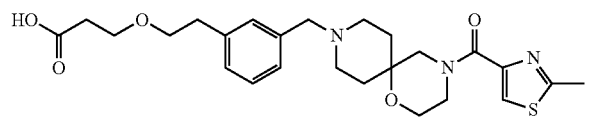 [SMILES: Cc1nc(C(=O)N2CCOC3(CCN(Cc4cccc(CCOCCC(=O)O)c4)CC3)C2)cs1]

tert-Butyl 3-(3-((4-(2-methylthiazole-4-carbonyl)-1-oxa-4,9-diazaspiro[5.5]undecan-9-yl)methyl)phenethoxy)propanoate (Example 277, step a) was dissolved in DCM (10 mL) and TFA (2 mL) was added. The resulting mixture was stirred for 2 h then evaporated. The residue was azeotroped with toluene and redissolved in MeCN (10 mL). This was applied to a SCX cartridge (50 g, Varian) which had been pre-wetted with MeCN. The cartridge was washed with MeCN (100 mL) and eluted with 880 aqueous ammonia in MeCN (1:4, 100 mL). The eluent was evaporated to afford the subtitled compound. Material used directly in the next step.

c) N-Cyclohexyl-N-(2,2-dimethoxyethyl)-3-(3-((4-(2-methylthiazole-4-carbonyl)-1-oxa-4,9-diazaspiro[5.5]undecan-9-yl)methyl)phenethoxy)propanamide 3-(3-((4-(2-Methylthiazole-4-carbonyl)-1-oxa-4,9-diazaspiro[5.5]undecan-9-yl)methyl)phenethoxy)propanoic acid (Example 277, step b) was dissolved in DMF (10 mL), and N-(2,2-dimethoxyethyl)cyclohexanamine (WO2008075025) (0.93 g), triethylamine (2.88 mL) and T3P (3.95 mL) were added. The reaction was stirred overnight and partioned between water (100 mL) and ethyl acetate (100 mL). The layers were separated and the aqueous extracted with ethyl acetate (2×100 mL). The combined organics were washed with saturated sodium bicarbonate solution (100 mL), brine (100 mL), dried over sodium sulphate, filtered and evaporated. The residue was purified by flash silica column chromatography eluting with 47.5:47.5:5 ethyl acetate:i-hexane:triethylamine to 95:5 ethyl acetate:triethylamine gradient to afford the subtitled compound as a colorless oil. Yield 0.9 g.

$^1$H NMR (400 MHz, DMSO, 90° C.) δ 7.85 (s, 1H), 7.26-7.05 (m, 4H), 4.46-4.37 (m, 1H), 3.68-3.55 (m, 11H), 3.43 (s, 2H), 3.33-3.22 (m, 8H), 2.77 (t, J=6.9 Hz, 2H), 2.68 (s, 3H), 2.56 (t, J=6.7 Hz, 2H), 2.38-2.32 (m, 4H), 1.78-1.65 (m, 4H), 1.63-1.42 (m, 6H), 1.33-1.19 (m, 2H), 1.15-1.00 (m, 2H).-

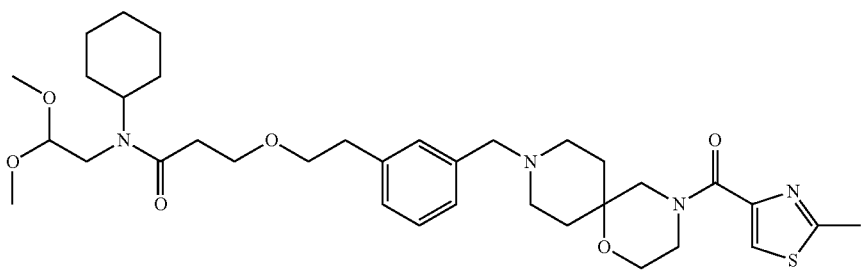 [SMILES: COC(CN(C(=O)CCOCCc1cccc(CN2CCC3(CC2)CN(C(=O)c2csc(C)n2)CCO3)c1)C1CCCCC1)OC]

d) N-Cyclohexyl-3-(3-((4-(2-methylthiazole-4-carbonyl)-1-oxa-4,9-diazaspiro[5.5]undecan-9-yl)methyl)phenethoxy)-N-(2-oxoethyl)propanamide

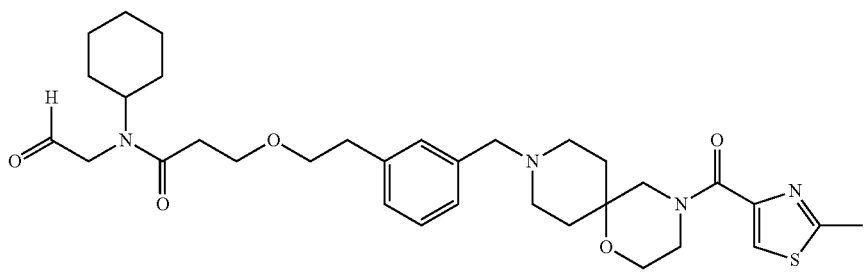 [SMILES: Cc1nc(C(=O)N2CCOC3(CCN(Cc4cccc(CCOCCC(=O)N(CC=O)C5CCCCC5)c4)CC3)C2)cs1]

Tosic acid (1384 mg) was added to a solution of N-cyclohexyl-N-(2,2-dimethoxyethyl)-3-(3-((4-(2-methylthiazole-4-carbonyl)-1-oxa-4,9-diazaspiro[5.5]undecan-9-yl)methyl)phenethoxy)propanamide (Example 277, step c) (683 mg) in DCM (10 mL) and the resulting mixture stirred at ambient temperature for 4 h. Sodium bicarbonate solution (saturated, 10 mL) was cautiously added and the mixture stirred until bubbling ceased (10 min). The reaction was diluted with DCM (50 mL) and the aqeuous separated. The organic was washed with saturated sodium bicarbonate solution (2×20 mL), brine (20 mL), dried over sodium sulphate, filtered and evaporated to afford the subtitled compound.

m/z 611 (M+H)$^+$ (APCI+)

e) (R)—N-Cyclohexyl-N-(2-(2-hydroxy-2-(4-hydroxy-2-oxo-2,3-dihydrobenzo[d]thiazol-7-yl)ethylamino)ethyl)-3-(3-((4-(2-methylthiazole-4-carbonyl)-1-oxa-4,9-diazaspiro[5.5]undecan-9-yl)methyl)phenethoxy)propanamide ditrifluoroacetate A solution of N-cyclohexyl-3-(3-((4-(2-methylthiazole-4-carbonyl)-1-oxa-4,9-diazaspiro[5.5]undecan-9-yl)methyl)phenethoxy)-N-(2-oxoethyl)propanamide (Example 277, step d) (0.122 g) in methanol (3 mL) was added to a mixture of (R)-7-(2-amino-1-hydroxyethyl)-4-hydroxybenzo[d]thiazol-2(3H)-one, HCl (WO2007027134, example 1, step d) (0.079 g) and acetic acid (0.011 mL). The resulting mixture was stirred for 5 min then cooled to 0° C. Sodium cyanoborohydride (0.019 g) was then added and the mixture allowed to warm to ambient temperature and stirred for 2 h. Solvent evaporated and the residue purified by flash silica column chromatography eluting with 95:5:0.5 to 89:10:1 DCM:MeOH:880 aqueous ammonia. The fractions containing product were combined, evaporated and purified by HPLC (Sunfire, Gradient: 5-40% acetonitrile in 0.2% aqueous TFA). The fractions containing product were combined, evaporated and triturated with diethyl ether to afford the titled compound as a white solid. Yield 0.085 g.

m/z 821 (M+H)$^+$ (MultiMode+)

$^1$H NMR (400 MHz, DMSO, 90° C.) δ 11.26 (s, 1H), 7.90 (s, 1H), 7.41-7.28 (m, 4H), 6.93 (d, J=8.2 Hz, 1H), 6.77 (d, J=8.2 Hz, 1H), 4.89 (dd, J=8.7, 4.1 Hz, 1H), 4.29 (s, 2H),

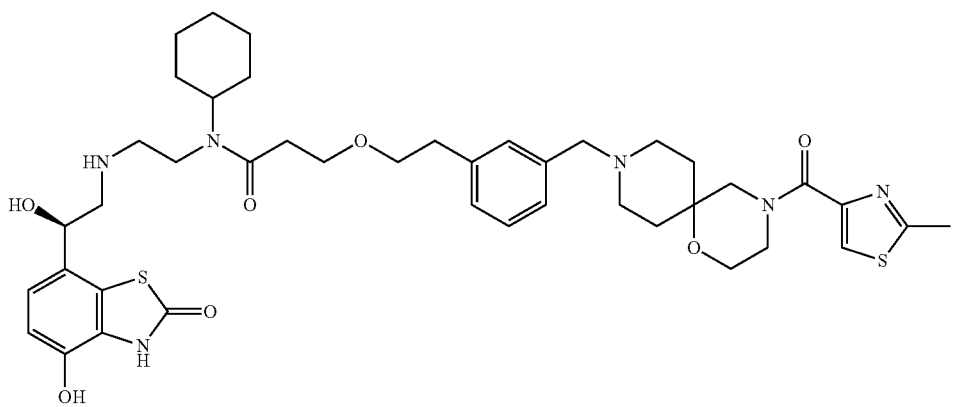 [SMILES: Cc1nc(C(=O)N2CCOC3(CCN(Cc4cccc(CCOCCC(=O)N(CCNC[C@H](O)c5ccc(O)c6[nH]c(=O)sc56)C5CCCCC5)c4)CC3)C2)cs1]

3.74-3.43 (m, 13H), 3.29-2.98 (m, 8H), 2.83 (t, J=6.7 Hz, 2H), 2.71-2.56 (m, 5H), 1.98-1.01 (m, 14H). 5 exchangables not observed.

EXAMPLE 278

(R)-4-hydroxy-7-(1-hydroxy-2-(2-(4-((4-(2-isopropylthiazole-4-carbonyl)-1-oxa-4,9-diazaspiro[5.5]undecan-9-yl)methyl)thiophen-2-yl)ethylamino)ethyl)benzo[d]thiazol-2(3H)-one ditrifluoroacetate

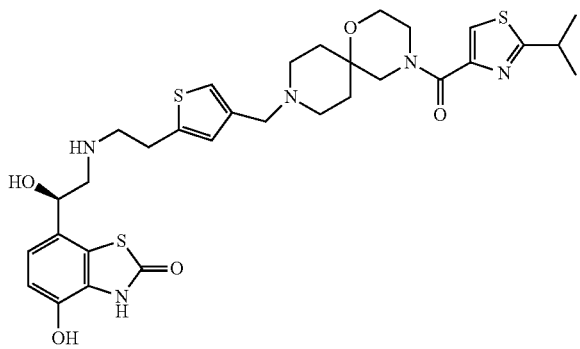 [SMILES: CC(C)c1nc(C(=O)N2CCOC3(CCN(Cc4csc(CCNC[C@H](O)c5ccc(O)c6[nH]c(=O)sc56)c4)CC3)C2)cs1]

a) tert-butyl(2-(5-chlorothiophen-2-yl)ethoxy)dimethylsilane

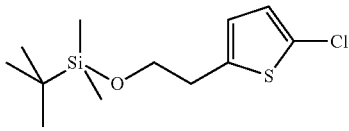 [SMILES: CC(C)(C)[Si](C)(C)OCCc1ccc(Cl)s1]

N-chlorosuccinimide (0.83 g) was added portionwise to a solution of tert-butyldimethyl(2-(thiophen-2-yl)ethoxy)silane (1.5 g) (example 4 step a) in chloroform (50 mL) and heated to reflux for 3 days. The yellow solution was diluted with DCM (100 mL) and washed with saturated sodium bicarbonate solution (2×100 mL), brine (100 mL), dried over sodium sulphate, filtered and evaporated in vacuo. The residue was purified by silica gel chromatography eluting with iso-hexane. The fractions containing product were combined and evaporated in vacuo to give the subtitled compound as a clear oil. Yield 1 g.

$^1$H NMR (300 MHz, CDCl$_3$) δ 6.69 (d, J=3.5 Hz, 1H), 6.57-6.54 (m, 1H), 3.75 (t, J=6.5 Hz, 2H), 2.89 (t, J=6.4 Hz, 2H), 0.87 (s, 9H), 0.01 (s, 6H)

b) 5-(2-(tert-butyldimethylsilyloxy)ethyl)-2-chlorothiophene-3-carbaldehyde

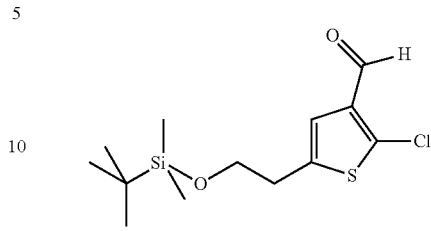

tert-butyl(2-(5-chlorothiophen-2-yl)ethoxy)dimethylsilane (0.8 g) (example 278, step a) was added dropwise over 5 min to a stirred solution of butyl lithium (2.5M in hexanes 1.7 mL) and 2,2,6,6-tetramethylpiperidine (0.73 mL) in THF (25 mL) at −78° C. The resulting mixture was stirred for 2 hrs and DMF (0.67 mL) was added. The mixture was stirred for a further 1 hr and allowed to warm to RT. The reaction was cautiously poured into HCl solution (0.5M, 200 mL) and extracted with ethyl acetate (3×100 mL). The combined organic solutions were washed with water (2×100 mL), brine (100 mL), dried over sodium sulphate, filtered and evaporated in vacuo. The resulting oil was purified by silica gel chromatography eluting with iso-hexane to 5% ether in iso-hexane gradient. The fractions containing product were combined and evaporated in vacuo to give the subtitle compound as a clear oil. Yield (0.8 g)

$^1$H NMR (400 MHz, CDCl$_3$) δ 9.98 (s, 1H), 7.06-7.04 (m, 1H), 3.79 (t, J=6.0 Hz, 2H), 2.95-2.85 (m, 2H), 0.90 (s, 9H), 0.05 (s, 6H)

c) 5-(2-(tert-butyldimethylsilyloxy)ethyl)thiophene-3-carbaldehyde

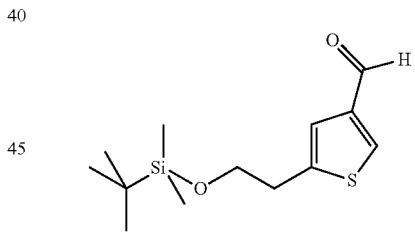

5-(2-(tert-butyldimethylsilyloxy)ethyl)-2-chlorothiophene-3-carbaldehyde (0.8 g) (example 278, step b) in a mixture of ethanol (50 mL) and triethylamine (0.91 mL) with 10% palladium on carbon catalyst (0.28 g) was stirred vigorously under 4 bar pressure of hydrogen for 18 hours. The mixture was filtered through celite and the filter pad washed with ethanol (50 mL). The combined filtrate and washings were evaporated and azeotroped with toluene (20 mL) to give a yellow oil. The oil was dissolved in DCM (100 mL), manganese dioxide (2.3 g) was added and the resulting suspension refluxed overnight. The mixture was filtered through celite and the filter pad washed with DCM (50 mL). The combined filtrate and washings were evaporated in vacuo to give the subtitled compound as a yellow oil. Yield 0.6 g.

$^1$H NMR (300 MHz, CDCl$_3$) δ 9.80 (s, 1H), 7.93-7.90 (m, 1H), 3.80 (t, J=6.2 Hz, 2H), 2.99 (t, J=5.9 Hz, 2H), 0.88 (s, 9H), 0.01 (s, 6H)+one H obscured by solvent peak d) (9-((5-(2-(tert-butyldimethylsilyloxy)ethyl)thiophen-3-yl)methyl)-1-oxa-4,9-diazaspiro[5.5]undecan-4-yl)(2-isopropylthiazol-4-yl)methanone

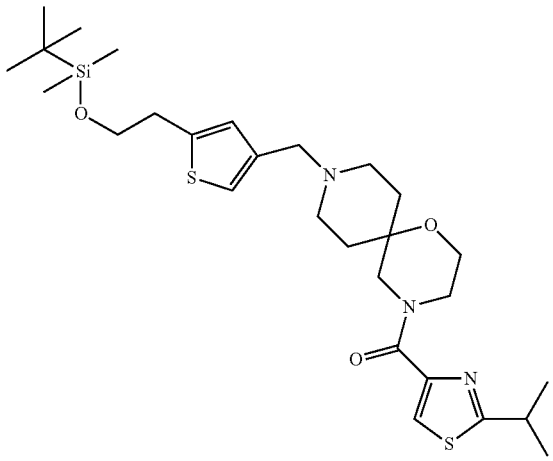 [SMILES: CC(C)c1nc(C(=O)N2CCOC3(CCN(Cc4csc(CCO[Si](C)(C)C(C)(C)C)c4)CC3)C2)cs1]

5-(2-(tert-butyldimethylsilyloxy)ethyl)thiophene-3-carbaldehyde (0.6 g) (example 278, step c) was added to (2-isopropylthiazol-4-yl)(1-oxa-4,9-diazaspiro[5.5]undecan-4-yl)methanone (0.94 g) (example 22, step b) in a mixture of N-methyl-2-pyrrolidinone (5 mL) and acetic acid (0.13 mL) and stirred for 30 min. Sodium triacetoxyborohydride (0.71 g) was then added and the mixture stirred overnight. The reaction was poured into water (100 mL), the pH was adjusted to 8 using saturated sodium bicarbonate solution and the resulting aqueous solution extracted with ethyl acetate (3×100 mL). The combined organic solutions were washed with water (3×100 mL), brine (100 mL), dried over sodium sulphate, filtered and evaporated. The residue was purified by silica gel chromatography eluting with 77.5:17.5:5 i-hexane:ethyl acetate:triethylamine to 47.5:47.5:5 i-hexane:ethyl acetate:triethylamine gradient. The fractions containing product were combined and evaporated in vacuo to give the subtitled compound as a clear oil. Yield 0.8 g.

564 (M+H)$^+$ (APCI)

$^1$H NMR (400 MHz, D$_6$-DMSO, 90° C.) δ 7.91 (s, 1H), 6.97 (s, 1H), 6.77 (s, 1H), 3.79 (t, J=6.3 Hz, 2H), 3.69-3.55 (m, 4H), 3.41-3.27 (m, 3H), 2.92 (td, J=6.3, 0.8 Hz, 2H), 2.42-2.23 (m, 6H), 1.75-1.64 (m, 2H), 1.59-1.47 (m, 2H), 1.37 (d, J=6.9 Hz, 6H), 0.89 (s, 9H), 0 (s, 6H)

e) (9-((5-(2-hydroxyethyl)thiophen-3-yl)methyl)-1-oxa-4,9-diazaspiro[5.5]undecan-4-yl)(2-isopropylthiazol-4-yl)methanone

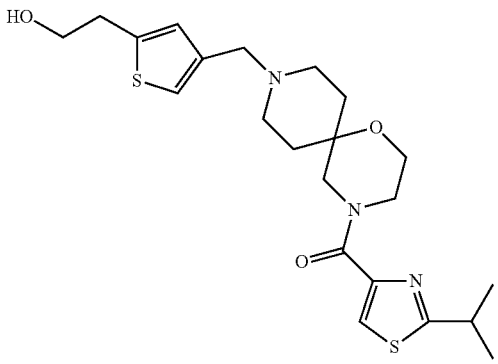 [SMILES: CC(C)c1nc(C(=O)N2CCOC3(CCN(Cc4csc(CCO)c4)CC3)C2)cs1]

Tetrabutylammonium fluoride (1M in tetrahydrofuran, 2.1 mL) was added to a solution of (9-((5-(2-(tert-butyldimethylsilyloxy)ethyl)thiophen-3-yl)methyl)-1-oxa-4,9-diazaspiro[5.5]undecan-4-yl)(2-isopropylthiazol-4-yl)methanone (example 278, step d) (0.80 g) in tetrahydrofuran (10 mL). After 2 h, the solution was evaporated in vacuo and the residue partitioned between saturated sodium bicarbonate solution (50 mL) and ethyl acetate (50 mL). The layers were separated and the aqueous phase extracted with ethyl acetate (2×50 mL). The combined organic solutions were washed with brine (50 mL), dried over sodium sulphate, filtered and evaporated. The residue was purified by silica gel chromatography, eluting with 20:1 ethyl acetate:triethylamine. The fractions containing product were combined and evaporated in vacuo to give the subtitled compound as a gum. Yield 0.61 g.

450 (M+H)$^+$ (APCI)

$^1$H NMR (400 MHz, D$_6$-DMSO, 90° C.) δ 7.90 (s, 1H), 6.94 (s, 1H), 6.74 (s, 1H), 4.41 (t, J=5.1 Hz, 1H), 3.72-3.55 (m, 4H), 3.41-3.24 (m, 3H), 3.00 (s, 2H), 2.88 (t, J=6.7 Hz, 2H), 2.43-2.26 (m, 6H), 1.75-1.30 (m, 10H)

f) (R)-4-hydroxy-7-(1-hydroxy-2-(2-(4-((4-(2-isopropylthiazole-4-carbonyl)-1-oxa-4,9-diazaspiro[5.5]undecan-9-yl)methyl)thiophen-2-yl)ethylamino)ethyl)benzo[d]thiazol-2(3H)-one ditrifluoroacetate

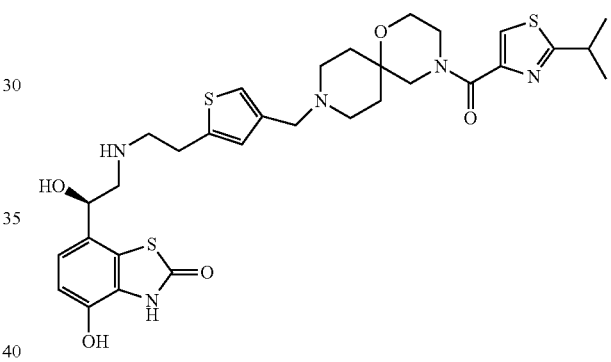

A solution of (9-((5-(2-hydroxyethyl)thiophen-3-yl)methyl)-1-oxa-4,9-diazaspiro[5.5]undecan-4-yl)(2-isopropylthiazol-4-yl)methanone (0.35 g) (example 278, step e) in dichloromethane (10 mL) was treated with trifluoroacetic acid (0.06 mL) followed by Dess-Martin periodinane (0.56 g) and the resultant mixture stirred at RT for 1 hour. The reaction mixture was treated with saturated sodium thiosulphate solution (10 mL) and saturated sodium bicarbonate solution (10 mL) and ethyl acetate (10 mL) and stirred vigorously for 5 minutes. The mixture was extracted with ethyl acetate (2×30 mL). The combined organic solutions were washed with saturated sodium bicarbonate solution, dried over sodium sulphate, filtered, treated with acetic acid (0.09 mL) and the solvent evaporated under reduced pressure. The residue was dissolved in methanol (5 mL) and (R)-7-(2-amino-1-hydroxyethyl)-4-hydroxybenzo[d]thiazol-2(3H)-one hydrochloride (WO2007027134, example 1, step d) (0.15 g) was then added and the mixture stirred for 5 min before cooling in an ice bath. Sodium cyanoborohydride (0.07 g) was then added and the mixture allowed to warm to RT and stirred overnight. The solvent was evaporated in vacuo. Purification was by silica gel chromatography eluting with 94.5:5:0.5 to 89:10:1 DCM:methanol:'880' aqueous ammonia gradient. The fractions containing product were combined and evaporated in vacuo. Further purification was by preparative HPLC (Sunfire™, Gradient: 10-30% acetonitrile in 0.2% aqueous TFA). The fractions containing product were combined, evaporated in vacuo, azeotroped with acetonitrile and the residue triturated with ether to give the titled compound as a white solid. Yield 0.10 g.

m/z 658 (M+H)⁺ (Multimode)

$^1$H NMR (500 MHz, D$_6$-DMSO) δ 11.68 (s, 1H), 10.42-10.01 (m, 2H), 9.06 (s, 1H), 8.86 (s, 1H), 8.04 (s, 1H), 7.59 (s, 1H), 7.03 (s, 1H), 6.92 (d, J=8.4 Hz, 1H), 6.79 (d, J=8.3 Hz, 1H), 6.52 (s, 1H), 4.94-4.86 (m, 1H), 4.42-4.23 (m, 2H), 3.82-3.48 (m, 6H), 3.34-2.91 (m, 11H), 2.14-2.02 (m, 2H), 1.83-1.59 (m, 2H), 1.33 (d, J=6.8 Hz, 6H)

EXAMPLE 279

(R)-4-Hydroxy-7-(1-hydroxy-2-(9-(4-(2-isopropylthiazole-4-carbonyl)-1-oxa-4,9-diazaspiro[5.5]undecan-9-yl)-3,3-dimethylnonylamino)ethyl)benzo[d]thiazol-2(3H)-one formate

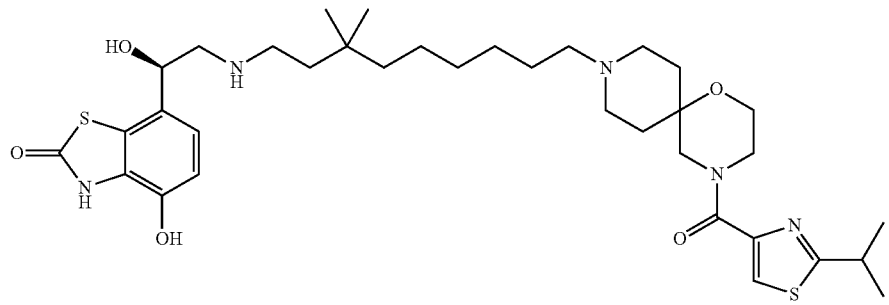 [SMILES: CC(C)c1nc(C(=O)N2CCOC3(CCN(CCCCCCC(C)(C)CCNC[C@H](O)c4ccc(O)c5[nH]c(=O)sc45)CC3)C2)cs1]

a) Ethyl 8-(tert-butyldimethylsilyloxy)-2,2-dimethyloctanoate

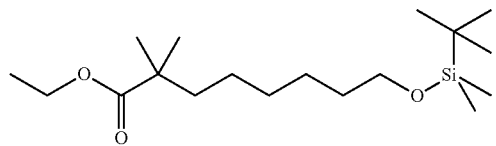 [SMILES: CCOC(=O)C(C)(C)CCCCCCO[Si](C)(C)C(C)(C)C]

n-Butyl lithium (32.8 mL) was added to a solution of diisopropylamine (1M in toluene, 11.64 mL) in THF (60 mL) at 0° C. to 5° C. over 15 minutes, and this mixture was stirred for 30 minutes. The reaction mixture was cooled to −78° C. then isobutyric acid ethyl ester (10 mL) was added dropwise over 15 minutes. The mixture was stirred at −78° C. for 1 hour, then (6-bromohexyloxy)-tert-butyldimethylsilane (23 mL) was added dropwise and the reaction mixture was stirred at −78° C. for a further 60 minutes. The cooling bath was removed and the mixture stirred at room temperature overnight before being poured onto a saturated aqueous solution of ammonium chloride (300 mL) and extracted with ethyl acetate (2×300 mL). The combined organic layers were washed with water (250 mL), dried over magnesium sulfate, filtered and evaporated to give the crude product. Purification was by silica gel chromatography eluting with 0-40% ethyl acetate in cyclohexane to afford the subtitled compound as a pale amber liquid. Yield 20 g.

$^1$H NMR (400 MHz, CDCl$_3$): δ 4.11 (q, J=7.1 Hz, 2H); 3.59 (t, J=6.6 Hz, 2H); 1.54-1.45 (m, 4H); 1.35-1.18 (m, 9H); 1.15 (s, 6H); 0.89 (s, 9H); 0.05-0.03 (m, 6H).

b) 8-(tert-Butyldimethylsilyloxy)-2,2-dimethyloctan-1-ol

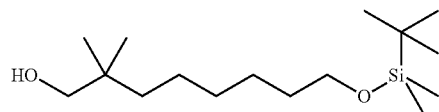 [SMILES: CC(C)(CO)CCCCCCO[Si](C)(C)C(C)(C)C]

Ethyl 8-(tert-butyldimethylsilyloxy)-2,2-dimethyloctanoate (example 279, step a) (20 g) in dry ether under nitrogen (300 mL) was cooled to 0° C. in an ice bath then diisobutylaluminium hydride (1M in toluene, 133 mL) was added dropwise. The reaction mixture was stirred at 0° C. for 1 hour then quenched with saturated aqueous potassium sodium tartrate (Rochelle's salt, 400 mL) and stirred overnight. The mixture was extracted with ethyl acetate (3×300 mL) then the combined organic layers were washed with brine, dried over magnesium sulfate, filtered and evaporated. Purification was by silica gel chromatography eluting with 0-20% ethyl acetate in cyclohexane to afford the subtitled compound as a colourless liquid. Yield 10.11 g.

$^1$H NMR (400 MHz, CDCl$_3$): δ 3.60 (t, J=6.6 Hz, 2H); 3.31 (s, 2Hi); 1.56-1.46 (m, 2H); 1.38-1.18 (m, 8H); 0.89 (s, 9H); 0.86 (s, 6H); 0.06-0.03 (m, 6H) plus one exchangeable not observed.

c) Mixture of (E)-tert-Butyl(9-methoxy-7,7-dimethylnon-8-enyloxy)dimethylsilane and (Z)-tert-Butyl(9-methoxy-7,7-dimethylnon-8-enyloxy)dimethylsilane

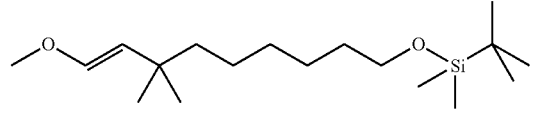 [SMILES: CO/C=C/C(C)(C)CCCCCCO[Si](C)(C)C(C)(C)C]

Oxalyl Chloride (5.9 mL) was added at −70° C. to a solution of dimethylsulfoxide (4.98 mL) in dry dichloromethane (60 mL) and the mixture stirred for 1 hour. 8-(tert-Butyldimethylsilyloxy)-2,2-dimethyloctan-1-ol (example 279, step b) (10.11 g), dissolved in dichloromethane (20 mL), was added dropwise and the mixture allowed to stir for 1 hour. Triethylamine (19.4 mL) was then added and stirring continued for 1 hour. The cooling bath was removed and the mixture allowed to warm to room temperature, at which point DCM (15 mL) was added. 1N HCl was added dropwise to dissolve the salts present in the reaction mixture and the layers separated. The aqueous layer was extracted with DCM (2×250 mL) then the combined organic layers were washed with saturated aqueous sodium carbonate (250 mL), dried over magnesium sulfate, filtered and concentrated under vacuum to give an orange liquid. The residue was filtered through a short plug of silica using diethyl ether as the eluent to afford 8-(tert-butyl-dimethyl-silanyloxy)-2,2-dimethyl-octanal as a yellow liquid which was used without further purification.

Potassium tert-butoxide (15.3 g) and (methoxymethyl)triphenylphosphonium chloride (48 g) in dry THF (350 mL) were cooled to 0° C. and stirred for 30 minutes. 8-(tert-butyl-dimethyl-silanyloxy)-2,2-dimethyl-octanal (10.03 g) was dissolved in dry THF (150 mL) and added to the reaction mixture, which was then stirred at 0° C. for 1 hour. The mixture was allowed to warm to room temperature and stirred for 30 minutes before addition of saturated sodium bicarbonate solution (300 mL) followed by extraction with diethyl ether (3×300 mL). The combined organic layers were washed with brine (300 mL), dried over magnesium sulfate, filtered and evaporated under vacuum to give the crude product. Cyclohexane (300 mL) was added and the mixture agitated for 5 minutes. The solvent was decanted off and this process was repeated. Evaporation of the cyclohexane layer gave a yellow liquid with some white solid present. The solid was removed by filtration then the filtrate was purified by silica gel chromatography eluting with 0-40% ethyl acetate in cyclohexane. Further purification was achieved by dissolving the material (3.2 g) in acetone (50 mL), treating with sodium iodide (3.05 g) followed by Merrifield resin (6.4 g) and stirring the mixture over the weekend. The resin was filtered and washed with acetone (100 mL), DCM (50 mL) and methanol (50 mL). The filtrate was evaporated and taken up into DCM (200 mL), washed with water (2×60 mL) and the organic layer dried over magnesium sulfate and evaporated under reduced pressure to give the subtitled product as a pale yellow liquid and as a mixture of cis/trans isomers. Yield 2.6 g.

$^1$H NMR (400 MHz, CDCl$_3$): δ 6.16 (d, J=12.9 Hz, 0.6H); 5.69 (d, J=7.0 Hz, 0.4H); 4.73 (d, J=12.9 Hz, 0.6H); 4.09 (d, J=7.0 Hz, 0.4H); 3.61-3.56 (m, 2H); 3.53-3.47 (m, 3H); 1.56-1.45 (m, 2H); 1.38-1.16 (m, 8H); 1.05 (d, J=10.1 Hz, 3H); 0.97 (s, 3H); 0.92-0.86 (m, 9H); 0.06-0.02 (m, 6H).

d) A mixture of (E)-9-Methoxy-7,7-dimethylnon-8-en-1-ol and (Z)-9-Methoxy-7,7-dimethylnon-8-en-1-ol

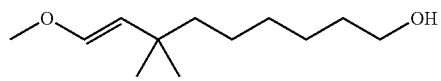

(E)-tert-Butyl(9-methoxy-7,7-dimethylnon-8-enyloxy) dimethylsilane (example 279, step c) (2.57 g) was dissolved in tetrahydrofuran (60 mL) and tetrabutylammonium fluoride (16.4 mL) was added and the reaction mixture allowed to stir at room temperature for 4 hours. The reaction mixture was quenched with water (50 mL) and extracted with diethyl ether (3×100 mL). The organic layer was dried over magnesium sulfate, filtered and concentrated under vacuum to give the subtitled compound as a pale yellow liquid and as a mixture of cis/trans isomers, which was used without further purification. Yield 1.2 g $^1$H NMR (400 MHz, CDCl$_3$): δ 6.16 (d, J=12.9 Hz, 0.5H); 5.70 (d, J=7.0 Hz, 0.5H); 4.74 (d, J=12.9 Hz, 0.5H); 4.11 (d, J=7.0 Hz, 0.5H); 3.68-3.61 (m, 2H); 3.52 (s, 1.5H); 3.49 (s, 1.5H); 1.62-1.51 (m, 2H); 1.40-1.21 (m, 8H); 1.07 (s, 3H); 0.98 (s, 3H) plus one exchangeable not observed.

e) 7,7-Dimethyl-9-oxononyl methanesulfonate

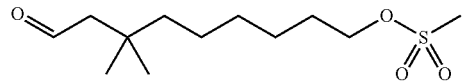 [SMILES: CC(C)(CC=O)CCCCCCOS(C)(=O)=O]

A mixture of (E)-9-methoxy-7,7-dimethylnon-8-en-1-ol and (Z)-9-methoxy-7,7-dimethylnon-8-en-1-ol (example 279, step d) (1.6 g) was dissolved in dichloromethane (15 mL) and triethylamine (1.33 mL) was added then the mixture was cooled to 0° C. in an ice bath under argon. Methanesulfonyl chloride (0.68 mL) was added dropwise over 5 minutes and the reaction mixture was stirred at 0° C. for 15 minutes and then at room temperature for 1 hour. The reaction mixture was washed with brine (2×30 mL), dried over magnesium sulfate, filtered and evaporated under vacuum to give the crude product. Purification was by silica gel chromatography, eluting with 0-100% ethyl acetate in cyclohexane to afford the subtitled compound as a colourless oil. Yield 1.2 g.

$^1$H NMR (400 MHz, CDCl$_3$): δ 9.85-9.81 (m, 1H); 4.25-4.18 (m, 2H); 3.00 (s, 3H); 2.25 (m, 2H); 1.80-1.69 (m, 2H); 1.47-1.37 (m, 2H), 1.31 (s, 6H); 1.05-1.01 (m, 6H).

f) 9-(4-(2-Isopropylthiazole-4-carbonyl)-1-oxa-4,9-diazaspiro[5.5]undecan-9-yl)-3,3-dimethylnonanal (2-Isopropyl-thiazol-4-yl)-(1-oxa-4,9-diaza-spiro[5.5]undec-4-yl)-methanone (0.262 g) (prepared from the trifluoroacetate salt as in Example 102, step c) was dissolved in acetonitrile (4 mL) and triethylamine (0.22 mL) was added. This solution was then added to a solution of 7,7-dimethyl-9-oxononyl methanesulfonate (Example 279, step e) (0.291 g) in acetonitrile (4 mL) and the resultant mixture heated at 80° C. overnight. The solvents were removed under vacuum. Purification was by silica gel chromatography eluting with 0-10% Methanol in DCM to afford the subtitled compound as a colourless oil. Yield 0.361 g.

$^1$H NMR (400 MHz, CDCl$_3$): δ 9.80-9.77 (m, 1H); 7.81 (s, 1H); 4.12-3.80 (m, 2H); 3.73 (s, 3H); 3.68-3.58 (m, 1H); 3.34-3.22 (m, 1H); 2.90-2.33 (m, 6H); 2.21 (d, J=3.17 Hz, 2H); 1.99-1.65 (m, 6H); 1.63-1.47 (m, 2H); 1.37 (d, J=6.9 Hz, 6H); 1.31-1.20 (m, 6H); 1.00 (s, 6H).

g) (R)-4-Hydroxy-7-(1-hydroxy-2-(9-(4-(2-isopropylthiazole-4-carbonyl)-1-oxa-4,9-diazaspiro[5.5]undecan-9-yl)-3,3-dimethylnonylamino)ethyl)benzo[d]thiazol-2(3H)-one, formate

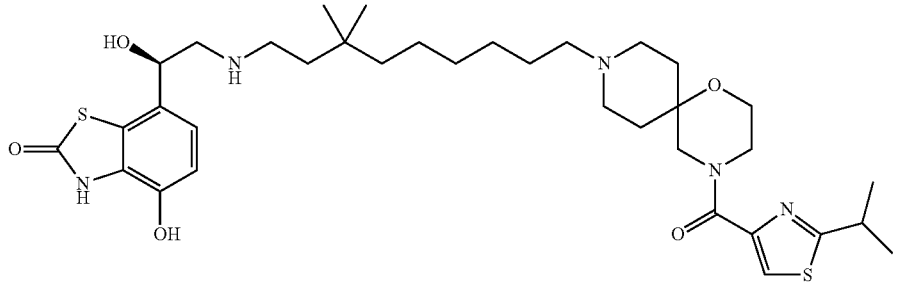 [SMILES: CC(C)c1nc(C(=O)N2CCOC3(CCN(CCCCCCC(C)(C)CCNC[C@H](O)c4ccc(O)c5[nH]c(=O)sc45)CC3)C2)cs1]

Acetic acid (0.035 mL) was added to a stirred solution of 9-(4-(2-isopropylthiazole-4-carbonyl)-1-oxa-4,9-diazaspiro[5.5]undecan-9-yl)-3,3-dimethylnonanal (example 279, step f) (195 mg) and (R)-7-(2-amino-1-hydroxyethyl)-4-hydroxybenzo[d]thiazol-2(3H)-one hydrochloride (WO2007027134, example 1, step d) (161 mg) in methanol (10 mL) and after a minute sodium cyanoborohydride (51 mg) was added and the reaction mixture stirred at room temperature for 1.5 h. The mixture was concentrated and then partitioned between THF (12 mL) and a mixture of brine and saturated sodium bicarbonate solution (10:1, 12 mL). The layers were separated and the organic phase dried over sodium sulfate, filtered and evaporated. The resulting material was purified by preparative HPLC (Phenomenex Gemini®, Gradient: 5-40% acetonitrile in 0.1% aqueous formic acid). The fractions containing product were combined and freeze-dried to afford the titled compound as a white solid. Yield 0.038 g.

m/z 688 (M+H)$^+$ $^1$H NMR (400 MHz, D$_6$-DMSO, 80° C.): δ 8.12 (s, 1.6H); 7.89 (s, 1H); 6.88 (d, J=8.3 Hz, 1H); 6.70 (d, J=8.3 Hz, 1H); 4.59 (t, J=6.2 Hz, 1H); 3.64 (d, J=9.5 Hz, 6H); 2.75 (d, J=6.7 Hz, 2H); 2.61-2.53 (m, 2H); 2.40-2.21 (m, 6H); 1.72-1.63 (m, 2H); 1.58-1.47 (m, 2H); 1.43-1.30 (m, 10H); 1.29-1.09 (m, 8H); 0.82 (s, 6H) plus one signal obscured by solvent and four exchangeables not observed.

EXAMPLE 280

(R)-4-Hydroxy-7-(1-hydroxy-2-(10-(4-(2-isopropylthiazole-4-carbonyl)-1-oxa-4,9-diazaspiro[5.5]undecan-9-yl)decan-2-ylamino)ethyl)benzo[d]thiazol-2(3H)-one formate a) 10-Bromodecan-2-ol

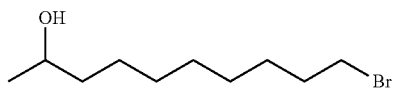

To a solution of 9-bromo-nonanol (1.7 g) in DCM (100 mL) was added diisopropylethylamine (3.91 mL) then DMSO (1.62 mL) and the mixture cooled to −14° C. then sulfur trioxide pyridine complex (3.64 g) was added portionwise. The mixture was stirred for 30 minutes then left to stand overnight. Water was added and the phases separated. The organic layer was washed with 1M sodium hydrogen sulphate (×3), saturated aqueous sodium bicarbonate solution and brine. The organic phase was separated and dried using a hydrophobic flit then evaporated to afford the aldehyde as a yellow liquid (2.32 g).

To a solution of the aldehyde (750 mg) in dry ether (20 mL) at 0° C. was added methyl lithium (1.6M in ether, 2.1 mL) dropwise. After 45 minutes the mixture was poured onto 2M sulfuric acid with stirring and the phases were separated. The organic layer was washed with saturated aqueous sodium bicarbonate solution then dried over sodium sulfate, filtered and evaporated. Purification was by silica gel chromatography eluting with 0-30% ethyl acetate in cyclohexane to afford the titled compound as a straw coloured liquid. Yield 0.286 g.

$^1$H NMR (400 MHz, CDCl$_3$): δ 3.83-3.75 (m, 1H); 3.41 (t, J=6.9 Hz, 2H); 1.90-1.80 (m, 2H); 1.50-1.37 (m, 6H); 1.36-1.26 (s, 6H); 1.19 (d, J=6.2 Hz, 3H) plus one exchangeable not observed.

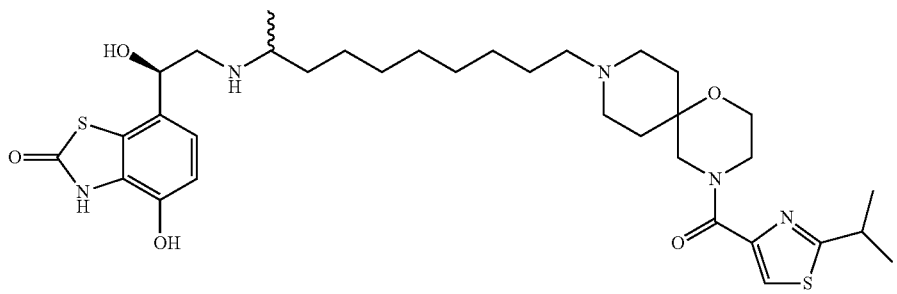 [SMILES: CC(CCCCCCCCN1CCC2(CC1)CN(C(=O)c1csc(C(C)C)n1)CCO2)NC[C@H](O)c1ccc(O)c2[nH]c(=O)sc12]

b) (9-(9-Hydroxydecyl)-1-oxa-4,9-diazaspiro[5.5]undecan-4-yl)(2-isopropylthiazol-4-yl)methanone

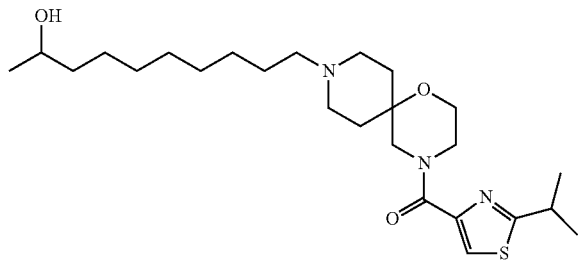 [SMILES: CC(O)CCCCCCCCN1CCC2(CC1)CN(C(=O)c1csc(C(C)C)n1)CCO2]

(2-Isopropyl-thiazol-4-yl)-(1-oxa-4,9-diaza-spiro[5.5]undec-4-yl)-methanone trifluoroacetate (example 22, step b) (500 mg) was applied to a methanol wetted SCX-2 cartridge, washed with methanol then eluted using 2N ammonia in methanol and evaporated to afford the free base (276 mg). This material was mixed with 10-bromodecan-2-ol (example 280, step a, 280 mg) and triethylamine (0.247 mL) in acetonitrile (10 mL) and heated at 60° C. for 18 h. The solvent was removed by evaporation and the crude material purified by silica gel chromatography eluting with 0-20% methanol in DCM to afford the titled compound. Yield 0.298 g.

$^1$H NMR (400 MHz, D$_6$-DMSO): δ 8.99 (s, 1H); 8.00 (s, 1H); 4.23 (d, J=4.7 Hz, 1H); 3.78-3.44 (m, 8H); 3.11-2.77 (m, 4H); 2.08-1.92 (m, 2H); 1.76-1.48 (m, 4H); 1.30 (d, J=6.9 Hz, 7H); 1.26-1.16 (m, 12H); 0.98 (d, J=6.1 Hz, 3H).

c) 10-(4-(2-Isopropylthiazole-4-carbonyl)-1-oxa-4,9-diazaspiro[5.5]undecan-9-yl)decan-2-one

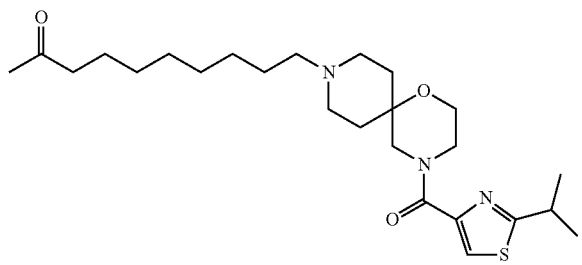 [SMILES: CC(=O)CCCCCCCCN1CCC2(CC1)CN(C(=O)c1csc(C(C)C)n1)CCO2]

To a solution of (9-(9-hydroxydecyl)-1-oxa-4,9-diazaspiro[5.5]undecan-4-yl)(2-isopropylthiazol-4-yl)methanone (example 280, step b) (287 mg) in DCM (10 mL) at 0° C. under nitrogen was added trifluoroacetic acid (0.048 mL). The mixture was stirred for 5 minutes then Dess-Martin periodinane (392 mg) was added. The reaction mixture was stirred at room temperature for 5 hours then a further amount of Dess-Martin periodinane (392 mg) was added at 0° C. then stirred at room temperature for 1.75 h. Saturated sodium thiosulfate solution (20 mL), saturated aqueous sodium bicarbonate solution (20 mL) and ethyl acetate were added and the mixture stirred then the phases separated. The aqueous layer was extracted with ethyl acetate (×2) and the combined organics were washed with saturated aqueous sodium bicarbonate solution. Acetic acid (0.053 mL) was added then the organics were dried over sodium sulfate, filtered and evaporated to afford the titled compound as a yellow gum. Yield 0.338 g.

$^1$H NMR (400 MHz, CDCl$_3$): δ 7.85 (s, 1H); 4.07-3.72 (m, 5H); 3.36-3.21 (m, 2H); 2.96-2.82 (m, 3H); 2.47-2.37 (m, 4H); 2.12 (s, 3H); 2.11-2.02 (m, 2H); 1.85-1.75 (m, 2H); 1.62-1.49 (m, 3H); 1.46-1.36 (m, 7H); 1.35-1.20 (m, 9H).

d) (R)-4-Hydroxy-7-(1-hydroxy-2-(10-(4-(2-isopropylthiazole-4-carbonyl)-1-oxa-4,9-diazaspiro[5.5]undecan-9-yl)decan-2-ylamino)ethyl)benzo[d]thiazol-2(3H)-one formate

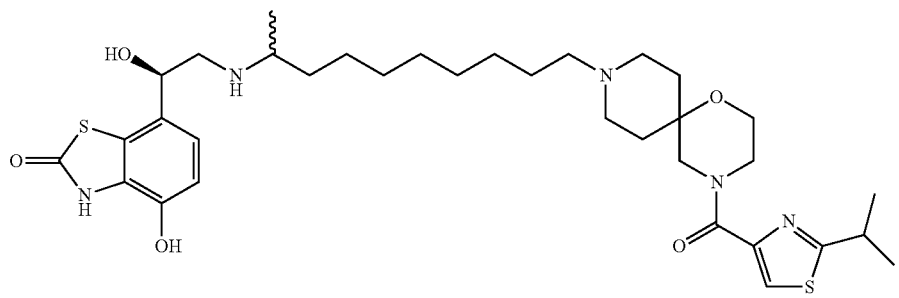 [SMILES: CC(CCCCCCCCN1CCC2(CC1)CN(C(=O)c1csc(C(C)C)n1)CCO2)NC[C@H](O)c1ccc(O)c2[nH]c(=O)sc12]

Acetic acid (0.053 mL) was added to a mixture of 10-(4-(2-isopropylthiazole-4-carbonyl)-1-oxa-4,9-diazaspiro[5.5]undecan-9-yl)decan-2-one (example 280, step c) (335 mg) and (R)-7-(2-amino-1-hydroxyethyl)-4-hydroxybenzo[d]thiazol-2(3H)-one hydrochloride (WO2007027134, example 1, step d) (243 mg) in dry methanol with 3 Å molecular sieves at room temperature under nitrogen and stirred for 5 minutes. The mixture was cooled to 0° C. and sodium triacetoxyborohydride (131 mg) was added. The reaction mixture was stirred, warming to room temperature overnight. The mixture was filtered and evaporated. Purification was by preparative HPLC (Phenomenex Gemini®, Gradient: 10-40% acetonitrile in 0.1% aqueous formic acid). The fractions containing product were combined and freeze-dried to afford the titled compound as a white solid. Yield 0.032 g.

m/z 674 (M+H)$^+$ $^1$H NMR (400 MHz, D$_6$-DMSO, 80° C.): δ 8.15 (s, 2H); 7.88 (s, 1H); 6.87 (d, J=8.3 Hz, 1H); 6.69 (d, J=8.3 Hz, 1H); 4.57-4.50 (m, 1H); 3.71-3.58 (m, 8H); 3.36-3.25 (m, 2H); 2.79-2.59 (m, 3H); 2.40-2.31 (m, 2H); 2.32-2.22 (m, 4H); 1.73-1.63 (m, 2H); 1.59-1.48 (m, 2H); 1.44-1.32 (m, 8H); 1.31-1.16 (s, 10H); 0.99-0.93 (m, 2H) plus 4 exchangeables not observed.

EXAMPLE 281

(R)-4-Hydroxy-7-(1-hydroxy-2-(4-(3-(4-(2-isopropylthiazole-4-carbonyl)-1-oxa-4,9-diazaspiro[5.5]undecan-9-yl)propylthio)butylamino)ethyl)benzo[d]thiazol-2(3H)-one formate

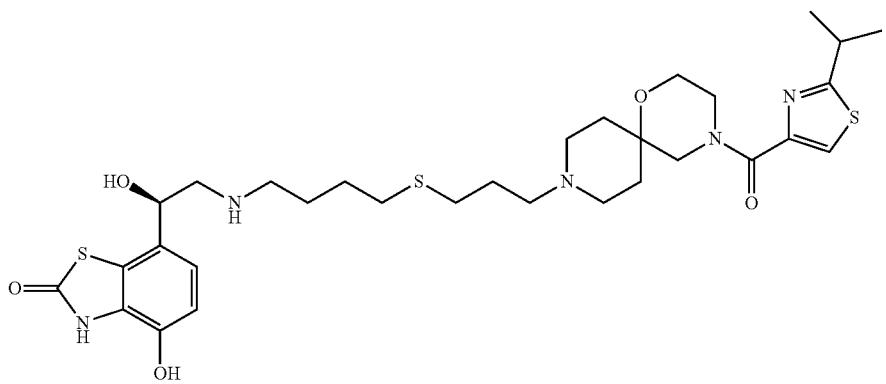 [SMILES: CC(C)c1nc(C(=O)N2CCOC3(CCN(CCCSCCCCNC[C@H](O)c4ccc(O)c5[nH]c(=O)sc45)CC3)C2)cs1]

a) 4-(2-(1,3-Dioxolan-2-yl)ethylthio)butan-1-ol

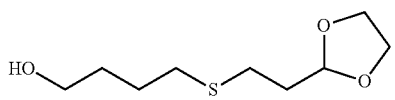 [SMILES: OCCCCSCCC1OCCO1]

A solution of 4-mercaptobutanol (4.936 g) in dry acetonitrile under argon was cooled to 0° C. and sodium hydride (60% in mineral oil, 2.044 g) was added portionwise. The mixture was stirred for 1 hour at 0° C. then 2-(2-bromoethyl)-1,3-dioxolane (9.26 g) was added and the resultant grey suspension was warmed to room temperature and stirred overnight. The reaction was quenched by addition of saturated aqueous sodium bicarbonate solution (150 mL) and then extracted with ethyl acetate (3×150 mL). The organics were combined and washed with brine (150 mL), dried over sodium sulfate, filtered and dried to afford the crude product. Purification was by silica gel chromatography eluting with 0-50% ethyl acetate in cyclohexane to afford the subtitled compound as a yellow oil. Yield 7.3 g.

$^1$H NMR (400 MHz, CDCl$_3$): δ 4.98-4.93 (m, 1H); 4.01-3.93 (m, 2H); 3.89-3.83 (m, 2H); 3.69-3.63 (m, 2H); 2.65-2.58 (m, 2H); 2.59-2.53 (m, 2H); 1.98-1.91 (m, 2H); 1.73-1.62 (m, 4H) plus one exchangeable not observed.

b) (9-(3-(4-Hydroxybutylthio)propyl)-1-oxa-4,9-diazaspiro[5.5]undecan-4-yl)(2-isopropylthiazol-4-yl)methanone

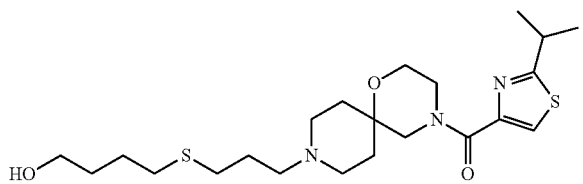 [SMILES: CC(C)c1nc(C(=O)N2CCOC3(CCN(CCCSCCCCO)CC3)C2)cs1]

4-(2-(1,3-Dioxolan-2-yl)ethylthio)butan-1-ol (example 281, step a) (500 mg) was dissolved in an 80% solution of aqueous formic acid (6 mL) and the reaction mixture was stirred at room temperature over the weekend. The mixture was diluted with water (10 mL) and extracted with ether (3×10 mL) then the organics were washed with brine (10 mL), dried over sodium sulphate, filtered and evaporated to afford 3-(4-hydroxy-butylsulfanyl)-propionaldehyde as an oil. This was dissolved in dry methanol and (2-isopropyl-thiazol-4-yl)-(1-oxa-4,9-diaza-spiro[5.5]undec-4-yl)-methanone trifluoroacetate (Example 22, step b) (606 mg) and 3 Å molecular sieves were added. Acetic acid (0.2 mL) was added and the mixture stirred for 5 minutes under argon before cooling to 0° C. and addition of sodium triacetoxyborohydride (633 mg). The cooling bath was removed and the reaction mixture stirred at room temperature overnight. The mixture was filtered then applied directly to an SCX-2 cartridge and washed with methanol before eluting the product with 2N ammonia in methanol. Further purification was by silica gel chromatography eluting with 10% methanol in DCM to afford the subtitled compound as a pale green oil. Yield 0.37 g.

$^1$H NMR (400 MHz, CDCl$_3$): δ 7.85 (s, 1H); 4.02-3.87 (m, 2H); 3.80-3.73 (m, 3H); 3.69-3.63 (m, 3H); 3.39-3.23 (m, 5H); 2.86-2.74 (m, 2H); 2.67-2.59 (m, 2H); 2.58-2.50 (m, 5H); 1.96-1.81 (m, 4H); 1.74-1.63 (m, 4H); 1.41 (d, J=6.9 Hz, 6H).

c) (R)-4-Hydroxy-7-(1-hydroxy-2-(4-(3-(4-(2-isopropylthiazole-4-carbonyl)-1-oxa-4,9-diazaspiro[5.5]undecan-9-yl)propylthio)butylamino)ethyl)benzo[d]thiazol-(3H)-one formate mic acid). The fractions containing product were combined and freeze-dried to give the titled compound as a white solid. Yield 0.006 g.

m/z 664 (M+H)$^+$

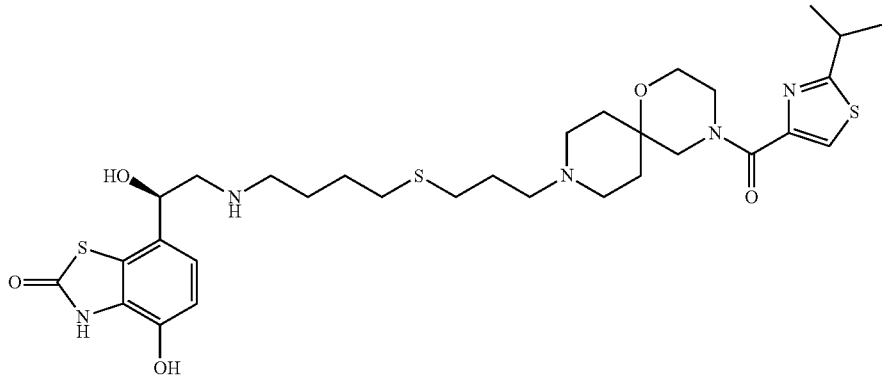 [SMILES: CC(C)c1nc(C(=O)N2CCOC3(CCN(CCCSCCCCNC[C@H](O)c4ccc(O)c5[nH]c(=O)sc45)CC3)C2)cs1]

Oxalyl chloride (0.068 mL) was dissolved in dry DCM (2 mL) and the solution cooled to −78° C. DMSO (0.12 mL) in DCM (0.03 mL) was added dropwise and the mixture stirred. After 15 minutes a solution of (9-(3-(4-hydroxybutylthio)propyl)-1-oxa-4,9-diazaspiro[5.5]undecan-4-yl)(2-isopropylthiazol-4-yl)methanone (example 281, step b) (290 mg) in DCM (1 mL) was added dropwise and stirring continued for 15 minutes before dropwise addition of triethylamine (0.44 mL). The cooling bath was removed and the reaction allowed to warm to room temperature. After 1 hour the reaction mixture was poured onto saturated aqueous ammonium chloride (3 mL) and DCM (3 mL) added. The layers were separated and the aqueous phase was extracted with DCM (2×5 mL). The organics were combined, washed with brine (5 mL), dried over sodium sulfate and evaporated to afford the crude aldehyde.

$^1$H NMR (400 MHz, D$_4$-MeOH): δ 8.48 (s, 1.8H); 7.88 (s, 1H); 6.95 (d, J=8.3 Hz, 1H); 6.73 (d, J=8.3 Hz, 1H); 4.97-4.90 (m, 1H); 3.89-3.56 (m, 6H); 3.38-3.24 (m, 1H); 3.13-3.04 (m, 2H); 3.04-2.96 (m, 2H); 2.97-2.61 (m, 6H); 2.60-2.49 (m, 4H); 2.04-1.91 (m, 2H); 1.91-1.70 (m, 5H); 1.70-1.57 (m, 3H); 1.38 (d, J=6.9 Hz, 6H) plus 4 exchangeables not observed.

EXAMPLE 282

4-Hydroxy-7-((1R)-1-hydroxy-2-(4-(3-(4-(2-isopropylthiazole-4-carbonyl)-1-oxa-4,9-diazaspiro[5.5]undecan-9-yl)propylsulfinyl)butylamino)ethyl)benzo[d]thiazol-2(3H)-one formate

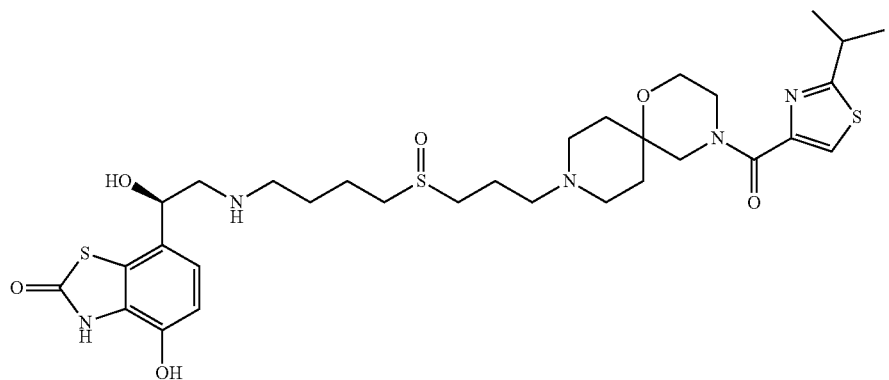 [SMILES: CC(C)c1nc(C(=O)N2CCOC3(CCN(CCCS(=O)CCCCNC[C@H](O)c4ccc(O)c5[nH]c(=O)sc45)CC3)C2)cs1]

The aldehyde (195 mg) was stirred with (R)-7-(2-amino-1-hydroxyethyl)-4-hydroxybenzo[d]thiazol-2(3H)-one hydrochloride (WO2007027134, example 1, step d) (170 mg) in dry methanol (8 mL) and 3 Å molecular sieves and acetic acid (0.07 mL) were added. After stirring for 5 minutes the reaction mixture was cooled to 0° C. and sodium triacetoxyborohydride (200 mg) was added. The cooling bath was removed and the reaction mixture stirred at room temperature over the weekend. The mixture was filtered and evaporated. Purification was by preparative HPLC (Phenomenex Gemini®, Gradient: 5-40% acetonitrile in 0.1% aqueous for- Trifluoroacetic acid (0.06 mL) was added to a solution of (9-(3-(4-hydroxybutylthio)propyl)-1-oxa-4,9-diazaspiro[5.5]undecan-4-yl)(2-isopropylthiazol-4-yl)methanone (Example 281, step b) (360 mg) in dry DCM (14 mL) under argon. The solution was cooled to 0° C. and left to stir for 5 minutes before addition of Dess-Martin periodinane (502 mg). The reaction mixture was stirred at room temperature for 1 hour then quenched by addition of saturated sodium thiosulfate (14 mL) and saturated aqueous sodium bicarbonate solution (14 mL). Ethyl acetate (30 mL) was added and the mixture stirred for 5 minutes then the phases separated. The aqueous layer was extracted with ethyl acetate (2×30 mL). Acetic acid (0.053 mL) was added to the combined organics, which were then dried over sodium sulfate, filtered and evaporated to afford the aldehyde as an oil. This was dissolved in dry methanol (15 mL) together with (R)-7-(2-amino-1-hydroxyethyl)-4-hydroxybenzo[d]thiazol-2(3H)-one hydrochloride (WO2007027134, example 1, step d) (311 mg) and 3 Å molecular sieves and acetic acid (0.07 mL) were added. After stirring for 5 minutes the reaction mixture was cooled to 0° C. and sodium triacetoxyborohydride (200 mg) was added and stirring continued at room temperature overnight. The mixture was filtered and evaporated. Purification was by preparative HPLC (Phenomenex Gemini®, Gradient: 5-40% acetonitrile in 0.1% aqueous formic acid). The fractions containing product were combined and freeze-dried to afford the titled compound as a white solid. Yield 0.018 g.

m/z 680 (M+H)$^+$ $^1$H NMR (400 MHz, D$_4$-MeOH): δ 8.40 (s, 2H); 7.88 (s, 1H); 6.96 (d, J=8.3 Hz, 1H); 6.73 (d, J=8.3 Hz, 1H); 4.98-4.92 (m, 1H); 3.90-3.56 (m, 6H); 3.36-3.24 (m, 1H); 3.19-3.03 (m, 4H); 3.04-2.67 (m, 10H); 2.15-1.95 (m, 4H); 1.93-1.56 (m, 6H); 1.38 (d, J=6.9 Hz, 6H) plus 4 exchangeables not observed.

EXAMPLE 283

4-Hydroxy-7-((1R)-1-hydroxy-2-(9-(4-(2-isopropylthiazole-4-carbonyl)-1-oxa-4,9-diazaspiro[5.5]undecan-9-yl)-2-methylnonylamino)ethyl)benzo[d]thiazol-2(3H)-one formate

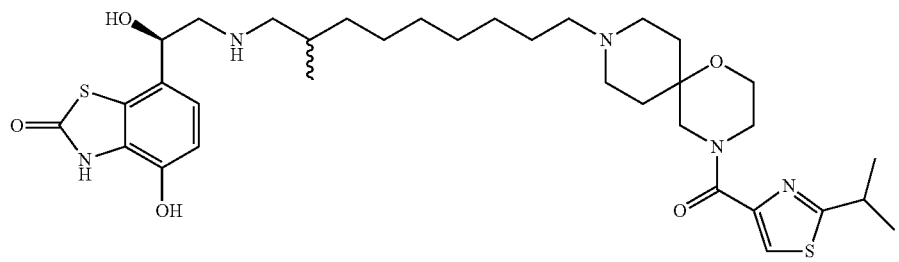

the solution stirred at −78° C. for 1 hour. 1,7-dibromoheptane (6.63 mL) was added and stirring continued at −78° C. for 1 hour then the cooling bath was removed and the reaction mixture was stirred at room temperature overnight. Saturated aqueous ammonium chloride (30 mL) was added to the reaction followed by ethyl acetate (30 mL). The layers were separated and the aqueous phase was extracted with ethyl acetate (2×30 mL). The organics were combined, washed with saturated aqueous sodium bicarbonate solution (50 mL), brine (50 mL), dried over sodium sulfate and evaporated. Purification was by silica gel chromatography eluting with 1-5% ethyl acetate in petroleum ether (40-60° C.) to give ethyl 9-bromo-2-methylnonanoate, which was used without further purification. This material (0.84 g) was dissolved in dry ether (27 mL) and cooled to 0° C. under argon. Diisobutylaluminium hydride (1M in toluene, 6.7 mL) was added dropwise and the reaction was stirred at 0° C. for 1 h 15 minutes. The reaction was quenched by addition of saturated aqueous potassium sodium tartrate and the resulting mixture was stirred for 15 minutes. Ethyl acetate (60 mL) and water (20 mL) were added and the phases separated. The aqueous layer was extracted with ethyl acetate (3×30 mL) then the combined organics were washed with brine, dried over sodium sulfate, filtered and evaporated. Purification was by silica gel chromatography eluting with 0 to 10% ethyl acetate in cyclohexane to afford the subtitled compound as a colourless oil. Yield 0.23 g.

$^1$H NMR (400 MHz, CDCl$_3$): δ 3.51 (dd, J=10.5, 5.8 Hz, 1H); 3.46-3.38 (m, 3H); 1.90-1.80 (m, 2H); 1.66-1.55 (m, 2H); 1.47-1.22 (m, 9H); 0.92 (d, J=6.7 Hz, 3H) plus one exchangeable not observed.

a) 9-Bromo-2-methylnonan-1-ol

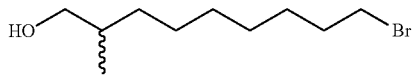

To a solution of diisopropylamine (5.42 mL) in dry THF (30 mL) under argon at 0° C. was added 2.5M n-butyl lithium (15.5 mL) slowly, keeping the temperature below 10° C. The solution was stirred at 0° C. for 30 minutes before cooling to −78° C. Ethyl propionate (4.01 mL) was added dropwise and b) (9-(9-Hydroxy-8-methylnonyl)-1-oxa-4,9-diazaspiro[5.5]undecan-4-yl)(2-isopropylthiazol-4-yl)methanone

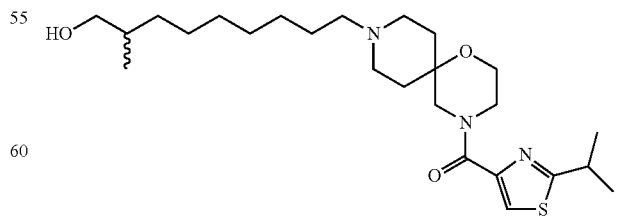

(2-Isopropyl-thiazol-4-yl)-(1-oxa-4,9-diaza-spiro[5.5]undec-4-yl)-methanone ditrifluoroacetate (Example 22, step b)

(500 mg) was applied to a methanol wetted SCX-2 cartridge, washed with methanol then eluted using 2N ammonia in methanol and evaporated to afford the free base (279 mg). This was dissolved in acetonitrile (10 mL) together with 9-bromo-2-methylnonan-1-ol (example 283, step a) (220 mg) and triethylamine (0.223 mL) was added. The reaction mixture was heated to 60° C. overnight then concentrated. Purification was by silica gel chromatography eluting with 0 to 10% methanol in DCM to afford the subtitled compound as a pale brown solid. Yield 0.38 g.

$^1$H NMR (400 MHz, CDCl$_3$): δ 7.87 (s, 1H); 4.06-3.90 (m, 2H); 3.83-3.71 (s, 4H); 3.52-3.37 (m, 4H); 3.05-2.85 (m, 4H); 2.48-2.32 (m, 2H); 2.15-2.05 (m, 2H); 1.97-1.84 (m, 2H); 1.66-1.50 (m, 4H); 1.48-1.39 (m, 6H); 1.38-1.21 (m, 8H); 0.91 (d, J=6.7 Hz, 3H) plus one exchangeable not observed.

reaction mixture was stirred at this temperature for 1 hour then at room temperature for 2 hours. A further amount of carbon tetrabromide (150 mg) was added, the mixture cooled to 0° C. and triphenylphosphine (114 mg) in DCM (1 mL) added dropwise. Stirred at room temperature for 1 hour then water was added and the phases separated. The organic phase was evaporated and the product purified by silica gel chromatography eluting with 0-10% methanol in DCM to afford the subtitled compound as an orange gum. Yield 0.088 g.

$^1$H NMR (400 MHz, CDCl$_3$): δ 7.87 (s, 1H); 4.03-3.91 (m, 2H); 3.81-3.70 (m, 4H); 3.43-3.313 (m, 4H); 3.06-2.86 (m, 4H); 2.49-2.34 (m, 2H); 2.15-2.05 (m, 2H); 1.98-1.86 (m, 2H); 1.57-1.50 (m, 2H); 1.47-1.39 (m, 6H); 1.37-1.19 (m, 10H); 1.00 (d, J=6.6 Hz, 3H).

d) 4-Hydroxy-7-((1R)-1-hydroxy-2-(9-(4-(2-isopropylthiazole-4-carbonyl)-1-oxa-4,9-diazaspiro[5.5]undecan-9-yl)-2-methylnonylamino)ethyl)benzo[d]thiazol-2(3H)-one formate

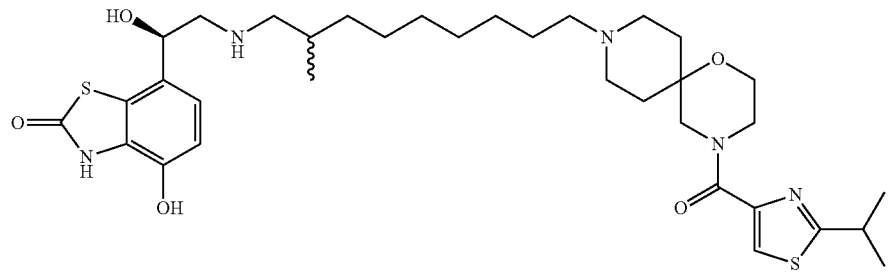

c) (9-(9-Bromo-8-methylnonyl)-1-oxa-4,9-diazaspiro[5.5]undecan-4-yl)(2-isopropylthiazol-4-yl)methanone

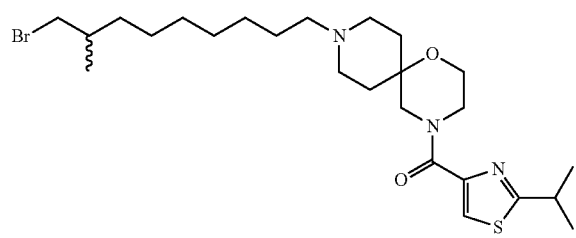 [SMILES: CC(CBr)CCCCCCCN1CCC2(CC1)CN(C(=O)c1csc(C(C)C)n1)CCO2]

(9-(9-Hydroxy-8-methylnonyl)-1-oxa-4,9-diazaspiro[5.5]undecan-4-yl)(2-isopropylthiazol-4-yl)methanone (example 283, step b) (100 mg), carbon tetrabromide (143 mg) and imidazole (30 mg) were dissolved in DCM (5 mL). The solution was cooled to 0° C. and a solution of triphenylphosphine (85 mg) in DCM (1 mL) was added dropwise. The (R)-7-(2-Amino-1-hydroxyethyl)-4-hydroxybenzo[d]thiazol-2(3H)-one hydrochloride (WO2007027134, example 1, step d) (263 mg) was dissolved in methanol (10 mL) and sodium methoxide (54 mg) was added and the mixture stirred for 25 minutes. The solid was collected by filtration and washed with methanol and air dried to afford the free base (150 mg). Some of this material (61 mg) was dissolved in DMF (3.5 mL) and was mixed with (9-(9-Bromo-8-methylnonyl)-1-oxa-4,9-diazaspiro[5.5]undecan-4-yl)(2-isopropylthiazol-4-yl)methanone (example 283, step c) (71 mg) and diisopropylethylamine (0.023 mL). The reaction mixture was heated to 50° C. overnight then cooled and partitioned between ethyl acetate (10 mL) and water (10 mL). The organics were dried over sodium sulfate, filtered and concentrated. Purification was by preparative HPLC (Phenomenex Gemini®, Gradient: 5-40% acetonitrile in 0.1% aqueous formic acid). The fractions containing product were combined and freeze-dried to afford the titled compound as a white solid. Yield 0.002 g.

m/z 674 (M+H)$^+$ $^1$H NMR (400 MHz, D$_4$-MeOH): δ 8.51 (s, 1H); 7.87 (s, 1H); 6.92 (d, J=8.3 Hz, 1H); 6.70 (d, J=8.3 Hz, 1H); 3.85-3.55 (s, 6H); 2.92-2.80 (m, 2H); 2.76-2.34 (m, 8H); 1.97-1.82 (m, 2H); 1.77-1.44 (m, 5H); 1.37 (d, J=6.9 Hz, 6H); 1.36-1.17 (m, 9H); 1.17-1.04 (m, 1H); 0.92 (dd, J=6.6, 3.2 Hz, 3H) plus two signals obscured by solvent and four exchangeables not observed.

EXAMPLE 284

(R)-4-Hydroxy-7-(1-hydroxy-2-(7-(4-(5-isopropylthiophene-3-carbonyl)-1-oxa-4,9-diazaspiro[5.5]undecan-9-yl)heptylamino)ethyl)benzo[d]thiazol-2(3H)-one formate

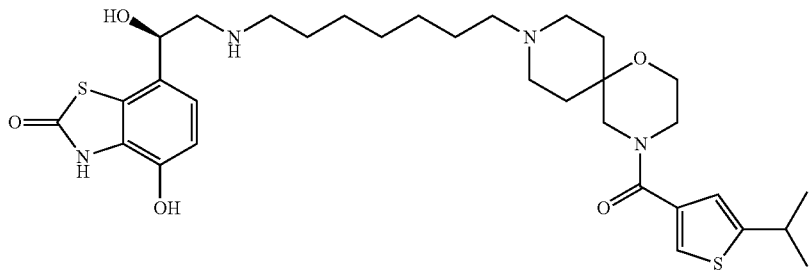 [SMILES: CC(C)c1cc(C(=O)N2CCOC3(CCN(CCCCCCCNC[C@H](O)c4ccc(O)c5[nH]c(=O)sc45)CC3)C2)cs1]

a) (9-(7-Hydroxyheptyl)-1-oxa-4,9-diazaspiro[5.5]undecan-4-yl)(5-isopropylthiophen-3-yl)methanone

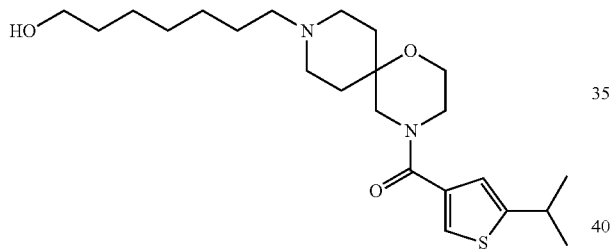

A solution of 7-bromo-1-heptanol (380 mg) in acetonitrile (3.9 mL) was added to a solution of (5-isopropylthiophen-3-yl)(1-oxa-4,9-diazaspiro[5.5]undecan-4-yl)methanone (Example 275, step i) (400 mg) and triethylamine (0.361 mL) in acetonitrile (8.6 mL). The resulting mixture was stirred at 60° C. for 16 hours. The solvent was removed under vacuum and the residue taken up in DCM (25 mL) and washed with brine (25 mL) and water (20 mL), then dried over sodium sulphate, filtered and evaporated. Purification was by silica gel chromatography eluting with 0 to 10% methanol in DCM to afford the subtitled compound as a pale brown solid. Yield 0.305 g.

¹H NMR (400 MHz, CDCl₃): δ 7.26 (s, 1H); 6.84 (s, 1H); 3.74-3.67 (m, 4H); 3.63 (t, J=6.4 Hz, 2H); 3.57-3.48 (m, 2H); 3.35-3.10 (m, 2H); 2.99-2.70 (m, 3H); 2.28-1.98 (m, 4H); 1.92-1.74 (m, 2H); 1.67-1.47 (m, 4H); 1.41-1.34 (m, 5H); 1.34 (d, J=6.9 Hz, 6H); 1.28-1.23 (m, 1H) plus one exchangeable not observed.

b) (R)-4-Hydroxy-7-(1-hydroxy-2-(7-(4-(5-isopropylthiophene-3-carbonyl)-1-oxa-4,9-diazaspiro[5.5]undecan-9-yl)heptylamino)ethyl)benzo[d]thiazol-2(3H)-one formate

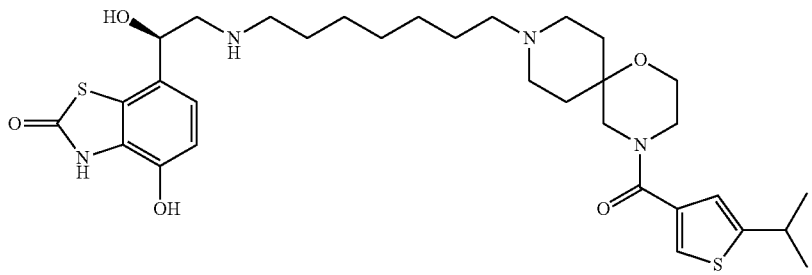 [SMILES: CC(C)c1cc(C(=O)N2CCOC3(CCN(CCCCCCCNC[C@H](O)c4ccc(O)c5[nH]c(=O)sc45)CC3)C2)cs1]

Trifluoroacetic acid (0.054 mL) was added to a solution of (9-(7-hydroxyheptyl)-1-oxa-4,9-diazaspiro[5.5]undecan-4-yl)(5-isopropylthiophen-3-yl)methanone (example 284, step a) (295 mg) in DCM (7.5 mL). The mixture was stirred for 5 minutes then Dess-Martin periodinane (503 mg) was added and stirring continued for 1 hour 50 minutes. The reaction mixture was quenched by addition of saturated sodium thiosulfate solution (4 mL) and saturated aqueous sodium bicarbonate solution (4 mL). Ethyl acetate (25 mL) was added and the mixture vigorously stirred for 5 minutes then the phases separated. The aqueous layer was extracted with ethyl acetate (5 mL). The organics were combined, washed with brine (5 mL) then acetic acid (0.080 mL) was added and the solution dried over sodium sulfate, filtered and evaporated to afford the aldehyde as an oil (504 mg). This was dissolved in dry methanol (5 mL) then (R)-7-(2-amino-1-hydroxyethyl)-4-hydroxybenzo[d]thiazol-2(3H)-one hydrochloride (WO2007027134, example 1, step d) (202 mg) was added and the mixture stirred for 5 minutes. The reaction mixture was cooled to 0° C. and sodium cyanoborohydride (66 mg) was added and stirring continued at 0° C. for 2 hours then at room temperature overnight. The mixture was concentrated under vacuum and partitioned between THF (6 mL) and a mixture of brine and saturated sodium bicarbonate solution (10:1, 6 mL). The layers were separated and the organic phase dried over sodium sulfate, filtered and evaporated and the residue azeotroped with acetonitrile. Purification was by preparative HPLC (Phenomenex Gemini®, Gradient: 5-40% acetonitrile in 0.1% aqueous formic acid). The fractions containing product were combined and freeze-dried to afford the titled compound as a white solid. Yield 0.037 g.

m/z 631 (M+H)$^+$ $^1$H NMR (400 MHz, D$_4$-MeOH): δ 8.49 (s, 2H); 7.45 (s, 1H); 6.95 (d, J=8.3 Hz, 1H); 6.91 (s, 1H); 6.73 (d, J=8.3 Hz, 1H); 4.93 (dd, J=9.1, 4.5 Hz, 1H); 3.79-3.47 (m, 6H); 3.20-3.04 (m, 3H); 3.01-2.94 (m, 3H); 2.92-2.70 (m, 4H); 2.08-1.97 (m, 2H); 1.75-1.56 (m, 6H); 1.43-1.33 (m, 6H); 1.30 (d, J=6.9 Hz, 6H) plus one signal obscured by solvent and four exchangeables not observed.

EXAMPLE 285

(R)-4-Hydroxy-7-(1-hydroxy-2-(9-(4-(2-isopropylthiazole-4-carbonyl)-1-oxa-4,9-diazaspiro[5.5]undecan-9-yl)-4,4-dimethylnonylamino)ethyl)benzo[d]thiazol-2(3H)-one formate

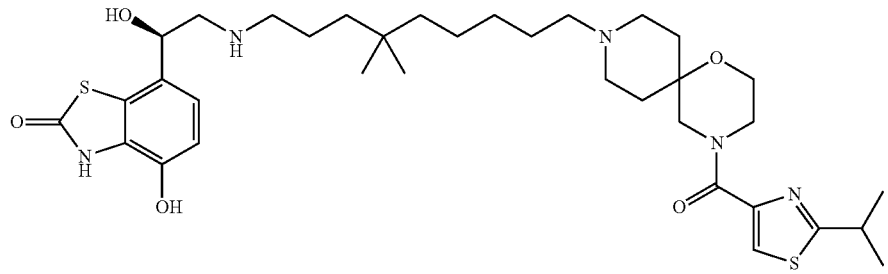 [SMILES: CC(C)c1nc(C(=O)N2CCOC3(CCN(CCCCCC(C)(C)CCCNC[C@H](O)c4ccc(O)c5[nH]c(=O)sc45)CC3)C2)cs1]

a) 2-(5-Bromopentyloxy)tetrahydro-2H-pyran

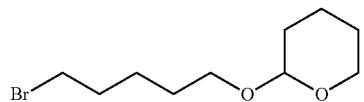 [SMILES: BrCCCCCOC1CCCCO1]

To a solution of 5-bromopentanol (10 g) in DCM (150 mL) was added pyridinium p-toluenesulfonate (1.5 g) followed by 3,4-dihydro-2H-pyran (8.1 mL) and the reaction mixture was stirred at room temperature under nitrogen for 21 hours. The solution was diluted with ether then washed with diluted brine (1:1 brine:water, 140 mL) before the organics were dried over sodium sulfate, filtered and evaporated. Purification was by silica gel chromatography eluting with 0 to 50% ethyl acetate in cyclohexane to afford the subtitled compound as a colourless liquid. Yield 14.14 g.

$^1$H NMR (400 MHz, CDCl$_3$): δ 4.59-4.56 (m, 1H); 3.91-3.82 (m, 1H); 3.79-3.71 (m, 1H); 3.57-3.47 (m, 1H); 3.44-3.36 (m, 3H); 1.94-1.76 (m, 3H); 1.76-1.66 (m, 1H); 1.65-1.46 (m, 8H).

b) Ethyl 2,2-dimethyl-7-(tetrahydro-2H-pyran-2-yloxy)heptanoate

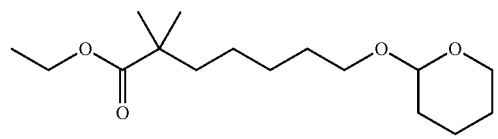 [SMILES: CCOC(=O)C(C)(C)CCCCCOC1CCCCO1]

A solution of diisopropylamine (1.78 mL) in dry THF (10 mL) at 0° C. under nitrogen was treated dropwise with n-butyl lithium (2.5M in hexanes, 5.09 mL) to generate a pale yellow solution which was stirred at 0° C. for 30 minutes then cooled to −78° C. and treated dropwise with ethyl isobutyrate (1.55 mL). The solution was stirred at −78° C. for 45 minutes then a solution of 2-(5-bromopentyloxy)tetrahydro-2H-pyran (example 285, step a) (3.20 g) in dry THF (1 mL) was added dropwise. The reaction mixture was stirred at −78° C. for 10 minutes then was allowed to warm to room temperature overnight. The reaction mixture was cooled to 0° C. then treated with saturated aqueous ammonium chloride solution (3 mL) and extracted with ethyl acetate. The aqueous phase was extracted with ethyl acetate (×2) and the combined organic phase was washed with water, saturated aqueous sodium bicarbonate solution and brine then dried over sodium sulfate, filtered and evaporated. Purification was by silica gel chromatography eluting with 0-5% ethyl acetate in cyclohexane to afford the subtitled compound as colourless liquid. Yield 2.22 g.

$^1$H NMR (400 MHz, CDCl$_3$): δ 4.59-4.55 (m, 1H); 4.11 (q, J=7.1 Hz, 2H); 3.90-3.82 (m, 1H); 3.72 (dt, J=9.6, 6.8 Hz, 1H); 3.53-3.45 (m, 1H); 3.37 (dt, J=9.6, 6.6 Hz, 1H); 1.88-1.77 (m, 1H); 1.75-1.67 (m, 1H); 1.64-1.48 (m, 8H); 1.40-1.30 (m, 2H); 1.29-1.20 (m, 5H); 1.15 (s, 6H).

c) 2,2-Dimethyl-7-(tetrahydro-2H-pyran-2-yloxy)heptan-1-ol

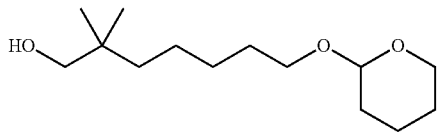 [SMILES: CC(C)(CO)CCCCCOC1CCCCO1]

A solution of ethyl 2,2-dimethyl-7-(tetrahydro-2H-pyran-2-yloxy)heptanoate (example 285, step b) (2.22 g) in dry ether (22 mL) at 0° C. under nitrogen, was treated dropwise over 5 minutes with diisobutylaluminium hydride (1M in toluene, 17.1 mL). After 1 hour at 0° C. the reaction mixture was treated cautiously with aqueous potassium sodium tartrate, diluted with ether and the resultant mixture was stirred vigorously for 1.5 hours. The phases were separated and the aqueous phase was extracted with ether (×2). The combined organic phase was washed with water and brine, dried over magnesium sulfate, filtered and evaporated. Purification was by silica gel chromatography eluting with 0 to 50% ethyl acetate in cyclohexane to afford the subtitled compound as a colourless oil. Yield 1.83 g.

$^1$H NMR (400 MHz, CDCl$_3$): δ 4.58-4.55 (m, 1H); 3.91-3.83 (m, 1H); 3.77-3.69 (m, 1H); 3.53-3.46 (m, 1H); 3.39 (dt, J=9.6, 6.6 Hz, 1H); 3.31 (d, J=4.1 Hz, 2H); 1.90-1.78 (m, 1H); 1.76-1.64 (m, 1H); 1.64-1.48 (m, 4H); 1.40-1.20 (m, 8H); 0.86 (s, 6H) plus one exchangeable not observed.

d) (E)-Ethyl 4,4-dimethyl-9-(tetrahydro-2H-pyran-2-yloxy)non-2-enoate

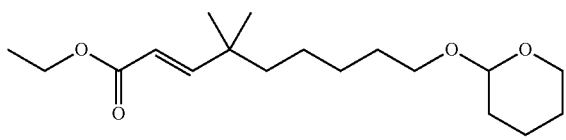 [SMILES: CCOC(=O)/C=C/C(C)(C)CCCCCOC1CCCCO1]

A solution of oxalyl chloride (0.78 mL) in dry DCM (20 mL) at −78° C. was treated dropwise with a solution of DMSO (1.26 mL) in DCM (0.3 mL). After 15 minutes a solution of 2,2-dimethyl-7-(tetrahydro-2H-pyran-2-yloxy)heptan-1-ol (example 285, step c) (1.73 g) in DCM (10 mL) was added dropwise and stirring continued for 15 minutes before addition of triethylamine (4.93 mL) dropwise. The cooling bath was removed and the reaction allowed to warm to room temperature. After 1 hour the reaction mixture was treated with saturated aqueous ammonium chloride solution and the layers were separated. The aqueous phase was extracted with DCM (×2) and the combined organics were washed with brine, dried over magnesium sulfate, filtered and evaporated to afford the crude aldehyde. This was taken up in DCM, washed with water, dried over magnesium sulfate, filtered and evaporated to afford the aldehyde as a colourless oil, which was used directly.

A solution of triethyl phosphonoacetate (1.62 mL) in acetonitrile (8 mL) was treated with lithium chloride (0.43 g) and then cooled to 0° C. and triethylamine (1.23 mL) added dropwise as a solution in acetonitrile (2.5 mL). The reaction mixture was stirred at 0° C. for 15 minutes then a solution of 2,2-dimethyl-7-(tetrahydro-pyran-2-yloxy)-heptanal (1.65 g) in acetonitrile (6 mL) was added. The resultant mixture was allowed to warm to room temperature and was stirred for 3 hours before treating with saturated aqueous ammonium chloride solution, ether and water. The layers were separated and the aqueous phase was extracted with ether (×2) and the combined organics were washed with brine, dried over magnesium sulphate, filtered and evaporated to afford the crude product. Purification was by silica gel chromatography eluting with 0 to 40% ethyl acetate in cyclohexane to afford the subtitled compound as a colourless oil. Yield 0.89 g.

$^1$H NMR (400 MHz, CDCl$_3$): δ 6.91 (d, J=15.9 Hz, 1H); 5.71 (dd, J=15.9, 1.9 Hz, 1H); 4.59-4.55 (m, 1H); 4.19 (q, J=7.1 Hz, 2H); 3.90-3.82 (m, 1H); 3.76-3.68 (m, 1H); 3.53-3.46 (m, 1H); 3.40-3.33 (m, 1H); 1.89-1.77 (m, 1H); 1.76-1.66 (m, 1H); 1.64-1.48 (m, 6H); 1.39-1.19 (m, 9H); 1.05-1.03 (m, 6H).

e) Ethyl 4,4-dimethyl-9-(tetrahydro-2H-pyran-2-yloxy)nonanoate

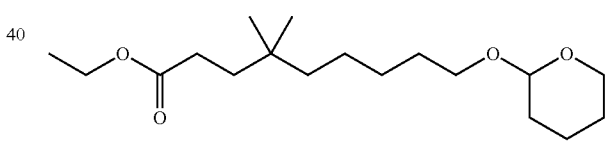

A solution of (E)-Ethyl 4,4-dimethyl-9-(tetrahydro-2H-pyran-2-yloxy)non-2-enoate (example 285, step d) (0.89 g) in IMS (industrial methylated spirits) (10 mL) was treated with palladium on carbon (spatula tip) under nitrogen then the flask was purged with hydrogen (×3) then stirred under an atmosphere of hydrogen overnight. A further portion of palladium on carbon was added and hydrogenation resumed for a further 24 hours. The catalyst was removed by filtration through diatomaceous earth and the filtrate was evaporated to afford the subtitled compound as a colourless oil. Yield 0.86 g.

$^1$H NMR (400 MHz, CDCl$_3$): δ 4.59-4.56 (m, 1H); 4.12 (q, J=7.1 Hz, 2H); 3.90-3.83 (m, 1H); 3.75-3.68 (m, 1H); 3.53-3.46 (m, 1H); 3.41-3.34 (m, 1H); 2.26-2.19 (m, 2H); 1.88-1.79 (m, 2H); 1.76-1.66 (m, 2H); 1.66-1.43 (m, 6H); 1.40-1.14 (m, 9H); 0.84 (s, 6H).

f) Ethyl 9-hydroxy-4,4-dimethylnonanoate

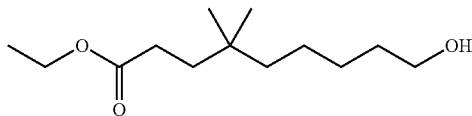 [SMILES: CCOC(=O)CCC(C)(C)CCCCCO]

To a solution of ethyl 4,4-dimethyl-9-(tetrahydro-2H-pyran-2-yloxy)nonanoate (example 285, step e) (0.86 g) in methanol (10 mL) was added p-toluenesulfonic acid monohydrate (52 mg) and the reaction mixture was stirred at room temperature for 2 hours. The mixture was diluted with ethyl acetate and water and the phases separated. The aqueous layer was extracted with ethyl acetate (×2) and the combined organic phase was washed with 10% citric acid, saturated aqueous sodium bicarbonate solution and brine then dried over magnesium sulfate, filtered and evaporated. Purification was by silica gel chromatography eluting with 0-50% ethyl acetate in cyclohexane to afford the subtitled compound as colourless oil. Yield 0.44 g.

$^1$H NMR (400 MHz, CDCl$_3$): δ 4.12 (q, J=7.1 Hz, 2H); 3.67-3.61 (t, J=6.4 Hz, 2H); 2.28-2.20 (m, 2H); 1.61-1.50 (m, 4H); 1.49-1.37 (m, 1H); 1.38-1.22 (m, 7H); 1.21-1.12 (m, 2H); 0.85 (s, 6H).

g) Ethyl 9-bromo-4,4-dimethylnonanoate

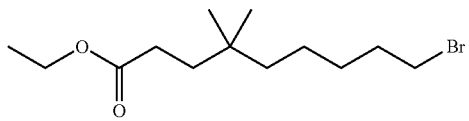 [SMILES: CCOC(=O)CCC(C)(C)CCCCCBr]

A solution of ethyl 9-hydroxy-4,4-dimethylnonanoate (example 285, step f) (0.44 g) in DCM (19 mL) at 0° C. was treated with carbon tetrabromide (0.76 g) followed by triphenylphosphine (0.60 g) and the reaction mixture was stirred at room temperature overnight. Further amounts of carbon tetrabromide (0.76 g) and triphenylphosphine (0.60 g) were added and stirring continued for 3 hours. The solvent was removed by evaporation then the mixture was triturated with cyclohexane and the resultant solid removed by filtration. The solid was washed with cyclohexane and the filtrate was concentrated to about 15 mL and left to stand overnight. The solid which came out of solution was removed by filtration, washed with cyclohexane and the filtrate evaporated to afford the subtitled compound as a pale brown oil. Yield 0.56 g.

$^1$H NMR (300 MHz, CDCl$_3$): δ 4.12 (q, J=7.1 Hz, 2H); 3.41 (t, J=6.8 Hz, 2H); 2.28-2.20 (m, 2H); 1.93-1.80 (m, 2H); 1.59-1.49 (m, 2H); 1.46-1.34 (m, 2H); 1.32-1.21 (m, 5H); 1.22-1.13 (m, 2H); 0.85 (s, 6H).

h) 9-Bromo-4,4-dimethylnonan-1-ol

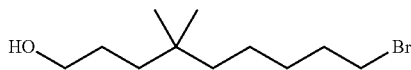

A solution of ethyl 9-bromo-4,4-dimethylnonanoate (example 285, step g) (0.56 g) in dry ether (19 mL) under nitrogen at 0° C. was treated with diisobutylaluminium hydride (1M in toluene, 4.20 mL) and the reaction mixture was stirred at 0° C. for 1 hour 15 minutes. The reaction mixture was treated cautiously with aqueous potassium sodium tartrate solution and stirred for 1 hour. The phases were separated and the aqueous layer was extracted with ether (×2) then the combined organic phase was washed with brine, dried over magnesium sulfate, filtered and evaporated to afford the subtitled compound as a colourless oil. Yield 0.42 g.

$^1$H NMR (400 MHz, CDCl$_3$): δ 3.62 (t, J=6.7 Hz, 2H); 3.41 (t, J=6.9 Hz, 2H); 1.91-1.82 (m, 2H); 1.55-1.45 (m, 2H); 1.46-1.35 (m, 2H); 1.30-1.15 (m, 6H); 0.85 (s, 6H) plus one exchangeable not observed.

i) (9-(9-Hydroxy-6,6-dimethylnonyl)-1-oxa-4,9-diazaspiro[5.5]undecan-4-yl)(2-isopropylthiazol-4-yl)methanone

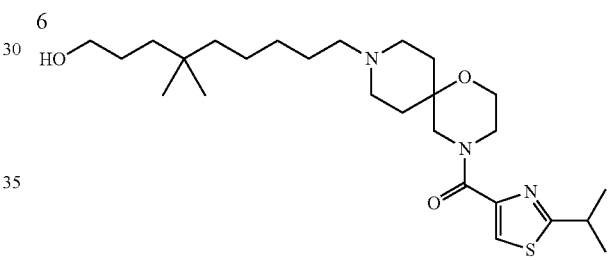

(2-Isopropyl-thiazol-4-yl)-(1-oxa-4,9-diaza-spiro[5.5]undec-4-yl)-methanone ditrifluoroacetate (Example 22, step b) (0.40 g) was applied to a methanol-wetted SCX-2 cartridge, washed with methanol then eluted using 2N ammonia in methanol and evaporated to afford the free base (227 mg). This material was treated with 9-bromo-4,4-dimethylnonan-1-ol (example 285, step h) (0.11 g) in acetonitrile (8.8 mL) followed by triethylamine (0.20 mL). The mixture was heated at 60° C. for 21 h then the solvent was removed by evaporation. Purification was by silica gel chromatography eluting with 75% ethyl acetate in cyclohexane with 5% triethylamine, up to 100% ethyl acetate plus 5% triethylamine to afford the subtitled compound as a colourless gum. Yield 0.295 g.

$^1$H NMR (400 MHz, D$_6$-DMSO): δ 8.00 (s, 1H); 4.35-4.30 (m, 1H); 3.76-3.45 (m, 6H); 3.37-3.28 (m, 1H); 2.41-2.03 (m, 6H); 1.72-1.58 (m, 2H); 1.57-1.44 (m, 2H); 1.43-1.28 (m, 10H); 1.27-1.05 (m, 9H); 0.81 (s, 6H) plus one exchangeable not observed.

j) (R)-4-Hydroxy-7-(1-hydroxy-2-(9-(4-(2-isopropylthiazole-4-carbonyl)-1-oxa-4,9-diazaspiro[5.5]undecan-9-yl)-4,4-dimethylnonylamino)ethyl)benzo[d]thiazol-2(3H)-one formate

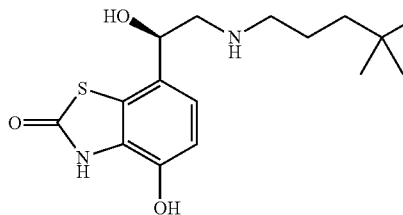
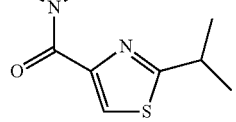

A solution of (9-(9-hydroxy-6,6-dimethylnonyl)-1-oxa-4,9-diazaspiro[5.5]undecan-4-yl)(2-isopropylthiazol-4-yl)methanone (example 285, step i) (0.255 g) in DCM (5.3 mL) at 0° C. under nitrogen was treated with trifluoroacetic acid (0.04 mL) and stirred for 5 minutes then Dess-Martin periodinane (0.339 g) was added. The solution was stirred at room temperature for 1 hour then a further amount of Dess-Martin periodinane (0.113 g) was added and stirring continued for 30 minutes. The reaction mixture was treated with saturated sodium thiosulfate solution and saturated aqueous sodium bicarbonate solution (1:1), diluted with DCM and stirred for 10 minutes. Ethyl acetate was added and the phases were separated. The aqueous layer was extracted with ethyl acetate ($\times 2$). The organics were combined, washed with saturated aqueous sodium bicarbonate solution then dried over magnesium sulfate then acetic acid (0.046 mL) was added and the solution evaporated to afford the aldehyde (0.362 g). This was suspended in dry methanol (9 mL) and treated with (R)-7-(2-amino-1-hydroxyethyl)-4-hydroxybenzo[d]thiazol-2(3H)-one hydrochloride (WO2007027134, example 1, step d) (0.210 g), 3 Å molecular sieves and acetic acid (0.046 mL) and the mixture stirred for 5 minutes. The reaction mixture was cooled to 0° C. and sodium triacetoxyborohydride (113 mg) was added and stirring continued at room temperature for 24 hours. The mixture was filtered then concentrated under vacuum. Purification was by silica gel chromatography eluting with 5, 6, 7, 8, 9, 10 and 12% of a (10% aqueous ammonia in methanol solution) in DCM followed by preparative HPLC (Phenomenex Gemini®, Gradient: 5-40% acetonitrile in 0.1% aqueous formic acid). The fractions containing product were combined and freeze-dried to afford the titled compound as a white solid. Yield 0.024 g.

m/z 688 (M+H)$^+$ $^1$H NMR (400 MHz, D$_6$-DMSO, 80° C.): δ 8.26-8.13 (m, 1H); 7.89 (s, 1H); 6.87 (d, J=8.3 Hz, 1H); 6.69 (d, J=8.3 Hz, 1H); 4.61-4.53 (m, 1H); 3.69-3.63 (m, 6H); 3.37-3.24 (m, 1H); 2.76-2.66 (m, 2H); 2.59-2.50 (m, 2H); 2.40-2.31 (m, 2H); 2.31-2.20 (m, 4H); 1.72-1.63 (m, 2H); 1.58-1.47 (m, 2H); 1.44-1.29 (m, 10H); 1.29-1.09 (m, 8H); 0.80 (s, 6H) plus four exchangeables not observed.

The compounds of the invention may be tested for pharmaceutical activity using assays know in the art, such as for example:

Assay for Adrenergic B2 Mediated cAMP Production
Cell Preparation

H292 cells are grown in 225 cm2 flasks incubator at 37° C., 5% CO$_2$ in RPMI medium containing 10% (v/v) FBS (foetal bovine serum) and 2 mM L-glutamine.

Experimental Method

Adherent H292 cells re removed from tissue culture flasks by treatment with Accutase™ cell detachment solution for 15 minutes. Flasks are incubated for 15 minutes in a humidified incubator at 37° C., 5% CO$_2$. Detached cells are re-suspended in RPMI media (containing 10% (v/v) FBS and 2 mM L-glutamine) at 0.1×10$^6$ cells per mL. 10000 cells in 100 μL are added to each well of a tissue-culture-treated 96-well plate and the cells incubated overnight in a humidified incubator at 37° C., 5% CO$_2$. The culture media is removed and cells are washed twice with 100 μL assay buffer and replaced with 50 μL assay buffer (HBSS solution containing 10 mM HEPES pH7.4 and 5 mM glucose). Cells are rested at room temperature for 20 minutes after which time 25 μL of rolipram (1.2 mM made up in assay buffer containing 2.4% (v/v) dimethylsulphoxide) is added. Cells are incubated with rolipram for 10 minutes after which time test compounds are added and the cells are incubated for 60 minutes at room temperature. The final rolipram concentration in the assay is 300 M and final vehicle concentration is 1% (v/v) dimethylsulphoxide. The reaction is stopped by removing supernatants, washing once with 100 μL assay buffer and replacing with 50 μL lysis buffer. The cell monolayer is frozen at −80° C. for 30 minutes (or overnight).

AlphaScreen™ cAMP Detection

The concentration of cAMP (cyclic adenosine monophosphate) in the cell lysate is determined using AlphaScreen™ methodology. The frozen cell plate is thawed for 20 minutes on a plate shaker then 10 μL of the cell lysate is transferred to a 96-well white plate. 40 μL of mixed AlphaScreen™ detection beads pre-incubated with biotinylated cAMP, is added to each well and the plate incubated at room temperature for 3 hours in the dark. The AlphaScreen™ signal is measured using an EnVision spectrophotometer (Perkin-Elmer Inc.) with the recommended manufacturer's settings cAMP concentrations are determined by reference to a calibration curve determined in the same experiment using standard cAMP concentrations. Concentration response curves for agonists are constructed and data is fitted to a four parameter logistic equation to determine both the pEC$_{50}$ and Intrinsic Activity. Intrinsic Activity is expressed as a fraction relative to the maximum activity determined for formoterol in each experiment.

Muscarinic 3 Receptor Binding Assay

The affinity (pIC$_{50}$) of compounds binding to the M$_3$ receptor is determined by competition binding of [$^3$H]N-methyl scopolamine (NMS) to CHO-K1 (Chinese Hamster Ovary) cell membranes expressing the human muscarinic acetylcholine M$_3$ receptor (M$_3$-ACh) in a scintillation proximity assay (SPA) format.

SPA beads are precoated with membranes and then incubated at 2 mg of beads per well with serial dilutions of compounds of the invention, [$^3$H]NMS at 0.1 nM, quarter Kd (experimentally determined dissociation constant) and assay buffer (20 mM HEPES pH 7.4 containing 5 mM MgCl$_2$). The assay is conducted in a final volume of 200 μL, in the presence of 1% (v/v) dimethyl sulphoxide (DMSO). Total binding of [$^3$H]NMS is determined in the absence of competing compound and non-specific binding of [$^3$H]NMS is determined in the presence of 1 μM atropine. The plates are incubated for 16 hours at room temperature and then read on Wallac Microbeta™ using a normalised $^3$H protocol. The pIC$_{50}$, defined as the negative logarithm of the molar concentration of compound required for 50% reduction in specific [$^3$H]-NMS binding, is determined.

Compounds of the invention were tested in the above assays and the following results obtained:

| Example No | B2 pEC50 (intrinsic activity) | M3 pIC50 |
|---|---|---|
| 1 | 7.2 (0.8) | 8.5 |
| 2 | 7.9 (0.8) | 9.5 |
| 3 | 8.1 (1.0) | 9 |
| 4 | 7.8 (0.9) | 8.9 |
| 5 | 7.1 (0.9) | 8.6 |
| 6 | 8.4 (0.9) | 9.5 |
| 7 | 8.2 (0.8) | 9.3 |
| 8 | 7.4 (1.0) | 8.4 |
| 9 | 8.3 (0.9) | 8.7 |

| Example number | $\beta_2$ pEC$_{50}$ | $\beta_2$ Intrinsic activity | M$_3$ pIC$_{50}$ |
|---|---|---|---|
| 10 | 6.5 | 0.9 | 8.3 |
| 11 | 8.8 | 0.8 | 10 |
| 12 | 8 | 1 | 9 |
| 13 | 7.4 | 0.8 | 10.1 |
| 14 | 8.3 | 0.9 | 8.2 |
| 15 | 8.6 | 0.9 | 8.9 |
| 16 | 7.8 | 0.9 | 8.1 |
| 17 | 7.3 | 0.5 | 7.3 |
| 18 | 7.2 | 1 | 8.6 |
| 19 | 8.5 | 0.9 | 8.8 |
| 20 | 6.7 | 0.8 | 7.5 |
| 21 | 6.7 | 0.5 | 9 |
| 22 | 8 | 0.9 | 9.9 |
| 23 | 7.8 | 0.9 | 9.6 |
| 24 | 8.3 | 1 | 7.6 |
| 25 | 7.8 | 0.8 | 9 |
| 26 | 7.9 | 0.8 | 9.2 |
| 27 | 8.9 | 1 | 8.6 |
| 28 | 8 | 1 | 8.6 |
| 29 | 8.8 | 1 | 8.4 |
| 30 | 8.6 | 0.9 | 7.8 |
| 31 | 8.3 | 0.9 | 7.2 |
| 32 | 8.5 | 1.1 | 7.4 |
| 33 | 8.2 | 1 | 7.9 |
| 34 | 8.5 | 1 | 7.7 |
| 35 | 7.9 | 1 | 7.6 |
| 36 | 8.2 | 1 | 9.3 |
| 37 | 8.5 | 0.9 | 8.5 |
| 38 | 7.7 | 0.8 | 8.6 |
| 39 | 7 | 0.9 | 9.5 |
| 40 | 7.9 | 1.1 | 9.4 |
| 41 | 8.2 | 1.1 | 6.9 |
| 42 | 8.1 | 1 | 9.2 |
| 43 | 8.3 | 0.8 | 7.4 |
| 44 | 8.6 | 1 | 8.5 |
| 45 | 8 | 0.8 | 8.3 |
| 46 | 7.1 | 1 | 8.2 |
| 47 | 7.8 | 0.9 | 9.3 |
| 48 | 8.3 | 0.9 | 9.1 |
| 49 | 8.1 | 0.9 | 7.4 |
| 50 | 8.1 | 0.9 | 7.4 |
| 51 | 8.5 | 0.9 | 7.8 |
| 52 | 8.3 | 0.9 | 8.1 |
| 53 | 8 | 1 | 7.9 |
| 54 | 8.2 | 0.9 | 6.7 |
| 55 | 8.2 | 1 | 7.2 |
| 56 | 8.1 | 1 | 8.6 |
| 57 | 8.2 | 1.1 | 9.1 |
| 58 | 8 | 0.9 | 8.2 |
| 59 | 7.8 | 1 | 8.1 |
| 60 | 8.3 | 1 | 8.4 |
| 61 | 7.2 | 0.9 | 8.3 |
| 62 | 6.6 | 0.9 | 6.6 |
| 63 | 8.3 | 1 | <6 |
| 64 | 7.3 | 0.9 | 9.7 |
| 65 | 7 | 0.9 | 9.2 |
| 66 | 7.8 | 0.9 | 9.1 |
| 67 | 7.8 | 0.9 | 8.5 |
| 68 | 8.2 | 0.8 | 7.6 |
| 69 | 7.8 | 0.9 | 7.7 |
| 70 | 8.1 | 0.8 | 8.5 |
| 71 | 7.7 | 0.8 | 8.3 |
| 72 | 8.1 | 0.8 | 8 |
| 73 | 8.1 | 0.9 | 8.1 |
| 74 | 7.9 | 0.9 | 7.7 |
| 75 | 7.6 | 0.8 | 8.7 |
| 76 | 7.5 | 0.9 | 8.7 |
| 77 | 7.1 | 1 | 8.6 |
| 78 | 7.8 | 0.9 | 8 |
| 79 | 8.2 | 0.9 | 6.9 |
| 80 | 8.2 | 0.8 | 8.3 |
| 81 | 8.1 | 0.7 | 8.2 |
| 82 | 8.4 | 0.9 | 9.4 |
| 83 | 7.9 | 0.8 | 9.3 |
| 84 | 8.3 | 0.9 | 9.1 |
| 85 | 8.1 | 0.8 | 7.3 |
| 86 | 8.6 | 0.8 | 9.8 |
| 87 | 8.5 | 0.9 | 9.3 |
| 88 | 7.9 | 1 | 8.7 |
| 89 | 8.8 | 1 | 7.5 |
| 90 | 6.7 | 0.9 | 7.1 |
| 91 | 8.9 | 0.7 | 8.7 |
| 92 | 6.1 | 0.9 | 6.9 |
| 93 | 8.6 | 0.8 | 8.6 |
| 94 | 5.9 | 0.7 | 7.9 |
| 95 | NV* | NV* | 8.8 |
| 96 | NV* | NV* | 9.6 |
| 97 | <5.5 | 1.5 | 8.2 |
| 98 | 5.7 | 0.4 | 8.9 |
| 99 | 8.1 | 0.8 | 8.8 |
| 100 | 8.3 | 0.9 | 8.8 |
| 101 | 6.8 | 1 | 9.5 |
| 102 | 6.7 | 0.9 | 9 |
| 103 | 6.6 | 1 | 9 |
| 104 | 7.1 | 0.9 | 8.5 |
| 105 | 7.8 | 0.8 | 9.9 |
| 106 | 7 | 0.8 | 6.7 |
| 107 | 7.4 | 0.9 | 8.2 |
| 108 | 6.9 | 0.9 | 8.4 |
| 109 | 8.1 | 0.9 | 9.7 |
| 110 | 7.2 | 0.8 | 7.7 |
| 111 | 7.5 | 0.8 | 9.1 |
| 112 | 6.9 | 0.9 | 6.3 |
| 113 | 7.7 | 0.8 | 7.7 |
| 114 | 7.2 | 0.9 | 6.5 |
| 115 | 8.2 | 0.8 | 8.1 |
| 118 | 8.2 | 1 | 7.7 |
| 124 | 8.4 | 0.9 | 7.9 |
| 130 | 7.9 | 1 | 7.1 |
| 141 | 8.2 | 0.9 | 7.6 |
| 149 | 8.1 | 0.9 | 7.6 |
| 173 | 8.6 | 0.8 | 8.1 |
| 178 | 8.3 | 0.8 | 7.5 |
| 190 | 7.9 | 0.9 | 8.7 |
| 198 | 7.9 | 0.8 | 8.5 |
| 201 | 7.5 | 0.9 | 8.2 |
| 202 | 7.7 | 0.9 | 8.1 |
| 209 | 7.6 | 0.9 | 8.7 |

| Example number | $\beta_2$ pEC$_{50}$ | $\beta_2$ Intrinsic activity | M$_3$ pIC$_{50}$ |
| --- | --- | --- | --- |
| 210 | 7.8 | 0.8 | 8.1 |
| 213 | 7.9 | 0.8 | 9.1 |
| 217 | 7.4 | 0.9 | 9.2 |
| 218 | 7.6 | 0.9 | 9.4 |
| 219 | 7.3 | 0.8 | 9 |
| 220 | 7.6 | 0.8 | 9.2 |
| 221 | 7.5 | 0.9 | 8.9 |
| 259 | 6.7 | 0.9 | 8.3 |
| 264 | 7.7 | 1 | 8.1 |
| 265 | 7.9 | 1 | 9.1 |
| 266 | 8.1 | 0.7 | 9.5 |
| 267 | 8 | 0.9 | 8.8 |
| 268 | 8 | 1 | 8.8 |
| 269 | 7.5 | 1.1 | 8.2 |
| 270 | 6.6 | 0.7 | 7.1 |
| 271 | 8.2 | 1 | 30% inhibtion at 1 µM |
| 272 | 8 | 1 | 6.1 |
| 273 | 6.4 | 0.5 | 7.1 |
| 274 | 7.6 | 1.0 | 8.6 |
| 275 | 7.3 | 1 | 8.8 |
| 276 | 7.4 | 1 | 8.7 |
| 277 | 7.5 | 0.9 | 10 |
| 278 | 8.4 | 1.0 | 9.4 |
| 279 | 6.5 | 0.9 | 8.1 |
| 280 | 8.3 | 1.2 | 9.1 |
| 281 | 7.5 | 0.8 | 8.8 |
| 282 | 7.3 | 1 | 7.7 |
| 283 | 7.1 | 1.1 | 8.9 |
| 284 | 7.9 | 0.9 | 8.7 |
| 285 | 7.8 | 1 | 8.4 |

NV* = inactive up to a max concentration of 3.2 µM of test compound.

The following experimental procedure was used to measure the beta-2% effect at 1 µM for the compounds of Examples 116-263.

Adrenergic $\beta_2$ Mediated cAMP Production

Cell Preparation

H292 cells are grown in 225 cm2 flasks incubator at 37° C., 5% CO$_2$ in RPMI medium containing 10% (v/v) FBS (foetal bovine serum) and 2 mM L-glutamine.

Experimental Method

Compounds were prepared by an initial first dilution into DMSO to give 1 mM stock concentration. This was followed by a 1 in 10 dilution of the stock concentration (10 µl stock compound +90 µl DMSO) to give 0.1 mM compound.

A compound addition plate was prepared by making a further 1 in 25 dilution in assay buffer (HBSS solution containing 10 mM HEPES pH7.4 and 5 mM glucose) containing 4% dimethylsulfoxide. The final compound concentration in assay is 1 µM.

Adherent H292 cells are removed from tissue culture flasks by treatment with Accutase™ cell detachment solution for 15 minutes. Flasks are incubated for 15 minutes in a humidified incubator at 37° C., 5% CO$_2$. Detached cells are re-suspended in RPMI media (containing 10% (v/v) FBS and 2 mM L-glutamine) at 0.1×10$^6$ cells per mL. 10000 cells in 100 µL are added to each well of a tissue-culture-treated 96-well plate and the cells incubated overnight in a humidified incubator at 37° C., 5% CO$_2$. The culture media is removed and cells are washed twice with 100 µL assay buffer and replaced with 50 µL assay buffer (HBSS solution containing 10 mM HEPES pH7.4 and 5 mM glucose). Cells are rested at room temperature for 20 minutes after which time 25 µL of rolipram (1.2 mM made up in assay buffer) is added. Cells are incubated with rolipram for 10 minutes after which time 25 µl test compounds are added and the cells are incubated for 60 minutes at room temperature. The final rolipram concentration in the assay is 300 µM and final vehicle concentration is 1% (v/v) dimethylsulphoxide. The reaction is stopped by removing supernatants, washing once with 100 µL assay buffer and replacing with 50 µL lysis buffer. The cell monolayer is frozen at −80° C. for 30 minutes (or overnight).

AlphaScreen™ cAMP Detection

The concentration of cAMP (cyclic adenosine monophosphate) in the cell lysate is determined using AlphaScreen™ methodology. The frozen cell plate is thawed for 20 minutes on a plate shaker then 10 µL of the cell lysate is transferred to a 96-well white plate. 40 µL of mixed AlphaScreen™ detection beads (containing equal volumes of donor beads (pre-incubated with biotinylated cAMP in the dark for 30 minutes) and acceptor beads is added to each well and the plate incubated at room temperature for 3 hours in the dark. The AlphaScreen™ signal is measured using an EnVision spectrophotometer (Perkin-Elmer Inc.) with the recommended manufacturer's settings. Concentration of cAMP produced per well were calculated with reference to the cAMP standard curve determined in the same experiment and expressed as a percentage of the maximum response generated by 1E-07M formoterol.

The following experimental procedure was used to determine the M3% inhibition at 1 µM of the compounds of Examples 116-263.

Muscarinic 3 Receptor Binding Assay

The activity (% inhibition specific binding) of compounds—on the M$_3$ receptor is determined by competition binding of [$^3$H]N-methyl scopolamine (NMS) to CHO-K1 (Chinese Hamster Ovary) cell membranes expressing the human muscarinic acetylcholine M$_3$ receptor (M$_3$-ACh) in a scintillation proximity assay (SPA) format.

SPA beads are precoated with membranes and then incubated at 2 mg of beads per well with 1 µM compound of the invention, [$^3$H]NMS at 0.1 nM, quarter Kd (experimentally determined dissociation constant) and assay buffer (20 mM HEPES pH 7.4 containing 5 mM MgCl$_2$). The assay is conducted in a final volume of 200 µL, in the presence of 1% (v/v) dimethyl sulphoxide (DMSO). Total binding of [$^3$H]NMS is determined in the absence of competing compound and non-specific binding of [$^3$H]NMS is determined in the presence of 1 µM atropine. The plates are incubated for 16 hours at room temperature and then read on Wallac Microbeta™ using a normalised $^3$H protocol. The compound activity at 1 µM, defined as % inhibition specific [$^3$H]-NMS binding, is determined.

| Example no. | M$_3$ (% inhibition at 1 µM) | $\beta_2$ (% effect at 1 µM) |
| --- | --- | --- |
| 116 | 3 | 111 |
| 117 | 22 | 101 |
| 118 | 95 | 101 |
| 119 | 60 | 100 |
| 120 | 82 | 101 |
| 121 | 28 | 85 |
| 122 | 86 | 82 |
| 123 | 62 | 97 |
| 124 | 97 | 100 |
| 125 | 52 | 97 |
| 126 | 50 | 98 |
| 127 | 78 | 97 |
| 128 | 14 | 112 |
| 129 | 20 | 90 |
| 130 | 90 | 109 |
| 131 | 41 | 95 |
| 132 | 85 | 92 |

| Example no. | M₃ (% inhibition at 1 μM) | β₂ (% effect at 1 μM) |
| --- | --- | --- |
| 133 | 56 | 110 |
| 134 | 4 | 116 |
| 135 | 1 | 106 |
| 136 | 26 | 111 |
| 137 | 13 | 112 |
| 138 | 27 | 92 |
| 139 | 34 | 101 |
| 140 | 76 | 109 |
| 141 | 91 | 105 |
| 142 | −3 | 100 |
| 143 | 2 | 108 |
| 144 | 35 | 101 |
| 145 | 7 | 53 |
| 146 | 41 | 96 |
| 147 | 66 | 102 |
| 148 | 4 | 104 |
| 149 | 92 | 113 |
| 150 | 91 | 100 |
| 151 | 71 | 98 |
| 152 | 13 | 110 |
| 153 | 67 | 98 |
| 154 | 28 | 102 |
| 155 | 4 | 101 |
| 156 | 3 | 106 |
| 157 | 13 | 102 |
| 158 | 72 | 95 |
| 159 | 3 | 90 |
| 160 | 5 | 91 |
| 161 | 42 | 87 |
| 162 | 8 | 91 |
| 163 | 25 | 95 |
| 164 | 35 | 99 |
| 165 | 11 | 89 |
| 166 | 69 | 95 |
| 167 | 8 | 100 |
| 168 | 29 | 95 |
| 169 | −2 | 92 |
| 170 | 42 | 102 |
| 171 | 11 | 86 |
| 172 | 19 | 98 |
| 173 | 99 | 93 |
| 174 | 41 | 89 |
| 175 | 3 | 94 |
| 176 | 16 | 87 |
| 177 | 1 | 78 |
| 178 | 89 | 94 |
| 179 | 66 | 95 |
| 180 | 51 | 92 |
| 181 | 10 | 86 |
| 182 | 16 | 88 |
| 183 | 97 | 91 |
| 184 | 96 | 89 |
| 185 | 95 | 81 |
| 186 | 95 | 86 |
| 187 | 84 | 92 |
| 188 | 96 | 93 |
| 189 | 96 | 93 |
| 190 | 99 | 77 |
| 191 | 94 | 82 |
| 192 | 96 | 88 |
| 193 | 99 | 91 |
| 194 | 85 | 92 |
| 195 | 88 | 86 |
| 196 | 95 | 89 |
| 197 | 97 | 78 |
| 198 | 99 | 82 |
| 199 | 91 | 91 |
| 200 | 70 | 92 |
| 201 | 98 | 105 |
| 202 | 99 | 98 |
| 203 | 94 | 99 |
| 204 | 97 | 101 |
| 205 | 91 | 85 |
| 206 | 95 | 95 |
| 207 | 94 | 101 |
| 208 | 88 | 98 |
| 209 | 99 | 84 |
| 210 | 95 | 92 |
| 211 | 68 | 91 |
| 212 | 88 | 93 |
| 213 | 99 | 87 |
| 214 | 91 | 82 |
| 215 | 94 | 89 |
| 216 | 90 | 88 |
| 217 | 100 | 103 |
| 218 | 100 | 95 |
| 219 | 99 | 92 |
| 220 | 100 | 109 |
| 221 | 99 | 93 |
| 222 | 91 | 87 |
| 223 | 56 | 87 |
| 224 | 70 | 89 |
| 225 | 60 | 74 |
| 226 | 53 | 76 |
| 227 | 48 | 80 |
| 228 | 22 | 67 |
| 229 | 67 | 83 |
| 230 | 31 | 70 |
| 231 | 91 | 53 |
| 232 | 56 | 83 |
| 233 | 51 | 82 |
| 234 | 80 | 78 |
| 235 | 29 | 97 |
| 236 | 30 | 73 |
| 237 | 46 | 62 |
| 238 | 57 | 73 |
| 239 | 90 | 76 |
| 240 | 34 | 92 |
| 241 | 11 | 85 |
| 242 | 83 | 43 |
| 243 | 78 | 84 |
| 244 | 48 | 60 |
| 245 | 51 | 76 |
| 246 | 38 | 72 |
| 247 | 60 | 75 |
| 248 | 44 | 70 |
| 249 | 31 | 76 |
| 250 | 91 | 77 |
| 251 | 51 | 68 |
| 252 | 10 | 88 |
| 253 | 35 | 73 |
| 254 | 92 | 71 |
| 255 | 32 | 66 |
| 256 | 38 | 76 |
| 257 | 36 | 56 |
| 258 | 96 | 55 |
| 259 | 99 | 68 |
| 260 | 93 | 56 |
| 261 | 90 | 70 |
| 262 | 82 | 69 |
| 263 | 37 | 74 |

Figure 1:
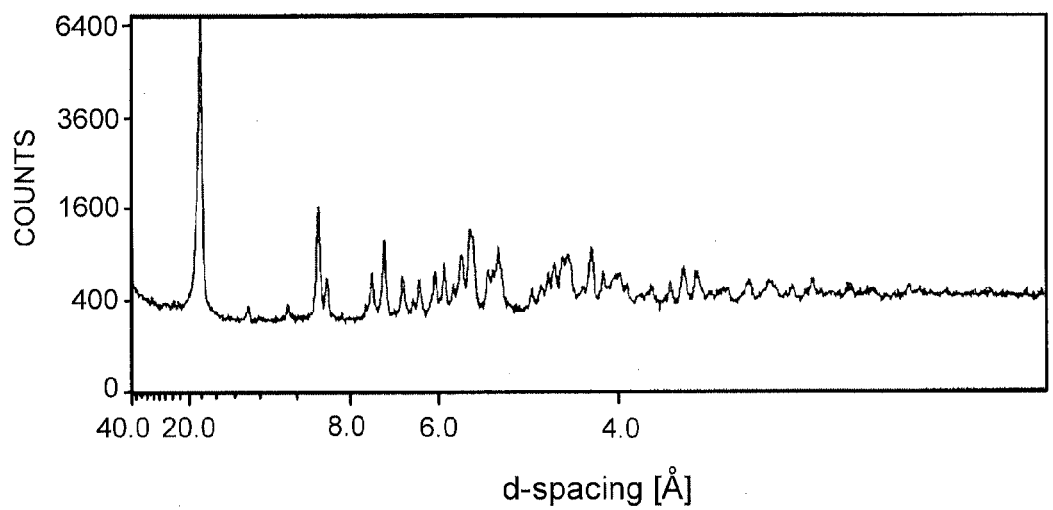
FIG. 1: X-ray powder diffraction pattern of pattern of di(1S)-(+)-10-camphorsulfonic acid salt modification A—Example 47B.
Figure 2:
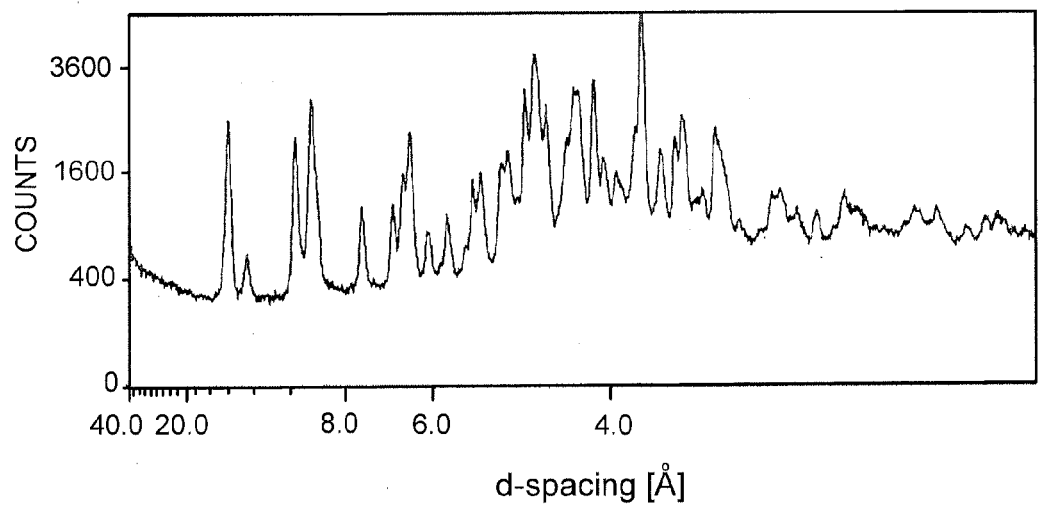
FIG. 2: X-ray powder diffraction pattern of fumarate salt modification A—Example 47C.
Figure 3:
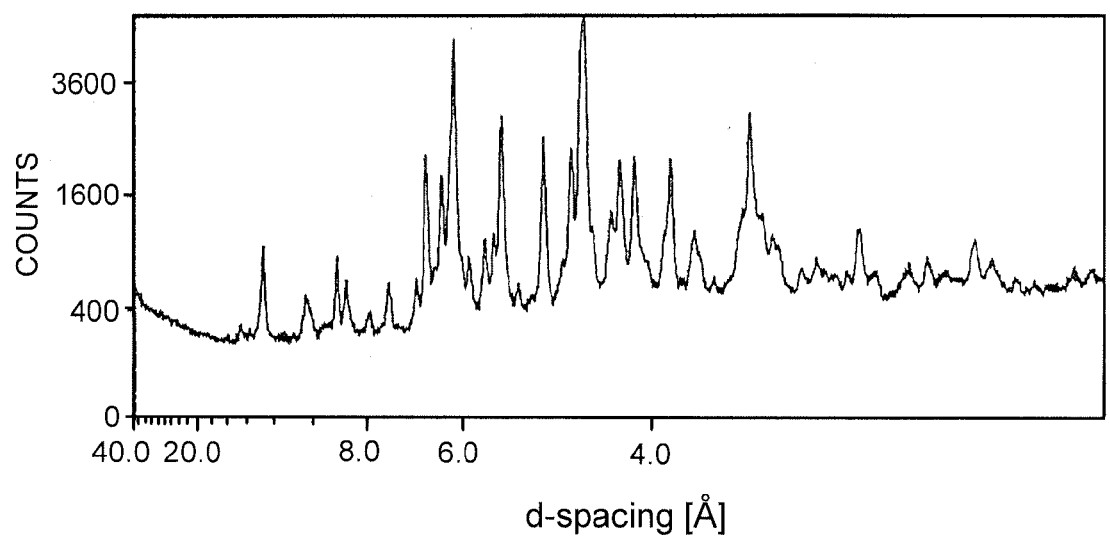
FIG. 3: X-ray powder diffraction pattern of fumarate salt modification B—Example 47D

The invention claimed is:
1. A method of treating chronic obstructive pulmonary disease which comprises administering to a patient in need thereof a therapeutically effective amount of (R)-7-(2-(2-fluoro-5-((4-(2-isopropylthiazole-4-carbonyl)-1-oxa-4,9-diazaspiro[5.5]undecan-9-yl)methyl)phenethylamino)-1-hydroxyethyl)-4-hydroxybenzo[d]thiazol-2(3H)-one,

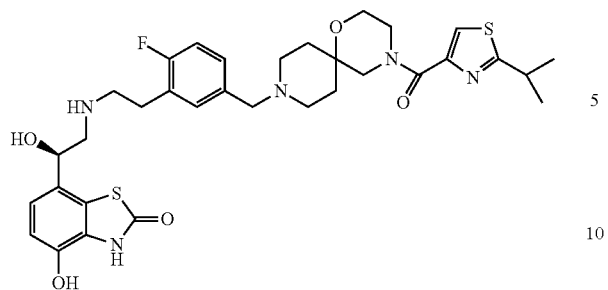
or a pharmaceutically acceptable salt thereof.
* * * * *